US008828996B2

(12) United States Patent
Hadida-Ruah et al.

(10) Patent No.: US 8,828,996 B2
(45) Date of Patent: Sep. 9, 2014

(54) MORPHOLINE-SPIROCYCLIC PIPERIDINE AMIDES AS MODULATORS OF ION CHANNELS

(75) Inventors: Sara Sabina Hadida-Ruah, La Jolla, CA (US); Hayley Marie Binch, Encinitas, CA (US); Michael Paul DeNinno, San Diego, CA (US); Lev Tyler Dewey Fanning, San Marcos, CA (US); Bryan A. Frieman, La Jolla, CA (US); Peter Diederik Jan Grootenhuis, San Diego, CA (US); Nicole Hilgraf, San Diego, CA (US); Pramod Joshi, San Diego, CA (US); Edward Adam Kallel, Escondido, CA (US); Mark Thomas Miller, San Diego, CA (US); Joseph Pontillo, San Diego, CA (US); Alina Silina, San Diego, CA (US); Urvi Jagdishbhai Sheth, San Diego, CA (US); Dennis James Hurley, San Marcos, CA (US); Vijayalaksmi Arumugam, San Marcos, CA (US)

(73) Assignee: Vertex Pharmaceuticals Incorporated, Boston, MA (US)

( * ) Notice: Subject to any disclaimer, the term of this patent is extended or adjusted under 35 U.S.C. 154(b) by 154 days.

(21) Appl. No.: 13/418,737

(22) Filed: Mar. 13, 2012

(65) Prior Publication Data

US 2012/0264749 A1   Oct. 18, 2012

Related U.S. Application Data

(60) Provisional application No. 61/452,538, filed on Mar. 14, 2011, provisional application No. 61/567,809, filed on Dec. 7, 2011.

(51) Int. Cl.
*C07D 498/10* (2006.01)
*A61K 31/537* (2006.01)

(52) U.S. Cl.
USPC ............... 514/232.2; 514/235.8; 514/235.5

(58) Field of Classification Search
USPC ................ 544/71; 514/232.2, 235.8, 235.5
See application file for complete search history.

(56) References Cited

U.S. PATENT DOCUMENTS

| | | | |
|---|---|---|---|
| 3,939,159 A | 2/1976 | Dornauer et al. |
| 4,353,901 A | 10/1982 | Clark |
| 5,206,240 A | 4/1993 | Baldwin et al. |
| 2002/0013325 A1 | 1/2002 | Fisher et al. |
| 2002/0082264 A1 | 6/2002 | Nikolic et al. |
| 2002/0151712 A1 | 10/2002 | Lin et al. |
| 2004/0014744 A1 | 1/2004 | Haviv et al. |
| 2004/0266802 A1 | 12/2004 | Calvet et al. |
| 2005/0209262 A1 | 9/2005 | Tomori et al. |
| 2006/0052597 A1 | 3/2006 | Best et al. |
| 2007/0066584 A1 | 3/2007 | Yao et al. |
| 2007/0078120 A1 | 4/2007 | Ban et al. |
| 2007/0117824 A1 | 5/2007 | Berk et al. |
| 2008/0255154 A1 | 10/2008 | Yao et al. |
| 2009/0169567 A1 | 7/2009 | Kokubo et al. |
| 2009/0192182 A1 | 7/2009 | Kusumi et al. |
| 2009/0325992 A1 | 12/2009 | Hanada et al. |
| 2010/0113418 A1 | 5/2010 | Fukatsu et al. |
| 2011/0306607 A1 | 12/2011 | Hadida-Ruah et al. |
| 2012/0196869 A1 | 8/2012 | Hadida Ruah et al. |
| 2012/0245136 A1 | 9/2012 | Hadida-Ruah et al. |

FOREIGN PATENT DOCUMENTS

| | | |
|---|---|---|
| CA | 2489255 | 12/2003 |
| EP | 0 002 937 | 7/1979 |
| EP | 0 370 732 | 5/1990 |
| EP | 0 431 943 | 6/1991 |
| EP | 2 123 652 | 11/2009 |
| GB | 1 590 155 | 5/1981 |
| JP | 4 297458 | 10/1992 |
| WO | WO 92/15304 | 9/1992 |
| WO | WO 95/15327 | 6/1995 |
| WO | WO 95/30642 | 11/1995 |
| WO | WO 97/02248 | 1/1997 |
| WO | WO 97/11940 | 4/1997 |
| WO | WO 9711940 A1 * | 4/1997 |
| WO | WO 97/16729 | 5/1997 |
| WO | WO 02/20509 | 3/2002 |
| WO | WO 03/095427 | 11/2003 |
| WO | WO 03/104240 | 12/2003 |
| WO | WO 2004/037800 | 5/2004 |
| WO | WO 2004/037828 | 5/2004 |
| WO | WO 2004/054974 | 7/2004 |
| WO | WO 2004/076418 | 9/2004 |
| WO | WO 2004/092179 | 10/2004 |
| WO | WO 2005/003128 | 1/2005 |
| WO | WO 2005/110992 | 11/2005 |
| WO | WO 2005/121090 | 12/2005 |
| WO | WO 2006/105442 | 10/2006 |

(Continued)

OTHER PUBLICATIONS

Artico, M., et al. "One-Pot Synthesis of Novel Spiro-Annelated Pyrrole-Containing Heterocyclic Systems from Suitable Synthons", J. Heterocyclic Chem., 1992, p. 241-245, vol. 29.
Fletcher, Stephen, et al., "4-(Phenylsulfonyl)piperidines: Novel, Selective, and Bioavailable 5-HT$_{2A}$ Receptor Antagonists", J. Med. Chem, 2002, p. 492-503, vol. 45.
Shen, Hong C., et al. "Discovery of spirocyclic secondary amine-derived ureas as highly potent, selective and bioavailable soluble epoxide hydrolase inhibitors", Bioorganic & Medicinal Chemistry Letters, 2009, p. 3398-3404, vol. 19.

(Continued)

*Primary Examiner* — Kahsay Habte
(74) *Attorney, Agent, or Firm* — Brinks Gilson & Lione

(57) ABSTRACT

The invention relates to morpholine spirocyclic piperidine amide compounds useful as inhibitors of ion channels. The invention also provides pharmaceutically acceptable compositions comprising the compounds of the invention and methods of using the compositions in the treatment of various disorders.

79 Claims, No Drawings

(56) References Cited

FOREIGN PATENT DOCUMENTS

| | | |
|---|---|---|
| WO | WO 2006/117669 | 11/2006 |
| WO | WO 2007/011809 | 1/2007 |
| WO | WO 2007/011811 | 1/2007 |
| WO | WO 2007/050124 | 5/2007 |
| WO | WO 2007/124045 | 11/2007 |
| WO | WO 2007/128782 | 11/2007 |
| WO | WO 2007/136605 | 11/2007 |
| WO | WO 2008/045564 | 4/2008 |
| WO | WO 2008/065508 | 6/2008 |
| WO | WO 2008/088688 | 7/2008 |
| WO | WO 2008/088692 | 7/2008 |
| WO | WO 2009/127609 | 10/2009 |
| WO | WO 2009/144554 | 12/2009 |
| WO | WO 2010/002010 | 1/2010 |
| WO | WO 2010/009195 | 1/2010 |
| WO | WO 2010/027567 | 3/2010 |
| WO | WO 2010/051476 | 5/2010 |
| WO | WO 2010/051497 | 5/2010 |
| WO | WO 2010/114957 | 10/2010 |
| WO | WO 2010/151595 | 12/2010 |
| WO | WO 2010/151597 | 12/2010 |
| WO | WO 2011/025690 | 3/2011 |
| WO | WO 2011/092198 | 8/2011 |
| WO | WO 2011/140425 | 11/2011 |
| WO | WO 2012/106499 | 8/2012 |
| WO | WO 2012/112743 | 8/2012 |

OTHER PUBLICATIONS

International Search Report completed Jul. 10, 2012, in International Application No. PCT/US2012/028882, filed Mar. 13, 2012.

* cited by examiner

MORPHOLINE-SPIROCYCLIC PIPERIDINE AMIDES AS MODULATORS OF ION CHANNELS

CROSS REFERENCE TO RELATED APPLICATIONS

This application claims priority to U.S. provisional patent application Ser. Nos. 61/452,538, filed Mar. 14, 2011, and 61/567,809, filed Dec. 7, 2011, the entire contents of all applications are incorporated herein by reference.

TECHNICAL FIELD OF THE INVENTION

The invention relates to compounds useful as inhibitors of ion channels. The invention also provides pharmaceutically acceptable compositions comprising the compounds of the invention and methods of using the compositions in the treatment of various disorders.

BACKGROUND OF THE INVENTION

Pain is a protective mechanism that allows healthy animals to avoid tissue damage and to prevent further damage to injured tissue. Nonetheless there are many conditions where pain persists beyond its usefulness, or where patients would benefit from inhibition of pain. Voltage-gated sodium channels are believed to play a critical role in pain signaling. This belief is based on the known roles of these channels in normal physiology, pathological states arising from mutations in sodium channel genes, preclinical work in animal models of disease, and the clinical usefulness of known sodium channel modulating agents (Cummins, T. R., Sheets, P. L., and Waxman, S. G., The roles of sodium channels in nociception: Implications for mechanisms of pain. *Pain* 131 (3), 243 (2007); England, S., Voltage-gated sodium channels: the search for subtype-selective analgesics. *Expert Opin Investig Drugs* 17 (12), 1849 (2008); Krafte, D. S. and Bannon, A. W., Sodium channels and nociception: recent concepts and therapeutic opportunities. *Curr Opin Pharmacol* 8 (1), 50 (2008)).

Voltage-gated sodium channels (NaV's) are key biological mediators of electrical signaling. NaV's are the primary mediators of the rapid upstroke of the action potential of many excitable cell types (e.g. neurons, skeletal myocytes, cardiac myocytes), and thus are critical for the initiation of signaling in those cells (Hille, Bertil, *Ion Channels of Excitable Membranes*, Third ed. (Sinauer Associates, Inc., Sunderland, Mass., 2001)). Because of the role NaV's play in the initiation and propagation of neuronal signals, antagonists that reduce NaV currents can prevent or reduce neural signaling. Thus NaV channels are considered likely targets in pathologic states where reduced excitability is predicted to alleviate the clinical symptoms, such as pain, epilepsy, and some cardiac arrhythmias (Chahine, M., Chatelier, A., Babich, O., and Krupp, J. J., Voltage-gated sodium channels in neurological disorders. *CNS Neurol Disord Drug Targets* 7 (2), 144 (2008)).

The NaV's form a subfamily of the voltage-gated ion channel super-family and comprises 9 isoforms, designated NaV 1.1-NaV 1.9. The tissue localizations of the nine isoforms vary greatly. NaV 1.4 is the primary sodium channel of skeletal muscle, and NaV 1.5 is primary sodium channel of cardiac myocytes. NaV's 1.7, 1.8 and 1.9 are primarily localized to the peripheral nervous system, while NaV's 1.1, 1.2, 1.3, and 1.6 are neuronal channels found in both the central and peripheral nervous systems. The functional behaviors of the nine isoforms are similar but distinct in the specifics of their voltage-dependent and kinetic behavior (Catterall, W. A., Goldin, A. L., and Waxman, S. G., International Union of Pharmacology. XLVII. Nomenclature and structure-function relationships of voltage-gated sodium channels. *Pharmacol Rev* 57 (4), 397 (2005)).

NaV channels have been identified as the primary target for some clinically useful pharmaceutical agents that reduce pain (Cummins, T. R., Sheets, P. L., and Waxman, S. G., The roles of sodium channels in nociception: Implications for mechanisms of pain. *Pain* 131 (3), 243 (2007)). The local anesthetic drugs such as lidocaine block pain by inhibiting NaV channels. These compounds provide excellent local pain reduction but suffer the drawback of abolishing normal acute pain and sensory inputs. Systemic administration of these compounds results in dose limiting side effects that are generally ascribed to block of neural channels in the CNS (nausea, sedation, confusion, ataxia). Cardiac side effects can also occur, and indeed these compounds are also used as class 1 anti-arrhythmics, presumably due to block of NaV 1.5 channels in the heart. Other compounds that have proven effective at reducing pain have also been suggested to act by sodium channel blockade including carbamazepine, lamotragine, and tricyclic antidepressants (Soderpalm, B., Anticonvulsants: aspects of their mechanisms of action. *Eur J Pain* 6 SupplA, 3 (2002); Wang, G. K., Mitchell, J., and Wang, S. Y., Block of persistent late $Na^+$ currents by antidepressant sertraline and paroxetine. *J Membr Biol* 222 (2), 79 (2008)). These compounds are likewise dose limited by adverse effects similar to those seen with the local anesthetics. Antagonists that specifically block only the isoform(s) critical for nocioception are expected to have increased efficacy since the reduction of adverse effects caused by block of off-target channels should enable higher dosing and thus more complete block of target channels isoforms.

Four NaV isoforms, NaV 1.3, 1.7, 1.8, and 1.9, have been specifically indicated as likely pain targets. NaV 1.3 is normally found in the pain sensing neurons of the dorsal root ganglia (DRG) only early in development and is lost soon after birth both in humans and in rodents. Nonetheless, nerve damaging injuries have been found to result in a return of the NaV 1.3 channels to DRG neurons and this may contribute to the abnormal pain signaling in various chronic pain conditions resulting from nerve damage (neuropathic pain). These data have led to the suggestion that pharmaceutical block of NaV 1.3 could be an effective treatment for neuropathic pain. In opposition to this idea, global genetic knockout of NaV 1.3 in mice does not prevent the development of allodynia in mouse models of neuropathic pain (Nassar, M. A. et al., Nerve injury induces robust allodynia and ectopic discharges in NaV 1.3 null mutant mice. *Mol Pain* 2, 33 (2006)). It remains unknown whether compensatory changes in other channels allow for normal neuropathic pain in NaV 1.3 knockout mice, though it has been reported that knockout of NaV 1.1 results in drastic upregulation of NaV 1.3. The converse effect in NaV 1.3 knockouts might explain these results.

NaV 1.7, 1.8, and 1.9 are highly expressed in DRG neurons, including the neurons whose axons make up the C-fibers and Aδ nerve fibers that are believed to carry most pain signals from the nociceptive terminals to the central nervous. Like NaV 1.3, NaV 1.7 expression increases after nerve injury and may contribute to neuropathic pain states. The localization of NaV 1.7, 1.8, and 1.9 in nocioceptors led to the hypothesis that reducing the sodium currents through these channels might alleviate pain. Indeed, specific interventions that reduce the levels of these channels have proven effective in animal models of pain.

Specific reduction of NaV 1.7 in rodents by multiple different techniques has resulted in the reduction of observable pain behaviors in model animals. Injection of a viral antisense NaV 1.7 cDNA construct greatly reduces normal pain responses due to inflammation or mechanical injury (Yeomans, D. C. et al., Decrease in inflammatory hyperalgesia by herpes vector-mediated knockdown of NaV 1.7 sodium channels in primary afferents. *Hum Gene Ther* 16 (2), 271 (2005)). Likewise, a genetic knockout of NaV 1.7 in a subset of nociceptor neurons reduced acute and inflammatory pain in mouse models (Nassar, M. A. et al., Nociceptor-specific gene deletion reveals a major role for NaV 1.7 (PN1) in acute and inflammatory pain. *Proc Natl Acad Sci USA* 101 (34), 12706 (2004)). Global knockouts of NaV 1.7 in mice lead to animals that die on the first day after birth. These mice fail to feed and this is the presumed cause of death.

Treatments that specifically reduce NaV 1.8 channels in rodent models effectively reduce pain sensitivity. Knockdown of NaV 1.8 in rats by intrathecal injection of antisense oligodeoxynucleotides reduces neuropathic pain behaviors, while leaving acute pain sensation intact (Lai, J. et al., Inhibition of neuropathic pain by decreased expression of the tetrodotoxin-resistant sodium channel, NaV1.8. *Pain* 95 (1-2), 143 (2002); Porreca, F. et al., A comparison of the potential role of the tetrodotoxin-insensitive sodium channels, PN3/SNS and NaN/SNS2, in rat models of chronic pain. *Proc Natl Acad Sci USA* 96 (14), 7640 (1999)). Global genetic knockout of NaV 1.8 in mice or specific destruction of NaV 1.8 expressing neurons greatly reduces perception of acute mechanical, inflammatory, and visceral pain (Akopian, A. N. et al., The tetrodotoxin-resistant sodium channel SNS has a specialized function in pain pathways. *Nat Neurosci* 2 (6), 541 (1999); Abrahamsen, B. et al., The cell and molecular basis of mechanical, cold, and inflammatory pain. *Science* 321 (5889), 702 (2008); Laird, J. M., Souslova, V., Wood, J. N., and Cervero, F., Deficits in visceral pain and referred hyperalgesia in NaV 1.8 (SNS/PN3)-null mice. *J Neurosci* 22 (19), 8352 (2002)). In contrast to the antisense experiments in rats, genetic knockout mice appear to develop neuropathic pain behaviors normally after nerve injury (Lai, J. et al., Inhibition of neuropathic pain by decreased expression of the tetrodotoxin-resistant sodium channel, NaV1.8. *Pain* 95 (1-2), 143 (2002); Akopian, A. N. et al., The tetrodotoxin-resistant sodium channel SNS has a specialized function in pain pathways. *Nat Neurosci* 2 (6), 541 (1999); Abrahamsen, B. et al., The cell and molecular basis of mechanical, cold, and inflammatory pain. *Science* 321 (5889), 702 (2008); Laird, J. M., Souslova, V., Wood, J. N., and Cervero, F., Deficits in visceral pain and referred hyperalgesia in NaV 1.8 (SNS/PN3)-null mice. *J Neurosci* 22 (19), 8352 (2002)).

NaV 1.9 global knock out mice have decreased sensitivity to inflammation induced pain, despite normal acute, and neuropathic pain behaviors (Amaya, F. et al., The voltage-gated sodium channel Na(v)1.9 is an effector of peripheral inflammatory pain hypersensitivity. *J Neurosci* 26 (50), 12852 (2006); Priest, B. T. et al., Contribution of the tetrodotoxin-resistant voltage-gated sodium channel NaV1.9 to sensory transmission and nociceptive behavior. *Proc Natl Acad Sci USA* 102 (26), 9382 (2005)). Spinal knockdown of NaV 1.9 had no apparent effect on pain behavior in rats (Porreca, F. et al., A comparison of the potential role of the tetrodotoxin-insensitive sodium channels, PN3/SNS and NaN/SNS2, in rat models of chronic pain. *Proc Natl Acad Sci USA* 96 (14), 7640 (1999)).

The understanding of the role of NaV channels in human physiology and pathology has been greatly advanced by the discovery and analysis of naturally occurring human mutations. NaV 1.1 and NaV 1.2 mutations result in various forms of epilepsy (Fujiwara, T., Clinical spectrum of mutations in SCN1A gene: severe myoclonic epilepsy in infancy and related epilepsies. *Epilepsy Res* 70 Suppl 1, S223 (2006); George, A. L., Jr., Inherited disorders of voltage-gated sodium channels. *J Clin Invest* 115 (8), 1990 (2005); Misra, S, N., Kahlig, K. M., and George, A. L., Jr., Impaired NaV1.2 function and reduced cell surface expression in benign familial neonatal-infantile seizures. *Epilepsia* 49 (9), 1535 (2008)). Mutations of the NaV 1.4 cause muscular disorders like paramyotonia congenital (Vicart, S., Sternberg, D., Fontaine, B., and Meola, G., Human skeletal muscle sodium channelopathies. *Neurol Sci* 26 (4), 194 (2005)). NaV 1.5 mutations result in cardiac abnormalities like Brugada Syndrome and long QT syndrome (Bennett, P. B., Yazawa, K., Makita, N., and George, A. L., Jr., Molecular mechanism for an inherited cardiac arrhythmia. *Nature* 376 (6542), 683 (1995); Darbar, D. et al., Cardiac sodium channel (SCN5A) variants associated with atrial fibrillation. *Circulation* 117 (15), 1927 (2008); Wang, Q. et al., SCN5A mutations associated with an inherited cardiac arrhythmia, long QT syndrome. *Cell* 80 (5), 805 (1995)).

Recent discoveries have demonstrated that mutations in the gene that encodes the NaV 1.7 channel (SCN9A) can cause both enhanced and reduced pain syndromes. Work by Waxman's group and others have identified at least 15 mutations that result in enhanced current through NaV 1.7 and are linked to dominant congenital pain syndromes. Mutations that lower the threshold for NaV 1.7 activation cause inherited erythromelalgia (IEM). IEM patients exhibit abnormal burning pain in their extremities. Mutations that interfere with the normal inactivation properties of NaV 1.7 lead to prolonged sodium currents and cause paroxysmal extreme pain disorder (PEPD). PEPD patients exhibit periocular, perimandibular, and rectal pain symptoms that progresses throughout life (Drenth, J. P. et al., SCN9A mutations define primary erythermalgia as a neuropathic disorder of voltage gated sodium channels. *J Invest Dermatol* 124 (6), 1333 (2005); Estacion, M. et al., NaV 1.7 gain-of-function mutations as a continuum: A1632E displays physiological changes associated with erythromelalgia and paroxysmal extreme pain disorder mutations and produces symptoms of both disorders. *J Neurosci* 28 (43), 11079 (2008)).

NaV 1.7 null mutations in human patients were recently described by several groups (Ahmad, S. et al., A stop codon mutation in SCN9A causes lack of pain sensation. *Hum Mol Genet.* 16 (17), 2114 (2007); Cox, J. J. et al., An SCN9A channelopathy causes congenital inability to experience pain. *Nature* 444 (7121), 894 (2006); Goldberg, Y. P. et al., Loss-of-function mutations in the NaV 1.7 gene underlie congenital indifference to pain in multiple human populations. *Clin Genet* 71 (4), 311 (2007)). In all cases patients exhibit congenital indifference to pain. These patients report no pain under any circumstances. Many of these patients suffer dire injuries early in childhood since they do not have the protective, normal pain that helps to prevent tissue damage and develop appropriate protective behaviors. Aside from the striking loss of pain sensation and reduced or absent of smell (Goldberg, Y. P. et al., Loss-of-function mutations in the NaV 1.7 gene underlie congenital indifference to pain in multiple human populations. *Clin Genet* 71 (4), 311 (2007)), these patients appear completely normal. Despite the normally high expression of NaV 1.7 in sympathetic neurons (Toledo-Aral, J. J. et al., Identification of PN1, a predominant voltage-dependent sodium channel expressed principally in peripheral neurons. *Proc Natl Acad Sci USA* 94 (4), 1527 (1997)) and adrenal chromatin cells (Klugbauer, N., Lacinova, L., Flockerzi, V., and Hofmann, F., Structure and functional expression of a new member of the tetrodotoxin-sensitive voltage-activated sodium channel family from human neuroendocrine cells. *EMBO J* 14 (6), 1084 (1995)), these NaV 1.7-null patients show no sign of neuroendocrine or sympathetic nervous dysfunction.

The gain of NaV 1.7 function mutations that cause pain, coupled with the loss of NaV 1.7 function mutations that abolish pain, provide strong evidence that NaV 1.7 plays an important role in human pain signaling. The relative good health of NaV 1.7-null patients indicates that ablation of NaV 1.7 is well tolerated in these patients.

Unfortunately, the efficacy of currently used sodium channel blockers for the disease states described above has been to a large extent limited by a number of side effects. These side effects include various CNS disturbances such as blurred vision, dizziness, nausea, and sedation as well more potentially life threatening cardiac arrhythmias and cardiac failure. Accordingly, there remains a need to develop additional Na channel antagonists, preferably those with higher potency and fewer side effects.

SUMMARY OF THE INVENTION

It has now been found that compounds of this invention, and pharmaceutically acceptable compositions thereof, are useful as inhibitors of voltage-gated sodium channels. These compounds have the general formula I:

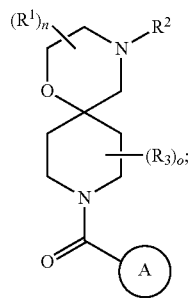

or a pharmaceutically acceptable salt thereof.

These compounds and pharmaceutically acceptable compositions are useful for treating or lessening the severity of a variety of diseases, disorders, or conditions, including, but not limited to, acute, chronic, neuropathic, or inflammatory pain, arthritis, migraine, cluster headaches, trigeminal neuralgia, herpetic neuralgia, general neuralgias, epilepsy or epilepsy conditions, neurodegenerative disorders, psychiatric disorders such as anxiety and depression, myotonia, arrhythmia, movement disorders, neuroendocrine disorders, ataxia, multiple sclerosis, irritable bowel syndrome, incontinence, visceral pain, osteoarthritis pain, postherpetic neuralgia, diabetic neuropathy, radicular pain, sciatica, back pain, head or neck pain, severe or intractable pain, nociceptive pain, breakthrough pain, postsurgical pain, or cancer pain.

DETAILED DESCRIPTION OF THE INVENTION

In one aspect, the invention provides compounds of formula I:

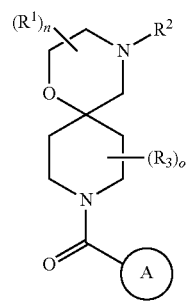

or a pharmaceutically acceptable salt thereof,
wherein, independently for each occurrence:
$R^1$ is C1-C6 alkyl, C1-C6 fluoroalkyl, C3-C8 cycloalkyl, halo, CN, $NR^8SO_2R^8$, $SO_2R^8$, $SR^8$, $SOR^8$, $NR^8COR^8$, $NR^8CO_2R^8$, $CON(R^8)_2$, $SO_2N(R^8)_2$, $CF_3$, optionally substituted heterocycloalkyl, phenyl, heteroaryl, or a straight chain, branched, or cyclic (C1-C8)-$R^9$ wherein up to two $CH_2$ units may be replaced with O, CO, S, SO, $SO_2$, N, $CF_2$, or $NR^8$, or two $R^1$ taken together form an oxo group;
$R^2$ is H, C1-C6 alkyl, C1-C6 fluoroalkyl, $CF_3$, optionally substituted cycloalkyl, aryl, heteroaryl or heterocycloalkyl, $COR^8$, $CO_2R^8$, $CON(R^8)_2$, $CF_3$, $CHF_2$, or a straight chain, branched, or cyclic (C1-C8)-$R^9$ wherein up to two $CH_2$ units may be replaced with O, CO, S, SO, $SO_2$, N, $CF_2$, or $NR^8$;
$R^3$ is C1-C6 alkyl or halo;
$R^8$ is H, C1-C6 alkyl, or C3-C8 cycloalkyl, a straight chain, branched, or cyclic (C1-C8)-$R^9$ wherein up to two $CH_2$ units may be replaced with O, CO, S, SO, $SO_2$, N, $CF_2$, or NR, or 2 $R^8$ taken together with the atoms to which they are attached form a ring;
$R^9$ is H, $CF_3$, $CHF_2$, $CH_2F$, $CO_2R$, OH, optionally substituted aryl, heteroaryl, C3-C8 cycloalkyl, heterocycloalkyl, $N(R)_2$, NRCOR, $CON(R)_2$, CN, or $SO_2R$;
R is H, C1-C6 alkyl, optionally substituted aryl, C3-C8 cycloalkyl, or heterocycloalkyl;
A is an optionally substituted aryl, heteroaryl or heterocyclic;
n is an integer from 0 to 4 inclusive; and
o is an integer from 0 to 4 inclusive.

In a further embodiment, $R^1$ is C1-C6 alkyl, C1-C6 fluoroalkyl, C3-C8 cycloalkyl, CN, $CON(R^8)_2$, $SO_2N(R^8)_2$, $CF_3$, optionally substituted heterocycloalkyl, phenyl, heteroaryl, or a straight chain, branched, or cyclic (C1-C8)-$R^9$ wherein up to two $CH_2$ units may be replaced with O, CO, S, SO, $SO_2$, N, $CF_2$, or $NR^8$, or two $R^1$ taken together form an oxo group.

For purposes of this invention, the chemical elements are identified in accordance with the Periodic Table of the Elements, CAS version, Handbook of Chemistry and Physics, 75th Ed. Additionally, general principles of organic chemistry are described in "Organic Chemistry", Thomas Sorrell, University Science Books, Sausalito: 1999, and "March's Advanced Organic Chemistry", 5th, Ed.: Smith, M. B. and March, J., John Wiley & Sons, New York: 2001, the entire contents of which are hereby incorporated by reference.

As described herein, compounds of the invention can optionally be substituted with one or more substituents, such as are illustrated generally above, or as exemplified by particular classes, subclasses, and species of the invention. The phrase "optionally substituted" is used interchangeably with the phrase "substituted or unsubstituted." As described herein, the variables $R^1$-$R^9$ in formula I encompass specific groups, such as, for example, alkyl and aryl. Unless otherwise noted, each of the specific groups for the variables $R^1$-$R^8$ can be optionally substituted with one or more substituents of halo, cyano, oxoalkoxy, hydroxy, amino, nitro, aryl, haloalkyl, and alkyl. For instance, an alkyl group can be optionally substituted with one or more of halo, cyano, oxoalkoxy, hydroxy, amino, nitro, aryl, haloalkyl, and alkyl. As an additional example, an aryl group can be optionally substituted with one or more of halo, cyano, alkoxy, hydroxy, nitro, haloalkyl, and alkyl. As one of ordinary skill in the art will recognize, combinations of substituents envisioned by this invention are those combinations that result in the formation of stable or chemically feasible compounds. The term "stable", as used herein, refers to compounds that are not substantially altered when subjected to conditions to allow for their production, detection, and preferably their recovery, purification, and use for one or more of the purposes disclosed herein. In some embodiments, a stable compound or chemically feasible compound is one that is not substantially altered when kept at a temperature of 40° C. or less, in the absence of moisture or other chemically reactive conditions, for at least a week. When two alkoxy groups are bound to the same atom or adjacent atoms, the two alkoxy groups can form a ring together with the atom(s) to which they are bound.

In general, the term "substituted," whether preceded by the term "optionally" or not, refers to the replacement of hydrogen radicals in a given structure with the radical of a specified substituent. Specific substituents are described above in the definitions and below in the description of compounds and examples thereof. Unless otherwise indicated, an optionally substituted group can have a substituent at each substitutable position of the group, and when more than one position in any given structure can be substituted with more than one substituent selected from a specified group, the substituent can be either the same or different at every position. A ring substituent, such as a heterocycloalkyl, can be bound to another ring, such as a cycloalkyl, to form a spiro-bicyclic ring system, e.g., both rings share one common atom. As one of ordinary skill in the art will recognize, combinations of substituents envisioned by this invention are those combinations that result in the formation of stable or chemically feasible compounds.

The phrase "up to", as used herein, refers to zero or any integer number that is equal or less than the number following the phrase. For example, "up to 3" means any one of 0, 1, 2, and 3. The term "aliphatic", "aliphatic group" or "alkyl" as used herein, means a straight-chain (i.e., unbranched) or branched, substituted or unsubstituted hydrocarbon chain that is completely saturated or that contains one or more units of unsaturation. Unless otherwise specified, aliphatic groups contain 1-20 aliphatic carbon atoms. In some embodiments, aliphatic groups contain 1-10 aliphatic carbon atoms. In other embodiments, aliphatic groups contain 1-8 aliphatic carbon atoms. In still other embodiments, aliphatic groups contain 1-6 aliphatic carbon atoms, and in yet other embodiments aliphatic groups contain 1-4 aliphatic carbon atoms. Suitable aliphatic groups include, but are not limited to, linear or branched, substituted or unsubstituted alkyl, alkenyl, alkynyl groups. The term "cycloaliphatic" or "cycloalkyl" mean a monocyclic hydrocarbon, bicyclic, or tricyclic hydrocarbon that is completely saturated or that contains one or more units of unsaturation, but which is not aromatic and has a single point of attachment to the rest of the molecule. In some embodiments, "cycloaliphatic" refers to a monocyclic $C_3$-$C_8$ hydrocarbon or bicyclic $C_8$-$C_{12}$ hydrocarbon that is completely saturated or that contains one or more units of unsaturation, but which is not aromatic, that has a single point of attachment to the rest of the molecule wherein any individual ring in said bicyclic ring system has 3-7 members.

The term "electron withdrawing group", as used herein means an atom or a group that is electronegative relative to hydrogen. See, e.g., "Advanced Organic Chemistry: Reactions, Mechanisms, and Structure," Jerry March, 4th Ed., John Wiley & Sons (1992), e.g., pp. 14-16, 18-19, etc. Exemplary such substituents include halo such as Cl, Br, or F, CN, COOH, $CF_3$, etc.

Unless otherwise specified, the term "heterocycle", "heterocyclyl", "heterocycloaliphatic", "heterocycloalkyl" or "heterocyclic" as used herein means non-aromatic, monocyclic, bicyclic, or tricyclic ring systems in which one or more ring atoms in one or more ring members is an independently selected heteroatom. Heterocyclic ring can be saturated or can contain one or more unsaturated bonds. In some embodiments, the "heterocycle", "heterocyclyl", "heterocycloaliphatic", "heterocycloalkyl" or "heterocyclic" group has three to fourteen ring members in which one or more ring members is a heteroatom independently selected from oxygen, sulfur, nitrogen, or phosphorus, and each ring in the ring system contains 3 to 7 ring members.

The term "heteroatom" means oxygen, sulfur, nitrogen, phosphorus, or silicon (including, any oxidized form of nitrogen, sulfur, phosphorus, or silicon; the quaternized form of any basic nitrogen or; a substitutable nitrogen of a heterocyclic ring, for example N (as in 3,4-dihydro-2H-pyrrolyl), NH (as in pyrrolidinyl) or $NR^+$ (as in N-substituted pyrrolidinyl)).

The term "unsaturated", as used herein, means that a moiety has one or more units of unsaturation but is not aromatic.

The term "alkoxy", or "thioalkyl", as used herein, refers to an alkyl group, as previously defined, attached to the principal carbon chain through an oxygen ("alkoxy") or sulfur ("thioalkyl") atom.

The term "aryl" used alone or as part of a larger moiety as in "aralkyl", "aralkoxy", or "aryloxyalkyl", refers to monocyclic, bicyclic, and tricyclic ring systems having a total of five to fourteen ring carbon atoms, wherein at least one ring in the system is aromatic and wherein each ring in the system contains 3 to 7 ring carbon atoms. The term "aryl" may be used interchangeably with the term "aryl ring". The term "heteroaryl", used alone or as part of a larger moiety as in "heteroaralkyl" or "heteroarylalkoxy", refers to monocyclic, bicyclic, and tricyclic ring systems having a total of five to fourteen ring members, wherein at least one ring in the system is aromatic, at least one ring in the system contains one or more heteroatoms, and wherein each ring in the system contains 3 to 7 ring members. The term "heteroaryl" may be used interchangeably with the term "heteroaryl ring" or the term "heteroaromatic".

The term "alkylidene chain" refers to a straight or branched carbon chain that may be fully saturated or have one or more units of unsaturation and has two points of attachment to the rest of the molecule.

Unless otherwise stated, structures depicted herein are also meant to include all isomeric (e.g., enantiomeric, diastereomeric, and geometric (or conformational)) forms of the structure; for example, the R and S configurations for each asymmetric center, (Z) and (E) double bond isomers, and (Z) and (E) conformational isomers. Therefore, single stereochemical isomers as well as enantiomeric, diastereomeric, and geometric (or conformational) mixtures of the present compounds are within the scope of the invention.

Unless otherwise stated, all tautomeric forms of the compounds of the invention are within the scope of the invention. Thus, included within the scope of the invention are tautomers of compounds of formula I.

Additionally, unless otherwise stated, structures depicted herein are also meant to include compounds that differ only in the presence of one or more isotopically enriched atoms. For example, compounds of formula I, wherein one or more hydrogen atoms are replaced deuterium or tritium, or one or more carbon atoms are replaced by a $^{13}$C- or $^{14}$C-enriched carbon are within the scope of this invention. Such compounds are useful, for example, as analytical tools, probes in biological assays, or sodium channel blockers with improved therapeutic profile.

In the formulas and drawings, a line transversing a ring and bonded to an R group such as in

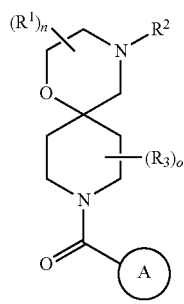

means that the R group can be bonded to any carbon, or if applicable, heteroatom such as N, of that ring as valency allows.

Within a definition of a term as for example, $R^1$, $R^2$, $R^3$, $R^4$, $R^5$, or $R^6$ when a $CH_2$ unit or, interchangeably, methylene unit may be replaced by O, CO, S, SO, $SO_2$ or $NR^8$, it is meant to include any $CH_2$ unit, including a $CH_2$ within a terminal methyl group. For example, —$CH_2CH_2CH_2SH$ is within the definition of C1-C6 alkyl wherein up to two $CH_2$ units may be replaced by S because the $CH_2$ unit of the terminal methyl group has been replaced by S.

In another embodiment, the invention features a compound of formula I and the attendant definitions, wherein $R^1$ is halo or optionally substituted aryl, heteroaryl, C1-C6 alkyl, C1-C6 fluoroalkyl, a straight chain, branched, or cyclic (C1-C8)-$R^9$ wherein up to two $CH_2$ units may be replaced with O, CO, S, SO, $SO_2$, N, or $NR^8$, or 2 $R^1$ taken together form an oxo group. In another embodiment, $R^1$ is F or optionally substituted phenyl, pyridyl, oxazole, thiazole, pyrazole, oxadiazole, $CH_2OCH_3$, $CH_2F$, $CH_2OCH(CH_3)_2$, $CH_2OCHF_2$, $CH_3$, $CH_2CH_3$, $CH_2OH$, $C(CH_3)_2OH$, $CH_2CH_2OH$, $CH_2OCH_2CH_3$, $CH(CH_2)_2$,

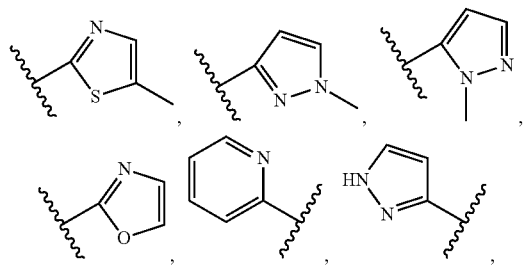

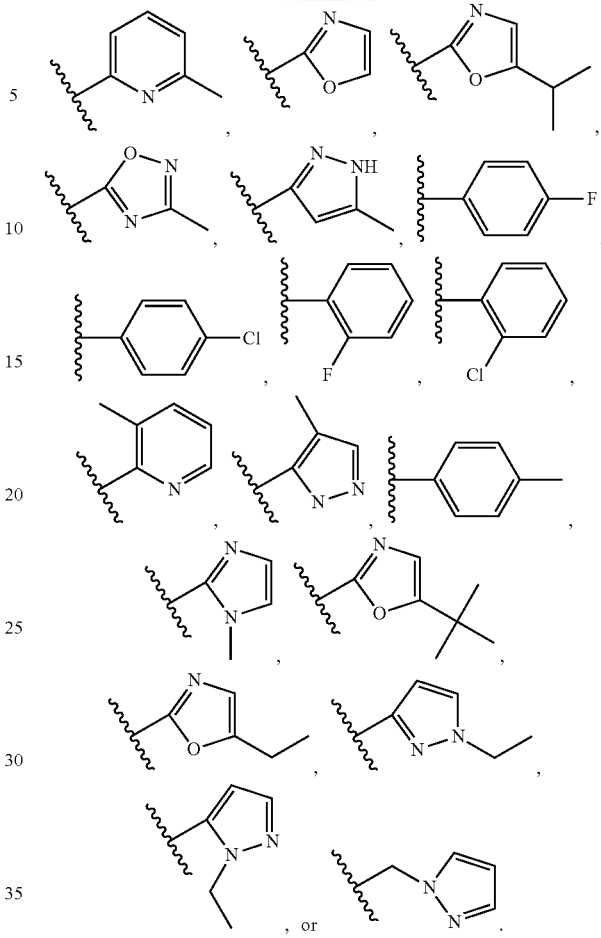

In another embodiment, the invention features a compound of formula I and the attendant definitions, wherein $R^2$ is H, C1-C6 alkyl, C1-C6 fluoroalkyl, $CF_3$, an optionally substituted cycloalkyl, aryl, heterocycloalkyl, heteroaryl, or a straight chain, branched, or cyclic (C1-C8)-$R^9$ wherein up to two $CH_2$ units may be replaced with O, CO, S, SO, $SO_2$, N, or $NR^8$. In another embodiment, $R^2$ is H, $CH_2CHF_2$, $CH_2CF_3$, $CH(CH_3)CH_2F$, $CH_2CH(CH_3)_2$, $CH_3$, $CH_2CH_3$, tBu, $CH_2CN$, $CH(CH_3)_2$, $CH(CH_2CH_3)_2$, $CH_2C(CH_3)_2OH$, $CH_2CH_2CH(CH_3)_2$, $CH_2CH_2OH$, $C(O)CH_3$, $C(O)CH_2CH_3$, $C(O)CH(CH_3)_2$, $CH_2CF_2CH_3$, $CH_2CCCH_3$, $CH_2C(O)tBu$, $CH_2CH_2OCH_3$, $CH_2OCH_3$, $CH_2C(O)CH_3$, $CH_2C(O)OCH_3$, $CH_2CH_2OCH_2CH_3$, $CH_2CCCH_2CH_3$, $CH_2CH_2OCH_2CH_3$, $CH_2CH_2SCH_3$, $CH_2CH_2CH_2OCH_3$, $CH_2CH(CH_2CH_3)_2$, n-butyl, n-propyl,

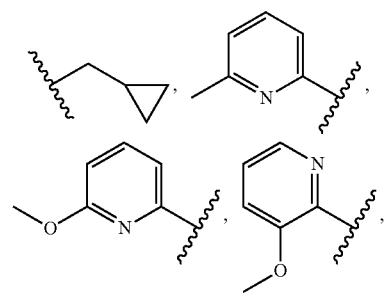

-continued

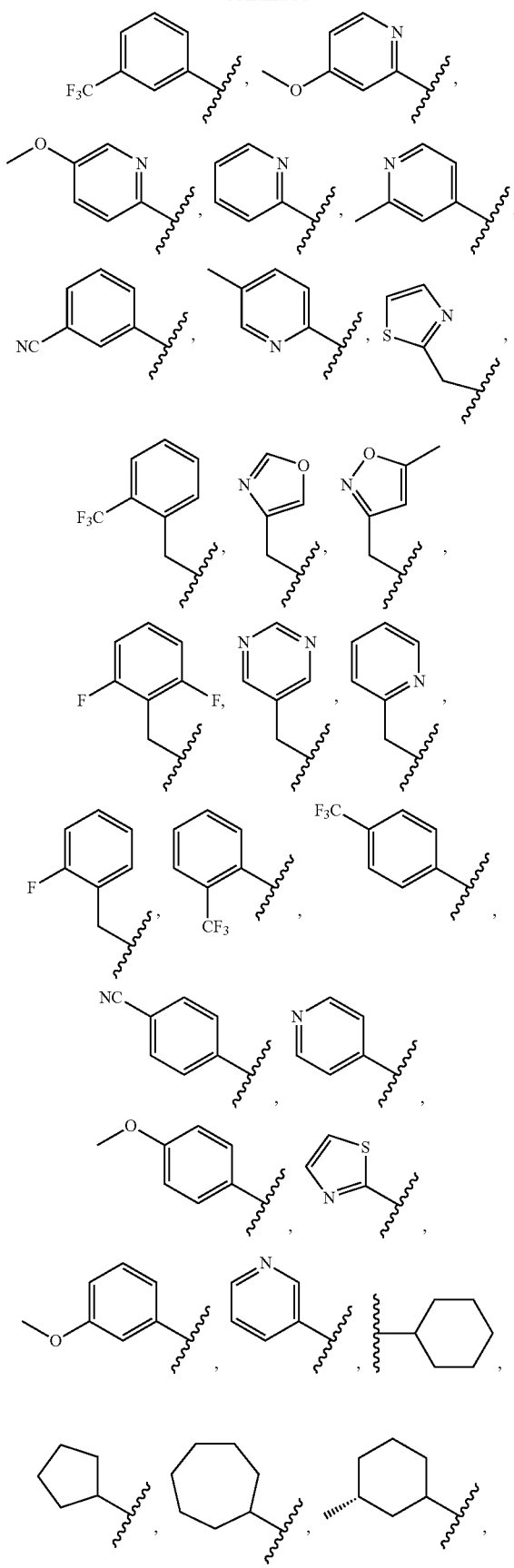

-continued

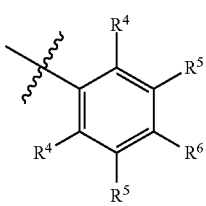

In another embodiment, the invention features a compound of formula I and the attendant definitions, wherein n is 0, 1, 2, or 3. In another embodiment, n is 1 or 2. In another embodiment, n is 1.

In another embodiment, the invention features a compound of formula I and the attendant definitions, wherein o is 0 or 1. In another embodiment, o is 0.

In another embodiment, the invention features a compound of formula I and the attendant definitions, wherein A is wherein:
$R^4$ is H, C1-C6 alkyl, C3-C8 cycloalkyl, C1-C6 alkoxy, halo, CN, OH, $OR^8$, $N(R^8)_2$, $NR^8SO_2R^8$, $SO_2R^8$, $SOR^8$, $SR^8$, $CO_2R^8$, $NR^8COR^8$, $NR^8CO_2R^8$, $CON(R^8)_2$, $SO_2N(R^8)_2$, $CHF_2$, $CF_3$, $OCF_3$, $OCHF_2$, $R^9$, heterocycloalkyl, heterocycloalkoxy, aryl, heteroaryl, or a straight chain, branched, or cyclic (C1-C8)-$R^9$ wherein up to three $CH_2$ units may be replaced with O, CO, S, SO, $SO_2$, N, $CF_2$, or $NR^8$;

$R^5$ is H, C1-C6 alkyl, C3-C8 cycloalkyl, C1-C6 alkoxy, C3-C8 cycloalkoxy, halo, CN, OH, $OR^8$, $N(R^8)_2$, $NR^8SO_2R^8$, $SO_2R^8$, $SOR^8$, $SR^8$, $CO_2R^8$, $NR^8COR^8$, $NR^8CO_2R^8$, $CON(R^8)_2$, $SO_2N(R^8)_2$, $CF_3$, $OCF_3$, $OCHF_2$, $R^9$, heterocycloalkyl, heterocycloalkoxy, aryl, heteroaryl, or a straight chain, branched, or cyclic (C1-C8)-$R^9$ wherein up to three $CH_2$ units may be replaced with O, CO, S, SO, $SO_2$, N, $CF_2$, or $NR^8$;

$R^6$ is H, C1-C6 alkyl, C3-C8 cycloalkyl, C1-C6 alkoxy, halo, CN, OH, $OR^8$, $N(R^8)_2$, $NR^8SO_2R^8$, $SO_2R^8$, $SOR^8$, $SR^8$, $CO_2R^8$, $NR^8COR^8$, $NR^8CO_2R^8$, $CON(R^8)_2$, $SO_2N(R^8)_2$, $CF_3$, $OCF_3$, $OCHF_2$, $R^9$, heterocycloalkyl, heterocycloalkoxy, aryl, heteroaryl, or a straight chain, branched, or cyclic (C1-C8)-$R^9$ wherein up to three $CH_2$ units may be replaced with O, CO, S, SO, $SO_2$, N, $CF_2$, or $NR^8$; or two occurrences of $R^4$ and $R^5$, or $R^5$ and $R^6$ together with the carbons to which they are attached form an optionally substituted ring comprising up to 2 heteroatoms.

In another embodiment, $R^4$ is H, C1-C6 alkyl, C1-C6 alkoxy, halo, $OCF_3$, $OCHF_2$, or a straight chain, branched, or cyclic (C1-C8)-$R^9$ wherein up to three $CH_2$ units may be replaced with O, CO, S, SO, $SO_2$, N, or $NR^7$. In another embodiment, $R^4$ is H, F, $CH_3$, $OCH_3$, $OCF_3$, or $OCHF_2$.

In another embodiment, $R^5$ is H, C1-C6 alkyl, C1-C6 alkoxy, halo, $CF_3$, CN, or a straight chain, branched, or cyclic (C1-C8)-$R^9$ wherein up to three $CH_2$ units may be replaced with O, CO, S, SO, $SO_2$, N, or $NR^8$. In another embodiment, $R^5$ is H, $CH_3$, $OCH_3$, $OCH_2CH_3$, $OCH(CH_3)_2$, F, Cl, CN, $CF_3$, or $CH_2OH$.

In another embodiment, $R^6$ is H, C1-C6 alkyl, C1-C6 alkoxy, $SO_2R^8$, $SO_2N(R^8)_2$, $R^9$, or a straight chain, branched, or cyclic (C1-C8)-$R^9$, wherein up to three $CH_2$ units may be replaced with O, S, SO, $SO_2$, N, or $NR^8$. In another embodiment, $R^6$ is H, $CH_2OH$, $OCH_3$, $OCH_2CH_3$, $OCH_2CH_2CH_3$, $OCH_2CH_2CH(CH_3)_2$, OtBu, tBu, $OCH(CH_3)_2$, $OCH_2C(CH_3)_2OCH_3$, $CH(OH)CH(CH_3)_2$, $C(OH)(CH_2CH_3)_2$, $OCH_2C(CH_3)_2OH$, $C(CH_3)_2OH$, $OCH_2CH_2OCH_3$, $OCH_2CH_2OH$, $OCH_2CH_2CH_2OH$, $CCCH_2OCH_3$, $SO_2CH_3$, $SO_2CH_2CH(CH_3)_2$, $SO_2CH(CH_3)_2$, $SO_2CH_2CH_3$, $SO_2C(CH_3)_3$, $CON(CH_2CH_3)_2$, $C(CH_3)_2CO_2CH_3$,

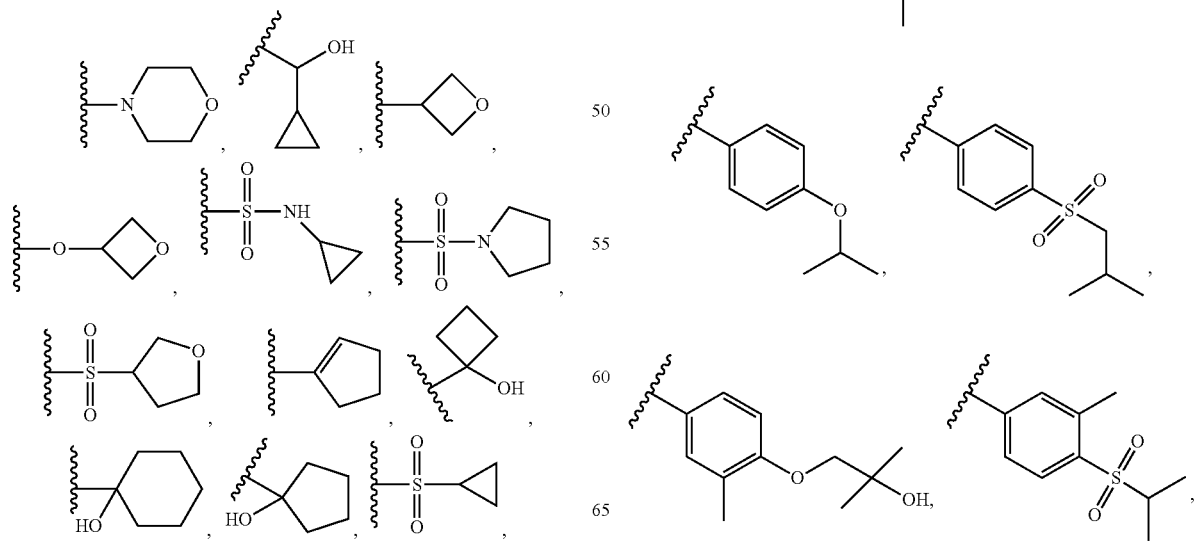

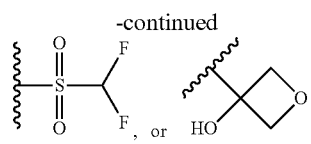

In another embodiment, the invention features a compound of formula I and the attendant definitions, wherein

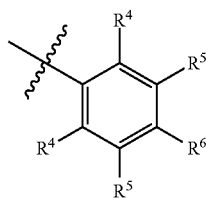

is selected from:

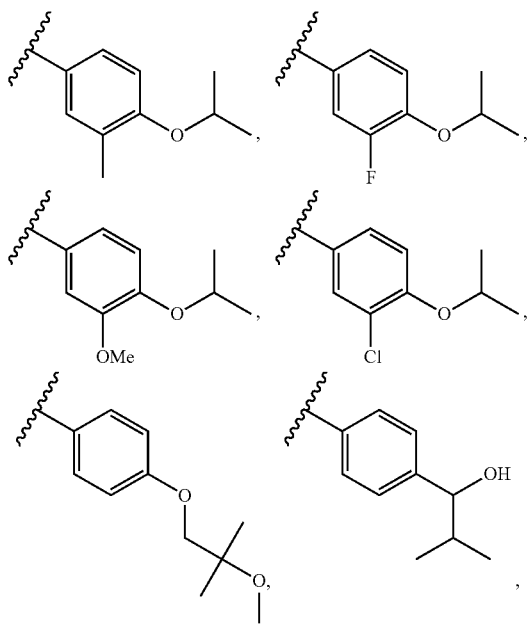

-continued
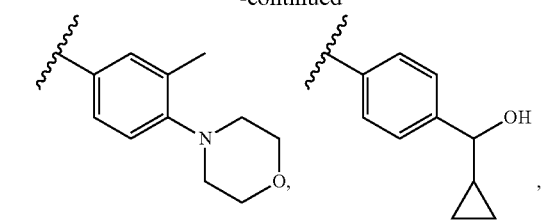
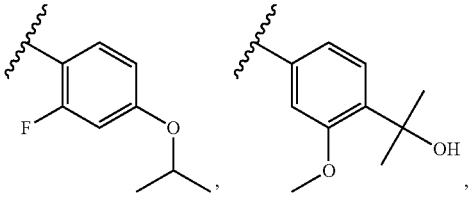
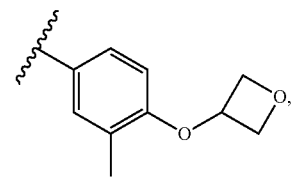
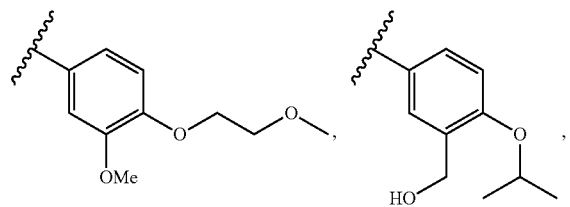
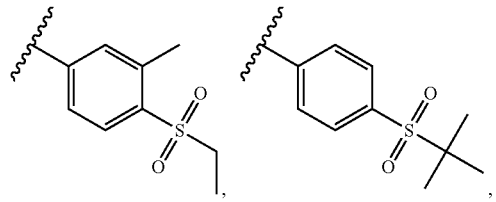
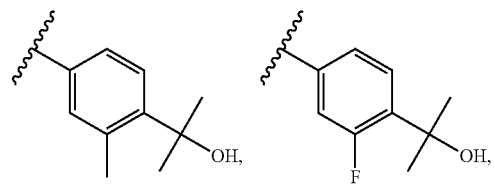
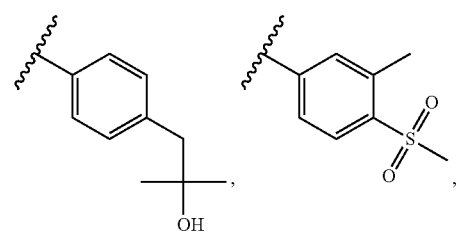
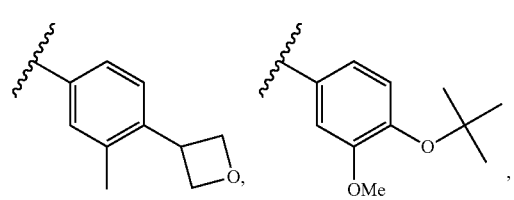
-continued
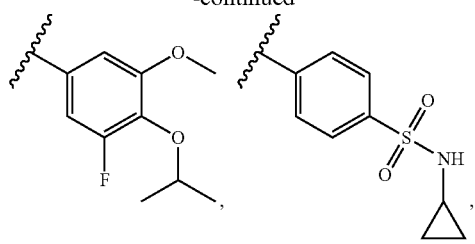
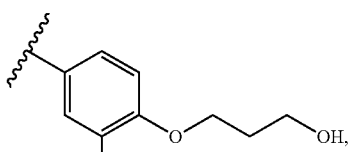
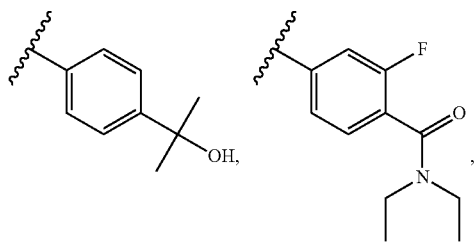
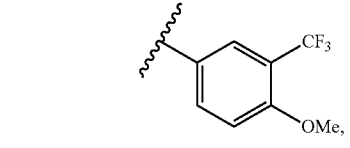
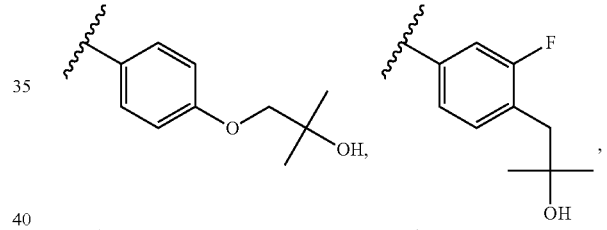
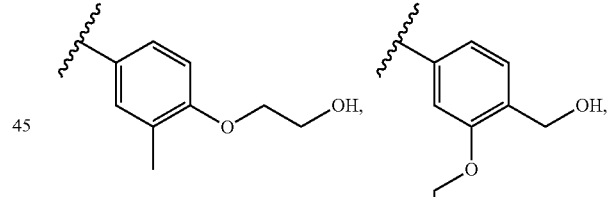
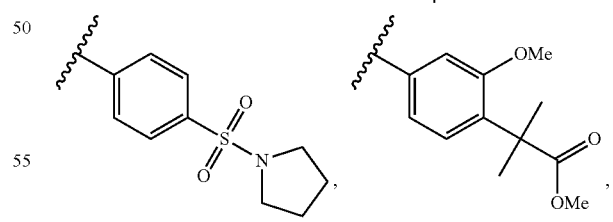
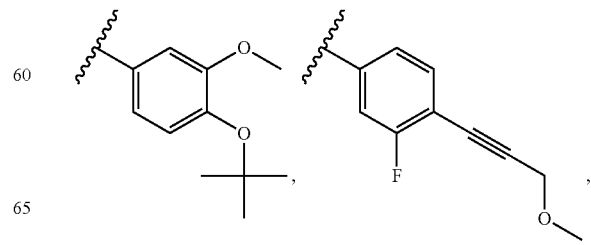

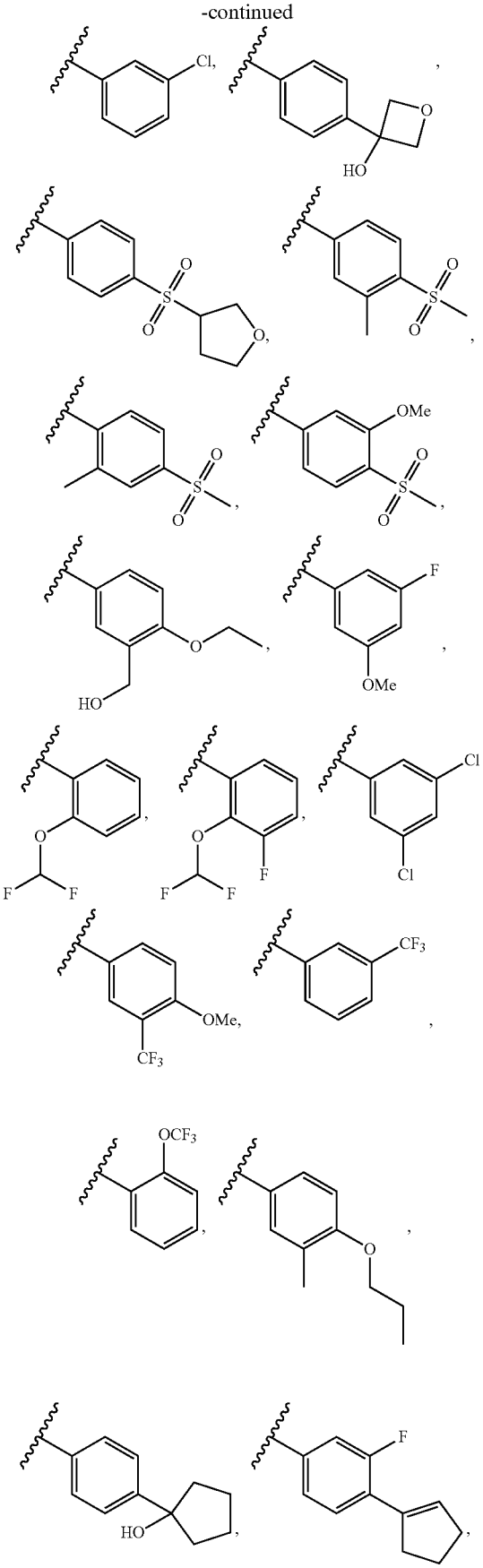
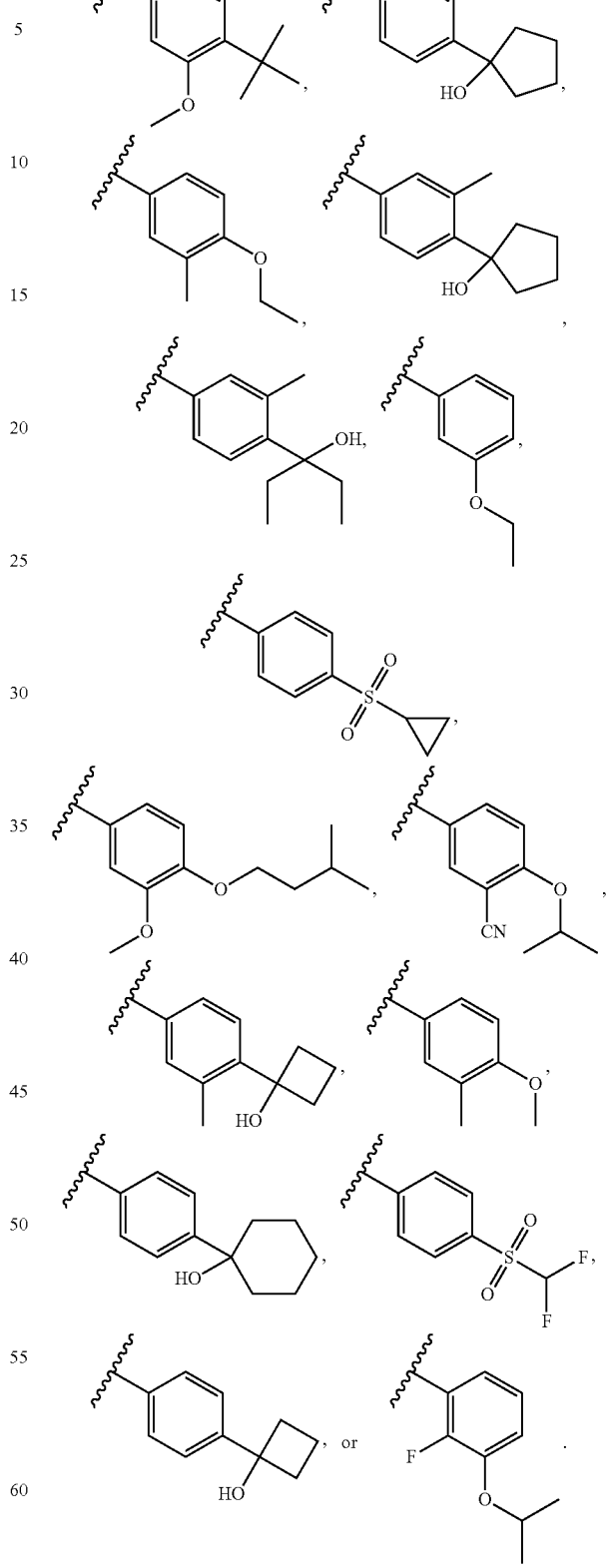
In another embodiment, the invention features a compound of formula I and the attendant definitions, wherein A is heteroaryl or heterocyclic. In another embodiment, A is a monocyclic heteroaryl comprising 1 to 3 heteroatoms independently selected from N, O, or S. In another embodiment, A is selected from a bicyclic heteroaryl comprising from 1 to 3 heteroatoms independently selected from N, O, or S.

In another embodiment, A is

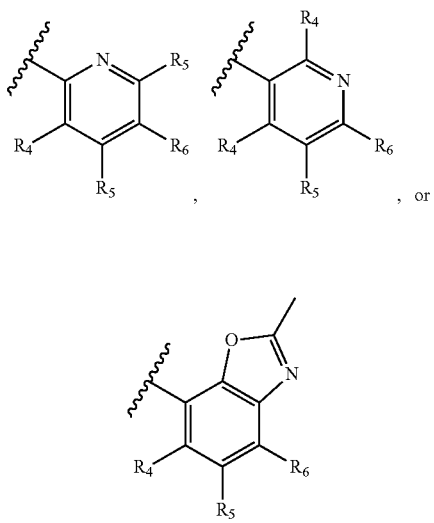

wherein:

- $R^4$ is H, C1-C6 alkyl, C3-C8 cycloalkyl, C1-C6 alkoxy, halo, CN, OH, $OR^8$, $N(R^8)_2$, $NR^8SO_2R^8$, $SO_2R^8$, $SOR^8$, $SR^8$, $CO_2R^8$, $NR^8COR^8$, $NR^8CO_2R^8$, $CON(R^8)_2$, $SO_2N(R^8)_2$, $CHF_2$, $CF_3$, $OCF_3$, $OCHF_2$, $R^9$, heterocycloalkyl, heterocycloalkoxy, aryl, heteroaryl, or a straight chain, branched, or cyclic (C1-C8)-$R^9$ wherein up to three $CH_2$ units may be replaced with O, CO, S, SO, $SO_2$, N, $CF_2$, or $NR^8$;
- $R^5$ is H, C1-C6 alkyl, C3-C8 cycloalkyl, C1-C6 alkoxy, C3-C8 cycloalkoxy, halo, CN, OH, $OR^8$, $N(R^8)_2$, $NR^8SO_2R^8$, $SO_2R^8$, $SOR^8$, $SR^8$, $CO_2R^8$, $NR^8COR^8$, $NR^8CO_2R^8$, $CON(R^8)_2$, $SO_2N(R^8)_2$, $CF_3$, $OCF_3$, $OCHF_2$, $R^9$, heterocycloalkyl, heterocycloalkoxy, aryl, heteroaryl, or a straight chain, branched, or cyclic (C1-C8)-$R^9$ wherein up to three $CH_2$ units may be replaced with O, CO, S, SO, $SO_2$, N, $CF_2$, or $NR^8$;
- $R^6$ is H, C1-C6 alkyl, C3-C8 cycloalkyl, C1-C6 alkoxy, halo, CN, OH, $OR^8$, $N(R^8)_2$, $NR^8SO_2R^8$, $SO_2R^8$, $SOR^8$, $SR^8$, $CO_2R^8$, $NR^8COR^8$, $NR^8CO_2R^8$, $CON(R^8)_2$, $SO_2N(R^8)_2$, $CF_3$, $OCF_3$, $OCHF_2$, $R^9$, heterocycloalkyl, heterocycloalkoxy, aryl, heteroaryl, or a straight chain, branched, or cyclic (C1-C8)-$R^9$ wherein up to three $CH_2$ units may be replaced with O, CO, S, SO, $SO_2$, N, $CF_2$, or $NR^8$; or
- two occurrences of $R^4$ and $R^5$, or $R^5$ and $R^6$ together with the carbons to which they are attached form an optionally substituted ring comprising up to 2 heteroatoms.

In another embodiment, $R^4$ is H or C1-C6 alkyl. In another embodiment, $R^4$ is H.

In another embodiment, $R^5$ is H, C1-C6 alkyl, or C1-C6 alkoxy. In another embodiment, $R^5$ is H, $CH_3$, or $OCH_3$.

In another embodiment, $R^6$ is H, CN, C1-C6 alkoxy, or $CF_3$. In another embodiment, $R^6$ is H, CN, $OCH_3$, or $CF_3$.

In another embodiment, the invention features a compound of formula I and the attendant definitions, wherein A is selected from the following:

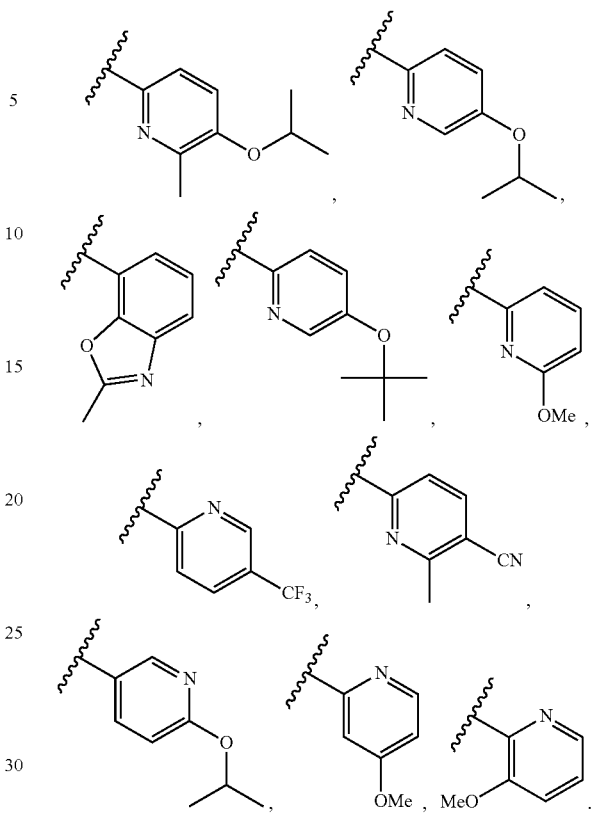

In another embodiment, the invention features the compounds of formula I and the attendant definitions, wherein the compound has formula IA:

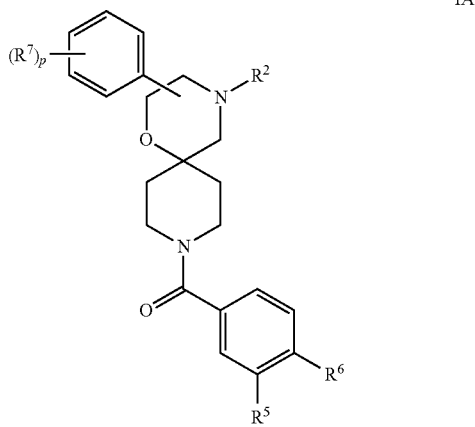

IA wherein:
- $R^2$ is H, C1-C6 alkyl, C1-C6 fluoroalkyl, an optionally substituted cycloalkyl, aryl, heteroaryl, or heterocycloalkyl, or a straight chain, branched, or cyclic (C1-C8)-$R^9$ wherein up to two $CH_2$ units may be replaced with O, CO, S, SO, $SO_2$, N, $CF_2$, or $NR^8$;
- $R^5$ is H, C1-C6 alkyl, C1-C6 alkoxy, C1-C6 fluoroalkyl, halo, $CF_3$, $OCF_3$, $OCHF_2$, or a straight chain, branched, or cyclic (C1-C8)-$R^9$ wherein up to three $CH_2$ units may be replaced with O, CO, S, SO, $SO_2$, N, $CF_2$, or $NR^8$;

$R^6$ is H, C1-C6 alkyl, C1-C6 alkoxy, CN, $SO_2R^8$, $CON(R^8)_2$, $SO_2N(R^8)_2$, heterocycloalkyl, or a straight chain, branched, or cyclic (C1-C8)-$R^9$ wherein up to three $CH_2$ units may be replaced with O, CO, S, SO, $SO_2$, N, $CF_2$, or $NR^8$;

$R^7$ is C1-C6 alkyl, C3-C8 cycloalkyl, C1-C6 alkoxy, halo, CN, OH, $OR^8$, $N(R^8)_2$, $CF_3$, $OCF_3$, or $OCHF_2$; and p is an integer from 0 to 3 inclusive.

In another embodiment, $R^2$ is selected from C1-C6 alkyl, C1-C6 fluoroalkyl, cycloalkyl, aryl, heterocycloalkyl, heteroaryl, or a straight chain, branched, or cyclic (C1-C8)-$R^9$ wherein up to two $CH_2$ units may be replaced with O, CO, S, SO, $SO_2$, N, $CF_2$, or $NR^8$. In another embodiment, $R^2$ is $CH_3$, $CH_2CH_3$, $CH(CH_3)_2$, $CH_2CH(CH_3)_2$, $CH_2CHF_2$, $CH_2CF_3$, $CH(CH_3)CH_2F$, $CH_2CN$, $CH_2CH_2OH$, $CH_2C(CH_3)_2OH$, $COCH_2CH_3$, or $COCH(CH_3)_2$.

In another embodiment, $R^5$ is selected from H, C1-C6 alkyl, C1-C6 alkoxy, C1-C6 fluororoalkyl, halo, or a straight chain, branched, or cyclic (C1-C8)-$R^9$ wherein up to three $CH_2$ units may be replaced with O, CO, S, SO, $SO_2$, N, $CF_2$, or $NR^8$. In another embodiment, $R^5$ is H, $CH_3$, $OCH_3$, $OCH_2CH_3$, $CF_3$, Cl, F, or $CH_2OH$.

In another embodiment, $R^6$ is selected from H, C1-C6 alkoxy, or a straight chain, branched, or cyclic (C1-C8)-$R^9$ wherein up to three $CH_2$ units may be replaced with O, CO, S, SO, $SO_2$, N, $CF_2$, or $NR^8$. In another embodiment, $R^6$ is H, $CH_2OH$, $OCH_2CH_3$, OtBu, $OCH(CH_3)_2$, $OCH_2C(CH_3)_2OCH_3$, $CH(OH)CH(CH_3)_2$, $OCH_2C(CH_3)_2OH$, $C(CH_3)_2OH$, $OCH_2CH_2OCH_3$, $OCH_2CH_2OH$, $OCH_2CH_2CH_2OH$, $CCCH_2OCH_3$, $SO_2CH_3$, $SO_2CH_2CH(CH_3)_2$, $SO_2CH(CH_3)_2$, $SO_2CH_2CH_3$, $SO_2C(CH_3)_3$, $CON(CH_2CH_3)_2$, $C(CH_3)_2CO_2CH_3$,

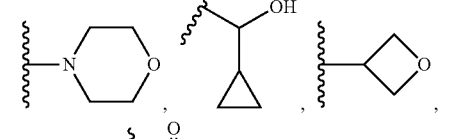

In another embodiment, $R^7$ is halo. In another embodiment, $R^7$ is F.

In another embodiment, the

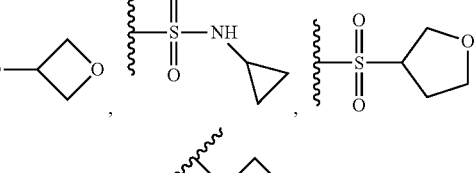

moiety is selected from:

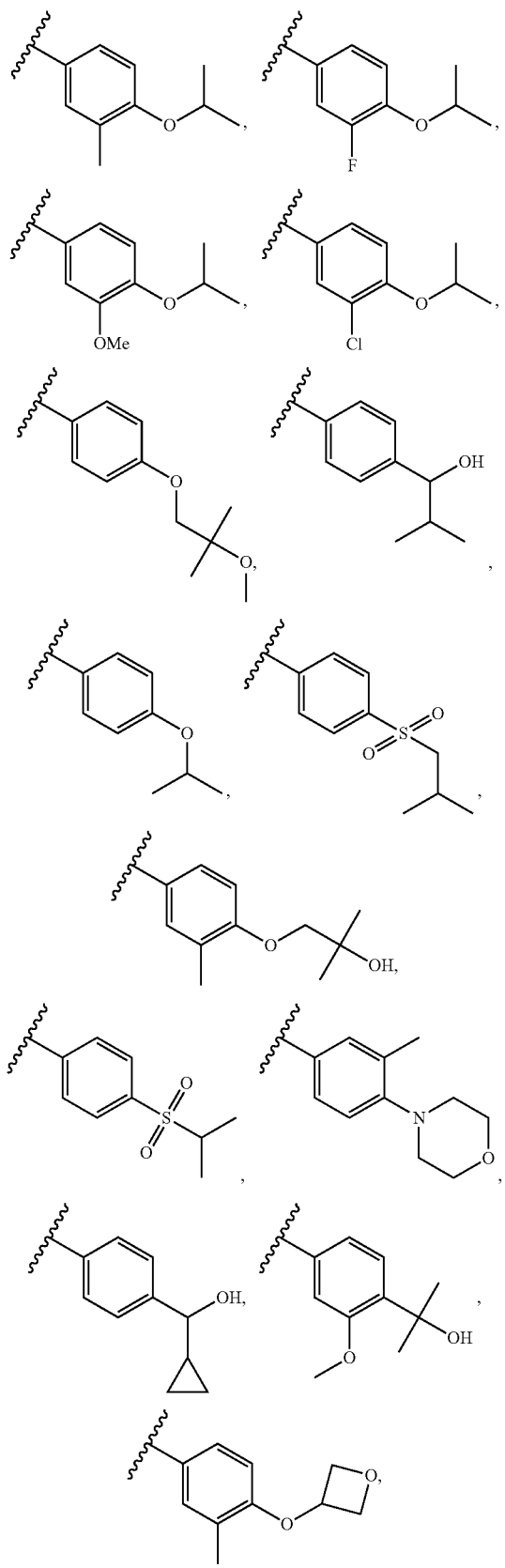

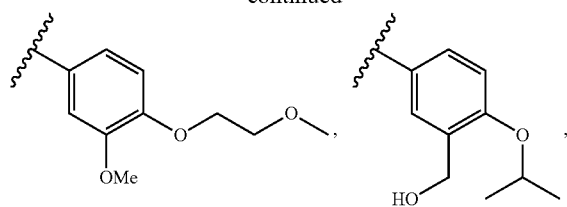
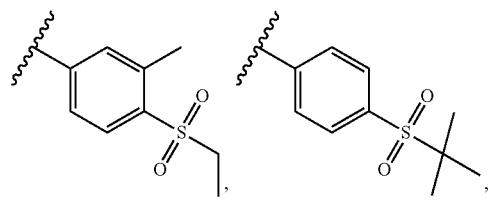
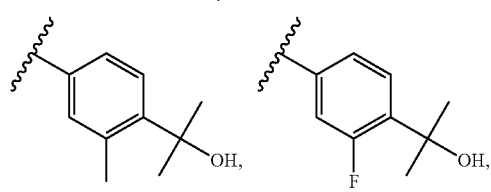
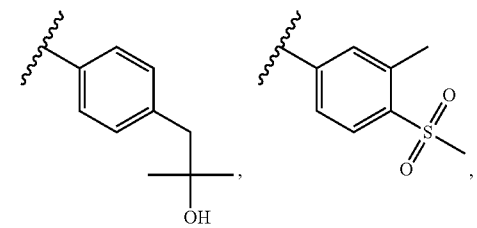
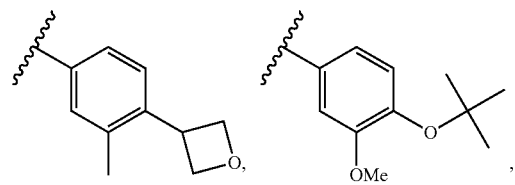
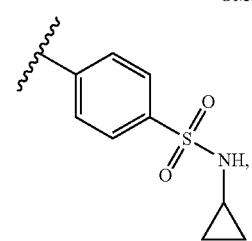
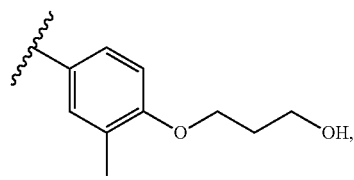
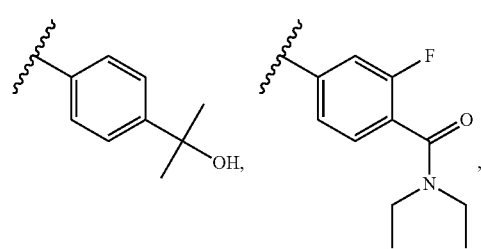
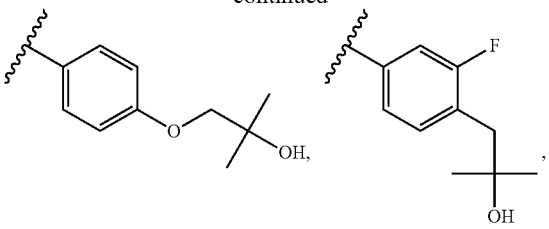
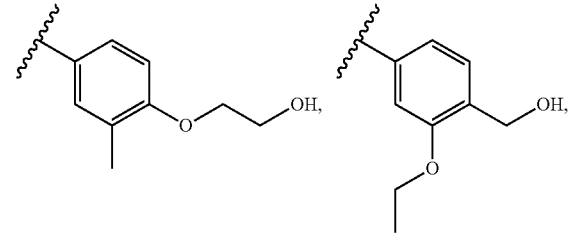
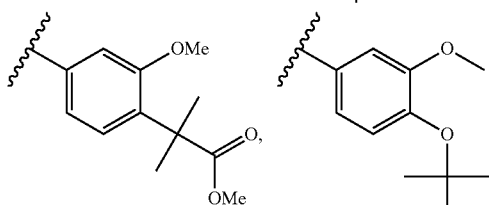
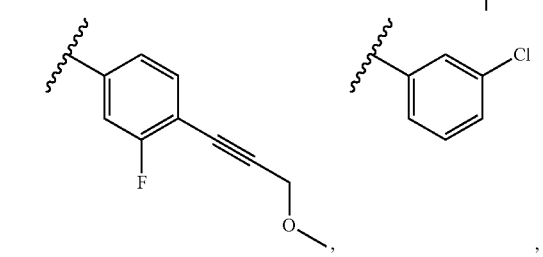
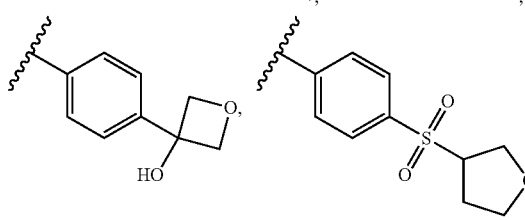
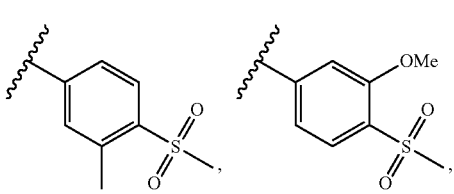
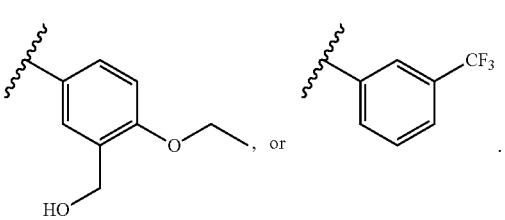
In another embodiment, the invention features a compound of formula I and the attendant definitions of the above embodiments, wherein the compound has formula IB:

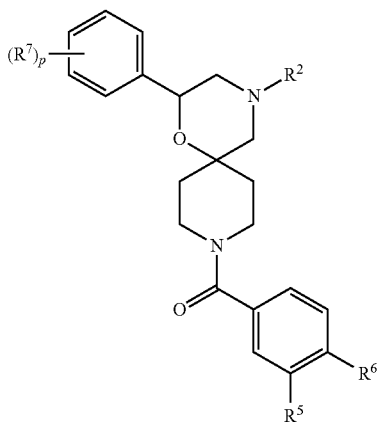

IB

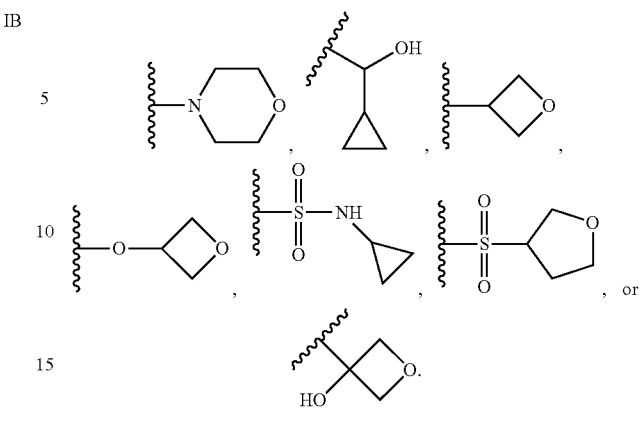

wherein:

- R² is H, C1-C6 alkyl, C1-C6 fluoroalkyl, an optionally substituted cycloalkyl, aryl, heteroaryl, or heterocycloalkyl, or a straight chain, branched, or cyclic (C1-C8)-R⁹ wherein up to two CH₂ units may be replaced with O, CO, S, SO, SO₂, N, CF₂, or NR⁸;
- R⁵ is H, C1-C6 alkyl, C1-C6 alkoxy, C1-C6 fluoroalkyl, halo, CF₃, OCF₃, OCHF₂, or a straight chain, branched, or cyclic (C1-C8)-R⁹ wherein up to three CH₂ units may be replaced with O, CO, S, SO, SO₂, N, CF₂, or NR⁸;
- R⁶ is H, C1-C6 alkyl, C1-C6 alkoxy, CN, SO₂R⁸, CON(R⁸)₂, SO₂N(R⁸)₂, heterocycloalkyl, or a straight chain, branched, or cyclic (C1-C8)-R⁹ wherein up to three CH₂ units may be replaced with O, CO, S, SO, SO₂, N, CF₂, or NR⁸;
- R⁷ is C1-C6 alkyl, C3-C8 cycloalkyl, C1-C6 alkoxy, halo, CN, OH, OR⁸, N(R⁸)₂, CF₃, OCF₃, or OCHF₂; and
- p is an integer from 0 to 3 inclusive.

In another embodiment, R² is selected from C1-C6 alkyl, C1-C6 fluoroalkyl, cycloalkyl, heterocycloalkyl, aryl, heteroaryl, or a straight chain, branched, or cyclic (C1-C8)-R⁹ wherein up to two CH₂ units may be replaced with O, CO, S, SO, SO₂, N, CF₂, or NR⁸. In another embodiment, R² is CH₃, CH₂CH₃, CH(CH₃)₂, CH₂CH(CH₃)₂, CH₂CHF₂, CH₂CF₃, CH(CH₃)CH₂F, CH₂CN, CH₂CH₂OH, CH₂C(CH₃)₂OH, COCH₂CH₃, or COCH(CH₃)₂.

In another embodiment, R⁵ is selected from H, C1-C6 alkyl, C1-C6 alkoxy, C1-C6 fluororoalkyl, halo, or a straight chain, branched, or cyclic (C1-C8)-R⁹ wherein up to three CH₂ units may be replaced with O, CO, S, SO, SO₂, N, CF₂, or NR⁸. In another embodiment, R⁵ is H, CH₃, OCH₃, OCH₂CH₃, CF₃, Cl, F, or CH₂OH.

In another embodiment, R⁶ is selected from H, C1-C6 alkoxy, or a straight chain, branched, or cyclic (C1-C8)-R⁹ wherein up to three CH₂ units may be replaced with O, CO, S, SO, SO₂, N, CF₂, or NR⁸. In another embodiment, R⁶ is H, CH₂OH, OCH₂CH₃, OtBu, OCH(CH₃)₂, OCH₂C(CH₃)₂OCH₃, CH(OH)CH(CH₃)₂, OCH₂C(CH₃)₂OH, C(CH₃)₂OH, OCH₂CH₂OCH₃, OCH₂CH₂OH, OCH₂CH₂CH₂OH, CCCH₂OCH₃, SO₂CH₃, SO₂CH₂CH(CH₃)₂, SO₂CH(CH₃)₂, SO₂CH₂CH₃, SO₂C(CH₃)₃, CON(CH₂CH₃)₂, C(CH₃)₂CO₂CH₃,

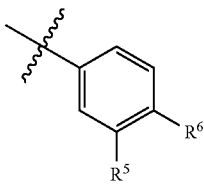

In another embodiment, R⁷ is halo. In another embodiment, R⁷ is F.

In another embodiment, the

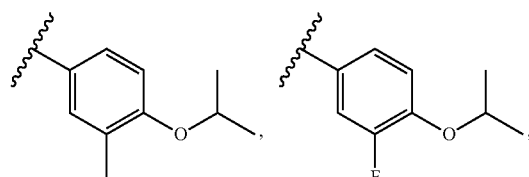

moiety is selected from:

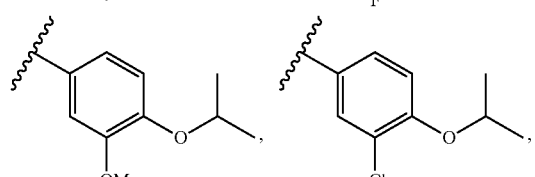

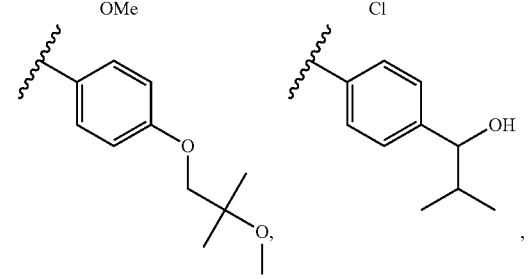

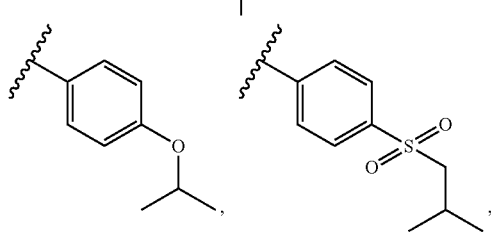

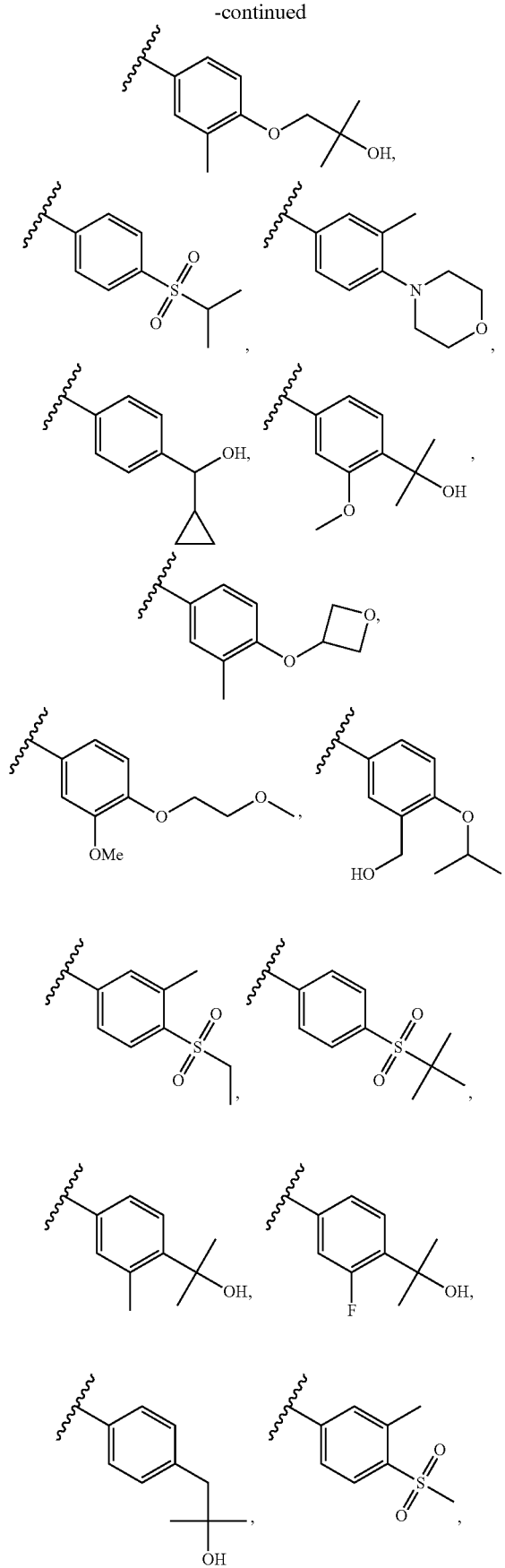
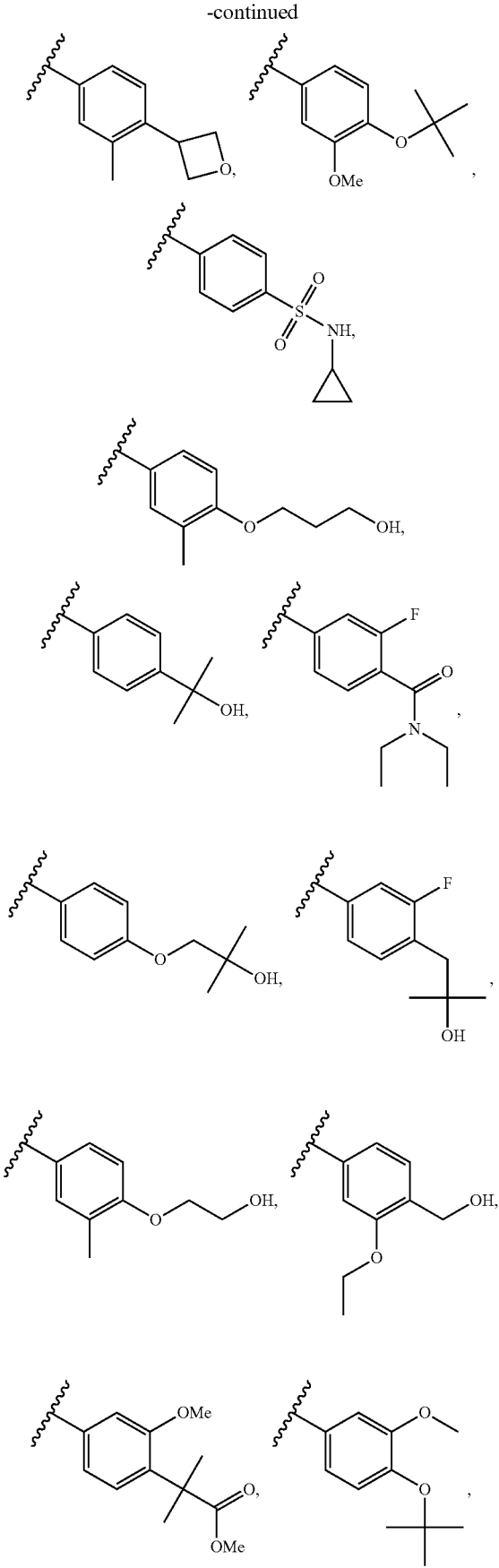

-continued

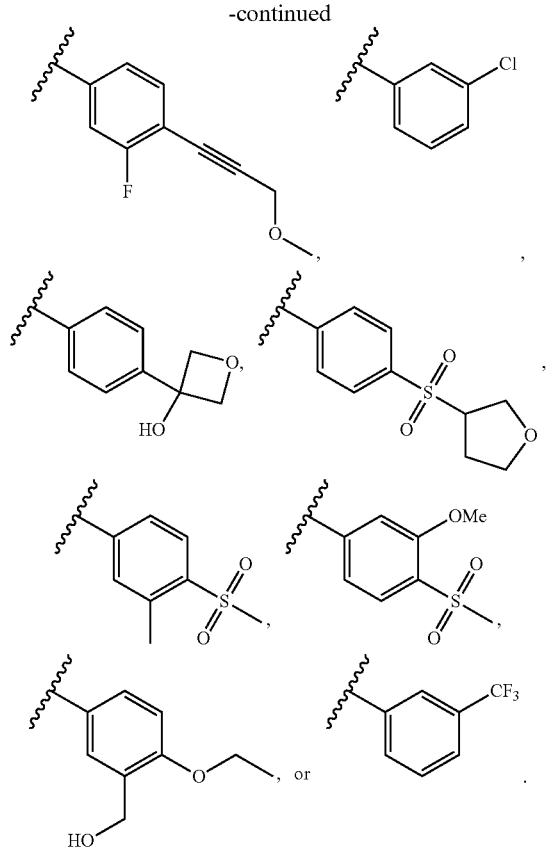

In another embodiment, the invention features a compound of formula I and the attendant definitions, wherein the compound has formula IC:

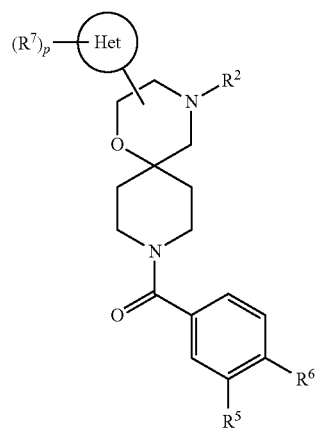

IC wherein,
the Het ring is a mono or bicyclic optionally substituted heterocyclic or heteroaryl ring;
$R^2$ is H, C1-C6 alkyl, C1-C6 fluoroalkyl, an optionally substituted aryl, heteroaryl, or heterocycloalkyl, or a straight chain, branched, or cyclic (C1-C8)-$R^9$ wherein up to two $CH_2$ units may be replaced with O, CO, S, SO, $SO_2$, N, $CF_2$, or $NR^8$;
$R^5$ is H, C1-C6 alkyl, C1-C6 alkoxy, halo, $CF_3$, $OCF_3$, $OCHF_2$, or a straight chain, branched, or cyclic (C1-C8)-$R^9$ wherein up to three $CH_2$ units may be replaced with O, CO, S, SO, $SO_2$, N, $CF_2$, or $NR^8$;
$R^6$ is H, C1-C6 alkyl, C1-C6 alkoxy, CN, $SO_2R^8$, $CON(R^8)_2$, $SO_2N(R^8)_2$, heterocycloalkyl, or a straight chain, branched, or cyclic (C1-C8)-$R^9$ wherein up to three $CH_2$ units may be replaced with O, CO, S, SO, $SO_2$, N, $CF_2$, or $NR^8$
$R^7$ is C1-C6 alkyl, C3-C8 cycloalkyl, C1-C6 alkoxy, halo, CN, OH, $OR^8$, $N(R^8)_2$, $CF_3$, $OCF_3$, or $OCHF_2$; and
p is an integer from 0 to 3 inclusive.

In another embodiment, the Het ring is an optionally substituted thiazole, pyridine, pyrazole, oxazole, or oxadiazole.
In another embodiment, p is 0 or 1.
In another embodiment, $R^7$ is C1-C6 alkyl.
In another embodiment, $R^7$ is $CH_3$, $CH_2CH_3$, $CH(CH_3)_2$, or tBu.
In another embodiment, the Het ring is

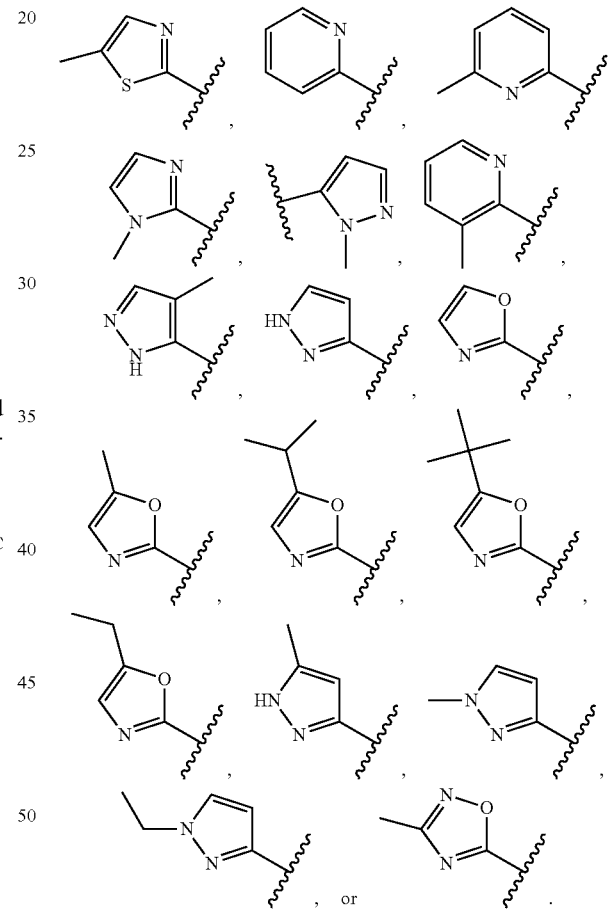

In another embodiment, $R^2$ is selected from C1-C6 alkyl or a straight chain, branched, or cyclic (C1-C8)-$R^9$ wherein up to two $CH_2$ units may be replaced with O, CO, S, SO, $SO_2$, N, $CF_2$, or $NR^8$. In another embodiment, $R^2$ is $CH_2CH_3$, tBu, $CH_2CHF_2$, $CH_2CF_3$, or

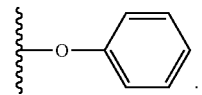

In another embodiment, $R^5$ is selected from H, C1-C6 alkyl, C1-C6 alkoxy, or halo. In another embodiment, $R^5$ is H, $CH_3$, $OCH_3$, F, or Cl.

In another embodiment, $R^6$ is H, C1-C6 alkoxy, or a straight chain, branched, or cyclic (C1-C8)-$R^9$ wherein up to three $CH_2$ units may be replaced with O, CO, S, SO, $SO_2$, N, $CF_2$, or $NR^8$. In another embodiment, $R^6$ is $OCH(CH_3)_2$, $C(CH_3)_2OH$, $OCH_2CH_2OH$, $OCH_2CH_2CH_2OH$,

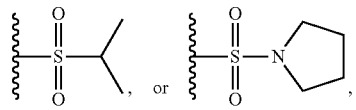, or ,

In another embodiment, the invention features a compound of formula I and the attendant definitions, wherein the compound has formula ID:

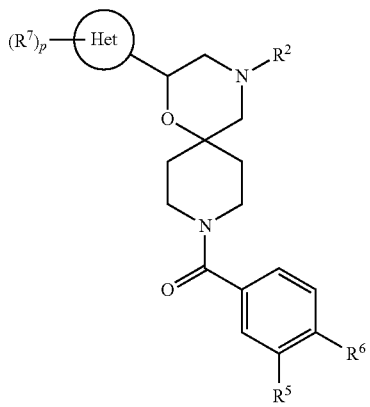

ID wherein,
the Het ring is a mono or bicyclic optionally substituted heterocyclic or heteroaryl ring;
$R^2$ is H, C1-C6 alkyl, C1-C6 fluoroalkyl, an optionally substituted aryl, heteroaryl, or heterocycloalkyl, or a straight chain, branched, or cyclic (C1-C8)-$R^9$ wherein up to two $CH_2$ units may be replaced with O, CO, S, SO, $SO_2$, N, $CF_2$, or $NR^8$;
$R^5$ is H, C1-C6 alkyl, C1-C6 alkoxy, halo, $CF_3$, $OCF_3$, $OCHF_2$, or a straight chain, branched, or cyclic (C1-C8)-$R^9$ wherein up to three $CH_2$ units may be replaced with O, CO, S, SO, $SO_2$, N, $CF_2$, or $NR^8$;
$R^6$ is H, C1-C6 alkyl, C1-C6 alkoxy, CN, $SO_2R^8$, $CON(R^8)_2$, $SO_2N(R^8)_2$, heterocycloalkyl, or a straight chain, branched, or cyclic (C1-C8)-$R^9$ wherein up to three $CH_2$ units may be replaced with O, CO, S, SO, $SO_2$, N, $CF_2$, or $NR^8$
$R^7$ is C1-C6 alkyl, C3-C8 cycloalkyl, C1-C6 alkoxy, halo, CN, OH, $OR^8$, $N(R^8)_2$, $CF_3$, $OCF_3$, or $OCHF_2$; and
p is an integer from 0 to 3 inclusive.

In another embodiment, the Het ring is an optionally substituted thiazole, pyridine, pyrazole, oxazole, or oxadiazole.
In another embodiment, p is 0 or 1.
In another embodiment, $R^7$ is C1-C6 alkyl.
In another embodiment, $R^7$ is $CH_3$, $CH_2CH_3$, $CH(CH_3)_2$, or tBu.

In another embodiment, the Het ring is

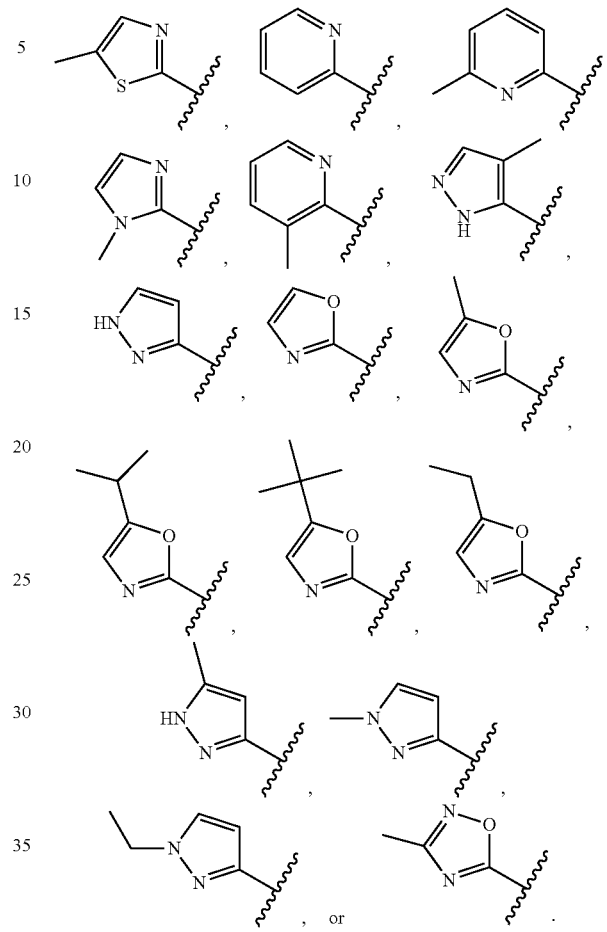

, or .

In another embodiment, $R^2$ is selected from C1-C6 alkyl or a straight chain, branched, or cyclic (C1-C8)-$R^9$ wherein up to two $CH_2$ units may be replaced with O, CO, S, SO, $SO_2$, N, $CF_2$, or $NR^8$. In another embodiment, $R^2$ is $CH_2CH_3$, tBu, $CH_2CHF_2$, $CH_2CF_3$, or

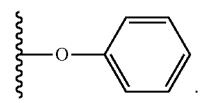 [SMILES: *Oc1ccccc1].

In another embodiment, $R^5$ is selected from H, C1-C6 alkyl, C1-C6 alkoxy, or halo. In another embodiment, $R^5$ is H, $CH_3$, $OCH_3$, F, or Cl.
In another embodiment, $R^6$ is H, C1-C6 alkoxy, or a straight chain, branched, or cyclic (C1-C8)-$R^9$ wherein up to three $CH_2$ units may be replaced with O, CO, S, SO, $SO_2$, N, $CF_2$, or $NR^8$. In another embodiment, $R^6$ is $OCH(CH_3)_2$, $C(CH_3)_2OH$, $OCH_2CH_2OH$, $OCH_2CH_2CH_2OH$,

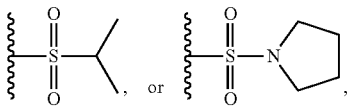, or ,

In another embodiment, the invention features a compound of formula I and the attendant definitions, wherein the compound is selected from the following table:
TABLE 1
| 1 |
|---|
| 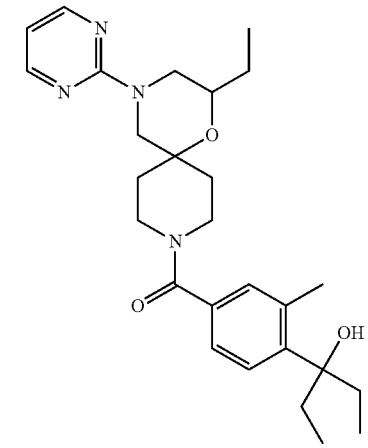 [SMILES: CCC1CN(c2ncccn2)CC2(CCN(C(=O)c3ccc(C(O)(CC)CC)c(C)c3)CC2)O1] |
| 2 |
| 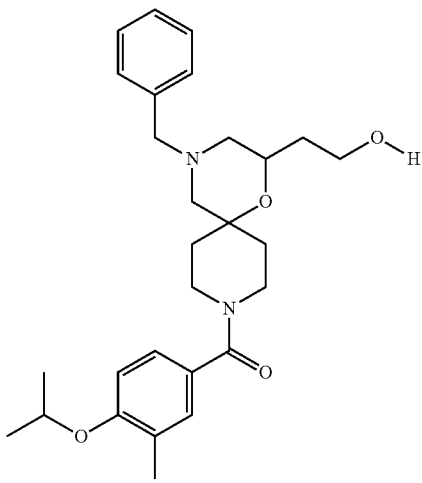 [SMILES: Cc1cc(C(=O)N2CCC3(CC2)CN(Cc2ccccc2)CC(CCO)O3)ccc1OC(C)C] |
| 3 |
| 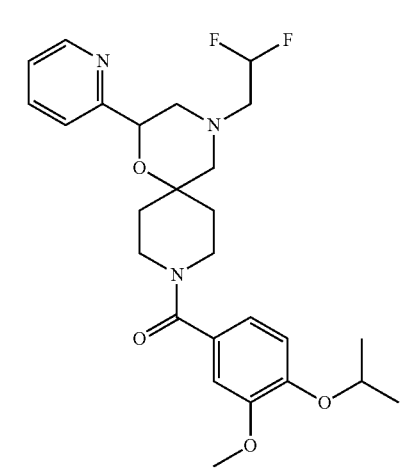 |
TABLE 1-continued
| 4 |
|---|
| 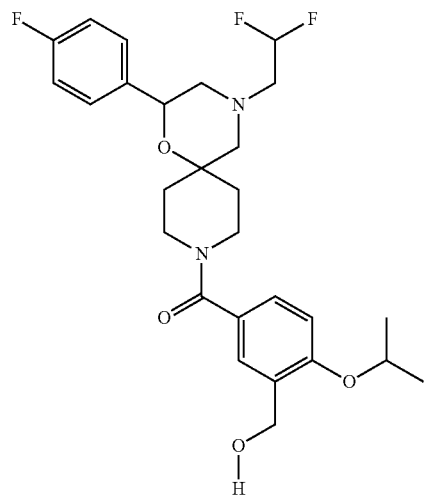 [SMILES: CC(C)Oc1ccc(C(=O)N2CCC3(CC2)CN(CC(F)F)CC(c2ccc(F)cc2)O3)cc1CO] |
| 5 |
| 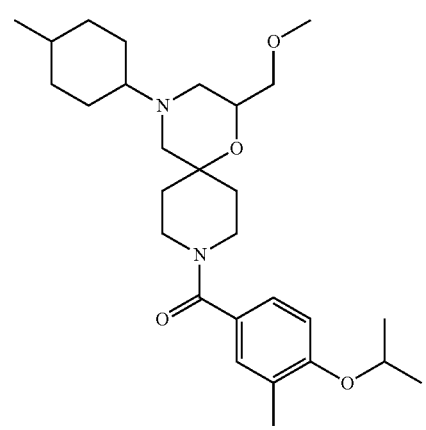 [SMILES: COCC1CN(C2CCC(C)CC2)CC2(CCN(C(=O)c3ccc(OC(C)C)c(C)c3)CC2)O1] |
| 6 |
| 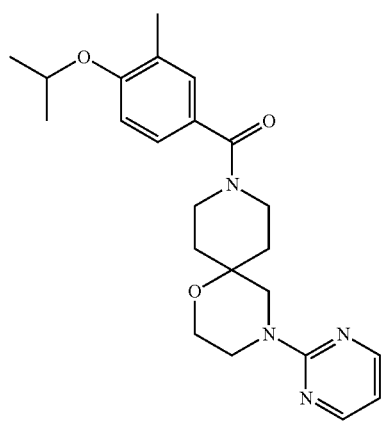 [SMILES: Cc1cc(C(=O)N2CCC3(CC2)CN(c2ncccn2)CCO3)ccc1OC(C)C] |

TABLE 1-continued
7
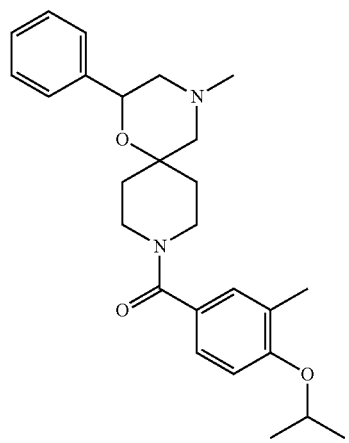 [SMILES: Cc1cc(C(=O)N2CCC3(CC2)CN(C)CC(c2ccccc2)O3)ccc1OC(C)C]
8
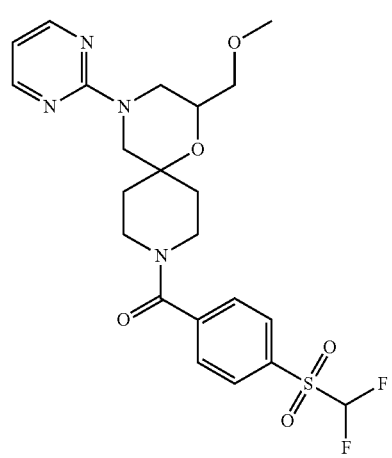 [SMILES: COCC1CN(c2ncccn2)CC2(CCN(C(=O)c3ccc(S(=O)(=O)C(F)F)cc3)CC2)O1]
9
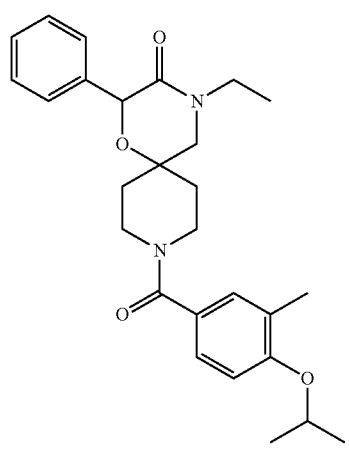 [SMILES: CCN1CC2(CCN(C(=O)c3ccc(OC(C)C)c(C)c3)CC2)OC(c2ccccc2)C1=O]
TABLE 1-continued
10
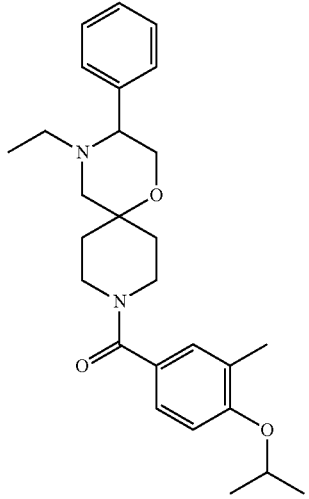 [SMILES: CCN1CC2(CCN(C(=O)c3ccc(OC(C)C)c(C)c3)CC2)OCC1c1ccccc1]
11
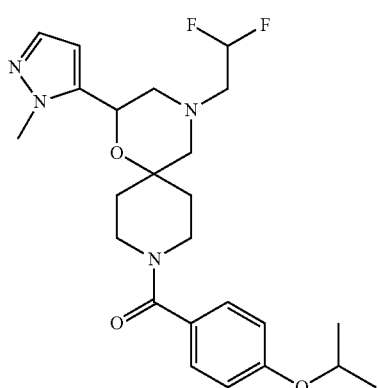
12
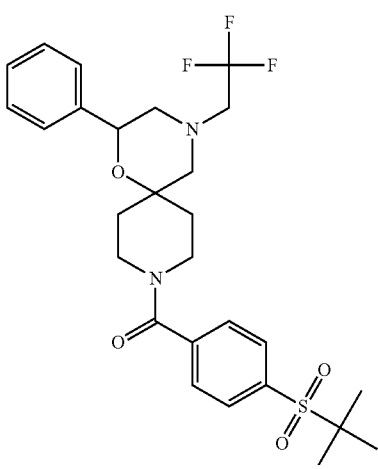 [SMILES: CC(C)(C)S(=O)(=O)c1ccc(C(=O)N2CCC3(CC2)CN(CC(F)(F)F)CC(c2ccccc2)O3)cc1]

TABLE 1-continued
13
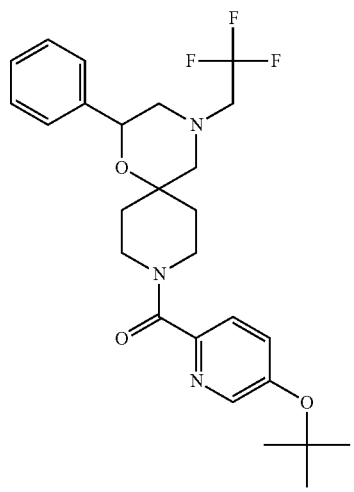 [SMILES: CC(C)(C)Oc1ccc(C(=O)N2CCC3(CC2)CN(CC(F)(F)F)CC(c2ccccc2)O3)nc1]
14
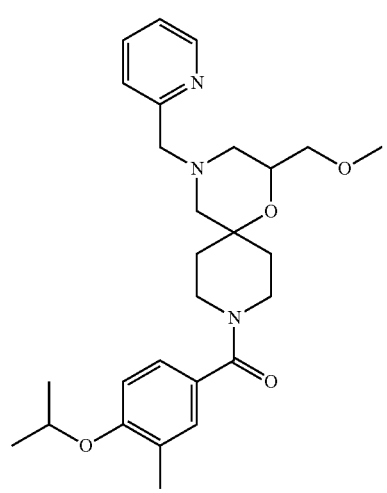 [SMILES: COCC1CN(Cc2ccccn2)CC2(CCN(C(=O)c3ccc(OC(C)C)c(C)c3)CC2)O1]
15
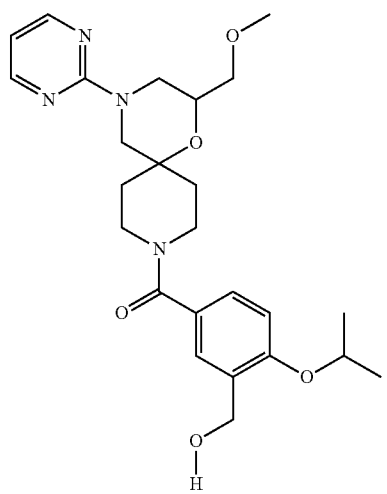 [SMILES: COCC1CN(c2ncccn2)CC2(CCN(C(=O)c3ccc(OC(C)C)c(CO)c3)CC2)O1]
TABLE 1-continued
16
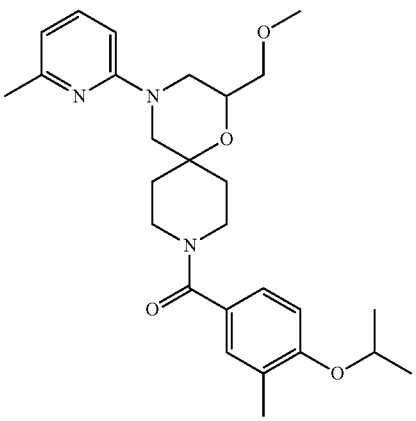 [SMILES: COCC1CN(c2cccc(C)n2)CC2(CCN(C(=O)c3ccc(OC(C)C)c(C)c3)CC2)O1]
17
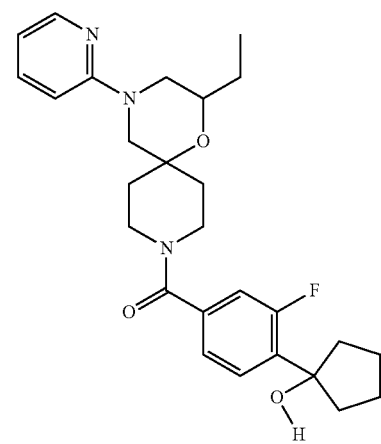 [SMILES: CCC1CN(c2ccccn2)CC2(CCN(C(=O)c3ccc(C4(O)CCCC4)c(F)c3)CC2)O1]
18
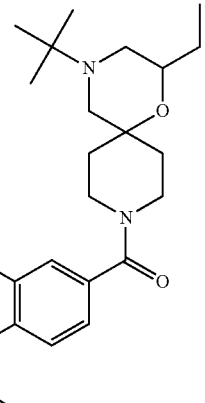

TABLE 1-continued
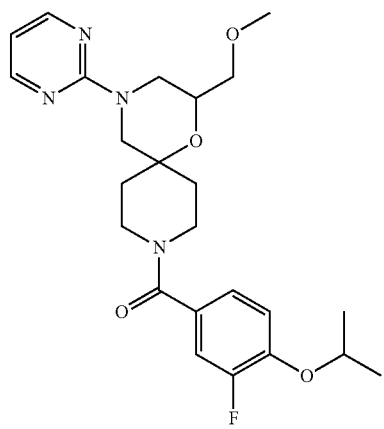 [SMILES: COCC1CN(c2ncccn2)CC2(CCN(C(=O)c3ccc(OC(C)C)c(F)c3)CC2)O1]
19
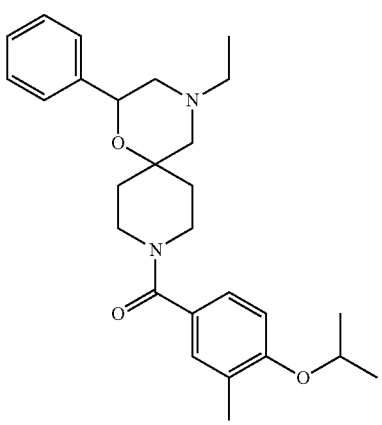
22
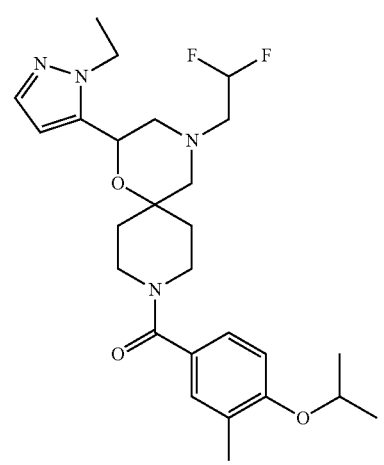 [SMILES: CCn1nccc1C1CN(CC(F)F)CC2(CCN(C(=O)c3ccc(OC(C)C)c(C)c3)CC2)O1]
20
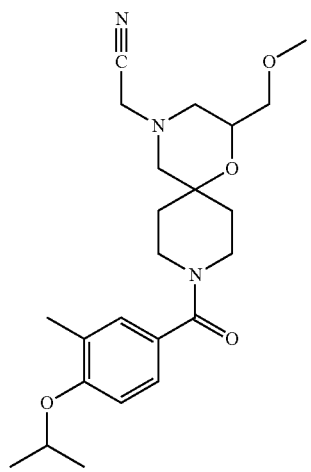
23
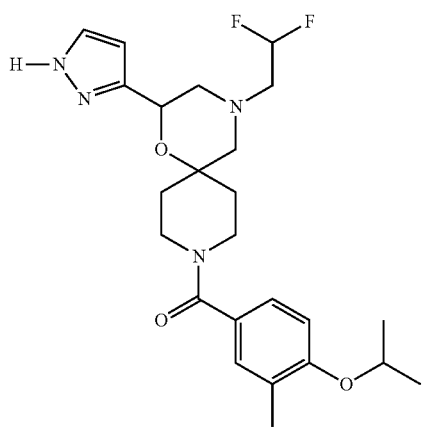 [SMILES: Cc1cc(C(=O)N2CCC3(CC2)CN(CC(F)F)CC(c2cc[nH]n2)O3)ccc1OC(C)C]
21
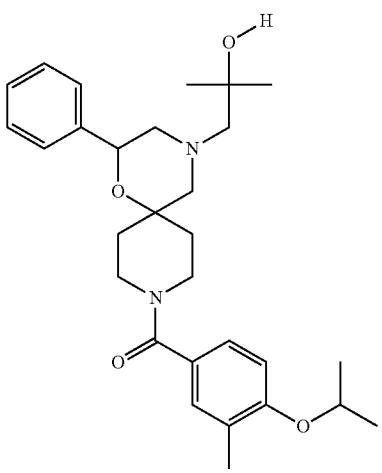 [SMILES: Cc1cc(C(=O)N2CCC3(CC2)CN(CC(C)(C)O)CC(c2ccccc2)O3)ccc1OC(C)C]
24

TABLE 1-continued
25
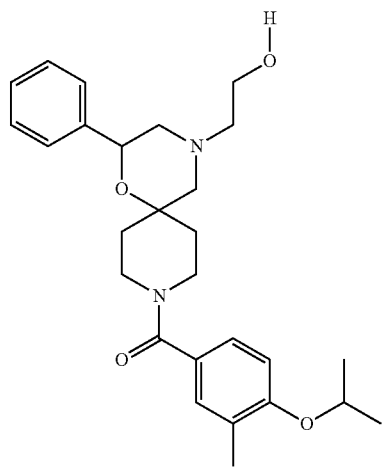 [SMILES: Cc1cc(C(=O)N2CCC3(CC2)CN(CCO)CC(c2ccccc2)O3)ccc1OC(C)C]
26
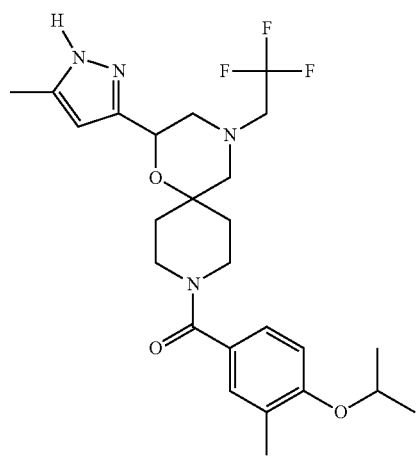 [SMILES: Cc1cc(C2CN(CC(F)(F)F)CC3(CCN(C(=O)c4ccc(OC(C)C)c(C)c4)CC3)O2)n[nH]1]
27
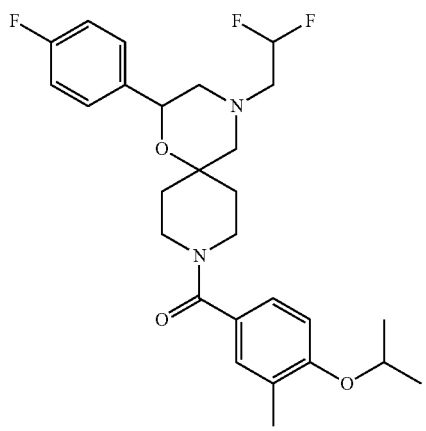 [SMILES: Cc1cc(C(=O)N2CCC3(CC2)CN(CC(F)F)CC(c2ccc(F)cc2)O3)ccc1OC(C)C]
TABLE 1-continued
28
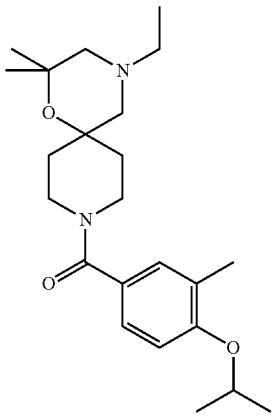 [SMILES: CCN1CC(C)(C)OC2(CCN(C(=O)c3ccc(OC(C)C)c(C)c3)CC2)C1]
29
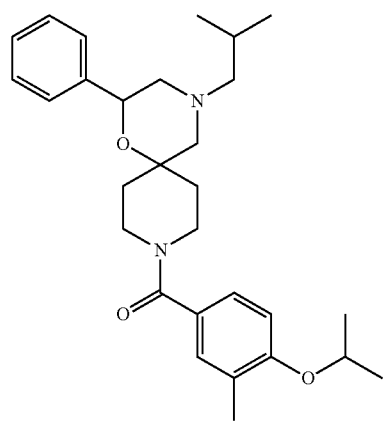 [SMILES: Cc1cc(C(=O)N2CCC3(CC2)CN(CC(C)C)CC(c2ccccc2)O3)ccc1OC(C)C]
30
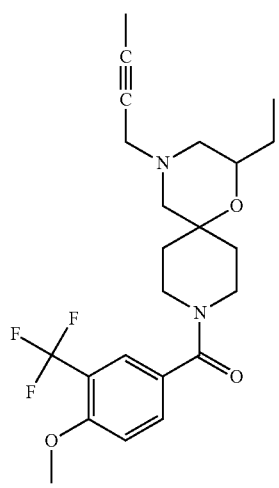 [SMILES: CC#CCN1CC(CC)OC2(CCN(C(=O)c3ccc(OC)c(C(F)(F)F)c3)CC2)C1]

TABLE 1-continued
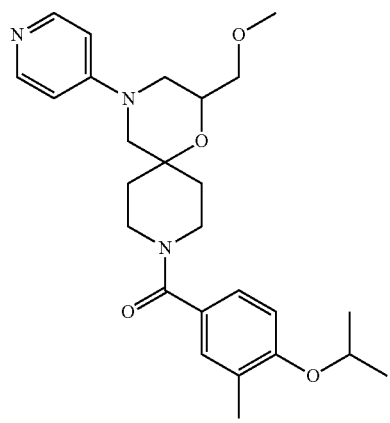 [SMILES: COCC1CN(c2ccncc2)CC2(CCN(C(=O)c3ccc(OC(C)C)c(C)c3)CC2)O1]
31
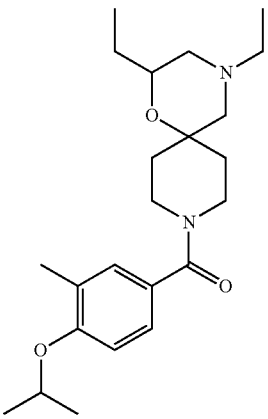
34
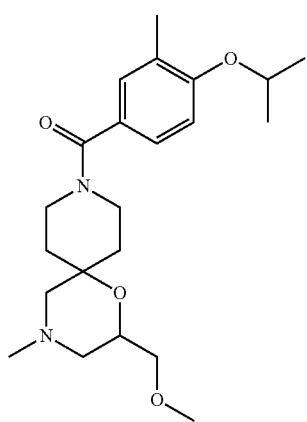 [SMILES: COCC1CN(C)CC2(CCN(C(=O)c3ccc(OC(C)C)c(C)c3)CC2)O1]
32
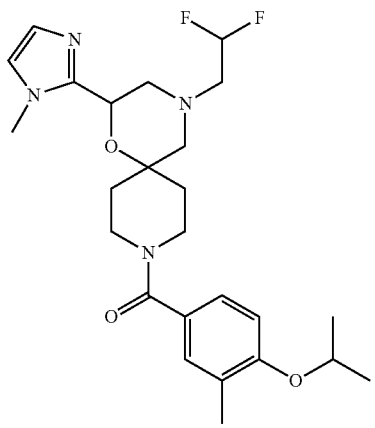
35
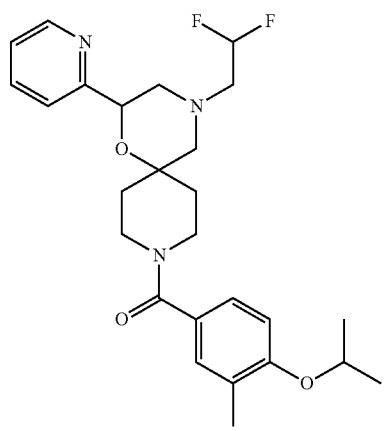
33
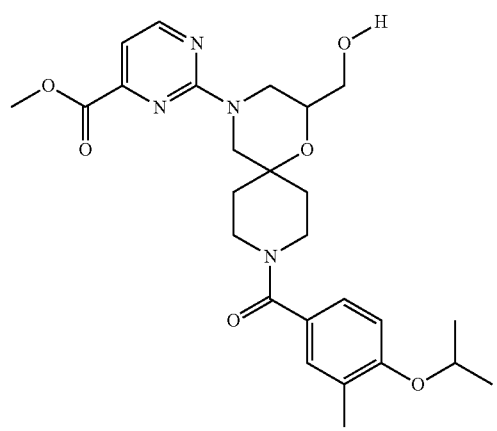 [SMILES: COC(=O)c1ccnc(N2CC(CO)OC3(CCN(C(=O)c4ccc(OC(C)C)c(C)c4)CC3)C2)n1]
36

TABLE 1-continued
37
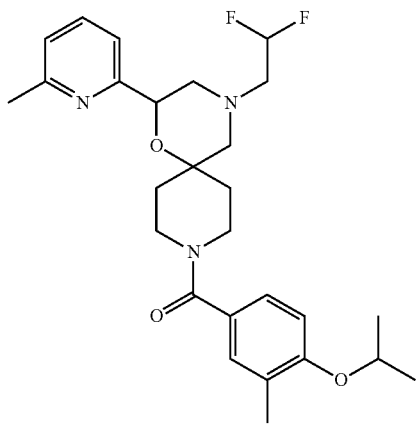 [SMILES: Cc1cccc(C2CN(CC(F)F)CC3(CCN(C(=O)c4ccc(OC(C)C)c(C)c4)CC3)O2)n1]
38
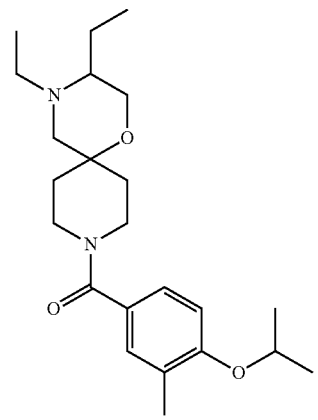
39
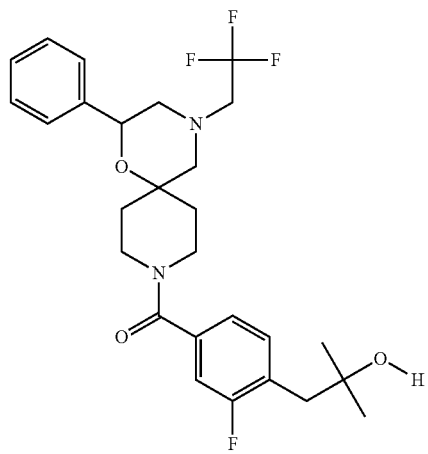 [SMILES: CC(C)(O)Cc1ccc(C(=O)N2CCC3(CC2)CN(CC(F)(F)F)CC(c2ccccc2)O3)cc1F]
TABLE 1-continued
40
41
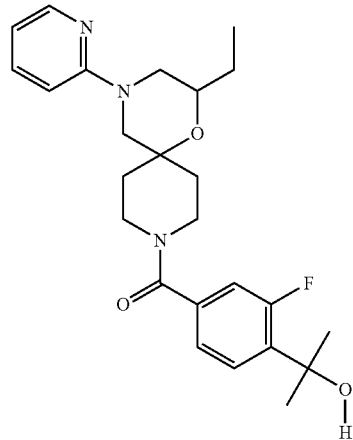 [SMILES: CCC1CN(c2ccccn2)CC2(CCN(C(=O)c3ccc(C(C)(C)O)c(F)c3)CC2)O1]
42

TABLE 1-continued
| 43 | 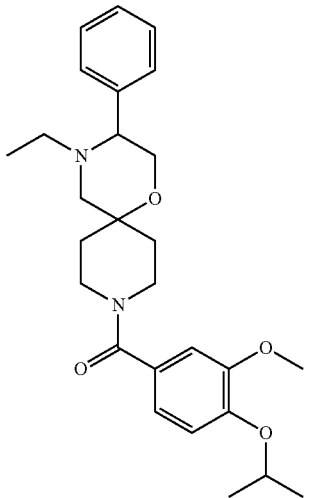 |
| 44 | 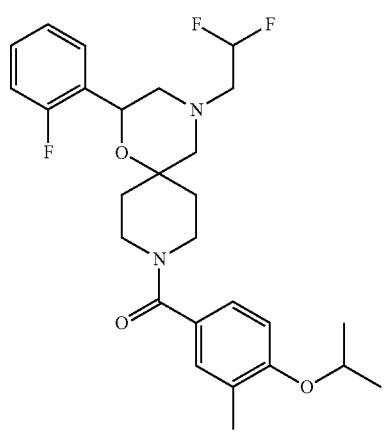 [SMILES: Cc1cc(C(=O)N2CCC3(CC2)CN(CC(F)F)CC(c2ccccc2F)O3)ccc1OC(C)C] |
| 45 | 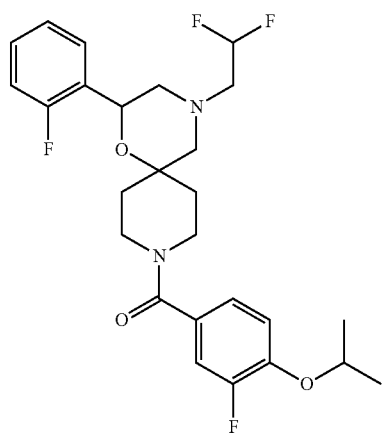 |
TABLE 1-continued
| 46 | 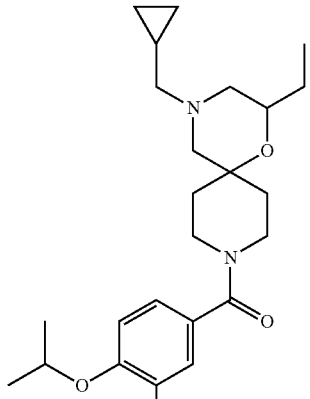 |
| 47 | 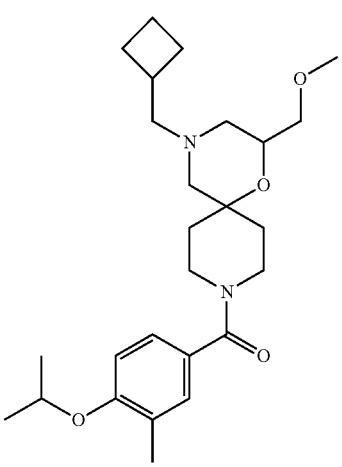 [SMILES: COCC1CN(CC2CCC2)CC2(CCN(C(=O)c3ccc(OC(C)C)c(C)c3)CC2)O1] |
| 48 | 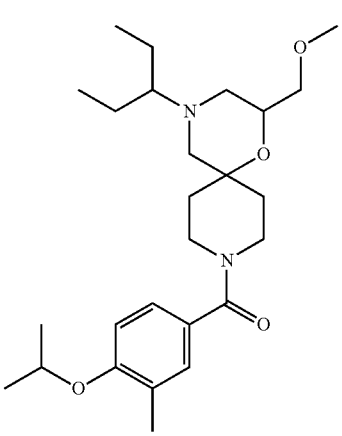 [SMILES: CCC(CC)N1CC(COC)OC2(CCN(C(=O)c3ccc(OC(C)C)c(C)c3)CC2)C1] |

TABLE 1-continued
49
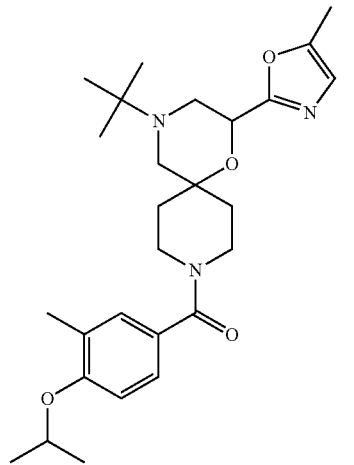 [SMILES: Cc1cnc(C2CN(C(C)(C)C)CC3(CCN(C(=O)c4ccc(OC(C)C)c(C)c4)CC3)O2)o1]
50
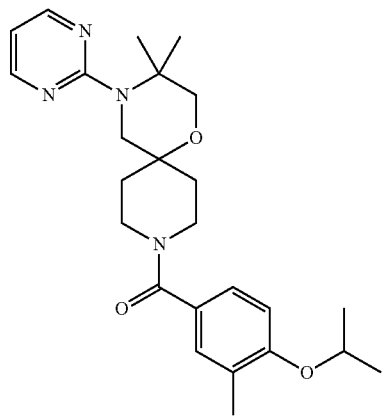 [SMILES: Cc1cc(C(=O)N2CCC3(CC2)CN(c2ncccn2)C(C)(C)CO3)ccc1OC(C)C]
52
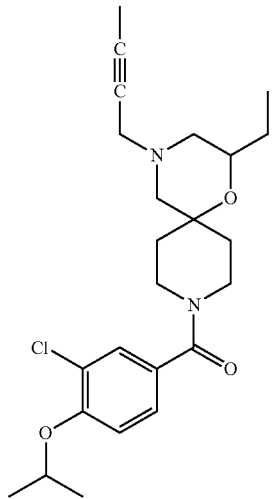
53
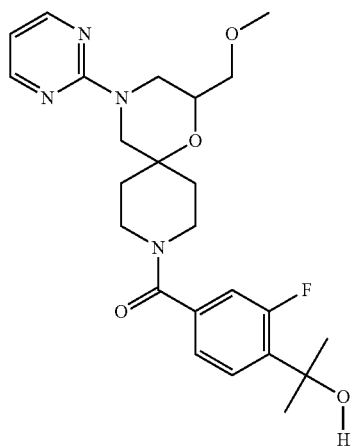 [SMILES: COCC1CN(c2ncccn2)CC2(CCN(C(=O)c3ccc(C(C)(C)O)c(F)c3)CC2)O1]
54
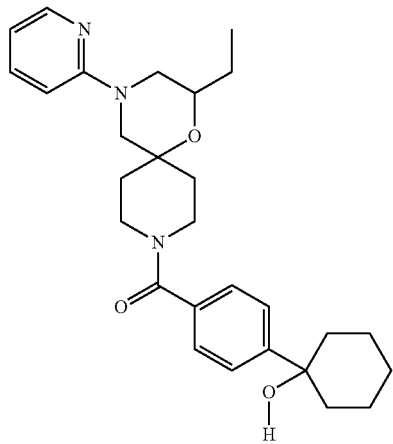

TABLE 1-continued
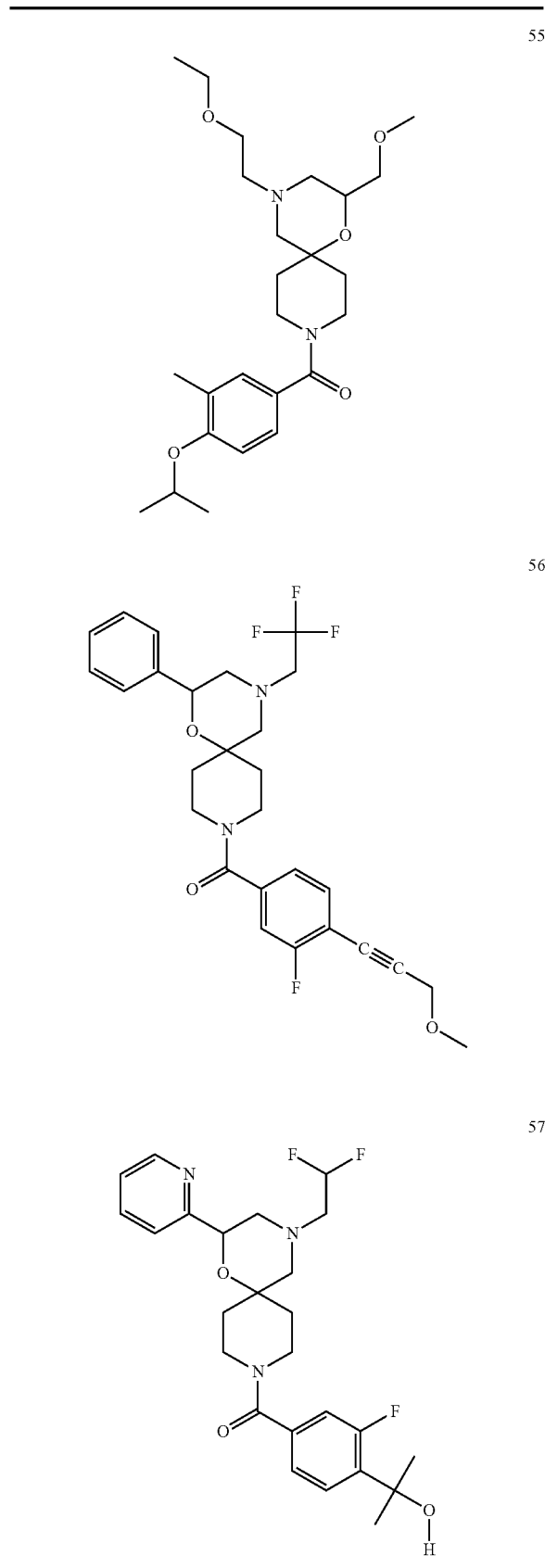
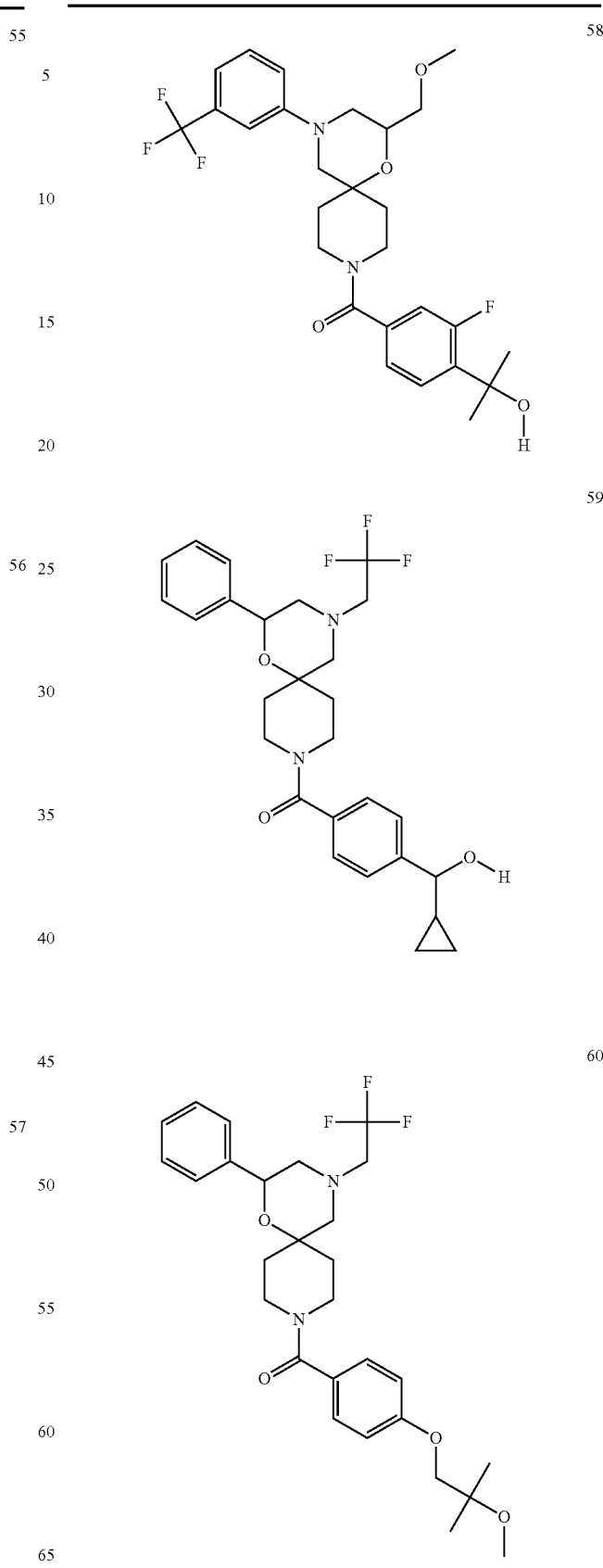

TABLE 1-continued
61
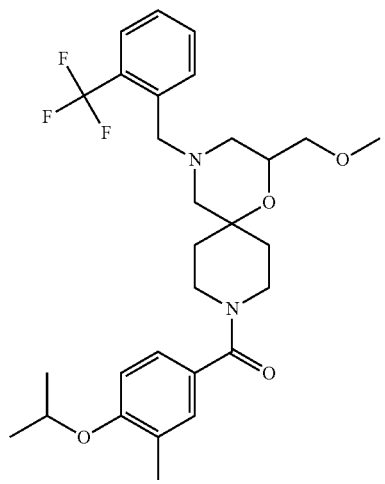 [SMILES: COCC1CN(Cc2ccccc2C(F)(F)F)CC2(CCN(C(=O)c3ccc(OC(C)C)c(C)c3)CC2)O1]
62
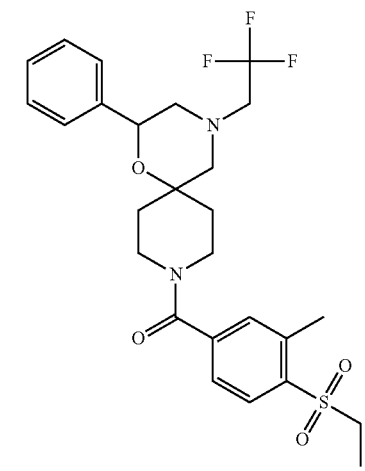 [SMILES: CCS(=O)(=O)c1ccc(C(=O)N2CCC3(CC2)CN(CC(F)(F)F)CC(c2ccccc2)O3)cc1C]
63
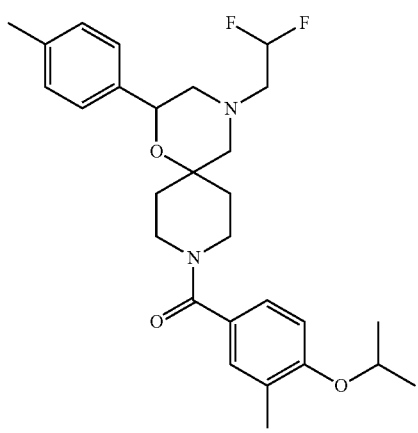 [SMILES: Cc1ccc(C2CN(CC(F)F)CC3(CCN(C(=O)c4ccc(OC(C)C)c(C)c4)CC3)O2)cc1]
TABLE 1-continued
64
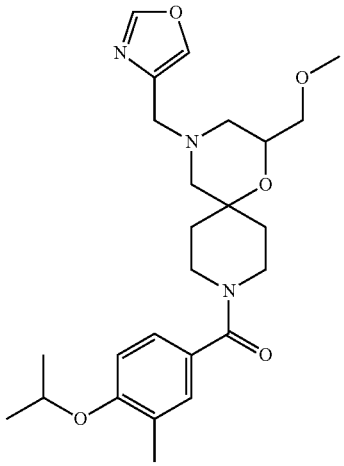 [SMILES: COCC1CN(Cc2cocn2)CC2(CCN(C(=O)c3ccc(OC(C)C)c(C)c3)CC2)O1]
65
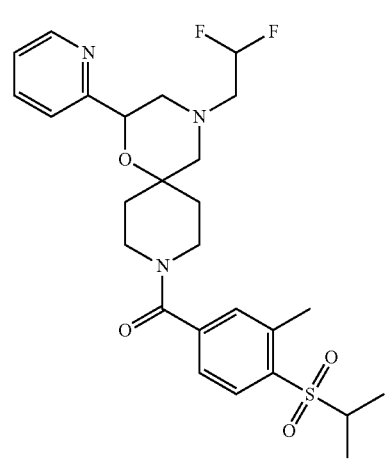 [SMILES: Cc1cc(C(=O)N2CCC3(CC2)CN(CC(F)F)CC(c2ccccn2)O3)ccc1S(=O)(=O)C(C)C]
66
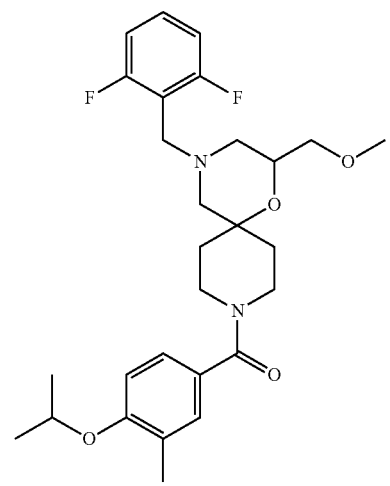 [SMILES: COCC1CN(Cc2c(F)cccc2F)CC2(CCN(C(=O)c3ccc(OC(C)C)c(C)c3)CC2)O1]

TABLE 1-continued
67
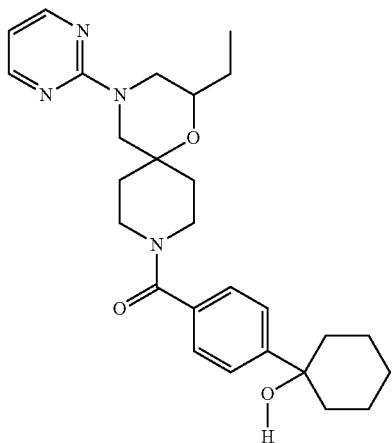 [SMILES: CCC1CN(c2ncccn2)CC2(CCN(C(=O)c3ccc(C4(O)CCCCC4)cc3)CC2)O1]
68
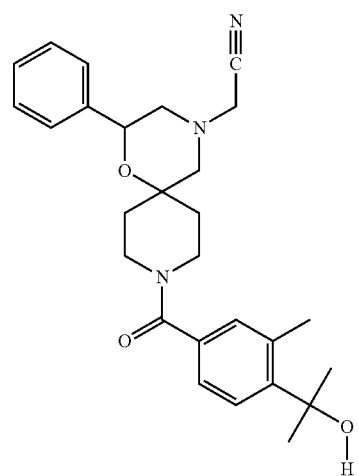 [SMILES: Cc1cc(C(=O)N2CCC3(CC2)CN(CC#N)CC(c2ccccc2)O3)ccc1C(C)(C)O]
69
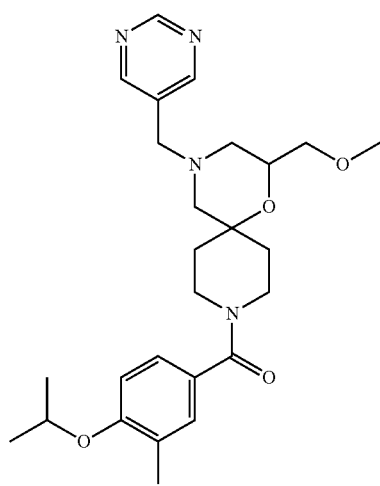 [SMILES: COCC1CN(Cc2cncnc2)CC2(CCN(C(=O)c3ccc(OC(C)C)c(C)c3)CC2)O1]
70
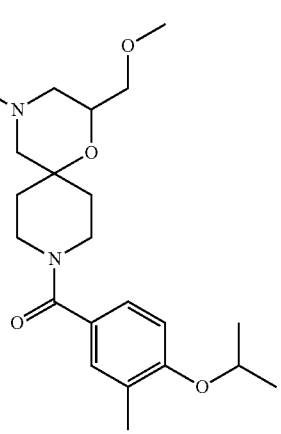
71
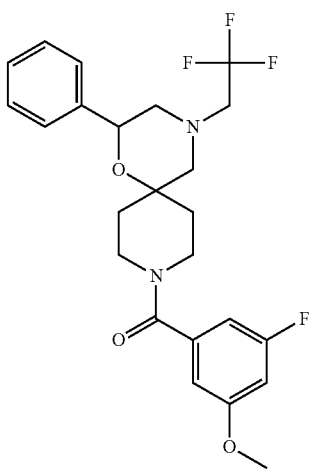 [SMILES: COc1cc(F)cc(C(=O)N2CCC3(CC2)CN(CC(F)(F)F)CC(c2ccccc2)O3)c1]
72
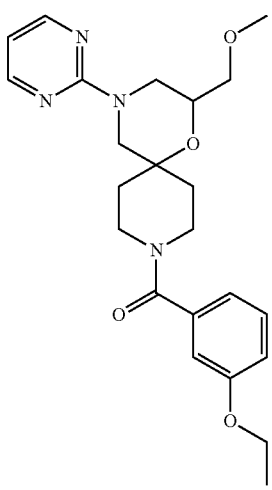 [SMILES: CCOc1cccc(C(=O)N2CCC3(CC2)CN(c2ncccn2)CC(COC)O3)c1]

TABLE 1-continued
| | |
|---|---|
| 73 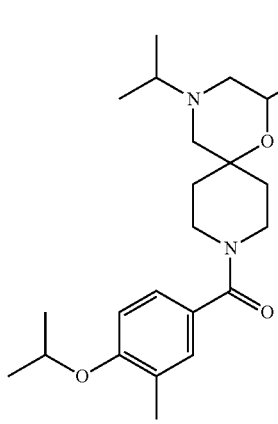 | 76 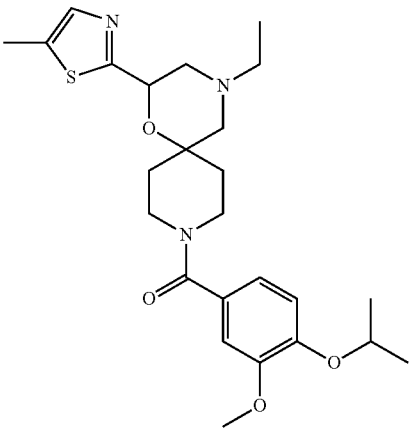 [SMILES: CCN1CC(c2ncc(C)s2)OC2(CCN(C(=O)c3ccc(OC(C)C)c(OC)c3)CC2)C1] |
| 74 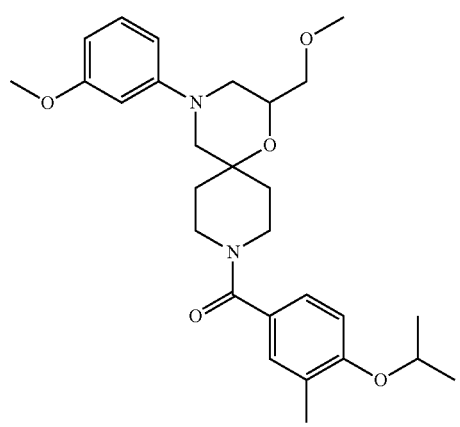 | 77 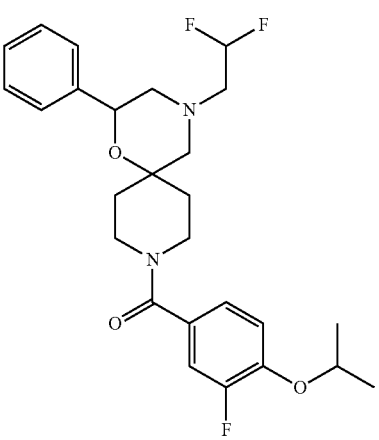 |
| 75 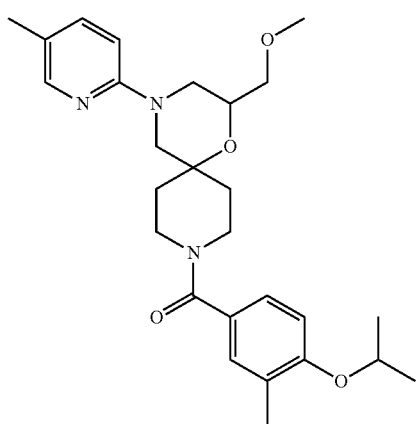 | 78 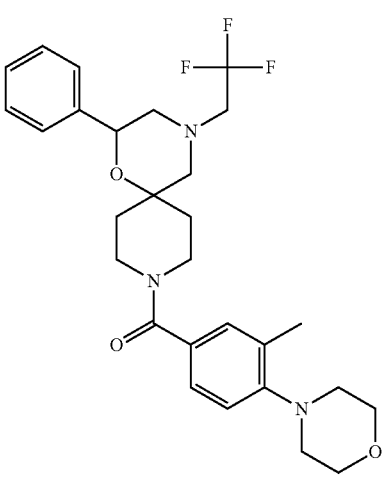 [SMILES: Cc1cc(C(=O)N2CCC3(CC2)CN(CC(F)(F)F)CC(c2ccccc2)O3)ccc1N1CCOCC1] |

TABLE 1-continued
79
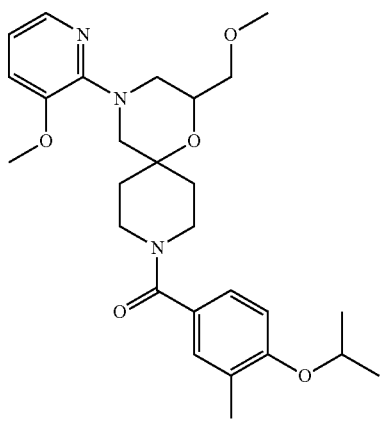 [SMILES: COCC1CN(c2ncccc2OC)CC2(CCN(C(=O)c3ccc(OC(C)C)c(C)c3)CC2)O1]
80
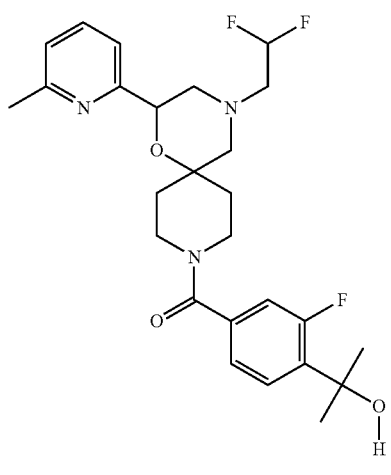 [SMILES: Cc1cccc(C2CN(CC(F)F)CC3(CCN(C(=O)c4ccc(C(C)(C)O)c(F)c4)CC3)O2)n1]
81
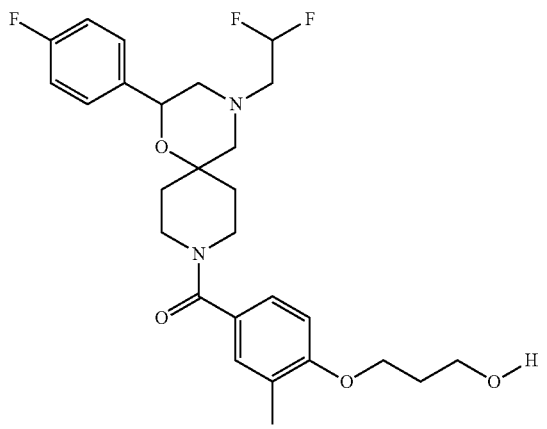 [SMILES: Cc1cc(C(=O)N2CCC3(CC2)CN(CC(F)F)CC(c2ccc(F)cc2)O3)ccc1OCCCO]
TABLE 1-continued
82
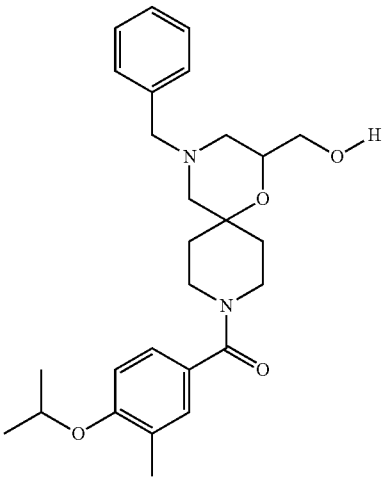 [SMILES: Cc1cc(C(=O)N2CCC3(CC2)CN(Cc2ccccc2)CC(CO)O3)ccc1OC(C)C]
83
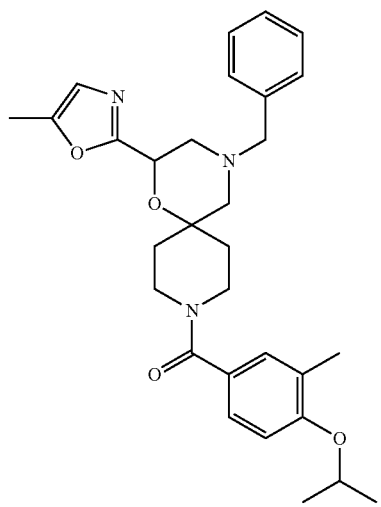 [SMILES: Cc1cnc(C2CN(Cc3ccccc3)CC3(CCN(C(=O)c4ccc(OC(C)C)c(C)c4)CC3)O2)o1]
84
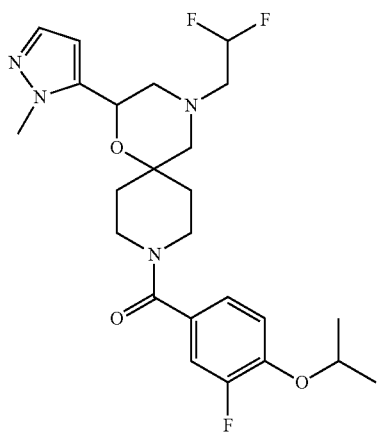 [SMILES: CC(C)Oc1ccc(C(=O)N2CCC3(CC2)CN(CC(F)F)CC(c2ccnn2C)O3)cc1F]

TABLE 1-continued
85
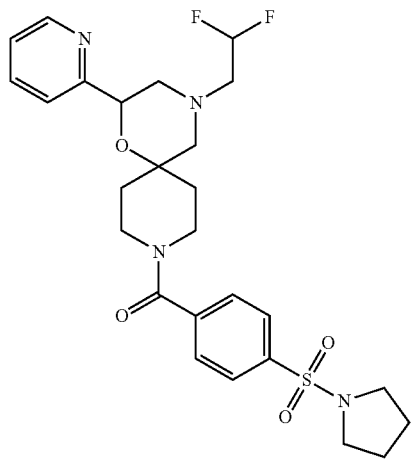 [SMILES: O=C(c1ccc(S(=O)(=O)N2CCCC2)cc1)N1CCC2(CC1)CN(CC(F)F)CC(c1ccccn1)O2]
86
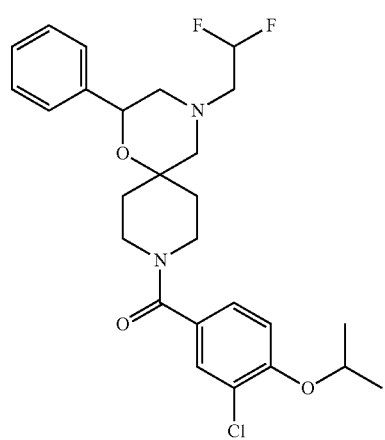 [SMILES: CC(C)Oc1ccc(C(=O)N2CCC3(CC2)CN(CC(F)F)CC(c2ccccc2)O3)cc1Cl]
87
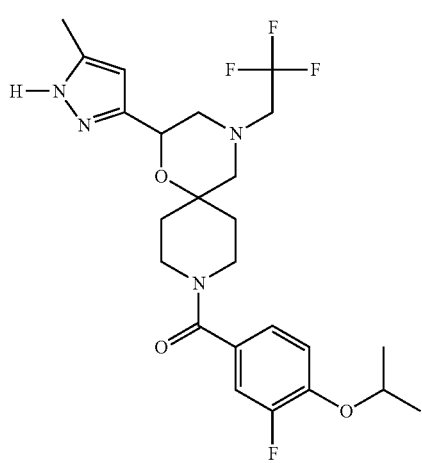 [SMILES: Cc1cc(C2CN(CC(F)(F)F)CC3(CCN(C(=O)c4ccc(OC(C)C)c(F)c4)CC3)O2)n[nH]1]
TABLE 1-continued
88
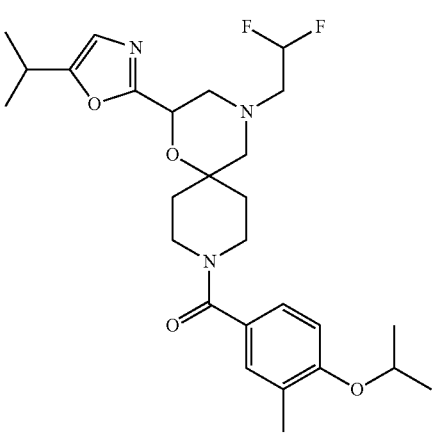 [SMILES: Cc1cc(C(=O)N2CCC3(CC2)CN(CC(F)F)CC(c2ncc(C(C)C)o2)O3)ccc1OC(C)C]
89
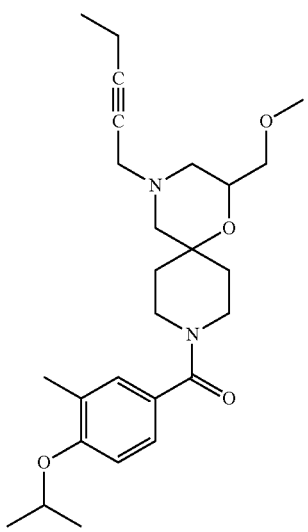 [SMILES: CCC#CCN1CC(COC)OC2(CCN(C(=O)c3ccc(OC(C)C)c(C)c3)CC2)C1]
90
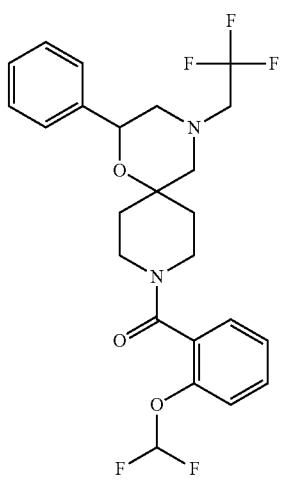 [SMILES: O=C(c1ccccc1OC(F)F)N1CCC2(CC1)CN(CC(F)(F)F)CC(c1ccccc1)O2]

TABLE 1-continued
91 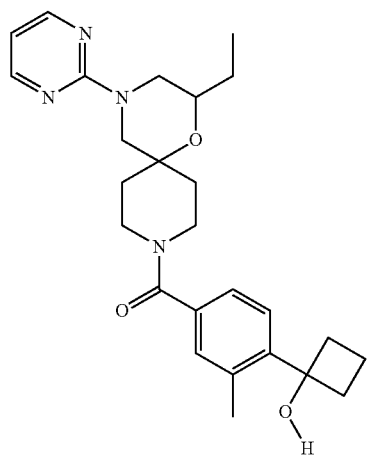 [SMILES: CCC1CN(c2ncccn2)CC2(CCN(C(=O)c3ccc(C4(O)CCC4)c(C)c3)CC2)O1]
92 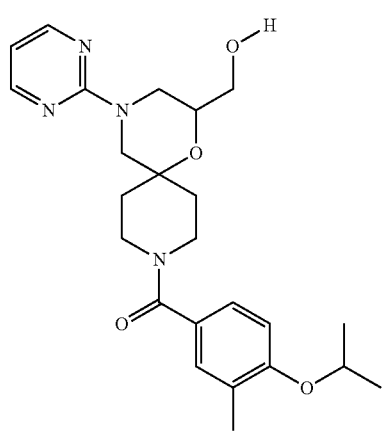 [SMILES: Cc1cc(C(=O)N2CCC3(CC2)CN(c2ncccn2)CC(CO)O3)ccc1OC(C)C]
93 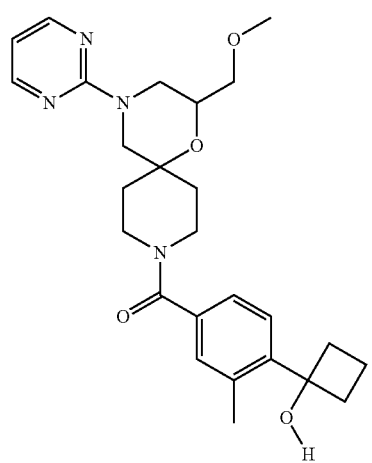 [SMILES: COCC1CN(c2ncccn2)CC2(CCN(C(=O)c3ccc(C4(O)CCC4)c(C)c3)CC2)O1]
TABLE 1-continued
94 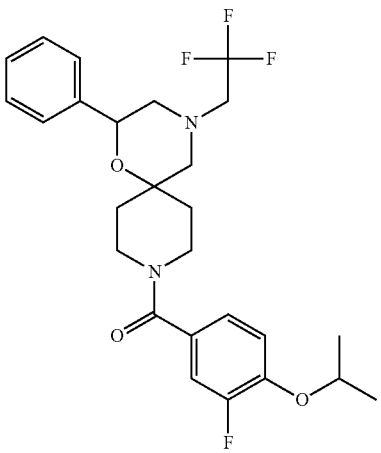 [SMILES: CC(C)Oc1ccc(C(=O)N2CCC3(CC2)CN(CC(F)(F)F)CC(c2ccccc2)O3)cc1F]
95 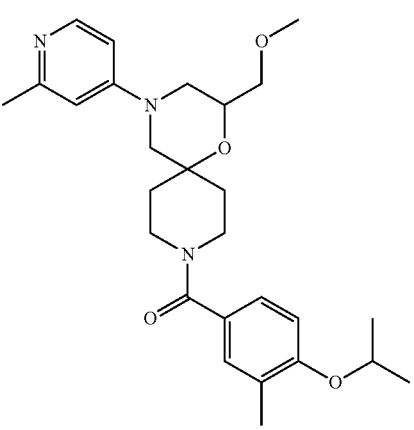 [SMILES: COCC1CN(c2ccnc(C)c2)CC2(CCN(C(=O)c3ccc(OC(C)C)c(C)c3)CC2)O1]
96 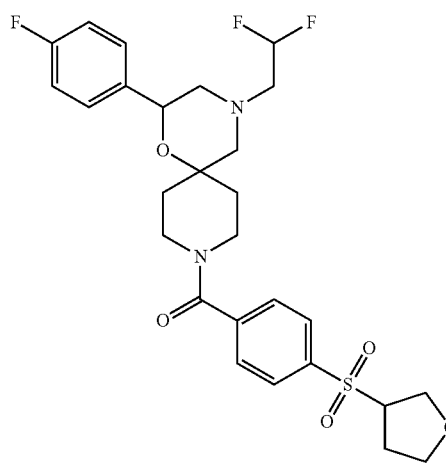

TABLE 1-continued
97 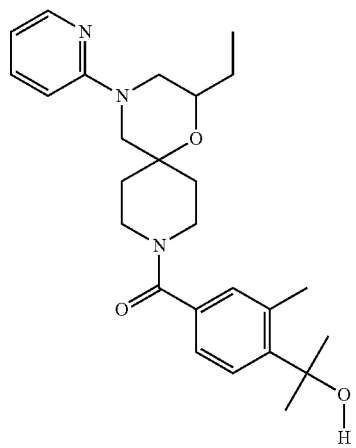 [SMILES: CCC1CN(c2ccccn2)CC2(CCN(C(=O)c3ccc(C(C)(C)O)c(C)c3)CC2)O1]
98 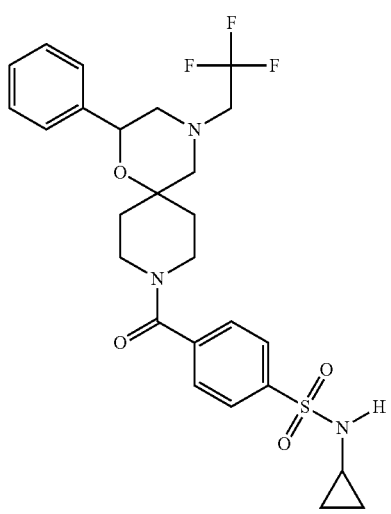 [SMILES: O=C(c1ccc(S(=O)(=O)NC2CC2)cc1)N1CCC2(CC1)CN(CC(F)(F)F)CC(c1ccccc1)O2]
99 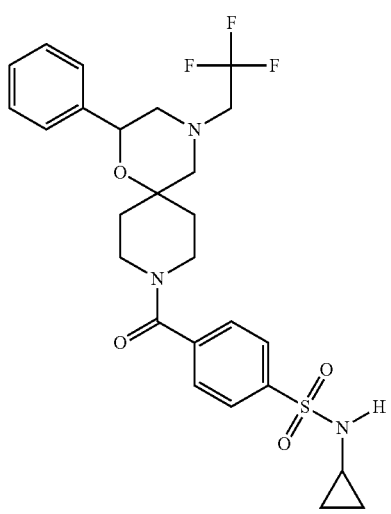 [SMILES: O=C(c1ccc(S(=O)(=O)NC2CC2)cc1)N1CCC2(CC1)CN(CC(F)(F)F)CC(c1ccccc1)O2]
TABLE 1-continued
100 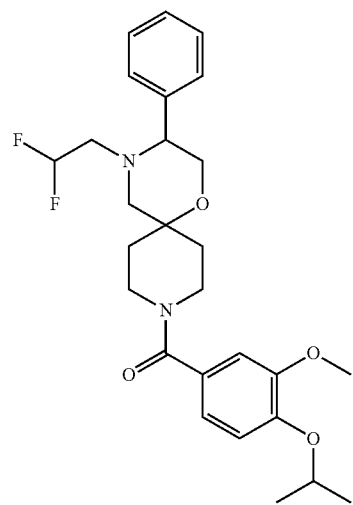 [SMILES: COc1cc(C(=O)N2CCC3(CC2)CN(CC(F)F)C(c2ccccc2)CO3)ccc1OC(C)C]
101 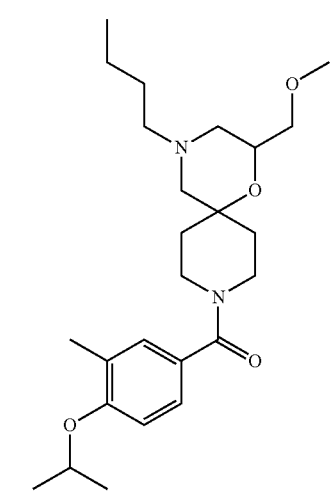 [SMILES: CCCCN1CC(COC)OC2(CCN(C(=O)c3ccc(OC(C)C)c(C)c3)CC2)C1]
102 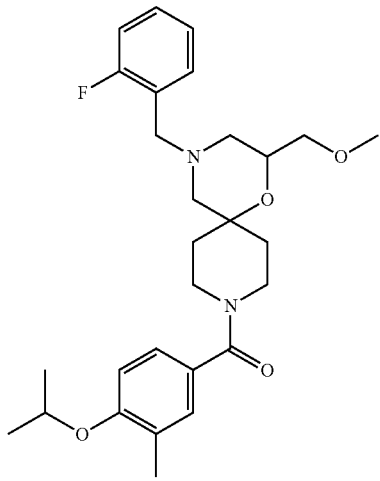 [SMILES: COCC1CN(Cc2ccccc2F)CC2(CCN(C(=O)c3ccc(OC(C)C)c(C)c3)CC2)O1]

TABLE 1-continued
103
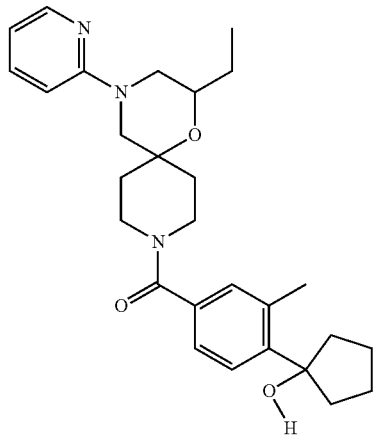
104
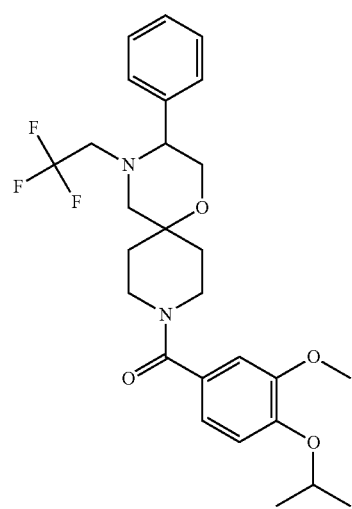 [SMILES: COc1cc(C(=O)N2CCC3(CC2)CN(CC(F)(F)F)C(c2ccccc2)CO3)ccc1OC(C)C]
105
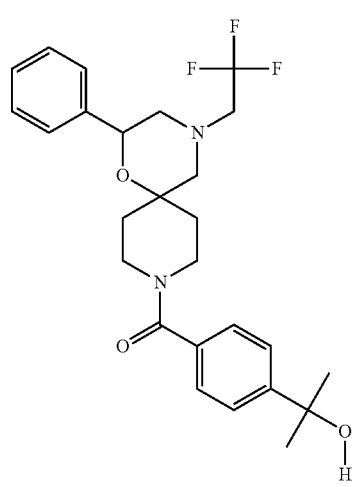 [SMILES: CC(C)(O)c1ccc(C(=O)N2CCC3(CC2)CN(CC(F)(F)F)CC(c2ccccc2)O3)cc1]
TABLE 1-continued
106
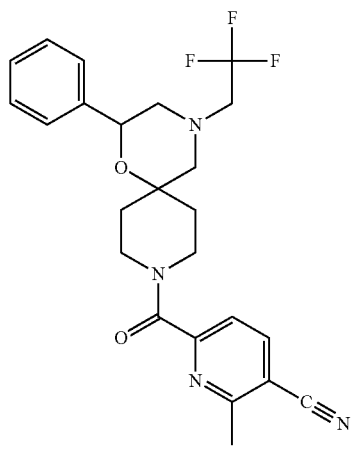 [SMILES: Cc1nc(C(=O)N2CCC3(CC2)CN(CC(F)(F)F)CC(c2ccccc2)O3)ccc1C#N]
107
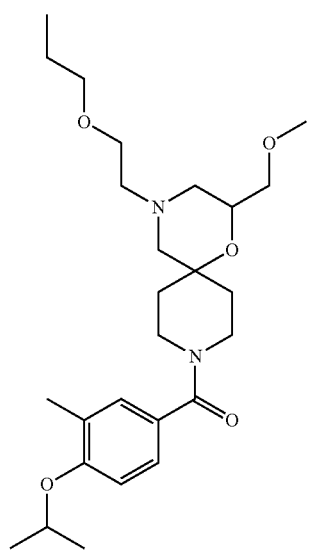 [SMILES: CCCOCCN1CC(COC)OC2(CCN(C(=O)c3ccc(OC(C)C)c(C)c3)CC2)C1]
108
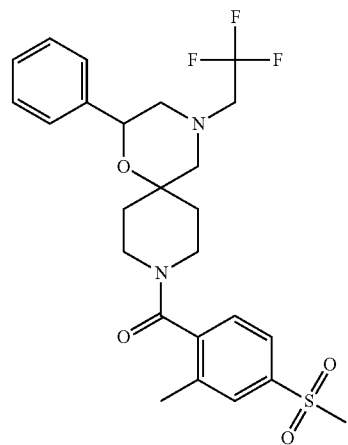 [SMILES: Cc1cc(S(C)(=O)=O)ccc1C(=O)N1CCC2(CC1)CN(CC(F)(F)F)CC(c1ccccc1)O2]

TABLE 1-continued
109
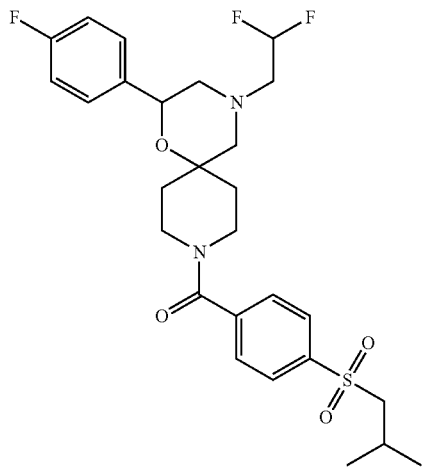 [SMILES: CC(C)CS(=O)(=O)c1ccc(C(=O)N2CCC3(CC2)CN(CC(F)F)CC(c2ccc(F)cc2)O3)cc1]
110
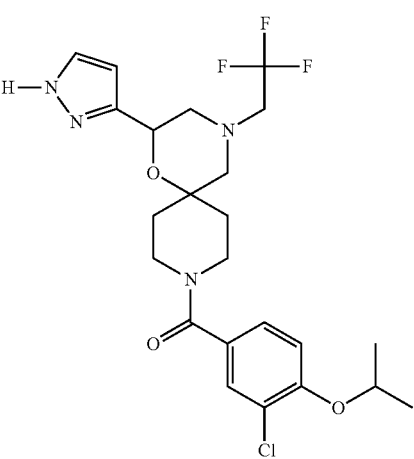 [SMILES: CC(C)Oc1ccc(C(=O)N2CCC3(CC2)CN(CC(F)(F)F)CC(c2cc[nH]n2)O3)cc1Cl]
111
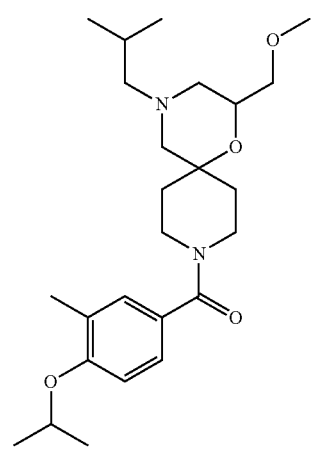 [SMILES: COCC1CN(CC(C)C)CC2(CCN(C(=O)c3ccc(OC(C)C)c(C)c3)CC2)O1]
TABLE 1-continued
112
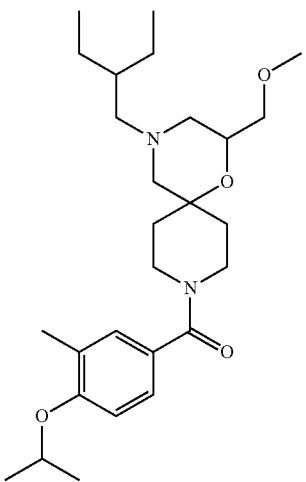 [SMILES: CCC(CC)CN1CC(COC)OC2(CCN(C(=O)c3ccc(OC(C)C)c(C)c3)CC2)C1]
113
114
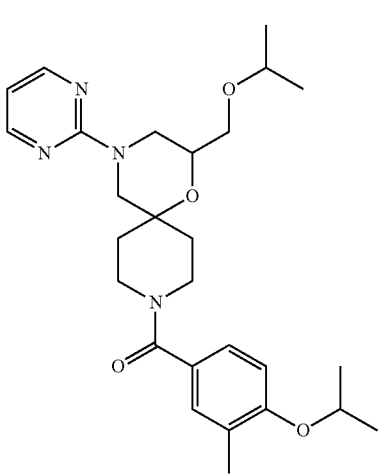 [SMILES: Cc1cc(C(=O)N2CCC3(CC2)CN(c2ncccn2)CC(COC(C)C)O3)ccc1OC(C)C]

TABLE 1-continued
115
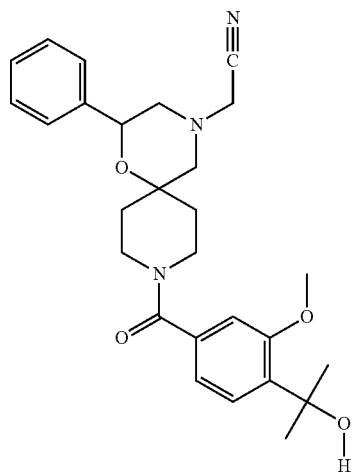 [SMILES: COc1cc(C(=O)N2CCC3(CC2)CN(CC#N)CC(c2ccccc2)O3)ccc1C(C)(C)O]
116
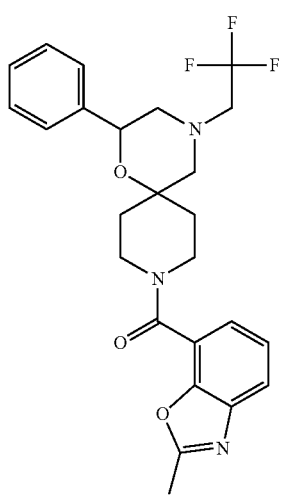 [SMILES: Cc1nc2cccc(C(=O)N3CCC4(CC3)CN(CC(F)(F)F)CC(c3ccccc3)O4)c2o1]
117
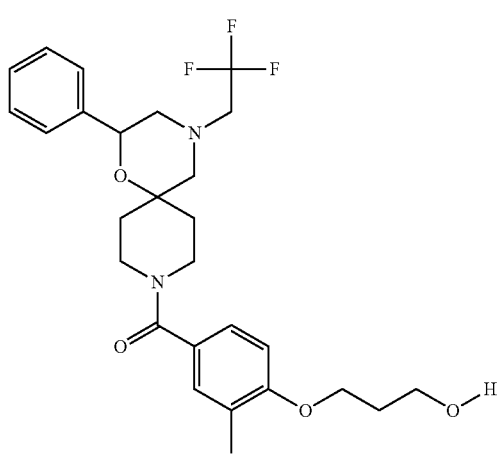 [SMILES: Cc1cc(C(=O)N2CCC3(CC2)CN(CC(F)(F)F)CC(c2ccccc2)O3)ccc1OCCCO]
118
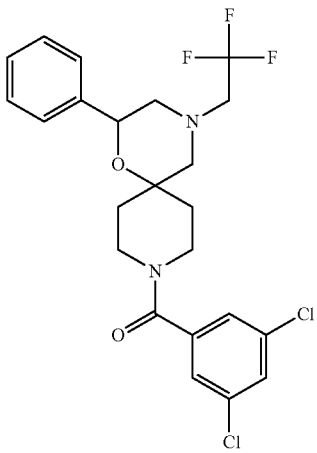 [SMILES: O=C(c1cc(Cl)cc(Cl)c1)N1CCC2(CC1)CN(CC(F)(F)F)CC(c1ccccc1)O2]
119
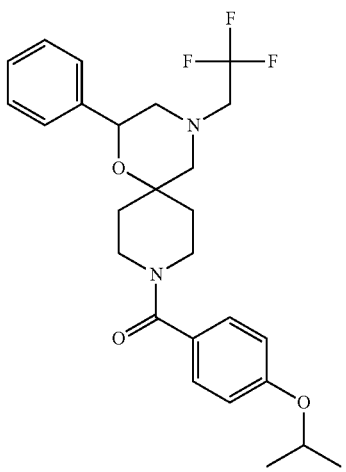
120
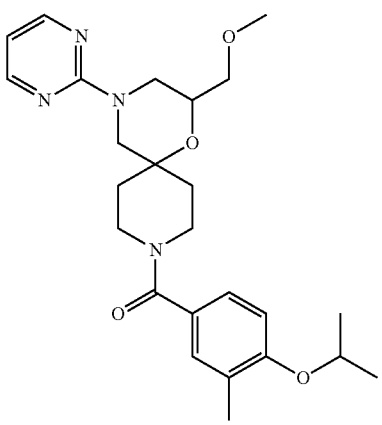

TABLE 1-continued
121
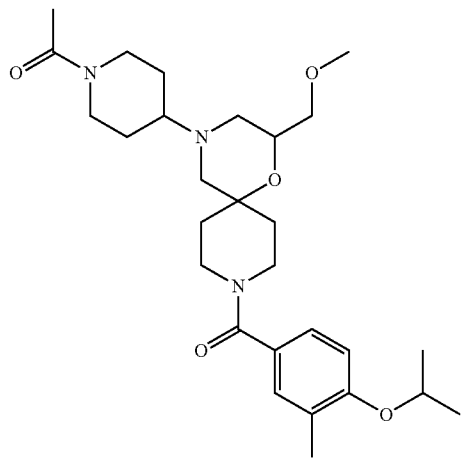 [SMILES: COCC1CN(C2CCN(C(C)=O)CC2)CC2(CCN(C(=O)c3ccc(OC(C)C)c(C)c3)CC2)O1]
122
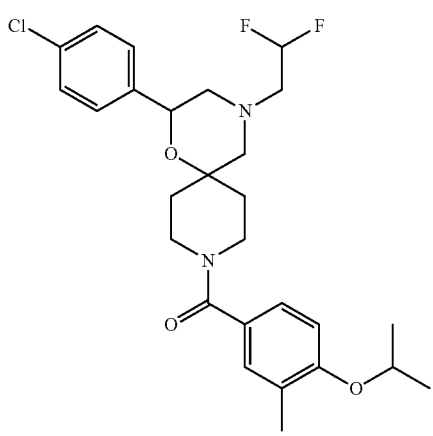 [SMILES: Cc1cc(C(=O)N2CCC3(CC2)CN(CC(F)F)CC(c2ccc(Cl)cc2)O3)ccc1OC(C)C]
123
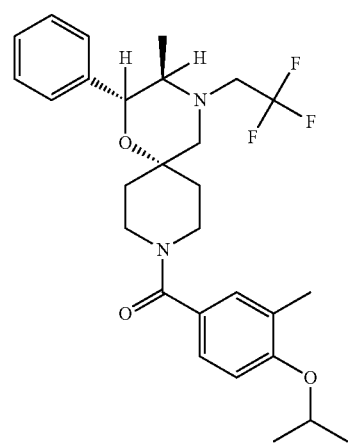
TABLE 1-continued
124
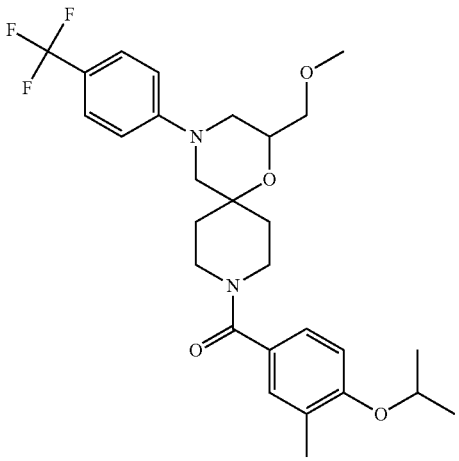 [SMILES: COCC1CN(c2ccc(C(F)(F)F)cc2)CC2(CCN(C(=O)c3ccc(OC(C)C)c(C)c3)CC2)O1]
125
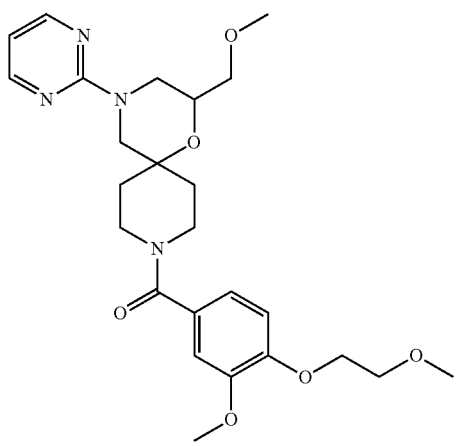 [SMILES: COCCOc1ccc(C(=O)N2CCC3(CC2)CN(c2ncccn2)CC(COC)O3)cc1OC]
126
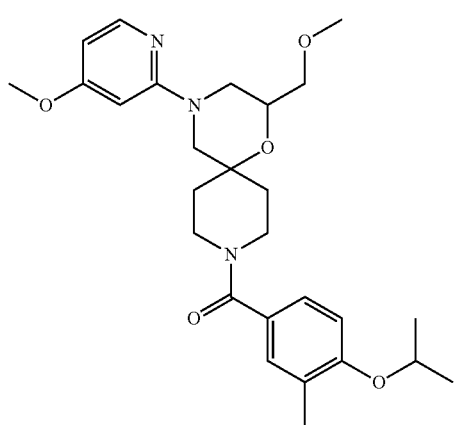 [SMILES: COCC1CN(c2cc(OC)ccn2)CC2(CCN(C(=O)c3ccc(OC(C)C)c(C)c3)CC2)O1]

TABLE 1-continued
127
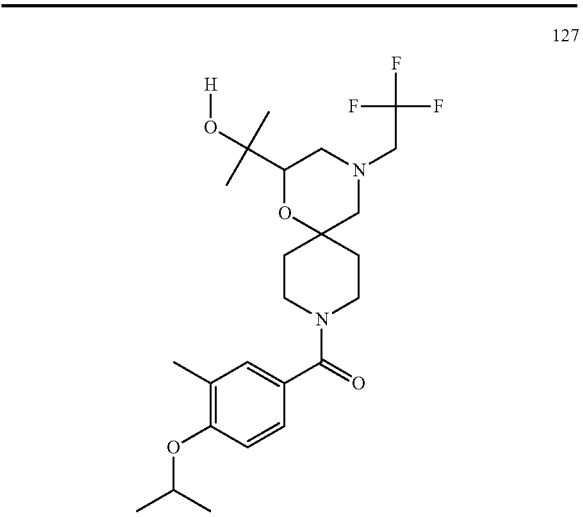
128
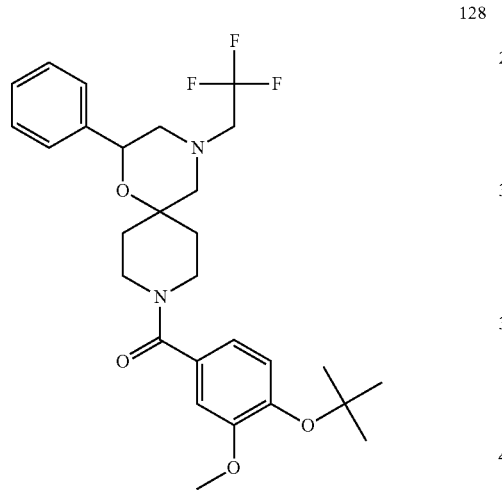
129
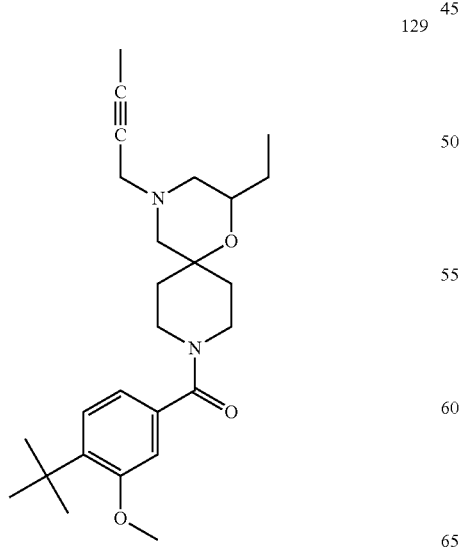
130
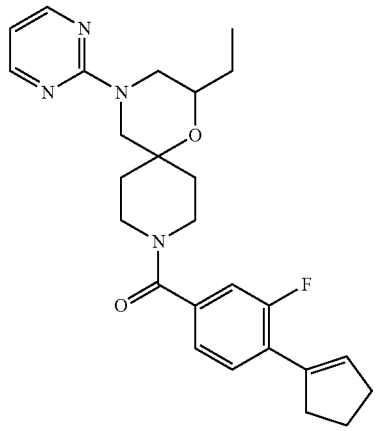 [SMILES: CCC1CN(c2ncccn2)CC2(CCN(C(=O)c3ccc(C4=CCCC4)c(F)c3)CC2)O1]
131
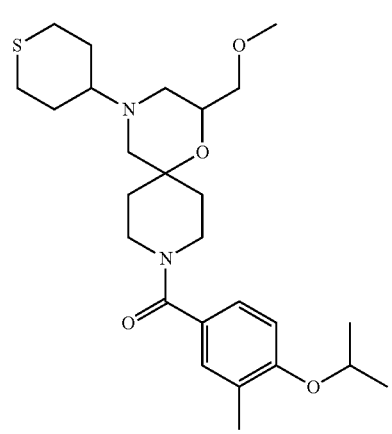 [SMILES: COCC1CN(C2CCSCC2)CC2(CCN(C(=O)c3ccc(OC(C)C)c(C)c3)CC2)O1]
132
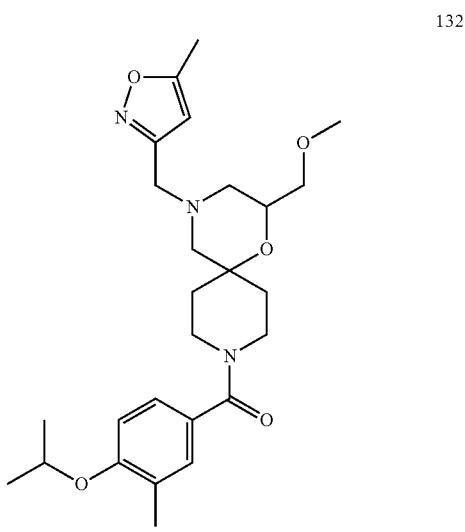

TABLE 1-continued
133
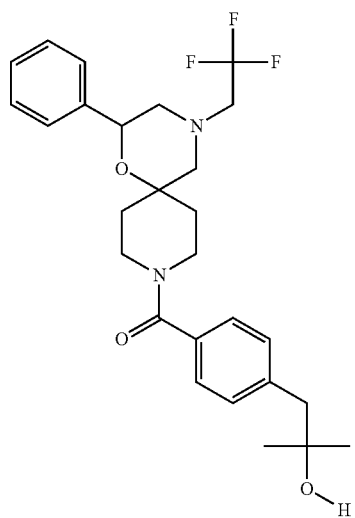 [SMILES: CC(C)(O)Cc1ccc(C(=O)N2CCC3(CC2)CN(CC(F)(F)F)CC(c2ccccc2)O3)cc1]
134
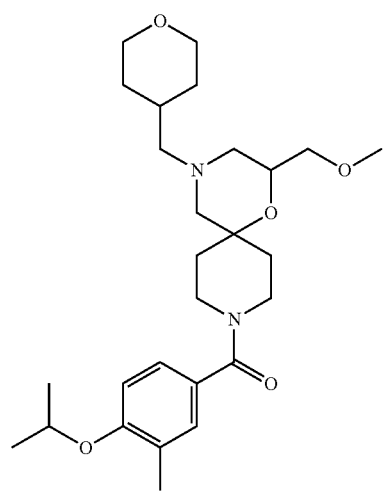 [SMILES: COCC1CN(CC2CCOCC2)CC2(CCN(C(=O)c3ccc(OC(C)C)c(C)c3)CC2)O1]
135
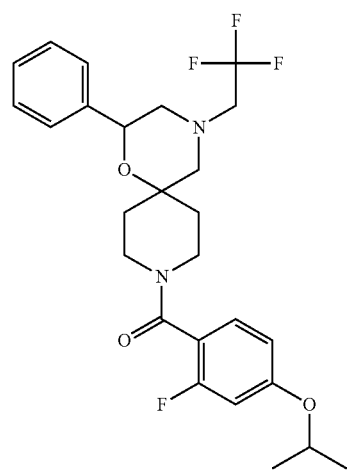 [SMILES: CC(C)Oc1ccc(C(=O)N2CCC3(CC2)CN(CC(F)(F)F)CC(c2ccccc2)O3)c(F)c1]
TABLE 1-continued
136
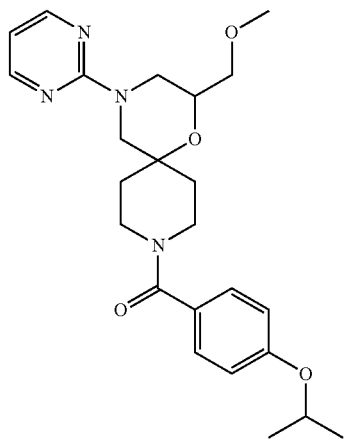 [SMILES: COCC1CN(c2ncccn2)CC2(CCN(C(=O)c3ccc(OC(C)C)cc3)CC2)O1]
137
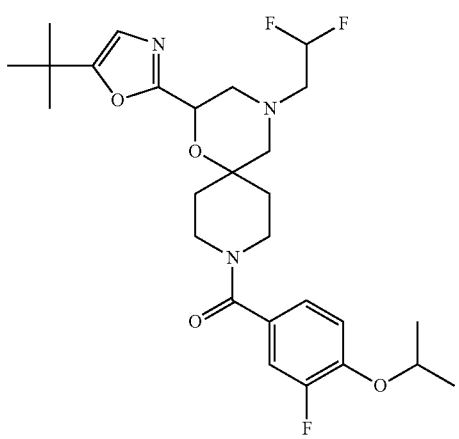 [SMILES: CC(C)Oc1ccc(C(=O)N2CCC3(CC2)CN(CC(F)F)CC(c2ncc(C(C)(C)C)o2)O3)cc1F]
138
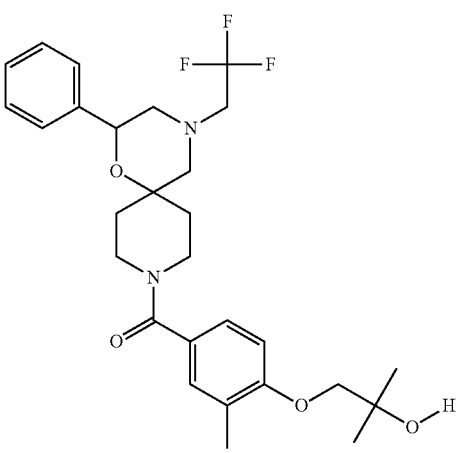 [SMILES: Cc1cc(C(=O)N2CCC3(CC2)CN(CC(F)(F)F)CC(c2ccccc2)O3)ccc1OCC(C)(C)O]

TABLE 1-continued
139
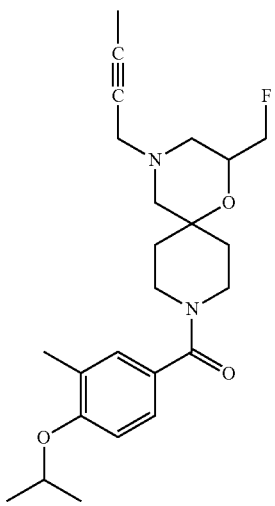 [SMILES: CC#CCN1CC(CF)OC2(CCN(C(=O)c3ccc(OC(C)C)c(C)c3)CC2)C1]
140
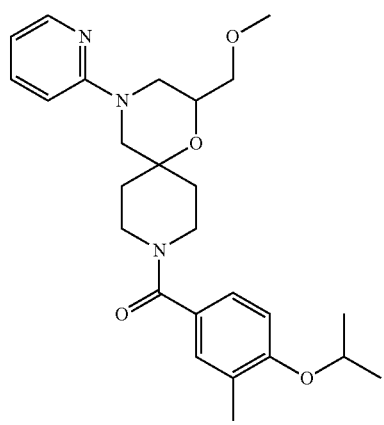 [SMILES: COCC1CN(c2ccccn2)CC2(CCN(C(=O)c3ccc(OC(C)C)c(C)c3)CC2)O1]
141
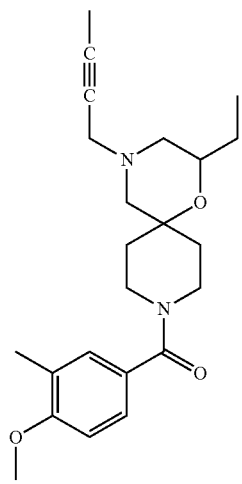 [SMILES: CC#CCN1CC(CC)OC2(CCN(C(=O)c3ccc(OC)c(C)c3)CC2)C1]
142
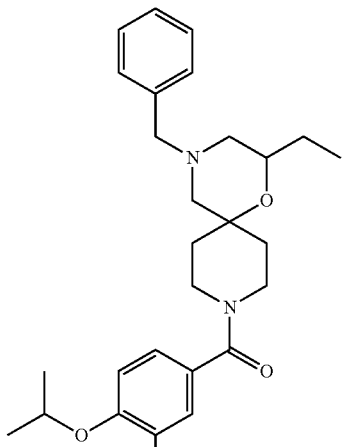
143
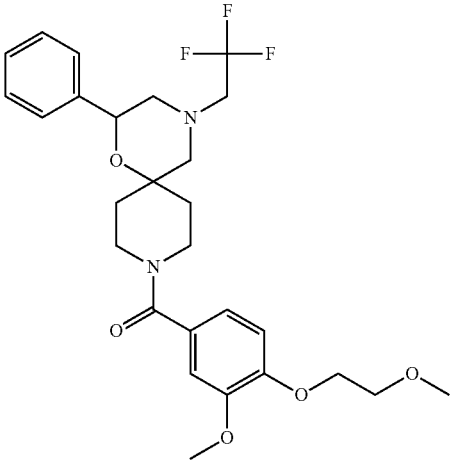 [SMILES: COCCOc1ccc(C(=O)N2CCC3(CC2)CN(CC(F)(F)F)CC(c2ccccc2)O3)cc1OC]
144
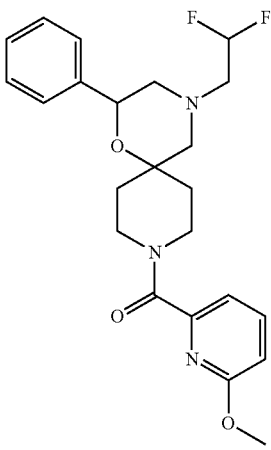 [SMILES: COc1cccc(C(=O)N2CCC3(CC2)CN(CC(F)F)CC(c2ccccc2)O3)n1]

TABLE 1-continued
| 145 | 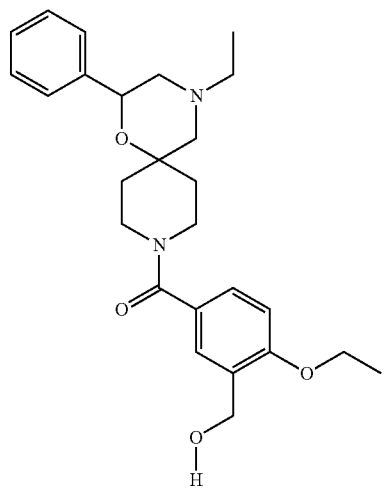 [SMILES: CCOc1ccc(C(=O)N2CCC3(CC2)CN(CC)CC(c2ccccc2)O3)cc1CO] |
| --- | --- |
| 146 | 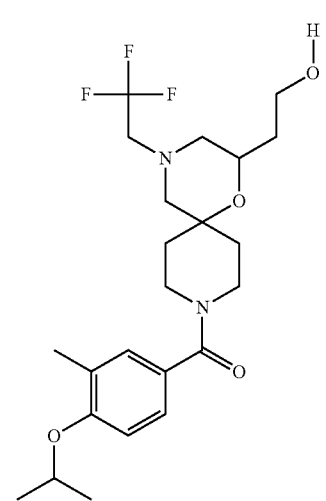 [SMILES: Cc1cc(C(=O)N2CCC3(CC2)CN(CC(F)(F)F)CC(CCO)O3)ccc1OC(C)C] |
| 147 | 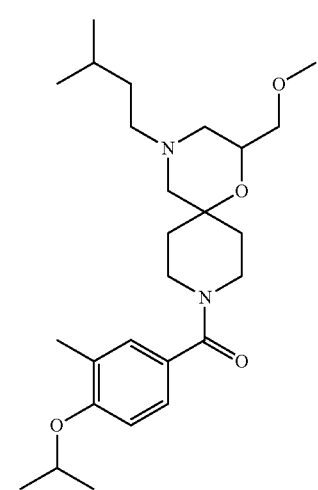 [SMILES: COCC1CN(CCC(C)C)CC2(CCN(C(=O)c3ccc(OC(C)C)c(C)c3)CC2)O1] |
| 148 | 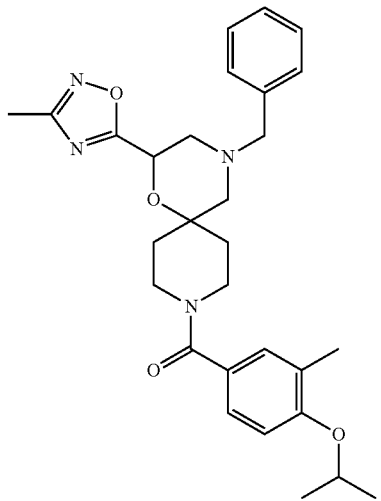 [SMILES: Cc1noc(C2CN(Cc3ccccc3)CC3(CCN(C(=O)c4ccc(OC(C)C)c(C)c4)CC3)O2)n1] |
| 149 | 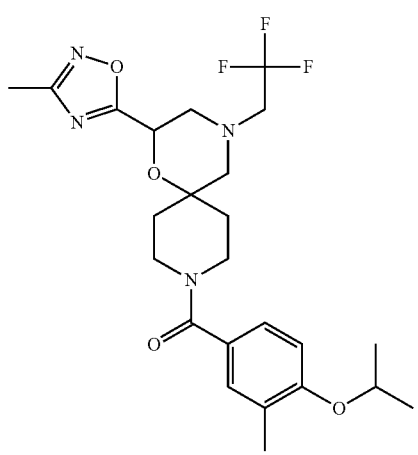 [SMILES: Cc1noc(C2CN(CC(F)(F)F)CC3(CCN(C(=O)c4ccc(OC(C)C)c(C)c4)CC3)O2)n1] |
| 150 | 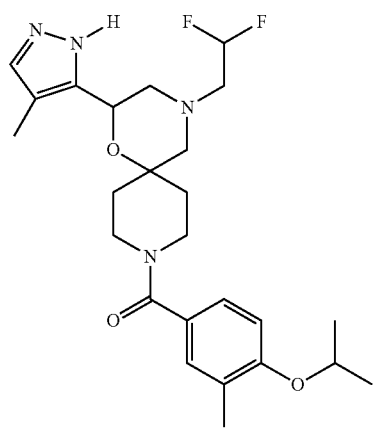 [SMILES: Cc1cc(C(=O)N2CCC3(CC2)CN(CC(F)F)CC(c2[nH]ncc2C)O3)ccc1OC(C)C] |

TABLE 1-continued
151
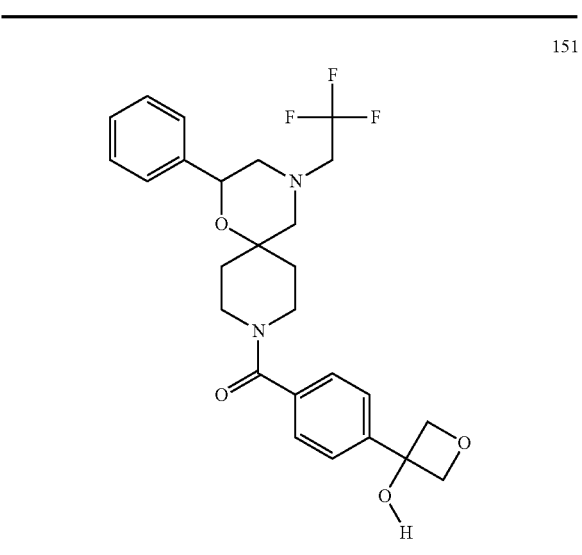
152
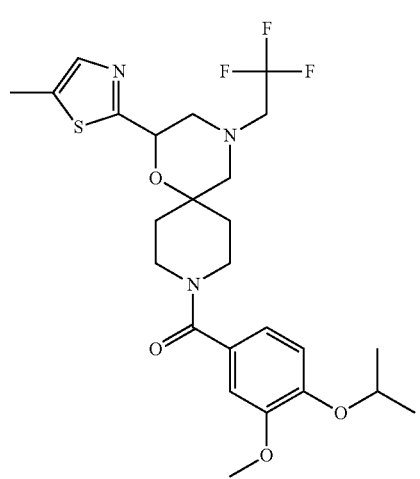 [SMILES: COc1cc(C(=O)N2CCC3(CC2)CN(CC(F)(F)F)CC(c2ncc(C)s2)O3)ccc1OC(C)C]
153
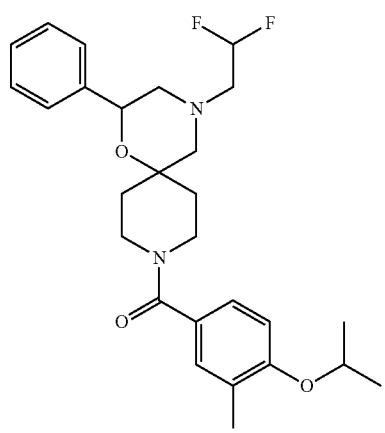 [SMILES: Cc1cc(C(=O)N2CCC3(CC2)CN(CC(F)F)CC(c2ccccc2)O3)ccc1OC(C)C]
TABLE 1-continued
154
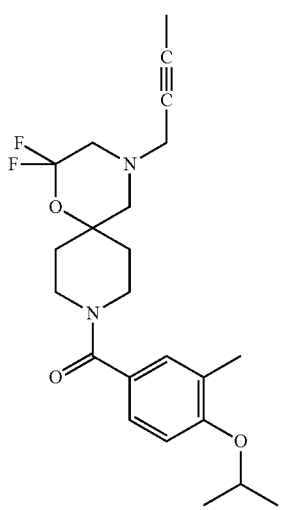 [SMILES: CC#CCN1CC(F)(F)OC2(CCN(C(=O)c3ccc(OC(C)C)c(C)c3)CC2)C1]
155
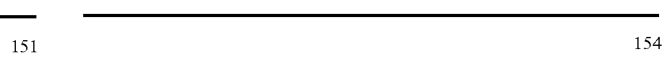
156
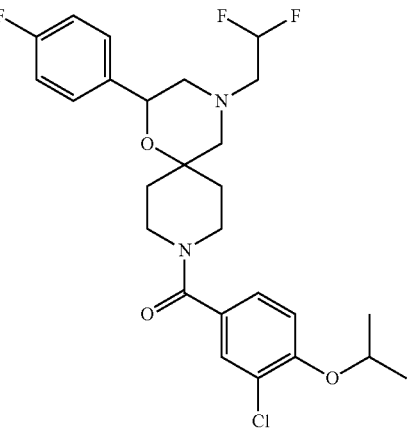

TABLE 1-continued
157 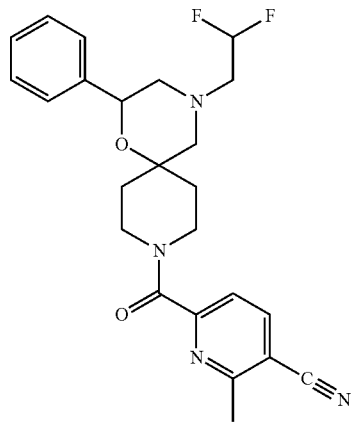 [SMILES: Cc1nc(C(=O)N2CCC3(CC2)CN(CC(F)F)CC(c2ccccc2)O3)ccc1C#N]
158 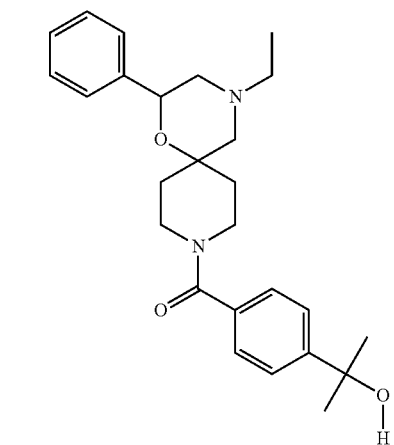 [SMILES: CCN1CC(c2ccccc2)OC2(CCN(C(=O)c3ccc(C(C)(C)O)cc3)CC2)C1]
159 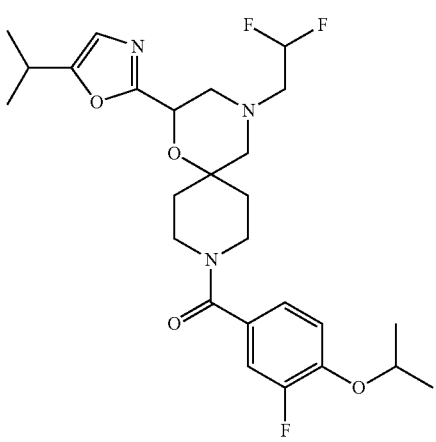 [SMILES: CC(C)Oc1ccc(C(=O)N2CCC3(CC2)CN(CC(F)F)CC(c2ncc(C(C)C)o2)O3)cc1F]
TABLE 1-continued
160 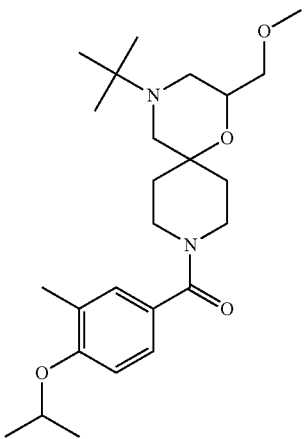 [SMILES: COCC1CN(C(C)(C)C)CC2(CCN(C(=O)c3ccc(OC(C)C)c(C)c3)CC2)O1]
161 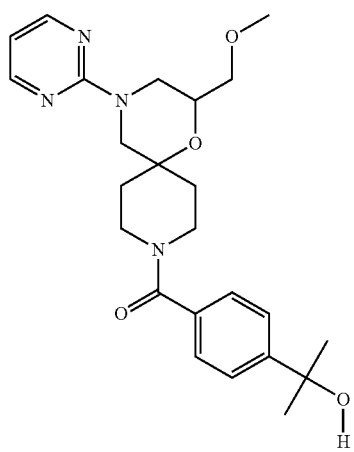 [SMILES: COCC1CN(c2ncccn2)CC2(CCN(C(=O)c3ccc(C(C)(C)O)cc3)CC2)O1]
162 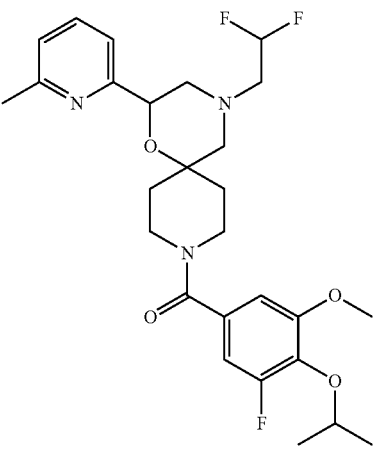

| 163 | 166 |
|---|---|
| 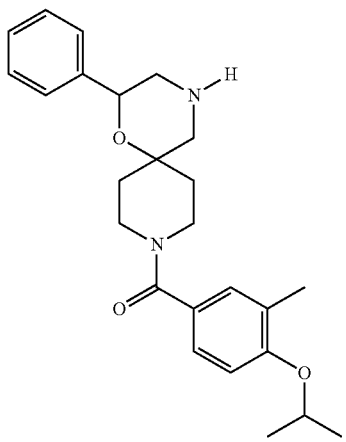 [SMILES: Cc1cc(C(=O)N2CCC3(CC2)CNCC(c2ccccc2)O3)ccc1OC(C)C] | |
| 164 | 167 |
|---|---|
| 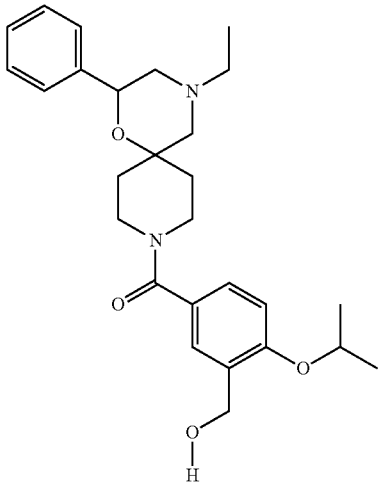 [SMILES: CCN1CC(c2ccccc2)OC2(CCN(C(=O)c3ccc(OC(C)C)c(CO)c3)CC2)C1] | 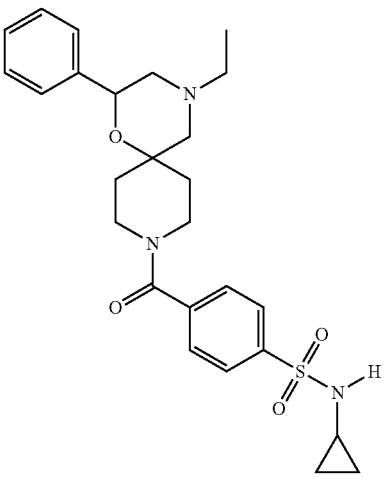 [SMILES: CCN1CC(c2ccccc2)OC2(CCN(C(=O)c3ccc(S(=O)(=O)NC4CC4)cc3)CC2)C1] |
| 165 | 168 |
|---|---|
| | 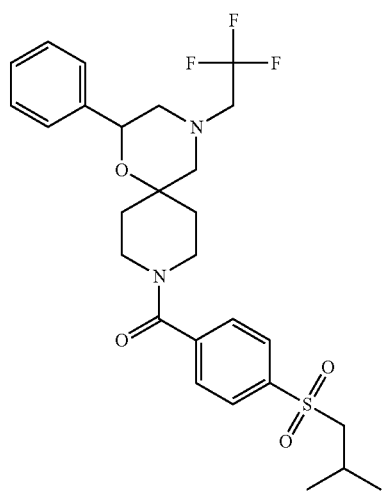 |

TABLE 1-continued
169
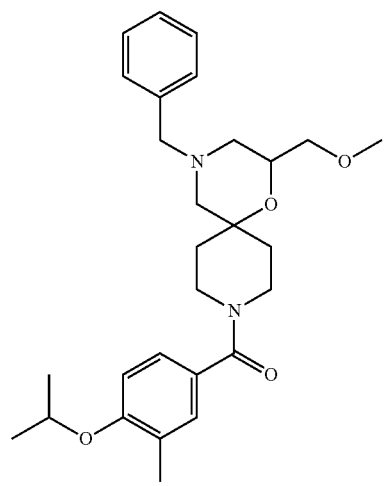 [SMILES: COCC1CN(Cc2ccccc2)CC2(CCN(C(=O)c3ccc(OC(C)C)c(C)c3)CC2)O1]
170
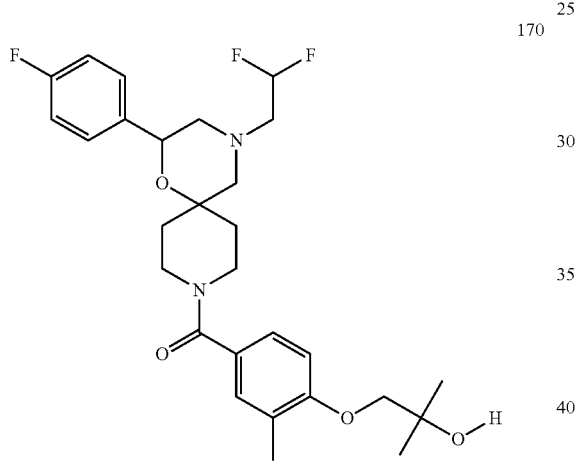
171
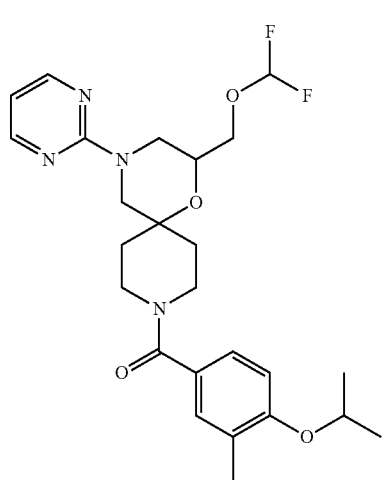 [SMILES: Cc1cc(C(=O)N2CCC3(CC2)CN(c2ncccn2)CC(COC(F)F)O3)ccc1OC(C)C]
TABLE 1-continued
172
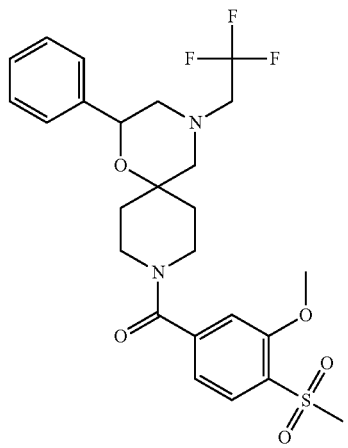 [SMILES: COc1cc(C(=O)N2CCC3(CC2)CN(CC(F)(F)F)CC(c2ccccc2)O3)ccc1S(C)(=O)=O]
173
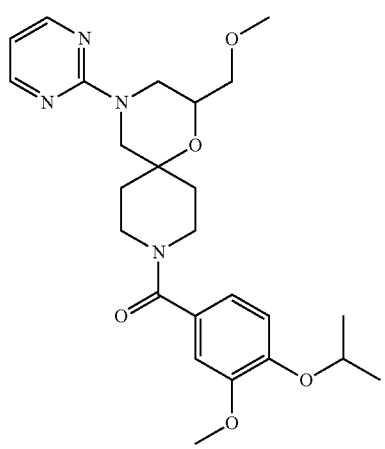 [SMILES: COCC1CN(c2ncccn2)CC2(CCN(C(=O)c3ccc(OC(C)C)c(OC)c3)CC2)O1]
174
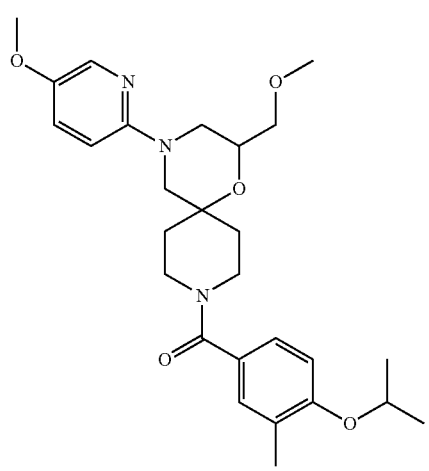

TABLE 1-continued
| | |
|---|---|
| 175 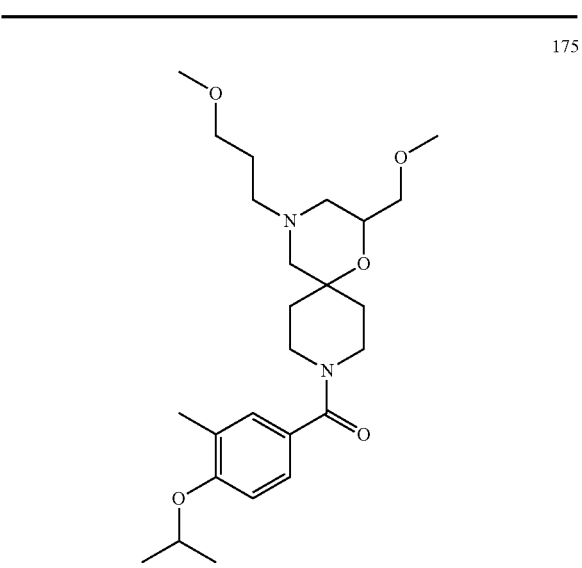 | 178 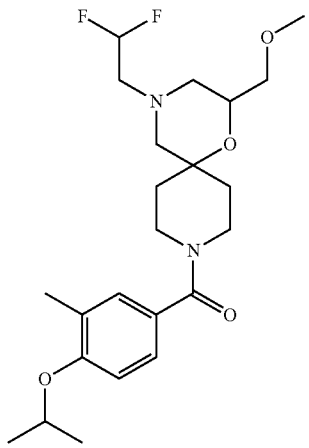 [SMILES: COCC1CN(CC(F)F)CC2(CCN(C(=O)c3ccc(OC(C)C)c(C)c3)CC2)O1] |
| 176 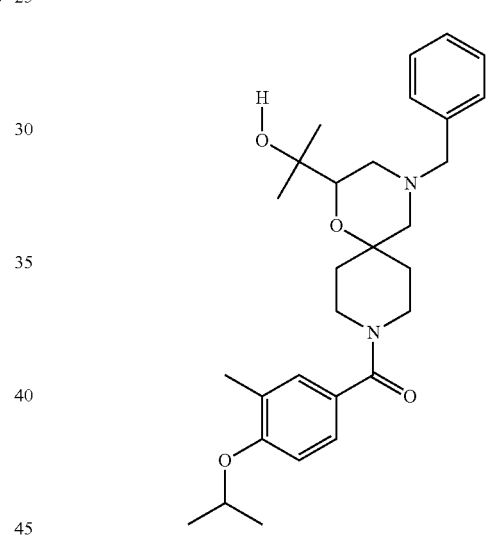 | 179 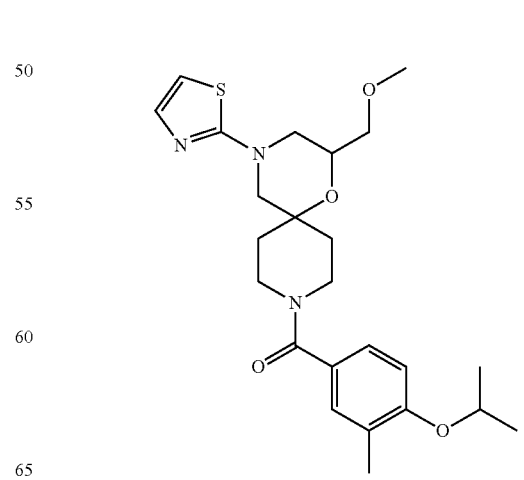 |
| 177 | 180 |

TABLE 1-continued
181
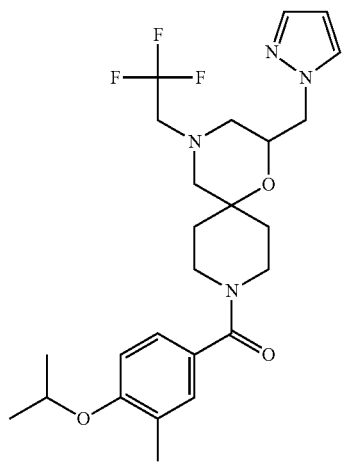 [SMILES: Cc1cc(C(=O)N2CCC3(CC2)CN(CC(F)(F)F)CC(Cn2cccn2)O3)ccc1OC(C)C]
182
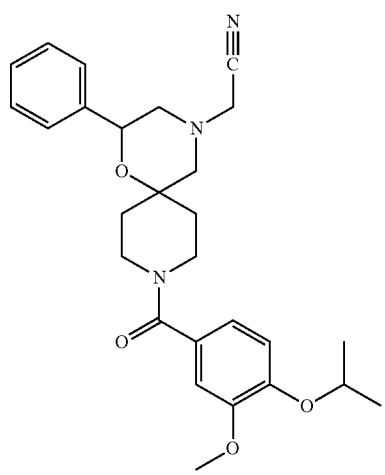 [SMILES: COc1cc(C(=O)N2CCC3(CC2)CN(CC#N)CC(c2ccccc2)O3)ccc1OC(C)C]
183
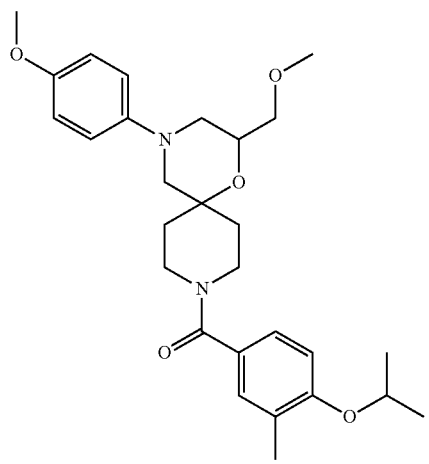
TABLE 1-continued
184
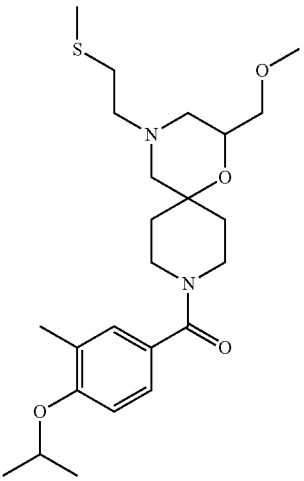
185
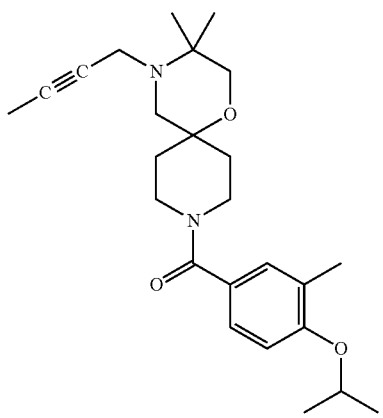 [SMILES: CC#CCN1CC2(CCN(C(=O)c3ccc(OC(C)C)c(C)c3)CC2)OCC1(C)C]
186
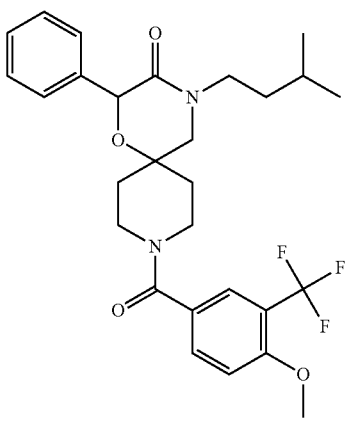 [SMILES: COc1ccc(C(=O)N2CCC3(CC2)CN(CCC(C)C)C(=O)C(c2ccccc2)O3)cc1C(F)(F)F]

TABLE 1-continued
187
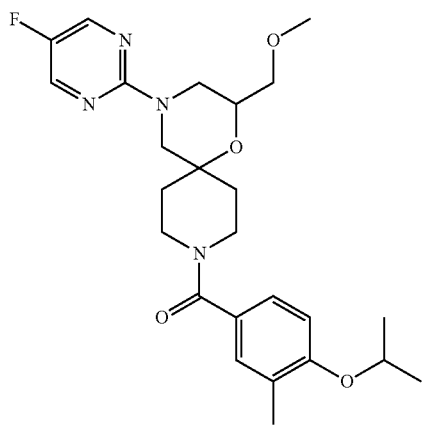 [SMILES: COCC1CN(c2ncc(F)cn2)CC2(CCN(C(=O)c3ccc(OC(C)C)c(C)c3)CC2)O1]
188
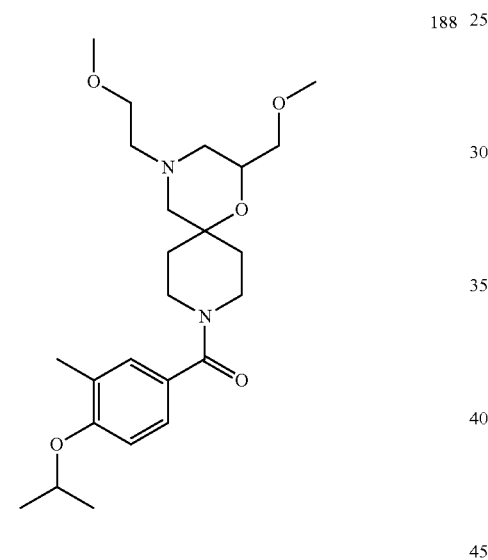
189
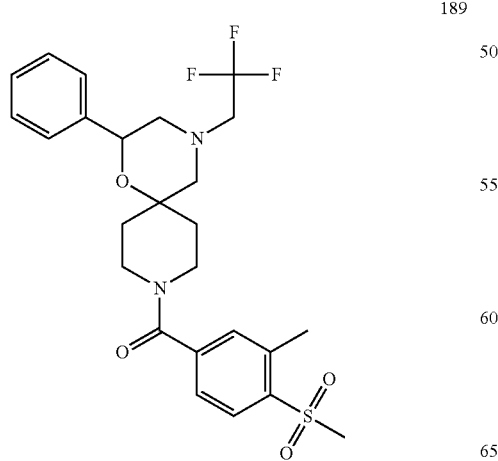
TABLE 1-continued
190
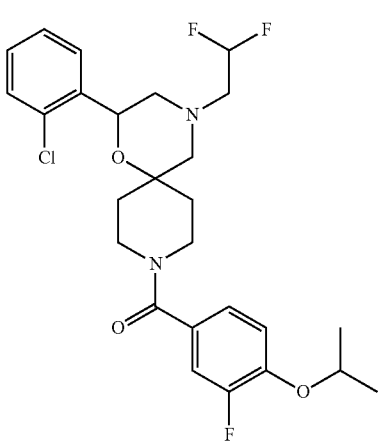
191
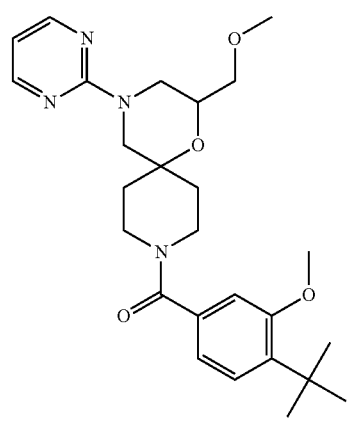 [SMILES: COCC1CN(c2ncccn2)CC2(CCN(C(=O)c3ccc(C(C)(C)C)c(OC)c3)CC2)O1]
192
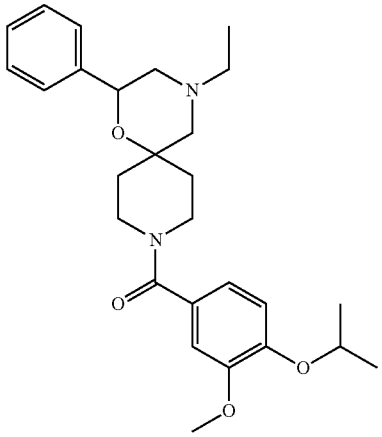 [SMILES: CCN1CC(c2ccccc2)OC2(CCN(C(=O)c3ccc(OC(C)C)c(OC)c3)CC2)C1]

TABLE 1-continued
193
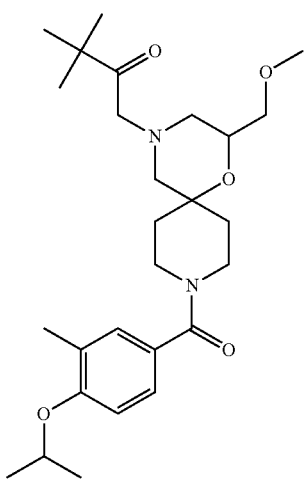 [SMILES: COCC1CN(CC(=O)C(C)(C)C)CC2(CCN(C(=O)c3ccc(OC(C)C)c(C)c3)CC2)O1]
194
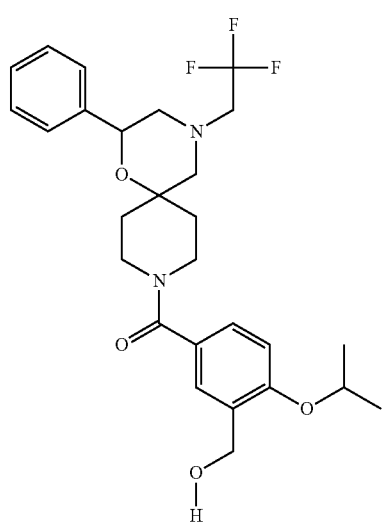 [SMILES: CC(C)Oc1ccc(C(=O)N2CCC3(CC2)CN(CC(F)(F)F)CC(c2ccccc2)O3)cc1CO]
195
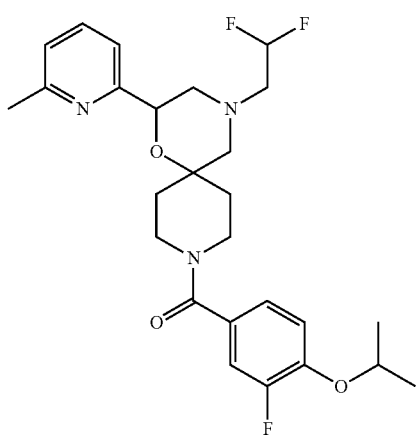 [SMILES: Cc1cccc(C2CN(CC(F)F)CC3(CCN(C(=O)c4ccc(OC(C)C)c(F)c4)CC3)O2)n1]
TABLE 1-continued
196
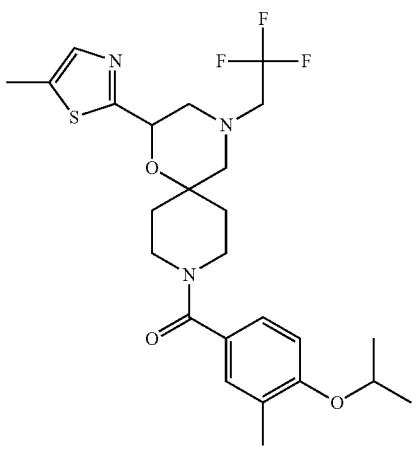 [SMILES: Cc1cnc(C2CN(CC(F)(F)F)CC3(CCN(C(=O)c4ccc(OC(C)C)c(C)c4)CC3)O2)s1]
197
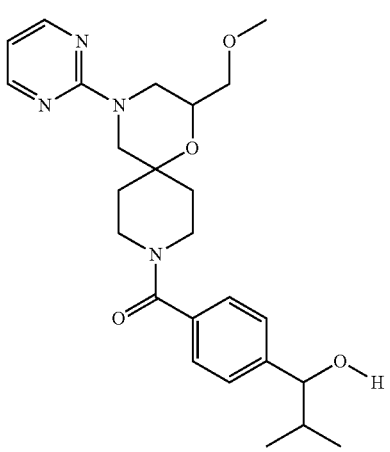 [SMILES: COCC1CN(c2ncccn2)CC2(CCN(C(=O)c3ccc(C(O)C(C)C)cc3)CC2)O1]
198
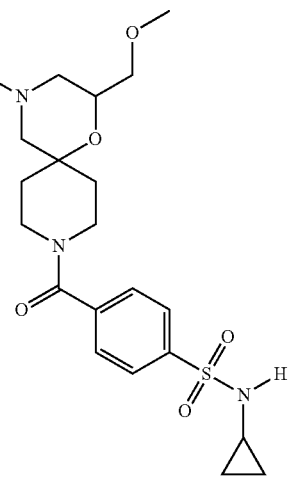

TABLE 1-continued
199
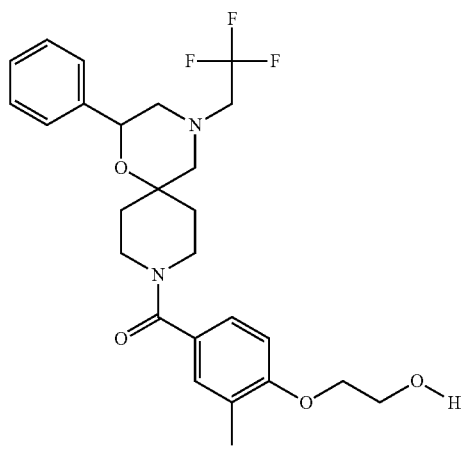 [SMILES: Cc1cc(C(=O)N2CCC3(CC2)CN(CC(F)(F)F)CC(c2ccccc2)O3)ccc1OCCO]
200
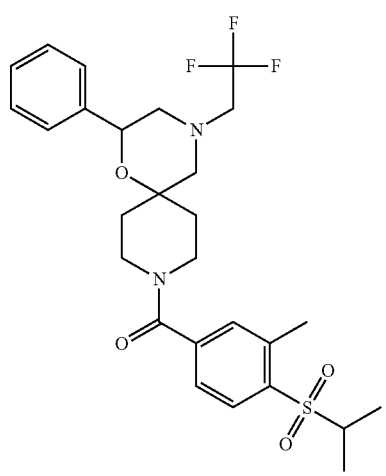 [SMILES: Cc1cc(C(=O)N2CCC3(CC2)CN(CC(F)(F)F)CC(c2ccccc2)O3)ccc1S(=O)(=O)C(C)C]
201
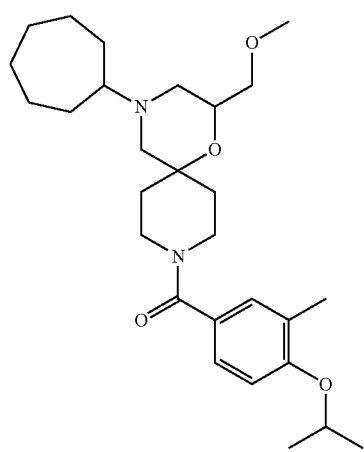 [SMILES: COCC1CN(C2CCCCCC2)CC2(CCN(C(=O)c3ccc(OC(C)C)c(C)c3)CC2)O1]
TABLE 1-continued
202
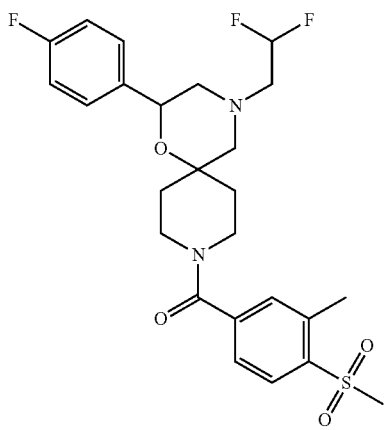
203
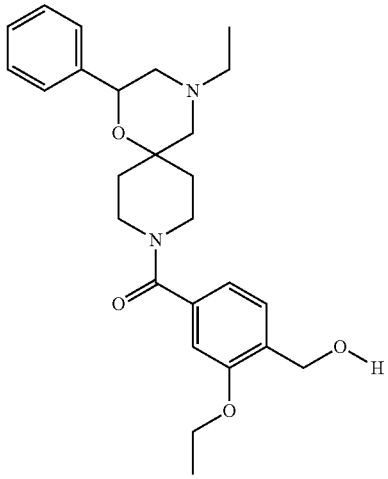 [SMILES: CCOc1cc(C(=O)N2CCC3(CC2)CN(CC)CC(c2ccccc2)O3)ccc1CO]
204
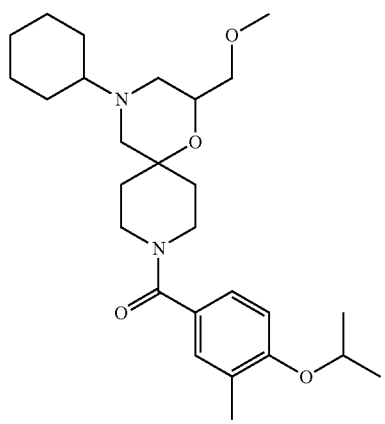 [SMILES: COCC1CN(C2CCCCC2)CC2(CCN(C(=O)c3ccc(OC(C)C)c(C)c3)CC2)O1]

TABLE 1-continued
205
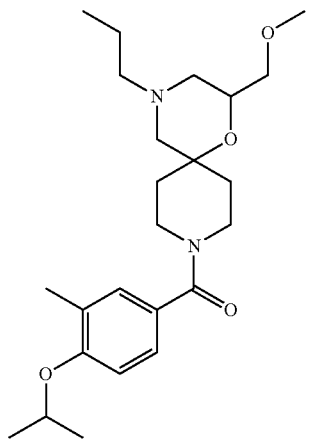 [SMILES: CCCN1CC(COC)OC2(CCN(C(=O)c3ccc(OC(C)C)c(C)c3)CC2)C1]
206
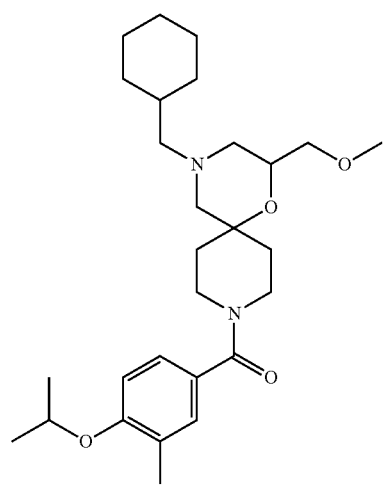 [SMILES: COCC1CN(CC2CCCCC2)CC2(CCN(C(=O)c3ccc(OC(C)C)c(C)c3)CC2)O1]
207
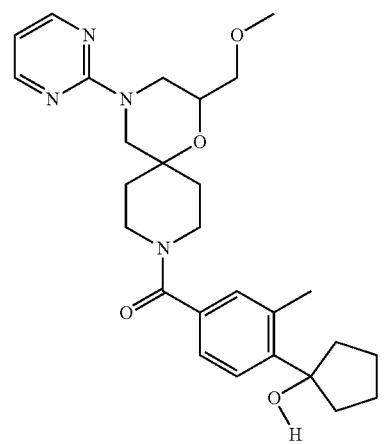 [SMILES: COCC1CN(c2ncccn2)CC2(CCN(C(=O)c3ccc(C4(O)CCCC4)c(C)c3)CC2)O1]
TABLE 1-continued
208
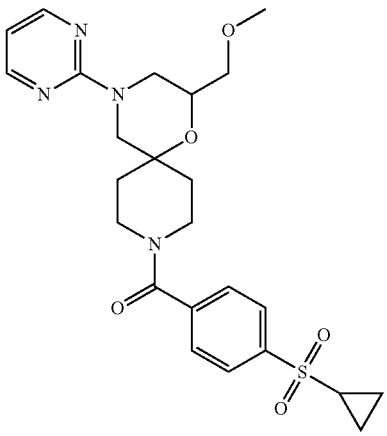 [SMILES: COCC1CN(c2ncccn2)CC2(CCN(C(=O)c3ccc(S(=O)(=O)C4CC4)cc3)CC2)O1]
209
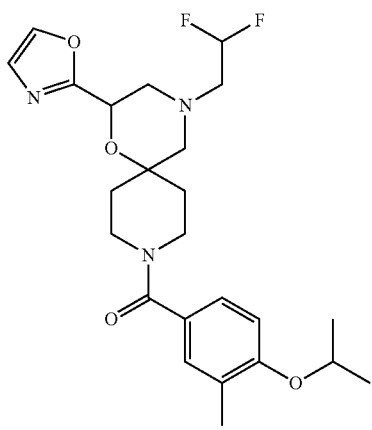 [SMILES: Cc1cc(C(=O)N2CCC3(CC2)CN(CC(F)F)CC(c2ncco2)O3)ccc1OC(C)C]
210
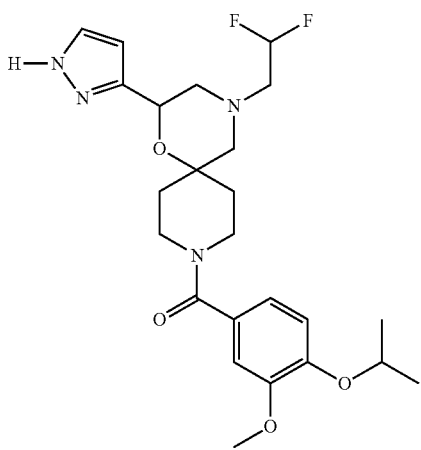 [SMILES: COc1cc(C(=O)N2CCC3(CC2)CN(CC(F)F)CC(c2cc[nH]n2)O3)ccc1OC(C)C]

TABLE 1-continued
211 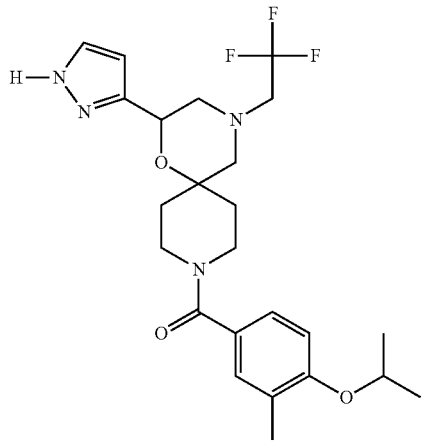 [SMILES: Cc1cc(C(=O)N2CCC3(CC2)CN(CC(F)(F)F)CC(c2cc[nH]n2)O3)ccc1OC(C)C]
214 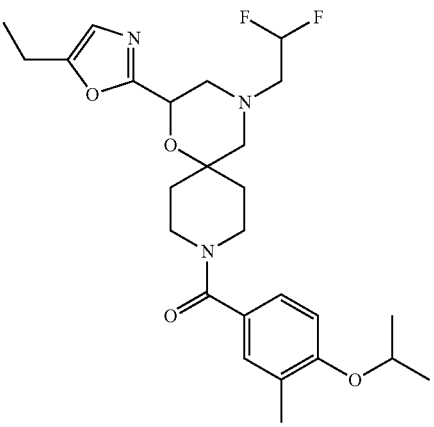
212 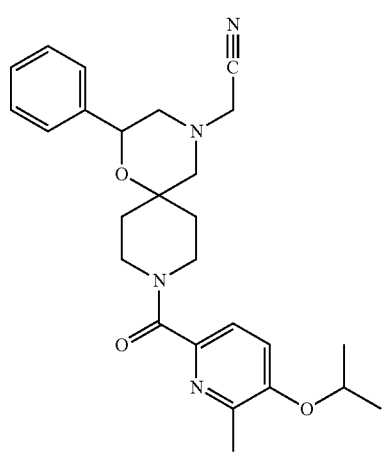 [SMILES: Cc1nc(C(=O)N2CCC3(CC2)CN(CC#N)CC(c2ccccc2)O3)ccc1OC(C)C]
215 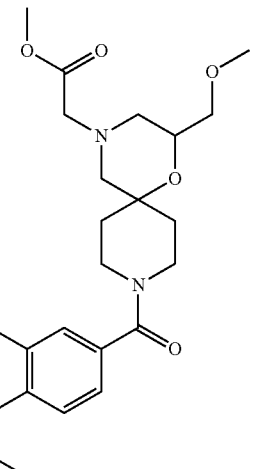
213 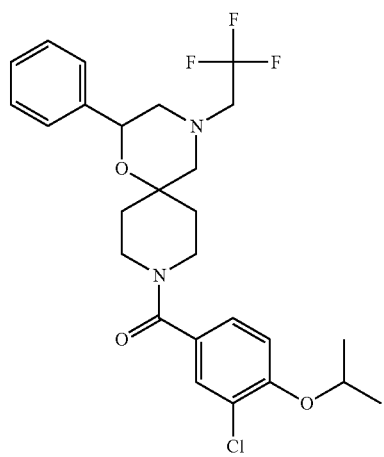
216 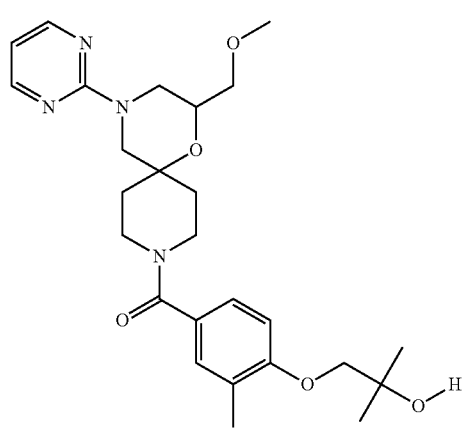 [SMILES: COCC1CN(c2ncccn2)CC2(CCN(C(=O)c3ccc(OCC(C)(C)O)c(C)c3)CC2)O1]

TABLE 1-continued
217
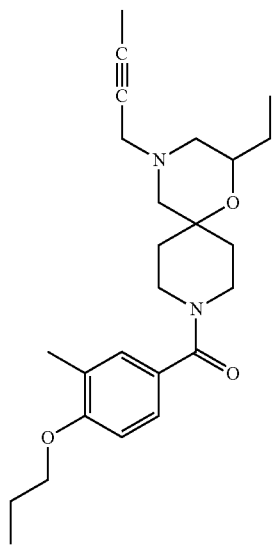 [SMILES: CC#CCN1CC(CC)OC2(CCN(C(=O)c3ccc(OCCC)c(C)c3)CC2)C1]
218
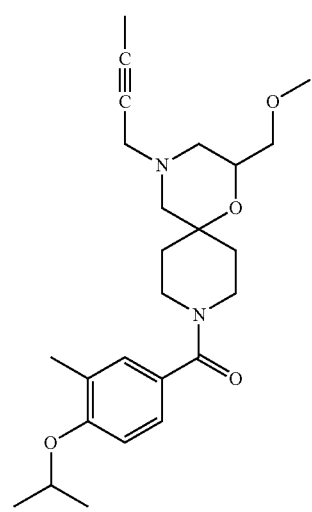 [SMILES: CC#CCN1CC(COC)OC2(CCN(C(=O)c3ccc(OC(C)C)c(C)c3)CC2)C1]
219
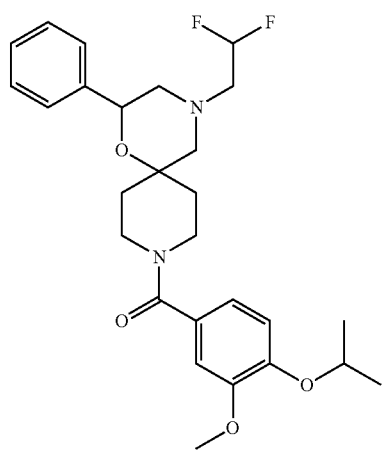
TABLE 1-continued
220
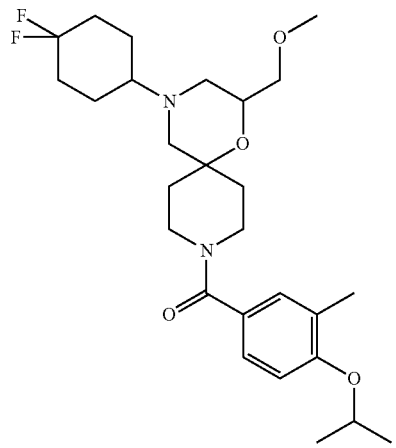 [SMILES: COCC1CN(C2CCC(F)(F)CC2)CC2(CCN(C(=O)c3ccc(OC(C)C)c(C)c3)CC2)O1]
221
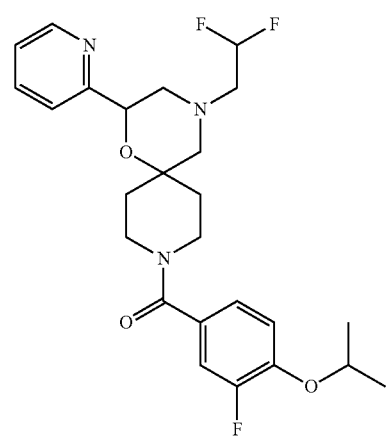
222
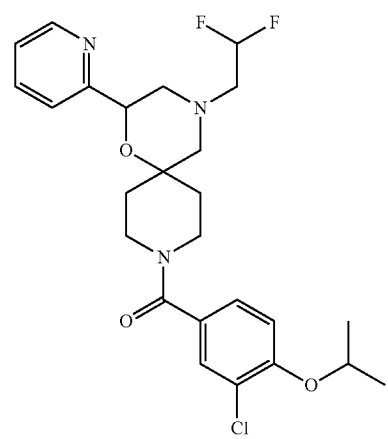 [SMILES: CC(C)Oc1ccc(C(=O)N2CCC3(CC2)CN(CC(F)F)CC(c2ccccn2)O3)cc1F]

TABLE 1-continued
223
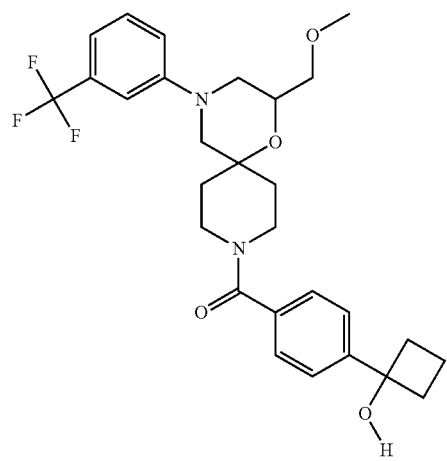 [SMILES: COCC1CN(c2cccc(C(F)(F)F)c2)CC2(CCN(C(=O)c3ccc(C4(O)CCC4)cc3)CC2)O1]
224
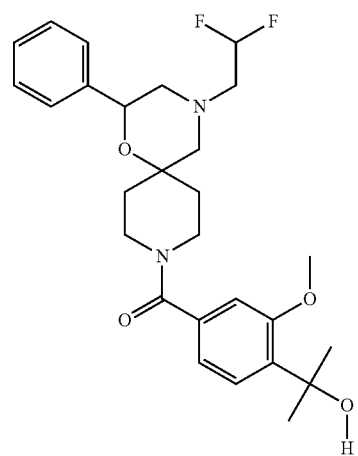 [SMILES: COc1cc(C(=O)N2CCC3(CC2)CN(CC(F)F)CC(c2ccccc2)O3)ccc1C(C)(C)O]
225
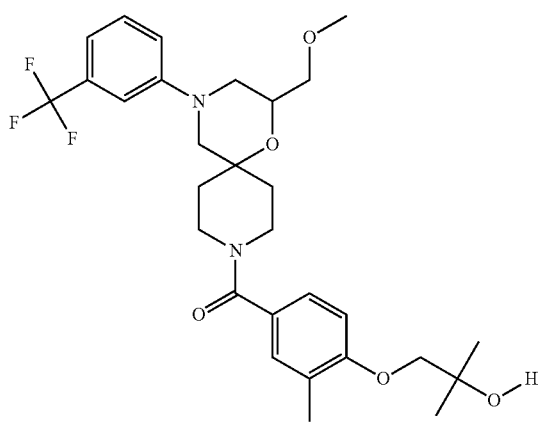 [SMILES: COCC1CN(c2cccc(C(F)(F)F)c2)CC2(CCN(C(=O)c3ccc(OCC(C)(C)O)c(C)c3)CC2)O1]
TABLE 1-continued
226
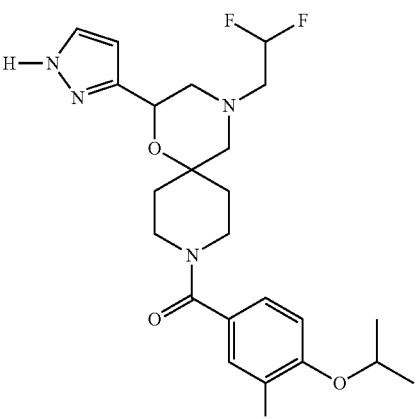
227
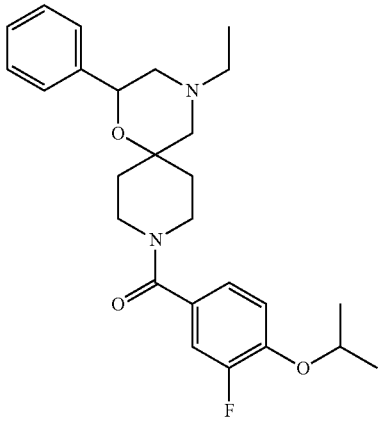 [SMILES: CCN1CC(c2ccccc2)OC2(CCN(C(=O)c3ccc(OC(C)C)c(F)c3)CC2)C1]
228
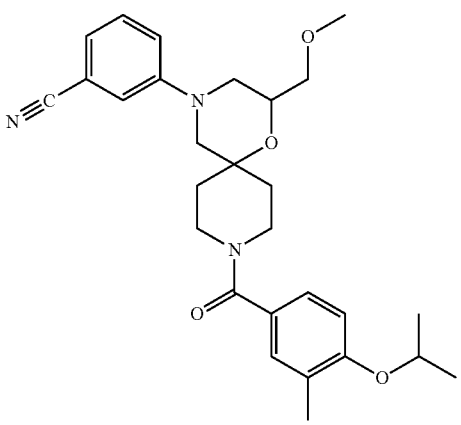 [SMILES: COCC1CN(c2cccc(C#N)c2)CC2(CCN(C(=O)c3ccc(OC(C)C)c(C)c3)CC2)O1]

TABLE 1-continued
229
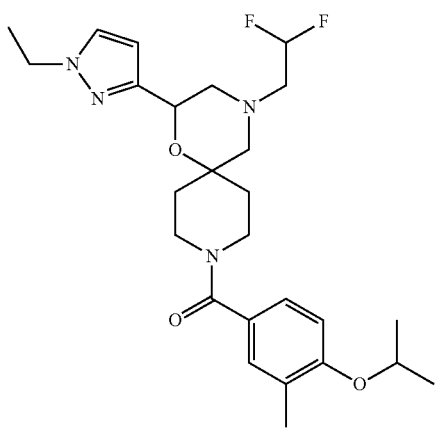 [SMILES: CCn1ccc(C2CN(CC(F)F)CC3(CCN(C(=O)c4ccc(OC(C)C)c(C)c4)CC3)O2)n1]
230
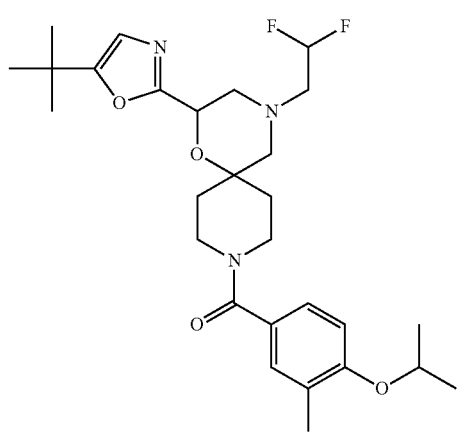 [SMILES: Cc1cc(C(=O)N2CCC3(CC2)CN(CC(F)F)CC(c2ncc(C(C)(C)C)o2)O3)ccc1OC(C)C]
231
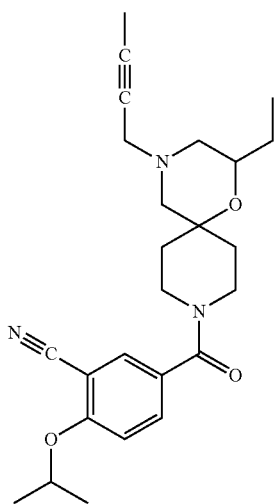 [SMILES: CC#CCN1CC(CC)OC2(CCN(C(=O)c3ccc(OC(C)C)c(C#N)c3)CC2)C1]
TABLE 1-continued
232
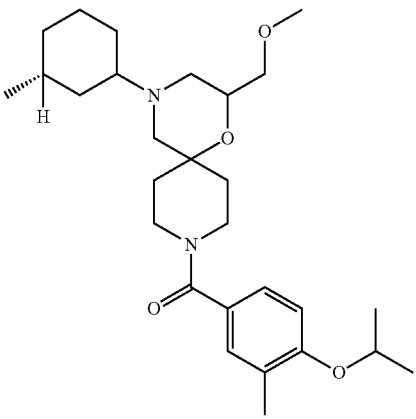 [SMILES: COCC1CN(C2CCC[C@@H](C)C2)CC2(CCN(C(=O)c3ccc(OC(C)C)c(C)c3)CC2)O1]
233
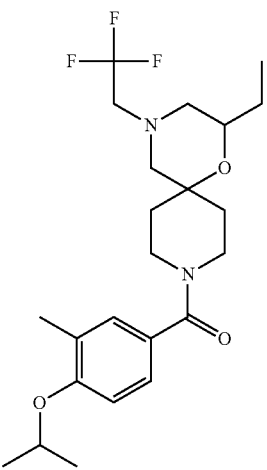 [SMILES: CCC1CN(CC(F)(F)F)CC2(CCN(C(=O)c3ccc(OC(C)C)c(C)c3)CC2)O1]
234
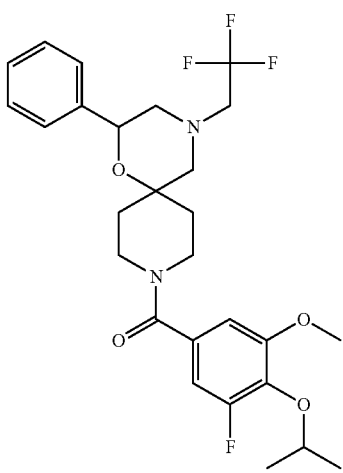 [SMILES: COc1cc(C(=O)N2CCC3(CC2)CN(CC(F)(F)F)CC(c2ccccc2)O3)cc(F)c1OC(C)C]

TABLE 1-continued
235
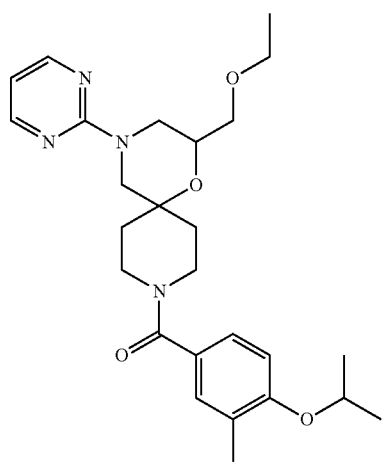
236
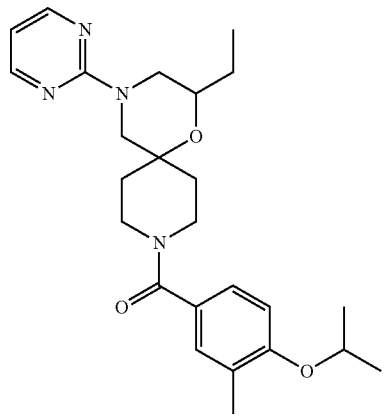
237
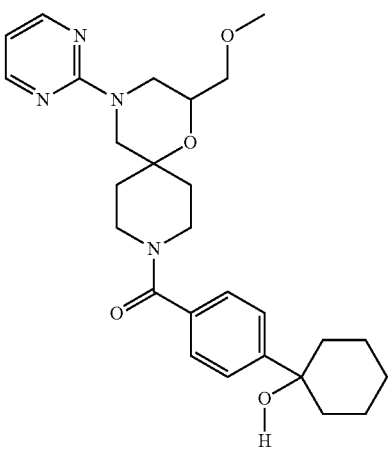 [SMILES: COCC1CN(c2ncccn2)CC2(CCN(C(=O)c3ccc(C4(O)CCCCC4)cc3)CC2)O1]
TABLE 1-continued
238
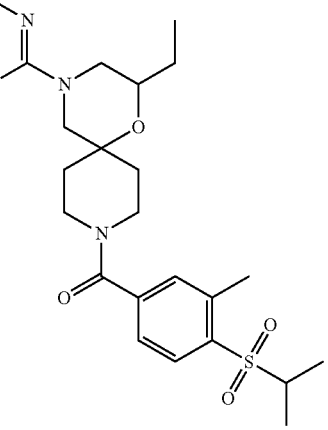
239
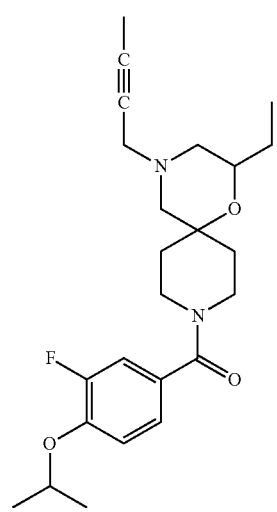
240
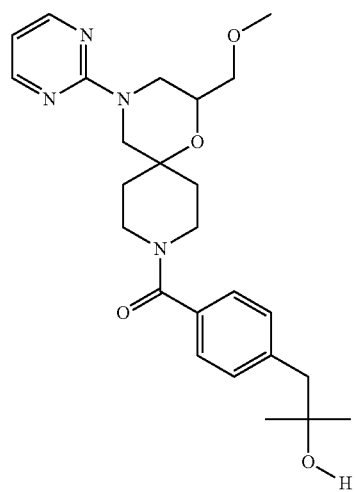 [SMILES: COCC1CN(c2ncccn2)CC2(CCN(C(=O)c3ccc(CC(C)(C)O)cc3)CC2)O1]

TABLE 1-continued
241
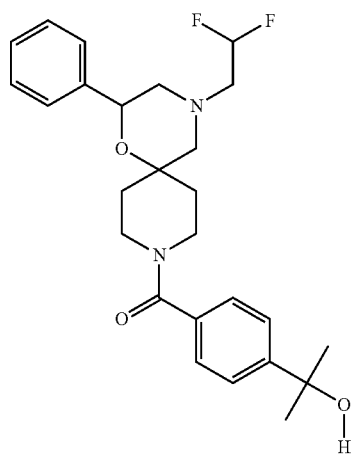 [SMILES: CC(C)(O)c1ccc(C(=O)N2CCC3(CC2)CN(CC(F)F)CC(c2ccccc2)O3)cc1]
242
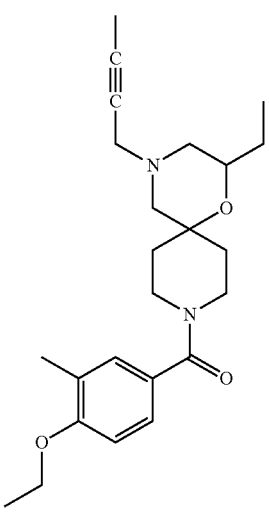 [SMILES: CC#CCN1CC(CC)OC2(CCN(C(=O)c3ccc(OCC)c(C)c3)CC2)C1]
243
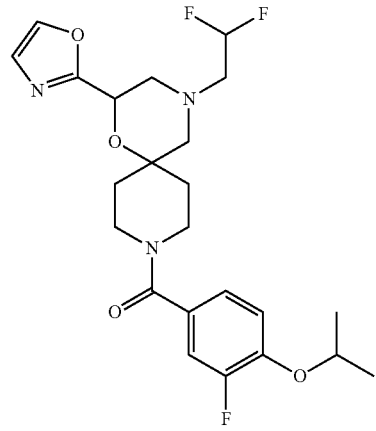 [SMILES: CC(C)Oc1ccc(C(=O)N2CCC3(CC2)CN(CC(F)F)CC(c2ncco2)O3)cc1F]
TABLE 1-continued
244
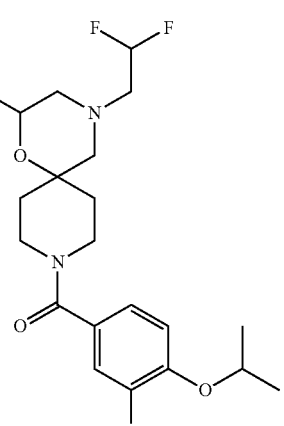
245
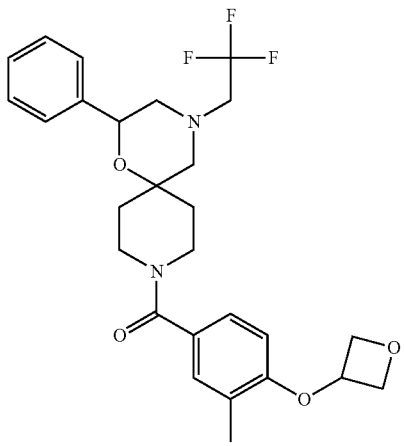 [SMILES: Cc1cc(C(=O)N2CCC3(CC2)CN(CC(F)(F)F)CC(c2ccccc2)O3)ccc1OC1COC1]
246

TABLE 1-continued
247
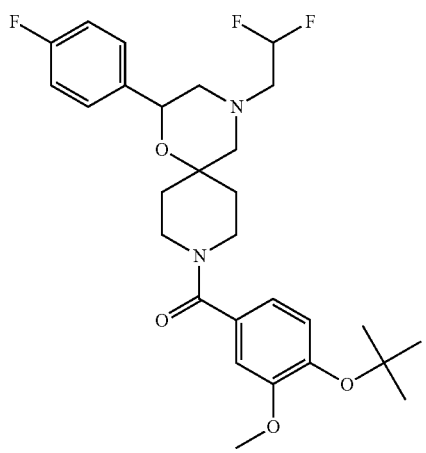 [SMILES: COc1cc(C(=O)N2CCC3(CC2)CN(CC(F)F)CC(c2ccc(F)cc2)O3)ccc1OC(C)(C)C]
248
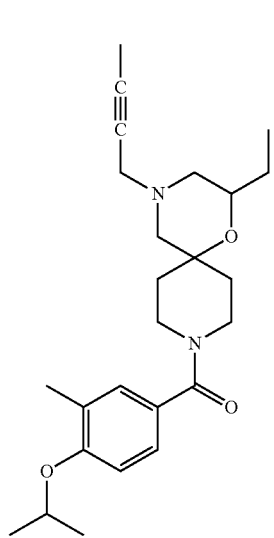 [SMILES: CC#CCN1CC(CC)OC2(CCN(C(=O)c3ccc(OC(C)C)c(C)c3)CC2)C1]
249
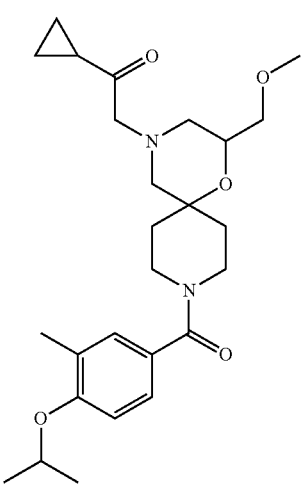 [SMILES: COCC1CN(CC(=O)C2CC2)CC2(CCN(C(=O)c3ccc(OC(C)C)c(C)c3)CC2)O1]
250
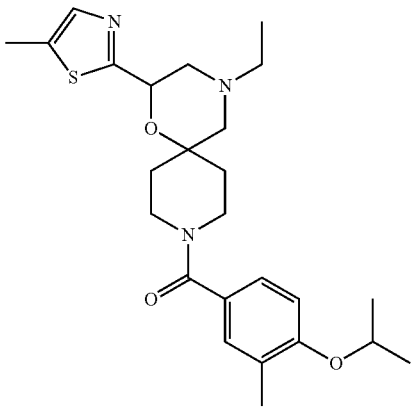 [SMILES: CCN1CC(c2ncc(C)s2)OC2(CCN(C(=O)c3ccc(OC(C)C)c(C)c3)CC2)C1]
251
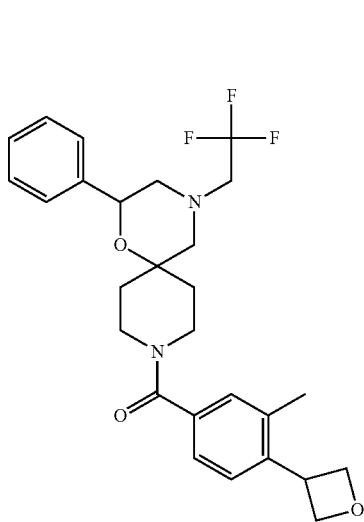 [SMILES: Cc1cc(C(=O)N2CCC3(CC2)CN(CC(F)(F)F)CC(c2ccccc2)O3)ccc1C1COC1]
252
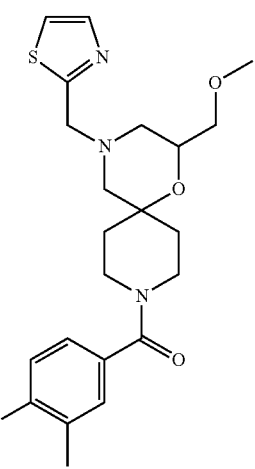

| 253 | 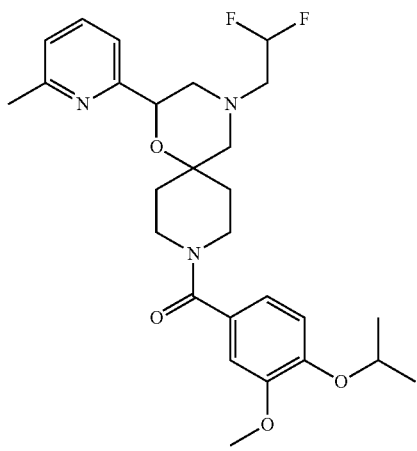 [SMILES: COc1cc(C(=O)N2CCC3(CC2)CN(CC(F)F)CC(c2cccc(C)n2)O3)ccc1OC(C)C] | 256 | 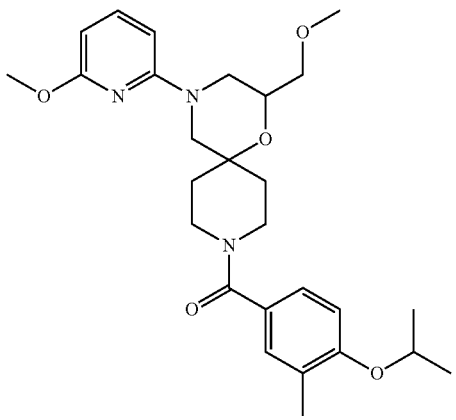 |
|---|---|---|---|
| 254 | 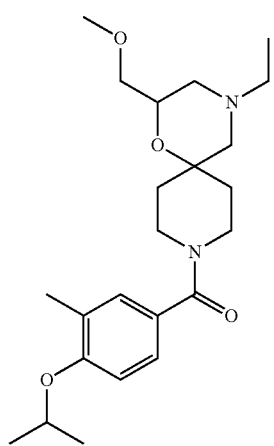 [SMILES: CCN1CC(COC)OC2(CCN(C(=O)c3ccc(OC(C)C)c(C)c3)CC2)C1] | 257 | 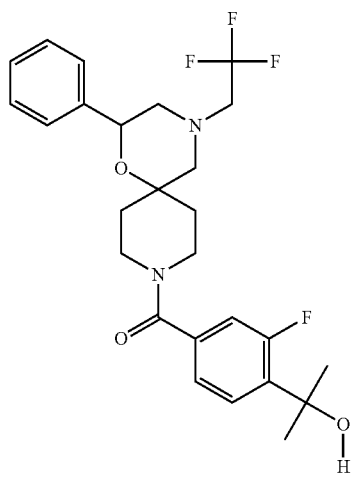 |
| 255 | 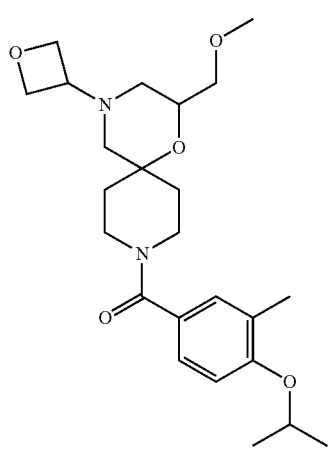 [SMILES: COCC1CN(C2COC2)CC2(CCN(C(=O)c3ccc(OC(C)C)c(C)c3)CC2)O1] | 258 | 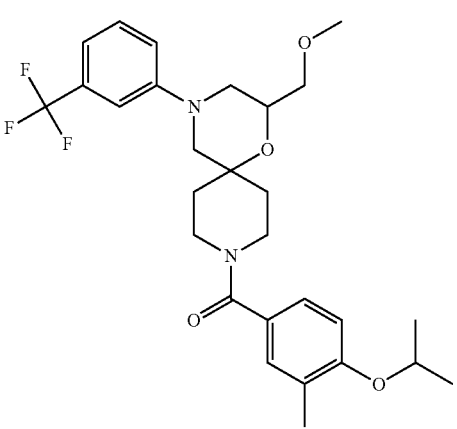 [SMILES: COCC1CN(c2cccc(C(F)(F)F)c2)CC2(CCN(C(=O)c3ccc(OC(C)C)c(C)c3)CC2)O1] |

TABLE 1-continued
259
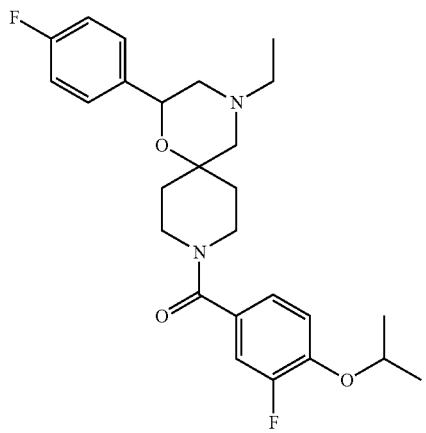 [SMILES: CCN1CC(c2ccc(F)cc2)OC2(CCN(C(=O)c3ccc(OC(C)C)c(F)c3)CC2)C1]
260
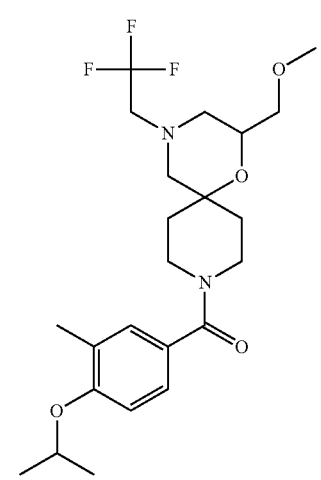 [SMILES: COCC1CN(CC(F)(F)F)CC2(CCN(C(=O)c3ccc(OC(C)C)c(C)c3)CC2)O1]
261
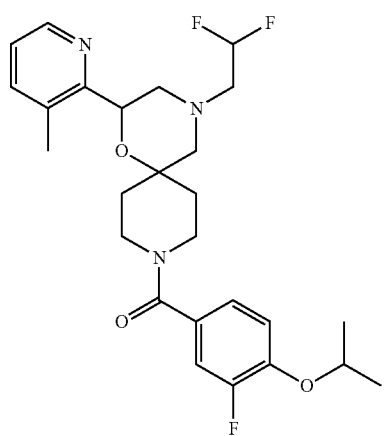 [SMILES: Cc1cccnc1C1CN(CC(F)F)CC2(CCN(C(=O)c3ccc(OC(C)C)c(F)c3)CC2)O1]
TABLE 1-continued
262
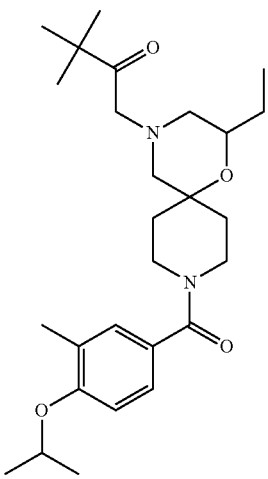 [SMILES: CCC1CN(CC(=O)C(C)(C)C)CC2(CCN(C(=O)c3ccc(OC(C)C)c(C)c3)CC2)O1]
263
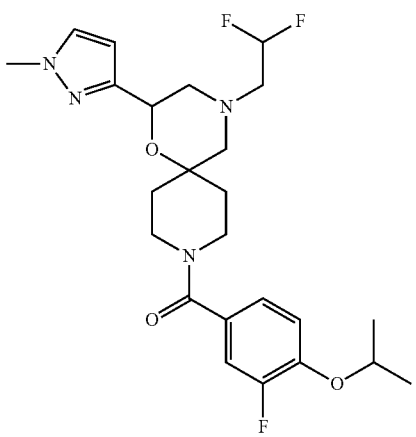 [SMILES: CC(C)Oc1ccc(C(=O)N2CCC3(CC2)CN(CC(F)F)CC(c2ccn(C)n2)O3)cc1F]
264
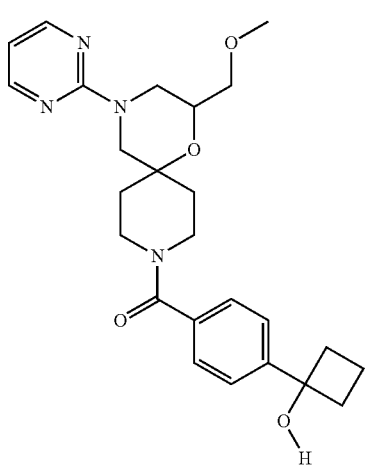 [SMILES: COCC1CN(c2ncccn2)CC2(CCN(C(=O)c3ccc(C4(O)CCC4)cc3)CC2)O1]

TABLE 1-continued
265 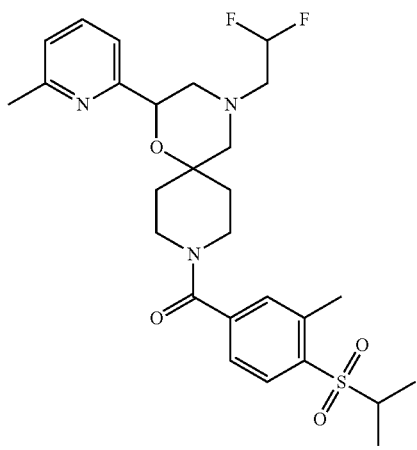 [SMILES: Cc1cccc(C2CN(CC(F)F)CC3(CCN(C(=O)c4ccc(S(=O)(=O)C(C)C)c(C)c4)CC3)O2)n1]
266 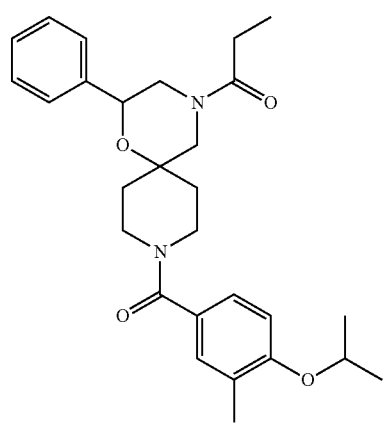 [SMILES: CCC(=O)N1CC(c2ccccc2)OC2(CCN(C(=O)c3ccc(OC(C)C)c(C)c3)CC2)C1]
267 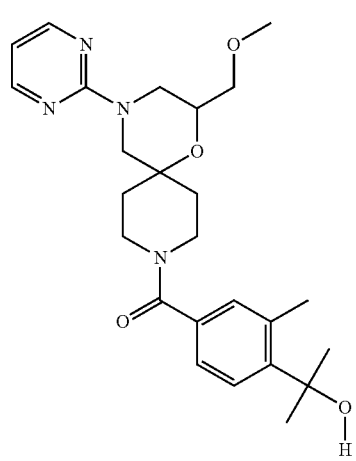 [SMILES: COCC1CN(c2ncccn2)CC2(CCN(C(=O)c3ccc(C(C)(C)O)c(C)c3)CC2)O1]
268 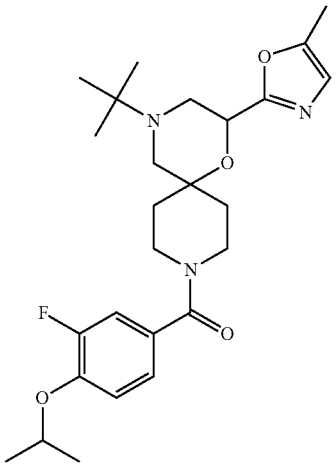 [SMILES: Cc1cnc(C2CN(C(C)(C)C)CC3(CCN(C(=O)c4ccc(OC(C)C)c(F)c4)CC3)O2)o1]
269 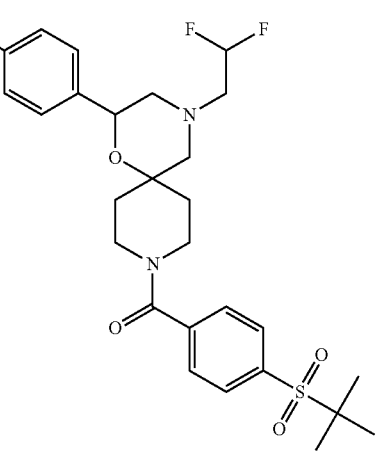
270 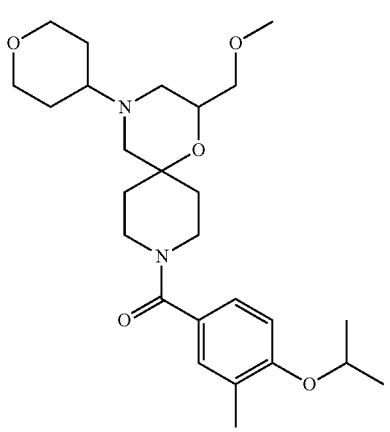 [SMILES: COCC1CN(C2CCOCC2)CC2(CCN(C(=O)c3ccc(OC(C)C)c(C)c3)CC2)O1]

TABLE 1-continued
271
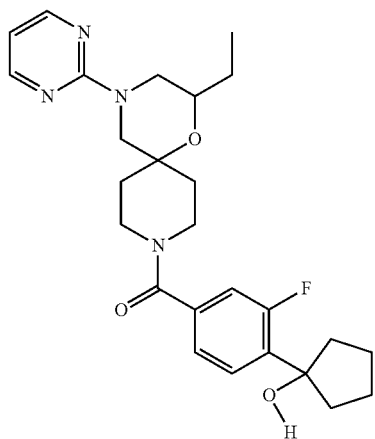
272
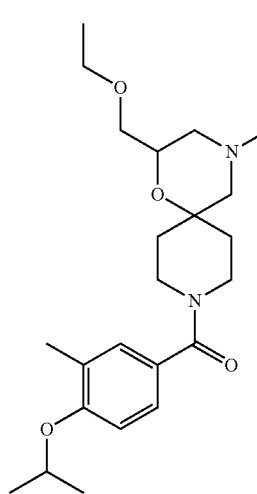
273
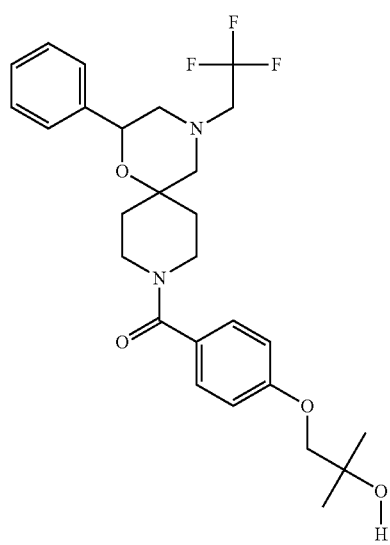 [SMILES: CC(C)(O)COc1ccc(C(=O)N2CCC3(CC2)CN(CC(F)(F)F)CC(c2ccccc2)O3)cc1]
TABLE 1-continued
274
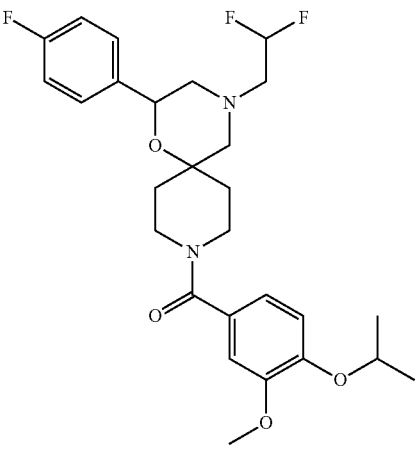 [SMILES: COc1cc(C(=O)N2CCC3(CC2)CN(CC(F)F)CC(c2ccc(F)cc2)O3)ccc1OC(C)C]
275
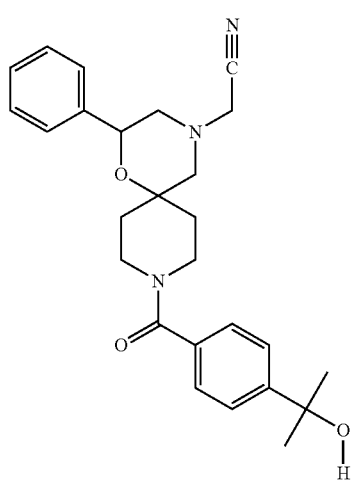 [SMILES: CC(C)(O)c1ccc(C(=O)N2CCC3(CC2)CN(CC#N)CC(c2ccccc2)O3)cc1]
276
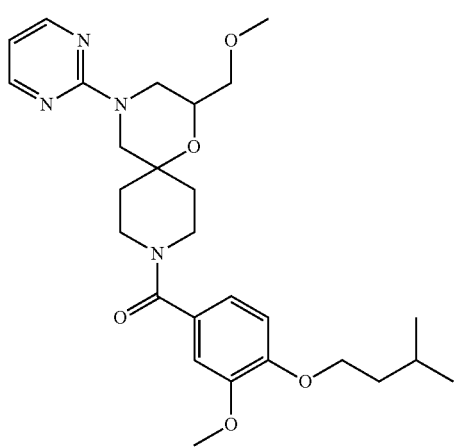

TABLE 1-continued
277
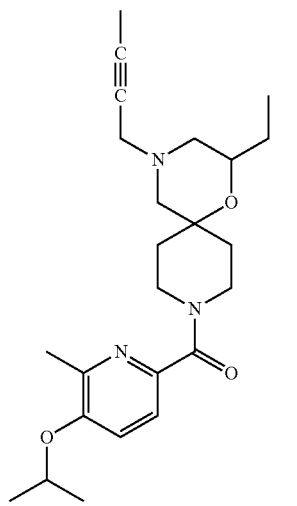 [SMILES: CC#CCN1CC(CC)OC2(CCN(C(=O)c3ccc(OC(C)C)c(C)n3)CC2)C1]
278
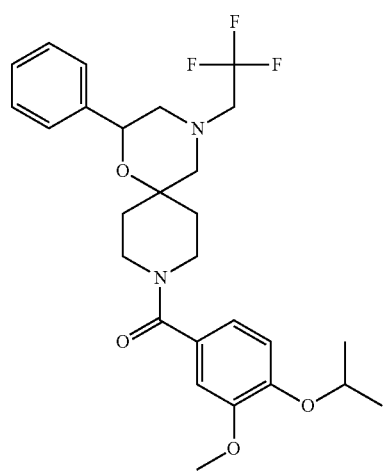 [SMILES: COc1cc(C(=O)N2CCC3(CC2)CN(CC(F)(F)F)CC(c2ccccc2)O3)ccc1OC(C)C]
279
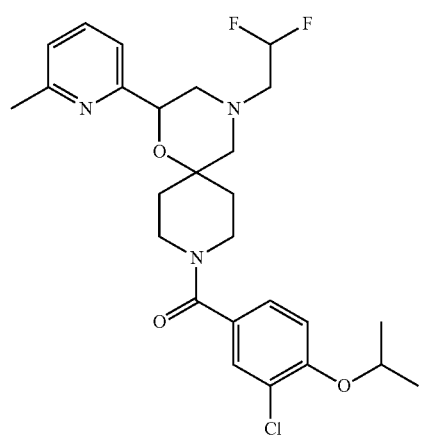 [SMILES: Cc1cccc(C2CN(CC(F)F)CC3(CCN(C(=O)c4ccc(OC(C)C)c(Cl)c4)CC3)O2)n1]
TABLE 1-continued
280
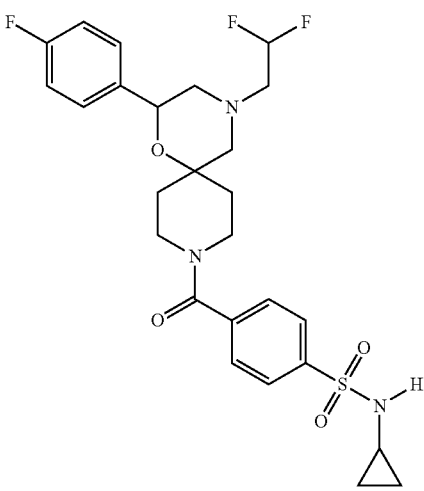 [SMILES: O=C(c1ccc(S(=O)(=O)NC2CC2)cc1)N1CCC2(CC1)CN(CC(F)F)CC(c1ccc(F)cc1)O2]
281
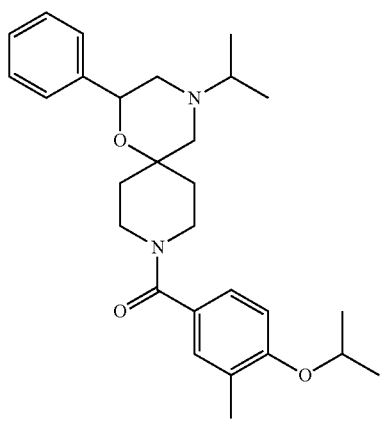 [SMILES: Cc1cc(C(=O)N2CCC3(CC2)CN(C(C)C)CC(c2ccccc2)O3)ccc1OC(C)C]
282
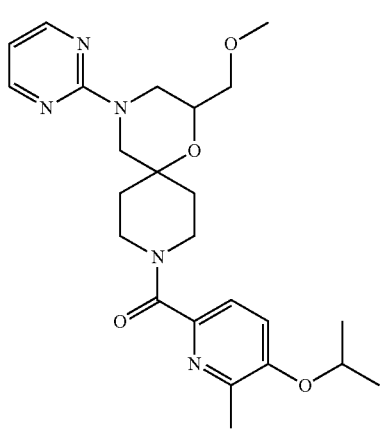 [SMILES: COCC1CN(c2ncccn2)CC2(CCN(C(=O)c3ccc(OC(C)C)c(C)n3)CC2)O1]

TABLE 1-continued
283
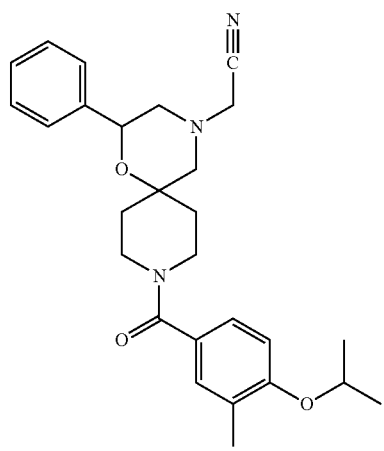 [SMILES: Cc1cc(C(=O)N2CCC3(CC2)CN(CC#N)CC(c2ccccc2)O3)ccc1OC(C)C]
284
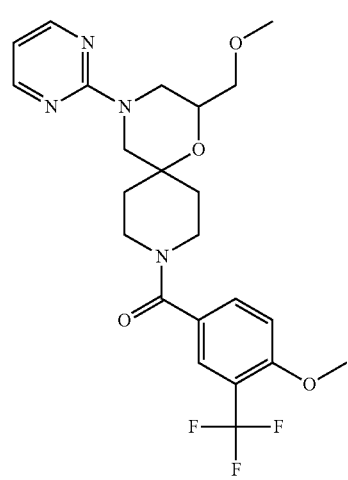 [SMILES: COCC1CN(c2ncccn2)CC2(CCN(C(=O)c3ccc(OC)c(C(F)(F)F)c3)CC2)O1]
285
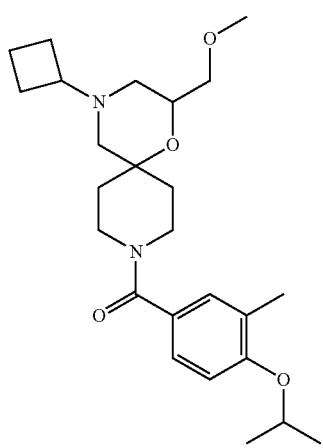 [SMILES: COCC1CN(C2CCC2)CC2(CCN(C(=O)c3ccc(OC(C)C)c(C)c3)CC2)O1]
TABLE 1-continued
286
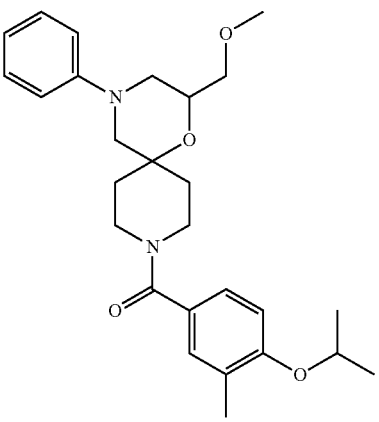
287
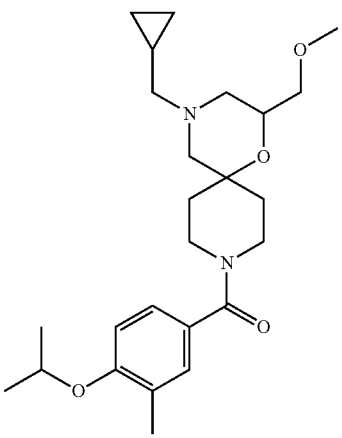 [SMILES: COCC1CN(CC2CC2)CC2(CCN(C(=O)c3ccc(OC(C)C)c(C)c3)CC2)O1]
288
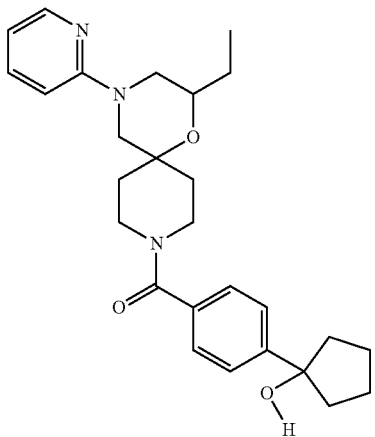 [SMILES: CCC1CN(c2ccccn2)CC2(CCN(C(=O)c3ccc(C4(O)CCCC4)cc3)CC2)O1]

TABLE 1-continued
289
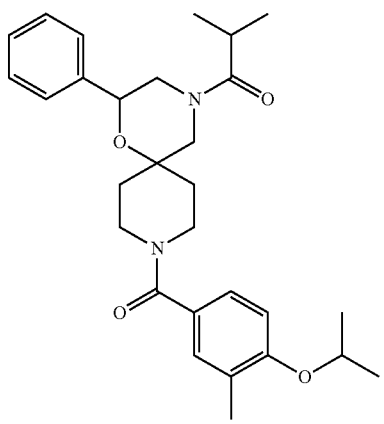 [SMILES: Cc1cc(C(=O)N2CCC3(CC2)CN(C(=O)C(C)C)CC(c2ccccc2)O3)ccc1OC(C)C]
290
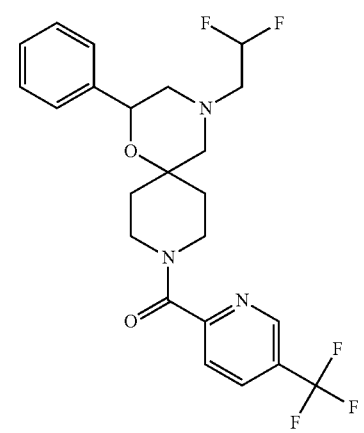 [SMILES: O=C(c1ccc(C(F)(F)F)cn1)N1CCC2(CC1)CN(CC(F)F)CC(c1ccccc1)O2]
291
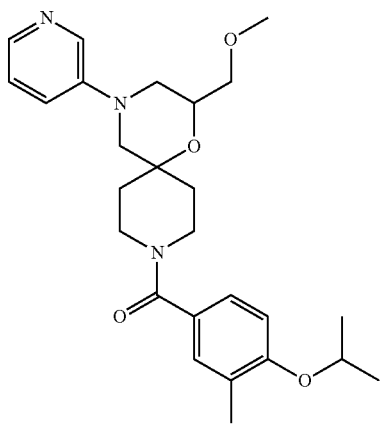 [SMILES: COCC1CN(c2cccnc2)CC2(CCN(C(=O)c3ccc(OC(C)C)c(C)c3)CC2)O1]
TABLE 1-continued
292
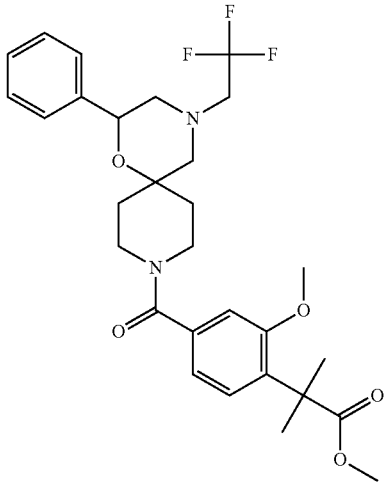 [SMILES: COC(=O)C(C)(C)c1ccc(C(=O)N2CCC3(CC2)CN(CC(F)(F)F)CC(c2ccccc2)O3)cc1OC]
293
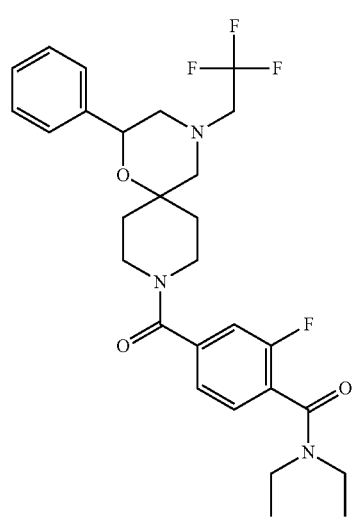 [SMILES: CCN(CC)C(=O)c1ccc(C(=O)N2CCC3(CC2)CN(CC(F)(F)F)CC(c2ccccc2)O3)cc1F]
294
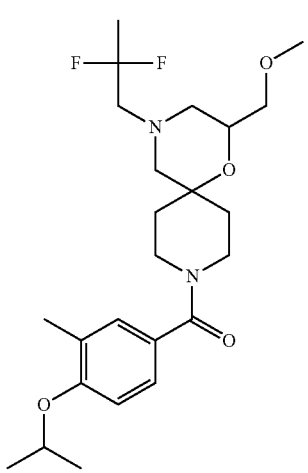 [SMILES: COCC1CN(CC(C)(F)F)CC2(CCN(C(=O)c3ccc(OC(C)C)c(C)c3)CC2)O1]

TABLE 1-continued
295
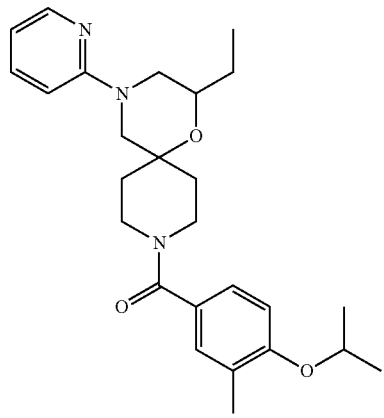
296
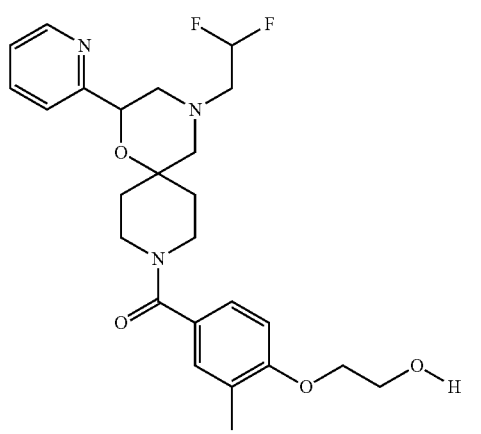 [SMILES: Cc1cc(C(=O)N2CCC3(CC2)CN(CC(F)F)CC(c2ccccn2)O3)ccc1OCCO]
297
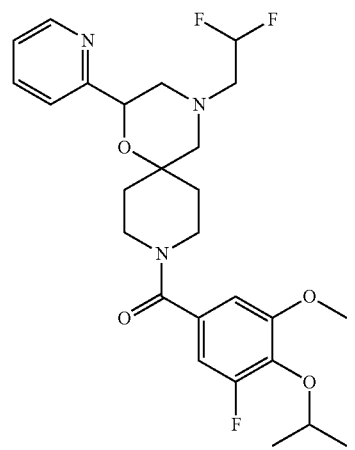 [SMILES: COc1cc(C(=O)N2CCC3(CC2)CN(CC(F)F)CC(c2ccccn2)O3)cc(F)c1OC(C)C]
298
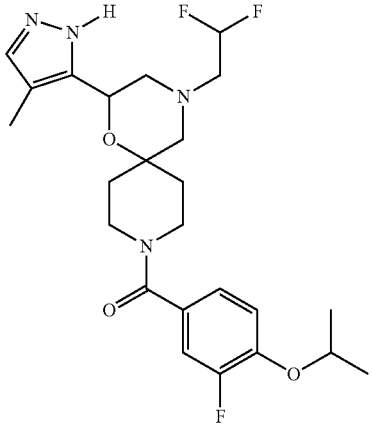 [SMILES: Cc1cn[nH]c1C1CN(CC(F)F)CC2(CCN(C(=O)c3ccc(OC(C)C)c(F)c3)CC2)O1]
299
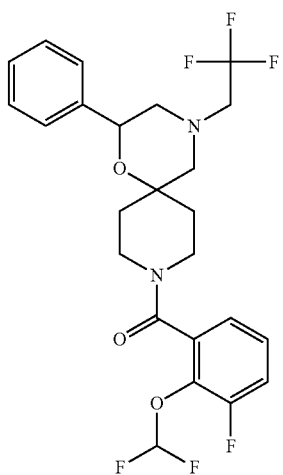 [SMILES: O=C(c1cccc(F)c1OC(F)F)N1CCC2(CC1)CN(CC(F)(F)F)CC(c1ccccc1)O2]
300
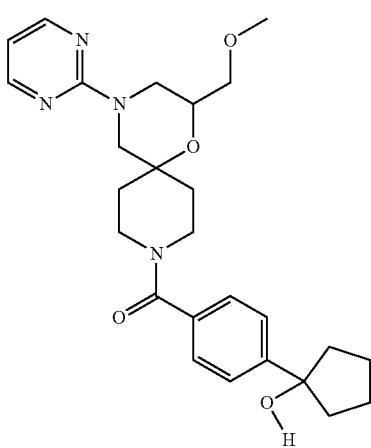 [SMILES: COCC1CN(c2ncccn2)CC2(CCN(C(=O)c3ccc(C4(O)CCCC4)cc3)CC2)O1]

TABLE 1-continued
301
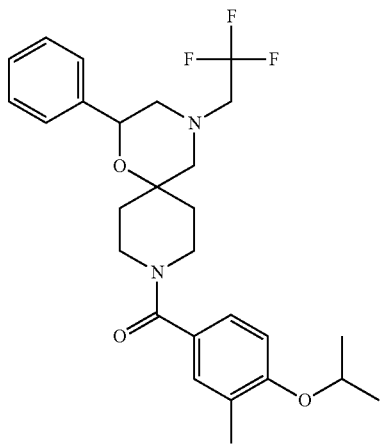 [SMILES: Cc1cc(C(=O)N2CCC3(CC2)CN(CC(F)(F)F)CC(c2ccccc2)O3)ccc1OC(C)C]
302
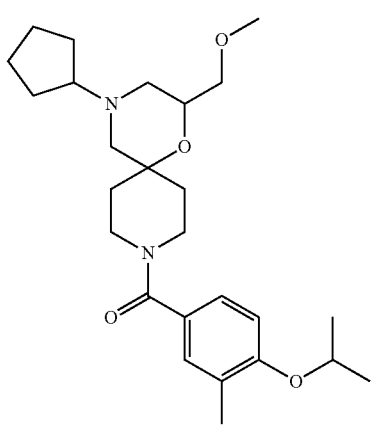 [SMILES: COCC1CN(C2CCCC2)CC2(CCN(C(=O)c3ccc(OC(C)C)c(C)c3)CC2)O1]
303
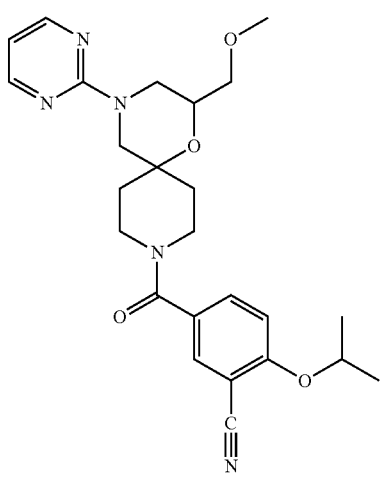 [SMILES: COCC1CN(c2ncccn2)CC2(CCN(C(=O)c3ccc(OC(C)C)c(C#N)c3)CC2)O1]
TABLE 1-continued
304
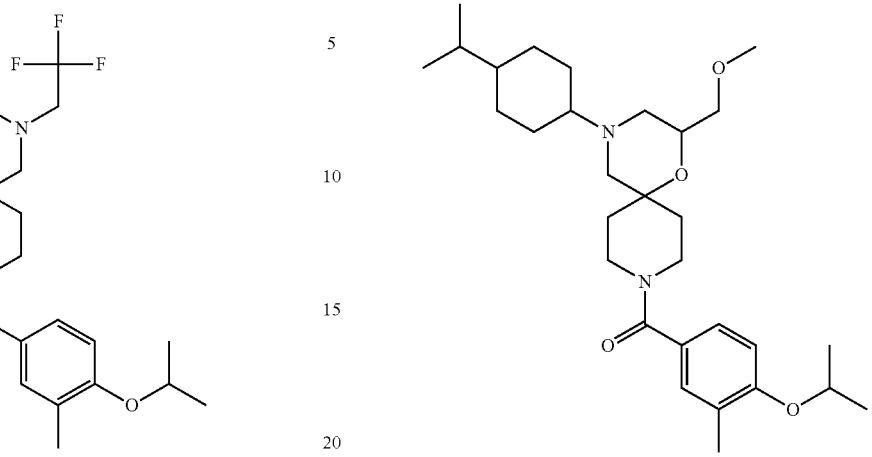
305
306
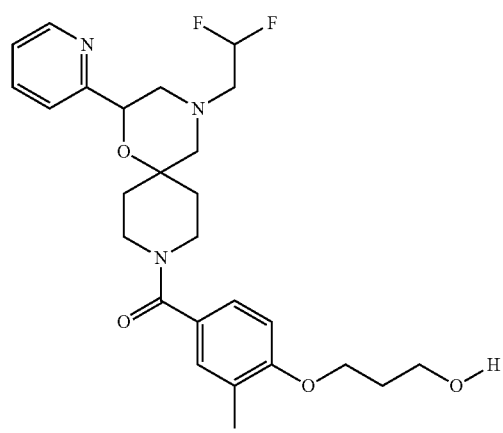 [SMILES: Cc1cc(C(=O)N2CCC3(CC2)CN(CC(F)F)CC(c2ccccn2)O3)ccc1OCCCO]
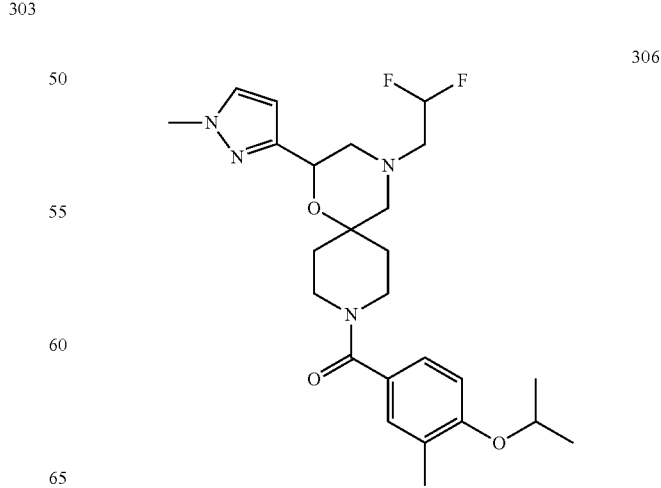

TABLE 1-continued

| | |
|---|---|
| 307 | 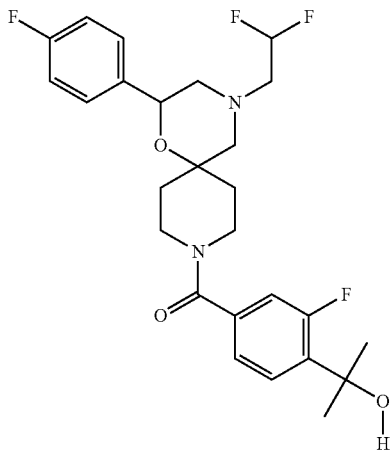 [SMILES: CC(C)(O)c1ccc(C(=O)N2CCC3(CC2)CN(CC(F)F)CC(c2ccc(F)cc2)O3)cc1F] |
| 308 | 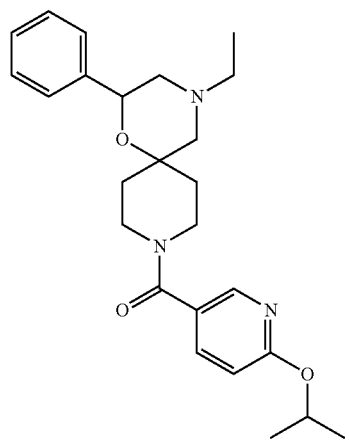 [SMILES: CCN1CC(c2ccccc2)OC2(CCN(C(=O)c3ccc(OC(C)C)nc3)CC2)C1] |
| 309 | 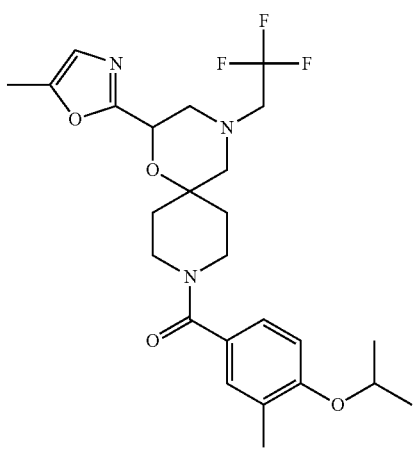 |

In another aspect, the invention features a pharmaceutical composition comprising a compound of the invention and a pharmaceutically acceptable carrier.

In another aspect, the invention features a method of inhibiting a voltage-gated sodium ion channel in:
a patient; or
a biological sample;
comprising administering to the patient, or contacting the biological sample, with a compound or composition of the invention. In another embodiment, the voltage-gated sodium ion channel is NaV 1.7.

In another aspect, the invention features a method of treating or lessening the severity in a subject of acute, chronic, neuropathic, or inflammatory pain, arthritis, migraine, cluster headaches, trigeminal neuralgia, herpatic neuralgia, general neuralgias, epilepsy or epilepsy conditions, neurodegenerative disorders, psychiatric disorders, anxiety, depression, dipolar disorder, myotonia, arrhythmia, movement disorders, neuroendocrine disorders, ataxia, multiple sclerosis, irritable bowel syndrome, incontinence, visceral pain, osteoarthritis pain, postherpetic neuralgia, diabetic neuropathy, radicular pain, sciatica, back pain, head or neck pain, severe or intractable pain, nociceptive pain, breakthrough pain, postsurgical pain, cancer pain, stroke, cerebral ischemia, traumatic brain injury, amyotrophic lateral sclerosis, stress- or exercise induced angina, palpitations, hypertension, migraine, or abnormal gastro-intestinal motility, comprising administering an effective amount of a compound or composition of the invention.

In another embodiment, the method is used for treating or lessening the severity of femur cancer pain; non-malignant chronic bone pain; rheumatoid arthritis; osteoarthritis; spinal stenosis; neuropathic low back pain; neuropathic low back pain; myofascial pain syndrome; fibromyalgia; temporomandibular joint pain; chronic visceral pain, abdominal pain; pancreatic; IBS pain; chronic and acute headache pain; migraine; tension headache, including, cluster headaches; chronic and acute neuropathic pain, post-herpetic neuralgia; diabetic neuropathy; HIV-associated neuropathy; trigeminal neuralgia; Charcot-Marie Tooth neuropathy; hereditary sensory neuropathies; peripheral nerve injury; painful neuromas; ectopic proximal and distal discharges; radiculopathy; chemotherapy induced neuropathic pain; radiotherapy-induced neuropathic pain; post-mastectomy pain; central pain; spinal cord injury pain; post-stroke pain; thalamic pain; complex regional pain syndrome; phantom pain; intractable pain; acute pain, acute post-operative pain; acute musculoskeletal pain; joint pain; mechanical low back pain; neck pain; tendonitis; injury/exercise pain; acute visceral pain, abdominal pain; pyelonephritis; appendicitis; cholecystitis; intestinal obstruction; hernias; chest pain, cardiac pain; pelvic pain, renal colic pain, acute obstetric pain, labor pain; cesarean section pain; acute inflammatory, burn and trauma pain; acute intermittent pain, endometriosis; acute herpes zoster pain; sickle cell anemia; acute pancreatitis; breakthrough pain; orofacial pain including sinusitis pain, dental pain; multiple sclerosis (MS) pain; pain in depression; leprosy pain; Behcet's disease pain; adiposis dolorosa; phlebitic pain; Guillain-Barre pain; painful legs and moving toes; Haglund syndrome; erythromelalgia pain; Fabry's disease pain; bladder and urogenital disease, including, urinary incontinence; hyperactivity bladder; painful bladder syndrome; interstitial cyctitis (IC); prostatitis; complex regional pain syndrome (CRPS), type I and type II; widespread pain, paroxysmal extreme pain, pruritis, tinnitis, or angina-induced pain.

The compounds of the invention may be prepared readily using the following methods. Illustrated below in Scheme 1 through Scheme 21 are methods for preparing the compounds of the invention.

Scheme 1
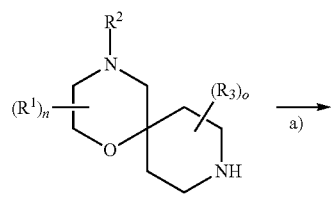
a) →
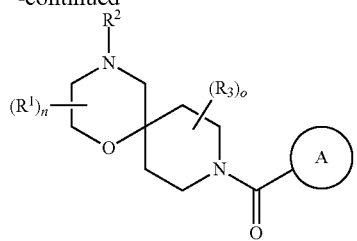
a) Acid, coupling reagent (e.g. EDCI or HATU), base (e.g. triethylamine or diisopropylethylamine); solvent (e.g. DMF or CH$_2$Cl$_2$)
Scheme 2
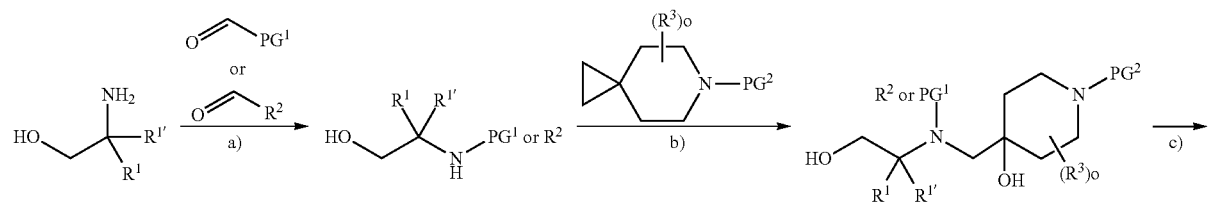
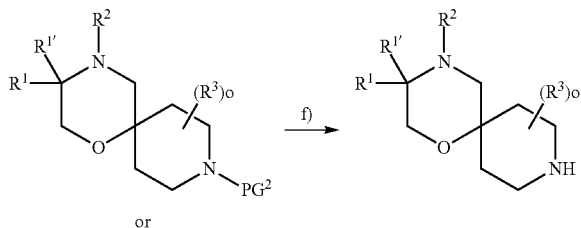
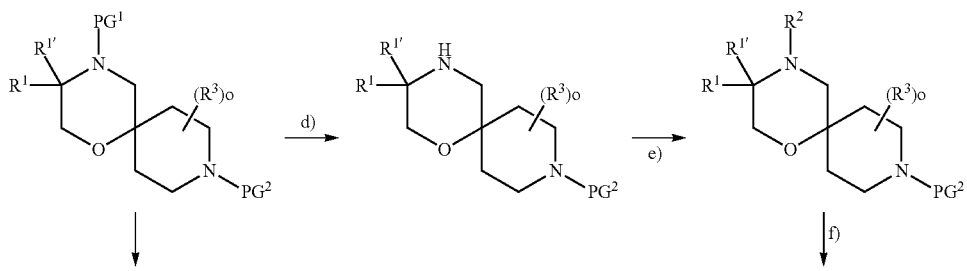

-continued

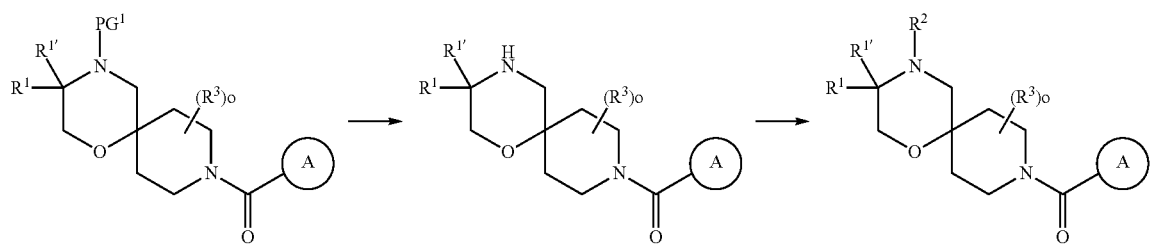

R¹ = alkyl or aryl; R¹' = H or alkyl; PG¹ = acid-stable protecting group (e.g. PMB, benzyl); PG² = acid-labile protecting group (e.g. Boc); R² = alkyl or aryl a) reducing agent (e.g. NaBH₄ or NaCNBH₃), solvent (e.g. MeOH); b) solvent (e.g. EtOH), reflux; c) H⁺: protic acid (e.g. methanesulfonic anhydride), base (e.g. iPr₂NEt), solvent (e.g. THF); d) For PG¹ as PMB or Bn: catalyst (e.g. Pd/C or Pd(OH)₂/C), hydrogen source (e.g. H₂ or ammonium formate), solvent (e.g. MeOH, EtOH or iPrOH,); e) R²X (X = halo, OTs): base (e.g. NaHCO3 or NaH, diisopropylethylamine), solvent (e.g. DMF or CH₂Cl₂) or R²X(X = CHO): reducing agent (e.g. NaCNBH₃ or NaBH₄), solvent (e.g. EtOH) f) PG² as acid labile protecting group: H⁺ (e.g. HCl or TFA), solvent (e.g. CH₂Cl₂ or dioxane).

Scheme 3

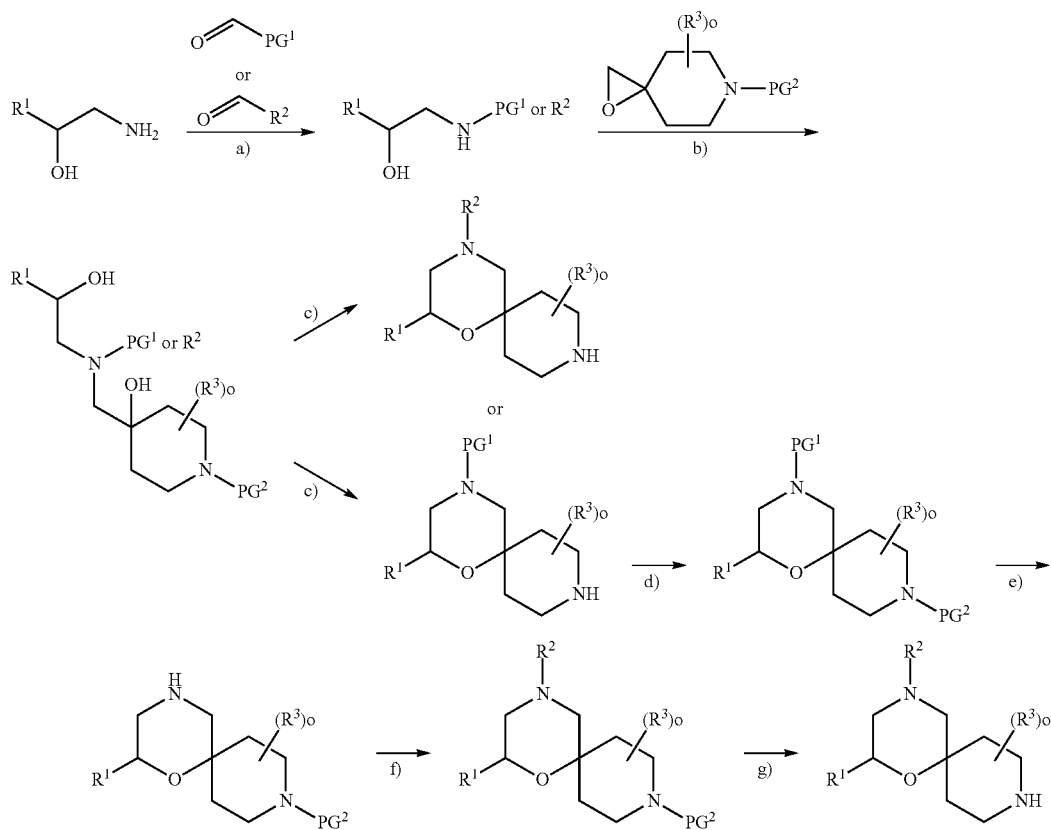

R¹ = optionally substituted phenyl; PG¹ = acid-stable protecting group (e.g. PMB, benzyl); PG² = acid-labile protecting group (e.g. Boc);

a) reducing agent (e.g. NaBH₄ or NaCNBH₃); solvent (e.g. MeOH); b) solvent (e.g. EtOH), reflux; c) H⁺: protic acid (e.g. HBr); d) for PG¹ = Boc; Boc₂O, base (e.g. Et₃N), solvent (e.g. DCM); e) for PG² = benzyl; catalyst (e.g. Pd/C or Pd(OH)₂/C), hydrogen source (e.g. H₂ or ammonium formate), solvent (e.g. MeOH, EtOH or iPrOH); f) R²X (X = halo, OTs): base (e.g. NaHCO₃ or NaH, diisopropylethylamine), solvent (e.g. DMF or CH₂Cl₂) or R²X(X=CHO): reducing agent (e.g. NaCNBH₃ or NaBH₄), solvent (e.g. EtOH) g) when PG² = Boc; H⁺ (e.g. HCl or TFA), solvent (e.g. dioxane or CH₂Cl₂).

Scheme 4

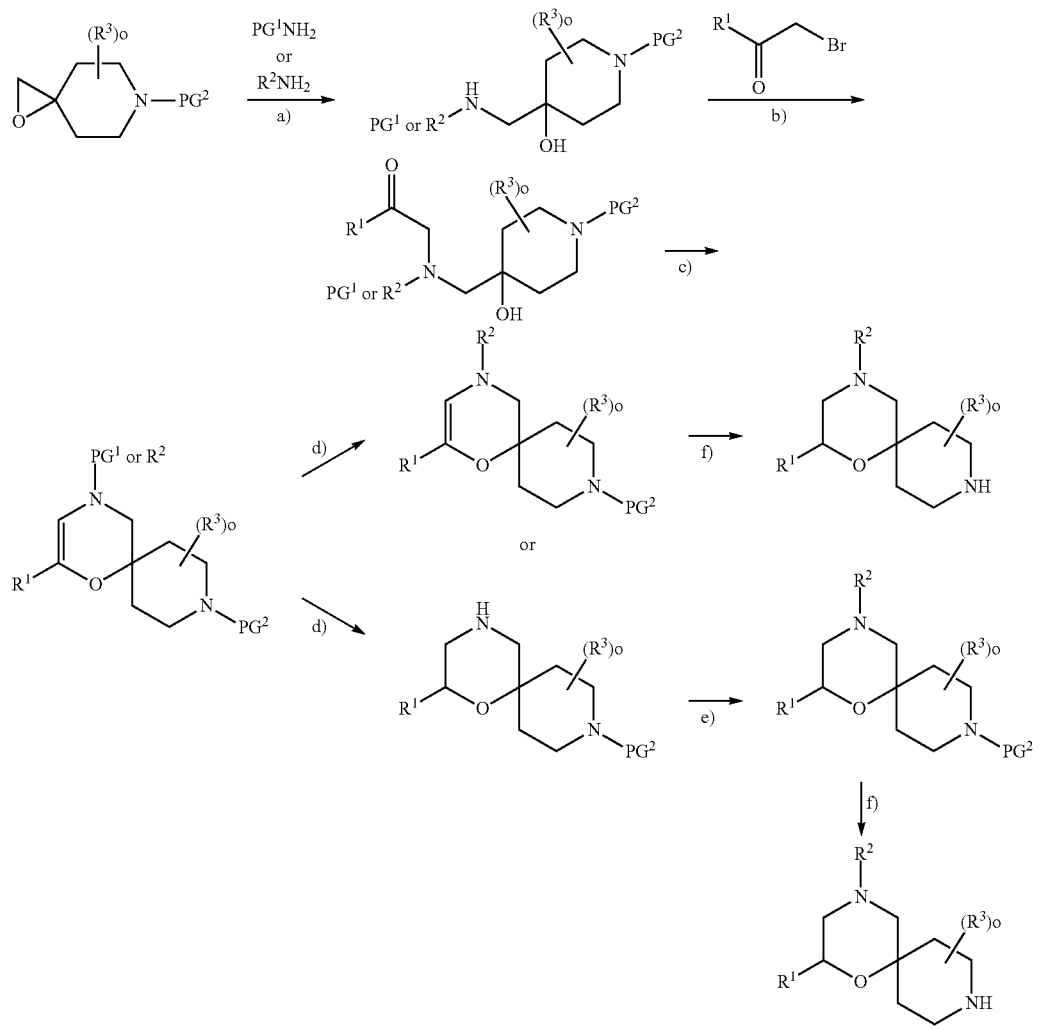

R¹ = optionally substituted 2-pyridil; PG¹ = acid-stable protecting group (e.g. benzyl); PG² = acid-labile protecting group (e.g. Boc)

a) base (e.g. ⁱPr₂NEt); solvent (e.g. DMF); b) base (e.g. ⁱPr₂NEt), solvent (e.g. DMF); c) H⁺ (e.g. p-toluenesulfonic acid), 80° C.; d) when PG¹ = benzyl; catalyst (e.g. Pd/C or Pd(OH)₂/C), hydrogen source (e.g. H₂ or ammonium formate), solvent (e.g. MeOH, EtOH or iPrOH,) e) R²X (X = halo, OTs): base (e.g. NaHCO₃ or NaH, diisopropylethylamine), solvent (e.g. DMF or CH₂Cl₂) or R²X (X=CHO ) : reducing agent (e.g. NaCNBH₃ or NaBH₄), solvent (e.g. EtOH) f) when PG² = Boc; H⁺ (e.g. HCl or TFA), solvent (e.g. dioxane or CH₂Cl₂)

Scheme 5

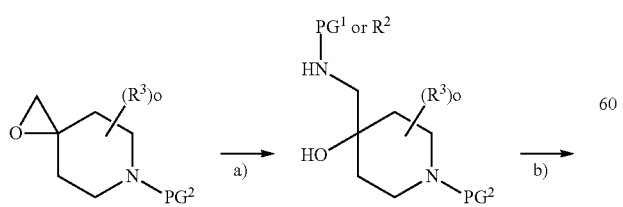

-continued

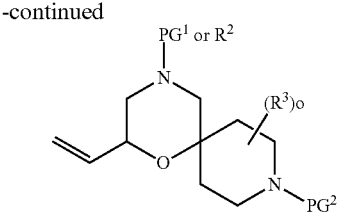

PG¹ = acid-stable protecting group (e.g. benzyl); PG² = acid-labile protecting group (e.g. Boc) a) Amine (e.g. benzylamine), solvent (e.g. methanol, ethanol, isopropanol); b) catalyst (e.g. Pd(PPh₃)₄), ligand (e.g. PPh₃), (Z)-but-2-ene-1,4--diyl diacetate, base (e.g. triethylamine, diisopropylethylamine), solvent (e.g. THF, diethyl ether, dioxane).

Scheme 6

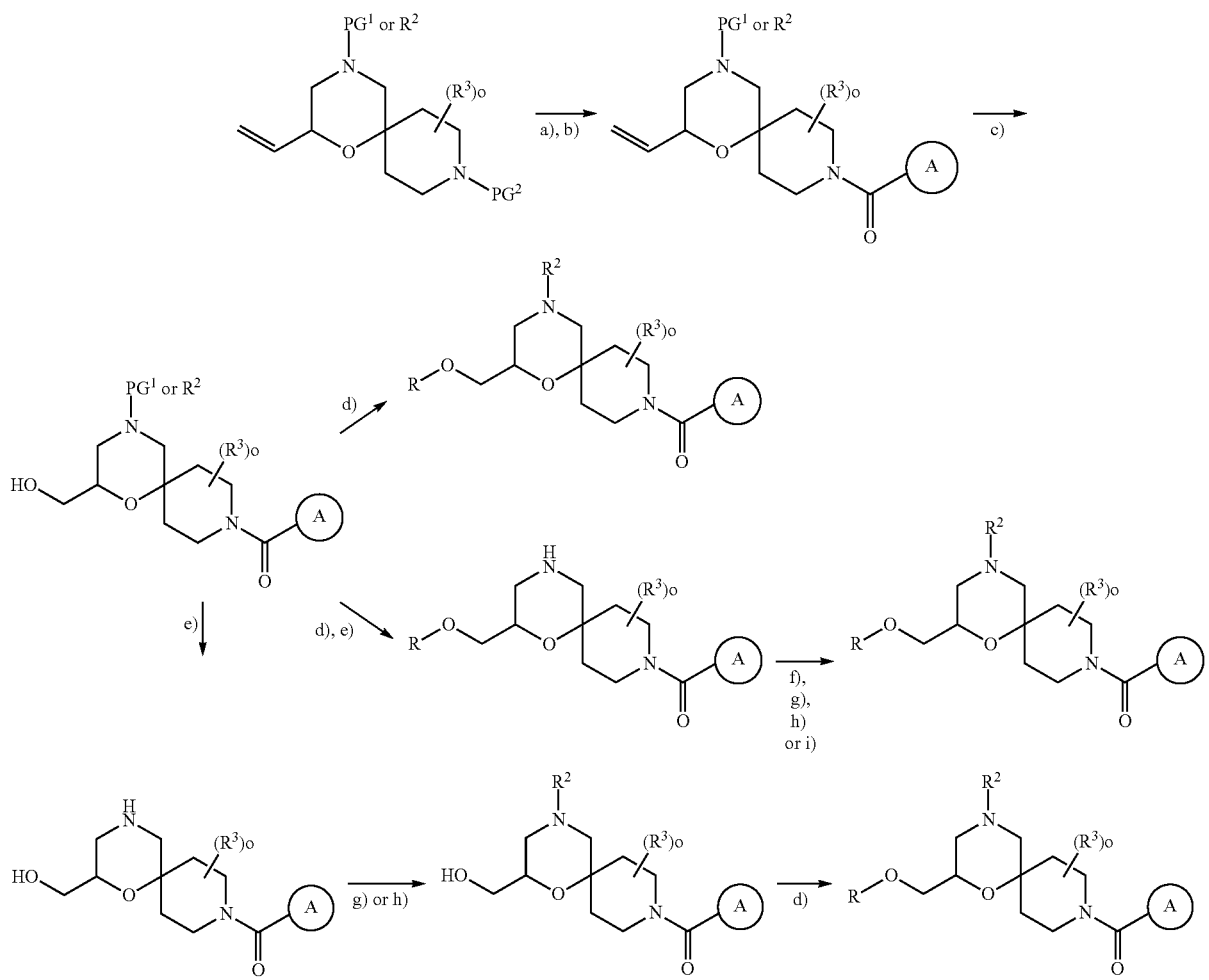

PG¹ = acid-stable protecting group (e.g. benzyl); PG² = acid-labile protecting group (e.g. Boc)
a) deprotection conditions for PG²: H⁺ (e.g. HCl or TFA); b) A—CO₂H, coupling agent (e.g. HATU or EDCI), base (e.g. Et₃N or iPr₂NEt), solvent (e.g. DMF, CH₃CN or CH₂Cl₂); c) ozone, reductive workup (e.g. NaBH₄), solvent (e.g. methanol, ethanol, isopropanol); d) R—X (X = leaving group: halo, OTs, OTf), base (e.g. NaH, KOtBu, NaOtBu), solvent (e.g. THF, DMF, CH₃CN); e) when PG¹ = benzyl; catalyst (e.g. Pd/C or Pd(OH)₂/C), hydrogen source (e.g. H₂ or ammonium formate), solvent (e.g. MeOH, EtOH or iPrOH,); f) R²—X (X = leaving group: halo, OTs, OTf), base (e.g. K₂CO₃, NaHCO₃, Et₃N), solvent (e.g. THF, DCM, EtOH,CH₃CN, DMF); g) reductive amination conditions, e.g. NaBH(OAc)₃, DCE, AcOH, TEA, appropriate ketone or aldehyde; h) nucelophilic aromatic substitution conditions, e.g. aryl halide, DMSO, K₂CO₃, heat; i) Pd-mediated amine arylation conditions: catalyst (e.g. Pd₂(dba)₃ or Pd(OAc)₂, ligand (e.g. rac-BINAP or DPPF), base (NaOtBu or KOH), solvent (e.g. toluene or dioxane).

Scheme 7

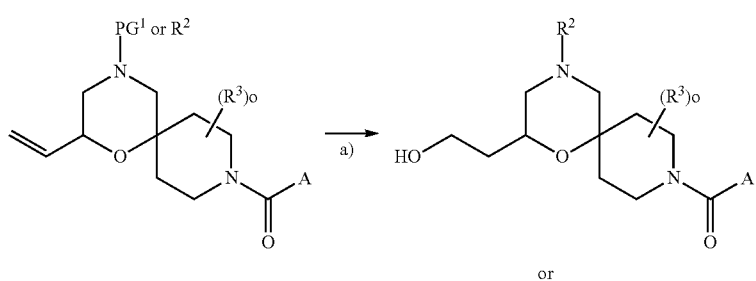

or

-continued

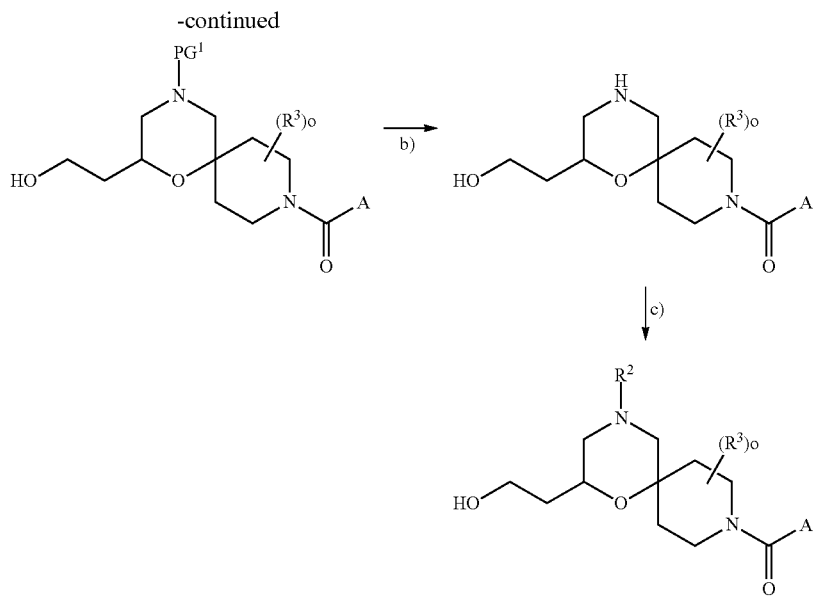

PG$^1$ = acid-stable protecting group (e.g. benzyl)
a) catecholborane, catalyst (e.g. Rh(PPh$_3$)$_3$Cl), solvent (e.g. THF, diethyl ether, dioxane; basic oxidative workup (e.g aq. H$_2$O$_2$/NaOH); b) when PG$^1$ = benzyl; catalyst (e.g. Pd/C or Pd(OH)$_2$/C), hydrogen source (e.g. H$_2$ or ammonium formate), solvent (e.g. MeOH, EtOH or iPrOH,); c) R$^2$—X (X = leaving group: halo, OTs, OTf), base (e.g. K$_2$CO$_3$, Et$_3$N), solvent (e.g. THF, DCM, EtOH, CH$_3$CN, DMF).

Scheme 8

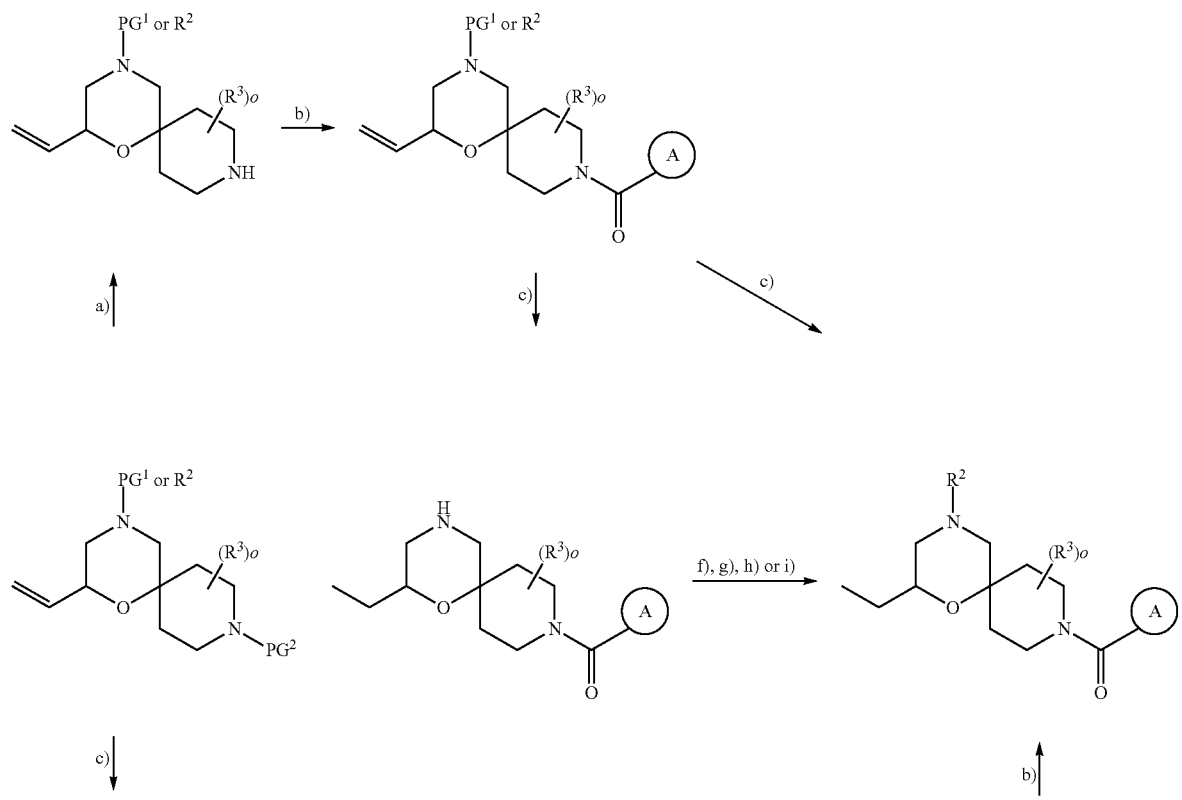

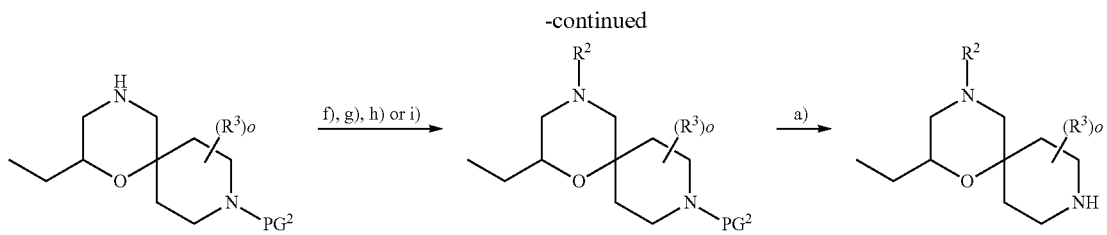

PG¹ = acid-stable protecting group (e.g. benzyl); PG² = acid-labile protecting group (e.g. Boc)
a) deprotection conditions for PG²: H⁺ (e.g. HCl or TFA); b) A—CO₂H, coupling agent (e.g. HATU or EDCI), base (e.g. Et₃N or iPr₂NEt), solvent (e.g. DMF, CH₃CN or CH₂Cl₂); c) when PG¹ = benzyl; catalyst (e.g. Pd/C or Pd(OH)₂/C, hydrogen source (e.g.ammonium formate), solvent (e.g. MeOH, EtOH or iPrOH,); f) R²—X (X = leaving group: halo, OTs, OTf), base (e.g. K₂CO₃, NaHCO₃, Et₃N), solvent (e.g. THF, DCM, EtOH, CH₃CN, DMF); g) reductive amination conditions, e.g. NaBH(OAc)₃, DCE, AcOH, TEA, appropriate ketone or aldehyde; h) nucelophilic substitution conditions, e.g. aryl halide, DMSO, heat; i) Pd-mediated amine arylation conditions: catalyst (e.g. Pd₂(dba)₃ or Pd(OAc)₂), ligand (e.g. rac-BINAP or DPPF), base (NaOtBu or KOH), solvent (e.g. toluene or dioxane).

Scheme 9

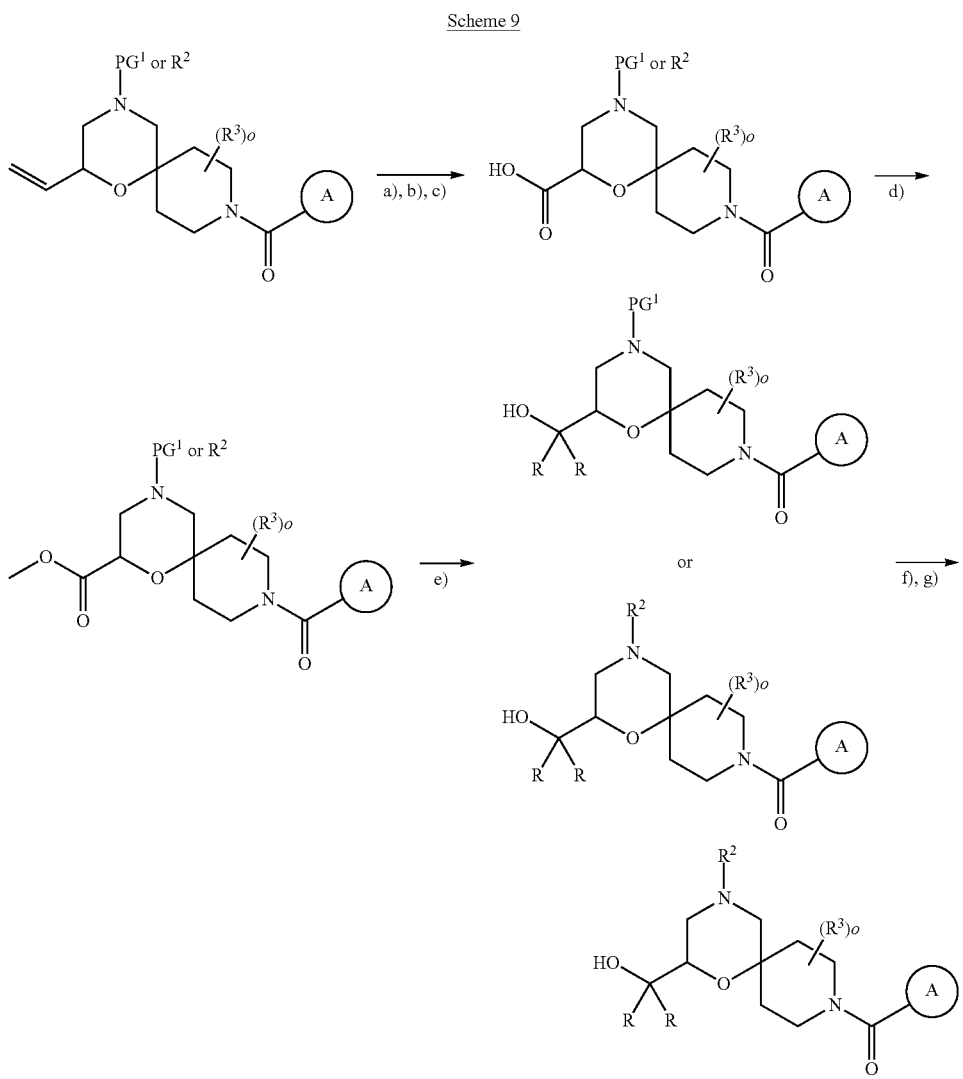

PG¹ = acid-stable protection group (e.g. benzyl); R¹ = alkyl.
a) Oxidant (e.g. OsO₄, NMO), solvent (e.g. acetone/water); b) Oxidant (e.g. NaIO₄), solvent (e.g. THF/water); c) Oxidant (e.g. NaClO₂), solvent (e.g. tBuOH/water); d) alkylating agent (e.g. MeI, dimethyl sulfate), base (e.g. K₂CO₃, NaHCO₃, Et₃N), solvent (e.g. THF, DMF);
e) Grignard reagent or alkyllithium (e.g. methylmagnesium halide or methyllithium), solvent (e.g. THF, diethyl ether, dioxane);
f) deprotection conditions e.g. when PG¹ = benzyl: catalyst (e.g. Pd/C or Pd(OH)₂/C), hydrogen source (e.g. H₂ or ammonium formate), solvent (e.g. MeOH, EtOH or iPrOH,); g) R²—X (X = leaving group: halo, OTs, OTf), base (e.g. K₂CO₃, NaHCO₃, Et₃N), solvent (e.g. THF, DCM, EtOH, CH₃CN, DMF).

Scheme 10

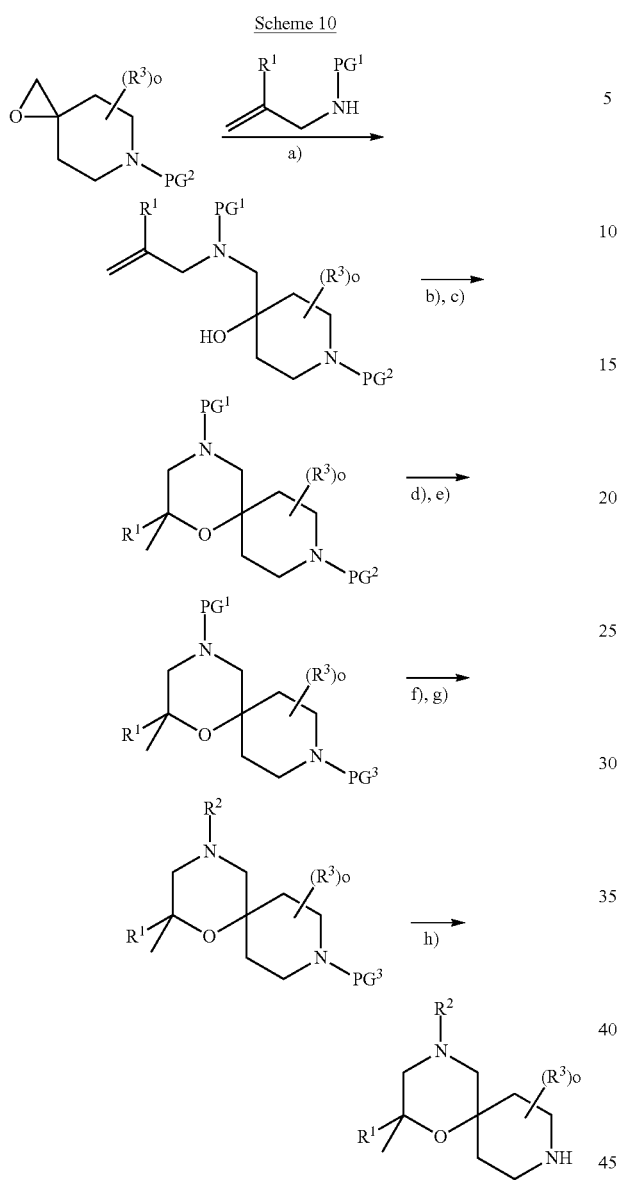

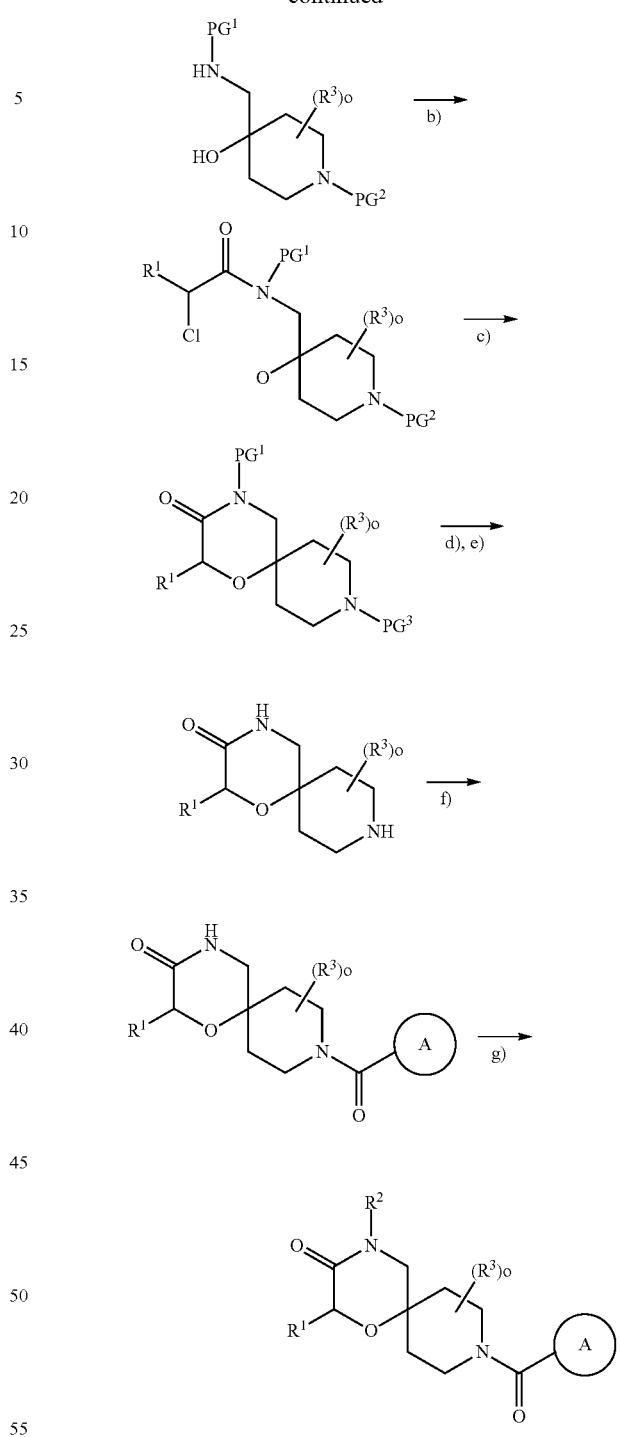

PG$^1$ = acid-stable protecting group (e.g. benzyl); PG$^2$ = acid-labile protecting group (e.g. Boc); PG$^3$ = base-labile protecting group (e.g. trifluoroacetate).
a) Protected amine (e.g. N-benzyl-2-methylprop-2-en-1-amine), solvent (e.g. methanol, ethanol, isopropanol); b) I$_2$, solvent (e.g. H$_2$O, DCM, MTBE, diethyl ether, THF), base (e.g. NaHCO$_3$, K$_2$CO$_3$, Et$_3$N); c) Reductant (e.g. NaBH$_4$ or LiAlH$_4$), solvent (e.g. DMSO or THF); d) PG$^2$ = Boc; H$^+$ (e.g. HCl OR TFA); e) PG$^3$ = trifluoroacetate; trifluoroacetic anhydride or ethyl trifluoroacetate, base (e.g. pyridine or Et$_3$N); f) PG$^1$ = benzyl; catalyst (e.g. Pd/C or Pd(OH)$_2$/C), hydrogen source (e.g. H$_2$ or ammonium formate), solvent (e.g. MeOH, EtOH or iPrOH,); g) R$^2$—X (X = leaving group: halo, OTs, OTf), base (e.g. K$_2$CO$_3$, NaHCO$_3$, Et$_3$N), solvent (e.g. THF, DCM, EtOH, CH$_3$CN, DMF); h) Base (e.g. NaOH, K$_2$CO$_3$, Na$_2$CO$_3$), solvent (e.g. MeOH, EtOH, H$_2$O).

PG$^1$ = acid-stable protecting group (e.g. para-methoxybenzyl); PG$^2$ = acid-labile protecting group (e.g. Boc); R$^1$ = optionally substituted phenyl.

a) Amine (e.g. p-methoxybenzylamine), solvent (e.g. methanol, ethanol, isopropanol); b) 2-halo-2-arylacetyl chloride, base (e.g. Et$_3$N, i-PrNEt$_2$, pyridine), solvent (e.g. THF, DCM, CH$_3$CN); c) Base (e.g. NaH, KOt-Bu, NaOt-Bu), solvent (e.g. THF, DMF, CH$_3$CN, DMSO, t-BuOH); d) PG$^1$ = PMB; oxidant (e.g. CAN or DDQ), solvent (e.g. H$_2$O/CH$_3$CN or DCM, DMF, dioxane); e) PG$^2$ = Boc; H$^+$ (e.g. HCl or TFA); f) A—CO$_2$H, coupling agent (e.g. HATU or EDCI), base (e.g. Et$_3$N or iPr$_2$NEt), solvent (e.g. DMF, CH$_3$CN or CH$_2$Cl$_2$); g) R$^2$—X (X = leaving group: halo, OTs, OTf), base (e.g. K$_2$CO$_3$, NaHCO$_3$, Et$_3$N), solvent (e.g. THF, DCM, EtOH, CH$_3$CN, DMF).

Scheme 11

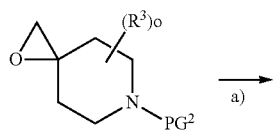

Scheme 12

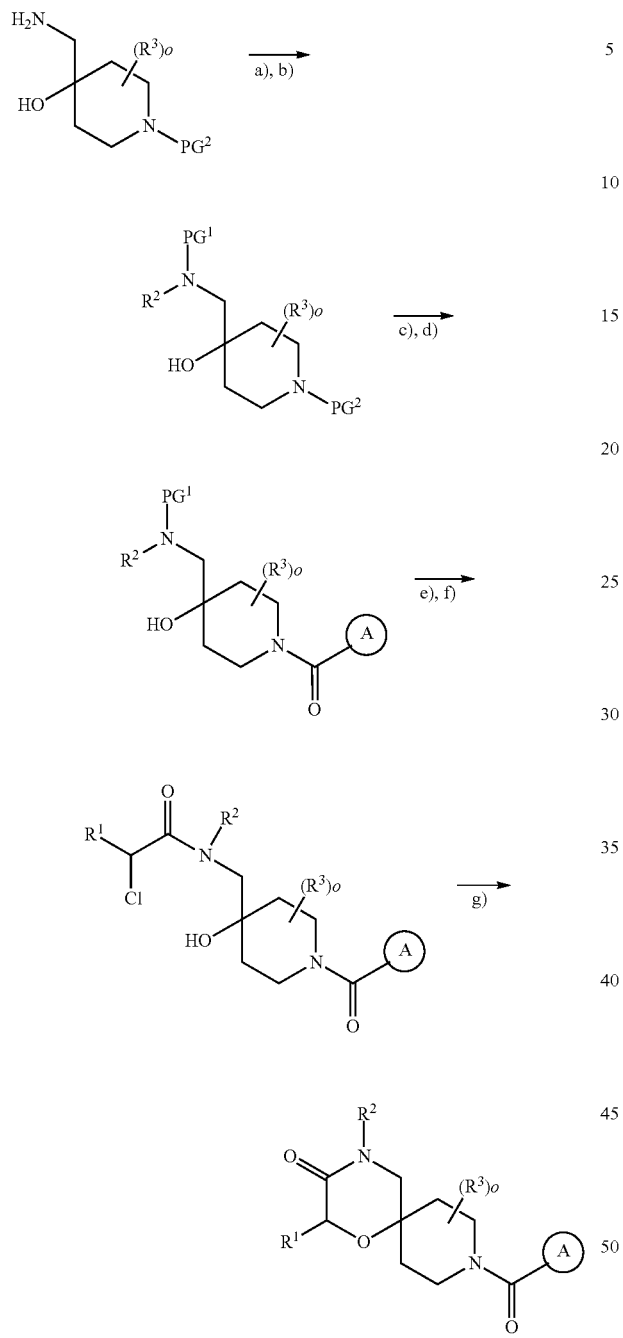

PG$^1$ = base-labile protecting group (e.g. trifluoroacetate);
PG$^2$ = acid-stable protecting group (e.g. benzyl); R = optionally substsituted phenyl. a) Aldehyde (e.g. 3-methylbutanal), reductant (e.g. NaBH$_4$, NaBH(OAc)$_3$, NaBH$_3$CN), solvent (e.g. methanol, THF, DCM, DCE);
b) PG$^1$ = trifluoroacetate; trifluoroacetic anhydride or ethyl trifluoroacetate, base (e.g. pyridine or Et$_3$N); c) PG$^2$ = benzyl; catalyst (e.g. Pd/C or Pd(OH)$_2$/C), hydrogen source (e.g. H$_2$ or ammonium formate), solvent (e.g. MeOH, EtOH or iPrOH,); d) A—CO$_2$H , coupling agent (e.g. HATU or EDCI), base (e.g. Et$_3$N or iPr$_2$NEt), solvent (e.g. DMF, CH$_3$CN or CH$_2$Cl$_2$); e) Base (e.g. NaOH, K$_2$CO$_3$, Na$_2$CO$_3$), solvent (e.g. MeOH, EtOH, H$_2$O); f) 2-halo-2-arylacetyl chloride, base (e.g. Et$_3$N, i-PrNEt$_2$, pryidine), solvent (e.g. THF, DCM, CH$_3$CN); g) Base (e.g. NaH, KOt-Bu, NaOt-Bu), solvent (e.g. THF, DMF, CH$_3$CN, DMSO, t-BuOH).

Scheme 13

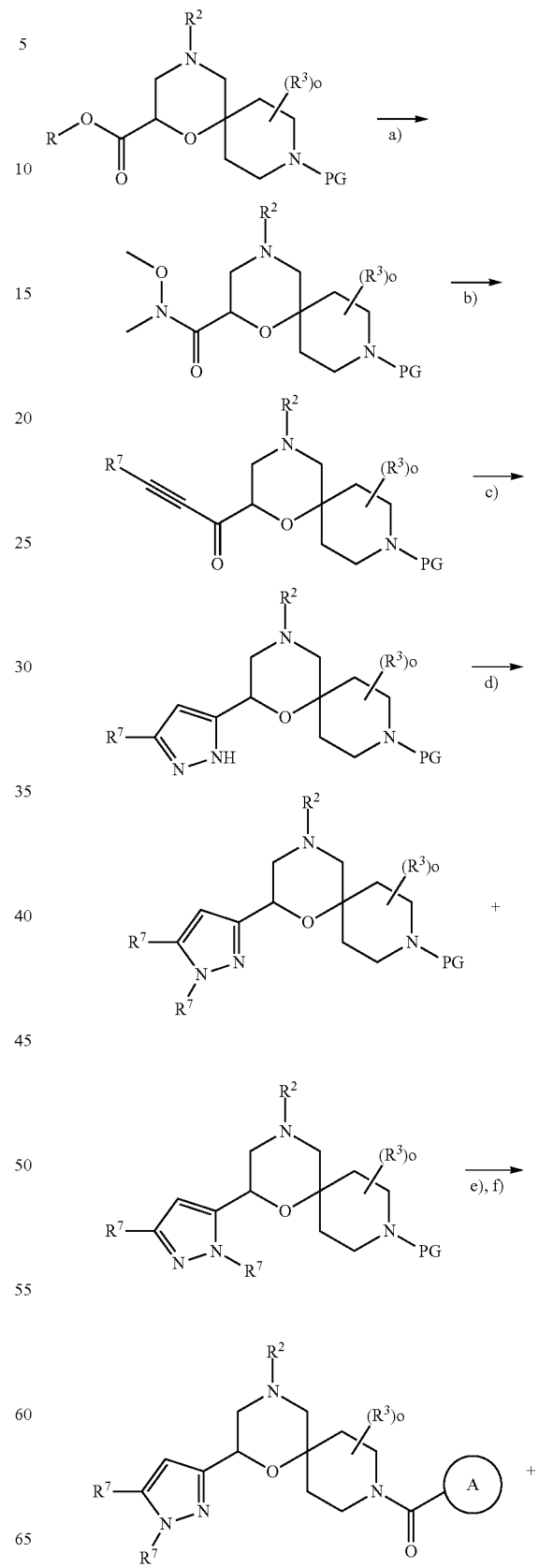

-continued

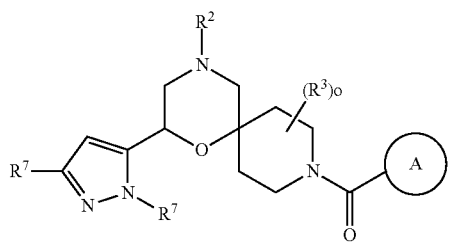

PG = acid-labile protecting group (e.g. Boc).

a) N,O-dimethylhydroxylamine, base (e.g. LiHMDS, NaHMDS, LDA), solvent (e.g. THF, diethyl ether); b) alkynylmagnesium halide, solvent (e.g. THF, diethyl ether); c) hydrazine, solvent (e.g. MeOH, EtOH, i-PrOH); d) $R^7$—X (X = leaving group: halo, OTs, OTf), base (e.g. NaH, KOt-Bu, NaOt-Bu), solvent (e.g. THF, DMF, $CH_3CN$, DMSO, t-BuOH); e) PG = Boc; $H^+$ (e.g. HCl or TFA); f) A—$CO_2H$, coupling agent (e.g. HATU or EDCI), base (e.g. $Et_3N$ or $iPr_2NEt$), solvent (e.g. DMF, $CH_3CN$ or $CH_2Cl_2$).

Scheme 14

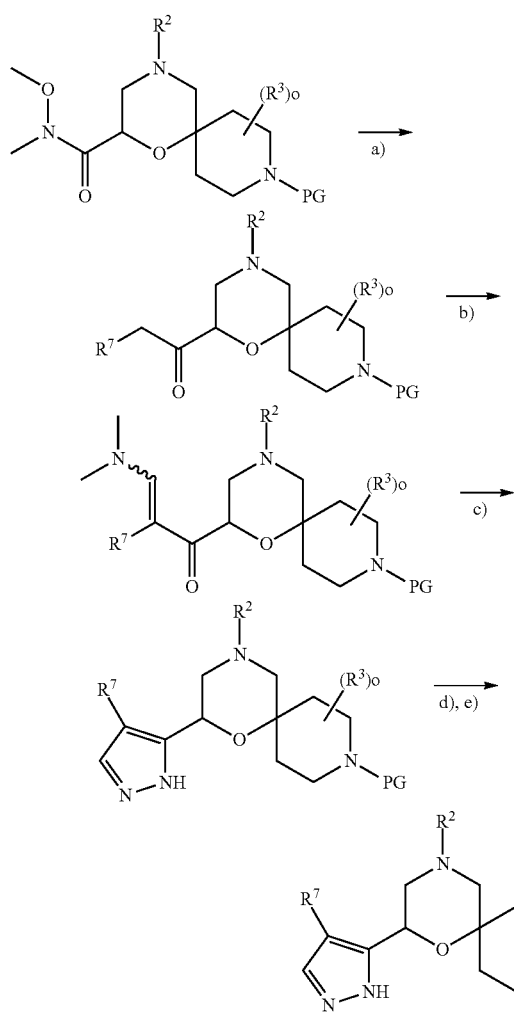

$PG^1$ = acid-labile protecting group (e.g. Boc); $R^7$ = alkyl.

a) Alkylmagnesium halide, solvent (e.g. THF, diethyl ether); b) DMF—DMA; c) hydrazine, solvent (e.g. MeOH, EtOH, i-PrOH); d) $PG^1$ = Boc; $H^+$ (e.g. HCl or TFA).

Scheme 15

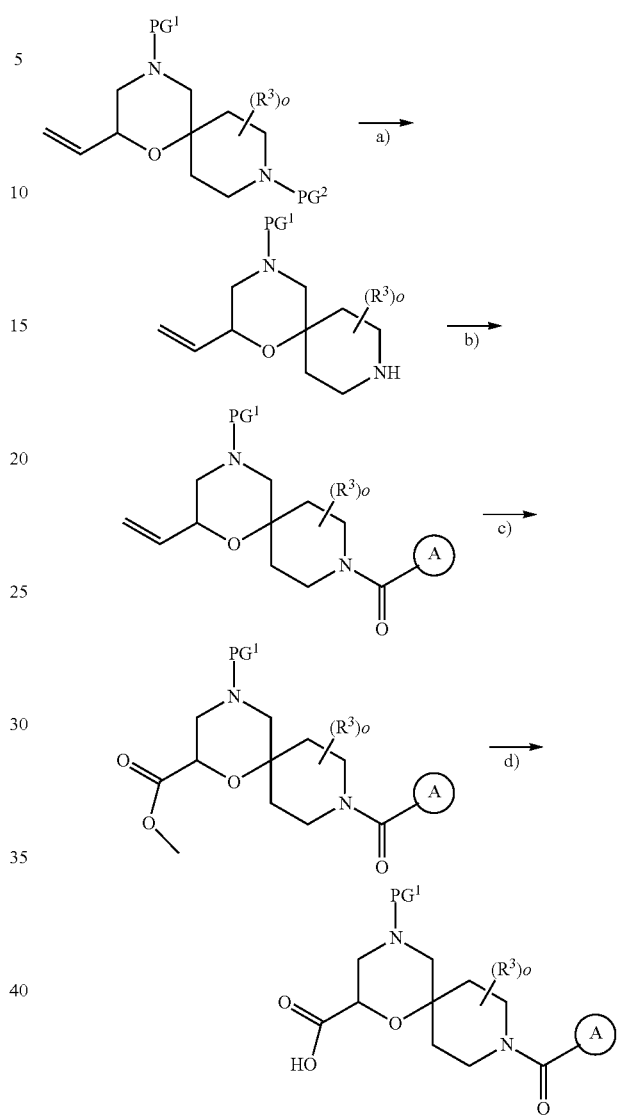

$PG^1$ = acid-stable protecting group (e.g. benzyl); $PG^2$ = acid-labile protecting group (e.g. Boc)
a) when $PG^1$ = Boc; $H^+$ (e.g. HCl or TFA), solvent (e.g. $^i$PrOH, EtOH, dioxane or $CH_2Cl_2$); b) A—$CO_2H$; coupling agent (e.g. HATU or EDCI), base (e.g. $Et_3N$ or $iPr_2NEt$), solvent (e.g. DMF, $CH_3CN$ or $CH_3Cl_2$)
c) i. Oxidant (e.g. $OsO_4$, NMO), solvent (e.g. acetone/water); ii. Oxidant (e.g. $NaIO_4$), solvent (e.g. THF/water); iii. Oxidant (e.g. $NaClO_2$), solvent (e.g. tBuOH/water);
d) base (e.g. LiOH or NaOH), solvent (e.g. THF or dioxane or MeOH), water.

Scheme 16

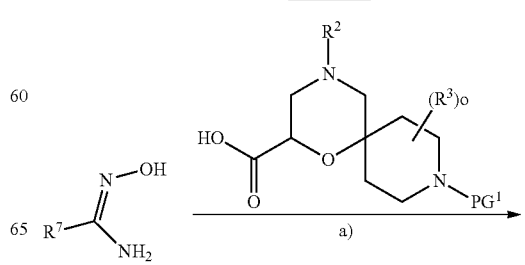

155

-continued

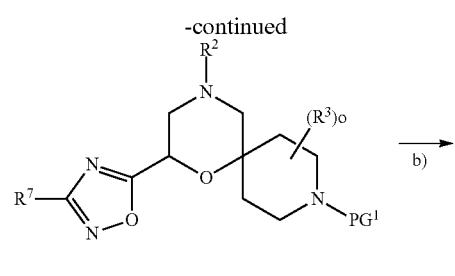

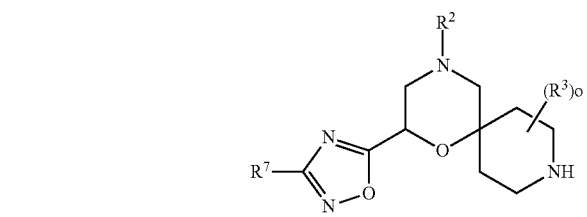

PG¹ = acid-labile protecting group (e.g. Boc)

a) Activating/dehydrating reagent (e.g. T3P, HATU, EDCI), base (e.g. Et₃N), solvent (e.g. 2-methyltetrahydrofuran, DMF); b) when PG¹ = Boc; H⁺ (e.g. HCl or TFA), solvent (e.g. ⁱPrOH, EtOH, dioxane or CH₂Cl₂)

Scheme 17

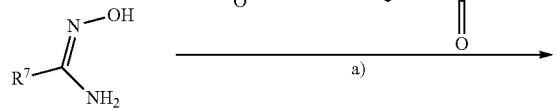

156

-continued

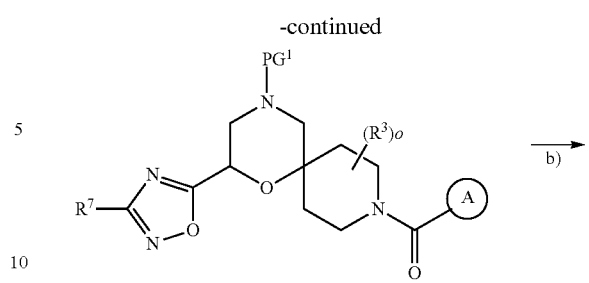

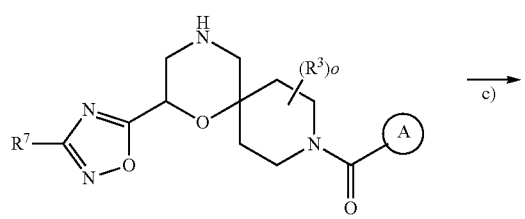

PG¹ = acid-stable protecting group (e.g. benzyl)

a) Activiating/dehydrating reagent (e.g. T₃P, HATU, EDCI), base (e.g. Et₃N), solvent (e.g. 2-methyltetrahydrofuran, DMF); b) when PG¹ = benzyl; i. 1-chloroethyl chloroforamte, solvent (e.g. DCE); ii. MeOH; c) R² — X (X = leaving group: halo, OTs, OTf), base (e.g. K₂CO₃, NaHCO₃, Et₃N), solvent (e.g. EtOH, CH₃CN).

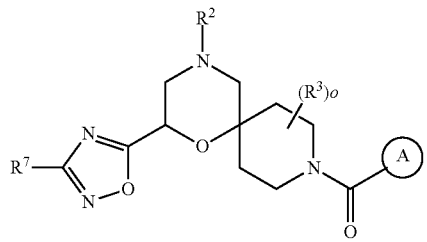

Scheme 18

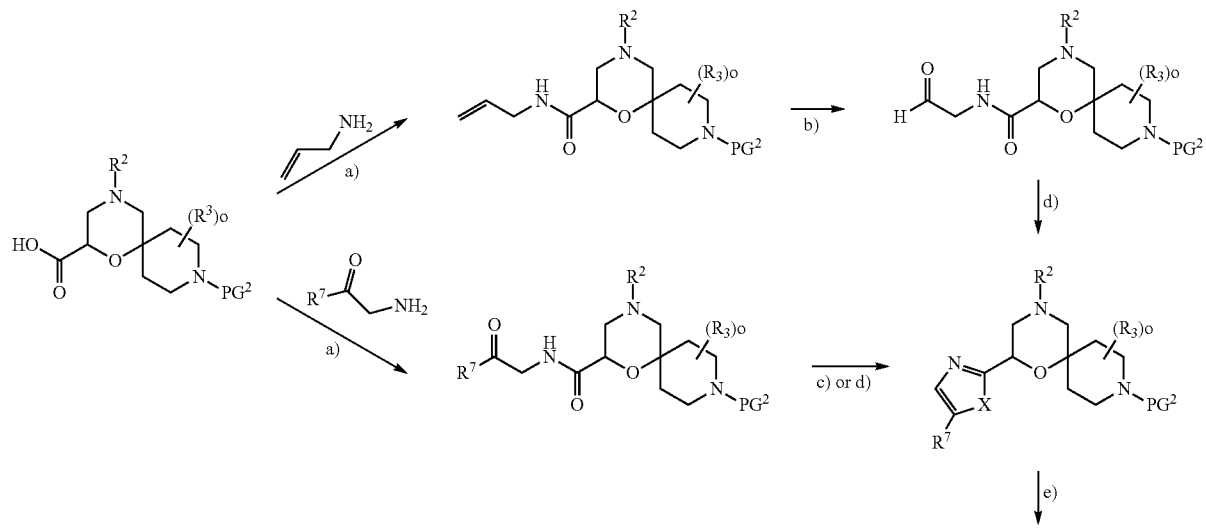

-continued

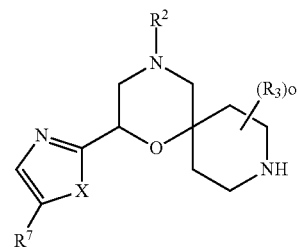

PG¹ = acid-labile protecting group (e.g. Boc)

a) Coupling agent (e.g. T3P, HATU, EDCI), base (e.g. Et₃N or DIEA), solvent (e.g. 2-methyltetrahydrofuran, DMF or CH₃CN); b) i. Oxidant (e.g. OsO₄, NMO), solvent (e.g. acetone/water); ii. Oxidant (e.g. NaIO₄), solvent (e.g. THF/water); c) X═S , (e.g. Lawesson's reagent or P₂S₅), solvent (e.g. THF or toluene); d) X═O, dehydrating reagent (e.g. POCl₃, I₂/Ph₃P or Burgess salt), base (e.g. Et₃N), solvent (e.g. toluene, DCM, THF); e) PG¹ = Boc; H⁺ (e.g. HCl or TFA), solvent (e.g. ⁱPrOH, EtOH, dioxane or CH₂Cl₂)

Scheme 19
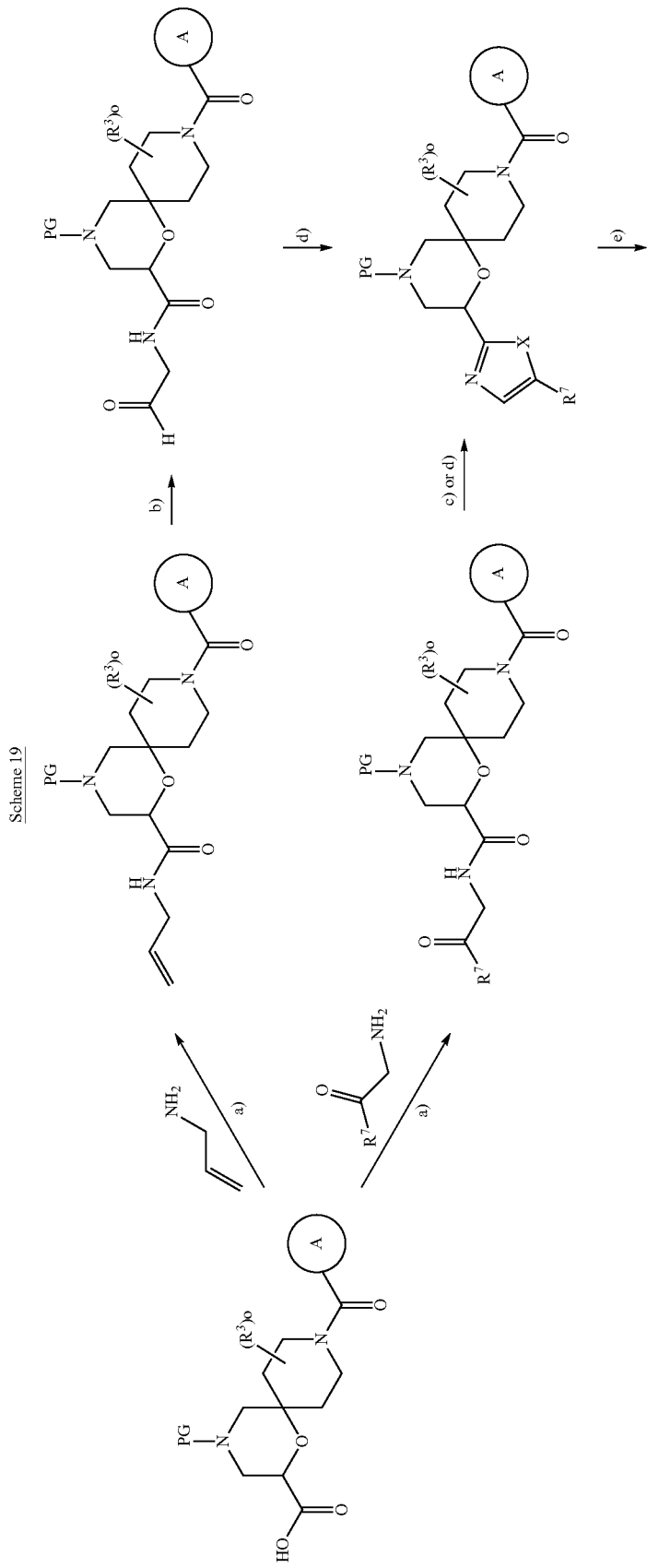

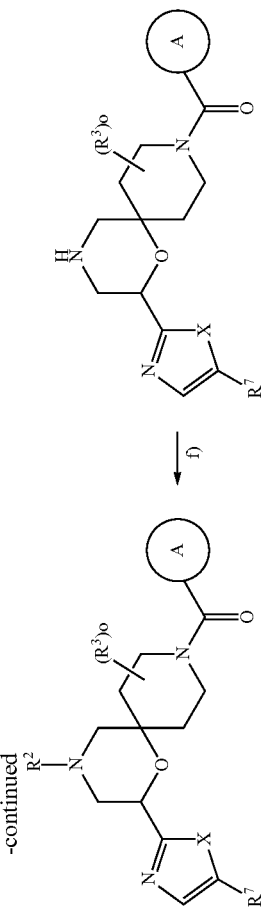

PG$^1$ = acid-labile protecting group (e.g. benzyl);

a) Coupling agent (e.g. T$_3$P, HATU, EDCI), base (e.g. Et$_3$N or DIEA), solvent (e.g. 2-methyltetrahydrofuran, DMF or CH$_3$CN); b) i. Oxidant (e.g. OsO$_4$, NMO), solvent (e.g. acetone/water); ii. Oxidant (e.g. NaIO$_4$), solvent (e.g. THF/water); c) X=S , (e.g. Lawesson's reagent or P$_2$S$_5$), solvent (e.g. THF or toluene); d) X=O, dehydrating reagent (e.g. POCl$_3$, I$_2$/Ph$_3$P or Burgess salt), base (e.g. Et$_3$N), solvent (e.g. toluene, DCM, THF); e) PG = benzyl; (e.g. Pd/C, or Pd(OH)$_2$/C, H$_2$ or ammonium formate) solvent (e.g. iPrOH, EtOH or CH$_3$CN); f) R$^2$—X (X = leaving group: halo, OTs, OTf), base (e.g. K$_2$CO$_3$, NaHCO$_3$, Et$_3$N), solvent (e.g. EtOH, CH$_3$CN).

Scheme 20

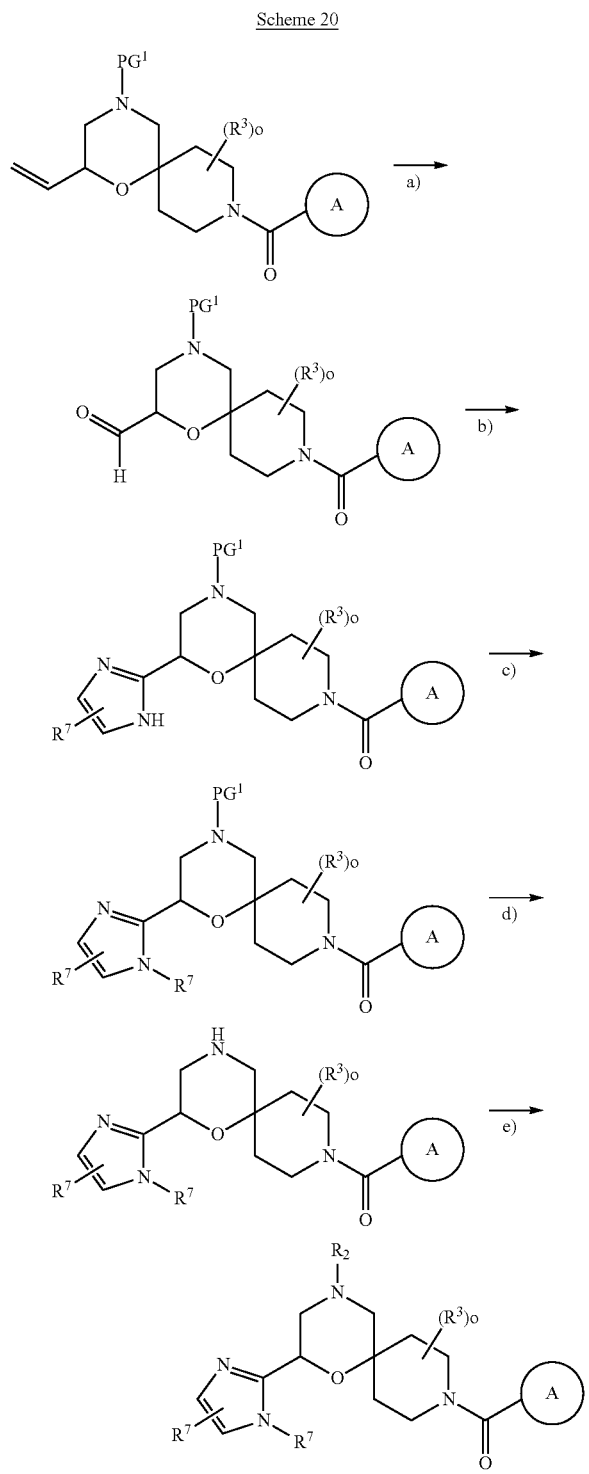

PG¹ = stable protecting group (e.g. benzyl)

a) i. Oxidant (e.g. OsO₄, NMO), solvent (e.g. acetone/water); ii. Oxidant (e.g. NaIO₄), solvent (e.g. THF/water); b) ammonium hydroxide, aldehyde/acyl equivalents (e.g. substituted/unsubstituted glyoxal, substituted 2-acetoxy ketones, alpha-bromo ketones), solvent (e.g. MeOH); c) NaH, MeI, DMF/THF; d) PG¹ = benzyl; (e.g. Pd/C, or Pd(OH)₂/C, H₂ or ammonium formate), solvent (e.g. iPrOH, EtOH or CH₃CN); e) R² — X (X = leaving group: halo, OTs, OTf), base (e.g. K₂CO₃, Et₃N), solvent (e.g. EtOH, CH₃CN).

Scheme 21

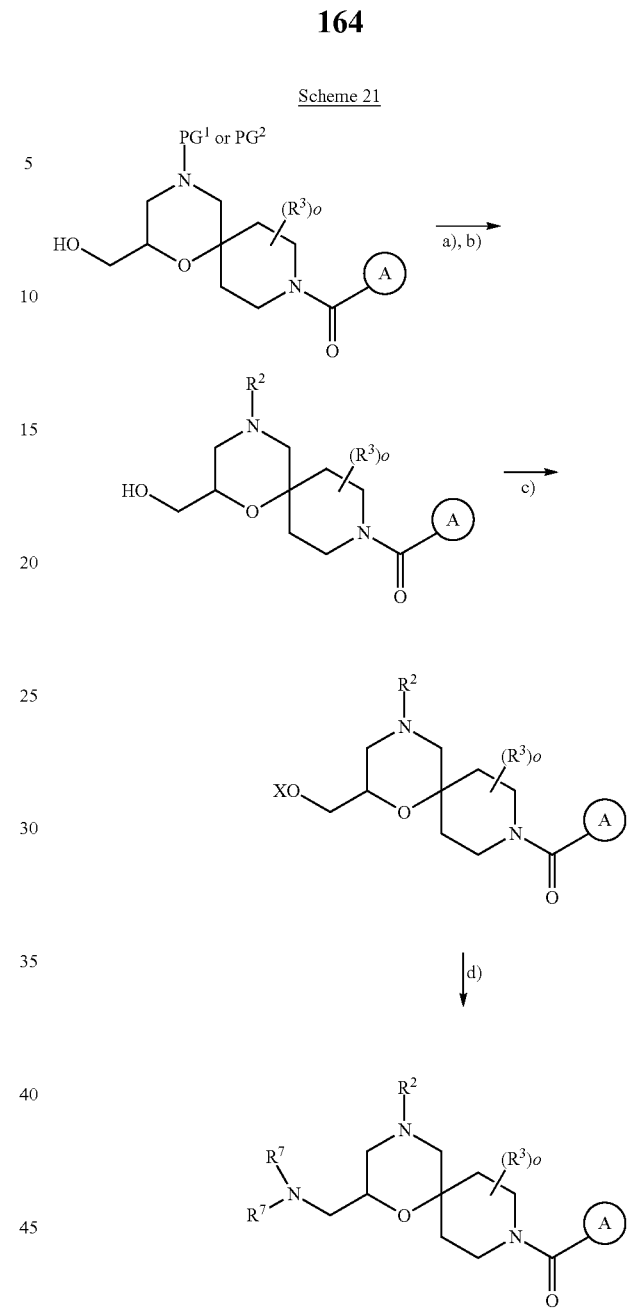

PG¹ = acid-stable protection group (e.g. benzyl); PG² = acid-labile protecting group (e.g. Boc) a) when PG¹ = benzyl; catalyst (e.g. Pd/C or Pd(OH)₂/C), hydrogen source (e.g. H₂ or ammonium formate), solvent (e.g. MeOH, EtOH or iPrOH,);
b) R² — X (X = leaving group: halo, OTs, OTf), base (e.g. K₂CO₃, NaHCO₃, Et₃N), solvent (e.g. THF, DCM, EtOH, CH₃CN, DMF); c) X (X = leaving group: MsCl, TsCl), base (e.g. Et₃N), solvent (e.g. THF, DMF); d) R⁷ — NH — R⁷
(R⁷, R⁷ = alkyl, cycloalkyl or heterocycle, base (e.g. NaH), solvent (e.g. DCM, THF, DMF).

Scheme 22

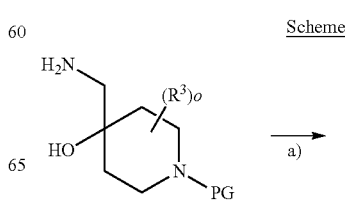

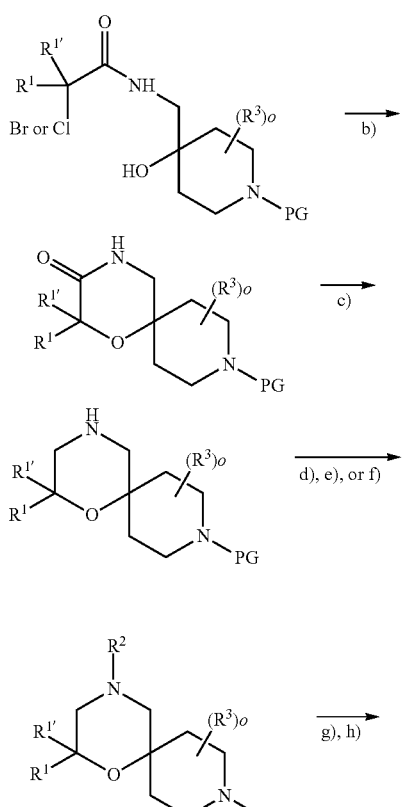

PG = acid-labile protecting group (e.g. Boc).
a) ethyl 2-halo-2,2-disubstituted acetate, solvent (e.g. DMF, THF, DCM, CH₃CN);
b) base (e.g. KOtBu), solvent (e.g. THF); c) reductase (e.g. borane-dimethylsulfide), solvent (e.g. THF); d) R² — X (X = leaving group: halo, OTs, OTf), base (e.g. K₂CO₃, NaHCO₃, Et₃N), solvent (e.g. THF, DCM, EtOH, CH₃CN, DMF);
e) reductive amination conditions, e.g. NaBH(OAc)₃, DCE, AcOH, TEA, appropriate ketone or aldehyde; f) nucelphilic substitution conditions, e.g. aryl halide, DMSO, heat; g) deprotection conditions for PG: H⁺ (e.g. HCl or TFA); h) A — CO₂H , coupling agent (e.g. HATU or EDCl), base (e.g. Et₃N iPrNEt), solvent (e.g. DMF, CH₃CN or CH₂Cl₂).

Scheme 23

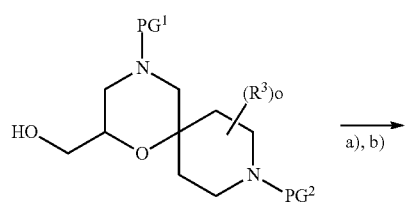

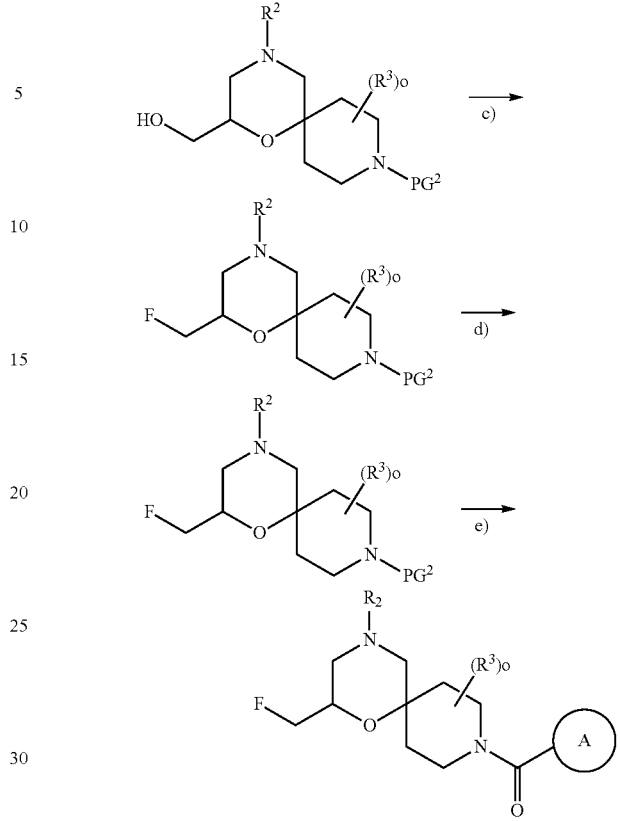

PG¹ = acid-stable protecting group (e.g. benzyl); PG² = acid-labile protecting group (e.g. Boc)

a) when PG¹ = benzyl; catalyst (e.g. Pd/C or Pd(OH)₂/C), hydrogen source (e.g. ammonium formate), solvent (e.g. MeOH, EtOH or iPrOH,); b) R²—X (X = leaving group: halo, OTs, OTf), base (e.g. K₂CO₃, NaHCO₃, Et₃N), solvent (e.g. THF, DCM, EtOH, CH₃CN, DMF); c) diethylaminosulfur trifluoride, DCM; d) deprotection conditions for PG²: H⁺ (e.g. HCl or TFA); e)  A — CO₂H, coupling agent (e.g. HATU or EDCl), base (e.g. Et₃N or iPr₂NEt), solvent (e.g. DMF, CH₃CN or CH₂Cl₂).

Uses, Formulation and Administration
Pharmaceutically Acceptable Compositions

As discussed above, the invention provides compounds that are inhibitors of voltage-gated sodium ion channels, and thus the present compounds are useful for the treatment of diseases, disorders, and conditions including, but not limited to acute, chronic, neuropathic, or inflammatory pain, arthritis, migraine, cluster headaches, trigeminal neuralgia, herpetic neuralgia, general neuralgias, epilepsy or epilepsy conditions, neurodegenerative disorders, psychiatric disorders such as anxiety and depression, myotonia, arrhythmia, movement disorders, neuroendocrine disorders, ataxia, multiple sclerosis, irritable bowel syndrome, and incontinence.

Accordingly, in another aspect of the invention, pharmaceutically acceptable compositions are provided, wherein these compositions comprise any of the compounds as described herein, and optionally comprise a pharmaceutically acceptable carrier, adjuvant or vehicle. In certain embodiments, these compositions optionally further comprise one or more additional therapeutic agents.

It will also be appreciated that certain of the compounds of invention can exist in free form for treatment, or where appropriate, as a pharmaceutically acceptable derivative thereof. According to the invention, a pharmaceutically acceptable derivative includes, but is not limited to, pharmaceutically acceptable salts, esters, salts of such esters, or any other adduct or derivative which upon administration to a subject in need is capable of providing, directly or indirectly, a compound as otherwise described herein, or a metabolite or residue thereof.

As used herein, the term "pharmaceutically acceptable salt" refers to those salts which are, within the scope of sound medical judgement, suitable for use in contact with the tissues of humans and lower animals without undue toxicity, irritation, allergic response and the like, and are commensurate with a reasonable benefit/risk ratio. A "pharmaceutically acceptable salt" means any non-toxic salt or salt of an ester of a compound of this invention that, upon administration to a recipient, is capable of providing, either directly or indirectly, a compound of this invention or an inhibitorily active metabolite or residue thereof. As used herein, the term "inhibitorily active metabolite or residue thereof" means that a metabolite or residue thereof is also an inhibitor of a voltage-gated sodium ion channel.

Pharmaceutically acceptable salts are well known in the art. For example, S. M. Berge, et al. describe pharmaceutically acceptable salts in detail in J. Pharmaceutical Sciences, 1977, 66, 1-19, incorporated herein by reference. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium and $N^+(C_{1-4}alkyl)_4$ salts. This invention also envisions the quaternization of any basic nitrogen-containing groups of the compounds disclosed herein. Water or oil-soluble or dispersable products may be obtained by such quaternization. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, loweralkyl sulfonate and aryl sulfonate.

As described above, the pharmaceutically acceptable compositions of the invention additionally comprise a pharmaceutically acceptable carrier, adjuvant, or vehicle, which, as used herein, includes any and all solvents, diluents, or other liquid vehicle, dispersion or suspension aids, surface active agents, isotonic agents, thickening or emulsifying agents, preservatives, solid binders, lubricants and the like, as suited to the particular dosage form desired. Remington's Pharmaceutical Sciences, Sixteenth Edition, E. W. Martin (Mack Publishing Co., Easton, Pa., 1980) discloses various carriers used in formulating pharmaceutically acceptable compositions and known techniques for the preparation thereof. Except insofar as any conventional carrier medium is incompatible with the compounds of the invention, such as by producing any undesirable biological effect or otherwise interacting in a deleterious manner with any other component(s) of the pharmaceutically acceptable composition, its use is contemplated to be within the scope of this invention. Some examples of materials which can serve as pharmaceutically acceptable carriers include, but are not limited to, ion exchangers, alumina, aluminum stearate, lecithin, serum proteins, such as human serum albumin, buffer substances such as phosphates, glycine, sorbic acid, or potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, polyacrylates, waxes, polyethylene-polyoxypropylene-block polymers, wool fat, sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols; such a propylene glycol or polyethylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

Uses of Compounds and Pharmaceutically Acceptable Compositions

In yet another aspect, a method for the treatment or lessening the severity of acute, chronic, neuropathic, or inflammatory pain, arthritis, migraine, cluster headaches, trigeminal neuralgia, herpetic neuralgia, general neuralgias, epilepsy or epilepsy conditions, neurodegenerative disorders, psychiatric disorders such as anxiety and depression, dipolar disorder, myotonia, arrhythmia, movement disorders, neuroendocrine disorders, ataxia, multiple sclerosis, irritable bowel syndrome, incontinence, visceral pain, osteoarthritis pain, postherpetic neuralgia, diabetic neuropathy, radicular pain, sciatica, back pain, head or neck pain, severe or intractable pain, nociceptive pain, breakthrough pain, postsurgical pain, or cancer pain is provided comprising administering an effective amount of a compound, or a pharmaceutically acceptable composition comprising a compound to a subject in need thereof.

In certain embodiments, a method of treatment or lessening the severity of stroke, cerebral ischemia, traumatic brain injury, amyotrophic lateral sclerosis, stress- or exercise induced angina, palpitations, hypertension, migraine, or abnormal gastro-intestinal motility is provided comprising administering an effective amount of a compound, or a pharmaceutically acceptable composition comprising a compound to a subject in need thereof.

In certain embodiments, a method for the treatment or lessening the severity of acute, chronic, neuropathic, or inflammatory pain is provided comprising administering an effective amount of a compound or a pharmaceutically acceptable composition to a subject in need thereof. In certain other embodiments, a method for the treatment or lessening the severity of radicular pain, sciatica, back pain, head pain, or neck pain is provided comprising administering an effective amount of a compound or a pharmaceutically acceptable composition to a subject in need thereof. In still other embodiments, a method for the treatment or lessening the severity of severe or intractable pain, acute pain, postsurgical pain, back pain, tinnitis or cancer pain is provided comprising administering an effective amount of a compound or a pharmaceutically acceptable composition to a subject in need thereof.

In certain embodiments, a method for the treatment or lessening the severity of femur cancer pain; non-malignant chronic bone pain; rheumatoid arthritis; osteoarthritis; spinal stenosis; neuropathic low back pain; neuropathic low back pain; myofascial pain syndrome; fibromyalgia; temporomandibular joint pain; chronic visceral pain, including, abdominal; pancreatic; IBS pain; chronic and acute headache pain; migraine; tension headache, including, cluster headaches; chronic and acute neuropathic pain, including, post-herpetic neuralgia; diabetic neuropathy; HIV-associated neuropathy; trigeminal neuralgia; Charcot-Marie Tooth neuropathy; hereditary sensory neuropathies; peripheral nerve injury; painful neuromas; ectopic proximal and distal discharges; radiculopathy; chemotherapy induced neuropathic pain; radiotherapy-induced neuropathic pain; post-mastectomy pain; central pain; spinal cord injury pain; post-stroke pain; thalamic pain; complex regional pain syndrome; phantom pain; intractable pain; acute pain, acute post-operative pain; acute musculoskeletal pain; joint pain; mechanical low back pain; neck pain; tendonitis; injury/exercise pain; acute visceral pain, including, abdominal pain; pyelonephritis; appendicitis; cholecystitis; intestinal obstruction; hernias; etc; chest pain, including, cardiac Pain; pelvic pain, renal colic pain, acute obstetric pain, including, labor pain; cesarean section pain; acute inflammatory, burn and trauma pain; acute intermittent pain, including, endometriosis; acute herpes zoster pain; sickle cell anemia; acute pancreatitis; breakthrough pain; orofacial pain including sinusitis pain, dental pain; multiple sclerosis (MS) pain; pain in depression; leprosy pain; behcet's disease pain; adiposis dolorosa; phlebitic pain; Guillain-Barre pain; painful legs and moving toes; Haglund syndrome; erythromelalgia pain; Fabry's disease pain; bladder and urogenital disease, including, urinary incontinence; hyperactivity bladder; painful bladder syndrome; interstitial cyctitis (IC); or prostatitis; complex regional pain syndrome (CRPS), type I and type II; angina-induced pain is provided, comprising administering an effective amount of a compound or a pharmaceutically acceptable composition to a subject in need thereof.

In certain embodiments of the invention an "effective amount" of the compound or pharmaceutically acceptable composition is that amount effective for treating or lessening the severity of one or more of acute, chronic, neuropathic, or inflammatory pain, arthritis, migraine, cluster headaches, trigeminal neuralgia, herpetic neuralgia, general neuralgias, epilepsy or epilepsy conditions, neurodegenerative disorders, psychiatric disorders such as anxiety and depression, myotonia, arrhythmia, movement disorders, neuroendocrine disorders, ataxia, multiple sclerosis, irritable bowel syndrome, incontinence, visceral pain, osteoarthritis pain, postherpetic neuralgia, diabetic neuropathy, radicular pain, sciatica, back pain, head or neck pain, severe or intractable pain, nociceptive pain, breakthrough pain, postsurgical pain, tinnitis or cancer pain.

The compounds and compositions, according to the method of the invention, may be administered using any amount and any route of administration effective for treating or lessening the severity of one or more of acute, chronic, neuropathic, or inflammatory pain, arthritis, migraine, cluster headaches, trigeminal neuralgia, herpetic neuralgia, general neuralgias, epilepsy or epilepsy conditions, neurodegenerative disorders, psychiatric disorders such as anxiety and depression, myotonia, arrhythmia, movement disorders, neuroendocrine disorders, ataxia, multiple sclerosis, irritable bowel syndrome, incontinence, visceral pain, osteoarthritis pain, postherpetic neuralgia, diabetic neuropathy, radicular pain, sciatica, back pain, head or neck pain, severe or intractable pain, nociceptive pain, breakthrough pain, postsurgical pain, tinnitis or cancer pain. The exact amount required will vary from subject to subject, depending on the species, age, and general condition of the subject, the severity of the infection, the particular agent, its mode of administration, and the like. The compounds of the invention are preferably formulated in dosage unit form for ease of administration and uniformity of dosage. The expression "dosage unit form" as used herein refers to a physically discrete unit of agent appropriate for the subject to be treated. It will be understood, however, that the total daily usage of the compounds and compositions of the invention will be decided by the attending physician within the scope of sound medical judgment. The specific effective dose level for any particular subject or organism will depend upon a variety of factors including the disorder being treated and the severity of the disorder; the activity of the specific compound employed; the specific composition employed; the age, body weight, general health, sex and diet of the subject; the time of administration, route of administration, and rate of excretion of the specific compound employed; the duration of the treatment; drugs used in combination or coincidental with the specific compound employed, and like factors well known in the medical arts. The term "subject" or "patient", as used herein, means an animal, preferably a mammal, and most preferably a human.

The pharmaceutically acceptable compositions of this invention can be administered to humans and other animals orally, rectally, parenterally, intracisternally, intravaginally, intraperitoneally, topically (as by powders, ointments, or drops), bucally, as an oral or nasal spray, or the like, depending on the severity of the infection being treated. In certain embodiments, the compounds of the invention may be administered orally or parenterally at dosage levels of about 0.01 mg/kg to about 50 mg/kg and preferably from about 1 mg/kg to about 25 mg/kg, of subject body weight per day, one or more times a day, to obtain the desired therapeutic effect.

Liquid dosage forms for oral administration include, but are not limited to, pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a compound of the invention, it is often desirable to slow the absorption of the compound from subcutaneous or intramuscular injection. This may be accomplished by the use of a liquid suspension of crystalline or amorphous material with poor water solubility. The rate of absorption of the compound then depends upon its rate of dissolution that, in turn, may depend upon crystal size and crystalline form. Alternatively, delayed absorption of a parenterally administered compound form is accomplished by dissolving or suspending the compound in an oil vehicle. Injectable depot forms are made by forming microencapsule matrices of the compound in biodegradable polymers such as polylactide-polyglycolide. Depending upon the ratio of compound to polymer and the nature of the particular polymer employed, the rate of compound release can be controlled. Examples of other biodegradable polymers include poly (orthoesters) and poly(anhydrides). Depot injectable formulations are also prepared by entrapping the compound in liposomes or microemulsions that are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar—agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes. Solid compositions of a similar type may also be employed as fillers in soft and hard-filled gelatin capsules using such excipients as lactose or milk sugar as well as high molecular weight polethylene glycols and the like.

The active compounds can also be in microencapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, eardrops, and eye drops are also contemplated as being within the scope of this invention. Additionally, the invention contemplates the use of transdermal patches, which have the added advantage of providing controlled delivery of a compound to the body. Such dosage forms are prepared by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

As described generally above, the compounds of the invention are useful as inhibitors of voltage-gated sodium ion channels. In one embodiment, the compounds and compositions of the invention are inhibitors of one or more of NaV1.1, NaV1.2, NaV1.3, NaV1.4, NaV1.5, NaV1.6, NaV1.7, NaV1.8, or NaV1.9, and thus, without wishing to be bound by any particular theory, the compounds and compositions are particularly useful for treating or lessening the severity of a disease, condition, or disorder where activation or hyperactivity of one or more of NaV1.1, NaV1.2, NaV1.3, NaV1.4, NaV1.5, NaV1.6, NaV1.7, NaV1.8, or NaV1.9 is implicated in the disease, condition, or disorder. When activation or hyperactivity of NaV1.1, NaV1.2, NaV1.3, NaV1.4, NaV1.5, NaV1.6, NaV1.7, NaV1.8, or NaV1.9 is implicated in a particular disease, condition, or disorder, the disease, condition, or disorder may also be referred to as a "NaV1.1, NaV1.2, NaV1.3, NaV1.4, NaV1.5, NaV1.6, NaV1.7, NaV1.8 or NaV1.9-mediated disease, condition or disorder". Accordingly, in another aspect, the invention provides a method for treating or lessening the severity of a disease, condition, or disorder where activation or hyperactivity of one or more of NaV1.1, NaV1.2, NaV1.3, NaV1.4, NaV1.5, NaV1.6, NaV1.7, NaV1.8, or NaV1.9 is implicated in the disease state.

The activity of a compound utilized in this invention as an inhibitor of NaV1.1, NaV1.2, NaV1.3, NaV1.4, NaV1.5, NaV1.6, NaV1.7, NaV1.8, or NaV1.9 may be assayed according to methods described generally in the Examples herein, or according to methods available to one of ordinary skill in the art.

In certain exemplary embodiments, compounds of the invention are useful as inhibitors of NaV1.7 and/or NaV1.8.

It will also be appreciated that the compounds and pharmaceutically acceptable compositions of the invention can be employed in combination therapies, that is, the compounds and pharmaceutically acceptable compositions can be administered concurrently with, prior to, or subsequent to, one or more other desired therapeutics or medical procedures. The particular combination of therapies (therapeutics or procedures) to employ in a combination regimen will take into account compatibility of the desired therapeutics and/or procedures and the desired therapeutic effect to be achieved. It will also be appreciated that the therapies employed may achieve a desired effect for the same disorder (for example, an inventive compound may be administered concurrently with another agent used to treat the same disorder), or they may achieve different effects (e.g., control of any adverse effects). As used herein, additional therapeutic agents that are normally administered to treat or prevent a particular disease, or condition, are known as "appropriate for the disease, or condition, being treated". For example, exemplary additional therapeutic agents include, but are not limited to: nonopioid analgesics (indoles such as Etodolac, Indomethacin, Sulindac, Tolmetin; naphthylalkanones such sa Nabumetone; oxicams such as Piroxicam; para-aminophenol derivatives, such as Acetaminophen; propionic acids such as Fenoprofen, Flurbiprofen, Ibuprofen, Ketoprofen, Naproxen, Naproxen sodium, Oxaprozin; salicylates such as Asprin, Choline magnesium trisalicylate, Diflunisal; fenamates such as meclofenamic acid, Mefenamic acid; and pyrazoles such as Phenylbutazone); or opioid (narcotic) agonists (such as Codeine, Fentanyl, Hydromorphone, Levorphanol, Meperidine, Methadone, Morphine, Oxycodone, Oxymorphone, Propoxyphene, Buprenorphine, Butorphanol, Dezocine, Nalbuphine, and Pentazocine). Additionally, nondrug analgesic approaches may be utilized in conjunction with administration of one or more compounds of the invention. For example, anesthesiologic (intraspinal infusion, neural blocade), neurosurgical (neurolysis of CNS pathways), neurostimulatory (transcutaneous electrical nerve stimulation, dorsal column stimulation), physiatric (physical therapy, orthotic devices, diathermy), or psychologic (cognitive methods-hypnosis, biofeedback, or behavioral methods) approaches may also be utilized. Additional appropriate therapeutic agents or approaches are described generally in The Merck Manual, Seventeenth Edition, Ed. Mark H. Beers and Robert Berkow, Merck Research Laboratories, 1999, and the Food and Drug Administration website, www.fda.gov, the entire contents of which are hereby incorporated by reference.

In another embodiment, additional appropriate therapeutic agents are selected from the following:

(1) an opioid analgesic, e.g. morphine, heroin, hydromorphone, oxymorphone, levorphanol, levallorphan, methadone, meperidine, fentanyl, cocaine, codeine, dihydrocodeine, oxycodone, hydrocodone, propoxyphene, nalmefene, nalorphine, naloxone, naltrexone, buprenorphine, butorphanol, nalbuphine or pentazocine;

(2) a nonsteroidal antiinflammatory drug (NSAID), e.g. aspirin, diclofenac, diflusinal, etodolac, fenbufen, fenoprofen, flufenisal, flurbiprofen, ibuprofen, indomethacin, ketoprofen, ketorolac, meclofenamic acid, mefenamic acid, meloxicam, nabumetone, naproxen, nimesulide, nitroflurbiprofen, olsalazine, oxaprozin, phenylbutazone, piroxicam, sulfasalazine, sulindac, tolmetin or zomepirac;

(3) a barbiturate sedative, e.g. amobarbital, aprobarbital, butabarbital, butabital, mephobarbital, metharbital, methohexital, pentobarbital, phenobartital, secobarbital, talbutal, theamylal or thiopental;

(4) a benzodiazepine having a sedative action, e.g. chlordiazepoxide, clorazepate, diazepam, flurazepam, lorazepam, oxazepam, temazepam or triazolam;

(5) an Hi antagonist having a sedative action, e.g. diphenhydramine, pyrilamine, promethazine, chlorpheniramine or chlorcyclizine;

(6) a sedative such as glutethimide, meprobamate, methaqualone or dichloralphenazone;

(7) a skeletal muscle relaxant, e.g. baclofen, carisoprodol, chlorzoxazone, cyclobenzaprine, methocarbamol or orphrenadine;

(8) an NMDA receptor antagonist, e.g. dextromethorphan ((+)-3-hydroxy-N-methylmorphinan) or its metabolite dextrorphan ((+)-3-hydroxy-N-methylmorphinan), ketamine, memantine, pyrroloquinine quinine, cis-4-(phosphonomethyl)-2-piperidinecarboxylic acid, budipine, EN-3231 (MorphiDex(R), a combination formulation of morphine and dextromethorphan), topiramate, neramexane or perzinfotel including an NR2B antagonist, e.g. ifenprodil, traxoprodil or (−)-(R)-6-{2-[4-(3-fluorophenyl)-4-hydroxy-1-piperidinyl]-1-hydroxyethyl-3,4-dihydro-2(1H)-quinolinone;

(9) an alpha-adrenergic, e.g. doxazosin, tamsulosin, clonidine, guanfacine, dexmetatomidine, modafinil, or 4-amino-6,7-dimethoxy-2-(5-methane-sulfonamido-1,2,3,4-tetrahydroisoquinol-2-yl)-5-(2-pyridyl)quinazoline;

(10) a tricyclic antidepressant, e.g. desipramine, imipramine, amitriptyline or nortriptyline;

(11) an anticonvulsant, e.g. carbamazepine, lamotrigine, topiratmate or valproate;

(12) a tachykinin (NK) antagonist, particularly an NK-3, NK-2 or NK-I antagonist, e.g. ([alpha]R,9R)-7-[3,5-bis(trifluoromethyl)benzyl]-8,9,10,11-tetrahydro-9-methyl-5-(4-methylphenyl)-7H-[1,4]diazocino[2,1-g][1,7]-naphthyridine-6-13-dione (TAK-637), 5-[[(2R,3S)-2-[(1R)-1-[3,5-bis(trifluoromethyl)phenyl]ethoxy-3-(4-fluorophenyl)-4-morpholinyl]-methyl]-1,2-dihydro-3H-1,2,4-triazol-3-one (MK-869), aprepitant, lanepitant, dapitant or 3-[[2-methoxy-5-(trifluoromethoxy)phenyl]-methylamino]-2-phenylpiperidine (2S,3S);

(13) a muscarinic antagonist, e.g. oxybutynin, tolterodine, propiverine, tropsium chloride, darifenacin, solifenacin, temiverine and ipratropium;

(14) a COX-2 selective inhibitor, e.g. celecoxib, rofecoxib, parecoxib, valdecoxib, deracoxib, etoricoxib, or lumiracoxib;

(15) a coal-tar analgesic, in particular paracetamol;

(16) a neuroleptic such as droperidol, chlorpromazine, haloperidol, perphenazine, thioridazine, mesoridazine, trifluoperazine, fluphenazine, clozapine, olanzapine, risperidone, ziprasidone, quetiapine, sertindole, aripiprazole, sonepiprazole, blonanserin, iloperidone, perospirone, raclopride, zotepine, bifeprunox, asenapine, lurasidone, amisulpride, balaperidone, palindore, eplivanserin, osanetant, rimonabant, meclinertant, Miraxion(R) or sarizotan;

(17) a vanilloid receptor agonist (e.g. resinferatoxin) or antagonist (e.g. capsazepine);

(18) a beta-adrenergic such as propranolol;

(19) a local anaesthetic such as mexiletine;

(20) a corticosteroid such as dexamethasone;

(21) a 5-HT receptor agonist or antagonist, particularly a 5-HTi B/I D agonist such as eletriptan, sumatriptan, naratriptan, zolmitriptan or rizatriptan;

(22) a 5-HT2A receptor antagonist such as R(+)-alpha-(2,3-dimethoxy-phenyl)-1-[2-(4-fluorophenylethyl)]-4-piperidinemethanol (MDL-100907);

(23) a cholinergic (nicotinic) analgesic, such as ispronicline (TC-1734), (E)-N-methyl-4-(3-pyridinyl)-3-buten-1-amine (RJR-2403), (R)-5-(2-azetidinylmethoxy)-2-chloropyridine (ABT-594) or nicotine;

(24) Tramadol®;

(25) a PDEV inhibitor, such as 5-[2-ethoxy-5-(4-methyl-1-piperazinyl-sulphonyl)phenyl]-1-methyl-3-n-propyl-1,6-dihydro-7H-pyrazolo[4,3-d]pyrimidin-7-one (sildenafil), (6R,12aR)-2,3,6,7,12,12a-hexahydro-2-methyl-6-(3,4-methylenedioxyphenyl)-pyrazino[2',1':6,1]-pyrido[3,4-b]indole-1,4-dione (IC-351 or tadalafil), 2-[2-ethoxy-5-(4-ethyl-piperazin-1-yl-1-sulphonyl)-phenyl]-5-methyl-7-propyl-3H-imidazo[5,1-f][1,2,4]triazin-4-one (vardenafil), 5-(5-acetyl-2-butoxy-3-pyridinyl)-3-ethyl-2-(1-ethyl-3-azetidinyl)-2,6-dihydro-7H-pyrazolo[4,3-d]pyrimidin-7-one, 5-(5-acetyl-2-propoxy-3-pyridinyl)-3-ethyl-2-(1-isopropyl-3-azetidinyl)-2,6-dihydro-7H-pyrazolo[4,3-<i]pyrimidm-7-one, 5-[2-ethoxy-5-(4-ethylpiperazin-1-ylsulphonyl)pyridin-3-yl]-3-ethyl-2-[2-methoxyethyl]-2,6-dihydro-7H-pyrazolo[4,3-d]pyrimidin-7-one, 4-[(3-chloro-4-methoxybenzyl)amino]-2-[(2S)-2-(hydroxymethyl) pyrrolidin-1-yl]-N-(pyrimidin-2-ylmethyl)pyrimidine-5-carboxamide, 3-(1-methyl-7-oxo-3-propyl-6,7-dihydro-1H-pyrazolo[4,3-d]pyrimidin-5-yl)-N-[2-(1-methylpyrrolidin-2-yl)ethyl]-4-propoxybenzenesulfonamide; (z) an alpha-2-delta ligand such as gabapentin, pregabalin, 3-methyl gabapentin, (1[alpha],3[alpha],5[alpha])(3-amino-methyl-bicyclo[3.2.0]hept-3-yl)-acetic acid, (3S,5R)-3-aminomethyl-5-methyl-heptanoic acid, (3S,5R)-3-amino-5-methyl-heptanoic acid, (3S,5R)-3-amino-5-methyl-octanoic acid, (2S,4S)-4-(3-chlorophenoxy)proline, (2S,4S)-4-(3-fluorobenzyl)-proline, [(1R,5R,6S)-6-(aminomethyl)bicyclo [3.2.0]hept-6-yl]acetic acid, 3-(1-aminomethyl-cyclohexyl-methyl)-4H-[1,2,4]oxadiazol-5-one, C-[1-(1H-tetrazol-5-ylmethyl)-cycloheptyl]-methylamine, (3S,4S)-(1-aminomethyl-3,4-dimethyl-cyclopentyl)-acetic acid, (3S, 5R)-3-aminomethyl-5-methyl-octanoic acid, (3S,5R)-3-amino-5-methyl-nonanoic acid, (3S,5R)-3-amino-5-methyl-octanoic acid, (3R,4R,5R)-3-amino-4,5-dimethyl-heptanoic acid and (3R,4R,5R)-3-amino-4,5-dimethyl-octanoic acid;

(26) a cannabinoid;

(27) metabotropic glutamate subtype 1 receptor (mGluR1) antagonist;

(28) a serotonin reuptake inhibitor such as sertraline, sertraline metabolite demethylsertraline, fluoxetine, norfluoxetine (fluoxetine desmethyl metabolite), fluvoxamine, paroxetine, citalopram, citalopram metabolite desmethylcitalopram, escitalopram, d,l-fenfluramine, femoxetine, ifoxetine, cyanodothiepin, litoxetine, dapoxetine, nefazodone, cericlamine and trazodone;

(29) a noradrenaline (norepinephrine) reuptake inhibitor, such as maprotiline, lofepramine, mirtazepine, oxaprotiline, fezolamine, tomoxetine, mianserin, buprorion, buprorion metabolite hydroxybuproprion, nomifensine and viloxazine (Vivalan(R)), especially a selective noradrenaline reuptake inhibitor such as reboxetine, in particular (S,S)-reboxetine;

(30) a dual serotonin-noradrenaline reuptake inhibitor, such as venlafaxine, venlafaxine metabolite O-desmethyl-venlafaxine, clomipramine, clomipramine metabolite desmethylclomipramine, duloxetine, milnacipran and imipramine;

(31) an inducible nitric oxide synthase (iNOS) inhibitor such as S-[2-[(1-iminoethyl)amino]ethyl]-homocysteine, S-[2-[(1-iminoethyl)-amino]ethyl]-4,4-dioxo-L-cysteine, S-[2-[(1-iminoethyl)amino]ethyl]-2-methyl-L-cysteine, (2S, 5Z)-2-amino-2-methyl-7-[(1-iminoethyl)amino]-5-heptenoic acid, 2-[[(1R,3S)-3-amino-4-hydroxy-1-(5-thiazolyl)-butyl]thio]-S-chloro-5-pyridinecarbonitrile; 2-[[(1R,3S)-3-amino-4-hydroxy-1-(5-thiazolyl)butyl]thio]-4-chlorobenzonitrile, (2S,4R)-2-amino-4-[[2-chloro-5-(trifluoromethyl)phenyl]thio]-5-thiazolebutanol, 2-[[(1R, 3S)-3-amino-4-hydroxy-1-(5-thiazolyl)butyl]thio]-6-(trifluoromethyl)-3 pyridinecarbonitrile, 2-[[(1R,3S)-3-amino-4-hydroxy-1-(5-thiazolyl)butyl]thio]-5-chlorobenzonitrile, N-[4-[2-(3-chlorobenzylamino)ethyl] phenyl]thiophene-2-carboxamidine, or guanidinoethyldisulfide;

(32) an acetylcholinesterase inhibitor such as donepezil;

(33) a prostaglandin E2 subtype 4 (EP4) antagonist such as N-[({2-[4-(2-ethyl-4,6-dimethyl-1H-imidazo[4,5-c]pyridin-1-yl)phenyl]ethyl}amino)-carbonyl]-4-methylbenzene-sulfonamide or 4-[(15)-1-({[5-chloro-2-(3-fluorophenoxy) pyridin-3-yl]carbonyl}amino)ethyl]benzoic acid;

(34) a leukotriene B4 antagonist; such as 1-(3-biphenyl-4-ylmethyl-4-hydroxy-chroman-7-yl)-cyclopentanecarboxylic acid (CP-105696), 5-[2-(2-Carboxyethyl)-3-[6-(4-methoxyphenyl)-5E-hexenyl]oxyphenoxy]-valeric acid (ONO-4057) or DPC-11870,

(35) a 5-lipoxygenase inhibitor, such as zileuton, 6-[(3-fluoro-5-[4-methoxy-3,4,5,6-tetrahydro-2H-pyran-4-yl]) phenoxy-methyl]-1-methyl-2-quinolone (ZD-2138), or 2,3, 5-trimethyl-6-(3-pyridylmethyl),1,4-benzoquinone (CV-6504);

(36) a sodium channel blocker, such as lidocaine;

(37) a 5-HT3 antagonist, such as ondansetron; and the pharmaceutically acceptable salts and solvates thereof.

The amount of additional therapeutic agent present in the compositions of this invention will be no more than the amount that would normally be administered in a composition comprising that therapeutic agent as the only active agent. Preferably the amount of additional therapeutic agent in the presently disclosed compositions will range from about 50% to 100% of the amount normally present in a composition comprising that agent as the only therapeutically active agent.

The compounds of this invention or pharmaceutically acceptable compositions thereof may also be incorporated into compositions for coating an implantable medical device, such as prostheses, artificial valves, vascular grafts, stents and catheters. Accordingly, the invention, in another aspect, includes a composition for coating an implantable device comprising a compound of the invention as described generally above, and in classes and subclasses herein, and a carrier suitable for coating said implantable device. In still another aspect, the invention includes an implantable device coated with a composition comprising a compound of the invention as described generally above, and in classes and subclasses herein, and a carrier suitable for coating said implantable device. Suitable coatings and the general preparation of coated implantable devices are described in U.S. Pat. Nos. 6,099,562; 5,886,026; and 5,304,121. The coatings are typically biocompatible polymeric materials such as a hydrogel polymer, polymethyldisiloxane, polycaprolactone, polyethylene glycol, polylactic acid, ethylene vinyl acetate, and mixtures thereof. The coatings may optionally be further covered by a suitable topcoat of fluorosilicone, polysaccharides, polyethylene glycol, phospholipids or combinations thereof to impart controlled release characteristics in the composition.

Another aspect of the invention relates to inhibiting one or more of NaV1.1, NaV1.2, NaV1.3, NaV1.4, NaV1.5, NaV1.6, NaV1.7, NaV1.8, or NaV1.9, activity in a biological sample or a subject, which method comprises administering to the subject, or contacting said biological sample with a compound of formula I or a composition comprising said compound. The term "biological sample", as used herein, includes, without limitation, cell cultures or extracts thereof; biopsied material obtained from a mammal or extracts thereof; and blood, saliva, urine, feces, semen, tears, or other body fluids or extracts thereof.

Inhibition of one or more of NaV1.1, NaV1.2, NaV1.3, NaV1.4, NaV1.5, NaV1.6, NaV1.7, NaV1.8, or NaV1.9, activity in a biological sample is useful for a variety of purposes that are known to one of skill in the art. Examples of such purposes include, but are not limited to, the study of sodium ion channels in biological and pathological phenomena; and the comparative evaluation of new sodium ion channel inhibitors.

EXAMPLES

General methods. $^1$H NMR (400 MHz or 300 MHz) and $^{13}$C NMR (100 MHz) spectra were obtained as solutions in deuterioacetonitrile (CD$_3$CN), chloroform-d (CDCl$_3$), deuteromethanol (MeOD-d4), or dimethyl sulfoxide-D$_6$ (DMSO). Mass spectra (MS) were obtained using an Applied Biosystems API EX LC/MS system equipped with a Phenomenex 50×4.60 mm luna-5μ C18 column. The LC/MS eluting system was 1-99% or 10-99% acetonitrile in H$_2$O with 0.035% v/v trifluoroacetic acid, 0.035% v/v formic acid, 5 mM HCl or 5 mM ammonium formate using a 3 or 15 minute linear gradient and a flow rate of 12 mL/minute. Silica gel chromatography was performed using silica gel-60 with a particle size of 230-400 mesh. Pyridine, dichloromethane (CH$_2$Cl$_2$), tetrahydrofuran (THF), dimethylformamide (DMF), acetonitrile (ACN), methanol (MeOH), and 1,4-dioxane were from Aldrich Sure-Seal bottles kept under dry nitrogen. All reactions were stirred magnetically unless otherwise noted.

Preparation of 10-phenyl-8-(2,2,2-trifluoroethyl)-11-oxa-3,8-diazaspiro[5.5]undecane

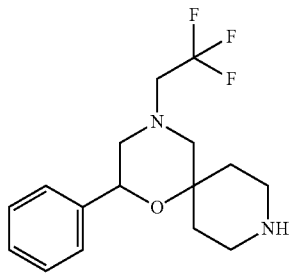 [SMILES: FC(F)(F)CN1CC(c2ccccc2)OC2(CCNCC2)C1]

Step 1:
To a solution of 2-amino-1-phenyl-ethanol (12.0 g, 87.48 mmol) in methanol (60 mL) was added benzaldehyde (9.3 g, 8.9 mL, 87.48 mmol) and the reaction mixture was stirred for 1 hour at room temperature. The reaction mixture was then cooled to 0° C. and sodium borohydride (3.3 g, 87.48 mmol) was added. The reaction mixture was gradually allowed to warm to room temperature and stirred overnight. The reaction mixture was concentrated in vacuo, diluted with water, and filtered. The residue was rinsed with cold isopropanol (3×), then dried in vacuo to give 2-(benzylamino)-1-phenylethanol as white crystals (14.0 g, 70%). ESI-MS m/z calc. 227.1. Found 228.2 (M+1)$^+$; Retention time:0.8 minutes (3 min run). $^1$H NMR (400 MHz, MeOD) δ 7.37-7.27 (m, 8H), 7.27-7.19 (m, 2H), 4.78 (dd, J=8.5, 4.5 Hz, 1H), 3.77 (q, J=13.0 Hz, 2H), 2.82-2.68 (m, 2H).

Step 2:
A solution of 2-(benzylamino)-1-phenylethanol (5.3 g, 23.44 mmol) and tert-butyl 1-oxa-6-azaspiro[2.5]octane-6-carboxylate (5.0 g, 23.44 mmol) in ethanol (30 mL) was heated overnight at 75° C. The solvent was evaporated and the crude material was used in the next step without further purification. ESI-MS m/z calc. 440.2. Found 441.7 (M+1)$^+$; Retention time:1.41 minutes (3 min run).

Step 3:
To tert-butyl 4-[[benzyl-(2-hydroxy-2-phenyl-ethyl)amino]methyl]-4-hydroxy-piperidine-1-carboxylate (6.2 g, 14.07 mmol) was added HBr (60 mL of 48% w/w,) and the reaction mixture was stirred at 55° C. for 10 hours. The reaction mixture was evaporated in vacuo, basified the aqueous with 50% aq. NaOH to pH13, then extracted with DCM (3×75 mL). The combined organics were dried over MgSO$_4$, filtered and concentrated in vacuo to give 4-benzyl-2-phenyl-1-oxa-4,9-diazaspiro[5.5]undecane (4.4 g, 97%) as a yellow oil, which was used directly without further purification. ESI-MS m/z calc. 322.2. Found 323.7 (M+1)$^+$; Retention time: 1.72 minutes (3 min run).

Step 4:
To crude 4-benzyl-2-phenyl-1-oxa-4,9-diazaspiro[5.5]undecane (4.1 g, 12.72 mmol) in DCM (15 mL) was added Boc$_2$O (2.8 g, 2.9 mL, 12.72 mmol) and the reaction mixture was stirred for 2 hours. The solvent was removed in vacuo and the residue was purified by silica gel column chromatography using 0-60% EtOAc/hexane as eluent to give tert-butyl 10-benzyl-8-phenyl-7-oxa-3,10-diazaspiro[5.5]undecane-3-carboxylate as a white foam (3.6 g, 66%). ESI-MS m/z calc. 422.3. Found 423.7 (M+1)$^+$; Retention time: 1.71 minutes (3 min run). $^1$H NMR (400 MHz, CDCl$_3$) δ 7.38-7.25 (m, 10H), 4.88-4.78 (m, 1H), 3.69 (s, 2H), 3.57 (d, J=13.3 Hz, 1H), 3.39 (d, J=13.3 Hz, 1H), 3.35-3.26 (m, 1H), 3.18-3.06 (m, 1H), 3.00-2.91 (m, 1H), 2.67-2.60 (m, 1H), 2.59-2.49 (m, 1H), 2.05-1.89 (m, 2H), 1.64-1.57 (m, 1H), 1.53-1.46 (m, 2H), 1.43 (s, 9H).

Step 5:
To tert-butyl 10-benzyl-8-phenyl-7-oxa-3,10-diazaspiro[5.5]undecane-3-carboxylate (1.58 g, 3.74 mmol) and Pd(OH)$_2$ (280 mg, 0.40 mmol) in ethanol (16 mL) was added ammonium formate (1.10 g, 17.39 mmol) and the reaction mixture was heated to 60° C. for 40 min. The reaction mixture was cooled, filtered, concentrated to 10% of original volume, diluted with ethyl acetate and washed with sat. aq. NaHCO$_3$ (pH 10)/brine. The aqueous was extracted further with ethyl acetate and the combined organics were dried over Na$_2$SO$_4$, filtered and concentrated in vacuo to give tert-butyl 8-phenyl-7-oxa-3,10-diazaspiro[5.5]undecane-3-carboxylate (1.15 g, 93%) as a white solid. ESI-MS m/z calc. 332.2. Found 333.3 (M+1)$^+$; Retention time: 1.13 minutes (3 min run). $^1$H NMR (400 MHz, CDCl$_3$) δ 7.40-7.23 (m, 5H), 4.69 (dd, J=10.7, 2.7 Hz, 1H), 3.76 (br. s, 2H), 3.31 (t, J=10.7 Hz, 1H), 3.17-3.02 (m, 2H), 2.75 (dd, J=35.5, 12.4 Hz, 2H), 2.63 (dd, J=12.3, 10.8 Hz, 1H), 2.49 (d, J=12.5 Hz, 1H), 1.69-1.57 (m, J=12.6 Hz, 1H), 1.57-1.39 (m, 11H).

Step 6:
To tert-butyl 10-phenyl-11-oxa-3,8-diazaspiro[5.5]undecane-3-carboxylate (0.98 g, 2.93 mmol) and NaHCO$_3$ (0.99 g, 11.73 mmol) in ethanol at room temperature was added 2,2,2-trifluoroethyl trifluoromethanesulfonate (0.82 g, 545 μL, 3.52 mmol) and the reaction mixture was heated at 80° C. for 6 hours. The reaction mixture was cooled, the solid precipitate was removed by filtration and the solvent was removed in vacuo. The residue was taken up in DCM and washed sequentially with 1:1 NaOH(1N): NaHCO$_3$ and then brine. The organics were separated, dried over sodium sulfate and concentrated in vacuo to give tert-butyl 10-phenyl-8-(2,2,2-trifluoroethyl)-11-oxa-3,8-diazaspiro[5.5]undecane-3-carboxylate (1.15 g, 95%). ESI-MS m/z calc. 414.2. Found 415.3 (M+1)$^+$; Retention time: 2.46 minutes (3 min run). $^1$H NMR (400 MHz, CDCl$_3$) δ 7.44-7.26 (m, 5H), 4.81 (dd, J=10.5, 2.6 Hz, 1H), 3.73 (s, 2H), 3.31 (s, 1H), 3.09 (s, 1H), 2.98 (m, 3H), 2.74 (dd, J=11.0, 1.5 Hz, 1H), 2.51 (d, J=14.1 Hz, 1H), 2.40-2.29 (m, 2H), 1.58 (s, 3H), 1.44 (s, 9H).

Step 7:

To tert-butyl 10-phenyl-8-(2,2,2-trifluoroethyl)-11-oxa-3,8-diazaspiro[5.5]undecane-3-carboxylate (779 mg, 1.86 mmol) in dichloromethane (5 mL) was added 2,2,2-trifluoroacetic acid (5 mL, 64.90 mmol) at room temperature. The reaction mixture was stirred for 40 minutes, then diluted with dichloromethane (75 mL) and the organic solution was washed with saturated sodium bicarbonate (twice) and then brine. The organic layer was dried over sodium sulfate, filtered and the solvent was removed in vacuo to give 10-phenyl-8-(2,2,2-trifluoroethyl)-11-oxa-3,8-diazaspiro[5.5]undecane as an amber oil (585 mg, 99%). ESI-MS m/z calc. 314.2. Found 315.3 (M+1)$^+$; Retention time: 1.29 minutes (3 min run). $^1$H NMR (400 MHz, CD$_3$CN) δ 7.44-7.25 (m, 5H), 4.82 (dd, J=10.6, 2.8 Hz, 1H), 3.74 (br s, 1H), 3.06 (q, J=9.8 Hz, 2H), 3.02-2.91 (m, 2H), 2.88 (dd, J=11.2, 1.5 Hz, 1H), 2.85-2.74 (m, 3H), 2.34 (d, J=14.8 Hz, 1H), 2.28 (dt, J=10.9, 5.3 Hz, 2H), 1.76-1.64 (m, J=16.0, 8.7, 5.3 Hz, 1H), 1.64-1.52 (m, 2H).

Preparation of 4-(2,2-difluoroethyl)-2-phenyl-1-oxa-4,9-diazaspiro[5.5]undecane

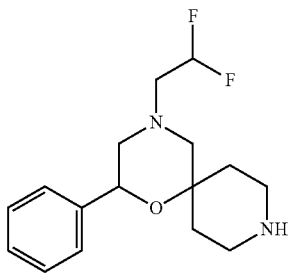 [SMILES: FC(F)CN1CC(c2ccccc2)OC2(CCNCC2)C1]

This compound was prepared using the procedure as described above, using 2-difluoroethyl trifluoromethanesulfonate as the alkylation reagent in step 6.

Preparation of 4-(2,2-difluoroethyl)-2-(4-fluorophenyl)-1-oxa-4,9-diazaspiro[5.5]undecane

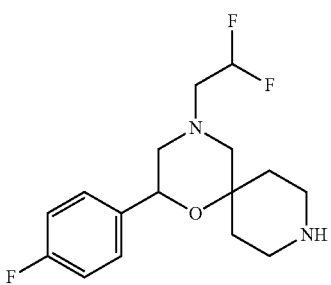 [SMILES: Fc1ccc(C2CN(CC(F)F)CC3(CCNCC3)O2)cc1]

This compound was prepared using the procedure as described above, starting with 2-amino-1-(4-fluorophenyl) ethanol in step 1 and using 2-difluoroethyl trifluoromethanesulfonate as the alkylation reagent in step 6. ESI-MS m/z calc. 314.2. Found 315.2 (M+1)$^+$; Retention time: 1.08 minutes (3 min run).

Preparation of 4-(2,2-difluoroethyl)-2-(4-fluorophenyl)-1-oxa-4,9-diazaspiro[5.5]undecane

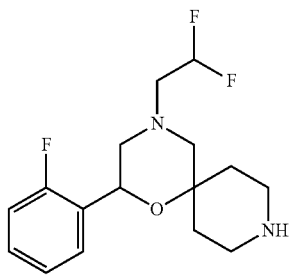 [SMILES: Fc1ccccc1C1CN(CC(F)F)CC2(CCNCC2)O1]

This compound was prepared using the procedure as described above, starting with 2-amino-1-(2-fluorophenyl) ethanol in step 1 and using 2-difluoroethyl trifluoromethanesulfonate as the alkylation reagent in step 6 ESI-MS m/z calc. 314.16058. Found 315.3 (M+1)$^+$; Retention time: 1.32 minutes (3 min run).

Preparation of 2-(2-phenyl-1-oxa-4,9-diazaspiro[5.5]undecan-4-yl)acetonitrile

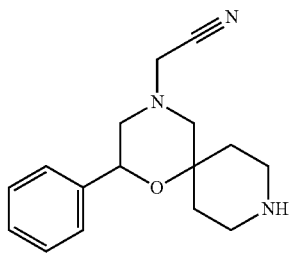 [SMILES: N#CCN1CC(c2ccccc2)OC2(CCNCC2)C1]

This compound was prepared using the procedure as described above, using 2-chloroacetonitrile as the alkylation reagent in step 6. ESI-MS m/z calc. 307.8. Found 309.4 (M+1)$^+$; Retention time: 0.89 minutes (3 min run).

Preparation of 4-benzyl-2-(4-chlorophenyl)-1-oxa-4,9-diazaspiro[5.5]undecane

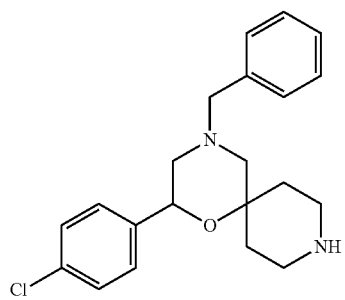 [SMILES: Clc1ccc(C2CN(Cc3ccccc3)CC3(CCNCC3)O2)cc1]

This compound was prepared using the steps 1-4 and 7 in the procedure as described above, starting with 2-amino-1-(4-chlorophenyl)ethanol in step 1. ESI-MS m/z calc. 356.9. Found 357.3 (M+1)$^+$; Retention time: 1.17 minutes (3 min run).

Preparation of 4-benzyl-2-(p-tolyl)-1-oxa-4,9-diazaspiro[5.5]undecane

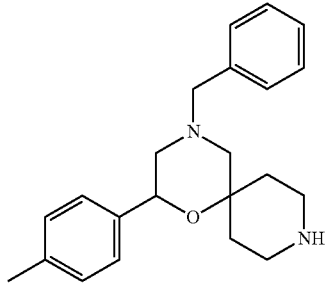 [SMILES: Cc1ccc(C2CN(Cc3ccccc3)CC3(CCNCC3)O2)cc1]

This compound was prepared using the steps 1-3 in the procedure as described above, starting with 2-amino-1-(p-tolyl)ethanol in step 1. ESI-MS m/z calc. 336.5. Found 337.3 (M+1)$^+$; Retention time: 0.65 minutes (3 min run).

Preparation of 8-ethyl-10-phenyl-11-oxa-3,8-diazaspiro[5.5]undecane

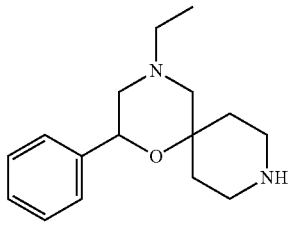 [SMILES: CCN1CC(c2ccccc2)OC2(CCNCC2)C1]

Step 1:
To a solution of tert-butyl 8-phenyl-7-oxa-3,10-diazaspiro[5.5]undecane-3-carboxylate (735 mg, 2.21 mmol) in methanol (10 mL) was added acetaldehyde (107 mg, 136 µL, 2.43 mmol), then sodium cyanoborohydride (195 mg, 1.5 mL, 3.10 mmol) and the reaction mixture was stirred for 2 hours. The reaction mixture was concentrated in vacuo, diluted with DCM (50 mL), washed with 1:1 aq. sat. NaHCO$_3$/25% NaOH (10 mL), and the aqueous layer was extracted with DCM (2×25 mL). The combined organics were dried (MgSO$_4$), concentrated in vacuo and purified by silica gel column chromatography using (0-75% EtOAc/DCM) as eluent to give tert-butyl 8-ethyl-10-phenyl-11-oxa-3,8-diazaspiro[5.5]undecane-3-carboxylate (540 mg, 68%) as a viscous yellow oil. ESI-MS m/z calc. 360.5. Found 361.7 (M+1)$^+$; Retention time: 1.15 minutes (3 min run).

Step 2:
To tert-butyl 8-ethyl-10-phenyl-11-oxa-3,8-diazaspiro[5.5]undecane-3-carboxylate (540 mg, 1.50 mmol) in DCM (1.5 mL) was added 2,2,2-trifluoroacetic acid (1 mL, 12.98 mmol) and the solution was stirred for 30 minutes. The reaction mixture was concentrated in vacuo, diluted with DCM (50 mL), washed with 1:1 sat. aq. Na$_2$CO$_3$/NaHCO$_3$ (10 ml) and the aqueous was extracted further with DCM (2×25 mL). The combined organics were dried (MgSO$_4$) and evaporated to give 8-ethyl-10-phenyl-11-oxa-3,8-diazaspiro[5.5]undecane (390 mg, 100%) as a pale yellow solid, which was used without further purification. ESI-MS m/z calc. 260.4. Found 261.3 (M+1)$^+$; Retention time: 0.3 minutes (3 min run).

Preparation of 8-isobutyl-10-phenyl-11-oxa-3,8-diazaspiro[5.5]undecane

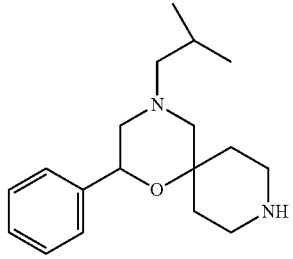 [SMILES: CC(C)CN1CC(c2ccccc2)OC2(CCNCC2)C1]

This compound was prepared following the above procedure, using 2-methylpropanal in step 1. ESI-MS m/z calc. 288.2. Found 289.3 (M+1)$^+$; Retention time: 0.79 minutes (3 min run).

Preparation of 4-ethyl-2-(4-fluorophenyl)-1-oxa-4,9-diazaspiro[5.5]undecane

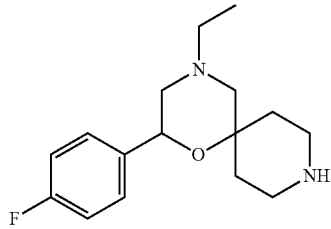 [SMILES: CCN1CC(c2ccc(F)cc2)OC2(CCNCC2)C1]

This compound was prepared following the above procedure, using tert-butyl 2-(4-fluorophenyl)-1-oxa-4,9-diazaspiro[5.5]undecane-9-carboxylate in step 1. ESI-MS m/z calc. 278.2. Found 279.3 (M+1)$^+$; Retention time: 0.20 minutes (3 min run).

Preparation of 4-ethyl-2,2-dimethyl-1-oxa-4,9-diazaspiro[5.5]undecane

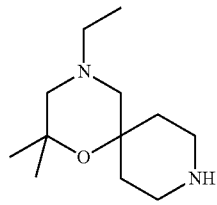

Step 1:
A mixture of N-benzyl-2-methyl-prop-2-en-1-amine (0.57 g, 3.52 mmol) and tert-butyl 1-oxa-6-azaspiro[2.5]octane-6-carboxylate (0.75 g, 3.52 mmol) in ethanol (4 mL) was heated at 80° C. in a sealed vial for 16 hours. The reaction mixture was cooled and concentrated in vacuo to give tert-butyl 4-[[benzyl(2-methylallyl)amino]methyl]-4-hydroxy-piperidine-1-carboxylate (1.32 g, 100%) as a colorless oil. ESI-MS m/z calc. 374.5. Found 375.7 (M+1)+; Retention time: 1.24 minutes (3 min run).

Step 2:

To a solution of tert-butyl 4-[[benzyl(2-methylallyl)amino]methyl]-4-hydroxy-piperidine-1-carboxylate (1.2 g, 3.20 mmol) in 2-methoxy-2-methyl-propane (11 mL) was added aq. NaHCO$_3$ (4.3 mL of 1 M, 4.30 mmol) then iodine (0.9 g, 181 µL, 3.52 mmol) and the reaction mixture was rapidly stirred for 16 hours. The reaction mixture was diluted with ethyl acetate (25 mL), quenched with 5 mL 1 M Na$_2$S$_2$O$_3$ aq., shaken vigorously and separated. The organic layer was washed with 1:1 sat. aq. NaHCO$_3$/1 M Na$_2$S$_2$O$_3$ aq. (10 mL), dried over MgSO$_4$ and concentrated in vacuo to give the iodide intermediate as a colorless oil. The oil was dissolved in DMSO (4 mL), and NaBH$_4$ (0.1 g, 3.81 mmol) was added and the reaction mixture was heated at 100° C. for 2 hours. A further aliquot of NaBH$_4$ (0.05 g, 1.32 mmol) was added and the reaction mixture was heated at 100° C. for 2 hours. After cooling, the reaction was quenched with 5 M aq. HCl (5 mL), stirred for 15 minutes, then added 5 M aq. NaOH (5 mL) and 1M aq. Na$_2$S$_2$O$_3$ (5 mL). The reaction mixture was vigorously stirred for 16 hours, then extracted with ethyl acetate (3×5 mL), dried over MgSO$_4$ then purified by silica gel column chromatography using 0-100% EtOAc/hexane as eluent to give tert-butyl 2-benzyl-4,4-dimethyl-5-oxa-2,9-diazaspiro[5.5]undecane-9-carboxylate (0.5 g, 42%) as a colorless oil. ESI-MS m/z calc. 374.5. Found 375.7 (M+1)+; Retention time: 1.24 minutes (3 min run).

Step 3:

To tert-butyl 2-benzyl-4,4-dimethyl-5-oxa-2,9-diazaspiro[5.5]undecane-9-carboxylate (560 mg, 1.50 mmol) was added hydrogen chloride (7.5 mL of 4 M in dioxane, 29.90 mmol), followed by ethanol (2 mL) and the reaction mixture was stirred for 30 minutes. The reaction mixture was concentrated in vacuo, dissolved in water (5 mL), washed with methyl tert-butyl ether (5 mL), basified with solid NaHCO$_3$ then adjusted to pH 13-14 with 50% aq. NaOH. The aqueous layer was extracted with ethyl acetate (3×25 mL), dried over MgSO$_4$ and concentrated to give 2-benzyl-4,4-dimethyl-5-oxa-2,9-diazaspiro[5.5]undecane (400 mg, 98%) as a yellow oil, which was used directly without further purification. ESI-MS m/z calc. 274.4. Found 275.5 (M+1)+; Retention time: 0.75 minutes (3 min run).

Step 4:

To 2-benzyl-4,4-dimethyl-5-oxa-2,9-diazaspiro[5.5]undecane (170 mg, 0.62 mmol) and pyridine (98 mg, 100 µL, 1.24 mmol) in DCM (2 mL) at −78° C. was added dropwise trifluoroacetic anhydride (130 mg, 86 µL, 0.62 mmol) and the reaction mixture was allowed to warm to room temperature over 16 hours. The reaction mixture was then concentrated in vacuo and purified by silica gel column chromatography using 0-100% EtOAc/DCM as eluent to give 1-(8-benzyl-10,10-dimethyl-11-oxa-3,8-diazaspiro[5.5]undecan-3-yl)-2,2,2-trifluoro-ethanone (160 mg, 70%)as a colorless oil. ESI-MS m/z calc. 370.4. Found 371.1 (M+1)+; Retention time: 1.48 minutes (3 min run).

Step 5:

A mixture of acetic acid (100 µL, 1.76 mmol), Pd(OH)$_2$ (11 mg, 0.02 mmol), 1-(8-benzyl-10,10-dimethyl-11-oxa-3,8-diazaspiro[5.5]undecan-3-yl)-2,2,2-trifluoro-ethanone (80 mg, 0.22 mmol), HCl (108 µL of 4 M in dioxane, 0.43 mmol) and ethanol (2 mL) was treated to an atmosphere of hydrogen at 85 psi for 3 days. The reaction mixture was filtered and the catalyst was washed with methanol, then concentrated in vacuo to give 1-(10,10-dimethyl-11-oxa-3,8-diazaspiro[5.5]undecan-3-yl)-2,2,2-trifluoro-ethanone acetic acid salt as a yellow solid. ESI-MS m/z calc. 280.1. Found 281.5 (M+1)+; Retention time: 0.91 minutes (3 min run).

Step 6:

To 1-(10,10-dimethyl-11-oxa-3,8-diazaspiro[5.5]undecan-3-yl)-2,2,2-trifluoro-ethanone acetic acid salt (90 mg, 0.26 mmol) in ethanol (1.4 mL) was added NaHCO$_3$ (89 mg, 1.06 mmol) then iodoethane (42 µL, 0.53 mmol). The reaction mixture was heated at 60° C. for 5 hours, then at room temperature for 72 hours, then microfiltered and purified by prep LCMS (1-99% ACN/Water, 5 mM HCl modifier) to give 148-ethyl-10,10-dimethyl-11-oxa-3,8-diazaspiro[5.5]undecan-3-yl)-2,2,2-trifluoro-ethanone hydrochloride salt (47 mg, 52%) as a white solid. ESI-MS m/z calc. 308.2. Found 309.7 (M+1)+; Retention time: 0.90 minutes (3 min run).

Step 7:

To 148-ethyl-10,10-dimethyl-11-oxa-3,8-diazaspiro[5.5] undecan-3-yl)-2,2,2-trifluoro-ethanone hydrochloride salt (47 mg, 0.14 mmol) and lithium hydroxide (10 mg, 0.42 mmol) was added water (0.15 mL) and THF (0.6 mL) and the reaction mixture was stirred at room temperature for 2 hours. The reaction mixture was concentrated in vacuo, partitioned between DCM (10 mL)/1:1 brine:NH$_4$OH (2 mL), extracted with DCM (5×10 mL), dried over MgSO$_4$ and concentrated in vacuo to give 4-ethyl-2,2-dimethyl-1-oxa-4,9-diazaspiro [5.5]undecane (24 mg, 81%). ESI-MS m/z calc. 212.2. Found 213.5 (M+1)+; Retention time: 0.19 minutes (3 min run).

Preparation of 9-(tert-butoxycarbonyl)-4-(2,2,2-trifluoroethyl)-1-oxa-4,9-diazaspiro[5.5]undecane-2-carboxylic acid

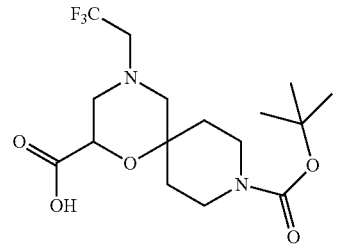 [SMILES: CC(C)(C)OC(=O)N1CCC2(CC1)CN(CC(F)(F)F)CC(C(=O)O)O2]

The synthesis of tert-butyl 4-[(benzylamino)methyl]-4-hydroxy-piperidine-1-carboxylate was carried out as described above.

Step 1:

To tetrakis(triphenylphosphine)palladium(0) (487 mg, 0.42 mmol) and triphenylphosphine (442 mg, 1.69 mmol) in degassed THF (75 mL) was added triethylamine (2.35 mL, 16.85 mmol). The reaction mixture was stirred for 1 hour under an atmosphere of nitrogen. A solution of tert-butyl 4-[(benzylamino)methyl]-4-hydroxy-piperidine-1-carboxylate (2.7 g, 8.43 mmol) in degassed THF (10 mL) was added via cannula, followed by the addition of [(Z)-4-acetoxybut-2-enyl]acetate (1.35 mL, 8.47 mmol) and the reaction mixture was stirred in a sealed pressure flask at 45° C. for 16 hours. The reaction mixture was concentrated in vacuo, diluted with ethyl acetate, chilled to −15° C., and the solid was removed by filtration over Celite®. The filtrate was concentrated in vacuo and the residue was purified by silica gel column chromatography using 0-60% EtOAc/hexane as eluent to give tert-butyl 10-benzyl-8-vinyl-7-oxa-3,10-diazaspiro[5.5]undecane-3-carboxylate (2.9 g, 92%) as a pale yellow oil. $^1$H NMR (400

MHz, CDCl₃) δ 7.38-7.19 (m, 5H), 5.77 (ddd, J=17.3, 10.6, 5.5 Hz, 1H), 5.36-5.23 (m, 1H), 5.13 (dt, J=10.6, 1.4 Hz, 1H), 4.25 (s, 1H), 3.64 (s, 2H), 3.53 (d, J=13.3 Hz, 1H), 3.37 (d, J=13.3 Hz, 1H), 3.29 (s, 1H), 3.10 (s, 1H), 2.84-2.72 (m, 1H), 2.55 (dd, J=11.1, 1.4 Hz, 1H), 2.41 (d, J=13.7 Hz, 1H), 1.95-1.75 (m, 2H), 1.50-1.34 (m, 11H).

Step 2:

To tert-butyl 10-benzyl-8-vinyl-7-oxa-3,10-diazaspiro[5.5]undecane-3-carboxylate (2.07 g, 5.56 mmol) and 4-methylmorpholine 4-oxide (725 mg, 6.19 mmol) in acetone (19 mL) and water (2 mL) was added osmium tetroxide in water (704 μL of 2.5% w/w, 0.06 mmol) dropwise and the solution was stirred for 2 hours. The reaction mixture was quenched with 1M sodium thiosulfate (50 mL) and stirred for 5 minutes, then extracted with EtOAc (4×50 mL), washed with sat. aq. NaHCO₃ (30 mL), and dried over MgSO₄, filtered and concentrated in vacuo to give the diol intermediate. The diol was diluted with DCM (20 mL), filtered over a plug of neutral alumina, washing extensively with 20% MeOH/DCM (>1 L). The filtrate was concentrated in vacuo to give tert-butyl 8-benzyl-10-(1,2-dihydroxyethyl)-11-oxa-3,8-diazaspiro[5.5]undecane-3-carboxylate (2.10 g, 93%) as a white foam. ESI-MS m/z calc. 406.5. Found 407.7 (M+1)⁺; Retention time: 1.13 (3 min run) ¹H NMR (400 MHz, DMSO) δ 7.36-7.27 (m, 4H), 7.27-7.21 (m, 1H), 4.62 (d, J=5.9 Hz, 1H), 4.34 (t, J=5.6 Hz, 1H), 3.74-3.49 (m, 4H), 3.45 (d, J=7.6 Hz, 2H), 3.42-3.33 (m, 2H), 3.23 (tt, J=5.7, 2.7 Hz, 1H), 2.94 (d, J=10.6 Hz, 1H), 2.59 (ddd, J=11.7, 8.5, 2.3 Hz, 1H), 2.35 (ddd, J=8.9, 5.2, 1.8 Hz, 1H), 1.81-1.67 (m, 2H), 1.38 (s, 9H), 1.34 (dd, J=6.7, 3.0 Hz, 2H), 1.29-1.18 (m, 1H).

Step 3:

To tert-butyl 8-benzyl-10-(1,2-dihydroxyethyl)-11-oxa-3,8-diazaspiro[5.5]undecane-3-carboxylate (1.5 g, 3.69 mmol) in THF (35 mL) was added NaIO₄ (2 g, 9.4 mmol) followed by the addition of H₂O (13 mL). The reaction mixture was stirred at room temp for 2.5 hours. The reaction mixture was filtered, then concentrated in vacuo and the residue was partitioned between sat. aq. sodium bicarbonate (50 mL) and ethyl acetate (50 mL). The aqueous layer was extracted further with ethyl acetate (2×50 mL). The organic layers were combined, dried over MgSO₄, filtered and concentrated in vacuo. To the intermediate aldehyde (~1.4 g) was added ᵗBuOH (17 mL) and 2-methylbut-2-ene (10.5 mL, 99.04 mmol) and the reaction mixture was cooled to 0° C. A solution of NaClO₂ (1.1 g, 9.65 mmol) and NaH₂PO₄ (1.33 g, 9.67 mmol) in water (17 mL) was added dropwise over 5 minutes, and the reaction mixture was stirred for 30 minutes at 0° C. The reaction mixture was warmed to room temperature, then extracted with ethyl acetate (4×50 mL) and the combined organics were dried over MgSO₄, filtered and concentrated in vacuo to give the crude acid as a yellow oil. The oil was dissolved in toluene (2.5 mL) and methanol (2.5 mL), then diazomethyl(trimethyl)silane (1.85 mL of 2 M in hexanes, 3.69 mmol) was added dropwise until faint yellow color persisted. Acetic acid was added to make solution colorless (2 drops). The reaction mixture was concentrated in vacuo then purified by silica gel column chromatography using 0-70% EtOAc/hexane as eluent to give 9-tert-butyl 2-methyl 4-benzyl-1-oxa-4,9-diazaspiro[5.5]undecane-2,9-dicarboxylate (1 g, 67%) as a colorless oil. ¹H NMR (400 MHz, CDCl₃) δ 7.37-7.20 (m, 5H), 4.43 (dd, J=10.5, 2.1 Hz, 1H), 3.74 (s, 3H), 3.57 (d, J=13.3 Hz, 3H), 3.45-3.29 (m, 2H), 3.14 (t, J=10.9 Hz, 1H), 3.08-3.01 (m, 1H), 2.56 (dd, J=11.3, 0.9 Hz, 1H), 2.30 (dd, J=8.7, 5.7 Hz, 1H), 2.13 (dd, J=19.9, 8.9 Hz, 1H), 1.91 (d, J=11.3 Hz, 1H), 1.69-1.46 (m, 3H), 1.43 (s, 9H). ESI-MS m/z calc. 404.5. Found 405.7 (M+1)⁺; Retention time: 1.62 (3 min run).

Step 4:

A mixture of 9-tert-butyl 2-methyl 4-benzyl-1-oxa-4,9-diazaspiro[5.5]undecane-2,9-dicarboxylate (670 mg, 1.66 mmol), ammonium formate (623 mg, 9.936 mmol) and palladium, 10 wt. % on activated carbon (353 mg, 3.31 mmol) in EtOH (5 mL) was heated at 65° C. for 50 minutes. The reaction mixture was cooled to room temperature, filtered and partitioned between EtOAc/1M aq. NaOH. The layers were separated and the organic layer was dried over Na₂SO₄, filtered and concentrated in vacuo to yield 9-tert-butyl 2-methyl 1-oxa-4,9-diazaspiro[5.5]undecane-2,9-dicarboxylate as a foam (386 mg, 74%). ESI-MS m/z calc. 314.2. Found 315.5 (M+1); Retention time: 0.99 minutes (3 min run).

Step 5:

2,2,2-Trifluoroethyl trifluoromethanesulfonate (164 μL, 1.06 mmol) was added to a solution of 9-tert-butyl 2-methyl 1-oxa-4,9-diazaspiro[5.5]undecane-2,9-dicarboxylate (222 mg, 0.71 mmol) and NaHCO₃ (237 mg, 2.83 mmol) in anhydrous EtOH (6 mL) at room temperature. The reaction mixture was purged with argon, sealed with a cap and heated at 70° C. for 12 hours. The reaction mixture was cooled to room temperature, filtered and concentrated in vacuo. The crude material was purified by silica gel column chromatography using 0 to 30% EtOAc in DCM as eluent to yield 9-tert-butyl 2-methyl 4-(2,2,2-trifluoroethyl)-1-oxa-4,9-diazaspiro[5.5]undecane-2,9-dicarboxylate (197 mg, 68%). ESI-MS m/z calc. 410.4. Found 411.5 (M+1)⁺; Retention time: 2.08 minutes (3 min run).

Step 6:

9-Tert-butyl 2-methyl 4-(2,2,2-trifluoroethyl)-1-oxa-4,9-diazaspiro[5.5]undecane-2,9-dicarboxylate (197 mg, 0.48 mmol) was dissolved in MeOH (1 mL)/H₂O (1 mL), followed by the addition of LiOH (46 mg, 1.92 mmol) and the reaction mixture was stirred for 2 hours at room temperature. The solvent was removed in vacuo and the residue was dissolved in water (2 mL) and cooled to 0° C., then acetic acid (115 mg, 109 μL, 1.92 mmol) was added dropwise (pH=5). The product was partitioned between EtOAc/water, the layers were separated and the aqueous layer was extracted once more with EtOAc. The organics were dried over Na₂SO₄, filtered and concentrated in vacuo to yield an oil. The oil was co-evaporated twice with toluene and dried under high vacuum to yield 9-(tert-butoxycarbonyl)-4-(2,2,2-trifluoroethyl)-1-oxa-4,9-diazaspiro[5.5]undecane-2-carboxylic acid (142 mg, 77%) as a white foam. ESI-MS m/z calc. 382.4. Found 383.5 (M+1)⁺; Retention time: 1.58 minutes (3 min run).

Preparation of 9-(tert-butoxycarbonyl)-4-(2,2-difluoroethyl)-1-oxa-4,9-diazaspiro[5.5]undecane-2-carboxylic acid

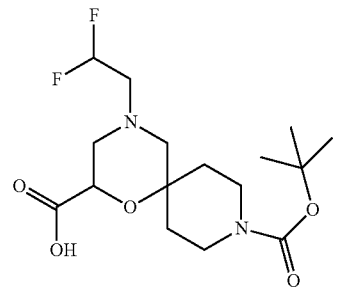 [SMILES: CC(C)(C)OC(=O)N1CCC2(CC1)CN(CC(F)F)CC(C(=O)O)O2]

This compound was prepared using the chemistry as described above using 2,2-difluoroethyl trifluoromethanesulfonate as the alkylating agent in step 5. ¹H NMR (400 MHz, DMSO) δ 6.28 (t, J=4.1 Hz, 1H), 6.14 (t, J=4.0 Hz, 1H), 6.00 (t, J=4.1 Hz, 1H), 4.20 (d, J=8.8 Hz, 1H), 3.49 (d, J=9.0 Hz, 2H), 3.22 (s, 1H), 3.04 (d, J=10.3 Hz, 2H), 2.72 (ddd, J=14.4, 13.7, 7.8 Hz, 3H), 2.23-1.94 (m, 3H), 1.58-1.28 (m, 11H); ESI-MS m/z calc. 364.4. Found 365.3 (M+1)+; Retention time: 1.36 minutes (3 min run).

Preparation of 9-(tert-butoxycarbonyl)-4-(tert-butyl)-1-oxa-4,9-diazaspiro[5.5]undecane-2-carboxylic acid

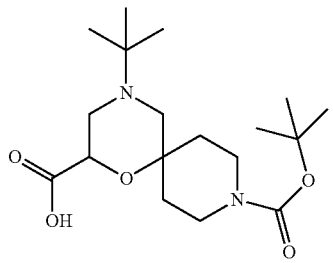 [SMILES: CC(C)(C)OC(=O)N1CCC2(CC1)CN(C(C)(C)C)CC(C(=O)O)O2]

This compound was prepared using steps 1-3 and 6 in the chemistry described above using tert-butyl 4-((tert-butylamino)methyl)-4-hydroxypiperidine-1-carboxylate in step 1. $^1$H NMR (400 MHz, CDCl$_3$) δ 4.32 (d, J=10.6 Hz, 1H), 4.21-4.16 (m, 1H), 3.84-3.50 (m, 3H), 3.33 (t, J=20.1 Hz, 2H), 3.14 (d, J=10.9 Hz, 1H), 2.78 (d, J=11.4 Hz, 1H), 2.23 (s, 1H), 2.09 (dt, J=24.2, 13.0 Hz, 4H), 1.59 (dd, J=49.3, 11.8 Hz, 3H), 1.42 (d, J=29.3 Hz, 12H), 1.00 (d, J=36.2 Hz, 10H); ESI-MS m/z calc. 356.2. Found 357.5 (M+1)+; Retention time: 0.66 minutes (3 min run).

Preparation of 9-(tert-butoxycarbonyl)-4-ethyl-1-oxa-4,9-diazaspiro[5.5]undecane-2-carboxylic acid

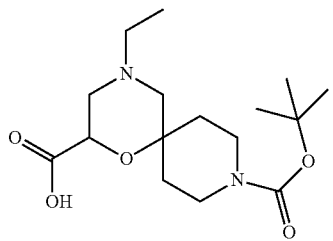 [SMILES: CCN1CC(C(=O)O)OC2(CCN(C(=O)OC(C)(C)C)CC2)C1]

This compound was prepared using steps 1-3 and 6 in the chemistry described above using tert-butyl 4-((ethylamino)methyl)-4-hydroxypiperidine-1-carboxylate in step 1. ESI-MS m/z calc. 328.5. Found 329.5 (M+1)+; Retention time: 1.44 minutes (3 min run).

Preparation of 4-(2,2-difluoroethyl)-2-(5-ethyloxazol-2-yl)-1-oxa-4,9-diazaspiro[5.5]undecane Step 1:
To 9-(tert-butoxycarbonyl)-4-(2,2-difluoroethyl)-1-oxa-4,9-diazaspiro[5.5]undecane-2-carboxylic acid (418 mg, 1.15 mmol), 1-aminobutan-2-one (156 mg, 1.26 mmol) and propane phosphonic acid anhydride (T3P) (1.095 g, 1.0 mL of 50% w/w, 1.72 mmol) in 2-methyltetrahydrofuran (3.1 mL) was added triethylamine (640 µL, 4.59 mmol) at room temperature. The reaction mixture was then heated at 40° C. for 5 hours. The reaction mixture was cooled quenched with sat. aq. NaHCO$_3$ and extracted with ethyl acetate. The combined organics were dried over Na$_2$SO$_4$, filtered and concentrated in vacuo, then purified by silica gel column chromatography using 0-50% EtOAc in DCM to yield tert-butyl difluoroethyl)-2-((2-oxobutyl)carbamoyl)-1-oxa-4,9-diazaspiro[5.5]undecane-9-carboxylate (300 mg, 60%) $^1$H NMR (400 MHz, CDCl$_3$) δ 7.40-7.30 (m, 1H), 6.09-5.64 (m, 1H), 4.31 (dd, J=11.0, 3.0 Hz, 1H), 4.21-4.05 (m, 2H), 3.77 (ddt, J=10.9, 7.5, 6.3 Hz, 2H), 3.39-3.17 (m, 2H), 3.14-2.95 (m, 1H), 2.80-2.63 (m, 3H), 2.50 (q, J=7.3 Hz, 2H), 2.41-2.27 (m, 1H), 2.25-2.11 (m, 2H), 1.67-1.51 (m, 3H), 1.46 (s, 9H), 1.13 (t, J=7.4 Hz, 3H). ESI-MS m/z calc. 433.2. Found 434.5 (M+1)+; Retention time: 1.78 minutes (3 min run).

Step 2:
To tert-butyl 4-(2,2-difluoroethyl)-242-oxobutyl)carbamoyl)-1-oxa-4,9-diazaspiro[5.5]undecane-9-carboxylate (200 mg, 0.46 mmol) in THF (2 mL) was added Burgess' salt (275 mg, 1.15 mmol) and the reaction mixture was heated at 75° C. under a nitrogen atmosphere for 2 hours. The reaction mixture was cooled to room temperature, and partitioned between EtOAc and saturated aq. NaHCO$_3$. The layers were separated and the aqueous layer was extracted once more with EtOAc. The combined organics were dried over Na$_2$SO$_4$, filtered and concentrated in vacuo to give an orange oil. The residue was purified by silica gel column chromatography using 0-20% EtOAc in DCM as eluent to yield tert-butyl 4-(2,2-difluoroethyl)-2-(5-ethyloxazol-2-yl)-1-oxa-4,9-diazaspiro[5.5]undecane-9-carboxylate (160 mg, 84%) as a colorless oil. ESI-MS m/z calc. 415.2. Found 416.5 (M+1)+; Retention time: 2.06 minutes (3 min run); $^1$H NMR (400 MHz, CDCl$_3$) δ 6.69 (s, 1H), 6.06-5.68 (m, 1H), 4.89 (dd, J=10.7, 2.5 Hz, 1H), 3.85-3.58 (m, 2H), 3.37-3.01 (m, 3H), 2.87-2.59 (m, 6H), 2.45 (d, J=13.6 Hz, 1H), 2.30 (d, J=11.3 Hz, 1H), 1.65-1.48 (m, 3H), 1.45 (s, 9H), 1.25 (t, J=7.6 Hz, 3H).

Step 3:
To a solution of tert-butyl 4-(2,2-difluoroethyl)-2-(5-ethyloxazol-2-yl)-1-oxa-4,9-diazaspiro[5.5]undecane-9-carboxylate (154 mg, 0.37 mmol) in DCM (0.4 mL) was added HCl (464 µL of 4 M solution in dioxane, 1.85 mmol) and the reaction mixture was stirred at room temperature for 1 hour. The solvent and excess HCl were removed under reduced pressure and the residue was triturated with Et$_2$O to yield 4-(2,2-difluoroethyl)-2-(5-ethyloxazol-2-yl)-1-oxa-4,9-diazaspiro[5.5]undecane hydrochloride salt (138 mg, 96%) as a white solid. ESI-MS m/z calc. 315.2. Found 316.3 (M+1)+; Retention time: 1.07 minutes (3 min run).

Preparation of 4-(2,2-difluoroethyl)-2-(5-isopropyloxazol-2-yl)-1-oxa-4,9-diazaspiro[5.5]undecane

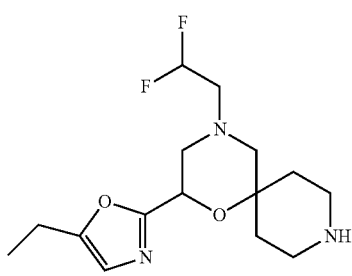 [SMILES: CCc1cnc(C2CN(CC(F)F)CC3(CCNCC3)O2)o1]

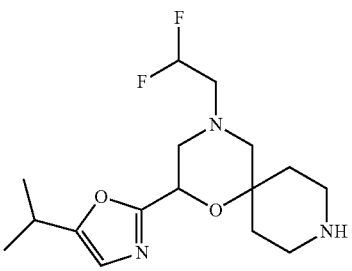 [SMILES: CC(C)c1cnc(C2CN(CC(F)F)CC3(CCNCC3)O2)o1]

This compound was prepared using the method described above using 1-amino-3-methyl-butan-2-one in step 1. ESI-MS m/z calc. 329.2. Found 330.3 (M+1)⁺; Retention time: 1.12 minutes (3 min run).

Preparation of 2-(5-(tert-butyl)oxazol-2-yl)-4-(2,2-difluoroethyl)-1-oxa-4,9-diazaspiro[5.5]undecane

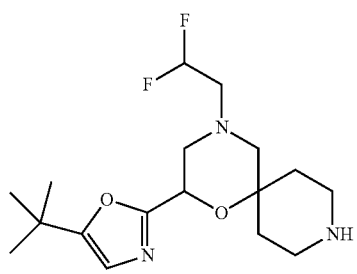 [SMILES: CC(C)(C)c1cnc(C2CN(CC(F)F)CC3(CCNCC3)O2)o1]

This compound was prepared using the method described above using 1-amino-3,3-dimethyl-butan-2-one in step 1. ESI-MS m/z calc. 343.20. Found 344.1 (M+1)⁺; Retention time: 1.23 minutes (3 min run).

Preparation of 8-tert-butyl-10-(5-methyloxazol-2-yl)-11-oxa-3,8-diazaspiro[5.5]undecane

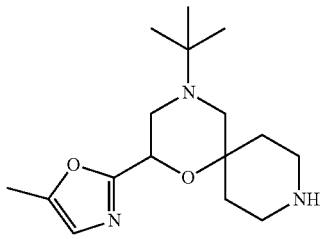 [SMILES: Cc1cnc(C2CN(C(C)(C)C)CC3(CCNCC3)O2)o1]

This compound was prepared using the method described above using 9-(tert-butoxycarbonyl)-4-(tert-butyl)-1-oxa-4,9-diazaspiro[5.5]undecane-2-carboxylic acid and 1-aminopropan-2-one in step 1. ESI-MS m/z calc. 293.4. Found 294.3 (M+1)⁺; Retention time: 0.39 minutes (3 min run).

Preparation of 4-(2,2-difluoroethyl)-2-(oxazol-2-yl)-1-oxa-4,9-diazaspiro[5.5]undecane

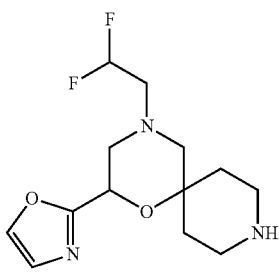 [SMILES: FC(F)CN1CC(c2ncco2)OC2(CCNCC2)C1]

Step 1:
To 9-(tert-butoxycarbonyl)-4-(2,2-difluoroethyl)-1-oxa-4,9-diazaspiro[5.5]undecane-2-carboxylic acid (520 mg, 1.43 mmol), prop-2-en-1-amine (118 μL, 1.57 mmol) and T3P (2.12 mL of 50% w/w, 3.59 mmol) in 2-methyltetrahydrofuran (4 mL) was added triethylamine (597 μL, 4.28 mmol) at room temperature and the reaction mixture was stirred for 2 hours. The reaction mixture was then quenched with saturated NaHCO₃ solution (3 mL) and stirred for an additional 10 minutes, then diluted with EtOAc and the layers were separated. The aqueous layer was extracted once more with EtOAc, and the combined organics were dried over Na₂SO₄, filtered and concentrated in vacuo to an oil. The residue was purified by silica gel column chromatography using 0-50% EtOAc in hexanes to yield tert-butyl 2-(allylcarbamoyl)-4-(2,2-difluoroethyl)-1-oxa-4,9-diazaspiro[5.5]undecane-9-carboxylate (480 mg, 83%). ESI-MS m/z calc. 403.2. Found 404.5 (M+1)⁺; Retention time: 1.78 minutes (3 min run).

Step 2:
To tert-butyl 2-(allylcarbamoyl)-4-(2,2-difluoroethyl)-1-oxa-4,9-diazaspiro[5.5]undecane-9-carboxylate (480 mg, 1.19 mmol) and 4-methylmorpholine 4-oxide (153 mg, 1.31 mmol) in acetone (4.5 mL) and water (480 μL) was added osmium tetroxide in water (75.63 μL of 4% w/w, 0.01 mmol) dropwise and the solution was stirred for 2.5 hours at room temperature. The reaction mixture was quenched with 1M sodium thiosulfate (12 mL) and stirred for 5 minutes, then extracted with EtOAc, washed with sat. aq. NaHCO₃, brine, dried over MgSO₄, filtered and concentrated in vacuo to give tert-butyl 4-(2,2-difluoroethyl)-2-((2,3-dihydroxypropyl)carbamoyl)-1-oxa-4,9-diazaspiro[5.5]undecane-9-carboxylate (520 mg, 99%) which was used without further purification. ESI-MS m/z calc. 437.2. Found 438.5 (M+1)⁺; Retention time: 1.54 minutes (3 min run).

Step 3:
To tert-butyl 4-(2,2-difluoroethyl)-2-((2,3-dihydroxypropyl)carbamoyl)-1-oxa-4,9-diazaspiro[5.5]undecane-9-carboxylate (422 mg, 0.96 mmol) in THF (10 mL) was added NaIO₄ (522 mg, 2.44 mmol) followed by H₂O (4 mL) the reaction mixture was stirred at room temperature for 2 hours. The reaction mixture was filtered and partitioned between sat. aq. sodium bicarbonate/ethyl acetate. The aqueous layer was extracted further with ethyl acetate (3×50 mL). The organics were combined, washed with sat. aq. sodium bicarbonate (50 mL), dried over MgSO₄, and concentrated in vacuo to yield tert-butyl 4-(2,2-difluoroethyl)-2-((2-oxoethyl)carbamoyl)-1-oxa-4,9-diazaspiro[5.5]undecane-9-carboxylate (377 mg, 96%) as a white solid, which was taken onto the next step without purification. ESI-MS m/z calc. 405.2. Found 406.5 (M+1)⁺; Retention time: 1.32 minutes (3 min run)

Step 4:
To tert-butyl 4-(2,2-difluoroethyl)-2-((2-oxoethyl)carbamoyl)-1-oxa-4,9-diazaspiro[5.5]undecane-9-carboxylate (331 mg, 0.82 mmol) in THF (3 mL) was added Burgess' Salt (486 mg, 2.04 mmol). The reaction mixture was heated at 70° C. for 20 minutes under an atmosphere of nitrogen. The reaction mixture was cooled to room temperature, partitioned between EtOAc and saturated aq. NaHCO₃, the layers separated and the aqueous layer was extracted once more with EtOAc. The combined organics were dried over Na₂SO₄, filtered and concentrated in vacuo to give an orange oil. The residue was purified by silica gel column chromatography using 0-30% EtOAc in DCM as eluent to yield tert-butyl difluoroethyl)-2-(oxazol-2-yl)-1-oxa-4,9-diazaspiro[5.5]undecane-9-carboxylate (121 mg, 38%) as an off white foam. ESI-MS m/z calc. 387.2. Found 388.3 (M+1)⁺; Retention time: 1.81 minutes (3 min run)

Step 5:
HCl (781 μL of 4 M in dioxane, 3.12 mmol) was added to a solution of tert-butyl 4-(2,2-difluoroethyl)-2-(oxazol-2-yl)-

1-oxa-4,9-diazaspiro[5.5]undecane-9-carboxylate (121 mg, 0.31 mmol) in DCM (0.7 mL) and the reaction mixture was stirred for 1 hour at room temperature. The solvent and excess HCl was removed under reduced pressure and the resulting solid was dissolved in methanol (3 mL) and purified by Waters mass directed LC/MS: (1-99% ACN/H$_2$O (5 mM HCl)). The desired fractions were combined and concentrated in vacuo to yield 4-(2,2-difluoroethyl)-2-(oxazol-2-yl)-1-oxa-4,9-diazaspiro[5.5]undecane hydrochloride salt (95 mg, 94%) as a white solid. ESI-MS m/z calc. 287.1. Found 288.3 (M+1)$^+$; Retention time: 0.96 minutes (3 min run); $^1$H NMR (400 MHz, DMSO) δ 8.15 (d, J=0.8 Hz, 1H), 7.23 (d, J=0.8 Hz, 1H), 6.22 (tt, J=55.1, 4.0 Hz, 1H), 4.94 (dd, J=10.8, 2.6 Hz, 1H), 3.19-2.79 (m, 8H), 2.65-2.54 (m, 2H), 2.25 (dd, J=11.9, 1.5 Hz, 1H), 1.83-1.70 (m, 2H), 1.65 (dd, J=15.1, 3.9 Hz, 1H).

Preparation of 10-(5-methylthiazol-2-yl)-8-(2,2,2-trifluoroethyl)-11-oxa-3,8-diazaspiro[5.5]undecane

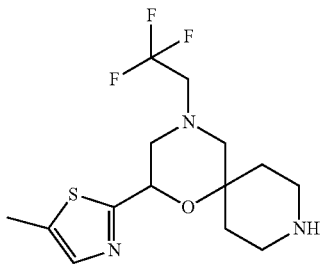 [SMILES: Cc1cnc(C2CN(CC(F)(F)F)CC3(CCNCC3)O2)s1]

Step 1:
T3P (591 mg, 553 μL of 50% w/w, 0.93 mmol) was added to a mixture of 9-(tert-butoxycarbonyl)-4-(2,2,2-trifluoroethyl)-1-oxa-4,9-diazaspiro[5.5]undecane-2-carboxylic acid (142 mg, 0.37 mmol), 1-aminopropan-2-one hydrochloride salt (41 mg, 0.37 mmol) and Et$_3$N (188 mg, 259 μL, 1.86 mmol) in 2-methyltetrahydrofuran (706 μL). The reaction mixture was then heated at 45° C. for 2 hours. The reaction mixture was cooled to room temperature and partitioned between EtOAc/saturated aq. NaHCO$_3$. The layers were separated and the aqueous layer was extracted with EtOAc (2×). The combined organics were dried over Na$_2$SO$_4$, filtered and concentrated in vacuo to a dark foam. The crude product was purified by silica gel column chromatography using 0-50% EtOAC in DCM as eluent to afford tert-butyl 10-(acetonylcarbamoyl)-8-(2,2,2-trifluoroethyl)-11-oxa-3,8-diazaspiro[5.5]undecane-3-carboxylate (80 mg, 49%) as a yellow solid. ESI-MS m/z calc. 437.5. Found 438.7 (M+1)$^+$; Retention time: 1.01 minutes (3 min run).

Step 2:
Tert-butyl 10-(acetonylcarbamoyl)-8-(2,2,2-trifluoroethyl)-11-oxa-3,8-diazaspiro[5.5]undecane-3-carboxylate (80 mg, 0.18 mmol) was dissolved in anhydrous THF (1.5 mL) followed by the addition of Lawesson's reagent (114 mg, 0.27 mmol) and the reaction mixture was heated at 70° C. for 1 hour under an atmosphere of nitrogen. The reaction mixture was cooled to room temperature and the solvent was removed under reduced pressure. The residue was purified by silica gel column chromatography using 0-10% EtOAc in DCM as eluent to yield tert-butyl 10-(5-methylthiazol-2-yl)-8-(2,2,2-trifluoroethyl)-11-oxa-3,8-diazaspiro[5.5]undecane-3-carboxylate (95 mg, 100%). ESI-MS m/z calc. 435.5. Found 436.5 (M+1)$^+$; Retention time: 1.67 minutes (3 min run); $^1$H NMR (400 MHz, CDCl$_3$) δ 7.54 (s, 1H), 5.20 (dd, J=9.4, 0.8 Hz, 1H), 3.82-3.76 (m, 2H), 3.43 (d, J=10.1 Hz, 1H), 3.31-3.21 (m, 1H), 3.09-2.94 (m, 3H), 2.72 (dd, J=11.4, 0.5 Hz, 1H), 2.50 (s, 1H), 2.46 (s, 3H), 2.45-2.38 (m, 2H), 1.79-1.67 (m, 1H), 1.65-1.57 (m, 1H), 1.53 (dd, J=11.2, 4.8 Hz, 1H), 1.45 (s, 9H).

Step 3:
Hydrogen chloride (229 μL of 4 M solution in dioxane, 0.9160 mmol) was added to tert-butyl 10-(5-methylthiazol-2-yl)-8-(2,2,2-trifluoroethyl)-11-oxa-3,8-diazaspiro[5.5]undecane-3-carboxylate (95 mg, 0.18 mmol) in anhydrous dichloromethane (1 mL) and the reaction mixture was stirred for 2 hours at room temperature. The excess HCl and solvent were removed under reduced pressure to yield 10-(5-methylthiazol-2-yl)-8-(2,2,2-trifluoroethyl)-11-oxa-3,8-diazaspiro[5.5]undecane hydrochloride salt (74 mg, 99%) as a light yellow solid. ESI-MS m/z calc. 335.1. Found 336.5 (M+1)$^+$; Retention time: 0.91 minutes (3 min run).

Preparation of 8-ethyl-10-(5-methylthiazol-2-yl)-11-oxa-3,8-diazaspiro[5.5]undecane

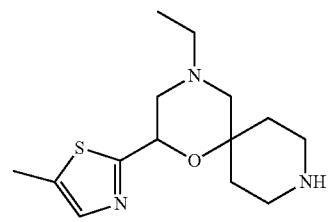 [SMILES: CCN1CC(c2ncc(C)s2)OC2(CCNCC2)C1]

This compound was prepared using the procedure as described above starting from 9-(tert-butoxycarbonyl)-4-ethyl-1-oxa-4,9-diazaspiro[5.5]undecane-2-carboxylic acid. ESI-MS m/z calc. 281.4. Found 282.5 (M+1)$^+$; Retention time: 0.20 minutes (3 min run).

Preparation of 8-(2,2-difluoroethyl)-10-(4-methyl-1H-pyrazol-5-yl)-11-oxa-3,8-diazaspiro[5.5]undecane

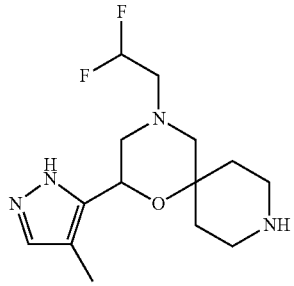 [SMILES: Cc1cn[nH]c1C1CN(CC(F)F)CC2(CCNCC2)O1]

Step 1:
To 3-tert-butyl O10-methyl 8-(2,2-difluoroethyl)-11-oxa-3,8-diazaspiro[5.5]undecane-3,10-dicarboxylate (1.50 g, 3.96 mmol) and powdered (N,O)-dimethylhydroxylamine hydrochloride salt (654 mg, 6.71 mmol) in THF (25 mL) at −78° C. was added lithium bis(trimethylsilyl)amine (12.6 mL of 1 M, 12.6 mmol) over a period of 5 minutes. The mixture was stirred at the same temperature for 15 minutes, it was then warmed to 0° C. and stirred for an additional 30 minutes. The reaction mixture was quenched with sat. aq. NH₄Cl (30 mL), extracted with ether (3×50 mL), and the combined organics were dried over MgSO₄, filtered and concentrated in vacuo. The crude material was purified by silica gel column chromatography (0-100% ethyl acetate/dichloromethane) to give tert-butyl difluoroethyl)-10-[methoxy(methyl)carbamoyl]-11-oxa-3,8-diazaspiro[5.5]undecane-3-carboxylate (1.38 g, 85%) as a colorless oil. ESI-MS m/z calc. 407.2. Found 408.5 (M+1)⁺; Retention time: 1.59 minutes (3 min run). ¹H NMR (400 MHz, CDCl₃) δ 5.93-5.61 (m, 1H), 4.66-4.58 (m, 1H), 3.72 (s, 3H), 3.65-3.46 (m, 2H), 3.33-3.22 (m, 1H), 3.14 (s, 3H), 2.83-2.77 (m, 1H), 2.70-2.57 (m, 3H), 2.47-2.40 (m, 1H), 2.28-2.12 (m, 2H), 1.61-1.48 (m, 3H), 1.46-1.35 (m, 10H).

Step 2:

To tert-butyl 8-(2,2-difluoroethyl)-10-[methoxy(methyl) carbamoyl]-11-oxa-3,8-diazaspiro[5.5]undecane-3-carboxylate (295 mg, 0.72 mmol) in THF (3 mL) at −78° C. under an atmosphere of nitrogen, was added ethylmagnesium bromide (1.7 mL of 1 M in THF, 1.7 mmol) dropwise. The reaction mixture was stirred at the same temperature for 0.5 hours, then at 0° C. for 1 hour. The reaction mixture was quenched with ethyl acetate (20 mL) and sat. aq. NaHCO₃ (10 mL). The aqueous layer was further extracted with EtOAc (2×20 mL), and the combined organics were dried over MgSO₄, filtered and concentrated in vacuo. The crude material was purified by silica gel column chromatography (0-100% ethyl acetate/hexane) to give tert-butyl 8-(2,2-difluoroethyl)-10-propanoyl-11-oxa-3,8-diazaspiro[5.5]undecane-3-carboxylate (227 mg, 83%) as a colorless oil. ESI-MS m/z calc. 376.2. Found 377.3 (M+1)⁺; Retention time: 1.76 minutes. ¹H NMR (400 MHz, CDCl₃) δ 6.01-5.70 (m, 1H), 4.21-4.15 (m, 1H), 3.91-3.75 (m, 2H), 3.33-3.22 (m, 1H), 3.15-2.98 (m, 2H), 2.79-2.57 (m, 5H), 2.43-2.35 (m, 1H), 2.19-2.06 (m, 2H), 1.61-1.39 (m, 12H), 1.06 (t, J=7.3 Hz, 3H).

Step 3:

tert-Butyl 8-(2,2-difluoroethyl)-10-propanoyl-11-oxa-3,8-diazaspiro[5.5]undecane-3-carboxylate (225 mg, 0.598 mmol) and DMF-DMA (1.0 mL, 7.53 mmol) were heated in a sealed vial at 105° C. overnight. The reaction mixture was concentrated and then diluted with methanol (1 mL). Hydrazine (60 μL, 1.9 mmol) was added in 3 aliquots every hour over 3 hours and then the reaction mixture was stirred for an additional 1 hour. The reaction mixture was diluted with methanol, microfiltered and purified by preparative LCMS (10-99% ACN/Water, HCl modifier) to give tert-butyl 8-(2,2-difluoroethyl)-10-(4-methyl-1H-pyrazol-5-yl)-11-oxa-3,8-diazaspiro[5.5]undecane-3-carboxylate (80 mg, 0.2 mmol, 33.42%) as a yellow oil. ESI-MS m/z calc. 400.2. Found 401.5 (M+1)⁺; Retention time: 1.36 minutes (3 min run).

Step 4:

To tert-butyl 8-(2,2-difluoroethyl)-10-(4-methyl-1H-pyrazol-5-yl)-11-oxa-3,8-diazaspiro[5.5]undecane-3-carboxylate (80 mg, 0.20 mmol) in ethanol (0.2 mL) was added HCl (500 μL of 4 M in dioxane, 2.00 mmol) and the reaction mixture was stirred for 1 hour. The reaction mixture was concentrated in vacuo to give, 8-(2,2-difluoroethyl)-10-(4-methyl-1H-pyrazol-5-yl)-11-oxa-3,8-diazaspiro[5.5]undecane hydrochloride salt as a yellow solid. ESI-MS m/z calc. 300.2. Found 301.3 (M+1)⁺; Retention time: 0.48 minutes (3 min run). ¹H NMR (400 MHz, DMSO) δ 8.74 (s, 2H), 7.45 (s, 1H), 6.49-6.08 (m, 1H), 5.76 (s, 1H), 4.88 (d, J=9.6 Hz, 1H), 3.21-2.57 (m, 10H), 2.06 (s, 3H), 1.81-1.56 (m, 4H).

Preparation of 8-(2,2-difluoroethyl)-10-(2-pyridyl)-11-oxa-3,8-diazaspiro[5.5]undecane

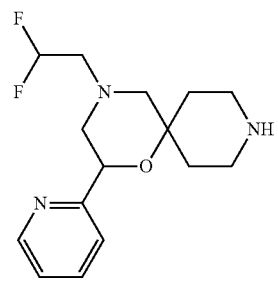 [SMILES: FC(F)CN1CC(c2ccccn2)OC2(CCNCC2)C1]

Step 1:

To tert-butyl 4-[(benzylamino)methyl]-4-hydroxy-piperidine-1-carboxylate (3.0 g, 9.36 mmol) in DMF (19 mL) at 0° C. was added diisopropyl ethylamine (3.4 mL, 19.66 mmol) followed by the addition of 2-bromo-1-(2-pyridyl)ethanone hydrobromide salt (2.6 g, 9.36 mmol) and reaction mixture was stirred for 2 hours warming from 0° C. to 10° C. The reaction mixture was diluted with ethyl acetate and washed with sat. NaHCO₃ solution and then brine. The organics were separated, dried over Na₂SO₄, filtered and concentrated in vacuo to give a residue, which was purified using silica gel column chromatography using MeOH/DCM (1-15%) as eluent to give tert-butyl 4-[[benzyl-[2-oxo-2-(2-pyridyl)ethyl]amino]methyl]-4-hydroxy-piperidine-1-carboxylate (3.8, 92%). ESI-MS m/z calc. 439.2. Found 440.0 (M+1)⁺; Retention time: 1.12 minutes (3 min run).

Step 2:

To tert-butyl 4-[[benzyl-[2-oxo-2-(2-pyridyl)ethyl]amino] methyl]-4-hydroxy-piperidine-1-carboxylate (190 mg, 0.43 mmol) in benzene (11 mL) was added 4-methylbenzenesulfonic acid (99 mg, 0.52 mmol) and reaction mixture was heated at 80° C. for 30 minutes. The reaction mixture was cooled, diluted with ethyl acetate and washed sequentially with sat. NaHCO₃ and brine solution. The organic layer was separated, dried over Na₂SO₄, filtered and concentrated in vacuo to give residue, which was purified using silica gel column chromatography using EtOAc/DCM (10-100%) as eluent to give tert-butyl 8-benzyl-10-(2-pyridyl)-11-oxa-3,8-diazaspiro[5.5]undec-9-ene-3-carboxylate (86 mg, 45%). ESI-MS m/z calc. 421.5. Found 422.2 (M+1)⁺; Retention time: 1.42 minutes (3 min run). ¹H NMR (400 MHz, CDCl₃) δ 8.40-8.34 (m, 1H), 7.56 (dd, J=4.0, 3.5 Hz, 1H), 7.37-7.27 (m, 6H), 7.07 (s, 1H), 6.92 (d, J=1.5 Hz, 1H), 4.22 (s, 2H), 3.99-3.76 (m, 2H), 3.17 (t, J=11.8 Hz, 2H), 2.78 (s, 2H), 1.83 (s, 2H), 1.44 (s, 9H), 1.40 (d, J=4.4 Hz, 2H).

Step 3:

To tert-butyl 8-benzyl-10-(2-pyridyl)-11-oxa-3,8-diazaspiro[5.5]undec-9-ene-3-carboxylate (80 mg, 0.19 mmol) in methanol (13 mL) was added Pd(OH)₂ (50 mg, 0.36 mmol) and ammonium formate (180 mg, 2.85 mmol) and the reaction mixture was heated at 70° C. for 1 hour. The reaction mixture was cooled, diluted with ethyl acetate and filtered through Celite®. The organic layer was washed with 1:1 NaOH:NaHCO₃ solution, dried over Na₂SO₄, filtered and concentrated in vacuo to yield tert-butyl 10-(2-pyridyl)-11-oxa-3,8-diazaspiro[5.5]undecane-3-carboxylate (63 mg, 100%) as an oil which was used in the next step without further purification. ESI-MS m/z calc. 333.4. Found 334.4 (M+1)⁺; Retention time: 1.00 minutes (3 min run).

Step 4:

To tert-butyl 10-(2-pyridyl)-11-oxa-3,8-diazaspiro[5.5]undecane-3-carboxylate (63 mg, 0.19 mmol) in ethanol was added sodium hydrogen carbonate (64 mg, 0.76 mmol) followed by the addition of 2,2-difluoroethyl trifluoromethanesulfonate (49 mg, 0.23 mmol) and reaction mixture was heated at 80° C. for 40 minutes. The reaction mixture was cooled to room temperature and diluted with DCM and the organic layer was washed with 1:1 NaOH:NaHCO₃ solution. The organics were separated, dried over Na₂SO₄, filtered and concentrated in vacuo to give tert-butyl 8-(2,2-difluoroethyl)-10-(2-pyridyl)-11-oxa-3,8-diazaspiro[5.5]undecane-3-carboxylate as an oil. To the oil was added HCl (237.5 μL of 4 M in dioxane, 0.95 mmol) at room temperature under an atmosphere of nitrogen and the reaction mixture was stirred for 30 minutes. The solvent was removed in vacuo and the residue was triturated with ether to give 8-(2,2-difluoroethyl)-10-(2-pyridyl)-11-oxa-3,8-diazaspiro[5.5]undecane (45 mg, 79%). ESI-MS m/z calc. 297.3. Found 298.4 (M+1)⁺; Retention time: 0.35 minutes (3 min run).

Preparation of 4-(2,2-difluoroethyl)-2-(6-methylpyridin-2-yl)-1-oxa-4,9-diazaspiro[5.5]undecane

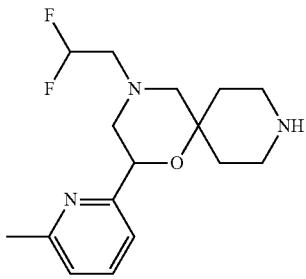 [SMILES: Cc1cccc(C2CN(CC(F)F)CC3(CCNCC3)O2)n1]

This compound was prepared using the chemistry as described above using 2-bromo-1-(6-methyl-2-pyridyl)ethanone in step 1. ESI-MS m/z calc. 311.2. Found 312.1 (M+1)⁺; Retention time: 0.3 minutes (3 min run).

Preparation of 4-(2,2-difluoroethyl)-2-(3-methylpyridin-2-yl)-1-oxa-4,9-diazaspiro[5.5]undecane

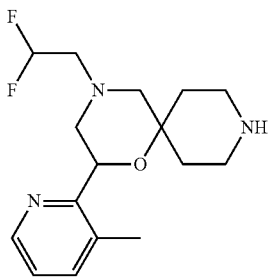 [SMILES: Cc1cccnc1C1CN(CC(F)F)CC2(CCNCC2)O1]

This compound was prepared using the chemistry as described above using 2-bromo-1-(3-methylpyridin-2-yl)ethanone in step 1. ESI-MS m/z calc. 311.4. Found 312.0 (M+1)⁺; Retention time: 0.23 minutes (3 min run).

Preparation of 8-(2,2-difluoroethyl)-10-(1H-pyrazol-3-yl)-11-oxa-3,8-diazaspiro[5.5]undecane

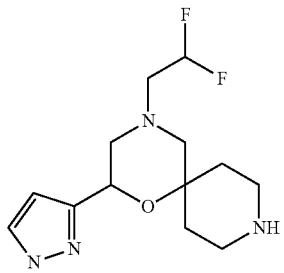 [SMILES: FC(F)CN1CC(c2cc[nH]n2)OC2(CCNCC2)C1]

Step 1:

To a mixture of 3-tert-butoxycarbonyl-8-(2,2-difluoroethyl)-11-oxa-3,8-diazaspiro[5.5]undecane-10-carboxylic acid (100 mg, 0.27 mmol), N,O-dimethylhydroxylamine hydrochloride salt (29 mg, 0.30 mmol) and T3P (245 μL of 50% w/w, 0.41 mmol) in 2-methyltetrahydrofuran (1 mL) was added triethylamine (153 μL, 1.10 mmol). The reaction mixture was stirred overnight, then diluted with ethyl acetate (5 mL), washed with sat. aq. NaHCO₃ (5 mL), dried over MgSO₄ and concentrated in vacuo to give the Weinreb amide intermediate. The intermediate was dissolved in THF (1 mL) and cooled to 0° C. under an atmosphere of nitrogen, and chloro(ethynyl)magnesium (1 mL of 0.6 M in THF, 0.60 mmol) was added dropwise. The reaction mixture was stirred at 0° C. for 2 h, then at room temperature for 1 hour. The reaction mixture was quenched with sat. aq. NH₄Cl, extracted with ethyl acetate, dried over MgSO₄ and purified by silica gel column chromatography using 0-100% EtOAc/hexanes eluent to give tert-butyl 8-(2,2-difluoroethyl)-10-prop-2-ynoyl-11-oxa-3,8-diazaspiro[5.5]undecane-3-carboxylate (25 mg, 24%) as a colorless oil. ESI-MS m/z calc. 372.4. Found 373.1 (M+1)⁺; Retention time: 1.82 (3 min run; ¹H NMR (400 MHz, CDCl₃) δ 5.84 (tt, J=55.8, 4.2 Hz, 1H), 4.30 (d, J=8.6 Hz, 1H), 3.78 (s, 2H), 3.38 (s, 1H), 3.34 (d, J=10.2 Hz, 1H), 3.13 (dd, J=30.8, 11.3 Hz, 2H), 2.86-2.56 (m, 3H), 2.35 (d, J=14.6 Hz, 1H), 2.22 (dd, J=22.1, 11.2 Hz, 2H), 1.70-1.36 (m, 12H).

Step 2:

A solution of tert-butyl 8-(2,2-difluoroethyl)-10-prop-2-ynoyl-11-oxa-3,8-diazaspiro[5.5]undecane-3-carboxylate (25 mg, 0.07 mmol), hydrazine (42 μL, 1.34 mmol) and ethanol (0.5 mL) was stirred for 1 hour at room temperature. The solution was concentrated in vacuo to give the crude pyrazole as a yellow oil. HCl (400 μL of 4 M in dioxane, 1.60 mmol) followed by ethanol (0.2 mL) was added and the reaction mixture was stirred for 15 minutes at room temperature. The reaction mixture was concentrated in vacuo to give 8-(2,2-difluoroethyl)-10-(1H-pyrazol-3-yl)-11-oxa-3,8-diazaspiro[5.5]undecane as a gummy yellow solid. ESI-MS m/z calc. 286.2. Found 287.1 (M+1)⁺; Retention time: 0.32 minutes (3 min run).

Preparation of 2-(1H-pyrazol-3-yl)-4-(2,2,2-trifluoroethyl)-1-oxa-4,9-diazaspiro[5.5]undecane

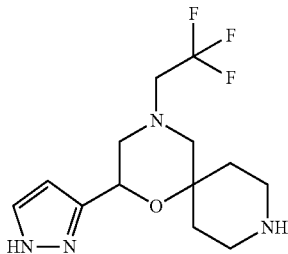 [SMILES: FC(F)(F)CN1CC(c2cc[nH]n2)OC2(CCNCC2)C1]

This compound was prepared using the chemistry as described above starting from 9-(tert-butoxycarbonyl)-4-(2,2,2-trifluoroethyl)-1-oxa-4,9-diazaspiro[5.5]undecane-2-carboxylic acid. ESI-MS m/z calc. 304.2. Found 305.3 (M+1)$^+$; Retention time: 0.76 minutes (3 min run).

Preparation of 2-(5-methyl-1H-pyrazol-3-yl)-4-(2,2,2-trifluoroethyl)-1-oxa-4,9-diazaspiro[5.5]undecane

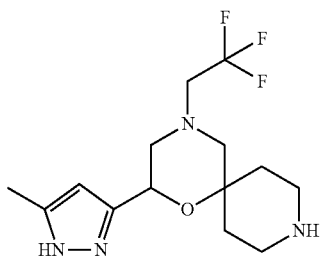 [SMILES: Cc1cc(C2CN(CC(F)(F)F)CC3(CCNCC3)O2)n[nH]1]

This compound was prepared using the chemistry as described above starting from 9-(tert-butoxycarbonyl)-4-(2,2,2-trifluoroethyl)-1-oxa-4,9-diazaspiro[5.5]undecane-2-carboxylic acid and using bromo-prop-1-ynyl-magnesium. ESI-MS m/z calc. 318.2. Found 319.1 (M+1)$^+$; Retention time: 0.85 minutes. (3 min run).

Preparation of 8-ethyl-9-phenyl-11-oxa-3,8-diazaspiro[5.5]undecane

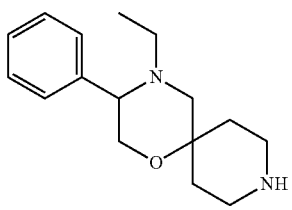 [SMILES: CCN1CC2(CCNCC2)OCC1c1ccccc1]

Step 1:

A solution of tert-butyl-1-oxa-6-azaspiro[2.5]octane-6-carboxylate (0.7 g, 3.42 mmol) and 2-[(4-methoxyphenyl)methylamino]-2-phenyl-ethanol (800 mg, 3.109 mmol) in ethanol (5 mL) was stirred at 60° C. for 72 hours. The reaction mixture was concentrated in vacuo and purified by silica gel column chromatography using 0 to 10% MeOH in DCM as eluent to yield tert-butyl 4-hydroxy-4-[[(2-hydroxy-1-phenyl-ethyl)-[(4-methoxyphenyl)methyl]amino]methyl]piperidine-1-carboxylate (1.2 g, 82%). ESI-MS m/z calc. 470.6. Found 471.5 (M+1)$^+$; Retention time: 1.45 minutes (3 min run).

Step 2:

To a solution of tert-butyl 4-hydroxy-4-[[(2-hydroxy-1-phenyl-ethyl)-[(4-methoxyphenyl)methyl]amino]methyl]piperidine-1-carboxylate (1.0 g, 2.13 mmol) in THF (10 mL) was added DIEA (1.1 mL, 6.38 mmol) followed by an addition of a solution of methylsulfonyl methanesulfonate (1.1 g, 6.38 mmol) in THF (2 mL) under an atmosphere of nitrogen at 0° C. The reaction mixture was warmed to room temperature and then heated at 40° C. for 16 hours. The reaction mixture was quenched with water and the aqueous layer was extracted with DCM. The organic layer was washed with a sat. solution of NaHCO$_3$, followed by washing with water. The organic layer was dried over MgSO$_4$ and concentrated in vacuo. The residue was purified by silica gel column chromatography using 0 to 100% DCM in hexanes as eluent to obtain tert-butyl 8-[(4-methoxyphenyl)methyl]-9-phenyl-11-oxa-3,8-diazaspiro[5.5]undecane-3-carboxylate (0.5 g, 51%). ESI-MS m/z calc. 452.6. Found 453.5 (M+1)$^+$; Retention time: 1.62 minutes (3 min run).

Step 3:

To tert-butyl 8-[(4-methoxyphenyl)methyl]-9-phenyl-11-oxa-3,8-diazaspiro[5.5]undecane-3-carboxylate (500 mg, 1.11 mmol), Pd (500 mg, 4.70 mmol) and ammonium formate (697 mg, 11.05 mmol) was added methanol. The reaction mixture was then heated at 70° C. for 16 hours. The reaction mixture was filtered through a plug of celite and the solvent was concentrated in vacuo to obtain tert-butyl 9-phenyl-11-oxa-3,8-diazaspiro[5.5]undecane-3-carboxylate (340 mg, 93%) as an oil. ESI-MS m/z calc. 332.4. Found 333.5 (M+1)$^+$; Retention time: 1.21 minutes (3 min run).

Step 4:

To a solution of tert-butyl 9-phenyl-11-oxa-3,8-diazaspiro[5.5]undecane-3-carboxylate (336 mg, 1.01 mmol) in ethanol (3 mL) was added acetaldehyde (62 µL, 1.11 mmol) then sodium cyanoborohydride (89 mg, 1.42 mmol) and the reaction mixture was stirred for 2 hours. The reaction mixture was concentrated in vacuo, partitioned between DCM (50 mL) and 1:1 aq. sat. NaHCO$_3$/25% NaOH (10 mL), and the aqueous layer was further extracted with DCM (2×25 mL). The combined organics were dried with MgSO$_4$ and concentrated in vacuo to give tert-butyl 8-ethyl-9-phenyl-11-oxa-3,8-diazaspiro[5.5]undecane-3-carboxylate (298 mg, 82%). ESI-MS m/z calc. 360.5. Found 361.7 (M+1)$^+$; Retention time: 1.30 minutes (3 min run).

Step 5:

To a solution of tert-butyl 8-ethyl-9-phenyl-11-oxa-3,8-diazaspiro[5.5]undecane-3-carboxylate (295 mg, 0.82 mmol) in DCM (3 mL) was added hydrogen chloride (2 mL of 4 M dioxane, 8.18 mmol). The reaction mixture was stirred for 1 hour. The solvent was decanted and the residue was triturated with methanol and hexanes. The solvent was concentrated in vacuo to obtain 8-ethyl-9-phenyl-11-oxa-3,8-diazaspiro[5.5]undecane hydrochloride salt (230 mg, 95%) as a fluffy solid. ESI-MS m/z calc. 260.2. Found 261.1 (M+1)$^+$; Retention time: 0.2 minutes (3 min run).

Preparation of tert-butyl 9-ethyl-11-oxa-3,8-diaza-spiro[5.5]undecane-3-carboxylate

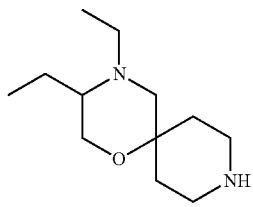

This compound was prepared using the chemistry as described above starting from tert-butyl 1-oxa-6-azaspiro[2.5]octane-6-carboxylate. ESI-MS m/z calc. 212.2. Found 213.5 (M+1)+; Retention time: 0.21 minutes (3 min run).

Preparation of 2-(methoxymethyl)-4-(pyrimidin-2-yl)-1-oxa-4,9-diazaspiro[5.5]undecane

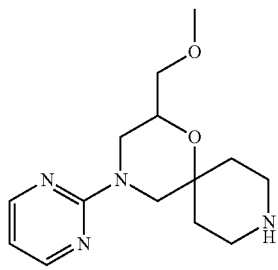 [SMILES: COCC1CN(c2ncccn2)CC2(CCNCC2)O1]

Step 1:
A mixture of tert-butyl 8-benzyl-10-(hydroxymethyl)-11-oxa-3,8-diazaspiro[5.5]undecane-3-carboxylate (4.10 g, 10.9 mmol), ammonium formate (6.87 g, 109 mmol) and Pd(OH)$_2$ (1.53 g, 10.9 mmol) was heated at 60° C. for 1 h. The reaction mixture was cooled, filtered, and concentrated in vacuo to provide tert-butyl 10-(hydroxymethyl)-11-oxa-3,8-diazaspiro[5.5]undecane-3-carboxylate (3.10 g, 10.8 mmol, 99%). ESI-MS m/z calc. 286.2. Found 287.2 (M+1)+; Retention time: 0.75 minutes (3 min run).

Step 2:
A solution of tert-butyl 10-(hydroxymethyl)-11-oxa-3,8-diazaspiro[5.5]undecane-3-carboxylate (3.10 g, 10.8 mmol), 2-chloropyrimidine (1.86 g, 16.2 mmol) and sodium carbonate (2.30 g, 21.7 mmol) in DMSO (15 mL) was heated at 110° C. for 1 h. The reaction mixture was diluted with ethyl acetate (200 mL), washed with water (4×100 mL), dried over Na$_2$SO$_4$, and concentrated in vacuo. Silica gel column chromatography (0-60% ethyl acetate/hexane) provided tert-butyl 10-(hydroxymethyl)-8-pyrimidin-2-yl-11-oxa-3,8-diazaspiro[5.5]undecane-3-carboxylate (3.18 g, 8.73 mmol, 80%). ESI-MS m/z calc. 364.2. Found 365.3 (M+1)+; Retention time: 1.21 minutes (3 min run). $^1$H NMR (400 MHz, CDCl$_3$) δ 8.29 (d, J=4.7 Hz, 2H), 6.50 (t, J=4.7 Hz, 1H), 4.64 (ddd, J=16.0, 8.5, 1.5 Hz, 2H), 3.90-3.80 (m, 1H), 3.79-3.56 (m, 4H), 3.44-3.22 (m, 1H), 3.13 (t, J=10.6 Hz, 1H), 2.90-2.71 (m, 2H), 2.19 (d, J=8.9 Hz, 1H), 1.98 (dd, J=10.6, 3.6 Hz, 1H), 1.69-1.58 (m, 2H), 1.45 (s, 9H).

Step 3:
To a solution of tert-butyl 10-(hydroxymethyl)-8-pyrimidin-2-yl-11-oxa-3,8-diazaspiro[5.5]undecane-3-carboxylate (1.45 g, 3.98 mmol) in dichloromethane (15 mL) was added triethylamine (1.66 mL, 11.9 mmol) and 4-(dimethylamino)-pyridine (195 mg, 1.59 mmol) at 0° C. Tosyl chloride (910 mg, 4.78 mmol) was then added in one portion. The reaction mixture was allowed to warm to room temperature and stirred for 16 h. The reaction mixture was quenched with water and the layers were separated. The aqueous layer was extracted with dichloromethane, and the combined organic layers washed with saturated sodium bicarbonate solution and brine. The organic layer was dried over Na$_2$SO$_4$, filtered and concentrated in vacuo. Silica gel column chromatography (0-80% ethyl acetate/hexanes) provided tert-butyl 4-(pyrimidin-2-yl)-2-(tosyloxymethyl)-1-oxa-4,9-diazaspiro[5.5]undecane-9-carboxylate (1.83 g, 3.53 mmol, 89%). ESI-MS m/z calc. 518.2. Found 519.3 (M+1)+; Retention time: 1.83 minutes (3 min run). $^1$H NMR (400 MHz, MeOD) δ 8.31 (d, J=4.8 Hz, 2H), 7.82 (d, J=8.3 Hz, 2H), 7.45 (d, J=8.2 Hz, 2H), 6.60 (t, J=4.8 Hz, 1H), 4.67-4.48 (m, 2H), 4.12 (d, J=4.6 Hz, 2H), 3.89 (ddd, J=12.0, 7.5, 4.6 Hz, 1H), 3.71-3.56 (m, 2H), 3.05 (ddd, J=20.6, 17.0, 8.8 Hz, 2H), 2.80-2.65 (m, 2H), 2.46 (s, 3H), 1.88 (d, J=14.1 Hz, 1H), 1.50 (dt, J=7.9, 4.0 Hz, 2H), 1.45 (s, 9H), 1.38-1.27 (m, 1H).

Step 4:
Tert-butyl 4-(pyrimidin-2-yl)-2-(tosyloxymethyl)-1-oxa-4,9-diazaspiro[5.5]undecane-9-carboxylate (1.83 g, 3.53 mmol) was dissolved in a solution of sodium methoxide (71 mL of 0.5 M in methanol, 35 mmol) and refluxed for 18 h. The solvent was evaporated to dryness and the residue dissolved in dichloromethane (200 mL). The solution was washed with water and brine, dried over Na$_2$SO$_4$, filtered and concentrated in vacuo. Silica gel chromatography (5-80% ethyl acetate/hexanes) provided tert-butyl 10-(methoxymethyl)-8-pyrimidin-2-yl-11-oxa-3,8-diazaspiro[5.5]undecane-3-carboxylate as colorless oil. ESI-MS m/z calc. 378.2. Found 379.3 (M+1)+; Retention time: 1.54 minutes (3 min run). $^1$H NMR (400 MHz, MeOD) δ 8.31 (d, J=4.8 Hz, 2H), 6.58 (t, J=4.8 Hz, 1H), 4.72-4.52 (m, 2H), 3.91 (ddd, J=10.9, 7.9, 4.9 Hz, 1H), 3.76-3.59 (m, 2H), 3.56-3.44 (m, 2H), 3.40 (s, 3H), 3.13 (t, J=11.1 Hz, 1H), 2.85-2.65 (m, 2H), 1.98 (d, J=14.6 Hz, 2H), 1.59 (dd, J=8.7, 4.5 Hz, 2H), 1.45 (s, 9H), 1.44-1.37 (m, 1H).

Step 5:
Tert-butyl 10-(methoxymethyl)-8-pyrimidin-2-yl-11-oxa-3,8-diazaspiro[5.5]undecane-3-carboxylate (1.18 g, 3.12 mmol) was dissolved in dichloromethane (2 mL) and treated with a solution of HCl (1.6 mL of 4 M in dioxane, 6.2 mmol). The mixture was allowed to stir for 2 h. The reaction mixture was evaporated to dryness to provide 2-(methoxymethyl)-4-(pyrimidin-2-yl)-1-oxa-4,9-diazaspiro[5.5]undecane hydrochloride. ESI-MS m/z calc. 278.2. Found 279.2 M+1)+; Retention time: 0.68 min (3 min run). $^1$H NMR (400 MHz, MeOD) δ 8.59 (d, J=5.2 Hz, 2H), 6.99 (t, J=5.2 Hz, 1H), 4.52 (ddd, J=44.3, 13.4, 1.7 Hz, 2H), 4.12-3.97 (m, 1H), 3.56 (ddd, J=26.1, 10.3, 4.9 Hz, 2H), 3.42 (s, 3H), 3.34 (dd, J=10.9, 5.0 Hz, 2H), 3.27-3.19 (m, 2H), 3.13 (dd, J=13.2, 11.1 Hz, 2H), 2.42 (d, J=15.2 Hz, 1H), 1.94 (dd, J=10.7, 4.3 Hz, 2H), 1.74 (ddd, J=15.3, 12.8, 4.4 Hz, 1H).

Preparation of 2-ethyl-4-(pyridin-2-yl)-1-oxa-4,9-diazaspiro[5.5]undecane

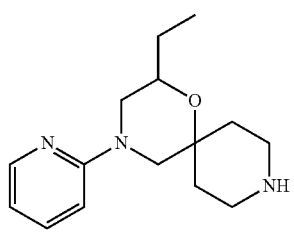 [SMILES: CCC1CN(c2ccccn2)CC2(CCNCC2)O1]

Step 1:

To a solution of tert-butyl 10-benzyl-8-vinyl-7-oxa-3,10-diazaspiro[5.5]undecane-3-carboxylate (3.10 g, 8.32 mmol) in methanol (60 mL) was added Pd(OH)$_2$ (1.40 g, 9.99 mmol) and ammonium formate (10.5 g, 166 mmol) and the mixture heated at 55° C. for 20 min. The reaction mixture was filtered, concentrated to ~10 mL, then diluted with dichloromethane and saturated sodium bicarbonate solution. The organic layer was separated and the aqueous layer extracted with dichloromethane (5×20 mL). The combined organic layers were dried over Na$_2$SO$_4$, filtered, and concentrated in vacuo to provide tert-butyl 4-ethyl-5-oxa-2,9-diazaspiro[5.5]undecane-9-carboxylate (2.27 g, 7.99 mmol, 96%). ESI-MS m/z calc. 284.21. Found 285.1 (M+1)$^+$; Retention time: 1.09 minutes (3 min run).

Step 2:

A solution of rac-BINAP (43.8 mg, 0.070 mmol) and Pd$_2$(dba)$_3$ (32.2 mg, 0.0352 mmol) in toluene (1 mL) was stirred under nitrogen atmosphere in a sealed vial at 90° C. for 10 min, then cooled to 40° C. and cannulated into a stirring solution of tert-butyl 4-ethyl-5-oxa-2,9-diazaspiro[5.5]undecane-9-carboxylate (500 mg, 1.76 mmol) and 2-chloropyridine (200 mg, 165 µL, 1.76 mmol) in toluene (6 mL). The solution was treated with sodium tert-butoxide (275 mg, 2.87 mmol), flushed with nitrogen and stirred for 3 h at 90° C. The reaction mixture was cooled, diluted with ethyl acetate (100 mL), filtered through Celite and concentrated in vacuo. Silica gel chromatography (120 g silica, 10-70% ethyl acetate/hexane) provided tert-butyl 10-ethyl-8-(2-pyridyl)-11-oxa-3,8-diazaspiro[5.5]undecane-3-carboxylate (486 mg, 1.34 mmol, 76%) as an orange-colored oil. ESI-MS m/z calc. 361.2. Found 362.3 (M+1)$^+$; Retention time: 1.25 minutes (3 min run). $^1$H NMR (400 MHz, DMSO-d$_6$) δ 8.08 (dd, J=4.9, 1.4 Hz, 1H), 7.51 (ddd, J=8.8, 7.1, 2.0 Hz, 1H), 6.85 (d, J=8.7 Hz, 1H), 6.61 (dd, J=6.7, 4.9 Hz, 1H), 4.24 (d, J=12.0 Hz, 1H), 4.11 (d, J=12.9 Hz, 1H), 3.75-3.51 (m, 3H), 3.15 (br s, 1H), 2.91 (br s, 1H), 2.59 (d, J=13.0 Hz, 1H), 2.40 (dd, J=12.6, 10.9 Hz, 1H), 2.02 (d, J=13.3 Hz, 1H), 1.60-1.42 (m, 4H), 1.39 (s, 9H), 1.36-1.26 (m, 1H), 0.95 (t, J=7.5 Hz, 3H).

Step 3:

Tert-butyl 10-ethyl-8-(2-pyridyl)-11-oxa-3,8-diazaspiro[5.5]undecane-3-carboxylate (480 mg, 1.33 mmol) was dissolved in dichloromethane (5 mL) at 0° C. and treated dropwise with HCl in dioxane (2.65 mL of 4 M, 10.6 mmol). The reaction was then allowed to warm to room temperature and stirred for 1 h. The reaction mixture was diluted with dichloromethane (50 mL) and saturated sodium bicarbonate solution. The organic layer was separated and the aqueous layer extracted with dichloromethane (3×20 mL). The aqueous layer was further diluted with 25 mL of 1 N NaOH and extracted with dichloromethane (3×20 mL). The combined organic extracts were dried over Na$_2$SO$_4$, filtered, and concentrated to provide 10-ethyl-8-(2-pyridyl)-11-oxa-3,8-diazaspiro[5.5]undecane (345 mg, 1.32 mmol, 99%) an orange-colored oil. ESI-MS m/z calc. 261.2. Found 262.3 (M+1)$^+$; Retention time: 0.3 minutes (3 min run). $^1$H NMR (400 MHz, DMSO-d$_6$) δ 8.08 (dd, J=4.9, 1.4 Hz, 1H), 7.50 (ddd, J=8.8, 7.1, 2.0 Hz, 1H), 6.84 (d, J=8.6 Hz, 1H), 6.60 (dd, J=6.6, 5.0 Hz, 1H), 4.17 (t, J=11.3 Hz, 2H), 3.58-3.54 (m, 2H), 2.96-2.84 (m, 1H), 2.81-2.71 (m, 1H), 2.71-2.65 (m, 2H), 2.55 (d, J=12.9 Hz, 1H), 2.40 (dd, J=12.6, 11.0 Hz, 1H), 1.93 (d, J=13.9 Hz, 1H), 1.59-1.38 (m, 5H), 0.96 (t, J=7.5 Hz, 3H).

Preparation of 4-(but-2-ynyl)-2-(fluoromethyl)-1-oxa-4,9-diazaspiro[5.5]undecane

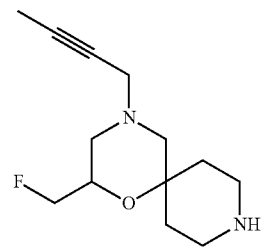 [SMILES: CC#CCN1CC(CF)OC2(CCNCC2)C1]

Step 1:

To a solution of tert-butyl 8-benzyl-10-(hydroxymethyl)-11-oxa-3,8-diazaspiro[5.5]undecane-3-carboxylate (2.00 g, 5.31 mmol) in methanol (38 mL) was added Pd(OH)$_2$ (671 mg, 4.78 mmol) and ammonium formate (4.02 g, 63.7 mmol) and the mixture heated at 50° C. for 1 h. Additional catalyst (2.6 mmol) and ammonium formate (25 mmol) were added and the reaction heated for an additional 2 h. The reaction mixture was filtered and concentrated to ~10 mL volume. The concentrate was diluted with dichloromethane and saturated sodium bicarbonate solution. The organic layer was separated and the aqueous layer washed with dichloromethane (5×50 mL). The combined organics were dried over Na$_2$SO$_4$, filtered, and concentrated to provide tert-butyl 10-(hydroxymethyl)-11-oxa-3,8-diazaspiro[5.5]undecane-3-carboxylate (1.37 g, 4.77 mmol, 90%) as an amber-colored glass. ESI-MS m/z calc. 286.2. Found 287.3 (M+1)$^+$; Retention time: 0.65 minutes (3 min run).

Step 2:

Tert-butyl 10-(hydroxymethyl)-11-oxa-3,8-diazaspiro[5.5]undecane-3-carboxylate (1.35 g, 4.71 mmol), K$_2$CO$_3$ (3.26 g, 23.6 mmol) and 1-bromobut-2-yne (495 µL, 5.66 mmol) were combined in N,N-dimethylformamide (15 mL) and heated for 48 h at 45° C. under nitrogen. The reaction mixture was diluted with ethyl acetate (150 mL) and filtered. The filtrate was washed with water, 50% saturated sodium bicarbonate solution, and brine. The organic layer was dried over Na$_2$SO$_4$, filtered, and concentrated in vacuo. The desired fractions obtained from silica gel chromatography (5-20% methanol/dichloromethane) were combined and concentrated, then brought up in ethyl acetate, filtered and concentrated in vacuo to provide tert-butyl-8-but-2-ynyl-10-(hydroxymethyl)-11-oxa-3,8-diazaspiro[5.5]undecane-3-carboxylate (1.12 g, 3.31 mmol, 70%). ESI-MS m/z calc. 338.2. Found 339.3 (M+1)$^+$; Retention time: 0.86 minutes (3 min run).

Step 3:

To a solution of diethylaminosulfur trifluoride (19.5 µL, 0.148 mmol) in dichloromethane (1.0 mL) at −78° C. was added dropwise a solution of tert-butyl 8-but-2-ynyl-10-(hydroxymethyl)-11-oxa-3,8-diazaspiro[5.5]undecane-3-carboxylate (50.0 mg, 0.148 mmol) in dichloromethane (1 mL). The reaction was stirred for 10 min at −78° C. then allowed to warm to room temperature and stirred for 16 h. Silica gel chromatography (4 g silica, 0-15% methanol/dichloromethane) provided tert-butyl 8-but-2-ynyl-10-(fluoromethyl)-11-oxa-3,8-diazaspiro[5.5]undecane-3-carboxylate (23.0 mg, 46%). ESI-MS m/z calc. 340.2. Found 341.3

(M+1)⁺; Retention time: 1.16 minutes (3 min run). ¹H NMR (400 MHz, CDCl₃) δ 4.52-4.40 (m, 1H), 4.39-4.28 (m, 1H), 4.06-3.91 (m, 1H), 3.71 (br s, 2H), 3.35-3.14 (m, 3H), 3.08 (t, J=11.4 Hz, 1H), 2.78 (d, J=10.3 Hz, 1H), 2.58 (d, J=11.1 Hz, 1H), 2.31 (d, J=13.5 Hz, 1H), 2.06 (t, J=12.5 Hz, 2H), 1.84 (t, J=2.3 Hz, 3H), 1.57-1.44 (m, 12H).

Step 4:

Tert-butyl 8-but-2-ynyl-10-(fluoromethyl)-11-oxa-3,8-diazaspiro[5.5]undecane-3-carboxylate (23.0 mg, 0.0676 mmol) was dissolved in dichloromethane (2 mL) and treated with HCl in dioxane (1.69 mL of 4 M, 6.76 mmol). The reaction mixture was stirred for 2 h, then diluted with dichloromethane (10 mL) and 1:1 saturated sodium bicarbonate/1 M NaOH (10 mL). The organic layer was separated, dried over Na₂SO₄, and concentrated to yield 8-but-2-ynyl-10-(fluoromethyl)-11-oxa-3,8-diazaspiro[5.5]undecane hydrochloride (16.0 mg, 0.0666 mmol, 98%). ESI-MS m/z calc. 240.2. Found 241.5 (M+1)⁺; Retention time: 0.22 minutes (3 min run).

Preparation of 4-(but-2-ynyl)-2,2-difluoro-1-oxa-4,9-diazaspiro[5.5]undecane

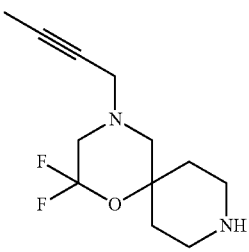 [SMILES: CC#CCN1CC(F)(F)OC2(CCNCC2)C1]

Step 1:

To a solution of tert-butyl 4-(aminomethyl)-4-hydroxy-piperidine-1-carboxylate (3.00 g, 13.0 mmol) in N,N-dimethylformamide (30 mL) was added ethyl 2-bromo-2,2-difluoroacetate (2.65 g, 13.0 mmol) and the reaction mixture stirred for 1 h under nitrogen. The reaction mixture was mixture diluted with ethyl acetate and water (25 mL) and brine (25 mL). The organic layer was dried over Na₂SO₄, filtered and concentrated to provide tert-butyl 4-[[(2-bromo-2,2-difluoro-acetyl)amino]methyl]-4-hydroxy-piperidine-1-carboxylate (4.98 g, 12.9 mmol, 99%). ¹H NMR (400 MHz, DMSO-d₆) δ 9.04 (t, J=5.9 Hz, 1H), 4.66 (s, 1H), 3.65 (d, J=12.7 Hz, 2H), 3.16 (d, J=6.1 Hz, 2H), 3.02 (s, 2H), 1.38 (m, 13H).

Step 2:

To a stirring solution of potassium tert-butoxide (7.23 mL of 1 M, 7.23 mmol) in tetrahydrofuran (20 mL) at 70° C. was added a solution of tert-butyl 4-[[(2-bromo-2,2-difluoro-acetyl)amino]methyl]-4-hydroxy-piperidine-1-carboxylate (1.4 g, 3.62 mmol) in tetrahydrofuran (20 mL) over 15 min. After 20 min the reaction mixture was diluted with 1:1 brine/saturated NH₄Cl and ethyl acetate. The organic layer was separated, washed with brine, dried over Na₂SO₄, filtered and concentrated in vacuo. Silica gel chromatography (40 g silica, 30-100% ethyl acetate/hexane, product visualized by TLC with ninhydrin staining+heat) provided tert-butyl 4,4-difluoro-3-oxo-2,9-diazaspiro[5.5]undecane-9-carboxylate (340 mg, 1.11 mmol, 31%) as a white solid. ESI-MS m/z calc. 306.1. Found 307.5 (M+1)⁺; Retention time: 1.32 minutes (3 min run). ¹H NMR (400 MHz, DMSO-d₆) δ 9.00 (s, 1H), 3.75 (d, J=13.3 Hz, 2H), 3.45 (d, J=3.2 Hz, 2H), 3.07 (br s, 2H), 1.79 (d, J=13.6 Hz, 2H), 1.72-1.60 (m, 2H), 1.41 (s, 9H).

Step 3:

Borane dimethylsulfide (36.3 μL, 0.408 mmol) was added dropwise to a solution of tert-butyl 10,10-difluoro-9-oxo-11-oxa-3,8-diazaspiro[5.5]undecane-3-carboxylate (125 mg, 0.408 mmol) in tetrahydrofuran (3 mL). The reaction mixture was heated at 55° C. for 2 h then cooled to room temperature. The mixture was quenched with the careful dropwise addition of methanol (~2 mL). N,N-dimethylethane-1,2-diamine (33.3 μL, 0.313 mmol) was then added and the mixture heated at 70° C. for 40 min. The reaction was concentrated, and silica gel chromatography (4 g silica, 1% triethylamine/4% methanol/dichloromethane)) provided tert-butyl 8-but-2-ynyl-10,10-difluoro-11-oxa-3,8-diazaspiro[5.5]undecane-3-carboxylate which was taken directly to the next reaction.

Step 4:

To a mixture of crude tert-butyl 10,10-difluoro-11-oxa-3,8-diazaspiro[5.5]undecane-3-carboxylate (65.0 mg, 0.222 mmol) and K₂CO₃ (61.5 mg, 0.445 mmol) in N,N-dimethylformamide (1.0 mL) was added 1-bromobut-2-yne (29.2 μL, 0.334 mmol) and the reaction heated at 45° C. for 48 h. The reaction was diluted with ethyl acetate and filtered. The filtrate was dried over Na₂SO₄, filtered and concentrated. Silica gel chromatography (4 g silica, 1-100% ethyl acetate/hexane) provided tert-butyl 8-but-2-ynyl-10,10-difluoro-11-oxa-3,8-diazaspiro[5.5]undecane-3-carboxylate (50.0 mg, 65%) as a colorless oil. ESI-MS m/z calc. 344.2. Found 345.3 (M+1)⁺; Retention time: 1.91 minutes (3 min run). ¹H NMR (400 MHz, CDCl₃) δ 3.80 (br s, 2H), 3.35 (q, J=2.2 Hz, 2H), 3.23 (t, J=12.1 Hz, 2H), 2.80 (t, J=8.5 Hz, 2H), 2.48 (s, 2H), 2.02 (d, J=13.2 Hz, 2H), 1.84 (t, J=2.3 Hz, 3H), 1.54-1.48 (m, 2H), 1.46 (s, 9H).

Step 5:

Tert-butyl 8-but-2-ynyl-10,10-difluoro-11-oxa-3,8-diazaspiro[5.5]undecane-3-carboxylate (50.0 mg, 0.145 mmol) was dissolved in dichloromethane (1 mL) and treated with HCl in dioxane (1.3 mL of 4 M, 5.1 mmol). The reaction mixture was stirred for 1 h then concentrated in vacuo several times with acetonitrile to yield a white solid. The solid was dissolved in 1:1 DCM/acetonitrile and stirred with solid K₂CO₃ for 1 h. The mixture was filtered and concentrated to provide 8-but-2-ynyl-10,10-difluoro-11-oxa-3,8-diazaspiro[5.5]undecane (34 mg, 96%). ESI-MS m/z calc. 244.1. Found 245.3 (M+1)⁺; Retention time: 0.79 minutes (3 min run).

Preparation of 4-tert-butyl-2-ethyl-1-oxa-4,9-diazaspiro[5.5]undecane

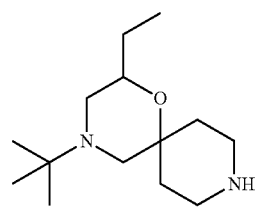 [SMILES: CCC1CN(C(C)(C)C)CC2(CCNCC2)O1]

Step 1:

To tetrakis(triphenylphosphine)palladium (0) (1.03 g, 0.891 mmol) and triphenylphosphine (934 mg, 3.56 mmol) in degassed tetrahydrofuran (150 mL) in a pressure flask was added triethylamine (5.0 mL, 36 mmol). The mixture was stirred for 1 h under nitrogen atmosphere. A solution of tert-butyl 4-[(tert-butylamino)methyl]-4-hydroxy-piperidine-1-carboxylate (5.10 g, 17.8 mmol) in degassed tetrahydrofuran (20 mL) was added via cannula, followed by [(Z)-4-acetoxybut-2-enyl]acetate (2.85 mL, 17.9 mmol) and the mixture was stirred at 45° C. for 16 h. Silica gel chromatography (0-40% ethyl acetate/hexane, ninhydrin stain on TLC to visualize) provided tert-butyl 4-tert-butyl-2-vinyl-1-oxa-4,9-diazaspiro[5.5]undecane-9-carboxylate (5.1 g, 15 mmol, 85%) as a pale yellow oil. $^1$H NMR (400 MHz, CDCl$_3$) d 5.97-5.65 (m, 1H), 5.29 (dt, J=17.3, 1.6 Hz, 1H), 5.17-5.07 (m, 1H), 4.13 (s, 1H), 3.64 (s, 2H), 3.32 (t, J=10.3 Hz, 1H), 3.12 (t, J=11.1 Hz, 1H), 2.85 (dt, J=11.0, 2.5 Hz, 1H), 2.68 (dd, J=11.1, 2.2 Hz, 1H), 2.33 (d, J=14.2 Hz, 1H), 2.00-1.73 (m, 2H), 1.66-1.49 (m, 3H), 1.51-1.35 (m, 11H), 1.09-0.91 (m, 9H).

Step 2:

To a solution of tert-butyl 4-tert-butyl-2-vinyl-1-oxa-4,9-diazaspiro[5.5]undecane-9-carboxylate (550 mg, 1.62 mmol) in methanol (10 mL) was added Pd(OH)$_2$ (447 mg, 3.18 mmol) and ammonium formate (2.19 g, 34.7 mmol) and the reaction mixture heated at 55° C. for 20 min. The reaction mixture was filtered, concentrated to ~10 mL and then diluted with dichloromethane and 1:1 saturated NaHCO$_3$ solution/1M NaOH. The dichloromethane layer was separated and the aqueous layer extracted with dichloromethane (5×20 mL). The combined organic layers were dried over Na$_2$SO$_4$, filtered and concentrated in vacuo to provide tert-butyl 8-tert-butyl-10-ethyl-11-oxa-3,8-diazaspiro[5.5]undecane-3-carboxylate (530 mg, 1.56 mmol, 96%) as a colorless oil. ESI-MS m/z calc. 340.3. Found 341.3 (M+1)$^+$; Retention time: 1.16 minutes (3 min run). $^1$H NMR (400 MHz, DMSO-d$_6$) δ 3.59 (t, J=11.7 Hz, 2H), 3.48-3.36 (m, 1H), 3.11 (br s, 1H), 2.91 (br s, 1H), 2.80 (d, J=10.7 Hz, 1H), 2.71 (dd, J=11.1, 1.7 Hz, 1H), 2.23 (d, J=14.0 Hz, 1H), 1.81 (d, J=11.1 Hz, 1H), 1.71 (t, J=10.6 Hz, 1H), 1.39 (s, 9H), 1.38-1.22 (m, 5H), 0.96 (s, 9H), 0.89 (t, J=7.4 Hz, 3H).

Step 3:

Tert-butyl 8-tert-butyl-10-ethyl-11-oxa-3,8-diazaspiro[5.5]undecane-3-carboxylate (530 mg, 1.56 mmol) was dissolved in dichloromethane and treated with a solution of HCl in dioxane (8.0 mL of 4 M, 33 mmol) and stirred for 15 min. The reaction mixture was diluted with dichloromethane and washed with 1:1 saturated NaHCO$_3$/1 M NaOH. The organic layer was dried over Na$_2$SO$_4$, filtered and concentrated to provide 8-tert-butyl-10-ethyl-11-oxa-3,8-diazaspiro[5.5]undecane (390 mg, 99%) as an oily solid. ESI-MS m/z calc. 240.2. Found 241.3 (M+1)$^+$; Retention time: 0.21 minutes (3 min run).

Preparation of 4-tert-butyl-2-(methoxymethyl)-1-oxa-4,9-diazaspiro[5.5]undecane

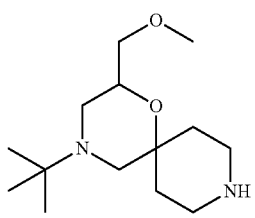 [SMILES: COCC1CN(C(C)(C)C)CC2(CCNCC2)O1]

Step 1:

To tert-butyl 4-tert-butyl-2-vinyl-1-oxa-4,9-diazaspiro[5.5]undecane-9-carboxylate (1.00 g, 2.95 mmol) and 4-methylmorpholine 4-oxide (381 mg, 3.25 mmol) in acetone (9.0 mL) and water (1.0 mL) was added a solution of osmium tetroxide in 2-methyl-2-propanol (370 μL of 2.5% w/w, 0.0295 mmol) and the solution stirred 2 h. The reaction quenched with 300 mL of 1 M sodium bisulfate and stirred for 5 min. The mixture was extracted with ethyl acetate (2×200 mL). The combined organic layers were washed with brine, dried over Na$_2$SO$_4$, filtered and concentrated in vacuo to provide tert-butyl 8-tert-butyl-10-(1,2-dihydroxyethyl)-11-oxa-3,8-diazaspiro[5.5]undecane-3-carboxylate as a white foamy solid. The crude material was taken directly to the next step. ESI-MS m/z calc. 372.3. Found 373.3 (M+1)$^+$; Retention time: 0.83 minutes (3 min run).

Step 2:

To a solution of tert-butyl 8-tert-butyl-10-(1,2-dihydroxyethyl)-11-oxa-3,8-diazaspiro[5.5]undecane-3-carboxylate (1.10 g, 2.95 mmol) in tetrahydrofuran (22 mL) was added sodium periodate (1.58 g, 7.38 mmol) and water (8.0 mL), resulting in a thick white precipitate. The reaction mixture was heated at 40° C. for 3 h, then additional sodium periodate added (2.95 mmol) and the mixture stirred for 16 h. The reaction mixture was filtered through Celite and rinsed with tetrahydrofuran (30 mL). The filtrate solution was cooled to 0° C. and treated portion-wise with sodium borohydride (223 mg, 5.91 mmol) over 5 min. The reaction mixture was stirred for 30 min then diluted with brine (400 mL) and ethyl acetate (400 mL). The organic phase was separated and the aqueous phase extracted with ethyl acetate (3×100 mL). The combined organic layers were dried over Na$_2$SO$_4$, filtered and concentrated in vacuo. Silica gel chromatography (80 g silica, 1-10% methanol/dichloromethane) provided tert-butyl 8-tert-butyl-10-(hydroxymethyl)-11-oxa-3,8-diazaspiro[5.5]undecane-3-carboxylate (720 mg, 2.10 mmol, 71%) as colorless oil. ESI-MS m/z calc. 342.3. Found 343.5 (M+1)$^+$; Retention time: 0.89 minutes (3 min run).

Step 3:

To a solution of tert-butyl 8-tert-butyl-10-(hydroxymethyl)-11-oxa-3,8-diazaspiro[5.5]undecane-3-carboxylate (720 mg, 2.10 mmol) in N,N-dimethylformamide (7.0 mL) was added sodium hydride (588 mg, 14.7 mmol) and the reaction stirred for 10 min. Methyl iodide (916 μL, 14.7 mmol) was added and the reaction mixture stirred for 20 min. The reaction was quenched with saturated aqueous NH$_4$Cl and extracted with ethyl acetate (2×25 mL). The combined organic layers were dried over Na$_2$SO$_4$, filtered and concentrated to provide tert-butyl 8-tert-butyl-10-(methoxymethyl)-11-oxa-3,8-diazaspiro[5.5]undecane-3-carboxylate (732 mg, 2.05 mmol, 98%). ESI-MS m/z calc. 356.3. Found 357.3 (M+1)$^+$; Retention time: 0.97 minutes (3 min run).

Step 4:

Tert-butyl 8-tert-butyl-10-(methoxymethyl)-11-oxa-3,8-diazaspiro[5.5]undecane-3-carboxylate (732 mg, 2.05 mmol) was dissolved in dichloromethane (10 mL) and treated dropwise with a solution of HCl in dioxane (12.8 mL of 4 M, 51.3 mmol). The reaction was stirred for 1.5 h and then diluted with dichloromethane. The organic phase was washed with 1:1 saturated NaHCO$_3$/1 M NaOH, dried over Na$_2$SO$_4$ and concentrated to provide 8-tert-butyl-10-(methoxymethyl)-11-oxa-3,8-diazaspiro[5.5]undecane (526 mg, 2.05 mmol, 99%) as a viscous amber colored oil. ESI-MS m/z calc. 256.2. Found 257.3 (M+1)$^+$; Retention time: 0.2 minutes (3 min run). $^1$H NMR (400 MHz, CDCl$_3$) δ 3.88-3.71 (m, 1H), 3.43-3.38 (m, 1H), 3.37 (d, J=2.5 Hz, 3H), 3.35-3.30 (m, 1H), 3.24 (td, J=12.2, 3.4 Hz, 1H), 3.15-3.07 (m, 1H), 3.02 (td, J=12.2, 3.0 Hz, 1H), 2.93-2.84 (m, 1H), 2.78-2.68 (m, 1H), 2.58 (d, J=8.9 Hz, 2H), 2.48-2.19 (m, 1H), 1.97 (d, J=11.4 Hz, 1H), 1.92 (ddd, J=16.6, 12.2, 9.6 Hz, 2H), 1.84-1.74 (m, 1H), 1.70-1.55 (m, 2H), 1.00 (s, 9H).

Preparation of 4-(2,2-difluoropropyl)-2-(methoxymethyl)-1-oxa-4,9-diazaspiro[5.5]undecane

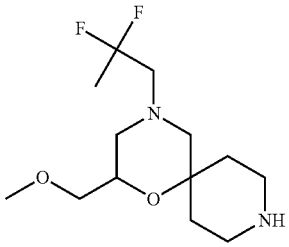 [SMILES: COCC1CN(CC(C)(F)F)CC2(CCNCC2)O1]

Step 1:

To a mixture of tert-butyl 10-(methoxymethyl)-11-oxa-3,8-diazaspiro[5.5]undecane-3-carboxylate and K₂CO₃ (115 mg, 0.832 mmol) in acetonitrile (1.4 mL) was added 1-bromopropan-2-one (304 mg, 2.00 mmol). The reaction mixture was heated under argon in a sealed tube for 16 h. The mixture was cooled, diluted with dichloromethane and washed with water. The organic layer was dried over Na₂SO₄, filtered and concentrated in vacuo to provide tert-butyl 2-(methoxymethyl)-4-(2-oxopropyl)-1-oxa-4,9-diazaspiro[5.5]undecane-9-carboxylate. ESI-MS m/z calc. 356.2. Found 357.3 (M+1)⁺; Retention time: 0.98 minutes (3 min run).

Step 2:

To a solution of tert-butyl 2-(methoxymethyl)-4-(2-oxopropyl)-1-oxa-4,9-diazaspiro[5.5]undecane-9-carboxylate in dichloromethane (1 mL) was added and N,N-diethylaminosulfur trifluoride (195 μL, 1.47 mmol). Cesium fluoride (9.0 mg, 0.059 mmol) was then added in two portions followed by trifluoroacetic acid (5 μL, 0.06 mmol). The reaction was stirred for 15 min then cooled to 0° C. and quenched with 5 mL of saturated aqueous NaHCO₃. The reaction was diluted with dichloromethane (5 mL) and the layers separated. The organic layer was washed with water, dried over Na₂SO₄, filtered and concentrated in vacuo to provide tert-butyl 8-(2,2-difluoropropyl)-10-(methoxymethyl)-11-oxa-3,8-diazaspiro[5.5]undecane-3-carboxylate as yellow oil. ESI-MS m/z calc. 378.2. Found 379.3 (M+1)⁺; Retention time: 1.53 minutes (3 min run).

Step 3:

Tert-butyl 8-(2,2-difluoropropyl)-10-(methoxymethyl)-11-oxa-3,8-diazaspiro[5.5]undecane-3-carboxylate (77.0 mg, 0.204 mmol) was treated with HCl in dioxane (509 μL of 4 M, 2.04 mmol) and stirred for 2 h. The solvent was evaporated to provide 4-(2,2-difluoropropyl)-2-(methoxymethyl)-1-oxa-4,9-diazaspiro[5.5]undecane hydrochloride as yellow solid (64 mg, 0.20 mmol, 99%). ESI-MS m/z calc. 278.2. Found 279.3 (M+1)⁺; Retention time: 0.79 minutes (3 min run).

Preparation of 5-Isopropoxy-6-methylpicolinic acid

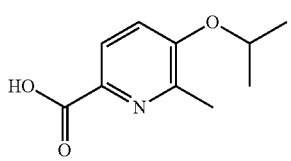

Step 1:

2-Methyl-3-pyridinol (8.3 g, 76.1 mmol) was suspended in acetonitrile (125 mL). A solution of NBS (27.7 g, 155.6 mmol) in acetonitrile (275 mL) was added to the suspension dropwise over 1 hour. The reaction mixture was heated at reflux for 1.5 hours. The reaction mixture was concentrated in vacuo and the residue was purified by silica gel column chromatography using dichloromethane as eluent to give 4,6-dibromo-2-methylpyridin-3-ol (15.8 g, 78%) as a yellow solid. ¹H NMR (300 MHz, DMSO) 2.41 (s, 3H), 7.70 (s, 1H), 9.98 (s, 1H).

Step 2:

4,6-Dibromo-2-methylpyridin-3-ol (15.8 g, 59.4 mmol) was dissolved in THF (200 mL). The solution was cooled to −78° C. and n-BuLi (50 mL, 125 mmol, 2.5 M in hexane) was added dropwise keeping the temperature below −78° C. The reaction mixture was allowed to stir at that temperature for 2 hours. The reaction mixture was quenched with water (50 mL) and was neutralized with 2 N HCl. The aqueous mixture was extracted with dichloromethane (2 times). The combined organic layers were dried (Na₂SO₄) and concentrated in vacuo to give 6-bromo-2-methylpyridin-3-ol (10.5 g, 95%) as a yellow oil. ¹H-NMR (300 MHz, DMSO) 2.29 (s, 3H), 7.08 (d, 1H), 7.26 (d, 1H), 10.08 (s, 1H).

Step 3:

6-Bromo-2-methylpyridin-3-ol (10.5 g, 55.9 mmol) was dissolved in DMF (100 mL). K₂CO₃ (19.3 g, 139.6 mmol) and 2-bromopropane (13.1 ml, 139.6 mmol) were added to the solution and the reaction mixture was heated at 100° C. overnight. The reaction mixture was poured onto a mixture of water and EtOAc (200 mL). The layers were separated and the aqueous layer was extracted with EtOAc (2×). The combined organic layers were dried (Na₂SO₄) and concentrated in vacuo. The crude oil was purified by silica gel column chromatography (0-20% ethyl acetate/heptanes) to give 6-bromo-3-isopropoxy-2-methylpyridine (10.9 g, 85%) as a yellow oil. ¹H-NMR (300 MHz, CDCl₃) 1.42 (d, 6H), 2.48 (s, 3H), 4.65 (m, 1H), 7.20 (d, 1H), 8.04 (d, 1H).

Step 4:

6-Bromo-3-isopropoxy-2-methylpyridine (2.00 g, 8.70 mmol), PdCl₂(PPh₃)₂ (0.18 g, 0.26 mmol) and Et₃N (1.8 ml, 13.04 mmol) were added to MeOH (5.2 mL) and acetonitrile (20 mL) in a Berghoff reactor. The reactor was charged with 10 bar CO (g) and was heated at 60° C. overnight. The reaction mixture was concentrated in vacuo and the residue was partitioned between DCM and water. The layers were separated and the organic layer was washed with brine and dried (Na₂SO₄). The mixture was concentrated in vacuo and purified by silica gel column chromatography to give methyl 5-isopropoxy-6-methylpicolinate (1.3 g, 71%) as a yellow oil. ¹H-NMR (300 MHz, CDCl₃) 1.40 (d, 6H), 2.53 (s, 3H), 3.98 (s, 3H), 4.62 (m, 1H), 7.12 (d, 1H), 7.98 (d, 1H).

Step 5:

5-Isopropoxy-6-methylpicolinate (1.3 g, 6.22 mmol) was dissolved in THF/water 2:1 (9 mL). LiOH*H₂O (0.26 g, 6.22 mmol) was added and the reaction mixture was stirred at room temperature overnight. The mixture was poured into a mixture of water and EtOAc and the layers were separated. The aqueous layer was acidified to pH 4 with 2 N HCl and was extracted with EtOAc (2×). The combined organics were dried (Na₂SO₄) and concentrated in vacuo to give 5-isopropoxy-6-methylpicolinic acid (860 mg, 74%) as a beige solid. $^1$H-NMR (300 MHz, DMSO) 1.31 (d, 6H), 4.73 (m, 1H), 7.44 (d, 1H), 7.86 (d, 1H).

Preparation of
4-(1-Hydroxy-1-methyl-ethyl)-3-methyl-benzoic acid

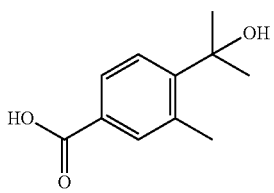

4-Bromo-3-methylbenzoic acid (3.96 g, 18.4 mmol) was dissolved in tetrahydrofuran (100 mL) and the solution was cooled to −78° C. n-Butyllithium in hexanes (16.2 mL of 2.5 M, 41 mmol) was added dropwise over 20 minutes. The reaction mixture was allowed to stir for 30 minutes at −78° C. and then acetone (1.35 mL, 18.4 mmol) was added in a dropwise manner. The reaction mixture was allowed to stir for 30 minutes at −78° C., and then allowed to warm to room temperature. The reaction mixture was then diluted with 1M aqueous sodium hydroxide (100 mL). The organic layer was discarded and then the aqueous layer was acidified with 4M aqueous hydrochloric acid. The aqueous layer was then extracted 3 times with ethyl acetate. The combined extracts were dried over sodium sulfate and then concentrated in vacuo. The crude material was purified by silica gel column chromatography using a gradient of 0-10% methanol in dichloromethane to give 4-(1-hydroxy-1-methyl-ethyl)-3-methyl-benzoic acid (1.51 g, 42%). $^1$H NMR (400 MHz, DMSO) δ 12.74 (s, 1H), 7.68 (dd, J=3.9, 2.5 Hz, 2H), 7.55 (d, J=8.7 Hz, 1H), 5.06 (s, 1H), 2.56 (s, 3H), 1.51 (s, 6H).

Preparation of
4-(2-Methoxyethoxy)-3-methylbenzoic acid

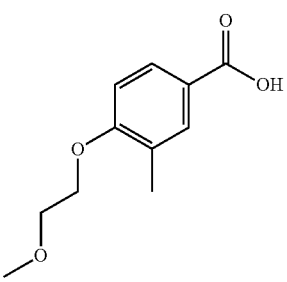

To a solution of 4-hydroxy-3-methyl-benzoic acid (2.0 g, 13 mmol) in THF (24 mL) was added tetrabutylphosphonium hydroxide (18 mL of 40% w/v, 26 mmol). The reaction mixture was cooled to 0° C. and then 1-bromo-2-methoxy-ethane (1.8 g, 1.2 mL, 13 mmol) was added. The reaction mixture was allowed to warm to room temperature overnight. The reaction mixture was acidified using 1M HCl and the aqueous layer was extracted with ethyl acetate. The organics were dried over sodium sulfate and concentrated in vacuo to yield 4-(2-methoxyethoxy)-3-methylbenzoic acid (182 mg, 6%).

ESI-MS m/z calc. 210.2. Found 209.2 (M-H)$^−$; Retention time: 0.96 minutes (3 min run).

The following compound was synthesized using the procedures described above: 4-(3-methoxypropoxy)-3-methylbenzoic acid.

Preparation of 4-tert-Butoxy-3-methoxybenzoic acid

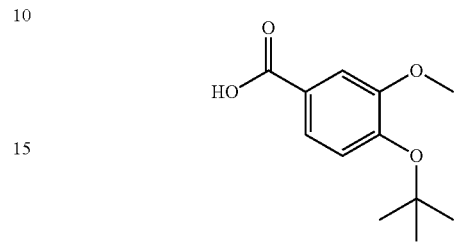

Step 1:
4-Hydroxy-3-methoxy-benzaldehyde (500 mg, 3.29 mmol), Boc$_2$O (1.74 g, 7.97 mmol), and Sc(OTf)$_3$ (80 mg, 0.16 mmol) were combined in dichloromethane (5 mL). The reaction mixture was allowed to stir at room temperature for 24 hours. Water (5 mL) and dichloromethane (5 mL) were added and the two phases were separated. The aqueous layer was extracted with dichloromethane (3×5 mL) and the combined organics were stirred with 10% aqueous potassium hydroxide until all remaining starting material was not observed in the organic phase (TLC, 40% ethyl acetate in hexanes). The two phases were separated and the dichloromethane layer was then washed twice with a saturated aqueous solution of sodium chloride, dried over sodium sulfate, filtered, and concentrated in vacuo to give 4-tert-butoxy-3-methoxybenzaldehyde (130 mg, 19%) as a yellow oil. ESI-MS m/z calc. 208.1. Found 209.2 (M+1)$^+$. Retention time: 0.96 minutes (6 min run).

Step 2:
4-tert-Butoxy-3-methoxybenzaldehyde (130 mg, 0.62 mmol) was suspended in a mixture of dioxane (520 μL) and potassium hydroxide (6.5 mL of 0.20 M, 1.3 mmol). KMnO$_4$ (150 mg, 0.93 mmol) was added and the reaction was stirred vigorously for 16 hours. The reaction mixture was filtered and then concentrated in vacuo to 3 mL. Hydrochloric acid (1M, 4 mL) was added and the resulting precipitate was filtered and washed with 1M HCl and a small amount of water to yield 4-tert-butoxy-3-methoxy-benzoic acid (68 mg, 49%) as a white solid. ESI-MS m/z calc. 224.1. Found 225.2 (M+1)$^+$. Retention time: 1.66 minutes (3 min run). $^1$H NMR (400 MHz, DMSO) δ 12.80 (s, 1H), 7.66-7.41 (m, 2H), 7.09 (d, J=8.8 Hz, 1H), 3.78 (s, 3H), 1.32 (s, 9H).

Preparation of
3-Methoxy-4-(2-methoxy-2-methylpropoxy)benzoic acid

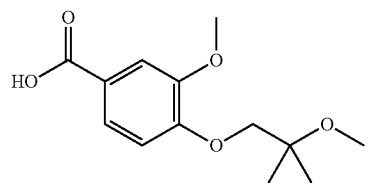 [SMILES: COc1cc(C(=O)O)ccc1OCC(C)(C)OC]

Step 1:

To a stirred solution of methyl 4-hydroxy-3-methoxy-benzoate (2 g, 10.98 mmol), 2-methylprop-2-en-1-ol (871.0 mg, 1.0 mL, 12.1 mmol) and triphenylphosphine (3.17 g, 2.8 mL, 12.1 mmol) in THF (63.28 mL) at 0° C. was added DIAD (2.44 g, 2.34 mL, 12.1 mmol). The ice bath was removed and the reaction was stirred at 55° C. for 16 hours. The reaction mixture was diluted with EtOAc and washed sequentially with $NaHCO_3$ (2×20 mL) and brine (2×20 mL) solutions. The organic layer was separated, dried over $Na_2SO_4$, filtered and the solvent was evaporated under reduced pressure. The crude product was purified with silica gel using (0-30%) ethyl acetate-hexanes to yield methyl 3-methoxy-4-(2-methylallyloxy)benzoate (1.94 g, 75%) as a viscous liquid. ESI-MS m/z calc. 236.1. Found 237.1 (M+1)+. Retention time: 1.63 minutes (3 min run). $^1$H NMR (400 MHz, DMSO) δ 7.56 (dd, J=8.4, 2.0 Hz, 1H), 7.47 (d, J=1.9 Hz, 1H), 7.06 (d, J=8.5 Hz, 1H), 5.07 (br s, 1H), 4.97 (br s, 1H), 4.55 (s, 2H), 3.83 (s, 3H), 3.82 (s, 3H), 1.78 (s, 3H).

Step 2:

To methyl 3-methoxy-4-(2-methylallyloxy)benzoate (313 mg, 1.33 mmol) in MeOH (2.5 mL) was added $H_2SO_4$ (71 µL, 1.3 mmol) and the reaction mixture was heated in a microwave vial at 100° C. for 15.5 hours. The reaction mixture was concentrated in vacuo and the crude product was purified by silica gel column chromatography using 0-30% ethyl acetate in hexane as eluent to yield methyl 3-methoxy-4-(2-methoxy-2-methyl-propoxy)benzoate (208 mg, 59%). ESI-MS m/z calc. 268.1. Found 269.5 (M+1)+; Retention time: 1.46 minutes (3 min run). $^1$H NMR (400 MHz, DMSO) δ 7.57 (dd, J=8.4, 2.0 Hz, 1H), 7.45 (d, J=1.9 Hz, 1H), 7.10 (d, J=8.5 Hz, 1H), 3.90 (s, 2H), 3.83 (s, 3H), 3.82 (s, 3H), 3.17 (s, 3H), 1.22 (s, 6H).

Step 3:

Methyl 3-methoxy-4-(2-methoxy-2-methyl-propoxy)benzoate (177 mg, 0.66 mmol), dioxane (1.9 mL) and NaOH (1.8 mL of 1 M, 1.80 mmol) were combined and the reaction mixture was heated at 80° C. for 15 minutes. The reaction mixture was concentrated in vacuo and the crude mixture was dissolved in water. The mixture was washed with EtOAc (3×). The aqueous layer was acidified with 1N HCl then washed with EtOAc (3×). The combined organic layers was dried over $Na_2SO_4$, filtered and the solvent was evaporated under reduced pressure to yield 3-methoxy-4-(2-methoxy-2-methyl-propoxy)benzoic acid (130 mg, 77%). ESI-MS m/z calc. 254.1. Found 255.5 (M+1)+; Retention time: 1.14 minutes (3 min run). $^1$H NMR (400 MHz, DMSO) δ 12.61 (s, 1H), 7.54 (dd, J=8.4, 1.9 Hz, 1H), 7.45 (d, J=1.8 Hz, 1H), 7.07 (d, J=8.5 Hz, 1H), 3.89 (s, 2H), 3.81 (s, 3H), 3.17 (s, 3H), 1.22 (s, 6H).

Preparation of
4-(2-Hydroxypropan-2-yl)-3-methoxybenzoic acid

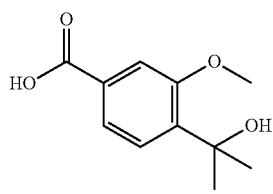

4-Bromo-3-methoxy-benzoic acid (2.00 g, 8.67 mmol) was dissolved in THF (50 mL) and the solution was cooled to −78° C. n-BuLi in hexanes (7.6 mL of 2.5 M, 19 mmol) was added dropwise over 15 minutes. The reaction mixture was allowed to stir for 30 minutes at −78° C. and then acetone (640 µL, 8.9 mmol) was added in a dropwise manner. The reaction mixture was allowed to stir for 30 minutes at −78° C., and then it was allowed to warm to room temperature. The reaction mixture was then diluted with 100 mL of 1M aqueous sodium hydroxide (100 mL). The organic layer was discarded and the aqueous layer was made acidic with 4M aqueous hydrochloric acid. The aqueous layer was then extracted 3 times with ethyl acetate. The combined extracts were dried over sodium sulfate and then evaporated to dryness. The crude material was purified by column chromatography using 0-5% methanol in dichloromethane as eluent to give 4-(2-hydroxypropan-2-yl)-3-methoxybenzoic acid (618 mg, 34%). ESI-MS m/z calc. 210.1. Found 209.1 (M−1)−; Retention time: 0.68 minutes (3 min run).

Preparation of
4-(Isopropylsulfonyl)-3-methylbenzoic acid

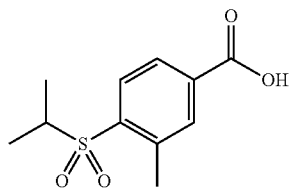 [SMILES: Cc1cc(C(=O)O)ccc1S(=O)(=O)C(C)C]

Step 1:

Butyllithium (16 mL of 1.6 M, 25.6 mmol) was added dropwise to a mixture of 4-bromo-3-methyl-benzoic acid (2.5 g, 11.6 mmol) and THF (63 mL) at −78° C. The reaction mixture was allowed to stir at −78° C. for 30 minutes before a solution of 2-isopropyldisulfanylpropane (1.7 g, 11.6 mmol) in THF (2 mL) was added dropwise. The mixture was allowed to stir at −78° C. for 30 minutes, then 30 minutes at room temperature. The reaction mixture was then diluted with 1M aqueous sodium hydroxide (100 mL). The organic layer was discarded and the aqueous layer was acidified with 4M aqueous hydrochloric acid. The aqueous layer was then extracted 3 times with ethyl acetate. The combined extracts were dried over sodium sulfate and concentrated in vacuo. The crude material was purified by silica gel column chromatography using a gradient of 0-5% MeOH in dichloromethane to give 4-(isopropylthio)-3-methylbenzoic acid (873 mg, 18%). MS m/z calc. 210.3. Found 211.2 (M+1)+. Retention time: 2.32 minutes (3 min run).

Step 2:

3-Chlorobenzenecarboperoxoic acid (933 mg, 4.2 mmol) was added to a mixture of 4-(isopropylthio)-3-methylbenzoic acid (250 mg, 1.2 mmol) and dichloromethane (5 mL) at 25° C. The reaction mixture was allowed to stir at 25° C. for 2 hours, then concentrated in vacuo. The white solid material was taken up in dichloromethane and was subjected to silica gel column chromatography (0-2% MeOH/dichloromethane) to give 4-isopropylsulfonyl-3-methyl-benzoic acid (90 mg, 31%) as a white solid. ESI-MS m/z calc. 242.3. Found 243.2 (M+1)+. Retention time: 1.57 minutes (3 min run). $^1$H NMR (400 MHz, DMSO) δ 13.50 (s, 1H), 8.50-7.66 (m, 3H), 3.50-3.47 (m, 1H), 2.67 (s, 3H), 1.19 (d, J=1.16 Hz, 6H).

Preparation of 3-Chloro-4-isopropoxybenzoic acid

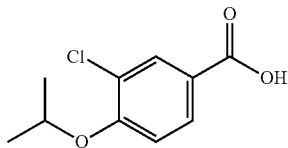

Step 1:
To a solution of 3-chloro-4-hydroxy-benzoic acid (1.0 g, 5.8 mmol) in methanol (30 mL) was added sulfuric acid (3 mL, 56.3 mmol) and the mixture was stirred at 60° C. for 12 hours. The reaction mixture was cooled to room temperature and the methanol was removed in vacuo. The residue was partitioned between a saturated solution of $K_2CO_3$ and ethyl acetate (3×30 mL), dried, filtered and concentrated in vacuo to yield methyl 3-chloro-4-hydroxy-benzoate (0.9 g, 83%) as a white solid. ESI-MS m/z calc 186.5. Found 187.5 (M+1)$^+$; Retention time: 1.17 minutes (3 min run). $^1$H NMR (400.0 MHz, CDCl$_3$) δ 8.05 (d, J=2.2 Hz, 1H), 7.90-7.87 (dd, J=8.8, 2.2H, 1H), 7.06 (d, J=8.8 Hz, 1H) and 3.90 (s, 3H).

Step 2:
To methyl 3-chloro-4-hydroxy-benzoate (3.0 g, 16.1 mmol) in DMF (19 mL) was added potassium carbonate (8.9 g, 64.3 mmol) followed by 2-iodopropane (5.5 g, 3.2 mL, 32.2 mmol). The reaction mixture was heated at 60° C. for 1.5 hours. The reaction mixture was cooled, filtered and diluted with EtOAc and the solvent was concentrated in vacuo. The material was dissolved in EtOAc and washed with water (3×10 mL) and brine (1×10 mL). The organic layer was dried over Na$_2$SO$_4$, filtered and the solvent was removed in vacuo to give methyl 3-chloro-4-isopropoxybenzoate. To the ester was added dioxane (47 mL) and sodium hydroxide (42.7 mL of 1 M, 42.7 mmol) and the reaction was heated at 80° C. for 15 minutes. The reaction was cooled and solvent was removed in vacuo. The resulting residue was dissolved in water and washed with EtOAc (3×10 mL) and the layers were separated. The aqueous layer was acidified to pH 1 and was extracted with EtOAc (3×10 mL). The organic layer was separated and dried over Na$_2$SO$_4$, filtered and the solvent was removed in vacuo to yield 3-chloro-4-isopropoxy-benzoic acid (2.86 g, 83%) as a white solid. ESI-MS m/z calc. 213.6. Found 215.3 (M+1)$^+$; Retention time: 1.51 minutes (3 min run). $^1$H NMR (400.0 MHz, CDCl$_3$) δ 8.05 (d, J=2.2 Hz, 1H), 7.90-7.87 (dd, J=8.8, 2.2H, 1H), 7.06 (d, J=8.8 Hz, 1H) and 3.90 (s, 3H) ppm.

Preparation of 4-isopropoxy-3-methyl-benzoic acid

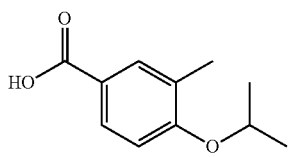

Step 1:
To a solution of 4-hydroxy-3-methylbenzoic acid (10.0 g, 65.7 mmol) and DMF (100 µL) in methanol (35 mL) was added dropwise thionyl chloride (7.8 g, 4.8 mL, 65.7 mmol). The reaction mixture was allowed to stir at room temperature for 2 hours. The reaction mixture was quenched with the addition of aqueous saturated sodium bicarbonate solution (50 mL) and methanol was removed in vacuo. The aqueous layer was then extracted with EtOAc (3×50 mL). The organic layers were dried over sodium sulfate, filtered and concentrated in vacuo to provide methyl 4-hydroxy-3-methyl-benzoate (10.5 g, 96%) as a light brown solid. ESI-MS m/z calc. 166.4. Found 167.4 (M+1)$^+$; Retention time: 1.09 minutes (3 min run).

Step 2:
To methyl 4-hydroxy-3-methyl-benzoate (1.0 g, 59.8 mmol) in dry DMF (62 mL) was added finely ground potassium carbonate (33.1 g, 239.3 mmol) followed by 2-iodopropane (20.3 g, 12.0 mL, 119.6 mmol). The reaction mixture was heated at 60° C. for 2 hours. The reaction mixture was cooled and diluted with ether (350 mL), and filtered over celite. The filtrate was washed with water (3×100 mL) and brine (100 mL) solution. The layers were separated and organics were dried over MgSO$_4$. The solvent was evaporated and resulting residue was purified by silica gel using 0-30% EtOAc/hexanes mixtures as eluent to give methyl 4-isopropoxy-3-methylbenzoate as a colorless oil (11.2 g, 89%). ESI-MS m/z calc. 208.25. Found 209.2 (M+1)$^+$; Retention time: 1.93 minutes (3 min run). Lithium hydroxide (4.4 g, 181.6 mmol) was added to a solution of methyl 4-isopropoxy-3-methylbenzoate (11.2 g, 53.8 mmol) in tetrahydrofuran (31 mL) and water (31 mL). The mixture was rapidly stirred and heated at 65° C. for 6 hours. The reaction mixture was cooled, diluted with water (75 mL) and extracted with ether (2×50 mL). The aqueous layer was acidified to pH 2 with 6N aq. HCl and extracted with ethyl acetate (4×75 mL). The combined organics were washed with water (75 mL) and brine solution (75 mL) and layers were separated. The organics were dried over MgSO$_4$ and concentrated in vacuo to give 4-isopropoxy-3-methyl-benzoic acid (9.5 g, 82%) as colorless crystals. ESI-MS m/z calc. 194.2. Found 195.3 (M+1)$^+$; Retention time: 1.53 minutes (3 min run). $^1$H NMR (400 MHz, DMSO) δ 7.78-7.71 (m, 2H), 7.02 (d, J=8.6 Hz, 1H), 4.70 (dt, J=12.1, 6.0 Hz, 1H), 2.15 (s, 3H), 1.30 (d, J=6.0 Hz, 6H).

Preparation of 4-(2-Methoxy-2-methyl-propoxy)benzoic acid

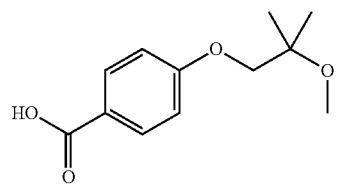 [SMILES: COC(C)(C)COc1ccc(C(=O)O)cc1]

Step 1:
A mixture of 1-chloro-2-methyl-propan-2-ol (10 mL), 4-hydroxybenzonitrile (2.0 g, 16.8 mmol), potassium carbonate (9.3 g, 67.3 mmol), water (6 mL) and ethanol (60 mL) was heated at 80° C. overnight. The reaction mixture was cooled, concentrated in vacuo and residue was diluted with ether (200 mL) and filtered. The filtrate was washed with water (50 mL) and brine solution (50 mL). The organics were separated and dried over MgSO$_4$ and purified by silica gel column chromatography using 0-100% EtOAc/DCM as eluent to give 4-(2-hydroxy-2-methyl-propoxy)benzonitrile (3.0 g, 94%) as a yellow solid. ESI-MS m/z calc. 191.1. Found 192.3 (M+1)⁺; Retention time: 1.05 minutes (3 min run).

Step 2:

To 4-(2-hydroxy-2-methyl-propoxy)benzonitrile (1 g, 5.2 mmol) in DMF (10 mL) was added sodium hydride (220 mg, 5.5 mmol) and the reaction mixture was stirred for 20 minutes. Iodomethane (816 mg, 358 µL, 5.8 mmol) was added and the reaction mixture was stirred for 1 hour at room temperature and 1 hour at 50° C. The reaction mixture was cooled and diluted with ether (250 mL) and washed with water (3×50 mL) and brine (50 mL) solution. The organics were separated and dried over MgSO₄ and concentrated in vacuo to give 4-(2-hydroxy-2-methylpropoxy)benzonitrile. ESI-MS m/z calc. 205.2. Found 206.3 (M+1)⁺; Retention time: 1.38 minutes (3 min run). To 4-(2-hydroxy-2-methylpropoxy)benzonitrile in ethanol (15 mL) was added sodium hydroxide (5.3 mL of 5 M, 26.1 mmol) and reaction was heated at 85° C. for 2 hours. The reaction mixture was cooled and concentrated in vacuo, then diluted with ethyl acetate (50 mL) and 3N HCl solution was added to adjust to pH 2 and the layers were separated. The aqueous layer was extracted with ethyl acetate (3×50 mL). The combined organics were washed with brine solution (2×50 mL), dried over MgSO₄ and concentrated in vacuo to give 4-(2-methoxy-2-methyl-propoxy)benzoic acid (0.9 g, 77%) as a white solid. ESI-MS m/z calc. 224.2. Found 225.3 (M+1)⁺; Retention time: 1.15 minutes (3 min run). ¹H NMR (400 MHz, DMSO) δ 7.98-7.73 (m, 2H), 7.10-6.90 (m, 2H), 3.90 (d, J=8.4 Hz, 2H), 3.15 (d, J=3.8 Hz, 3H), 1.19 (d, J=15.0 Hz, 6H).

Preparation of 4-(2-Hydroxy-2-methyl-propoxy)-3-methyl-benzoic acid

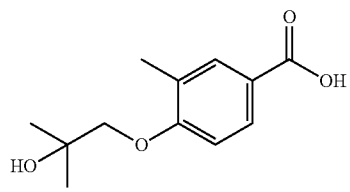 [SMILES: Cc1cc(C(=O)O)ccc1OCC(C)(C)O]

A mixture of 1-chloro-2-methyl-propan-2-ol (10 mL), 4-hydroxy-3-methyl-benzoic acid (2.0 g, 13.15 mmol), potassium carbonate (7.3 g, 52.71 mmol), water (6 mL) and ethanol (60 mL) was heated at 80° C. for 16 hours. The reaction mixture was cooled to room temperature and partitioned between 1N NaOH and EtOAc and the layers were separated. The organic layer was washed with 1N NaOH (2×10 mL) and the combined aqueous layers were washed with EtOAc. The combined organic layers were dried and concentrated in vacuo to give ethyl 4-(2-hydroxy-2-methyl-propoxy)-3-methyl-benzoate. The ester was dissolved in ethanol (15 mL) and water (2 mL), sodium hydroxide (1.1 g, 26.30 mmol) was added and the reaction mixture was stirred at 40° C. for 4 hours. The reaction mixture was poured into 1N NaOH solution and extracted with ether (2×10 mL). The aqueous layer was acidified to pH 2-3 using 6N HCl solution and extracted with EtOAc (3×10 mL). The organics were separated and washed with brine solution. The organic layer was dried (Na₂SO₄) and concentrated in vacuo and the resulting material was triturated with ether to give 4-(2-hydroxy-2-methyl-propoxy)-3-methyl-benzoic acid (2.2 g, 75%) as a white solid. ESI-MS m/z calc. 224.1. Found 225.5 (M+1); Retention time: 1.06 minutes (3 min run) ¹H NMR (400 MHz, DMSO) δ 7.75 (dd, J=8.5, 2.0 Hz, 1H), 7.73-7.70 (m, 1H), 6.96 (d, J=8.6 Hz, 1H), 4.67 (s, 1H, OH), 3.76 (s, 2H), 2.20 (s, 3H), 1.22 (s, 6H).

Preparation of 5-Isopropoxypyridine-2-carboxylic acid

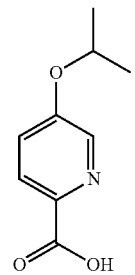

Step 1:

To a solution of 5-hydroxypyridine-2-carboxylic acid (1.0 g, 7.2 mmol) in methanol (15 mL) was added sulfuric acid (881 µL, 16.53 mmol) dropwise and the reaction mixture was stirred at room temperature overnight. The reaction mixture was concentrated in vacuo, diluted with DCM (100 mL), washed with sat. aq NaHCO₃ solution. The organic layer was separated and dried with sodium sulfate, filtered and concentrated in vacuo to give methyl 5-hydroxypyridine-2-carboxylate, which was used without further purification. ESI-MS m/z calc. 150.1. Found 154.1 (M+1)⁺; Retention time: 0.33 minutes (3 min run).

Step 2:

To methyl 5-hydroxypyridine-2-carboxylate (0.6 g, 3.92 mmol) in DMF (3.6 mL) was added potassium carbonate (2.2 g, 15.7 mmol) followed by 2-bromopropane (736 µL, 7.8 mmol) The reaction mixture was heated at 60° C. for 1.5 hours. The reaction mixture was cooled and filtered using EtOAc and the solvent was evaporated under reduced pressure. The residue was dissolved in EtOAc and washed with water (3×10 mL) and brine solution (10 mL). The organics were separated and dried over Na₂SO₄, filtered and concentrated in vacuo. The residue was purified by silica gel column chromatography using 0-50% EtOAc: hexanes as eluent to give methyl 5-isopropoxypyridine-2-carboxylate (555 mg, 73%) as a colorless oil. ESI-MS m/z calc. 195.1. Found 196.3 (M+1)⁺; Retention time: 1.09 minutes (3 min run). Lithium hydroxide (5.7 mL of 2 M, 11.37 mmol) was added to a solution of methyl 5-isopropoxypyridine-2-carboxylate (555 mg, 2.84 mmol) in dioxane (4 mL) and stirred at 55° C. for 2 hours. The reaction mixture was diluted with ethyl acetate and washed with water and layers were separated. The aqueous layer was acidified with 1N HCl solution and extracted with ethyl acetate. The organics were separated and dried over sodium sulfate, filtered and concentrated in vacuo to give 5-isopropoxypyridine-2-carboxylic acid (150 mg, 29%). ESI-MS m/z calc. 182.1. Found 182.3 (M+1)⁺; Retention time: 0.33 minutes (3 min run).

Preparation of 2-Fluoro-4-isopropoxy-benzoic acid

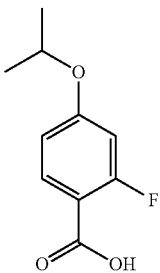

Step 1:

To a solution of 2-fluoro-4-hydroxy-benzoic acid (5.32 g, 34.1 mmol) in methanol (21 mL) was added thionyl chloride (4.86 g, 3 mL, 40.9 mmol) dropwise and the reaction mixture was stirred at 40° C. for 3 hours. The reaction mixture was concentrated in vacuo and diluted with DCM (100 mL) and washed with aqueous saturated NaHCO$_3$ (2×50 mL) solution. The organics were separated and dried with MgSO$_4$, filtered and concentrated in vacuo to give methyl 2-fluoro-4-hydroxy-benzoate (2.3 g, 40%). ESI-MS m/z calc. 170.1. Found 171.3 (M+1)$^+$; Retention time: 0.84 minutes (3 min run).

Step 2:

To a mixture of methyl 2-fluoro-4-hydroxy-benzoate (2.1 g, 12.4 mmol), potassium carbonate (6.8 g, 49.5 mmol) in dry DMF (13 mL) was added 2-iodopropane (2.5 mL, 24.8 mmol) and the reaction mixture was heated at 60° C. for 2 hours. The reaction was cooled and diluted with ether (50 mL) and filtered over Celite®. The filtrate was washed sequentially with water (3×25 mL) and brine solution (25 mL). The organic layer was separated and dried over MgSO$_4$ and solvent was concentrated in vacuo to give a residue which was purified by silica gel column chromatography using 5-45% EtOAc/hexanes to give methyl 2-fluoro-4-isopropoxybenzoate as a colorless oil (2.2 g, 83%). To a solution of methyl 2-fluoro-4-isopropoxybenzoate (2.2 g, 10.3 mmol) in THF (5.5 mL) was added a suspension of lithium hydroxide (0.9 g, 37.1 mmol) in water (5.5 mL). The reaction mixture was stirred at 70° C. for 2 hours. The reaction mixture was cooled to room temperature and the excess LiOH was removed by filtration. The filtrate was diluted with water (9 ml), and washed with ether (2×5 mL). The aqueous layer was separated and cooled to 0° C. and the pH was adjusted to pH 2 by addition of 6 M HCl solution. The aqueous layer was extracted with EtOAc (3×30 mL). The organics were separated and washed sequentially with water and brine. The organic layer was separated, dried and concentrated in vacuo to give 2-fluoro-4-isopropoxy-benzoic acid (2.45 g, 67%) as a white solid. $^1$H NMR (400 MHz, CDCl$_3$) δ 7.98 (t, J=8.8 Hz, 1H), 6.69 (ddd, J=15.1, 10.9, 2.0 Hz, 2H), 4.63 (dt, J=12.1, 6.0 Hz, 1H), 1.39 (d, J=6.1 Hz, 6H).

Preparation of 3-Methyl-4-(oxetan-3-yloxy)benzoic acid

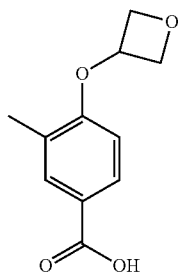

Step 1:

To a solution of 4-hydroxy-3-methylbenzoic acid (10.00 g, 65.7 mmol) and DMF (100 μL) in MeOH (35 mL) was added dropwise thionyl chloride (4.8 mL, 65.7 mmol) at room temperature. The reaction mixture was stirred at room temperature for 2 hours. The reaction mixture was quenched with the addition of aqueous saturated sodium bicarbonate solution (50 mL), and methanol was removed under reduced pressure. The residue was extracted with EtOAc (3×50 mL) and dried over sodium sulfate, filtered and concentrated in vacuo to provide methyl 4-hydroxy-3-methyl-benzoate (10.53 g, 96%) as a light brown solid. ESI-MS m/z calc. 166.0. Found 167.1 (M+1)$^+$; Retention time: 1.09 minutes (3 min run).

Step 2:

To methyl 4-hydroxy-3-methyl-benzoate (498 mg, 3 mmol) was added DMF (3 mL) and sodium hydride (240 mg, 6.0 mmol) followed by oxetan-3-ol (445 mg, 6 mmol) and the reaction mixture was heated at 80° C. for 4 hours. The reaction was cooled and quenched with brine solution and extracted with EtOAc (3×10 mL). The organic layer was separated and dried over sodium sulfate and evaporated to give methyl 3-methyl-4-(oxetan-3-yloxy)benzoate. To methyl 3-methyl-4-(oxetan-3-yloxy)benzoate was added sodium hydroxide (3 mL of 1 M NaOH, 3 mmol) solution and the reaction mixture was stirred for 1 hour. The reaction was acidified with 1 M HCl solution to pH 3 and extracted with EtOAc. The organics were separated and dried and concentrated in vacuo to give 3-methyl-4-(oxetan-3-yloxy)benzoic acid. ESI-MS m/z calc. 208.1. Found 209.3 (M+1)$^+$; Retention time: 1.04 minutes (3 min run).

Preparation of 4-Ethylsulfonyl-3-methyl-benzoic acid

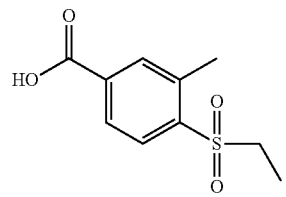

Step 1:

To a solution of 4-fluoro-3-methyl-benzoic acid (27.4 g, 178.0 mmol) in methanol (200 mL) was slowly added thionyl chloride (17.8 mL, 243.3 mmol). The solution was stirred at 35° C. for 7 hours. The solution was allowed to cool to room temperature and concentrated in vacuo to an oil. This oil was dissolved in EtOAc (75 mL) and washed sequentially with saturated aqueous sodium bicarbonate solution (2×75 mL) and brine solution (1×75 mL). The organic layer was separated and dried over sodium sulfate, filtered and concentrated in vacuo to provide methyl 4-fluoro-3-methyl-benzoate (25.4 g, 85%) as a red oil. ESI-MS m/z calc. 168.0. Found 169.2 (M+1)$^+$; Retention time: 1.48 minutes (3 min run). $^1$H NMR (400 MHz, CDCl$_3$) δ 7.92-7.88 (m, 1H), 7.88-7.83 (m, 1H), 7.04 (t, J=8.9 Hz, 1H), 3.90 (s, 3H), 2.31 (d, J=2.0 Hz, 3H).

Step 2:

To methyl 4-fluoro-3-methyl-benzoate (8.0 g, 47.6 mmol) in DMF (64 mL) was added ethylsulfanylsodium (10.0 g, 118.9 mmol) and the reaction was heated for 16 hours at 55° C. The reaction mixture was cooled to room temperature and quenched with brine solution and stirred for 20 minutes. The reaction mixture was extracted with EtOAc (3×10 mL). The aqueous layer was treated with Clorox® bleach solution (150 mL) and the reaction mixture immediately turned colorless. The reaction mixture was stirred for 10 minutes. The reaction was treated with 1N HCl solution to pH 1 and extracted with EtOAc (3×10 mL). The organics were separated and washed with brine solution (3×10 mL). The organic layer was dried over sodium sulfate and the solvent was removed in vacuo to provide 4-ethyl sulfonyl-3-methyl-benzoic acid (9.4 g, 86%) as a white solid. $^1$H NMR (400 MHz, CDCl$_3$) δ 8.13 (dd, J=13.8, 8.3 Hz, 3H), 3.22 (q, J=7.4 Hz, 2H), 2.79 (s, 3H), 1.31 (t, J=7.4 Hz, 3H).

Preparation of 4-Tert-butylsulfonylbenzoic acid

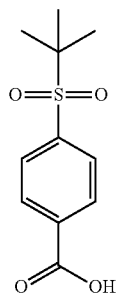

Step 1:
Ethyl 4-fluorobenzoate (1.5 g, 8.9 mmol) and tert-butylsulfanylsodium (2.0 g, 17.8 mmol) were combined in N,N-dimethylformamide (10 mL). The reaction mixture was heated to 80° C. for 2 hours. After this time, a precipitate formed and N,N-dimethylformamide (15 mL) was added and the reaction mixture was stirred for an additional 20 hours at 80° C. The reaction mixture was partitioned between ethyl acetate (100 mL) and water (100 mL). The aqueous layer was acidified with 4M hydrochloric acid, extracted with ethyl acetate (2×). The combined extracts were dried over sodium sulfate, filtered, and concentrated in vacuo to yield 4-(tert-butylthio)benzoic acid as a colorless oil. The oil was dissolved in acetic acid (10 mL) and hydrogen peroxide (5 mL of 30% w/w, 52.0 mmol) was added to the reaction mixture. The resulting mixture was heated to 80° C. for 2 hours. The reaction mixture was then allowed to cool to room temperature, and diluted with water (50 mL) and ethyl acetate (100 mL). The aqueous layer was extracted with ethyl acetate. The combined ethyl acetate extracts were dried over sodium sulfate, filtered, and concentrated in vacuo to yield 4-tert-butylsulfonylbenzoic acid (2.2 g, 92%) as a white solid. $^1$H NMR (400 MHz, DMSO) δ 13.59 (s, 1H), 8.18 (d, J=8.0 Hz, 2H), 7.94 (d, J=7.6 Hz, 2H), 1.25 (s, 9H); ESI-MS m/z calc. 242.1. Found 241.3 (M−1)$^-$; Retention time: 1.33 minutes (3 min run).

Preparation of 3-Fluoro-4-isopropoxy-5-methoxy-benzoic acid

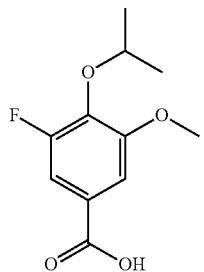 [SMILES: COc1cc(C(=O)O)cc(F)c1OC(C)C]

A solution of 3-fluoro-4-hydroxy-5-methoxy-benzaldehyde (250 mg, 1.5 mmol) in DMF (2.5 mL) was treated with potassium carbonate (812 mg, 5.9 mmol) and stirred for 30 minutes. 2-Iodopropane (500 mg, 2.9 mmol) was added over 10 minutes and reaction mixture was stirred for 20 hours. The reaction mixture was partitioned between EtOAc and saturated aqueous sodium chloride solution. The organic layer was washed with saturated sodium bicarbonate solution. The organic layer was separated and dried over sodium sulfate, filtered and concentrated in vacuo to give 3-fluoro-4-isopropoxy-5-methoxybenzaldehyde. To the aldehyde was added tert-butanol (6.7 mL) and 2-methylbut-2-ene (4 mL, 38.2 mmol) and the reaction mixture was cooled to 0° C. A solution of chlorite (345 mg, 3.8 mmol) and sodium dihydrogen phosphate hydrate (527 mg, 3.8 mmol) in water (6.7 mL) was added dropwise over 5 minutes, and the reaction mixture was stirred 30 minutes. The reaction mixture was warmed to room temperature and stirred for 12 hours. The reaction mixture was basified with 1 N NaOH solution and extracted with ethyl acetate (2×50 mL). The aqueous layer was acidified with 1 N HCl solution and extracted with EtOAc (4×50 mL). The combined organics were dried (Na$_2$SO$_4$), filtered, and concentrated in vacuo to afford 3-fluoro-4-isopropoxy-5-methoxybenzoic acid (190 mg, 56%) as a white solid. ESI-MS m/z calc. 228.0. Found 229.3 (M−1)$^+$; Retention time: 1.57 minutes (3 min run).

Preparation of 4-(Cyclopropylsulfamoyl)benzoic acid

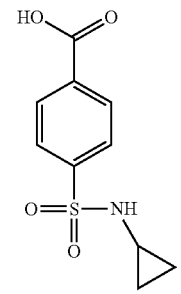

To 4-chlorosulfonylbenzoic acid (10.0 g, 45.3 mmol) in dichloromethane (350 mL) at 0° C. was added cyclopropanamine (15.5 g, 19 mL, 271.9 mmol). The reaction mixture was allowed to warm to room temperature over 16 hours. The solvent was evaporated under reduced pressure. The residue was dissolved in water (150 mL) and acidified using hydrochloric acid. The aqueous layer was extracted with EtOAc (2×200 mL). The organic layer was dried over sodium sulfate, filtered and concentrated in vacuo to give 4-(cyclopropylsulfamoyl)benzoic acid (10.0 g, 92%) as a white solid. ESI-MS m/z calc. 241.0. Found 242.5 (M+1)$^+$; Retention time: 0.84 minutes (3 min run); $^1$H NMR (400 MHz, DMSO) δ 13.27 (s, 1H), 7.97 (d, J=8.3 Hz, 2H), 7.91 (d, J=2.5 Hz, 1H), 7.75 (d, J=8.3 Hz, 2H), 2.03-1.90 (m, 1H), 0.38-0.28 (m, 2H), 0.23-0.15 (m, 2H).

Preparation of 4-(3-Hydroxypropoxy)-3-methyl-benzoic acid

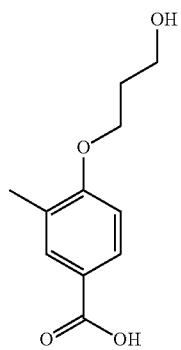

Step 1:

To a solution of methyl 4-hydroxy-3-methyl-benzoate (3.03 g, 18.2 mmol) in DMF (9 mL) was added 3-bromopropan-1-ol (3.80 g, 2.4 mL, 27.4 mmol) and cesium carbonate (17.8 g, 54.7 mmol) and the reaction mixture was heated at 60° C. for 16 hours. The reaction mixture was cooled to room temperature and then partitioned between water (250 mL) and ethyl acetate (2×100 ml). The organic layers were combined, washed with brine solution (50 mL), dried over Na$_2$SO$_4$, filtered and concentrated in vacuo to yield a crude oil that was purified by silica gel column chromatography eluting with EtOAc/hexanes (10-100%) to give methyl 4-(3-hydroxypropoxy)-3-methyl-benzoate (1.87 g, 46%) as a white solid. ESI-MS m/z calc. 224.0. Found 225.0 (M+1)$^+$; Retention time: 1.27 minutes (3 min run); $^1$H NMR (400 MHz, CDCl$_3$) δ 7.94-7.77 (m, 2H), 6.85 (d, J=8.5 Hz, 1H), 4.18 (t, J=5.9 Hz, 2H), 3.98-3.82 (m, 5H), 2.24 (s, 3H), 2.10 (p, J=5.9 Hz, 2H).

Step 2:

To a solution of methyl 4-(3-hydroxypropoxy)-3-methyl-benzoate (0.9 g, 4.01 mmol) in dioxane (8 mL) was added 1N NaOH (5 mL) and the reaction mixture was heated at 70° C. for 22 hours. The solvent was concentrated in vacuo and the crude residue was dissolved in water (20 mL) and extracted with ethyl acetate (1×20 mL). The aqueous layer was acidified with 1 M HCl solution and extracted with ethyl acetate (2×20 mL). The organics were separated, dried with Na$_2$SO$_4$ and concentrated in vacuo to give 4-(3-hydroxypropoxy)-3-methyl-benzoic acid (0.7 g, 87%) as a white solid. ESI-MS m/z calc. 210.0. Found 211.0 (M+1)$^+$; Retention time: 0.95 minutes (3 min run); $^1$H NMR (400 MHz, DMSO) δ 12.5 (bs, 1H), 7.97-7.60 (m, 2H), 7.01 (d, J=8.6 Hz, 1H), 4.57 (s, 1H), 4.11 (t, J=6.2 Hz, 2H), 3.59 (t, J=5.5 Hz, 2H), 2.19 (s, 3H), 1.89 (p, J=6.2 Hz, 2H).

Preparation of 3-Fluoro-4-(1-hydroxy-1-methyl-ethyl)benzoic acid

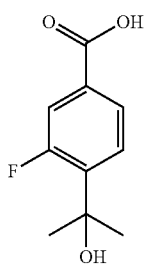

Step 1:

4-Bromo-3-fluoro-benzoic acid (5.0 g, 22.8 mmol) was dissolved THF (60 mL) and the solution was cooled to −78° C. n-Butyllithium (20 mL of 2.5 M in hexanes, 50.2 mmol) was added dropwise and the mixture was allowed to stir for 1 minute at −78° C., then acetone (3.7 mL, 50.2 mmol) was added dropwise. The reaction mixture was allowed to warm to room temperature and stirred for 16 hours. The reaction mixture was quenched with sat. NH$_4$Cl solution, diluted with saturated citric acid solution and the aqueous layer was extracted with EtOAc (3×20 mL). The combined organic layers were washed with brine, dried over MgSO$_4$, filtered and concentrated in vacuo. The desired compound was contaminated with 3-fluoro-4-hydroxybenzoic acid and the mixture was taken forward without any purification. ESI-MS m/z calc. 198.2. Found 197 (M−1)$^+$; Retention time: 2.13 minutes (15 min run).

Step 2:

To a solution of 3-fluoro-4-(1-hydroxy-1-methyl-ethyl) benzoic acid (9.1 g, 45.7 mmol) in DMF (40 mL) was added cesium carbonate (22.3 g, 68.5 mmol) followed by benzyl bromide (11.7 g, 8.1 mL, 68.5 mmol) and reaction mixture was stirred at room temperature for 16 hours. The reaction mixture was partitioned between EtOAc and H$_2$O. The aqueous layer was extracted with EtOAc (3×20 mL). The combined organic layers were washed sequentially with H$_2$O (3×10 mL), brine solution. The organics were separated and dried over MgSO$_4$, filtered and concentrated in vacuo. The resulting residue was purified by silica gel column chromatography eluting with 10-20% EtOAc-hexanes to provide benzyl 3-fluoro-4-(1-hydroxy-1-methyl-ethyl)benzoate (2.8 g, 21%) ESI-MS m/z calc. 288.2. Found 289.3 (M+1)$^+$; Retention time: 1.79 min (3 min run). To a solution of benzyl 3-fluoro-4-(1-hydroxy-1-methyl-ethyl)benzoate (2.8 g, 9.71 mmol) in MeOH (50 mL) was added palladium on carbon (100 mg, 0.09 mmol) and the reaction mixture was subjected to an atmosphere of hydrogen for 16 hours. The catalyst was removed via filtration over Celite® and the solvent removed in vacuo to provide 3-fluoro-4-(1-hydroxy-1-methyl-ethyl) benzoic acid (1.8 g, 96%) as a white solid. ESI-MS m/z calc. 198.2. Found 199.9 (M+1)$^+$; Retention time: 0.91 minutes (3 min run).

Preparation of 4-(2-Hydroxy-2-methyl-propyl)benzoic acid

Step 1:

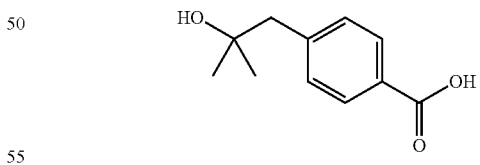

A solution of bromo(methyl)magnesium in diethyl ether (25 mL of 3 M, 74.5 mmol) in THF (8 mL) and toluene (25 mL) was added to a solution of ethyl 2-(4-bromophenyl) acetate (8.23 g, 33.9 mmol) in Et$_2$O (165 mL) and the reaction mixture was stirred at 40° C. for 1 hour. The reaction mixture was quenched by the addition of saturated aqueous ammonium chloride (200 mL) and the phases were separated. The organics were dried over sodium sulfate, filtered and concentrated in vacuo. The resulting residue was purified by silica gel column chromatography eluting with 0-30% EtOAc-hexanes to give 1-(4-bromophenyl)-2-methyl-propan-2-ol (5.68 g, 73%), as a clear oil. ESI-MS m/z calc. 228.1. Found 229.5 (M+1)+; Retention time: 1.45 minutes (3 min run).

Step 2:

1-(4-bromophenyl)-2-methyl-propan-2-ol (2.77 g, 12.1 mmol) was dissolved in dry THF (30 mL) and the solution was cooled to −78° C. Tert-butyllithium in pentane (15 mL of 1.7 M, 25.4 mmol) was added dropwise over 10 minutes and the reaction mixture was stirred at −78° C. for 2 hours. The reaction mixture was added via cannula to crushed solid $CO_2$ (53.2 g, 1.21 mol) in $Et_2O$ under a flow of nitrogen gas. The reaction mixture was allowed to warm to room temperature, diluted with EtOAc and washed with water. The aqueous phase was acidified (pH 2) with 1N HCl solution and the aqueous layer was extracted with EtOAc. The organics were dried over sodium sulfate, filtered and concentrated in vacuo to give 4-(2-hydroxy-2-methyl-propyl)benzoic acid (620 mg, 26%) as a white solid. ESI-MS m/z calc. 194.0. Found 195.3 (M+1)+; Retention time: 0.93 minutes (3 min run).

Preparation of 3-Methyl-4-(oxetan-3-yl)benzoic acid

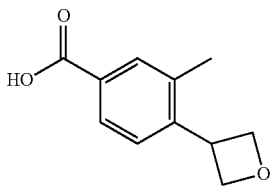

Step 1:

To (4-cyano-2-methyl-phenyl)boronic acid (1.75 g, 10.90 mmol), nickel iodide (0.10 g, 0.33 mmol), (1S,2S)-2-aminocyclohexan-1-ol (0.05 g, 0.33 mmol) and NaHMDS (2.01 g, 10.90 mmol) in isopropanol (10 mL) under an atmosphere of nitrogen was added 3-iodooxetane (1.00 g, 5.40 mmol) in isopropanol (1 mL) via cannula. The reaction mixture was heated at 90° C. for 2 hours, then cooled, diluted with ethanol (20 mL) and filtered over Celite®. The filtrate was concentrated in vacuo, then the residue was purified by silica gel column chromatography using 0-60% EtOAc/hexane as eluant to give 3-methyl-4-(oxetan-3-yl)benzonitrile (0.62 g, 65%) as a white solid. ESI-MS m/z calc. 173.1. Found 174.3 (M+1)+; Retention time: 1.09 minutes (3 min run).

Step 2:

To 3-methyl-4-(oxetan-3-yl)benzonitrile (500 mg, 2.89 mmol) in ethanol (7.5 mL) was added NaOH (3 mL of 5 M, 15.00 mmol) and the reaction mixture was heated at 85° C. for 1 hour. The reaction mixture was cooled to room temperature, concentrated in vacuo and diluted with ethyl acetate (20 mL). 6N HCl solution (~3 mL) was added until pH 6 was reached, then the aqueous layer was extracted with ethyl acetate (2×20 mL), and the combined organics were washed with brine solution (10 mL). The organics were separated, dried over $MgSO_4$ and concentrated in vacuo to give a white solid, which was triturated with ether to give a mixture (2:3 by NMR) of acid and amide. ESI-MS m/z (acid) calc. 192.1. Found 193.3 (M+1)+; Retention time: 0.88 minutes (3 min run). ESI-MS m/z (amide) calc. 191.1. Found 192.3 (M+1)+; Retention time: 0.47 min (3 min run).

Preparation of 2-(Difluoromethoxy)-3-fluoro-benzoic acid

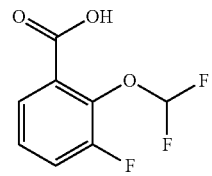 [SMILES: O=C(O)c1cccc(F)c1OC(F)F]

Step 1:

To a solution of 3-fluoro-2-hydroxy-benzoic acid (5.0 g, 32 mmol) in methanol (20 mL) was added thionyl chloride (5.0 g, 42 mmol) dropwise and the reaction mixture was stirred at 40° C. for 3 hours, then heated at 50° C. for 16 hours. The reaction mixture was cooled and concentrated in vacuo and resulting residue was purified by silica gel column chromatography using 0-50% ethyl acetate/hexanes mixtures as eluant to give methyl 3-fluoro-2-hydroxy-benzoate (5.1 g, 94%) as white crystals. ESI-MS m/z calc. 170.0. Found 170.9 (M+1)+; Retention time: 1.33 minutes (3 min run).

Step 2:

A mixture of methyl 3-fluoro-2-hydroxy-benzoate (1.5 g, 8.8 mmol), 2-chloro-2,2-difluoro-acetic acid (1.62 g, 1.05 mL, 10.6 mmol) and potassium carbonate (1.46 g, 10.6 mmol) were heated in DMF (5 mL) at 120° C. for 5 hours. The reaction mixture was diluted with water (20 mL) and extracted with ether (2×10 mL). The organics were separated and washed sequentially with water (5 mL) and brine solution (5 mL). The organics were dried ($MgSO_4$) and concentrated in vacuo to give residue which was purified by silica gel column chromatography using 0-30% EtOAc/hexanes as eluent to give methyl 2-(difluoromethoxy)-3-fluorobenzoate (0.8 g, 39%). To methyl 2-(difluoromethoxy)-3-fluorobenzoate (0.8 g, 3.64 mmol) was added 12% aq. NaOH (3 mL) and the reaction mixture was heated at 50° C. for 1 hour. The aqueous layer was extracted with 1:1 ether/hexane (2×5 mL). The aqueous layer was acidified to pH 1 with 6 N HCl solution to give a suspension. The solid was filtered and washed with water, then dried in vacuo to give 2-(difluoromethoxy)-3-fluoro-benzoic acid (555 mg, 31%) as an off-white solid. $^1$H NMR (400 MHz, $CDCl_3$) δ 7.83 (d, J=7.8 Hz, 1H), 7.43 (dd, J=13.1, 4.8 Hz, 1H), 7.35 (td, J=8.1, 4.9 Hz, 1H), 6.68 (t, J=74.4 Hz, 1H).

Preparation of 4-(1-Hydroxy-1-methyl-ethyl)benzoic acid

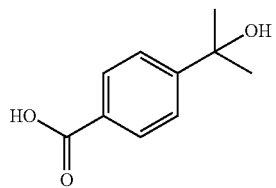

4-Isopropylbenzoic acid (5.0 g, 30.5 mmol) was dissolved in a solution of potassium hydroxide (4.1 g, 2 mL, 73.1 mmol)

in water (125 mL). To the reaction mixture was added a solution of potassium permanganate (9.6 g, 60.9 mmol) in water (125 mL). The combined mixture was allowed to stir at 60° C. for 2 hours. The reaction mixture was cooled to 0° C. and treated with ethylene glycol (100 μL) and cooled to 0° C. The solid were removed by filtration and the filtrate was acidified to pH 1 by addition of 6 N HCl solution. The solid was removed by filtration, and the filtrate was extracted with diethyl ether (3×200 mL). The combined organic extracts were dried over sodium sulfate, filtered and concentrated in vacuo to provide 4-(1-hydroxy-1-methyl-ethyl)benzoic acid (5.1 g, 93%) as a white solid. ESI-MS m/z calc. 180.1. Found 181.2 (M+1)+; Retention time: 0.6 minutes (3 min run). $^1$H NMR (400 MHz, MeOD) δ 8.00-7.95 (m, 2H), 7.61-7.56 (m, 2H), 2.64 (s, 1H), 1.54 (s, 6H).

Preparation of 4-(Diethylcarbamoyl)-3-fluoro-benzoic acid

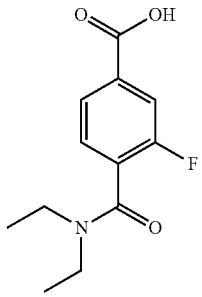 [SMILES: CCN(CC)C(=O)c1ccc(C(=O)O)cc1F]

To 4-cyano-2-fluoro-benzoic acid (2.0 g, 12.1 mmol) in DMF (18 mL) at room temperature was added N-ethylethanamine (1.5 g, 2.1 mL, 13.3 mmol) followed by 0-(7-azabenzotriazol-1-yl)-N,N,N',N'-tetramethyluronium hexafluorophosphate (4.6 g, 12.1 mmol) and diisopropylethylamine (3.9 g, 5.3 mL, 30.3 mmol) and the reaction mixture was stirred for 3 hours. The reaction mixture was diluted with EtOAc and washed with brine solution. The organics were separated, dried and concentrated in vacuo. The residue was purified by silica gel column chromatography using EtOAc-DCM (10-100%) as eluent to give 4-cyano-N,N-diethyl-2-fluoro-benzamide (2.0 g, 75%). $^1$H NMR (400 MHz, CDCl$_3$) δ 7.51 (dd, J=7.8, 1.3 Hz, 1H), 7.47-7.37 (m, 2H), 3.56 (q, J=7.0 Hz, 2H), 3.16 (q, J=7.1 Hz, 2H), 1.24 (td, J=7.1, 2.0 Hz, 4H). To 4-cyano-N,N-diethyl-2-fluoro-benzamide (1.75 g, 7.9 mmol) was added a 2:1 mixture of THF:MeOH (15 mL), followed by 4 N NaOH solution (10 mL, 39.6 mmol) and the reaction mixture was heated at 65° C. for 2.5 hours. The reaction mixture was cooled, diluted with EtOAc and washed with 2 M HCl solution. The organics were separated, dried and concentrated in vacuo to give 4-(diethylcarbamoyl)-3-fluoro-benzoic acid (1.91 g, 66%) as a solid. ESI-MS m/z calc. 239.24. Found 240.2 (M+1); Retention time: 0.99 minutes (3 min run).

Preparation of 5-Tert-butoxypyridine-2-carboxylic acid

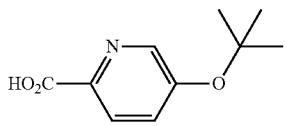

To NaO$^t$Bu (1.57 g, 16.4 mmol) in HMPA (6 mL) was added DMF (6 mL), followed by 5-fluoropyridine-2-carbonitrile (1 g, 8.19 mmol) and the reaction mixture was stirred for 16 hours under an atmosphere of nitrogen. The reaction mixture was diluted with water (100 mL) and extracted with DCM (3×50 mL) and layers were separated. The organics were washed sequentially with water (50 mL) and sat. aq. NaHCO$_3$ solution (50 mL) and the organic layer was separated, dried over MgSO$_4$ and concentrated in vacuo. The residue was purified by silica gel column chromatography eluting with 0-50% EtOAc/hexanes to give 5-tert-butoxypyridine-2-carbonitrile (0.90 g, 62%) as a yellow solid. ESI-MS m/z calc. 176.0. Found 177.5 (M+1)+; Retention time: 1.3 minutes (3 min run). $^1$H NMR (400 MHz, CDCl$_3$) δ 8.38 (dd, J=2.7, 0.5 Hz, 1H), 7.67-7.56 (m, 1H), 7.41-7.31 (m, 1H), 1.52-1.38 (m, 10H). To 5-tert-butoxypyridine-2-carbonitrile (0.75 g, 4.26 mmol) in ethanol (10 mL) was added NaOH (4.3 mL of 5 M, 21.3 mmol) and the reaction mixture was heated at 85° C. for 1 hour. The reaction mixture was cooled, concentrated in vacuo and diluted with ethyl acetate (50 mL). The organic layer was washed with mixture of brine solution (10 mL) and 6N HCl (3 mL). The organic layer was separated, dried over MgSO$_4$ and concentrated in vacuo to give 5-tert-butoxypyridine-2-carboxylic acid (0.82 g, 99%) as a yellow solid. ESI-MS m/z calc. 195.1. Found 196.1 (M+1)+; Retention time: 0.62 minutes (3 min run).

Preparation of 3-Fluoro-4-(2-hydroxy-2-methyl-propyl)benzoic acid

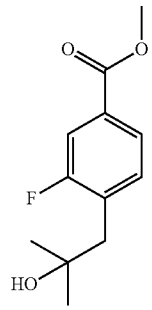

Step 1:
Trimethylsilyl diazomethane (11.6 mL of 2 M in toluene, 23.2 mmol) was added dropwise to a solution of 2-(4-bromo-2-fluoro-phenyl)acetic acid (4.5 g, 19.3 mmol) in a mixture of toluene (7.65 mL)/methanol (7.65 mL) under a nitrogen atmosphere at room temperature. The reaction mixture was then quenched with a few drops of acetic acid and the solvents were concentrated in vacuo. The residue was purified by silica gel column chromatography using 0-10% EtOAc-hexanes as eluent to yield methyl 2-(4-bromo-2-fluoro-phenyl)acetate (4.3 g, 91%). $^1$H NMR (400 MHz, CDCl$_3$) δ 7.28-7.22 (m, 2H), 7.15 (t, J=8.0 Hz, 1H), 3.71 (s, 3H), 3.63 (d, J=1.0 Hz, 2H).

Step 2:
A solution of methyl 2-(4-bromo-2-fluoro-phenyl)acetate (4.0 g, 16.2 mmol) in THF (56 mL) was cooled to 0° C. under a nitrogen atmosphere and to this solution was added methylmagnesium bromide solution (16.2 mL of 3 M in diethyl ether, 48.6 mmol) over 30 minutes. The reaction mixture was stirred for 2 hours, then quenched with saturated aqueous ammonium chloride solution and extracted with EtOAc. The aqueous layer was extracted once more with EtOAc, and the combined organics were dried over Na$_2$SO$_4$, filtered and concentrated in vacuo. The resulting residue was purified by silica gel column chromatography using 0-15% EtOAc-hexanes as eluent to yield 1-(4-bromo-2-fluoro-phenyl)-2-methyl-propan-2-ol (3.0 g, 75%) as a colorless oil. ESI-MS m/z calc. 246.0. Found 231.1 (M−17)$^+$; Retention time: 1.53 minutes (3 min run); $^1$H NMR (400 MHz, CDCl$_3$) δ 7.26-7.21 (m, 2H), 7.14 (t, J=8.1 Hz, 1H), 2.78 (d, J=1.4 Hz, 2H), 1.24 (d, J=0.8 Hz, 6H).

Step 3:

A reaction vessel charged with 1-(4-bromo-2-fluoro-phenyl)-2-methyl-propan-2-ol (2.35 g, 9.51 mmol), palladium acetate (214 mg, 0.95 mmol), 3-diphenylphosphanylpropyl-diphenyl-phosphane (404 mg, 0.95 mmol) and triethylamine (4.24 mL, 30.4 mmol) in DMF (26 mL) was added MeOH (20 mL). The reaction vessel was charged to 50 psi with CO gas and heated at 80° C. for 15 hours. The reaction mixture was allowed to cool, partitioned between EtOAc and brine solution. The layers were separated and the aqueous layer was extracted once more with EtOAc. The combined organics were washed with brine (2×10 mL), dried over Na$_2$SO$_4$, filtered and concentrated in vacuo to an orange oil. The residue was purified by silica gel column chromatography using 0-30% EtOAc-hexanes as eluent to yield methyl 3-fluoro-4-(2-hydroxy-2-methyl-propyl)benzoate (1.83 g, 85%). ESI-MS m/z calc. 226.1. Found 227.5 (M+1)$^+$; Retention time: 1.29 minutes (3 min run); $^1$H NMR (400 MHz, CDCl$_3$) δ 7.78 (dd, J=7.9, 1.7 Hz, 1H), 7.71 (dd, J=10.3, 1.6 Hz, 1H), 7.34 (t, J=7.6 Hz, 1H), 3.92 (s, 3H), 2.88 (d, J=1.3 Hz, 2H), 1.26 (s, 6H).

Step 4:

Methyl 3-fluoro-4-(2-hydroxy-2-methyl-propyl)benzoate (1.59 g, 7.03 mmol) was dissolved in a mixture of THF (40 mL)/water (20 mL)/MeOH (20 mL) and LiOH (1.01 g, 42.2 mmol) was added. The reaction mixture was heated at 55° C. for 30 minutes. The reaction mixture was cooled to room temperature and the concentrated in vacuo. The residue was dissolved in water and cooled to 0° C. and treated with 1 M HCl solution (to pH 3). The resulting precipitate was filtered, washed with water and dried under high vacuum to yield 3-fluoro-4-(2-hydroxy-2-methyl-propyl)benzoic acid (999 mg, 67%) as a white solid. ESI-MS m/z calc. 212.1. Found 211.1 (M−1)$^+$; Retention time: 0.98 minutes (3 min run); $^1$H NMR (400 MHz, CDCl$_3$) δ 7.84 (dd, J=7.9, 1.6 Hz, 1H), 7.77 (dd, J=10.1, 1.6 Hz, 1H), 7.39 (d, J=15.1 Hz, 1H), 2.91 (s, 2H), 1.28 (s, 6H).

Preparation of 4-(2-Hydroxyethoxy)-3-methyl-benzoic acid

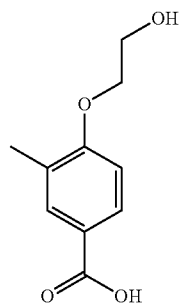

Step 1:

To a solution of methyl 4-hydroxy-3-methyl-benzoate (5.77 g, 34.7 mmol) in DMF (17 mL) was added 2-bromoethanol (6.51 g, 3.7 mL, 52.1 mmol) and cesium carbonate (33.95 g, 104.2 mmol) and the reaction mixture was heated at 60° C. for 16 hours. The reaction mixture was cooled to room temperature and then partioned between water (250 mL) and ethyl acetate (2×100 ml). The organic layers were combined, dried over Na$_2$SO$_4$, filtered and concentrated in vacuo to yield a crude oil that was purified by silica gel column chromatography using EtOAc/hexanes (10 to 100%) as eluent to give methyl 4-(2-hydroxyethoxy)-3-methyl-benzoate (1.87 g, 26%) as a white solid. ESI-MS m/z calc. 210.1. Found 211.1 (M+1)$^+$; Retention time: 1.08 minutes (3 min run); $^1$H NMR (400 MHz, CDCl$_3$) δ 7.94-7.79 (m, 2H), 6.84 (d, J=8.5 Hz, 1H), 4.23-4.08 (m, 2H), 4.08-3.96 (m, 2H), 3.88 (s, 3H), 2.34-2.18 (m, 3H).

Step 2:

To a solution of methyl 4-(2-hydroxyethoxy)-3-methyl-benzoate (1.87 g, 8.9 mmol) in dioxane (16 mL) was added 1N NaOH (5 mL) and the reaction mixture was heated at 70° C. for 18 hours. 5M NaOH (0.5 ml) was added and the reaction was stirred at 70° C. for 22 hours. The reaction mixture was cooled and solvent was concentrated in vacuo and the crude residue was dissolved in water (20 mL) and extracted with ethyl acetate (2×20 mL). The aqueous layer was acidified with 1 M HCl solution and extracted with ethyl acetate (2×20 mL). The organics were separated, dried with Na$_2$SO$_4$ and concentrated in vacuo to give 4-(2-hydroxyethoxy)-3-methyl-benzoic acid (0.77 g, 44%) as a white solid. ESI-MS m/z calc. 196.1. Found 197.0 (M+1)$^+$; Retention time: 0.72 minutes (3 min run). $^1$H NMR (400 MHz, DMSO) δ 12.51 (s, 1H), 7.96-7.49 (m, 2H), 7.00 (d, J=8.6 Hz, 1H), 4.87 (t, J=5.4 Hz, 1H), 4.06 (t, J=5.0 Hz, 2H), 3.75 (q, J=5.1 Hz, 2H), 2.17 (d, J=20.3 Hz, 3H).

Preparation of 4-Pyrrolidin-1-ylsulfonylbenzoic acid

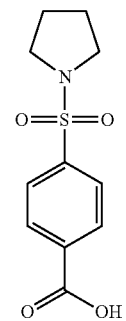 [SMILES: O=C(O)c1ccc(S(=O)(=O)N2CCCC2)cc1]

To a solution of 4-chlorosulfonylbenzoic acid (2 g, 9.07 mmol) in dichloromethane (10 mL) was added a solution of pyrrolidine (1.29 g, 1.51 mL, 18.1 mmol) in dichloromethane (10 mL) and the reaction mixture was stirred at room temperature for 24 hours. The reaction mixture was filtered and the white solid obtained was washed with water (50 ml) and diethyl ether (10 ml) and dried under vacuum to give 4-pyrrolidin-1-ylsulfonylbenzoic acid (700 mg, 30%). ESI-MS m/z calc. 255.0. Found 256.3 (M+1)$^+$; Retention time: 1.18 minutes (3 min run); $^1$H NMR (400 MHz, DMSO) δ 13.49 (s, 1H), 8.15 (d, J=8.5 Hz, 2H), 7.92 (d, J=8.5 Hz, 2H), 3.17 (t, J=6.7 Hz, 4H), 1.65 (t, J=6.7 Hz, 4H).

Preparation of
3-Fluoro-4-(3-methoxyprop-1-ynyl)benzoic acid

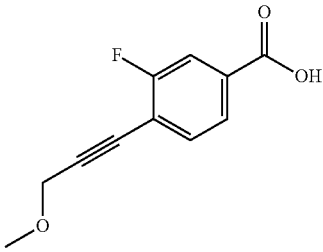

Step 1:
To a mixture of methyl 4-bromo-3-fluoro-benzoate (2.5 g, 10.7 mmol) and copper (I) iodide (204 mg, 1.07 mmol) and palladium dichlorobis(triphenylphosphine) complex (753 mg, 1.07 mmol) under an atmosphere of argon was added DMF (21 mL) and the reaction mixture was cooled to 0° C. Triethylamine (1.95 mL, 13.9 mmol) was added followed by 3-methoxyprop-1-yne (997 µL, 11.8 mmol) and the reaction mixture was stirred at 60° C. for 70 minutes. The reaction mixture was cooled, diluted with EtOAc and filtered over Celite®. The filtrate was washed sequentially with 1 M HCl, 10% NH$_4$OH and brine. The organic layer was separated, dried and concentrated in vacuo and the resulting residue was purified by silica gel column chromatography using EtOAc-hexanes (10-100%) as eluent to give methyl 3-fluoro-4-(3-methoxyprop-1-ynyl)benzoate (1.45 g, 61%). ESI-MS m/z calc. 222.2. Found 223.2 (M+1)$^+$; Retention time: 1.53 minutes (3 min run); $^1$H NMR (400 MHz, CDCl$_3$) δ 7.75 (ddd, J=11.2, 8.8, 1.5 Hz, 2H), 7.50 (dd, J=7.9, 7.0 Hz, 1H), 4.37 (s, 2H), 3.92 (s, 3H), 3.47 (s, 3H).

Step 2:
To methyl 3-fluoro-4-(3-methoxyprop-1-ynyl)benzoate (1.4 g, 6.3 mmol) in 2:1 mixture of THF: MeOH (15 mL) at room temperature was added 4 M sodium hydroxide solution (1.9 mL, 7.56 mmol) and reaction mixture was stirred for 1 hour. The solvent was removed in vacuo and the reaction mixture was extracted with ethyl ether, and layers were separated. The aqueous layer was acidified with 1M HCl solution and extracted with ethyl ether. The organics were separated, dried and concentrated in vacuo to give 4-(3-hydroxypropoxy)-3-methyl-benzoic acid (1.1 g, 85%) as a white solid. ESI-MS m/z calc. 208.2. Found 209.2 (M+1)$^+$; Retention time: 1.22 minutes (3 min run); $^1$H NMR (400 MHz, CDCl$_3$) δ 7.85 (dd, J=8.0, 1.4 Hz, 1H), 7.80 (dd, J=9.5, 1.3 Hz, 1H), 7.59-7.49 (m, 1H), 4.39 (s, 2H), 3.48 (s, 3H).

Preparation of 4-(3-Hydroxyoxetan-3-yl)benzoic acid

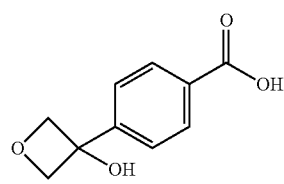 [SMILES: O=C(O)c1ccc(C2(O)COC2)cc1]

To 4-bromobenzoic acid (434 mg, 2.16 mmol) in THF (9 mL) at −78° C. was added dropwise n-butyllithium (2.84 mL of 1.6 M in hexanes, 4.54 mmol). The reaction mixture was stirred for 30 minutes, then oxetan-3-one (218 mg, 3.03 mmol) in THF (1 mL) was added dropwise. The reaction mixture was stirred for 30 minutes at −78° C. and allowed to warm to room temperature over 30 minutes. The reaction mixture was diluted with ethyl acetate (15 mL) and acidified to pH 2 with 2 N HCl. The layers were separated and the aqueous was re-extracted with ethyl acetate (15 mL). The combined organics were washed with brine solution (10 mL), dried over MgSO$_4$ and concentrated in vacuo to give a white solid as a 1:1 mixture of 4-(3-hydroxyoxetan-3-yl)benzoic acid/benzoic acid (380 mg, 91%).

Preparation of
4-Tetrahydrofuran-3-ylsulfonylbenzoic acid

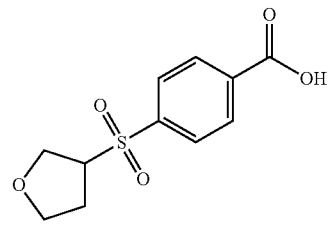 [SMILES: O=C(O)c1ccc(S(=O)(=O)C2CCOC2)cc1]

Step 1:
To a suspension of methyl 4-sulfanylbenzoate (0.85 g, 5.05 mmol), potassium carbonate (1.39 g, 10.1 mmol) in DMF (10 mL) at room temperature was added 3-iodotetrahydrofuran (1.00 g, 5.05 mmol). The resulting suspension was stirred for 16 hours. The reaction mixture was diluted with DCM (25 mL), filtered and the solvent was evaporated under reduced pressure. The residue was dissolved in DCM (25 mL) and washed with water (3×15 mL) and saturated aqueous brine solution (1×15 mL). The organic layer was dried over sodium sulfate, filtered and concentrated in vacuo to yield methyl 4-tetrahydrofuran-3-ylsulfanylbenzoate (1.03 g, 86%) as a yellow solid. ESI-MS m/z calc. 238.1. Found 239.3 (M+1)$^+$; Retention time: 1.47 minutes (3 min run); $^1$H NMR (400 MHz, DMSO) δ 7.91-7.83 (m, 2H), 7.48-7.39 (m, 2H), 4.16-4.08 (m, 2H), 3.91-3.72 (m, 5H), 3.55 (q, J=7.6 Hz, 1H), 2.49-2.35 (m, 1H), 1.86-1.74 (m, 1H).

Step 2:
Methyl 4-tetrahydrofuran-3-ylsulfanylbenzoate (1.01 g, 4.24 mmol) was dissolved in methanol (25 mL), followed by the addition of water (2.5 mL), and Oxone (2.61 g, 4.24 mmol). The reaction mixture was stirred at room temperature for 24 hours. An additional 0.1 eq of Oxone (0.26 g) was added and the reaction mixture was stirred for 2 hours, then filtered and the solvent was concentrated in vacuo. The resulting residue was dissolved in dichloromethane (30 mL) and washed with water (2×25 mL). The organic layer was dried over sodium sulfate, filtered and concentrated in vacuo to yield methyl 4-tetrahydrofuran-3-ylsulfonylbenzoate (1.07 g, 93%) as a yellow solid. ESI-MS m/z calc. 270.1. Found 271.3 (M+1)$^+$; Retention time: 1.02 minutes (3 min run).

Step 3:
To methyl 4-tetrahydrofuran-3-ylsulfonylbenzoate (1.07 g, 3.96 mmol) in dioxane (11 mL) was added 1 M sodium hydroxide (10.5 mL, 10.5 mmol) and the reaction was heated at 80° C. for 10 minutes. The solvent was evaporated under reduced pressure. The residue was dissolved in water (30 mL) and washed with ethyl acetate (3×25 mL). The aqueous layer was acidified with hydrochloric acid. The aqueous layer was extracted with ethyl acetate (2×30 mL). The organic layer was dried over sodium sulfate, filtered and concentrated in vacuo to yield 4-tetrahydrofuran-3-ylsulfonylbenzoic acid (0.86 g, 85%) as a white solid. ESI-MS m/z calc. 256.0. Found 257.3 (M+1)$^+$; Retention time: 0.69 minutes (3 min run); $^1$H NMR (400 MHz, DMSO) δ 13.59 (s, 1H), 8.19 (d, J=8.3 Hz, 2H), 8.05 (d, J=8.3 Hz, 2H), 4.38-4.15 (m, 1H), 4.06-3.97 (m, 1H), 3.87-3.71 (m, 2H), 3.72-3.54 (m, 1H), 2.20-2.06 (m, 2H).

Preparation of 3-Methyl-4-methylsulfonyl-benzoic acid

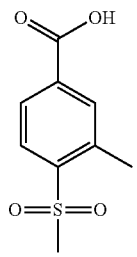

Step 1:
Thionyl chloride (5.8 g, 3.5 mL, 48.7 mmol) was added dropwise to a solution of 4-fluoro-3-methyl-benzoic acid (5.0 g, 32.4 mmol) in methanol (40 mL). The reaction mixture was stirred at 35° C. for 16 hours. The reaction mixture was concentrated in vacuo and the resulting methyl 4-fluoro-3-methylbenzoate was used in the next step without further purification. ESI-MS m/z calc. 167.1. Found 168.2 (M+1)$^+$; Retention time: 1.57 minutes (3 min run). The crude ester was dissolved in DMF (20 mL) and powdered sodium thiomethoxide (2.3 g, 32.4 mmol) was added and the reaction mixture was stirred at room temperature for 1 hour and at 80° C. for 1 hour. The reaction mixture was concentrated in vacuo, the residue was partitioned between 1M HCl solution and ethyl acetate. The layers were separated and the organic was washed with 1M hydrochloric acid solution. The ethyl acetate layer was then dried over magnesium sulfate, filtered, and concentrated in vacuo to give methyl 3-methyl-4-(methylthio)benzoate. ESI-MS m/z calc. 182.2. Found 183.1 (M+1)$^+$; Retention time: 1.48 minutes (3 min run). Methyl 3-methyl-4-(methylthio)benzoate (32.4 mmol) was heated in a mixture of acetic acid (80 mL) and hydrogen peroxide (40 mL of 30% w/w,) at 80° C. for 30 minutes. The reaction mixture was cooled, concentrated in vacuo and then partitioned between water and ethyl acetate. The layers were separated and the organic was washed sequentially with water (1×20 mL), sat. NaHCO$_3$ (1×20 mL) and brine (1×20 mL), then dried over MgSO$_4$ and concentrated in vacuo. The residue was triturated with ethyl ether to give methyl 3-methyl-4-methylsulfonyl-benzoate (5.8 g) as a white solid. The mother liquor was concentrated in vacuo then triturated with hexanes (3×) to give a second crop (1.2 g) (combined yield 95%). ESI-MS m/z calc. 228.3. Found 229.5 (M+1)$^+$; Retention time: 1.04 minutes (3 min run); $^1$H NMR (400 MHz, CDCl$_3$) δ 8.20-8.09 (m, 1H), 8.04-8.00 (m, 2H), 3.96 (s, 3H), 3.10 (s, 3H), 2.77 (s, 3H).

Step 2:
To a mixture of methyl 3-methyl-4-methylsulfonyl-benzoate (5.8 g, 25.4 mmol) in dioxane (25 mL) was added NaOH (20 g, 125.0 mmol) (aq. 25%) and the reaction mixture was heated at 75° C. for 1 hour. The reaction mixture was cooled and was concentrated in vacuo to half the volume and adjusted to pH 2 with 6N HCl solution. The aqueous layer was extracted with ethyl acetate (3×100 mL). The organics were washed with brine solution (50 mL), dried over MgSO$_4$ and concentrated in vacuo to give 3-methyl-4-methylsulfonyl-benzoic acid (5.3 g, 97%) as a white solid. ESI-MS m/z calc. 214.5. Found 215.5 (M+1)$^+$; Retention time: 0.67 minutes (3 min run); $^1$H NMR (400 MHz, DMSO) δ 13.48 (s, 1H), 8.13-7.81 (m, 3H), 3.33 (s, 3H), 2.70 (s, 3H).

Preparation of 4-Ethoxy-3-(hydroxymethyl)benzoic acid

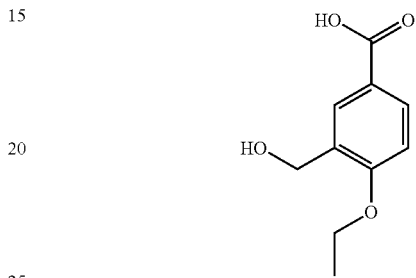

Step 1:
A suspension of methyl 3-formyl-4-hydroxy-benzoate (3.0 g, 16.7 mmol), bromoethane (2.7 g, 1.85 mL, 24.9 mmol) and powdered K$_2$CO$_3$ (6.9 g, 49.9 mmol) in DMF (15 mL) was heated at 40° C. for 16 hours. After 16 hours, a further aliquot of bromoethane (1 mL) was added and the reaction mixture was heated for a further 2 hours. The reaction mixture was diluted with DCM (50 mL), filtered and concentrated in vacuo to give a yellow solid, which was diluted with ether (200 mL), washed sequentially with water (50 mL), sat. aq. NaHCO$_3$ (50 mL) and brine solution (50 mL). The organics were separated, dried over MgSO$_4$ and concentrated in vacuo to give methyl 4-ethoxy-3-formylbenzoate (3.52 g, 100%) as a white solid. ESI-MS m/z calc. 208.0. Found 209.3 (M+1)$^+$; Retention time: 1.34 minutes (3 min run). Methyl 4-ethoxy-3-formylbenzoate (1.73 g, 8.91 mmol) was dissolved in THF (20 mL) and cooled to 0° C. LiBH$_4$ (100 mg, 4.59 mmol) was added and the reaction mixture was stirred for 1 hour, then slowly quenched with dropwise addition of acetic acid. The reaction mixture was concentrated in vacuo, diluted with ethyl acetate (50 mL), washed sequentially with sat. aq. NaHCO$_3$ (20 mL) and brine (20 mL). The organics were separated, dried over MgSO$_4$ and purified by silica gel column chromatography using 0-100% EtOAc/DCM as eluent to give methyl 4-ethoxy-3-(hydroxymethyl)benzoate (1.6 g, 46%) as a white solid. ESI-MS m/z calc. 210.0. Found 211.3 (M+1)$^+$; Retention time: 1.11 minutes (3 min run); $^1$H NMR (400 MHz, CDCl$_3$) δ 8.05-7.86 (m, 2H), 6.99-6.79 (m, 1H), 4.72 (s, 2H), 4.16 (q, J=7.0 Hz, 2H), 3.89 (s, 3H), 1.64 (d, J=7.0 Hz, 2H), 1.47 (t, J=7.0 Hz, 3H).

Step 2:
To a solution of methyl 4-ethoxy-3-(hydroxymethyl)benzoate (1.6 g, 7.61 mmol) in dioxane (10 mL) was added NaOH (6.0 g, 37.5 mmol) and the reaction mixture was heated at 50° C. for 2 hours. The reaction mixture was concentrated in vacuo to half-volume, acidified to pH 2 with aq. 6N HCl solution. The resulting suspension was filtered, the solid rinsed with water and acetonitrile, then dried in vacuo to give 4-ethoxy-3-(hydroxymethyl)benzoic acid (740 mg, 50%) as a white solid. $^1$H NMR (400 MHz, DMSO) δ 12.51 (s, 1H), 8.00 (s, 1H), 7.81 (dd, J=8.5, 2.2 Hz, 1H), 7.01 (d, J=8.6 Hz, 1H), 5.13 (t, J=5.7 Hz, 1H), 4.50 (d, J=5.2 Hz, 2H), 4.11 (q, J=7.0 Hz, 2H), 1.34 (t, J=7.0 Hz, 3H).

Preparation of 2-Methyl-4-methylsulfonyl-benzoic acid

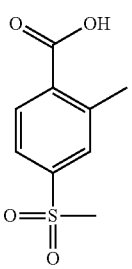

Thionyl chloride (2 mL, 27.4 mmol) was added dropwise to a solution of 4-fluoro-2-methyl-benzoic acid (1.25 g, 8.11 mmol) in methanol (10 mL). The reaction mixture was stirred at 60° C. for 2 hours. The reaction mixture was concentrated in vacuo and methyl 4-fluoro-2-methylbenzoate was used in the next step without further purification. Methyl 4-fluoro-2-methylbenzoate was dissolved in DMF (5 mL) and sodium thiomethoxide (1.1 g, 15.7 mmol) was added and the reaction mixture was heated to 80° C. for 2 hours. The reaction mixture was then partitioned between 1M hydrochloric acid and ethyl acetate. The layers were separated and the organic layer was washed with 1M hydrochloric acid, dried over magnesium sulfate, filtered, and concentrated in vacuo to give 2-methyl-4-(methylthio)benzoic acid which was carried to the next step without further purification. 2-Methyl-4-(methylthio)benzoic acid was suspended in acetic acid (10 mL) and hydrogen peroxide (5 mL of 30% w/w) was added and the reaction mixture was heated to 80° C. for 2 hours. The reaction mixture was concentrated in vacuo, then partitioned between 0.2 M HCl (25 mL) and ethyl acetate (50 mL). The layers were separated and the aqueous extracted with ethyl acetate (50 mL). The combined organics washed with brine (20 mL), dried over MgSO$_4$ and concentrated in vacuo. The resulting solid was rinsed with ether (2×10 mL) and dried in vacuo to give 2-methyl-4-methylsulfonyl-benzoic acid (0.87 g, 50%) as a white solid. ESI-MS m/z calc. 214.0. Found 215.5 (M+1)$^+$; Retention time: 0.48 minutes (3 min run); $^1$H NMR (400 MHz, DMSO) δ 7.99 (d, J=8.1 Hz, 1H), 7.87 (s, 1H), 7.82 (d, J=8.0 Hz, 1H), 3.25 (s, 3H), 2.59 (s, 3H).

Preparation of 3-Methoxy-4-methylsulfonyl-benzoic acid

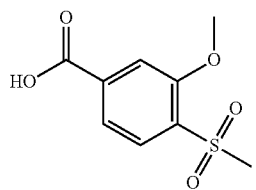

To 3-fluoro-4-methylsulfonyl-benzoic acid (490 mg, 2.25 mmol), sodium hydride (270 mg, 6.74 mmol), methanol (1.55 g, 2.0 mL, 48.3 mmol) was added DMF (5 mL) and reaction mixture was heated at 100° C. for 1 hour. The reaction mixture was cooled and diluted with EtOAc and acidified using 1 M HCl solution. The organic layer was separated, washed with saturated aqueous brine solution (3×), dried over sodium sulfate and concentrated in vacuo to give 3-methoxy-4-methylsulfonyl-benzoic acid (496 mg, 95%). ESI-MS m/z calc. 230.0. Found 231.3 (M+1)$^+$; Retention time: 0.49 minutes (3 min run).

Preparation of 4-[Cyclopropyl(hydroxy)methyl]benzoic acid

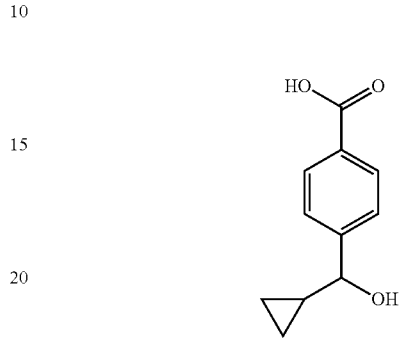

Step 1:
(4-Ethoxycarbonylphenyl)-iodo-zinc (20 mL of 0.5 M in THF, 10.0 mmol) was added over 10 min to dichloro-bis (triphenylphosphoranyl)palladium (211 mg, 0.3 mmol) in THF (20 mL) under an atmosphere of nitrogen at 0° C. The reaction mixture was stirred for 15 minutes, cyclopropanecarbonyl chloride (941 mg, 817 µL, 9.0 mmol) was added dropwise at 0° C. and stirred for 2 hours. The reaction mixture was quenched with 1M HCl (20 mL), extracted with ethyl acetate (2×50 mL). The organic layer was washed sequentially with sat. aq. NaHCO$_3$ (5 mL) and brine solution (50 mL), dried over MgSO$_4$ and purified by silica gel column chromatography using 0-30% EtOAc/hexanes as eluent to give ethyl 4-(cyclopropanecarbonyl)benzoate (1.54 g, 71%) as a pale yellow oil. ESI-MS m/z calc. 218.0. Found 219.3 (M+1)$^+$; Retention time: 1.57 minutes (3 min run).

Step 2:
To ethyl 4-(cyclopropanecarbonyl)benzoate (400 mg, 1.83 mmol) in ethanol (10 mL) was added at room temperature NaBH$_4$ (69 mg, 1.83 mmol) and the reaction mixture was stirred for 1 hour. The reaction mixture was then concentrated in vacuo and NaOH (1.5 g, 9.38 mmol) and dioxane (1.5 mL) were added and the reaction mixture was heated at 80° C. for 3 hours. The reaction mixture was concentrated in vacuo to half the volume and pH was adjusted to 2 with 3 N HCl. The aqueous layer was extracted with ethyl acetate (3×10 mL), and the combined organics were washed with brine solution (5 mL), dried over MgSO$_4$ and concentrated in vacuo to give 4-[cyclopropyl(hydroxy)methyl]benzoic acid (300 mg, 85%). ESI-MS m/z calc. 192.2. Found 193.5 (M+1)$^+$; Retention time: 0.78 minutes (3 min run); $^1$H NMR (400 MHz, DMSO) δ 7.89 (d, J=8.1 Hz, 2H), 7.49 (d, J=8.1 Hz, 2H), 5.33 (d, J=4.4 Hz, 1H), 4.04 (dd, J=7.3, 4.3 Hz, 1H), 1.12-0.87 (m, 1H), 0.54-0.20 (m, 4H).

Preparation of 3-Fluoro-4-isopropoxy-benzoic acid

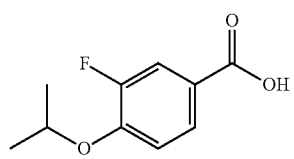

Step 1:

To methyl 3-fluoro-4-hydroxy-benzoate (2.0 g, 11.8 mmol) in DMF (12 mL) was added $K_2CO_3$ (6.50 g, 47.04 mmol) followed by 2-iodopropane (2.35 mL, 23.5 mmol). The reaction mixture was heated at 60° C. for 1.5 hours. The reaction mixture was cooled and diluted with EtOAc, filtered and the solvent was evaporated in vacuo. The resulting residue was dissolved in EtOAc and washed sequentially with water (3×10 mL) and brine solution (1×10 mL). The organics were separated and dried over $Na_2SO_4$, filtered and concentrated in vacuo to give the desired ester. ESI-MS m/z calc. 212.2. Found 213.3 (M+1)+; Retention time: 1.7 minutes (3 min run). $^1$H NMR (400 MHz, DMSO) δ 7.76 (ddd, J=8.6, 2.1, 1.2 Hz, 1H), 7.69 (dd, J=11.9, 2.1 Hz, 1H), 7.31 (t, J=8.6 Hz, 1H), 4.79 (dt, J=12.1, 6.0 Hz, 1H), 3.82 (s, 3H), 1.32 (d, J=6.5 Hz, 6H).

Step 2:

To the ester from above was added dioxane (31 mL) and NaOH solution (31.2 mL of 1 M, 31.2 mmol) and the reaction was heated at 80° C. for 20 minutes, then concentrated in vacuo. The crude mixture was dissolved in water and washed with EtOAc (3×10 mL). The layers were separated and the aqueous layer was acidified using 1 M HCl solution. The aqueous layer was extracted with EtOAc (3×10 mL). The organic layer was dried over $Na_2SO_4$, filtered and concentrated in vacuo to yield 3-fluoro-4-isopropoxy-benzoic acid (1.7 g, 72%) as a white solid. ESI-MS m/z calc. 198.1. Found 199.1 (M+1)+; Retention time: 1.7 minutes (3 min run). $^1$H NMR (400 MHz, DMSO) δ 12.90 (br s, 1H), 7.73 (ddd, J=8.6, 2.0, 1.1 Hz, 1H), 7.65 (dd, J=11.9, 2.1 Hz, 1H), 7.28 (t, J=8.6 Hz, 1H), 4.77 (hept, J=6.1 Hz, 1H), 1.32 (d, J=6.0 Hz, 6H).

Preparation of 4-Isopropoxy-3-methoxy-benzoic acid

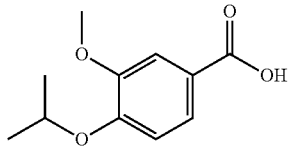

Step 1:

2-Bromopropane (3.39 mL, 36.2 mmol) was added to a suspension of 4-bromo-2-methoxy-phenol (5 g, 24.1 mmol), $K_2CO_3$ (6.67 g, 48.3 mmol) and DMSO (71 mL) at room temperature. The heterogeneous mixture was stirred at 55° C. for 2 hours, then cooled to room temperature and diluted with water. The reaction mixture was extracted with $Et_2O$ and the extract was washed successively with 10% aq. NaOH solution, water, then brine solution. The organics were separated and dried over sodium sulfate, filtered and concentrated in vacuo to give 4-bromo-1-isopropoxy-2-methoxy-benzene (5.83 g, 94%) as a pale yellow oil. ESI-MS m/z calc. 244.0. Found 245.0 (M+1)+; Retention time: 1.93 minutes (3 min run). $^1$H NMR (400 MHz, CDCl$_3$) δ 7.03-6.95 (m, 2H), 6.76 (dd, J=7.7, 1.1 Hz, 1H), 4.47 (dt, J=12.2, 6.1 Hz, 1H), 3.84 (s, 3H), 1.35 (d, J=6.1 Hz, 6H).

Step 2:

Under an atmosphere of nitrogen, tert-butyllithium (2.14 mL of 1.6 M in toluene, 3.42 mmol) was added dropwise to a solution of 4-bromo-1-isopropoxy-2-methoxy-benzene (400 mg, 1.63 mmol) in THF (6 mL) at −78° C. The reaction mixture was allowed to stir for 1 hour at −78° C., then added dropwise to a flask containing $CO_2$ (1.8 g, 40.8 mmol) (solid, dry ice) in THF (2 mL). The reaction mixture was allowed to stir for 30 minutes warming to room temperature. Water (20 mL) was added to the reaction mixture and the volatiles were removed in vacuo. The resultant aqueous layer was acidified with 1N HCl solution to pH 1 and was extracted with ethyl acetate (3×15 mL). The organics were separated and the combined organics were washed with brine solution, dried over sodium sulfate, filtered and concentrated in vacuo to give 4-isopropoxy-3-methoxy-benzoic acid (310 mg, 85%) as a white solid. ESI-MS m/z calc. 210.1. Found 211.1 (M+1)+; Retention time: 1.23 minutes (3 min run). $^1$H NMR (400 MHz, DMSO) δ 12.63 (s, 1H), 7.53 (dd, J=8.4, 2.0 Hz, 1H), 7.44 (d, J=2.0 Hz, 1H), 7.04 (d, J=8.7 Hz, 1H), 4.67 (dt, J=12.1, 6.0 Hz, 1H), 3.78 (s, 3H), 1.28 (d, J=6.0 Hz, 6H).

Preparation of 4-Isobutylsulfonylbenzoic acid

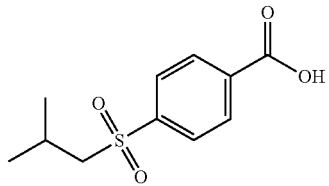 [SMILES: CC(C)CS(=O)(=O)c1ccc(C(=O)O)cc1]

Step 1:

Potassium carbonate (1.2 g, 8.9 mmol) was added to a mixture of methyl 4-sulfanylbenzoate (1.0 g, 6.0 mmol), 1-bromo-2-methyl-propane (1.2 g, 970 μL, 8.9 mmol), and DMF (10 mL) at room temperature. The reaction mixture was allowed to stir for 4 hours and the resulting solid was removed by filtration. The filtrate were partitioned between ethyl acetate (100 mL) and water (100 mL). The layers were separated and the organic layer was washed with brine solution, then dried over sodium sulfate, filtered and concentrated in vacuo to give methyl 4-isobutylsulfanylbenzoate (1.1 g, 83%) as a clear oil. ESI-MS m/z calc. 242.0. Found 243.2 (M+1)+; Retention time: 1.73 minutes (3 min run). $^1$H NMR (400 MHz, CDCl$_3$) δ 8.30 (d, J=8.3 Hz, 2H), 8.05 (d, J=8.3 Hz, 2H), 3.03 (d, J=6.5 Hz, 2H), 2.27 (dt, J=13.3, 6.6 Hz, 1H), 1.08 (d, J=6.7 Hz, 6H).

Step 2:

3-Chlorobenzenecarboperoxoic acid (3.6 g, 15.6 mmol) was added to a solution of methyl 4-isobutylsulfanylbenzoate (1.0 g, 4.5 mmol) in DCM (20 mL) at room temperature. The reaction mixture was allowed to stir for 2 hours, then concentrated in vacuo. The resulting residue was purified by silica gel column chromatography using (0-100%) ethyl acetate/hexanes as eluent to give methyl 4-isobutylsulfonylbenzoate. ESI-MS m/z calc. 256.1. Found 257.2 (M+1)+; Retention time: 1.96 minutes (3 min run). $^1$H NMR (400 MHz, CDCl$_3$) δ 8.23 (d, J=8.4 Hz, 2H), 8.00 (d, J=8.3 Hz, 2H), 3.98 (s, 3H), 3.02 (d, J=6.5 Hz, 2H), 2.25 (dp, J=13.3, 6.6 Hz, 1H), 1.07 (d, J=6.7 Hz, 6H).

Step 3:

A mixture of methyl 4-isobutylsulfonylbenzoate (1.0 g, 3.9 mmol), NaOH solution (10 mL of 1 M, 10.00 mmol), and dioxane (10 mL) was heated at 80° C. for 1.5 hours. The reaction mixture was cooled to room temperature, then concentrated in vacuo. The solid residue was dissolved in water and washed with ethyl acetate (1×10 mL). The aqueous layer was acidified with 1N HCl solution and was extracted with ethyl acetate (2×10 mL) and layers were separated. The combined organics were washed with brine, dried over sodium sulfate, and concentrated in vacuo. The residue was purified by silica gel column chromatography using (0-100%) ethyl acetate/hexanes as eluent to give 4-isobutylsulfonylbenzoic acid (1.0 g, 98%). ESI-MS m/z calc. 242.1. Found 243.2 (M+1)⁺; Retention time: 1.73 minutes (3 min run). ¹H NMR (400 MHz, CDCl₃) δ 8.30 (d, J=8.3 Hz, 2H), 8.05 (d, J=8.3 Hz, 2H), 3.03 (d, J=6.5 Hz, 2H), 2.27 (dt, J=13.3, 6.6 Hz, 1H), 1.08 (d, J=6.7 Hz, 6H).

Preparation of 4-(2-Hydroxy-2-methyl-propoxy)benzoic acid

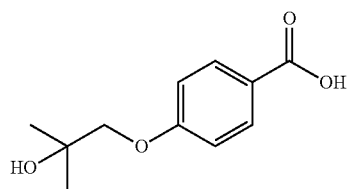

Step 1:

A mixture of 1-chloro-2-methyl-propan-2-ol (10 mL), 4-hydroxybenzonitrile (2 g, 16.8 mmol), K₂CO₃ (9.3 g, 67.3 mmol) in water (6 mL) and ethanol (60 mL) was heated at 80° C. for 16 hours. The reaction mixture was cooled and the solvent was concentrated in vacuo. The residue was diluted with ether (200 mL) and filtered and the filtrate was washed sequentially with water (50 mL) and brine solution (50 mL). The organics were separated and dried over MgSO₄ and solvent was removed in vacuo to give a residue which was purified by silica gel column chromatography using (0-100%) EtOAc/DCM as eluent to give 4-(2-hydroxy-2-methyl-propoxy)benzonitrile (3.0 g, 94%) as a yellow solid. ESI-MS m/z calc. 191.1. Found 192.3 (M+1)⁺; Retention time: 1.05 minutes (3 min run).

Step 2:

To 4-(2-hydroxy-2-methyl-propoxy)benzonitrile (1.0 g, 5.2 mmol) in ethanol (15 mL) was added NaOH solution (5 mL of 5 M, 25 mmol) and the reaction mixture was heated at 85° C. for 1 hour, concentrated in vacuo and diluted with ethyl acetate (50 mL). To the organic layer was added a mixture of brine solution (10 mL) and 6N HCl (3 mL, to adjust to pH 6). The organic layer was separated, dried over MgSO₄ and concentrated in vacuo to give a yellow solid, which was triturated twice with diethyl ether to give 4-(2-hydroxy-2-methyl-propoxy)benzoic acid (0.8 g, 76%) as a white solid. ESI-MS m/z calc. 195.1. Found 196.1 (M+1)⁺; Retention time: 0.62 minutes (3 min run). ¹H NMR (400 MHz, DMSO) δ 12.59 (s, 1H), 7.98-7.66 (m, 2H), 7.09-6.81 (m, 2H), 4.66 (d, J=9.3 Hz, 1H), 3.77 (d, J=7.9 Hz, 2H), 1.30-1.00 (s, 6H).

Preparation of 3-(Hydroxymethyl)-4-isopropoxy-benzoic acid

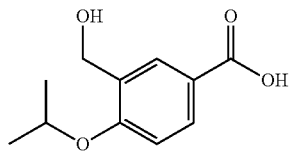

Step 1:

To a mixture of methyl 3-formyl-4-hydroxy-benzoate (10.0 g, 55.5 mmol), potassium carbonate (30.7 g, 222.0 mmol) and N,N-dimethylformamide (62.5 mL) was added 2-iodopropane (18.9 g, 11.1 mL, 111.0 mmol) and the reaction mixture was heated at 60° C. for 18 hours. The reaction mixture was filtered, the filtrate was concentrated in vacuo to give a residue which was dissolved in ethyl acetate (150 mL) and washed sequentially with water (3×75 mL) and brine solution (1×75 mL). The layers were separated and the organic layer was dried over sodium sulfate, filtered and concentrated in vacuo to yield methyl 3-formyl-4-isopropoxy-benzoate (12.2 g, 99%) as a yellow viscous liquid. ESI-MS m/z calc. 222.2. Found 223.3 (M+1)⁺; Retention time: 1.51 minutes (3 min run). ¹H NMR (400 MHz, DMSO) δ 10.35 (s, 1H), 8.23 (d, J=2.3 Hz, 1H), 8.17 (dd, J=8.8, 2.3 Hz, 1H), 7.39 (d, J=8.9 Hz, 1H), 4.98-4.83 (m, 1H), 3.85 (s, 3H), 1.38 (d, J=6.0 Hz, 6H).

Step 2:

Methyl 3-formyl-4-isopropoxy-benzoate (180 mg, 0.8 mmol) was dissolved in tetrahydrofuran (5 mL) and lithium borohydride (35 mg, 1.6 mmol) was added. The reaction mixture was stirred at room temperature for 30 minutes, then quenched with methanol (3 mL). The reaction mixture was neutralized by the addition of a saturated aqueous solution of sodium bicarbonate (3 mL) and extracted with ethyl acetate (3×10 mL). The organic layers were washed with brine solution (1×10 mL), dried over sodium sulfate, filtered and concentrated in vacuo to yield methyl 3-(hydroxymethyl)-4-isopropoxy-benzoate (180 mg, 99%) as a viscous liquid. ESI-MS m/z calc. 224.3. Found 225.3 (M+1)⁺; Retention time: 1.26 minutes (3 min run); ¹H NMR (400 MHz, DMSO) δ 8.09 (s, 1H), 7.89 (d, J=8.6 Hz, 1H), 7.13 (d, J=8.6 Hz, 1H), 5.25 (t, J=5.6 Hz, 1H), 4.86-4.68 (m, 1H), 4.54 (d, J=5.6 Hz, 2H), 3.87 (s, 3H), 1.35 (d, J=6.0 Hz, 6H).

Step 3:

To methyl 3-(hydroxymethyl)-4-isopropoxy-benzoate (180 mg, 0.8 mmol) in dioxane (2 mL) was added sodium hydroxide (2.1 mL of 1 M, 2.1 mmol) and the reaction mixture was heated at 80° C. for 50 minutes. The solvent was evaporated under reduced pressure. The residue was dissolved in water (10 mL) and washed with ethyl acetate (3×10 mL). The layers were separated and aqueous layer was acidified with hydrochloric acid. The aqueous layer was extracted with ethyl aceatate (3×10 mL). The organic layer was separated, dried over sodium sulfate, filtered and concentrated in vacuo to yield 3-(hydroxymethyl)-4-isopropoxy-benzoic acid (150 mg, 89%) as a white solid. ESI-MS m/z calc. 210.2. Found 211.3 (M+1)⁺; Retention time: 1.01 minutes (3 min run).

Preparation of 3-Methoxy-4-(2-methoxy-1,1-dimethyl-2-oxo-ethyl)benzoic acid

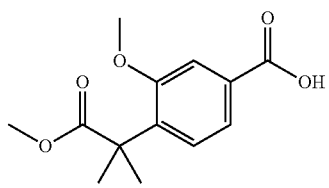 [SMILES: COC(=O)C(C)(C)c1ccc(C(=O)O)cc1OC]

Step 1:

To MgSO₄ (4.8 g, 1.8 mL, 40 mmol) in DCM (40 mL) was added H₂SO₄ (1.0 g, 533 µL, 10 mmol) at 0° C. and the reaction mixture was allowed to stir for 30 minutes. 4-Bromo-3-methoxy-benzoic acid (2.3 g, 10 mmol) was added followed by 2-methylpropan-2-ol (3.7 g, 4.8 mL, 50 mmol). The reaction mixture was allowed to stir at room temperature for 16 hours. MgSO$_4$ was removed by filtration and 1N NaOH solution was added until pH 9 was achieved. The layers were separated and the organic layer was dried over sodium sulfate, filtered and concentrated in vacuo to yield tert-butyl 4-bromo-3-methoxy-benzoate (0.4 g, 14%).

Step 2:

To difluorozinc (36 mg, 0.35 mmol) and Pd ($^t$Bu$_3$P)$_2$ (7 mg, 0.01 mmol) under an atmosphere of nitrogen was added tert-butyl 4-bromo-3-methoxy-benzoate (200 mg, 0.69 mmol) dissolved in DMF (2.5 mL), followed by (1-methoxy-2-methyl-prop-1-enoxy)-trimethylsilane (182 mg, 1.05 mmol). The reaction mixture was heated at 80° C. for 16 hours. The reaction mixture was cooled, filtered and partitioned between EtOAc and brine solution. The organics were separated, dried over sodium sulfate and concentrated in vacuo. The resulting residue was dissolved in DCM (1 mL) and treated with TFA (794 mg, 537 µL, 6.97 mmol). The reaction mixture was allowed to stir for 2 hours and the solvent was concentrated in vacuo, the residue was dissolved in DMF, filtered and purified by HPLC using MeOH:H$_2$O mixture (1-99%) with HCl modifier (5 mM) to give 3-methoxy-4-(2-methoxy-1,1-dimethyl-2-oxo-ethyl)benzoic acid (55 mg, 31%). ESI-MS m/z calc. 252.0. Found 253.2 (M+1)$^+$; Retention time: 2.46 minutes (3 min run).

Preparation of 4-ethoxy-3-methylbenzoic acid

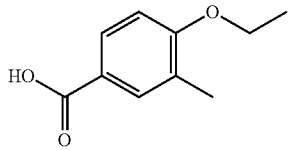

Step 1:

To a solution of 4-hydroxy-3-methyl-benzoic acid (1.00 g, 6.57 mmol) in N,N-dimethylformamide (10 mL) was added potassium carbonate (2.73 g, 19.7 mmol) and bromoethane (3.58 g, 2.44 mL, 32.9 mmol). The reaction mixture heated at 45° C. for 48 h in a sealed tube. The reaction mixture allowed to cool then diluted with water and ether. The ether layer was washed with 50% saturated NaHCO$_3$ (50 mL) and brine (50 mL), dried over Na$_2$SO$_4$, and concentrated in vacuo to provide ethyl 4-ethoxy-3-methylbenzoate as an orange-colored oil. The crude product was taken directly to the next step. ESI-MS m/z calc. 208.10994. Found 209.3 (M+1)$^+$; Retention time: 1.78 minutes (3 min run).

Step 2:

The crude ethyl 4-ethoxy-3-methyl-benzoate was suspended in a solution of NaOH (10.5 g, 263 mmol) in water (50 mL) and methanol (25 mL). The reaction mixture was refluxed for 1 h. The reaction mixture was cooled to 0° C., acidified with 12 M HCl (24.7 mL, 296 mmol) and the resulting solid filtered. The solid was slurried with acetonitrile and filtered to provide 4-ethoxy-3-methyl-benzoic acid (760 mg, 4.22 mmol, 64%) as a light pink solid. ESI-MS m/z calc. 180.07864. Found 181.3 (M+1)$^+$; Retention time: 1.31 minutes (3 min run). $^1$H NMR (400 MHz, DMSO-d$_6$) δ 12.50 (s, 1H), 7.77 (dd, J=8.5, 2.2 Hz, 1H), 7.73 (d, J=1.5 Hz, 1H), 7.00 (d, J=8.6 Hz, 1H), 4.11 (q, J=7.0 Hz, 2H), 2.17 (s, 3H), 1.36 (t, J=7.0 Hz, 3H).

Preparation of 3-methyl-4-propoxybenzoic acid

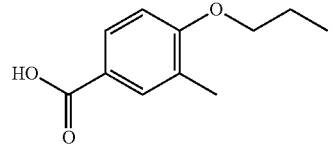

Step 1:

To a solution of 4-hydroxy-3-methyl-benzoic acid (3.00 g, 19.7 mmol) in N,N-dimethylformamide (30 mL) was added and 1-iodopropane (16.8 g, 9.62 mL, 98.6 mmol). The reaction mixture was stirred at 60° C. for 3 h. The reaction mixture was allowed to cool then diluted with water and ether. The ether layer was washed with water (50 mL) and brine (50 mL), dried over Na$_2$SO$_4$, and concentrated. Silica gel chromatography (5-30% ethyl acetate/hexane) provided propyl 3-methyl-4-propoxybenzoate as an orange-colored oil that was taken directly to the next step.

Step 2:

The crude propyl 3-methyl-4-propoxybenzoate was dissolved in methanol (25 mL) and water (50 mL) and treated with solid sodium hydroxide (31.6 g, 789 mmol). The reaction mixture was refluxed for 1 h. The reaction mixture cooled to 0° C. and acidified with 12 M HCl (74 mL, 890 mmol). The resulting solid filtered to provide 3-methyl-4-propoxy-benzoic acid (3.22 g, 16.6 mmol, 84%) as a light pink solid. ESI-MS m/z calc. 194.0943. Found 195.3 (M+1)$^+$; Retention time: 1.41 minutes (3 min run). $^1$H NMR (400 MHz, DMSO-d$_6$) δ 12.50 (s, 1H), 7.77 (dd, J=8.5, 2.2 Hz, 1H), 7.73 (d, J=1.4 Hz, 1H), 6.99 (d, J=8.6 Hz, 1H), 4.01 (t, J=6.4 Hz, 2H), 2.18 (s, 3H), 1.82-1.69 (m, 2H), 1.01 (t, J=7.4 Hz, 3H).

Preparation of 4-(1-hydroxycyclobutyl)-3-methylbenzoic acid

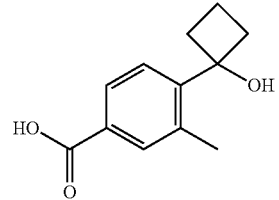

To a solution of 4-bromo-3-methyl-benzoic acid (2.95 g, 13.7 mmol) in tetrahydrofuran (53 mL) at −78° C. was added n-butyllithium (17.6 mL of 1.6 M in hexanes, 28 mmol) dropwise while maintaining the internal temperature below −65° C. resulting in a thin, light yellow slurry. The mixture was stirred at −78° C. for 30 min. Cyclobutanone (962 mg, 1.03 mL, 13.7 mmol) was added dropwise to the above slurry while maintaining the internal temperature below −65° C. The mixture was stirred at −78° C. for 10 min, warmed to room temperature and stirred for 2 h. The reaction mixture was quenched with saturated NH$_4$Cl (50 mL) and 1N HCl (25 mL) then extracted with ethyl acetate (3×100 mL). The combined organics were dried over Na$_2$SO$_4$, filtered and concentrated in vacuo. Silica gel chromatography (0-10% methanol/dichloromethane) provided the product as an off-white solid. The solid was slurried with hexanes, filtered, and dried to provide 4-(1-hydroxycyclobutyl)-3-methyl-benzoic acid (1.30 g, 6.30 mmol, 46%) as a white solid. ESI-MS m/z calc. 189.09155. Found 189.5 (M−OH)⁺; Retention time: 1.0 minute (3 min run). ¹H NMR (400 MHz, DMSO-$d_6$) δ 12.76 (s, 1H), 7.77-7.66 (m, 2H), 7.36 (d, J=7.8 Hz, 1H), 5.38 (s, 1H), 2.56-2.51 (m, 2H), 2.38 (s, 3H), 2.32-2.23 (m, 2H), 2.06-1.90 (m, 1H), 1.61-1.51 (m, 1H).

Preparation of
4-(1-hydroxycyclopentyl)-3-methylbenzoic acid

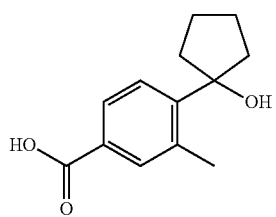 [SMILES: Cc1cc(C(=O)O)ccc1C1(O)CCCC1]

4-Bromo-3-methyl-benzoic acid (4.00 g, 18.6 mmol) was dissolved in tetrahydrofuran (80 mL) and the solution was cooled to −78° C. n-Butyllithium (16.4 mL of 2.5 M in hexanes, 40.9 mmol) was added dropwise over 20 min while maintaining the internal temperature below −65° C. resulting in a thin, light yellow slurry. The reaction mixture was allowed to stir for 30 min at −78° C. Cyclopentanone (1.57 g, 1.65 mL, 18.6 mmol) was then added in a dropwise manner. The mixture was stirred at −78° C. for 30 min, warmed to room temperature and stirred for 2 h. The reaction mixture was then diluted with 1 M NaOH (100 mL) and washed with diethyl ether. The organic layer was discarded and the aqueous layer was acidified with 4 M HCl to <pH 3. The aqueous layer was extracted with ethyl acetate (3×50 mL). The combined extracts were dried over $Na_2SO_4$ and concentrated in vacuo. The crude product was filtered through silica gel eluting with 0-10% methanol/dichloromethane, and all product containing fraction concentrated in vacuo. The resulting solid was slurried in dichloromethane and filtered to provide 4-(1-hydroxycyclopentyl)-3-methylbenzoic acid (1.10 g, 26%) as a white solid. ESI-MS m/z calc. 220.10994. Found 221.5 (M+1)⁺; Retention time: 1.16 minutes (3 min run). ¹H NMR (400 MHz, DMSO-$d_6$) δ 12.74 (s, 1H), 7.70 (d, J=1.4 Hz, 1H), 7.67 (dd, J=8.1, 1.7 Hz, 1H), 7.51 (d, J=8.2 Hz, 1H), 4.77 (s, 1H), 2.54 (s, 3H), 2.07-1.98 (m, 2H), 1.98-1.89 (m, 2H), 1.87-1.77 (m, 2H), 1.72-1.59 (m, 2H).

Preparation of
3-fluoro-4-(1-hydroxycyclopentyl)benzoic acid

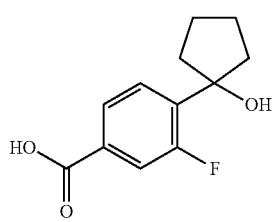 [SMILES: O=C(O)c1ccc(C2(O)CCCC2)c(F)c1]

4-Bromo-3-fluoro-benzoic acid (3.00 g, 13.7 mmol) was dissolved in tetrahydrofuran (60 mL) and the solution was cooled to −78° C. n-Butyllithium (18.8 mL of 1.6 M in hexanes, 30 mmol) was added dropwise over 20 min while maintaining the internal temperature under −70° C. The reaction mixture was allowed to stir for 30 min at −78° C. and then cyclopentanone (1.21 mL, 13.7 mmol) was added in a dropwise while maintaining the internal temperature below −70° C. The mixture was stirred at −78° C. for 30 min the allowed to warm to room temperature. The reaction mixture was diluted with saturated $NH_4Cl$ (50 mL) and 1 M HCl (25 mL) and extracted with dichloromethane (3×50 mL). The combined extracts were dried over $Na_2SO_4$ and concentrated in vacuo. Silica gel chromatography (0-5% methanol/dichloromethane) provided 3-fluoro-4-(1-hydroxycyclopentyl) benzoic acid (400 mg, 13%) as a white solid. ESI-MS m/z calc. 224.1. Found 225.3 (M+1)⁺; Retention time: 1.16 minutes (3 min run). ¹H NMR (400 MHz, DMSO-$d_6$) δ 13.12 (s, 1H), 7.80-7.70 (m, 2H), 7.60-7.51 (m, 1H), 5.13 (s, 1H), 2.08-1.95 (m, 2H), 1.95-1.81 (m, 4H), 1.81-1.67 (m, 2H).

Preparation of 4-(1-hydroxycyclopentyl)benzoic acid

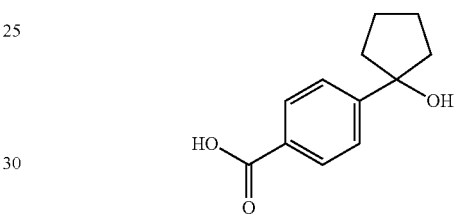

A solution of 4-bromobenzoic acid (4.02 g, 20.0 mmol) in tetrahydrofuran (100 mL) was purged with argon for 5 min. n-Butyllithium (16.0 mL of 2.5 M in hexanes, 40 mmol) was added dropwise at −78° C., resulting in a yellow thick syrup. The mixture was stirred at −78° C. for 30 min. Cyclopentanone (3.89 mL, 44.0 mmol) was added dropwise. The reaction was quenched immediately with saturated $NH_4Cl$ and allowed to warm to room temperature. The mixture was acidified with 1 N HCl to pH ~3 and extracted with ethyl acetate (3×50 mL). The combined organic layers were washed with brine, dried over $MgSO_4$ and concentrated in vacuo. The solid residue was suspended in hexanes, filtered, and the solid washed with additional hexanes. The solid was re-suspended in dichloromethane followed by hexanes. The resulting precipitate was filtered, washed with hexane and air dried to yield 4-(1-hydroxycyclopentyl)benzoic acid (1.25 g, 30%) as a white solid. ¹H NMR (400 MHz, DMSO-$d_6$) δ 12.78 (s, 1H), 7.88 (d, J=8.5 Hz, 2H), 7.58 (d, J=8.5 Hz, 2H), 4.93 (s, 1H), 1.93-1.71 (m, 8H).

Preparation of 4-(1-hydroxycyclohexyl)benzoic acid

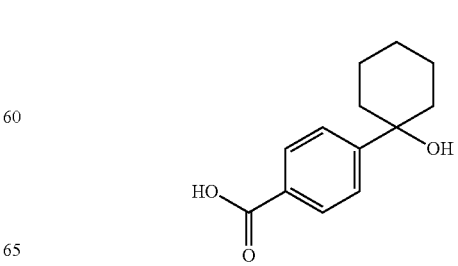

To a solution of 4-bromobenzoic acid (3.00 g, 14.9 mmol) in tetrahydrofuran (54 mL) at −78° C. was added n-butyllithium (19.1 mL of 1.6 M in hexanes, 30.6 mmol) dropwise while maintaining the internal temperature below −65° C. The mixture was stirred at −78° C. for 30 min. Cyclohexanone (1.55 mL, 14.9 mmol) was added dropwise while maintaining the reaction temperature below −65° C. The mixture was stirred at −78° C. for 10 min then allowed to warm to room temperature and stirred for 2 h. The reaction mixture was quenched with saturated NH₄Cl (50 mL) and 1N HCl (25 mL). The mixture was extracted with ethyl acetate (3×100 mL). The combined organics were dried over Na₂SO₄, filtered and concentrated in vacuo. The residue was stirred with 1:1 dichloromethane/hexane (20 mL) to provide a white solid, which was filtered and discarded. The filtrate was concentrated in vacuo and purified by silica gel chromatography (0-5% methanol/dichloromethane) to provide an off-white solid. The solid was stirred with hexane, filtered, and dried to provide 4-(1-hydroxycyclohexyl)benzoic acid (375 mg, 11%). ESI-MS m/z calc. 220.1. Found 221.3 (M+1)⁺; Retention time: 1.18 minutes (3 min run). ¹H NMR (400 MHz, DMSO-d₆) δ 12.77 (s, 1H), 7.88 (d, J=8.3 Hz, 2H), 7.60 (d, J=8.5 Hz, 2H), 4.84 (s, 1H), 1.81-1.46 (m, 9H), 1.35-1.17 (m, 1H).

Preparation of 4-(3-hydroxypentan-3-yl)-3-methylbenzoic acid

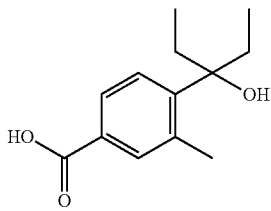 [SMILES: CCC(O)(CC)c1ccc(C(=O)O)cc1C]

4-Bromo-3-methyl-benzoic acid (3.00 g, 14.0 mmol) was dissolved in tetrahydrofuran (60 mL) and cooled to −78° C. n-Butyllithium (19.2 mL of 1.6 M in hexanes, 31 mmol) was added dropwise over 20 min while maintaining the internal temperature below −70° C., resulting in the formation of a yellow precipitate. The mixture was stirred for 30 min at −78° C. Pentan-3-one (1.48 mL, 14.0 mmol) was added dropwise while maintaining the internal temperature below −70° C. The reaction mixture was allowed to stir for 30 min at −78° C. then allowed to warm to room temperature. The reaction mixture was quenched with saturated NH₄Cl (50 mL), stirred for 10 min, then further diluted with 1 N HCl until pH<3. The mixture was then extracted with ethyl acetate (3×100 mL). The combined extracts were dried over Na₂SO₄ and concentrated in vacuo. Silica gel chromatography (0-5% methanol/dichloromethane) provided the product as an off-white solid, which was slurried in 1:1 dichloromethane/hexanes and filtered to provide 4-(1-ethyl-1-hydroxy-propyl)-3-methyl-benzoic acid (1.56 g, 50%) as a white solid. ESI-MS m/z calc. 222.1. Found 223.3 (M+1)⁺; Retention time: 1.22 minutes (3 min run). ¹H NMR (400 MHz, DMSO-d₆) δ 12.70 (s, 1H), 7.71-7.64 (m, 2H), 7.58 (d, J=8.1 Hz, 1H), 4.59 (s, 1H), 2.47 (s, 3H), 2.02-1.87 (m, 2H), 1.81-1.66 (m, 2H), 0.64 (t, J=7.4 Hz, 6H).

Preparation of 4-(3-hydroxypentan-3-yl)benzoic acid

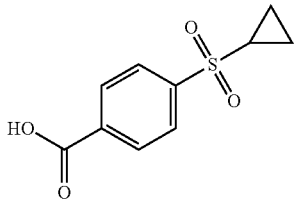 [SMILES: O=C(O)c1ccc(S(=O)(=O)C2CC2)cc1]

Step 1:
To a solution of methyl 4-sulfanylbenzoate (2.00 g, 11.9 mmol) in N,N-dimethylformamide (13 mL) was added potassium carbonate (6.57 g, 47.6 mmol) and 1-bromo-3-chloropropane (2.35 mL, 23.8 mmol). The mixture was heated at 60° C. for 16 h. The reaction mixture was filtered and the solvent removed in vacuo. The material was dissolved in dichloromethane (10 mL) and washed with water (3×10 mL) and a saturated aqueous NH₄Cl (10 mL). The organic layer was dried over Na₂SO₄, filtered and the solvent removed in vacuo. Silica gel chromatography (0-100% dichloromethane/hexane) provided methyl 4-(3-chloropropylsulfanyl)benzoate (1.87 g, 64%) as a colorless viscous liquid. ESI-MS m/z calc. 244.0. Found 245.1 (M+1)⁺; Retention time: 1.83 minutes (3 min run). ¹H NMR (400 MHz, DMSO-d₆) δ 7.88 (d, J=8.5 Hz, 2H), 7.43 (d, J=8.2 Hz, 2H), 3.84 (s, 3H), 3.79-3.61 (m, 2H), 3.18 (t, J=7.2 Hz, 2H), 2.20-1.97 (m, 2H).

Step 2:
Methyl 4-(3-chloropropylsulfanyl)benzoate (1.84 g, 7.52 mmol) was dissolved in methanol (46 mL), followed by the addition of water (4.6 mL) and Oxone (4.62 g, 7.52 mmol). The reaction mixture was stirred at room temperature for 14 h. The reaction mixture was filtered and the solvent removed in vacuo. The resulting solid was dissolved in dichloromethane and washed with water (2×10 mL). The organic layer was dried over Na₂SO₄, filtered and the solvent removed in vacuo to yield methyl 4-(3-chloropropylsulfonyl)benzoate (1.89 g, 91%) as a viscous liquid. ESI-MS m/z calc. 276.0. Found 277.1 (M+1)⁺; Retention time: 1.36 minutes (3 min run). ¹H NMR (400 MHz, DMSO-d₆) δ 8.21 (d, J=8.3 Hz, 2H), 8.07 (d, J=8.3 Hz, 2H), 3.92 (s, 3H), 3.73-3.46 (m, 4H), 2.21-1.79 (m, 2H).

Step 3:
To a solution of methyl 4-(3-chloropropylsulfonyl)benzoate (1.89 g, 6.83 mmol) in 2-methylpropan-2-ol (20 mL) was added potassium tert-butoxide (1.53 g, 13.7 mmol) and the slurry heated at 80° C. for 10 min. Additional 2-methylpropan-2-ol (20 mL) was added to facilitate stirring and the heating continued for 25 min. The reaction mixture was diluted with water (100 mL) and washed with ethyl acetate (3×100 mL). The aqueous layer was acidified with 1N HCl and extracted with ethyl acetate (3×100 mL). The combined organics were dried over Na₂SO₄, filtered and the solvent removed in vacuo to provide 4-cyclopropylsulfonylbenzoic acid (1.22 g, 79%) as a beige solid. ESI-MS m/z calc. 226.0. Found 227.3 (M+1)⁺; Retention time: 0.86 minutes (3 min run).

Preparation of (4-isopropoxy-3-methyl-phenyl)-[10-phenyl-8-(2,2,2-trifluoroethyl)-11-oxa-3,8-diazaspiro[5.5]undecan-3-yl]methanone

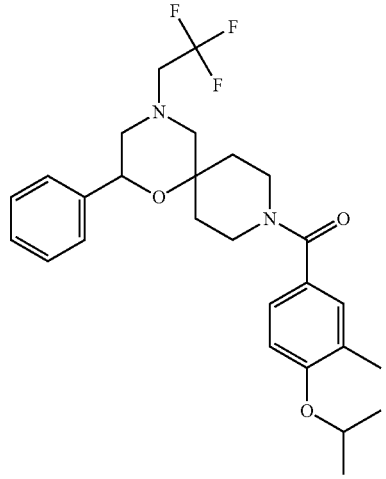 [SMILES: Cc1cc(C(=O)N2CCC3(CC2)CN(CC(F)(F)F)CC(c2ccccc2)O3)ccc1OC(C)C]

To 10-phenyl-8-(2,2,2-trifluoroethyl)-11-oxa-3,8-diazaspiro[5.5]undecane (hydrochloride salt) (150 mg, 0.39 mmol) and 4-isopropoxy-3-methyl-benzoic acid (75 mg, 0.39 mmol) in DMF (1 mL) was added at room temperature O—(7-azabenzotriazol-1-yl)-N,N,N',N'-tetramethyluronium hexafluorophosphate (162 mg, 0.43 mmol) and diisopropylethylamine (337 µL, 1.94 mmol) and reaction mixture was stirred at room temperature for 30 minutes. The reaction was diluted with ethyl acetate and washed with 1M NaOH and then brine solution. The organic layer was separated, dried over $MgSO_4$, filtered and concentrated in vacuo. The residue was purified by silica gel column chromatography using 10-60% EtOAc/hexane to give the desired compound as a white foam (147 mg, 73%) ESI-MS m/z calc. 490.2. Found 491.4 $(M+1)^+$; Retention time: 2.42 minutes (3 min run).

The following compounds were made using Method A as described above:

| Names | Acid names | Amine Names |
|---|---|---|
| (3-chloro-4-isopropoxy-phenyl)-[10-phenyl-8-(2,2,2-trifluoroethyl)-11-oxa-3,8-diazaspiro[5.5]undecan-3-yl]methanone | 3-chloro-4-isopropoxy-benzoic acid | 10-phenyl-8-(2,2,2-trifluoroethyl)-11-oxa-3,8-diazaspiro[5.5]undecane |
| (4-isopropoxy-3-methyl-phenyl)-[10-phenyl-8-(2,2,2-trifluoroethyl)-11-oxa-3,8-diazaspiro[5.5]undecan-3-yl]methanone | 4-isopropoxy-3-methyl-benzoic acid | 10-phenyl-8-(2,2,2-trifluoroethyl)-11-oxa-3,8-diazaspiro[5.5]undecane |
| (3-fluoro-4-isopropoxy-phenyl)-[10-phenyl-8-(2,2,2-trifluoroethyl)-11-oxa-3,8-diazaspiro[5.5]undecan-3-yl]methanone | 3-fluoro-4-isopropoxy-benzoic acid | 10-phenyl-8-(2,2,2-trifluoroethyl)-11-oxa-3,8-diazaspiro[5.5]undecane |
| [4-(2-methoxy-2-methyl-propoxy)phenyl]-[10-phenyl-8-(2,2,2-trifluoroethyl)-11-oxa-3,8-diazaspiro[5.5]undecan-3-yl]methanone | 4-(2-methoxy-2-methyl-propoxy)benzoic acid | 10-phenyl-8-(2,2,2-trifluoroethyl)-11-oxa-3,8-diazaspiro[5.5]undecane |
| (4-isopropoxy-3-methoxy-phenyl)-[10-phenyl-8-(2,2,2-trifluoroethyl)-11-oxa-3,8-diazaspiro[5.5]undecan-3-yl]methanone | 4-isopropoxy-3-methoxy-benzoic acid | 10-phenyl-8-(2,2,2-trifluoroethyl)-11-oxa-3,8-diazaspiro[5.5]undecane |
| (5-isopropoxy-6-methyl-2-pyridyl)-[10-phenyl-8-(2,2,2-trifluoroethyl)-11-oxa-3,8-diazaspiro[5.5]undecan-3-yl]methanone | 5-isopropoxy-6-methyl-pyridine-2-carboxylic acid | 10-phenyl-8-(2,2,2-trifluoroethyl)-11-oxa-3,8-diazaspiro[5.5]undecane |
| (4-isobutylsulfonylphenyl)-[10-phenyl-8-(2,2,2-trifluoroethyl)-11-oxa-3,8-diazaspiro[5.5]undecan-3-yl]methanone | 4-isobutylsulfonylbenzoic acid | 10-phenyl-8-(2,2,2-trifluoroethyl)-11-oxa-3,8-diazaspiro[5.5]undecane |
| [4-(2-hydroxy-2-methyl-propoxy)-3-methyl-phenyl]-[10-phenyl-8-(2,2,2-trifluoroethyl)-11-oxa-3,8-diazaspiro[5.5]undecan-3-yl]methanone | 4-(2-hydroxy-2-methyl-propoxy)-3-methyl-benzoic acid | 10-phenyl-8-(2,2,2-trifluoroethyl)-11-oxa-3,8-diazaspiro[5.5]undecane |
| (4-isopropylsulfonyl-3-methyl-phenyl)-[10-phenyl-8-(2,2,2-trifluoroethyl)-11-oxa-3,8-diazaspiro[5.5]undecan-3-yl]methanone | 4-isopropylsulfonyl-3-methyl-benzoic acid | 10-phenyl-8-(2,2,2-trifluoroethyl)-11-oxa-3,8-diazaspiro[5.5]undecane |
| (3-methyl-4-morpholino-phenyl)-[10-phenyl-8-(2,2,2-trifluoroethyl)-11-oxa-3,8-diazaspiro[5.5]undecan-3-yl]methanone | 3-methyl-4-morpholino-benzoic acid | 10-phenyl-8-(2,2,2-trifluoroethyl)-11-oxa-3,8-diazaspiro[5.5]undecane |

| Names | Acid names | Amine Names |
|---|---|---|
| (5-isopropoxy-2-pyridyl)-[10-phenyl-8-(2,2,2-trifluoroethyl)-11-oxa-3,8-diazaspiro[5.5]undecan-3-yl]methanone | 5-isopropoxypyridine-2-carboxylic acid | 10-phenyl-8-(2,2,2-trifluoroethyl)-11-oxa-3,8-diazaspiro[5.5]undecane |
| (2-fluoro-4-isopropoxy-phenyl)-[10-phenyl-8-(2,2,2-trifluoroethyl)-11-oxa-3,8-diazaspiro[5.5]undecan-3-yl]methanone | 2-fluoro-4-isopropoxy-benzoic acid | 10-phenyl-8-(2,2,2-trifluoroethyl)-11-oxa-3,8-diazaspiro[5.5]undecane |
| [3-methyl-4-(oxetan-3-yloxy)phenyl]-[10-phenyl-8-(2,2,2-trifluoroethyl)-11-oxa-3,8-diazaspiro[5.5]undecan-3-yl]methanone | 3-methyl-4-(oxetan-3-yloxy)benzoic acid | 10-phenyl-8-(2,2,2-trifluoroethyl)-11-oxa-3,8-diazaspiro[5.5]undecane |
| [3-methoxy-4-(2-methoxyethoxy)phenyl]-[10-phenyl-8-(2,2,2-trifluoroethyl)-11-oxa-3,8-diazaspiro[5.5]undecan-3-yl]methanone | 3-methoxy-4-(2-methoxyethoxy)benzoic acid | 10-phenyl-8-(2,2,2-trifluoroethyl)-11-oxa-3,8-diazaspiro[5.5]undecane |
| [3-(hydroxymethyl)-4-isopropoxy-phenyl]-[10-phenyl-8-(2,2,2-trifluoroethyl)-11-oxa-3,8-diazaspiro[5.5]undecan-3-yl]methanone | 3-(hydroxymethyl)-4-isopropoxy-benzoic acid | 10-phenyl-8-(2,2,2-trifluoroethyl)-11-oxa-3,8-diazaspiro[5.5]undecane |
| (4-isopropoxyphenyl)-[10-phenyl-8-(2,2,2-trifluoroethyl)-11-oxa-3,8-diazaspiro[5.5]undecan-3-yl]methanone | 4-isopropoxybenzoic acid | 10-phenyl-8-(2,2,2-trifluoroethyl)-11-oxa-3,8-diazaspiro[5.5]undecane |
| (4-ethylsulfonyl-3-methyl-phenyl)-[10-phenyl-8-(2,2,2-trifluoroethyl)-11-oxa-3,8-diazaspiro[5.5]undecan-3-yl]methanone | 4-ethylsulfonyl-3-methyl-benzoic acid | 10-phenyl-8-(2,2,2-trifluoroethyl)-11-oxa-3,8-diazaspiro[5.5]undecane |
| (4-tert-butylsulfonylphenyl)-[10-phenyl-8-(2,2,2-trifluoroethyl)-11-oxa-3,8-diazaspiro[5.5]undecan-3-yl]methanone | 4-tert-butylsulfonylbenzoic acid | 10-phenyl-8-(2,2,2-trifluoroethyl)-11-oxa-3,8-diazaspiro[5.5]undecane |
| [4-(1-hydroxy-1-methyl-ethyl)-3-methyl-phenyl]-[10-phenyl-8-(2,2,2-trifluoroethyl)-11-oxa-3,8-diazaspiro[5.5]undecan-3-yl]methanone | 4-(1-hydroxy-1-methyl-ethyl)-3-methyl-benzoic acid | 10-phenyl-8-(2,2,2-trifluoroethyl)-11-oxa-3,8-diazaspiro[5.5]undecane |
| (4-tert-butoxy-3-methoxy-phenyl)-[10-phenyl-8-(2,2,2-trifluoroethyl)-11-oxa-3,8-diazaspiro[5.5]undecan-3-yl]methanone | 4-tert-butoxy-3-methoxy-benzoic acid | 10-phenyl-8-(2,2,2-trifluoroethyl)-11-oxa-3,8-diazaspiro[5.5]undecane |
| (3-fluoro-4-isopropoxy-5-methoxy-phenyl)-[10-phenyl-8-(2,2,2-trifluoroethyl)-11-oxa-3,8-diazaspiro[5.5]undecan-3-yl]methanone | 3-fluoro-4-isopropoxy-5-methoxy-benzoic acid | 10-phenyl-8-(2,2,2-trifluoroethyl)-11-oxa-3,8-diazaspiro[5.5]undecane |

| Names | Acid names | Amine Names |
|---|---|---|
| N-cyclopropyl-4-[10-phenyl-8-(2,2,2-trifluoroethyl)-11-oxa-3,8-diazaspiro[5.5]undecane-3-carbonyl]benzenesulfonamide | 4-(cyclopropylsulfamoyl)benzoic acid | 10-phenyl-8-(2,2,2-trifluoroethyl)-11-oxa-3,8-diazaspiro[5.5]undecane |
| [4-(2-hydroxy-2-methyl-propyl)phenyl]-[10-phenyl-8-(2,2,2-trifluoroethyl)-11-oxa-3,8-diazaspiro[5.5]undecan-3-yl]methanone | 4-(2-hydroxy-2-methyl-propyl)benzoic acid | 10-phenyl-8-(2,2,2-trifluoroethyl)-11-oxa-3,8-diazaspiro[5.5]undecane |
| (3-methyl-4-methylsulfonyl-phenyl)-[10-phenyl-8-(2,2,2-trifluoroethyl)-11-oxa-3,8-diazaspiro[5.5]undecan-3-yl]methanone | 3-methyl-4-methylsulfonyl-benzoic acid | 10-phenyl-8-(2,2,2-trifluoroethyl)-11-oxa-3,8-diazaspiro[5.5]undecane |
| [3-methyl-4-(oxetan-3-yl)phenyl]-[10-phenyl-8-(2,2,2-trifluoroethyl)-11-oxa-3,8-diazaspiro[5.5]undecan-3-yl]methanone | 3-methyl-4-(oxetan-3-yl)benzoic acid | 10-phenyl-8-(2,2,2-trifluoroethyl)-11-oxa-3,8-diazaspiro[5.5]undecane |
| (2-methyl-1,3-benzoxazol-7-yl)-[10-phenyl-8-(2,2,2-trifluoroethyl)-11-oxa-3,8-diazaspiro[5.5]undecan-3-yl]methanone | 2-methyl-1,3-benzoxazole-7-carboxylic acid | 10-phenyl-8-(2,2,2-trifluoroethyl)-11-oxa-3,8-diazaspiro[5.5]undecane |
| [4-(1-hydroxy-1-methyl-ethyl)phenyl]-[10-phenyl-8-(2,2,2-trifluoroethyl)-11-oxa-3,8-diazaspiro[5.5]undecan-3-yl]methanone | 4-(1-hydroxy-1-methyl-ethyl)benzoic acid | 10-phenyl-8-(2,2,2-trifluoroethyl)-11-oxa-3,8-diazaspiro[5.5]undecane |
| [3-fluoro-4-(1-hydroxy-1-methyl-ethyl)phenyl]-[10-phenyl-8-(2,2,2-trifluoroethyl)-11-oxa-3,8-diazaspiro[5.5]undecan-3-yl]methanone | 3-fluoro-4-(1-hydroxy-1-methyl-ethyl)benzoic acid | 10-phenyl-8-(2,2,2-trifluoroethyl)-11-oxa-3,8-diazaspiro[5.5]undecane |
| N,N-diethyl-2-fluoro-4-[10-phenyl-8-(2,2,2-trifluoroethyl)-11-oxa-3,8-diazaspiro[5.5]undecane-3-carbonyl]benzamide | 4-(diethylcarbamoyl)-3-fluoro-benzoic acid | 10-phenyl-8-(2,2,2-trifluoroethyl)-11-oxa-3,8-diazaspiro[5.5]undecane |
| (5-tert-butoxy-2-pyridyl)-[10-phenyl-8-(2,2,2-trifluoroethyl)-11-oxa-3,8-diazaspiro[5.5]undecan-3-yl]methanone | 5-tert-butoxypyridine-2-carboxylic acid | 10-phenyl-8-(2,2,2-trifluoroethyl)-11-oxa-3,8-diazaspiro[5.5]undecane |
| [4-(2-hydroxy-2-methyl-propoxy)phenyl]-[10-phenyl-8-(2,2,2-trifluoroethyl)-11-oxa-3,8-diazaspiro[5.5]undecan-3-yl]methanone | 4-(2-hydroxy-2-methyl-propoxy)benzoic acid | 10-phenyl-8-(2,2,2-trifluoroethyl)-11-oxa-3,8-diazaspiro[5.5]undecane |
| [3-fluoro-4-(2-hydroxy-2-methyl-propyl)phenyl]-[10-phenyl-8-(2,2,2-trifluoroethyl)-11-oxa-3,8-diazaspiro[5.5]undecan-3-yl]methanone | 3-fluoro-4-(2-hydroxy-2-methyl-propyl)benzoic acid | 10-phenyl-8-(2,2,2-trifluoroethyl)-11-oxa-3,8-diazaspiro[5.5]undecane |

| Names | Acid names | Amine Names |
|---|---|---|
| methyl 2-[2-methoxy-4-[10-phenyl-8-(2,2,2-trifluoroethyl)-11-oxa-3,8-diazaspiro[5.5]undecane-3-carbonyl]phenyl]-2-methyl-propanoate | 3-methoxy-4-(2-methoxy-1,1-dimethyl-2-oxo-ethyl)benzoic acid | 10-phenyl-8-(2,2,2-trifluoroethyl)-11-oxa-3,8-diazaspiro[5.5]undecane |
| [3-fluoro-4-(3-methoxyprop-1-ynyl)phenyl]-[10-phenyl-8-(2,2,2-trifluoroethyl)-11-oxa-3,8-diazaspiro[5.5]undecan-3-yl]methanone | 3-fluoro-4-(3-methoxyprop-1-ynyl)benzoic acid | 10-phenyl-8-(2,2,2-trifluoroethyl)-11-oxa-3,8-diazaspiro[5.5]undecane |
| (3-chlorophenyl)-[10-phenyl-8-(2,2,2-trifluoroethyl)-11-oxa-3,8-diazaspiro[5.5]undecan-3-yl]methanone | 3-chlorobenzoic acid | 10-phenyl-8-(2,2,2-trifluoroethyl)-11-oxa-3,8-diazaspiro[5.5]undecane |
| [4-(3-hydroxyoxetan-3-yl)phenyl]-[10-phenyl-8-(2,2,2-trifluoroethyl)-11-oxa-3,8-diazaspiro[5.5]undecan-3-yl]methanone | 4-(3-hydroxyoxetan-3-yl)benzoic acid | 10-phenyl-8-(2,2,2-trifluoroethyl)-11-oxa-3,8-diazaspiro[5.5]undecane |
| (2-methyl-4-methylsulfonyl-phenyl)-[10-phenyl-8-(2,2,2-trifluoroethyl)-11-oxa-3,8-diazaspiro[5.5]undecan-3-yl]methanone | 2-methyl-4-methylsulfonyl-benzoic acid | 10-phenyl-8-(2,2,2-trifluoroethyl)-11-oxa-3,8-diazaspiro[5.5]undecane |
| 2-methyl-6-[10-phenyl-8-(2,2,2-trifluoroethyl)-11-oxa-3,8-diazaspiro[5.5]undecane-3-carbonyl]pyridine-3-carbonitrile | 5-cyano-6-methyl-pyridine-2-carboxylic acid | 10-phenyl-8-(2,2,2-trifluoroethyl)-11-oxa-3,8-diazaspiro[5.5]undecane |
| (3-methoxy-4-methylsulfonyl-phenyl)-[10-phenyl-8-(2,2,2-trifluoroethyl)-11-oxa-3,8-diazaspiro[5.5]undecan-3-yl]methanone | 3-methoxy-4-methylsulfonyl-benzoic acid | 10-phenyl-8-(2,2,2-trifluoroethyl)-11-oxa-3,8-diazaspiro[5.5]undecane |
| (3-fluoro-5-methoxy-phenyl)-[10-phenyl-8-(2,2,2-trifluoroethyl)-11-oxa-3,8-diazaspiro[5.5]undecan-3-yl]methanone | 3-fluoro-5-methoxy-benzoic acid | 10-phenyl-8-(2,2,2-trifluoroethyl)-11-oxa-3,8-diazaspiro[5.5]undecane |
| [2-(difluoromethoxy)phenyl]-[10-phenyl-8-(2,2,2-trifluoroethyl)-11-oxa-3,8-diazaspiro[5.5]undecan-3-yl]methanone | 2-(difluoromethoxy)benzoic acid | 10-phenyl-8-(2,2,2-trifluoroethyl)-11-oxa-3,8-diazaspiro[5.5]undecane |
| [2-(difluoromethoxy)-3-fluoro-phenyl]-[10-phenyl-8-(2,2,2-trifluoroethyl)-11-oxa-3,8-diazaspiro[5.5]undecan-3-yl]methanone | 2-(difluoromethoxy)-3-fluoro-benzoic acid | 10-phenyl-8-(2,2,2-trifluoroethyl)-11-oxa-3,8-diazaspiro[5.5]undecane |
| (3,5-dichlorophenyl)-[10-phenyl-8-(2,2,2-trifluoroethyl)-11-oxa-3,8-diazaspiro[5.5]undecan-3-yl]methanone | 3,5-dichlorobenzoic acid | 10-phenyl-8-(2,2,2-trifluoroethyl)-11-oxa-3,8-diazaspiro[5.5]undecane |

| Names | Acid names | Amine Names |
| --- | --- | --- |
| (3-chloro-4-isopropoxy-phenyl)-[8-(2,2-difluoroethyl)-10-phenyl-11-oxa-3,8-diazaspiro[5.5]undecan-3-yl]methanone | 3-chloro-4-isopropoxy-benzoic acid | 8-(2,2-difluoroethyl)-10-phenyl-11-oxa-3,8-diazaspiro[5.5]undecane |
| [8-(2,2-difluoroethyl)-10-phenyl-11-oxa-3,8-diazaspiro[5.5]undecan-3-yl]-(3-fluoro-4-isopropoxy-phenyl)methanone | 3-fluoro-4-isopropoxy-benzoic acid | 8-(2,2-difluoroethyl)-10-phenyl-11-oxa-3,8-diazaspiro[5.5]undecane |
| [8-(2,2-difluoroethyl)-10-phenyl-11-oxa-3,8-diazaspiro[5.5]undecan-3-yl]-(4-isopropoxy-3-methyl-phenyl)methanone | 4-isopropoxy-3-methyl-benzoic acid | 8-(2,2-difluoroethyl)-10-phenyl-11-oxa-3,8-diazaspiro[5.5]undecane |
| [8-(2,2-difluoroethyl)-10-phenyl-11-oxa-3,8-diazaspiro[5.5]undecan-3-yl]-(5-isopropoxy-6-methyl-2-pyridyl)methanone | 5-isopropoxy-6-methyl-pyridine-2-carboxylic acid | 8-(2,2-difluoroethyl)-10-phenyl-11-oxa-3,8-diazaspiro[5.5]undecane |
| [8-(2,2-difluoroethyl)-10-phenyl-11-oxa-3,8-diazaspiro[5.5]undecan-3-yl]-(4-isopropoxy-3-methoxy-phenyl)methanone | 4-isopropoxy-3-methoxy-benzoic acid | 8-(2,2-difluoroethyl)-10-phenyl-11-oxa-3,8-diazaspiro[5.5]undecane |
| [8-(2,2-difluoroethyl)-10-phenyl-11-oxa-3,8-diazaspiro[5.5]undecan-3-yl]-[4-(1-hydroxy-1-methyl-ethyl)-3-methoxy-phenyl]methanone | 4-(1-hydroxy-1-methyl-ethyl)-3-methoxy-benzoic acid | 8-(2,2-difluoroethyl)-10-phenyl-11-oxa-3,8-diazaspiro[5.5]undecane |
| [8-(2,2-difluoroethyl)-10-phenyl-11-oxa-3,8-diazaspiro[5.5]undecan-3-yl]-[4-(1-hydroxy-1-methyl-ethyl)-3-methyl-phenyl]methanone | 4-(1-hydroxy-1-methyl-ethyl)-3-methyl-benzoic acid | 8-(2,2-difluoroethyl)-10-phenyl-11-oxa-3,8-diazaspiro[5.5]undecane |
| [8-(2,2-difluoroethyl)-10-(2-pyridyl)-11-oxa-3,8-diazaspiro[5.5]undecan-3-yl]-(4-pyrrolidin-1-ylsulfonylphenyl)methanone | 4-pyrrolidin-1-ylsulfonylbenzoic acid | 8-(2,2-difluoroethyl)-10-(2-pyridyl)-11-oxa-3,8-diazaspiro[5.5]undecane |
| [8-(2,2-difluoroethyl)-10-phenyl-11-oxa-3,8-diazaspiro[5.5]undecan-3-yl]-[4-(1-hydroxy-1-methyl-ethyl)phenyl]methanone | 4-(1-hydroxy-1-methyl-ethyl)benzoic acid | 8-(2,2-difluoroethyl)-10-phenyl-11-oxa-3,8-diazaspiro[5.5]undecane |
| [3-ethoxy-4-(hydroxymethyl)phenyl]-(8-ethyl-10-phenyl-11-oxa-3,8-diazaspiro[5.5]undecan-3-yl)methanone | 3-ethoxy-4-(hydroxymethyl)benzoic acid | 8-ethyl-10-phenyl-11-oxa-3,8-diazaspiro[5.5]undecane |
| [8-(2,2-difluoroethyl)-10-phenyl-11-oxa-3,8-diazaspiro[5.5]undecan-3-yl]-(6-methoxy-2-pyridyl)methanone | 6-methoxypyridine-2-carboxylic acid | 8-(2,2-difluoroethyl)-10-phenyl-11-oxa-3,8-diazaspiro[5.5]undecane |
| [8-(2,2-difluoroethyl)-10-(2-pyridyl)-11-oxa-3,8-diazaspiro[5.5]undecan-3-yl]-(4-isopropylsulfonyl-3-methyl-phenyl)methanone | 4-isopropylsulfonyl-3-methyl-benzoic acid | 8-(2,2-difluoroethyl)-10-(2-pyridyl)-11-oxa-3,8-diazaspiro[5.5]undecane |

-continued

| Names | Acid names | Amine Names |
|---|---|---|
| [8-(2,2-difluoroethyl)-10-phenyl-11-oxa-3,8-diazaspiro[5.5]undecan-3-yl]-[5-(trifluoromethyl)-2-pyridyl]methanone | 5-(trifluoromethyl)pyridine-2-carboxylic acid | 8-(2,2-difluoroethyl)-10-phenyl-11-oxa-3,8-diazaspiro[5.5]undecane |
| 6-[8-(2,2-difluoroethyl)-10-phenyl-11-oxa-3,8-diazaspiro[5.5]undecane-3-carbonyl]-2-methyl-pyridine-3-carbonitrile | 5-cyano-6-methyl-pyridine-2-carboxylic acid | 8-(2,2-difluoroethyl)-10-phenyl-11-oxa-3,8-diazaspiro[5.5]undecane |
| [8-(2,2-difluoroethyl)-10-(2-pyridyl)-11-oxa-3,8-diazaspiro[5.5]undecan-3-yl]-(4-isopropoxy-3-methyl-phenyl)methanone | 4-isopropoxy-3-methyl-benzoic acid | 8-(2,2-difluoroethyl)-10-(2-pyridyl)-11-oxa-3,8-diazaspiro[5.5]undecane |
| [8-(2,2-difluoroethyl)-10-(2-pyridyl)-11-oxa-3,8-diazaspiro[5.5]undecan-3-yl]-(3-fluoro-4-isopropoxy-phenyl)methanone | 3-fluoro-4-isopropoxy-benzoic acid | 8-(2,2-difluoroethyl)-10-(2-pyridyl)-11-oxa-3,8-diazaspiro[5.5]undecane |
| (3-chloro-4-isopropoxy-phenyl)-[8-(2,2-difluoroethyl)-10-(2-pyridyl)-11-oxa-3,8-diazaspiro[5.5]undecan-3-yl]methanone | 3-chloro-4-isopropoxy-benzoic acid | 8-(2,2-difluoroethyl)-10-(2-pyridyl)-11-oxa-3,8-diazaspiro[5.5]undecane |
| [8-(2,2-difluoroethyl)-10-(2-pyridyl)-11-oxa-3,8-diazaspiro[5.5]undecan-3-yl]-(4-isopropoxy-3-methoxy-phenyl)methanone | 4-isopropoxy-3-methoxy-benzoic acid | 8-(2,2-difluoroethyl)-10-(2-pyridyl)-11-oxa-3,8-diazaspiro[5.5]undecane |
| [8-(2,2-difluoroethyl)-10-(2-pyridyl)-11-oxa-3,8-diazaspiro[5.5]undecan-3-yl]-(3-fluoro-4-isopropoxy-5-methoxy-phenyl)methanone | 3-fluoro-4-isopropoxy-5-methoxy-benzoic acid | 8-(2,2-difluoroethyl)-10-(2-pyridyl)-11-oxa-3,8-diazaspiro[5.5]undecane |
| [8-(2,2-difluoroethyl)-10-(2-pyridyl)-11-oxa-3,8-diazaspiro[5.5]undecan-3-yl]-[3-fluoro-4-(1-hydroxy-1-methyl-ethyl)phenyl]methanone | 3-fluoro-4-(1-hydroxy-1-methyl-ethyl)benzoic acid | 8-(2,2-difluoroethyl)-10-(2-pyridyl)-11-oxa-3,8-diazaspiro[5.5]undecane |
| [8-(2,2-difluoroethyl)-10-(2-pyridyl)-11-oxa-3,8-diazaspiro[5.5]undecan-3-yl]-[4-(2-hydroxyethoxy)-3-methyl-phenyl]methanone | 4-(2-hydroxyethoxy)-3-methyl-benzoic acid | 8-(2,2-difluoroethyl)-10-(2-pyridyl)-11-oxa-3,8-diazaspiro[5.5]undecane |
| [8-(2,2-difluoroethyl)-10-(1H-pyrazol-3-yl)-11-oxa-3,8-diazaspiro[5.5]undecan-3-yl]-(3-fluoro-4-isopropoxy-phenyl)methanone | 3-fluoro-4-isopropoxy-benzoic acid | 8-(2,2-difluoroethyl)-10-(1H-pyrazol-3-yl)-11-oxa-3,8-diazaspiro[5.5]undecane |
| [8-(2,2-difluoroethyl)-10-(1-methylpyrazol-3-yl)-11-oxa-3,8-diazaspiro[5.5]undecan-3-yl]-(4-isopropoxy-3-methyl-phenyl)methanone | 4-isopropoxy-3-methyl-benzoic acid | 8-(2,2-difluoroethyl)-10-(1-methylpyrazol-3-yl)-11-oxa-3,8-diazaspiro[5.5]undecane |
| [8-(2,2-difluoroethyl)-10-(2-methylpyrazol-3-yl)-11-oxa-3,8-diazaspiro[5.5]undecan-3-yl]-(4-isopropoxy-3-methyl-phenyl)methanone | 4-isopropoxy-3-methyl-benzoic acid | 8-(2,2-difluoroethyl)-10-(2-methylpyrazol-3-yl)-11-oxa-3,8-diazaspiro[5.5]undecane |

| Names | Acid names | Amine Names |
|---|---|---|
| [8-(2,2-difluoroethyl)-10-(1H-pyrazol-3-yl)-11-oxa-3,8-diazaspiro[5.5]undecan-3-yl]-(4-isopropoxy-3-methyl-phenyl)methanone | 4-isopropoxy-3-methyl-benzoic acid | 8-(2,2-difluoroethyl)-10-(1H-pyrazol-3-yl)-11-oxa-3,8-diazaspiro[5.5]undecan |
| (4-isopropoxy-3-methyl-phenyl)-[10-(1H-pyrazol-3-yl)-8-(2,2,2-trifluoroethyl)-11-oxa-3,8-diazaspiro[5.5]undecan-3-yl]methanone | 4-isopropoxy-3-methyl-benzoic acid | 10-(1H-pyrazol-3-yl)-8-(2,2,2-trifluoroethyl)-11-oxa-3,8-diazaspiro[5.5]undecane |
| (3-chloro-4-isopropoxy-phenyl)-[10-(1H-pyrazol-3-yl)-8-(2,2,2-trifluoroethyl)-11-oxa-3,8-diazaspiro[5.5]undecan-3-yl]methanone | 3-chloro-4-isopropoxy-benzoic acid | 10-(1H-pyrazol-3-yl)-8-(2,2,2-trifluoroethyl)-11-oxa-3,8-diazaspiro[5.5]undecane |
| [8-(2,2-difluoroethyl)-10-(1-ethylpyrazol-3-yl)-11-oxa-3,8-diazaspiro[5.5]undecan-3-yl]-(4-isopropoxy-3-methyl-phenyl)methanone | 4-isopropoxy-3-methyl-benzoic acid | 8-(2,2-difluoroethyl)-10-(1-ethylpyrazol-3-yl)-11-oxa-3,8-diazaspiro[5.5]undecane |
| [8-(2,2-difluoroethyl)-10-(1H-pyrazol-3-yl)-11-oxa-3,8-diazaspiro[5.5]undecan-3-yl]-(4-isopropoxy-3-methoxy-phenyl)methanone | 4-isopropoxy-3-methoxy-benzoic acid | 8-(2,2-difluoroethyl)-10-(1H-pyrazol-3-yl)-11-oxa-3,8-diazaspiro[5.5]undecane |
| [10-(5-tert-butyloxazol-2-yl)-8-(2,2-difluoroethyl)-11-oxa-3,8-diazaspiro[5.5]undecan-3-yl]-(4-isopropoxy-3-methyl-phenyl)methanone | 4-isopropoxy-3-methyl-benzoic acid | 10-(5-tert-butyloxazol-2-yl)-8-(2,2-difluoroethyl)-11-oxa-3,8-diazaspiro[5.5]undecane |
| [10-(5-tert-butyloxazol-2-yl)-8-(2,2-difluoroethyl)-11-oxa-3,8-diazaspiro[5.5]undecan-3-yl]-(3-fluoro-4-isopropoxy-phenyl)methanone | 3-fluoro-4-isopropoxy-benzoic acid | 10-(5-tert-butyloxazol-2-yl)-8-(2,2-difluoroethyl)-11-oxa-3,8-diazaspiro[5.5]undecane |
| [8-(2,2-difluoroethyl)-10-(4-fluorophenyl)-11-oxa-3,8-diazaspiro[5.5]undecan-3-yl]-(4-isopropoxy-3-methoxy-phenyl)methanone | 4-isopropoxy-3-methoxy-benzoic acid | 8-(2,2-difluoroethyl)-10-(4-fluorophenyl)-11-oxa-3,8-diazaspiro[5.5]undecane |
| [8-(2,2-difluoroethyl)-10-(4-fluorophenyl)-11-oxa-3,8-diazaspiro[5.5]undecan-3-yl]-(4-isopropoxy-3-methyl-phenyl)methanone | 4-isopropoxy-3-methyl-benzoic acid | 8-(2,2-difluoroethyl)-10-(4-fluorophenyl)-11-oxa-3,8-diazaspiro[5.5]undecane |
| (3-chloro-4-isopropoxy-phenyl)-[8-(2,2-difluoroethyl)-10-(4-fluorophenyl)-11-oxa-3,8-diazaspiro[5.5]undecan-3-yl]methanone | 3-chloro-4-isopropoxy-benzoic acid | 8-(2,2-difluoroethyl)-10-(4-fluorophenyl)-11-oxa-3,8-diazaspiro[5.5]undecane |

| Names | Acid names | Amine Names |
|---|---|---|
| [8-(2,2-difluoroethyl)-10-(4-fluorophenyl)-11-oxa-3,8-diazaspiro[5.5]undecan-3-yl]-(3-fluoro-4-isopropoxy-phenyl)methanone | 3-fluoro-4-isopropoxy-benzoic acid | 8-(2,2-difluoroethyl)-10-(4-fluorophenyl)-11-oxa-3,8-diazaspiro[5.5]undecane |
| [8-(2,2-difluoroethyl)-10-(4-fluorophenyl)-11-oxa-3,8-diazaspiro[5.5]undecan-3-yl]-[3-fluoro-4-(1-hydroxy-1-methyl-ethyl)phenyl]methanone | 3-fluoro-4-(1-hydroxy-1-methyl-ethyl)benzoic acid | 8-(2,2-difluoroethyl)-10-(4-fluorophenyl)-11-oxa-3,8-diazaspiro[5.5]undecane |
| [8-(2,2-difluoroethyl)-10-(4-fluorophenyl)-11-oxa-3,8-diazaspiro[5.5]undecan-3-yl]-[4-(2-hydroxy-2-methyl-propoxy)-3-methyl-phenyl]methanone | 4-(2-hydroxy-2-methyl-propoxy)-3-methyl-benzoic acid | 8-(2,2-difluoroethyl)-10-(4-fluorophenyl)-11-oxa-3,8-diazaspiro[5.5]undecane |
| [8-(2,2-difluoroethyl)-10-(4-fluorophenyl)-11-oxa-3,8-diazaspiro[5.5]undecan-3-yl]-(4-isobutylsulfonylphenyl)-methanone | 4-isobutylsulfonylbenzoic acid | 8-(2,2-difluoroethyl)-10-(4-fluorophenyl)-11-oxa-3,8-diazaspiro[5.5]undecane |
| (4-tert-butylsulfonylphenyl)-[8-(2,2-difluoroethyl)-10-(4-fluorophenyl)-11-oxa-3,8-diazaspiro[5.5]undecan-3-yl]methanone | 4-tert-butylsulfonylbenzoic acid | 8-(2,2-difluoroethyl)-10-(4-fluorophenyl)-11-oxa-3,8-diazaspiro[5.5]undecane |
| (4-tert-butoxy-3-methoxy-phenyl)-[8-(2,2-difluoroethyl)-10-(4-fluorophenyl)-11-oxa-3,8-diazaspiro[5.5]undecan-3-yl]methanone | 4-tert-butoxy-3-methoxy-benzoic acid | 8-(2,2-difluoroethyl)-10-(4-fluorophenyl)-11-oxa-3,8-diazaspiro[5.5]undecane |
| N-cyclopropyl-4-[8-(2,2-difluoroethyl)-10-(4-fluorophenyl)-11-oxa-3,8-diazaspiro[5.5]undecane-3-carbonyl]benzene-sulfonamide | 4-(cyclopropylsulfamoyl)benzoic acid | 8-(2,2-difluoroethyl)-10-(4-fluorophenyl)-11-oxa-3,8-diazaspiro[5.5]undecane |
| [8-(2,2-difluoroethyl)-10-(4-fluorophenyl)-11-oxa-3,8-diazaspiro[5.5]undecan-3-yl]-(4-tetrahydrofuran-3-ylsulfonylphenyl)-methanone | 4-tetrahydrofuran-3-ylsulfonylbenzoic acid | 8-(2,2-difluoroethyl)-10-(4-fluorophenyl)-11-oxa-3,8-diazaspiro[5.5]undecane |
| [8-(2,2-difluoroethyl)-10-(4-fluorophenyl)-11-oxa-3,8-diazaspiro[5.5]undecan-3-yl]-[3-(hydroxymethyl)-4-isopropoxy-phenyl]methanone | 3-(hydroxymethyl)-4-isopropoxy-benzoic acid | 8-(2,2-difluoroethyl)-10-(4-fluorophenyl)-11-oxa-3,8-diazaspiro[5.5]undecane |
| [8-(2,2-difluoroethyl)-10-(4-fluorophenyl)-11-oxa-3,8-diazaspiro[5.5]undecan-3-yl]-(3-methyl-4-methylsulfonyl-phenyl)methanone | 3-methyl-4-methylsulfonyl-benzoic acid | 8-(2,2-difluoroethyl)-10-(4-fluorophenyl)-11-oxa-3,8-diazaspiro[5.5]undecane |

-continued

| Names | Acid names | Amine Names |
|---|---|---|
| [8-(2,2-difluoroethyl)-10-(4-fluorophenyl)-11-oxa-3,8-diazaspiro[5.5]undecan-3-yl]-[4-(3-hydroxypropoxy)-3-methyl-phenyl]methanone | 4-(3-hydroxypropoxy)-3-methyl-benzoic acid | 8-(2,2-difluoroethyl)-10-(4-fluorophenyl)-11-oxa-3,8-diazaspiro[5.5]undecane |
| [8-(2,2-difluoroethyl)-10-(1-methylpyrazol-3-yl)-11-oxa-3,8-diazaspiro[5.5]undecan-3-yl]-(3-fluoro-4-isopropoxy-phenyl)methanone | 3-fluoro-4-isopropoxy-benzoic acid | 8-(2,2-difluoroethyl)-10-(1-methylpyrazol-3-yl)-11-oxa-3,8-diazaspiro[5.5]undecane |
| (3-fluoro-4-isopropoxy-phenyl)-[10-(5-methyl-1H-pyrazol-3-yl)-8-(2,2,2-trifluoroethyl)-11-oxa-3,8-diazaspiro[5.5]undecan-3-yl]methanone | 3-fluoro-4-isopropoxy-benzoic acid | 10-(5-methyl-1H-pyrazol-3-yl)-8-(2,2,2-trifluoroethyl)-11-oxa-3,8-diazaspiro[5.5]undecane |
| (4-isopropoxy-3-methyl-phenyl)-[10-(5-methyl-1H-pyrazol-3-yl)-8-(2,2,2-trifluoroethyl)-11-oxa-3,8-diazaspiro[5.5]undecan-3-yl]methanone | 4-isopropoxy-3-methyl-benzoic acid | 10-(5-methyl-1H-pyrazol-3-yl)-8-(2,2,2-trifluoroethyl)-11-oxa-3,8-diazaspiro[5.5]undecane |
| (3-fluoro-4-isopropoxy-phenyl)-[10-(1H-pyrazol-3-yl)-8-(2,2,2-trifluoroethyl)-11-oxa-3,8-diazaspiro[5.5]undecan-3-yl]methanone | 3-fluoro-4-isopropoxy-benzoic acid | 10-(1H-pyrazol-3-yl)-8-(2,2,2-trifluoroethyl)-11-oxa-3,8-diazaspiro[5.5]undecane |
| (8-isobutyl-10-phenyl-11-oxa-3,8-diazaspiro[5.5]undecan-3-yl)-(4-isopropoxy-3-methyl-phenyl)methanone | 4-isopropoxy-3-methyl-benzoic acid | 8-isobutyl-10-phenyl-11-oxa-3,8-diazaspiro[5.5]undecane |
| (8-ethyl-10-phenyl-11-oxa-3,8-diazaspiro[5.5]undecan-3-yl)-(6-isopropoxy-3-pyridyl)methanone | 6-isopropoxypyridine-3-carboxylic acid | 8-ethyl-10-phenyl-11-oxa-3,8-diazaspiro[5.5]undecane |
| (8-ethyl-10-phenyl-11-oxa-3,8-diazaspiro[5.5]undecan-3-yl)-[4-(1-hydroxy-1-methyl-ethyl)phenyl]methanone | 4-(1-hydroxy-1-methyl-ethyl)benzoic acid | 8-ethyl-10-phenyl-11-oxa-3,8-diazaspiro[5.5]undecane |
| [4-ethoxy-3-(hydroxymethyl)phenyl]-(8-ethyl-10-phenyl-11-oxa-3,8-diazaspiro[5.5]undecan-3-yl)methanone | 4-ethoxy-3-(hydroxymethyl)benzoic acid | 8-ethyl-10-phenyl-11-oxa-3,8-diazaspiro[5.5]undecane |
| (8-ethyl-10-phenyl-11-oxa-3,8-diazaspiro[5.5]undecan-3-yl)-(4-isopropoxy-3-methyl-phenyl)methanone | 4-isopropoxy-3-methyl-benzoic acid | 8-ethyl-10-phenyl-11-oxa-3,8-diazaspiro[5.5]undecane |
| (8-ethyl-10-phenyl-11-oxa-3,8-diazaspiro[5.5]undecan-3-yl)-(4-isopropoxy-3-methoxy-phenyl)methanone | 4-isopropoxy-3-methoxy-benzoic acid | 8-ethyl-10-phenyl-11-oxa-3,8-diazaspiro[5.5]undecane |
| (8-ethyl-10-phenyl-11-oxa-3,8-diazaspiro[5.5]undecan-3-yl)-(3-fluoro-4-isopropoxy-phenyl)methanone | 3-fluoro-4-isopropoxy-benzoic acid | 8-ethyl-10-phenyl-11-oxa-3,8-diazaspiro[5.5]undecane |

| Names | Acid names | Amine Names |
|---|---|---|
| (8-ethyl-10-phenyl-11-oxa-3,8-diazaspiro[5.5]undecan-3-yl)-[3-(hydroxymethyl)-4-isopropoxy-phenyl]methanone | 3-(hydroxymethyl)-4-isopropoxy-benzoic acid | 8-ethyl-10-phenyl-11-oxa-3,8-diazaspiro[5.5]undecane |
| N-cyclopropyl-4-(8-ethyl-10-phenyl-11-oxa-3,8-diazaspiro[5.5]undecane-3-carbonyl)benzene-sulfonamide | 4-(cyclopropylsulfamoyl)benzoic acid | 8-ethyl-10-phenyl-11-oxa-3,8-diazaspiro[5.5]undecane |
| [8-(2,2-difluoroethyl)-10-oxazol-2-yl-11-oxa-3,8-diazaspiro[5.5]undecan-3-yl]-(4-isopropoxy-3-methyl-phenyl)methanone | 4-isopropoxy-3-methyl-benzoic acid | 8-(2,2-difluoroethyl)-10-oxazol-2-yl-11-oxa-3,8-diazaspiro[5.5]undecane |
| [8-(2,2-difluoroethyl)-10-(6-methyl-2-pyridyl)-11-oxa-3,8-diazaspiro[5.5]undecan-3-yl]-[3-fluoro-4-(1-hydroxy-1-methyl-ethyl)phenyl]methanone | 3-fluoro-4-(1-hydroxy-1-methyl-ethyl)benzoic acid | 8-(2,2-difluoroethyl)-10-(6-methyl-2-pyridyl)-11-oxa-3,8-diazaspiro[5.5]undecane |
| [8-(2,2-difluoroethyl)-10-(6-methyl-2-pyridyl)-11-oxa-3,8-diazaspiro[5.5]undecan-3-yl]-(4-isopropoxy-3-methyl-phenyl)methanone | 4-isopropoxy-3-methyl-benzoic acid | 8-(2,2-difluoroethyl)-10-(6-methyl-2-pyridyl)-11-oxa-3,8-diazaspiro[5.5]undecane |
| (3-chloro-4-isopropoxy-phenyl)-[8-(2,2-difluoroethyl)-10-(6-methyl-2-pyridyl)-11-oxa-3,8-diazaspiro[5.5]undecan-3-yl]methanone | 3-chloro-4-isopropoxy-benzoic acid | 8-(2,2-difluoroethyl)-10-(6-methyl-2-pyridyl)-11-oxa-3,8-diazaspiro[5.5]undecane |
| [8-(2,2-difluoroethyl)-10-(6-methyl-2-pyridyl)-11-oxa-3,8-diazaspiro[5.5]undecan-3-yl]-(3-fluoro-4-isopropoxy-phenyl)methanone | 3-fluoro-4-isopropoxy-benzoic acid | 8-(2,2-difluoroethyl)-10-(6-methyl-2-pyridyl)-11-oxa-3,8-diazaspiro[5.5]undecane |
| [8-(2,2-difluoroethyl)-10-(6-methyl-2-pyridyl)-11-oxa-3,8-diazaspiro[5.5]undecan-3-yl]-(4-isopropoxy-3-methoxy-phenyl)methanone | 4-isopropoxy-3-methoxy-benzoic acid | 8-(2,2-difluoroethyl)-10-(6-methyl-2-pyridyl)-11-oxa-3,8-diazaspiro[5.5]undecane |
| [8-(2,2-difluoroethyl)-10-(6-methyl-2-pyridyl)-11-oxa-3,8-diazaspiro[5.5]undecan-3-yl]-(4-isopropylsulfonyl-3-methyl-phenyl)methanone | 4-isopropylsulfonyl-3-methyl-benzoic acid | 8-(2,2-difluoroethyl)-10-(6-methyl-2-pyridyl)-11-oxa-3,8-diazaspiro[5.5]undecane |
| [8-(2,2-difluoroethyl)-10-(6-methyl-2-pyridyl)-11-oxa-3,8-diazaspiro[5.5]undecan-3-yl]-(3-fluoro-4-isopropoxy-5-methoxy-phenyl)methanone | 3-fluoro-4-isopropoxy-5-methoxy-benzoic acid | 8-(2,2-difluoroethyl)-10-(6-methyl-2-pyridyl)-11-oxa-3,8-diazaspiro[5.5]undecan- |
| 2-[3-[4-(1-hydroxy-1-methyl-ethyl)benzoyl]-10-phenyl-11-oxa-3,8-diazaspiro[5.5]undecan-8-yl]acetonitrile | 4-(1-hydroxy-1-methyl-ethyl)benzoic acid | 2-(10-phenyl-11-oxa-3,8-diazaspiro[5.5]undecan-8-yl)acetonitrile |

| Names | Acid names | Amine Names |
|---|---|---|
| [4-(3-hydroxypropoxy)-3-methyl-phenyl]-[10-phenyl-8-(2,2,2-trifluoroethyl)-11-oxa-3,8-diazaspiro[5.5]undecan-3-yl]methanone | 4-(3-hydroxypropoxy)-3-methyl-benzoic acid | 10-phenyl-8-(2,2,2-trifluoroethyl)-11-oxa-3,8-diazaspiro[5.5]undecane |
| 2-[3-(5-isopropoxy-6-methyl-pyridine-2-carbonyl)-10-phenyl-11-oxa-3,8-diazaspiro[5.5]undecan-8-yl]acetonitrile | 5-isopropoxy-6-methyl-pyridine-2-carboxylic acid | 2-(10-phenyl-11-oxa-3,8-diazaspiro[5.5]undecan-8-yl)acetonitrile |
| [4-(2-hydroxyethoxy)-3-methyl-phenyl]-[10-phenyl-8-(2,2,2-trifluoroethyl)-11-oxa-3,8-diazaspiro[5.5]undecan-3-yl]methanone | 4-(2-hydroxyethoxy)-3-methyl-benzoic acid | 10-phenyl-8-(2,2,2-trifluoroethyl)-11-oxa-3,8-diazaspiro[5.5]undecane |
| 2-[3-[4-(1-hydroxy-1-methyl-ethyl)-3-methoxy-benzoyl]-10-phenyl-11-oxa-3,8-diazaspiro[5.5]undecan-8-yl]acetonitrile | 4-(1-hydroxy-1-methyl-ethyl)-3-methoxy-benzoic acid | 2-(10-phenyl-11-oxa-3,8-diazaspiro[5.5]undecan-8-yl)acetonitrile |
| 2-[3-[4-(1-hydroxy-1-methyl-ethyl)-3-methyl-benzoyl]-10-phenyl-11-oxa-3,8-diazaspiro[5.5]undecan-8-yl]acetonitrile | 4-(1-hydroxy-1-methyl-ethyl)-3-methyl-benzoic acid | 2-(10-phenyl-11-oxa-3,8-diazaspiro[5.5]undecan-8-yl)acetonitrile |
| 2-[3-(4-isopropoxy-3-methyl-benzoyl)-10-phenyl-11-oxa-3,8-diazaspiro[5.5]undecan-8-yl]acetonitrile | 4-isopropoxy-3-methyl-benzoic acid | 2-(10-phenyl-11-oxa-3,8-diazaspiro[5.5]undecan-8-yl)acetonitrile |
| 2-[3-(4-isopropoxy-3-methoxy-benzoyl)-10-phenyl-11-oxa-3,8-diazaspiro[5.5]undecan-8-yl]acetonitrile | 4-isopropoxy-3-methoxy-benzoic acid | 2-(10-phenyl-11-oxa-3,8-diazaspiro[5.5]undecan-8-yl)acetonitrile |
| [8-(2,2-difluoroethyl)-10-(5-isopropyloxazol-2-yl)-11-oxa-3,8-diazaspiro[5.5]undecan-3-yl]-(4-isopropoxy-3-methyl-phenyl)methanone | 4-isopropoxy-3-methyl-benzoic acid | 8-(2,2-difluoroethyl)-10-(5-isopropyloxazol-2-yl)-11-oxa-3,8-diazaspiro[5.5]undecane |
| [8-ethyl-10-(4-fluorophenyl)-11-oxa-3,8-diazaspiro[5.5]undecan-3-yl]-(3-fluoro-4-isopropoxy-phenyl)methanone | 3-fluoro-4-isopropoxy-benzoic acid | 8-ethyl-10-(4-fluorophenyl)-11-oxa-3,8-diazaspiro[5.5]undecane |
| [8-tert-butyl-10-(5-methyloxazol-2-yl)-11-oxa-3,8-diazaspiro[5.5]undecan-3-yl]-(4-isopropoxy-3-methyl-phenyl)methanone | 4-isopropoxy-3-methyl-benzoic acid | 8-tert-butyl-10-(5-methyl oxazol-2-yl)-11-oxa-3,8-diazaspiro[5.5]undecane |
| [8-tert-butyl-10-(5-methyloxazol-2-yl)-11-oxa-3,8-diazaspiro[5.5]undecan-3-yl]-(3-fluoro-4-isopropoxy-phenyl)methanone | 3-fluoro-4-isopropoxy-benzoic acid | 8-tert-butyl-10-(5-methyloxazol-2-yl)-11-oxa-3,8-diazaspiro[5.5]undecane |
| (8-ethyl-9-phenyl-11-oxa-3,8-diazaspiro[5.5]undecan-3-yl)-(4-isopropoxy-3-methyl-phenyl)methanone | 4-isopropoxy-3-methyl-benzoic acid | 8-ethyl-9-phenyl-11-oxa-3,8-diazaspiro[5.5]undecane |

| Names | Acid names | Amine Names |
| --- | --- | --- |
| (8-ethyl-9-phenyl-11-oxa-3,8-diazaspiro[5.5]undecan-3-yl)-(4-isopropoxy-3-methoxy-phenyl)methanone | 4-isopropoxy-3-methoxy-benzoic acid | 8-ethyl-9-phenyl-11-oxa-3,8-diazaspiro[5.5]undecane |
| [8-ethyl-10-(5-methylthiazol-2-yl)-11-oxa-3,8-diazaspiro[5.5]undecan-3-yl]-(4-isopropoxy-3-methyl-phenyl)methanone | 4-isopropoxy-3-methyl-benzoic acid | 8-ethyl-10-(5-methylthiazol-2-yl)-11-oxa-3,8-diazaspiro[5.5]undecane |
| [8-ethyl-10-(5-methylthiazol-2-yl)-11-oxa-3,8-diazaspiro[5.5]undecan-3-yl]-(4-isopropoxy-3-methoxy-phenyl)methanone | 4-isopropoxy-3-methoxy-benzoic acid | 8-ethyl-10-(5-methylthiazol-2-yl)-11-oxa-3,8-diazaspiro[5.5]undecane |
| [8-(2,2-difluoroethyl)-10-(5-ethyloxazol-2-yl)-11-oxa-3,8-diazaspiro[5.5]undecan-3-yl]-(4-isopropoxy-3-methyl-phenyl)methanone | 4-isopropoxy-3-methyl-benzoic acid | 8-(2,2-difluoroethyl)-10-(5-ethyloxazol-2-yl)-11-oxa-3,8-diazaspiro[5.5]undecane |
| 1-[3-(4-isopropoxy-3-methyl-benzoyl)-10-phenyl-11-oxa-3,8-diazaspiro[5.5]undecan-8-yl]propan-1-one | 4-isopropoxy-3-methylbenzoic acid | 1-(2-phenyl-1-oxa-4,9-diazaspiro[5.5]undecan-4-yl)propan-1-one |
| [8-(2,2-difluoroethyl)-10-(5-isopropyloxazol-2-yl)-11-oxa-3,8-diazaspiro[5.5]undecan-3-yl]-(3-fluoro-4-isopropoxy-phenyl)methanone | 3-fluoro-4-isopropoxy-benzoic acid | 8-(2,2-difluoroethyl)-10-(5-isopropyloxazol-2-yl)-11-oxa-3,8-diazaspiro[5.5]undecane |
| (8-ethyl-10,10-dimethyl-11-oxa-3,8-diazaspiro[5.5]undecan-3-yl)-(4-isopropoxy-3-methyl-phenyl)methanone | 4-isopropoxy-3-methyl-benzoic acid | 8-ethyl-10,10-dimethyl-11-oxa-3,8-diazaspiro[5.5]undecane |
| (8,9-diethyl-11-oxa-3,8-diazaspiro[5.5]undecan-3-yl)-(4-isopropoxy-3-methyl-phenyl)methanone | 4-isopropoxy-3-methyl-benzoic acid | 8,9-diethyl-11-oxa-3,8-diazaspiro[5.5]undecane |
| (4-isopropoxy-3-methyl-phenyl)-[10-(5-methylthiazol-2-yl)-8-(2,2,2-trifluoroethyl)-11-oxa-3,8-diazaspiro[5.5]undecan-3-yl]methanone | 4-isopropoxy-3-methyl-benzoic acid | 10-(5-methylthiazol-2-yl)-8-(2,2,2-trifluoroethyl)-11-oxa-3,8-diazaspiro[5.5]undecane |
| (4-isopropoxy-3-methoxy-phenyl)-[10-(5-methylthiazol-2-yl)-8-(2,2,2-trifluoroethyl)-11-oxa-3,8-diazaspiro[5.5]undecan-3-yl]methanone | 4-isopropoxy-3-methoxy-benzoic acid | 10-(5-methylthiazol-2-yl)-8-(2,2,2-trifluoroethyl)-11-oxa-3,8-diazaspiro[5.5]undecane |
| [8-(2,2-difluoroethyl)-10-(2-fluorophenyl)-11-oxa-3,8-diazaspiro[5.5]undecan-3-yl]-(3-fluoro-4-isopropoxy-phenyl)methanone | 4-isopropoxy-3-methylbenzoic acid | 4-(2,2-difluoroethyl)-2-(2-fluorophenyl)-1-oxa-4,9-diazaspiro[5.5]undecane |

| Names | Acid names | Amine Names |
|---|---|---|
| [8-(2,2-difluoroethyl)-10-(2-fluorophenyl)-11-oxa-3,8-diazaspiro[5.5]undecan-3-yl]-(4-isopropoxy-3-methyl-phenyl)methanone | 3-fluoro-4-isopropoxybenzoic acid | 4-(2,2-difluoroethyl)-2-(2-fluorophenyl)-1-oxa-4,9-diazaspiro[5.5]undecane |
| [8-(2,2-difluoroethyl)-10-oxazol-2-yl-11-oxa-3,8-diazaspiro[5.5]undecan-3-yl]-(3-fluoro-4-isopropoxy-phenyl)methanone | 3-fluoro-4-isopropoxybenzoic acid | 4-(2,2-difluoroethyl)-2-(oxazol-2-yl)-1-oxa-4,9-diazaspiro[5.5]undecane |
| [8-(2,2-difluoroethyl)-10-(3-methyl-2-pyridyl)-11-oxa-3,8-diazaspiro[5.5]undecan-3-yl]-(3-fluoro-4-isopropoxy-phenyl)methanone | 3-fluoro-4-isopropoxybenzoic acid | 4-(2,2-difluoroethyl)-2-(3-methylpyridin-2-yl)-1-oxa-4,9-diazaspiro[5.5]undecane |
| [8-(2,2-difluoroethyl)-10-(4-methyl-1H-pyrazol-5-yl)-11-oxa-3,8-diazaspiro[5.5]undecan-3-yl]-(4-isopropoxy-3-methyl-phenyl)methanone | 4-isopropoxy-3-methylbenzoic acid | 4-(2,2-difluoroethyl)-2-(4-methyl-1H-pyrazol-5-yl)-1-oxa-4,9-diazaspiro[5.5]undecane |
| [8-(2,2-difluoroethyl)-10-(4-methyl-1H-pyrazol-5-yl)-11-oxa-3,8-diazaspiro[5.5]undecan-3-yl]-(3-fluoro-4-isopropoxy-phenyl)methanone | 3-fluoro-4-isopropoxybenzoic acid | 4-(2,2-difluoroethyl)-2-(4-methyl-1H-pyrazol-5-yl)-1-oxa-4,9-diazaspiro[5.5]undecane |
| [8-tert-butyl-10-(methoxymethyl)-11-oxa-3,8-diazaspiro[5.5]undecan-3-yl]-(4-isopropoxy-3-methyl-phenyl)methanone | 4-isopropoxy-3-methyl-benzoic acid | 8-tert-butyl-10-(methoxymethyl)-11-oxa-3,8-diazaspiro[5.5]undecane |
| (8-tert-butyl-10-ethyl-11-oxa-3,8-diazaspiro[5.5]undecan-3-yl)-(4-isopropoxy-3-methyl-phenyl)methanone | 4-isopropoxy-3-methyl-benzoic acid | 8-tert-butyl-10-ethyl-11-oxa-3,8-diazaspiro[5.5]undecane |
| (8-but-2-ynyl-10-ethyl-11-oxa-3,8-diazaspiro[5.5]undecan-3-yl)-[4-methoxy-3-(trifluoromethyl)phenyl]methanone | 4-methoxy-3-(trifluoromethyl)benzoic acid | 8-but-2-ynyl-10-ethyl-11-oxa-3,8-diazaspiro[5.5]undecane |
| (8-but-2-ynyl-10-ethyl-11-oxa-3,8-diazaspiro[5.5]undecan-3-yl)-(5-isopropoxy-6-methyl-2-pyridyl)methanone | 5-isopropoxy-6-methyl-pyridine-2-carboxylic acid | 8-but-2-ynyl-10-ethyl-11-oxa-3,8-diazaspiro[5.5]undecane |
| 5-(8-but-2-ynyl-10-ethyl-11-oxa-3,8-diazaspiro[5.5]undecane-3-carbonyl)-2-isopropoxy-benzonitrile | 3-cyano-4-isopropoxy-benzoic acid | 8-but-2-ynyl-10-ethyl-11-oxa-3,8-diazaspiro[5.5]undecane |
| (8-but-2-ynyl-10-ethyl-11-oxa-3,8-diazaspiro[5.5]undecan-3-yl)-(3-chloro-4-isopropoxy-phenyl)methanone | 3-chloro-4-isopropoxy-benzoic acid | 8-but-2-ynyl-10-ethyl-11-oxa-3,8-diazaspiro[5.5]undecane |
| (8-but-2-ynyl-10-ethyl-11-oxa-3,8-diazaspiro[5.5]undecan-3-yl)-(3-fluoro-4-isopropoxy-phenyl)methanone | 3-fluoro-4-isopropoxy-benzoic acid | 8-but-2-ynyl-10-ethyl-11-oxa-3,8-diazaspiro[5.5]undecane |

| Names | Acid names | Amine Names |
| --- | --- | --- |
| (4-tert-butyl-3-methoxy-phenyl)-(8-but-2-ynyl-10-ethyl-11-oxa-3,8-diazaspiro[5.5]undecan-3-yl)methanone | 4-tert-butyl-3-methoxy-benzoic acid | 8-but-2-ynyl-10-ethyl-11-oxa-3,8-diazaspiro[5.5]undecane |
| [4-(1-hydroxycyclobutyl)phenyl]-[10-(methoxymethyl)-8-[3-(trifluoromethyl)phenyl]-11-oxa-3,8-diazaspiro[5.5]undecan-3-yl]methanone | 4-(1-hydroxycyclobutyl)benzoic acid | 10-(methoxymethyl)-8-[3-(trifluoromethyl)phenyl]-11-oxa-3,8-diazaspiro[5.5]undecane |
| [4-(2-hydroxy-2-methyl-propoxy)-3-methyl-phenyl]-[10-(methoxymethyl)-8-[3-(trifluoromethyl)phenyl]-11-oxa-3,8-diazaspiro[5.5]undecan-3-yl]methanone | 4-(2-hydroxy-2-methyl-propoxy)-3-methyl-benzoic acid | 10-(methoxymethyl)-8-[3-(trifluoromethyl)phenyl]-11-oxa-3,8-diazaspiro[5.5]undecane |
| (10-ethyl-8-pyrimidin-2-yl-11-oxa-3,8-diazaspiro[5.5]undecan-3-yl)-[4-(1-hydroxycyclobutyl)-3-methyl-phenyl]methanone | 4-(1-hydroxycyclobutyl)-3-methyl-benzoic acid | 10-ethyl-8-pyrimidin-2-yl-11-oxa-3,8-diazaspiro[5.5]undecane |
| [10-ethyl-8-(2-pyridyl)-11-oxa-3,8-diazaspiro[5.5]undecan-3-yl]-[4-(1-hydroxycyclobutyl)-3-methyl-phenyl]methanone | 4-(1-hydroxycyclobutyl)-3-methyl-benzoic acid | 10-ethyl-8-(2-pyridyl)-11-oxa-3,8-diazaspiro[5.5]undecane |
| [4-(1-hydroxycyclobutyl)-3-methyl-phenyl]-[10-(methoxymethyl)-8-pyrimidin-2-yl-11-oxa-3,8-diazaspiro[5.5]undecan-3-yl]methanone | 4-(1-hydroxycyclobutyl)-3-methyl-benzoic acid | 10-(methoxymethyl)-8-pyrimidin-2-yl-11-oxa-3,8-diazaspiro[5.5]undecane |
| [10-ethyl-8-(2-pyridyl)-11-oxa-3,8-diazaspiro[5.5]undecan-3-yl]-[4-(1-hydroxycyclohexyl)-phenyl]methanone | 4-(1-hydroxycyclohexyl)benzoic acid | 10-ethyl-8-(2-pyridyl)-11-oxa-3,8-diazaspiro[5.5]undecane |
| (10-ethyl-8-pyrimidin-2-yl-11-oxa-3,8-diazaspiro[5.5]undecan-3-yl)-[4-(1-hydroxycyclohexyl)-phenyl]methanone | 4-(1-hydroxycyclohexyl)benzoic acid | 10-ethyl-8-pyrimidin-2-yl-11-oxa-3,8-diazaspiro[5.5]undecane |
| [4-(1-hydroxycyclohexyl)-phenyl]-[10-(methoxymethyl)-8-pyrimidin-2-yl-11-oxa-3,8-diazaspiro[5.5]undecan-3-yl]methanone | 4-(1-hydroxycyclohexyl)benzoic acid | 10-(methoxymethyl)-8-pyrimidin-2-yl-11-oxa-3,8-diazaspiro[5.5]undecane |
| [10-ethyl-8-(2-pyridyl)-11-oxa-3,8-diazaspiro[5.5]undecan-3-yl]-[4-(1-hydroxycyclopentyl)phenyl]methanone | 4-(1-hydroxycyclopentyl)benzoic acid | 10-ethyl-8-(2-pyridyl)-11-oxa-3,8-diazaspiro[5.5]undecane |
| [10-ethyl-8-(2-pyridyl)-11-oxa-3,8-diazaspiro[5.5]undecan-3-yl]-[3-fluoro-4-(1-hydroxycyclopentyl)-phenyl]methanone | 3-fluoro-4-(1-hydroxycyclopentyl)benzoic acid | 10-ethyl-8-(2-pyridyl)-11-oxa-3,8-diazaspiro[5.5]undecane |

| Names | Acid names | Amine Names |
|---|---|---|
| [10-ethyl-8-(2-pyridyl)-11-oxa-3,8-diazaspiro[5.5]undecan-3-yl]-[4-(1-hydroxycyclopentyl)-3-methyl-phenyl]methanone | 4-(1-hydroxycyclopentyl)-3-methyl-benzoic acid | 10-ethyl-8-(2-pyridyl)-11-oxa-3,8-diazaspiro[5.5]undecane |
| [10-ethyl-8-(2-pyridyl)-11-oxa-3,8-diazaspiro[5.5]undecan-3-yl]-[3-fluoro-4-(1-hydroxy-1-methyl-ethyl)phenyl]methanone | 3-fluoro-4-(1-hydroxy-1-methyl-ethyl)benzoic acid | 10-ethyl-8-(2-pyridyl)-11-oxa-3,8-diazaspiro[5.5]undecane |
| [10-ethyl-8-(2-pyridyl)-11-oxa-3,8-diazaspiro[5.5]undecan-3-yl]-[4-(1-hydroxy-1-methyl-ethyl)-3-methyl-phenyl]methanone | 4-(1-hydroxy-1-methyl-ethyl)-3-methyl-benzoic acid | 10-ethyl-8-(2-pyridyl)-11-oxa-3,8-diazaspiro[5.5]undecane |
| (10-ethyl-8-pyrimidin-2-yl-11-oxa-3,8-diazaspiro[5.5]undecan-3-yl)-(4-isopropylsulfonyl-3-methyl-phenyl)methanone | 4-isopropylsulfonyl-3-methyl-benzoic acid | 10-ethyl-8-pyrimidin-2-yl-11-oxa-3,8-diazaspiro[5.5]undecane |
| (10-ethyl-8-pyrimidin-2-yl-11-oxa-3,8-diazaspiro[5.5]undecan-3-yl)-[3-fluoro-4-(1-hydroxycyclopentyl)-phenyl]methanone | 3-fluoro-4-(1-hydroxycyclopentyl)benzoic acid | 10-ethyl-8-pyrimidin-2-yl-11-oxa-3,8-diazaspiro[5.5]undecane |
| [4-(1-ethyl-1-hydroxy-propyl)-3-methyl-phenyl]-(10-ethyl-8-pyrimidin-2-yl-11-oxa-3,8-diazaspiro[5.5]undecan-3-yl)methanone | 4-(1-ethyl-1-hydroxy-propyl)-3-methyl-benzoic acid | 10-ethyl-8-pyrimidin-2-yl-11-oxa-3,8-diazaspiro[5.5]undecane |
| (10-ethyl-8-pyrimidin-2-yl-11-oxa-3,8-diazaspiro[5.5]undecan-3-yl)-[4-(1-hydroxycyclopentyl)-3-methyl-phenyl]methanone | 4-(1-hydroxycyclopentyl)-3-methyl-benzoic acid | 10-ethyl-8-pyrimidin-2-yl-11-oxa-3,8-diazaspiro[5.5]undecane |
| [4-(1-hydroxycyclopentyl)-3-methyl-phenyl]-[10-(methoxymethyl)-8-pyrimidin-2-yl-11-oxa-3,8-diazaspiro[5.5]undecan-3-yl]methanone | 4-(1-hydroxycyclopentyl)-3-methyl-benzoic acid | 10-(methoxymethyl)-8-pyrimidin-2-yl-11-oxa-3,8-diazaspiro[5.5]undecane |
| [4-(1-hydroxycyclopentyl)-phenyl]-[10-(methoxymethyl)-8-pyrimidin-2-yl-11-oxa-3,8-diazaspiro[5.5]undecan-3-yl]methanone | 4-(1-hydroxycyclopentyl)benzoic acid | 10-(methoxymethyl)-8-pyrimidin-2-yl-11-oxa-3,8-diazaspiro[5.5]undecane |
| [4-(1-hydroxycyclobutyl)-phenyl]-[10-(methoxymethyl)-8-pyrimidin-2-yl-11-oxa-3,8-diazaspiro[5.5]undecan-3-yl]methanone | 4-(1-hydroxycyclobutyl)benzoic acid | 10-(methoxymethyl)-8-pyrimidin-2-yl-11-oxa-3,8-diazaspiro[5.5]undecane |

-continued

| Names | Acid names | Amine Names |
|---|---|---|
| [4-(2-hydroxy-2-methyl-propoxy)-3-methyl-phenyl]-[10-(methoxymethyl)-8-pyrimidin-2-yl-11-oxa-3,8-diazaspiro[5.5]undecan-3-yl]methanone | 4-(2-hydroxy-2-methyl-propoxy)-3-methyl-benzoic acid | 10-(methoxymethyl)-8-pyrimidin-2-yl-11-oxa-3,8-diazaspiro[5.5]undecane |
| 2-isopropoxy-5-[10-(methoxymethyl)-8-pyrimidin-2-yl-11-oxa-3,8-diazaspiro[5.5]undecane-3-carbonyl]benzonitrile | 3-cyano-4-isopropoxy-benzoic acid | 10-(methoxymethyl)-8-pyrimidin-2-yl-11-oxa-3,8-diazaspiro[5.5]undecane |
| (4-tert-butyl-3-methoxy-phenyl)-[10-(methoxymethyl)-8-pyrimidin-2-yl-11-oxa-3,8-diazaspiro[5.5]undecan-3-yl]methanone | 4-tert-butyl-3-methoxy-benzoic acid | 10-(methoxymethyl)-8-pyrimidin-2-yl-11-oxa-3,8-diazaspiro[5.5]undecane |
| [3-methoxy-4-(2-methoxyethoxy)phenyl]-[10-(methoxymethyl)-8-pyrimidin-2-yl-11-oxa-3,8-diazaspiro[5.5]undecan-3-yl]methanone | 3-methoxy-4-(2-methoxyethoxy)benzoic acid | 10-(methoxymethyl)-8-pyrimidin-2-yl-11-oxa-3,8-diazaspiro[5.5]undecane |
| (5-isopropoxy-6-methyl-2-pyridyl)-[10-(methoxymethyl)-8-pyrimidin-2-yl-11-oxa-3,8-diazaspiro[5.5]undecan-3-yl]methanone | 5-isopropoxy-6-methyl-pyridine-2-carboxylic acid | 10-(methoxymethyl)-8-pyrimidin-2-yl-11-oxa-3,8-diazaspiro[5.5]undecane |
| (3-ethoxyphenyl)-[10-(methoxymethyl)-8-pyrimidin-2-yl-11-oxa-3,8-diazaspiro[5.5]undecan-3-yl]methanone | 3-ethoxybenzoic acid | 10-(methoxymethyl)-8-pyrimidin-2-yl-11-oxa-3,8-diazaspiro[5.5]undecane |
| (4-isopropoxyphenyl)-[10-(methoxymethyl)-8-pyrimidin-2-yl-11-oxa-3,8-diazaspiro[5.5]undecan-3-yl]methanone | 4-isopropoxybenzoic acid | 10-(methoxymethyl)-8-pyrimidin-2-yl-11-oxa-3,8-diazaspiro[5.5]undecane |
| (4-cyclopropylsulfonylphenyl)-[10-(methoxymethyl)-8-pyrimidin-2-yl-11-oxa-3,8-diazaspiro[5.5]undecan-3-yl]methanone | 4-cyclopropylsulfonylbenzoic acid | 10-(methoxymethyl)-8-pyrimidin-2-yl-11-oxa-3,8-diazaspiro[5.5]undecane |
| [4-(1-hydroxy-1-methyl-ethyl)-3-methyl-phenyl]-[10-(methoxymethyl)-8-pyrimidin-2-yl-11-oxa-3,8-diazaspiro[5.5]undecan-3-yl]methanone | 4-(1-hydroxy-1-methyl-ethyl)-3-methyl-benzoic acid | 10-(methoxymethyl)-8-pyrimidin-2-yl-11-oxa-3,8-diazaspiro[5.5]undecane |
| [4-(1-hydroxy-1-methyl-ethyl)phenyl]-[10-(methoxymethyl)-8-pyrimidin-2-yl-11-oxa-3,8-diazaspiro[5.5]undecan-3-yl]methanone | 4-(1-hydroxy-1-methyl-ethyl)benzoic acid | 10-(methoxymethyl)-8-pyrimidin-2-yl-11-oxa-3,8-diazaspiro[5.5]undecane |
| [3-fluoro-4-(1-hydroxy-1-methyl-ethyl)phenyl]-[10-(methoxymethyl)-8-pyrimidin-2-yl-11-oxa-3,8-diazaspiro[5.5]undecan-3-yl]methanone | 3-fluoro-4-(1-hydroxy-1-methyl-ethyl)benzoic acid | 10-(methoxymethyl)-8-pyrimidin-2-yl-11-oxa-3,8-diazaspiro[5.5]undecane |

-continued

| Names | Acid names | Amine Names |
|---|---|---|
| (3-fluoro-4-isopropoxy-phenyl)-[10-(methoxymethyl)-8-pyrimidin-2-yl-11-oxa-3,8-diazaspiro[5.5]undecan-3-yl]methanone | 3-fluoro-4-isopropoxy-benzoic acid | 10-(methoxymethyl)-8-pyrimidin-2-yl-11-oxa-3,8-diazaspiro[5.5]undecane |
| (4-isopentyloxy-3-methoxy-phenyl)-[10-(methoxymethyl)-8-pyrimidin-2-yl-11-oxa-3,8-diazaspiro[5.5]undecan-3-yl]methanone | 4-isopentyloxy-3-methoxy-benzoic acid | 10-(methoxymethyl)-8-pyrimidin-2-yl-11-oxa-3,8-diazaspiro[5.5]undecane |
| [4-(1-hydroxy-2-methyl-propyl)phenyl]-[10-(methoxymethyl)-8-pyrimidin-2-yl-11-oxa-3,8-diazaspiro[5.5]undecan-3-yl]methanone | 4-(1-hydroxy-2-methyl-propyl)benzoic acid | 10-(methoxymethyl)-8-pyrimidin-2-yl-11-oxa-3,8-diazaspiro[5.5]undecane |
| [2-(difluoromethoxy)-phenyl]-[10-(methoxymethyl)-8-pyrimidin-2-yl-11-oxa-3,8-diazaspiro[5.5]undecan-3-yl]methanone | 2-(difluoromethoxy)benzoic acid | 10-(methoxymethyl)-8-pyrimidin-2-yl-11-oxa-3,8-diazaspiro[5.5]undecane |
| [4-(2-hydroxy-2-methyl-propyl)phenyl]-[10-(methoxymethyl)-8-pyrimidin-2-yl-11-oxa-3,8-diazaspiro[5.5]undecan-3-yl]methanone | 4-(2-hydroxy-2-methyl-propyl)benzoic acid | 10-(methoxymethyl)-8-pyrimidin-2-yl-11-oxa-3,8-diazaspiro[5.5]undecane |
| [4-(difluoromethylsulfonyl)phenyl]-[10-(methoxymethyl)-8-pyrimidin-2-yl-11-oxa-3,8-diazaspiro[5.5]undecan-3-yl]methanone | 4-(difluoromethylsulfonyl)benzoic acid | 10-(methoxymethyl)-8-pyrimidin-2-yl-11-oxa-3,8-diazaspiro[5.5]undecane |
| [10-(methoxymethyl)-8-pyrimidin-2-yl-11-oxa-3,8-diazaspiro[5.5]undecan-3-yl]-[4-methoxy-3-(trifluoromethyl)phenyl]methanone | 4-methoxy-3-(trifluoromethyl)benzoic acid | 10-(methoxymethyl)-8-pyrimidin-2-yl-11-oxa-3,8-diazaspiro[5.5]undecane |
| [3-(hydroxymethyl)-4-isopropoxy-phenyl]-[10-(methoxymethyl)-8-pyrimidin-2-yl-11-oxa-3,8-diazaspiro[5.5]undecan-3-yl]methanone | 3-(hydroxymethyl)-4-isopropoxy-benzoic acid | 10-(methoxymethyl)-8-pyrimidin-2-yl-11-oxa-3,8-diazaspiro[5.5]undecane |
| (4-isopropoxy-3-methoxy-phenyl)-[10-(methoxymethyl)-8-pyrimidin-2-yl-11-oxa-3,8-diazaspiro[5.5]undecan-3-yl]methanone | 4-isopropoxy-3-methoxy-benzoic acid | 10-(methoxymethyl)-8-pyrimidin-2-yl-11-oxa-3,8-diazaspiro[5.5]undecane |
| N-cyclopropyl-4-[10-(methoxymethyl)-8-pyrimidin-2-yl-11-oxa-3,8-diazaspiro[5.5]undecane-3-carbonyl]benzenesulfonamide | 4-(cyclopropylsulfamoyl)benzoic acid | 10-(methoxymethyl)-8-pyrimidin-2-yl-11-oxa-3,8-diazaspiro[5.5]undecane |
| (8-but-2-ynyl-10-ethyl-11-oxa-3,8-diazaspiro[5.5]undecan-3-yl)-(3-methyl-4-propoxy-phenyl)methanone | 3-methyl-4-propoxy-benzoic acid | 8-but-2-ynyl-10-ethyl-11-oxa-3,8-diazaspiro[5.5]undecane |

| Names | Acid names | Amine Names |
|---|---|---|
| (8-but-2-ynyl-10-ethyl-11-oxa-3,8-diazaspiro[5.5]undecan-3-yl)-(4-ethoxy-3-methyl-phenyl)methanone | 4-ethoxy-3-methyl-benzoic acid | 8-but-2-ynyl-10-ethyl-11-oxa-3,8-diazaspiro[5.5]undecane |
| (8-but-2-ynyl-10-ethyl-11-oxa-3,8-diazaspiro[5.5]undecan-3-yl)-(4-methoxy-3-methyl-phenyl)methanone | 4-methoxy-3-methyl-benzoic acid | 8-but-2-ynyl-10-ethyl-11-oxa-3,8-diazaspiro[5.5]undecane |
| [3-fluoro-4-(1-hydroxy-1-methyl-ethyl)phenyl]-10-(methoxymethyl)-8-[3-(trifluoromethyl)phenyl]-11-oxa-3,8-diazaspiro[5.5]undecan-3-yl]methanone | 3-fluoro-4-(1-hydroxy-1-methyl-ethyl)benzoic acid | [10-(methoxymethyl)-8-[3-(trifluoromethyl)phenyl]-11-oxa-3,8-diazaspiro[5.5]undecane |
| (8-but-2-ynyl-10,10-difluoro-11-oxa-3,8-diazaspiro[5.5]undecan-3-yl)-(4-isopropoxy-3-methyl-phenyl)methanone | 4-isopropoxy-3-methyl-benzoic acid | 8-but-2-ynyl-10,10-difluoro-11-oxa-3,8-diazaspiro[5.5]undecane |
| [8-but-2-ynyl-10-(fluoromethyl)-11-oxa-3,8-diazaspiro[5.5]undecan-3-yl]-(4-isopropoxy-3-methyl-phenyl)methanone | 4-isopropoxy-3-methyl-benzoic acid | 8-but-2-ynyl-10-(fluoromethyl)-11-oxa-3,8-diazaspiro[5.5]undecane |
| [8-(2,2-difluoropropyl)-10-(methoxymethyl)-11-oxa-3,8-diazaspiro[5.5]undecan-3-yl]-(4-isopropoxy-3-methyl-phenyl)methanone | 4-isopropoxy-3-methyl-benzoic acid | 8-(2,2-difluoropropyl)-10-(methoxymethyl)-11-oxa-3,8-diazaspiro[5.5]undecane |

Preparation of (4-isopropoxy-3-methyl-phenyl)-(10-phenyl-11-oxa-3,8-diazaspiro[5.5]undecan-3-yl)methanone

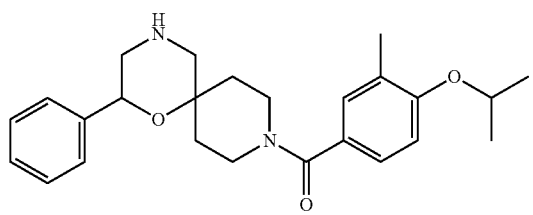 [SMILES: Cc1cc(C(=O)N2CCC3(CC2)CNCC(c2ccccc2)O3)ccc1OC(C)C]

Step 1:

A mixture of 4-benzyl-2-phenyl-1-oxa-4,9-diazaspiro[5.5]undecane (222 mg, 0.69 mmol), 4-isopropoxy-3-methyl-benzoic acid (140 mg, 0.72 mmol) and HATU (262 mg, 0.69 mmol) was stirred in a mixture of DCM (1 mL) and DMF (1 mL) for 5 minutes. Triethylamine (192 µL, 1.38 mmol) was added and the reaction mixture was stirred for 16 hours, then concentrated in vacuo, diluted with sat. aq. NaHCO₃, extracted with ethyl acetate (3×2 mL), dried over MgSO₄, filtered and concentrated in vacuo and purified by silica gel column chromatography using 0-60% EtOAc/DCM as eluent to give (10-benzyl-8-phenyl-7-oxa-3,10-diazaspiro[5.5]undecan-3-yl)-(4-isopropoxy-3-methyl-phenyl)methanone (343 mg, 100%) as a yellow oil. ESI-MS m/z calc. 406.5. Found 407.7 (M+1)⁺; Retention time: 1.13 minutes (3 min run).

Step 2:

To (10-benzyl-8-phenyl-7-oxa-3,10-diazaspiro[5.5]undecan-3-yl)-(4-isopropoxy-3-methyl-phenyl)methanone (264 mg, 0.53 mmol), ammonium formate (167 mg, 2.65 mmol), palladium (30 mg, 0.03 mmol) (10% on carbon) was added methanol (5 mL) and the reaction mixture was stirred at 75° C. for 40 minutes. The reaction mixture was cooled, filtered over celite and concentrated in vacuo. The residue was partitioned between ethyl acetate and 1:1 sat. aq. NaHCO₃/25% aq. NaOH, dried over MgSO₄, filtered and concentrated in vacuo to give (4-isopropoxy-3-methyl-phenyl)-(8-phenyl-7-oxa-3,10-diazaspiro[5.5]undecan-3-yl)methanone (170 mg, 79%), which was used directly without further purification in the next step. ESI-MS m/z calc. 408.5. Found 409.7 (M+1)⁺; Retention time: 1.24 minutes (3 min run)

Preparation of (4-isopropoxy-3-methyl-phenyl)-(8-methyl-10-phenyl-11-oxa-3,8-diazaspiro[5.5]undecan-3-yl)methanone

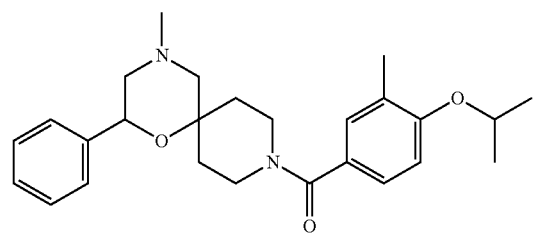 [SMILES: Cc1cc(C(=O)N2CCC3(CC2)CN(C)CC(c2ccccc2)O3)ccc1OC(C)C]

To (4-isopropoxy-3-methyl-phenyl)-(8-phenyl-7-oxa-3,10-diazaspiro[5.5]undecan-3-yl)methanone (22 mg, 0.05 mmol) in DCM (0.3 mL) was added iodomethane (15 mg, 7 µL, 0.11 mmol) followed by the addition of triethylamine (15 µL, 0.11 mmol) and the reaction mixture was stirred for 16 hours at room temperature. The reaction mixture was concentrated in vacuo, diluted with methanol, filtered and purified by prep LCMS (1-99% ACN/H$_2$O, 5 mM HCl modifier) to give (4-isopropoxy-3-methyl-phenyl)-(10-methyl-8-phenyl-7-oxa-3,10-diazaspiro[5.5]undecan-3-yl)methanone hydrochloride salt as a glassy solid (13 mg, 54%). ESI-MS m/z calc. 422.3. Found 423.5 (M+1)$^+$; Retention time: 1.31 minutes (3 min run).

Preparation of (4-isopropoxy-3-methyl-phenyl)-(8-isopropyl-10-phenyl-11-oxa-3,8-diazaspiro[5.5]undecan-3-yl)methanone

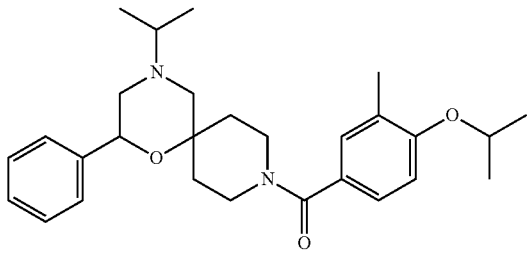 [SMILES: Cc1cc(C(=O)N2CCC3(CC2)CN(C(C)C)CC(c2ccccc2)O3)ccc1OC(C)C]

To (4-isopropoxy-3-methyl-phenyl)-(8-phenyl-7-oxa-3,10-diazaspiro[5.5]undecan-3-yl)methanone (30 mg, 0.07 mmol) and acetone (130 µL, 1.77 mmol) in DCE (0.5 mL) was added sodium triacetoxyborohydride (50 mg, 0.24 mmol) and the reaction mixture was stirred for 5 hours. The reaction mixture was concentrated in vacuo, diluted with methanol, microfiltered and purified by preparative LCMS (1-99% ACN/H$_2$O, 5 mM HCl modifier) to give (4-isopropoxy-3-methyl-phenyl)-(10-isopropyl-8-phenyl-7-oxa-3,10-diazaspiro[5.5]undecan-3-yl)methanone hydrochloride salt (13 mg, 36%) as a glassy solid. ESI-MS m/z calc. 450.2. Found 451.5 (M+1)$^+$; Retention time: 1.38 minutes (3 min run).

Preparation of [8-(2-hydroxy-2-methyl-propyl)-10-phenyl-11-oxa-3,8-diazaspiro[5.5]undecan-3-yl]-(4-isopropoxy-3-methyl-phenyl)methanone

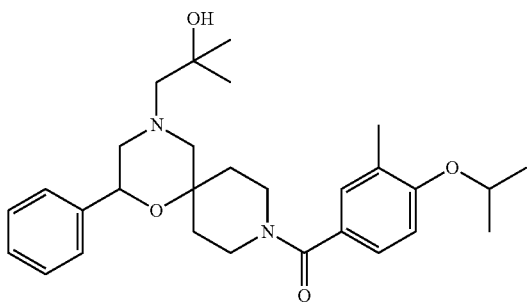 [SMILES: Cc1cc(C(=O)N2CCC3(CC2)CN(CC(C)(C)O)CC(c2ccccc2)O3)ccc1OC(C)C]

(4-Isopropoxy-3-methyl-phenyl)-(8-phenyl-7-oxa-3,10-diazaspiro[5.5]undecan-3-yl)methanone (21 mg, 0.05 mmol) and 2,2-dimethyloxirane (11 mg, 14 µL, 0.15 mmol) were stirred in ethanol (0.3 mL) at 40° C. for 16 hours. The reaction mixture was diluted with methanol, microfiltered, and purified by prep LCMS (10-99% ACN/Water, 5 mM HCl modifier) to give [10-(2-hydroxy-2-methyl-propyl)-8-phenyl-7-oxa-3,10-diazaspiro[5.5]undecan-3-yl]-(4-isopropoxy-3-methyl-phenyl)methanone hydrochloride salt (12 mg, 46%) as a glassy solid. ESI-MS m/z calc. 480.3. Found 481.7 (M+1)$^+$; Retention time: 1.49 minutes (3 min run).

Preparation of [8-(2-hydroxyethyl)-10-phenyl-11-oxa-3,8-diazaspiro[5.5]undecan-3-yl]-(4-isopropoxy-3-methyl-phenyl)methanone

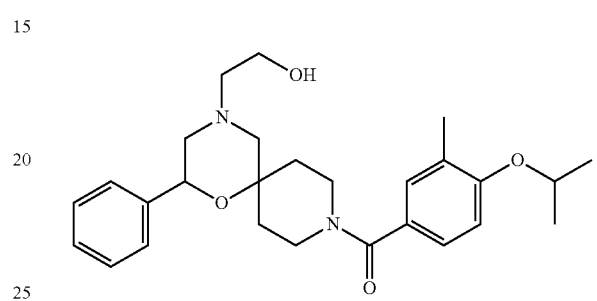

(4-Isopropoxy-3-methyl-phenyl)-(8-phenyl-7-oxa-3,10-diazaspiro[5.5]undecan-3-yl)methanone (21 mg, 0.05 mmol), 2-(2-bromoethoxy)tetrahydropyran (13 mg, 9 µL, 0.06 mmol) and K$_2$CO$_3$ (21 mg, 0.15 mmol) were combined in DMF (0.3 mL) and stirred at 40° C. for 16 hours. The reaction mixture was diluted with ether (3 mL), microfiltered and evaporated to give the THP-ether intermediate, which was dissolved in methanol (0.5 mL), then HCl (0.5 mL of 4 M in dioxane, 2.00 mmol) was added and the reaction mixture was stirred for 30 minutes. The reaction mixture was concentrated in vacuo, diluted with methanol, microfiltered and purified by prep LCMS (10-99% ACN/Water, 5 mM HCl modifier) to give 10-(2-hydroxyethyl)-8-phenyl-7-oxa-3,10-diazaspiro[5.5]undecan-3-yl-(4-isopropoxy-3-methyl-phenyl)methanone hydrochloride salt (10 mg, 40%) as a glassy solid. ESI-MS m/z calc. 452.3. Found 453.2 (M+1)$^+$; Retention time: 1.08 minutes (3 min run).

Preparation of (2-(4-chlorophenyl)-4-(2,2-difluoroethyl)-1-oxa-4,9-diazaspiro[5.5]undecan-9-yl)(4-isopropoxy-3-methylphenyl)methanone

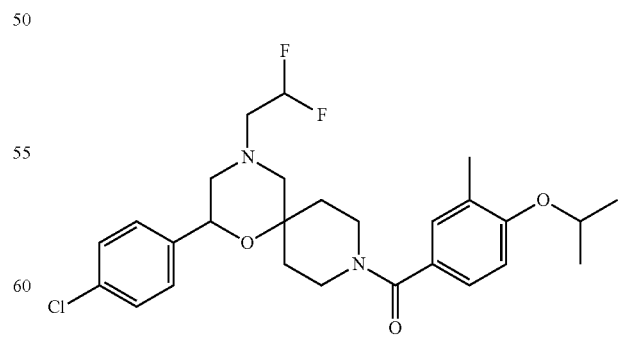

Step 1:
To a solution of 8-benzyl-10-(4-chlorophenyl)-11-oxa-3,8-diazaspiro[5.5]undecane (100 mg, 0.28 mmol) and 4-isopropoxy-3-methyl-benzoic acid (54 mg, 0.28 mmol) in DMF (1 mL) was added DIEA (98 μL, 0.56 mmol) followed by the addition of HATU (128 mg, 0.34 mmol). The reaction mixture was stirred for 10 minutes, then quenched with water and the aqueous layer was extracted with ethyl acetate. The combined organic layer was washed with water (twice). The organic layer was dried over MgSO$_4$, filtered and concentrated in vacuo. The residue was purified by silica gel column chromatography using 0 to 50% EtOAc/hexanes as eluent to obtain [8-benzyl-10-(4-chlorophenyl)-11-oxa-3,8-diazaspiro[5.5]undecan-3-yl]-(4-isopropoxy-3-methyl-phenyl)methanone (44 mg, 29%). ESI-MS m/z calc. 532.2. Found 533.3 (M+1)$^+$; Retention time: 2.17 minutes (3 min run).

Step 2:

1-Chloroethyl carbonochloridate (142 mg, 108 μL, 0.99 mmol) was added to a solution of [8-benzyl-10-(4-chlorophenyl)-11-oxa-3,8-diazaspiro[5.5]undecan-3-yl]-(4-isopropoxy-3-methyl-phenyl)methanone (44 mg, 0.08 mmol) in DCE (508 μL) at room temperature and then the reaction mixture was heated at reflux for 1 hour. The excess solvent was removed in vacuo and the carbamate intermediate was dissolved in MeOH (2 mL) and heated at reflux for 20 minutes. The reaction mixture was cooled to room temperature, filtered and purified by Waters mass directed LC/MS-HPLC: (1-99% ACN/H$_2$O (5 mM HCl)). The desired fractions were concentrated to dryness, dissolved in EtOAc and washed with 1M NaOH. The combined organics were dried over Na$_2$SO$_4$, filtered and concentrated in vacuo to yield [10-(4-chlorophenyl)-11-oxa-3,8-diazaspiro[5.5]undecan-3-yl]-(4-isopropoxy-3-methyl-phenyl)methanone (22 mg, 60%). ESI-MS m/z calc. 442.2. Found 443.5 (M+1)$^+$; Retention time: 1.51 minutes (3 min run)

Step 3:

2,2-difluoroethyl trifluoromethanesulfonate (17 mg, 0.08 mmol) was added to a solution of [10-(4-chlorophenyl)-11-oxa-3,8-diazaspiro[5.5]undecan-3-yl]-(4-isopropoxy-3-methyl-phenyl)methanone (22 mg, 0.05 mmol) and NaHCO$_3$ (13 mg, 0.15 mmol) in anhydrous ethanol (0.3 mL) at room temperature. The reaction mixture was purged with argon, sealed with a cap and heated at 70° C. for 40 minutes. The reaction mixture was cooled to room temperature, diluted with MeOH to 1 mL, microfiltered and purified by Waters mass directed LC/MS: (10-99% ACN/H$_2$O (5 mM HCl)) to yield [10-(4-chlorophenyl)-8-(2,2-difluoroethyl)-11-oxa-3,8-diazaspiro[5.5]undecan-3-yl]-(4-isopropoxy-3-methyl-phenyl)methanone (27 mg, 100%). ESI-MS m/z calc. 506.21478. Found 507.2 (M+1)$^+$; Retention time: 2.17 minutes (3 min run).

Preparation of (2-(2-chlorophenyl)-4-(2,2-difluoroethyl)-1-oxa-4,9-diazaspiro[5.5]undecan-9-yl)(3-fluoro-4-isopropoxyphenyl)methanone

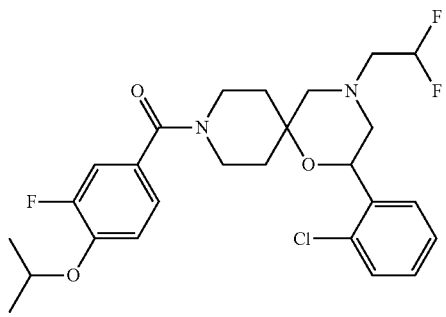 [SMILES: CC(C)Oc1ccc(C(=O)N2CCC3(CC2)CN(CC(F)F)CC(c2ccccc2Cl)O3)cc1F]

This compound was prepared following the above procedure, using 8-benzyl-10-(2-chlorophenyl)-11-oxa-3,8-diazaspiro[5.5]undecane in step 1 and using 3-fluoro-4-isopropoxy-benzoic acid as the acid reagent in step 3. ESI-MS m/z calc. 510.2. Found 511.5 (M+1)$^+$; Retention time: 2.25 minutes. $^1$H NMR (400 MHz, DMSO) δ 7.61 (dd, J=7.8, 1.2 Hz, 1H), 7.50-7.31 (m, 3H), 7.30-7.12 (m, 3H), 6.36-6.00 (m, 1H), 5.08 (d, J=13.4 Hz, 1H), 4.74-4.64 (m, 1H), 4.12-3.91 (m, 1H), 3.73-3.59 (m, 2H), 3.32 (dd, J=32.0, 10.6 Hz, 1H), 3.06 (dd, J=11.0, 3.1 Hz, 1H), 2.91 (dd, J=11.6, 2.6 Hz, 1H), 2.86-2.65 (m, 2H), 2.44-2.30 (m, 1H), 2.19 (d, J=9.6 Hz, 1H), 2.13-1.99 (m, 1H), 1.70-1.55 (m, 3H), 1.30 (d, J=6.0 Hz, 6H).

Preparation of (4-(2,2-difluoroethyl)-2-(p-tolyl)-1-oxa-4,9-diazaspiro[5.5]undecan-9-yl)(4-isopropoxy-3-methylphenyl)methanone

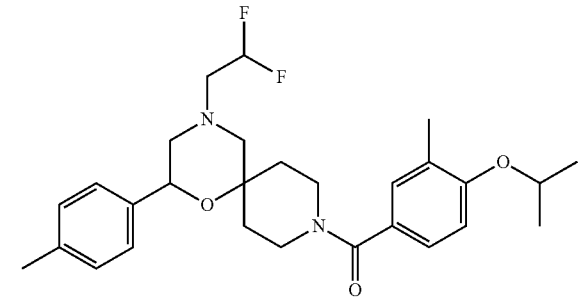 [SMILES: Cc1ccc(C2CN(CC(F)F)CC3(CCN(C(=O)c4ccc(OC(C)C)c(C)c4)CC3)O2)cc1]

Step 1:

A mixture of 8-benzyl-10-(p-tolyl)-11-oxa-3,8-diazaspiro[5.5]undecane (100 mg, 0.30 mmol), 4-isopropoxy-3-methyl-benzoic acid (61 mg, 0.31 mmol) and HATU (119 mg, 0.31 mmol) was stirred in DCM (450 μL) and DMF (450 μL) for 5 minutes. Triethylamine (83 μL, 0.59 mmol) was added and the reaction mixture was stirred overnight. The reaction mixture was diluted with sat. aq. NaHCO$_3$ (5 mL) and extracted with DCM (3×5 mL), dried over MgSO$_4$, filtered, concentrated in vacuo and purified by silica gel column chromatography (0-100% EtOAc/hexane) to give [8-benzyl-10-(p-tolyl)-11-oxa-3,8-diazaspiro[5.5]undecan-3-yl]-(4-isopropoxy-3-methyl-phenyl)methanone as a colorless oil (120 mg, 79%). ESI-MS m/z calc. 512.3. Found 513.3 (M+1)$^+$; Retention time: 1.86 minutes (3 min run).

Step 2:

To [8-benzyl-10-(p-tolyl)-11-oxa-3,8-diazaspiro[5.5]undecan-3-yl]-(4-isopropoxy-3-methyl-phenyl)methanone (120 mg, 0.23 mmol) in ethanol (1.2 mL) was added ammonium formate (69 mg, 1.09 mmol) and Pd(OH)$_2$ (18 mg, 0.025 mmol) and the reaction mixture was heated at 75° C. for 60 minutes. The reaction mixture was cooled, filtered, concentrated in vacuo and the residue was dissolved with ethyl acetate (10 mL) and washed with sat. aq. NaHCO$_3$ (5 mL). The aqueous layer was extracted further with ethyl acetate (2×10 mL). The combined organics were dried over MgSO$_4$, filtered and concentrated in vacuo to give the amine intermediate. The amine intermediate was dissolved in ethanol (600 μL) and NaHCO$_3$ (79 mg, 0.94 mmol) and 2,2-difluoroethyl trifluoromethanesulfonate (74 mg, 0.35 mmol) were added. The reaction mixture was heated at 40° C. overnight, filtered and then purified by preparative LCMS (10-99% ACN/water, HCl modifier as modifier) to give [8-(2,2-difluoroethyl)-10-(p-tolyl)-11-oxa-3,8-diazaspiro[5.5]undecan-3-yl]-(4-isopropoxy-3-methyl-phenyl)methanone. ESI-MS m/z calc. 486.3. Found 487.3 (M+1)$^+$; Retention time: 2.39 minutes (3 min run).

Preparation of (4-benzyl-2-(5-methyloxazol-2-yl)-1-oxa-4,9-diazaspiro[5.5]undecan-9-yl)(4-isopropoxy-3-methylphenyl)methanone

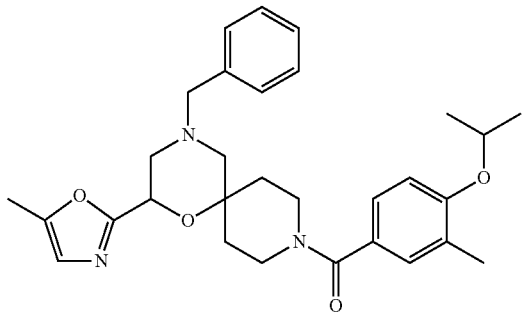 [SMILES: Cc1cnc(C2CN(Cc3ccccc3)CC3(CCN(C(=O)c4ccc(OC(C)C)c(C)c4)CC3)O2)o1]

Step 1:

To tert-butyl 8-benzyl-10-vinyl-11-oxa-3,8-diazaspiro[5.5]undecane-3-carboxylate (600 mg, 1.61 mmol) in ethanol (1 mL) was added HCl (4 mL of 4 M in dioxane, 16.11 mmol) and the mixture was stirred for 30 minutes. The reaction mixture was concentrated in vacuo, then DMF (4 mL), 4-isopropoxy-3-methyl-benzoic acid (313 mg, 1.61 mmol) and dimethylamino(triazolo[4,5-b]pyridin-3-yloxy)methylene]-dimethyl-ammonium hexafluorophosphate (613 mg, 1.61 mmol) were added and the reaction mixture was stirred for 10 minutes. Triethylamine (898 µL, 6.44 mmol) was added and the reaction mixture was stirred overnight at room temperature. The reaction mixture was concentrated in vacuo, diluted with DCM (5 mL), washed with 1 N aq. NaOH (2 mL) and brine (2 mL), dried over MgSO$_4$ and concentrated in vacuo. The residue was purified by silica gel column chromatography using 0-100% EtOAc/hexane as eluent to give (8-benzyl-10-vinyl-11-oxa-3,8-diazaspiro[5.5]undecan-3-yl)-(4-isopropoxy-3-methyl-phenyl)methanone as a pale yellow oil (715 mg, 99%). $^1$H NMR (400 MHz, CDCl$_3$) δ 7.35-7.22 (m, 5H), 7.20-7.14 (m, 2H), 6.79 (d, J=8.2 Hz, 1H), 5.83-5.74 (m, 1H), 5.34-5.26 (m, 1H), 5.15 (d, J=10.6 Hz, 1H), 4.59-4.50 (m, 1H), 4.33-4.14 (m, 2H), 3.59-3.14 (m, 7H), 2.79 (d, J=11.0 Hz, 1H), 2.56 (d, J=11.1 Hz, 1H), 2.19 (s, 3H), 1.91-1.80 (m, 2H), 1.69-1.39 (m, 2H), 1.34 (d, J=6.0 Hz, 6H); ESI-MS m/z calc. 448.6. Found 449.5 (M+1)$^+$; Retention time: 1.54 minutes (3 min run).

Step 2:

To (8-benzyl-10-vinyl-11-oxa-3,8-diazaspiro[5.5]undecan-3-yl)-(4-isopropoxy-3-methyl-phenyl)methanone (2.4 g, 5.6 mmol) and 4-methylmorpholine 4-oxide (698 mg, 5.96 mmol) in acetone (22 mL) and water (2.5 mL) was added osmium tetroxide (677 µL of 2.5% w/w, 0.05 mmol) dropwise and the reaction mixture was stirred for 2 hours. The reaction mixture was quenched with 1M sodium thiosulfate (100 mL) and stirred for 5 minutes, then extracted with EtOAc (4×100 mL), washed with sat. aq. sodium bicarbonate (100 mL) and dried over MgSO$_4$ and concentrated in vacuo to give the diol intermediate (~2.5 g). The reaction mixture was purified by basic alumina column chromatography using 0-20% MeOH/DCM as eluent to obtain [8-benzyl-10-(1,2-dihydroxyethyl)-11-oxa-3,8-diazaspiro[5.5]undecan-3-yl]-(4-isopropoxy-3-methyl-phenyl)methanone (2.18 g, 84%). ESI-MS m/z calc. 482.6. Found 483.7 (M+1)$^+$; Retention time: 1.10 minutes (3 min run).

Step 3:

To [8-benzyl-10-(1,2-dihydroxyethyl)-11-oxa-3,8-diazaspiro[5.5]undecan-3-yl]-(4-isopropoxy-3-methyl-phenyl)methanone (1.53 g, 3.17 mmol) in THF (28 mL) was added NaIO$_4$ (1.36 g, 6.34 mmol) followed by the addition of water (10 mL). The reaction mixture was stirred at room temperature for 2 hours, then filtered through celite, and concentrated in vacuo. The residue was partitioned between sat. aq. sodium bicarbonate (50 mL) and ethyl acetate (50 mL) and the aqueous layer was extracted further with ethyl acetate (3×50 mL). The organics were combined, washed with sat. aq. sodium bicarbonate (50 mL), dried over MgSO$_4$, and concentrated in vacuo. To the intermediate aldehyde (~1.4 g) was added 2-methylpropan-2-ol (17 mL) and 2-methylbut-2-ene (9 mL, 85.08 mmol) and the reaction mixture was cooled to 0° C. A solution of NaClO$_2$ (938 mg, 8.29 mmol) and NaH$_2$PO$_4$ (1.15 g, 8.31 mmol) in water (17 mL) was added dropwise over 5 minutes, and the reaction mixture was stirred for 30 minutes. The reaction mixture was warmed to room temperature, then extracted with ethyl acetate (4×50 mL) and the combined organic layer was washed with brine (15 mL), dried over MgSO$_4$, filtered and concentrated in vacuo to give 8-benzyl-3-(4-isopropoxy-3-methyl-benzoyl)-11-oxa-3,8-diazaspiro[5.5]undecane-10-carboxylic acid as a white foam (1.48 g, 100%). ESI-MS m/z calc. 466.6. Found 467.5 (M+1)$^+$; Retention time: 1.27 minutes (3 min run).

Step 4:

To 8-benzyl-3-(4-isopropoxy-3-methyl-benzoyl)-11-oxa-3,8-diazaspiro[5.5]undecane-10-carboxylic acid (201 mg, 0.43 mmol), 1-aminopropan-2-one (47 mg, 0.43 mmol) and T3P (641 µL of 50% w/w, 1.08 mmol) was added 2-methyltetrahydrofuran (1 mL) and the reaction mixture was then heated at 75° C. for 2 hours. The reaction mixture was cooled to room temperature and partitioned between EtOAc/saturated aq. NaHCO$_3$. The layers were separated and the aqueous layer was extracted with EtOAc (2×). The combined organics were dried over Na$_2$SO$_4$, filtered and concentrated in vacuo to a dark foam. The crude product was purified by silica gel column chromatography using 20-70% EtOAC in DCM as eluent to afford N-acetonyl-8-benzyl-3-(4-isopropoxy-3-methyl-benzoyl)-11-oxa-3,8-diazaspiro[5.5]undecane-10-carboxamide (92 mg, 41%) as a yellow solid. ESI-MS m/z calc. 521.6. Found 522.5 (M+1)$^+$; Retention time: 1.48 minutes (3 min run).

Step 5:

To N-acetonyl-8-benzyl-3-(4-isopropoxy-3-methyl-benzoyl)-11-oxa-3,8-diazaspiro[5.5]undecane-10-carboxamide (136 mg, 0.26 mmol) in THF (3 mL) was added Burgess' Salt (155 mg, 0.65 mmol) and the reaction mixture was heated at 75° C. in a sealed vial for 2 hours. The solvents were removed under reduced pressure, and the residue was dissolved in DMF (1 mL), filtered and purified by Waters preparative LC/MS (1-99% ACN/H$_2$O (5 mM HCl)). The desired fractions were concentrated in vacuo and the residue partitioned between EtOAc/saturated aqueous NaHCO$_3$ solution. The layers were separated and the aqueous layer was extracted with EtOAc (2×). The combined organics were dried over Na$_2$SO$_4$, filtered and concentrated in vacuo to yield 8-benzyl-10-(5-methyloxazol-2-yl)-11-oxa-3,8-diazaspiro[5.5]undecan-3-yl]-(4-isopropoxy-3-methyl-phenyl)methanone (76 mg, 58%) as a foam. ESI-MS m/z calc. 503.6. Found 504.5 (M+1)⁺; Retention time: 1.74 minutes (3 min run).

Preparation of (4-isopropoxy-3-methylphenyl)(2-(5-methyloxazol-2-yl)-4-(2,2,2-trifluoroethyl)-1-oxa-4,9-diazaspiro[5.5]undecan-9-yl)methanone

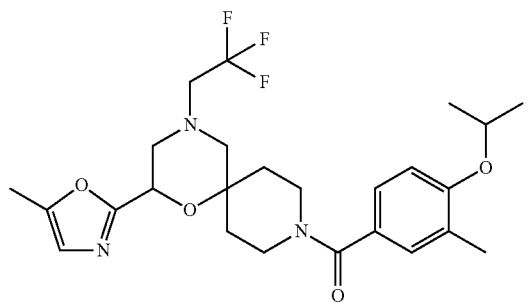 [SMILES: Cc1cnc(C2CN(CC(F)(F)F)CC3(CCN(C(=O)c4ccc(OC(C)C)c(C)c4)CC3)O2)o1]

Step 1:

A mixture of 8-benzyl-10-(5-methyloxazol-2-yl)-11-oxa-3,8-diazaspiro[5.5]undecan-3-yl-(4-isopropoxy-3-methyl-phenyl)methanone (46 mg, 0.09 mmol), palladium, 10 wt. % on activated carbon (19 mg, 0.18 mmol) and ammonium formate (35 mg, 0.55 mmol) in EtOH (750 µL) was heated to 65° C. for 50 minutes. The reaction mixture was cooled to room temperature, microfiltered and 80% of the solvent was removed in vacuo and then diluted with DMF (1 mL) and purified by Waters prep LC/MS (1-99% ACN/H₂O (5 mM HCl)) to yield (4-isopropoxy-3-methyl-phenyl)-[10-(5-methyloxazol-2-yl)-11-oxa-3,8-diazaspiro[5.5]undecan-3-yl] methanone hydrochloride salt (32 mg, 78%). ESI-MS m/z calc. 413.2. Found 414.7 (M+1)⁺; Retention time: 0.99 minutes (3 min run).

Step 2:

A mixture of (4-isopropoxy-3-methyl-phenyl)-[10-(5-methyloxazol-2-yl)-11-oxa-3,8-diazaspiro[5.5]undecan-3-yl] methanone hydrochloride salt (32 mg, 0.07 mmol), 2,2,2-trifluoroethyl trifluoromethanesulfonate (17 µL, 0.11 mmol) and NaHCO₃ (24 mg, 0.28 mmol) in anhydrous EtOH (800 µL) was heated at 80° C. in a sealed vial for 18 hours. The reaction mixture was allowed to cool to room temperature, microfiltered and purified by Waters mass directed LC/MS: (10-99% ACN/H₂O (5 mM HCl)) and concentrated in vacuo to yield (4-isopropoxy-3-methyl-phenyl)-[10-(5-methyloxazol-2-yl)-8-(2,2,2-trifluoroethyl)-11-oxa-3,8-diazaspiro[5.5]undecan-3-yl]methanone (3 mg, 9%) as a white solid. ESI-MS m/z calc. 495.5. Found 496.7 (M+1)⁺; Retention time: 1.99 minutes (3 min run); ¹H NMR (400 MHz, DMSO) δ 7.27-7.13 (m, 2H), 6.96 (d, J=9.0 Hz, 1H), 6.82 (d, J=1.2 Hz, 1H), 4.86 (dd, J=12.0, 4.7 Hz, 1H), 4.71-4.54 (m, 1H), 3.32-3.14 (m, 5H), 3.07 (dd, J=11.5, 2.6 Hz, 1H), 2.90-2.83 (m, 1H), 2.70 (dd, J=18.3, 7.2 Hz, 1H), 2.41-2.23 (m, 6H), 2.13 (s, 3H), 1.64-1.39 (m, 3H), 1.29 (d, J=6.0 Hz, 6H).

Preparation of [8-(2,2-difluoroethyl)-10-(1-methylimidazol-2-yl)-11-oxa-3,8-diazaspiro[5.5]undecan-3-yl]-(4-isopropoxy-3-methyl-phenyl)methanone

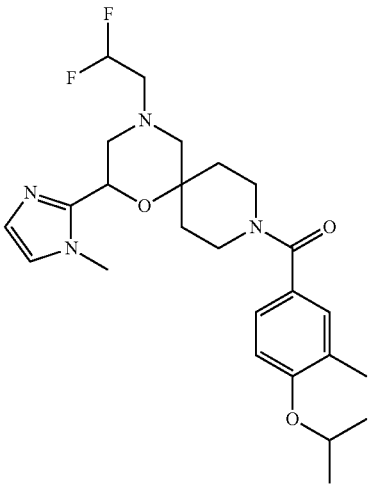 [SMILES: Cc1cc(C(=O)N2CCC3(CC2)CN(CC(F)F)CC(c2nccn2C)O3)ccc1OC(C)C]

Step 1:

To a solution of [8-benzyl-10-(1,2-dihydroxyethyl)-11-oxa-3,8-diazaspiro[5.5]undecan-3-yl]-(4-isopropoxy-3-methyl-phenyl)methanone (417 mg, 0.86 mmol) in THF (10 mL) was added NaIO₄ (468 mg, 2.19 mmol) and H₂O (4 mL). The reaction mixture was stirred at room temperature for 2 hours. The reaction mixture was filtered and partitioned between sat. aq. sodium bicarbonate/ethyl acetate. The aqueous layer was extracted further with ethyl acetate (3×50 mL). The organics were combined, washed with sat. aq. sodium bicarbonate (50 mL), dried over MgSO₄, filtered and concentrated in vacuo to yield 8-benzyl-3-(4-isopropoxy-3-methyl-benzoyl)-11-oxa-3,8-diazaspiro[5.5]undecane-10-carbaldehyde (384 mg, 99%) as a white solid. ESI-MS m/z calc. 450.3. Found 451.3 (M+1)⁺; Retention time: 1.33 minutes (3 min run).

Step 2:

Oxaldehyde (543.1 µL of 40% w/w, 4.75 mmol) was added to a solution of 8-benzyl-3-(4-isopropoxy-3-methyl-benzoyl)-11-oxa-3,8-diazaspiro[5.5]undecane-10-carbaldehyde (306 mg, 0.68 mmol) and ammonium hydroxide (881.4 µL of 30% w/w, 6.79 mmol) in MeOH (3 mL) and the reaction mixture was stirred at room temperature. After 3 hours, an additional 0.5 eq of oxaldehyde and 1.0 eq. of ammonium hydroxide were added and the reaction mixture was stirred for an additional 14 hours. The reaction mixture was partitioned between EtOAc and saturated aqueous NaHCO₃, the layers were separated and the aqueous layer was extracted once more with EtOAc. The combined organics were dried over Na₂SO₄, filtered and concentrated in vacuo to give a dark oil. The residue was purified by silica gel column chromatography using 0-5% MeOH in DCM to yield [8-benzyl-10-(1H-imidazol-2-yl)-11-oxa-3,8-diazaspiro[5.5]undecan-3-yl]-(4-isopropoxy-3-methyl-phenyl)methanone (236 mg, 71%) as a yellow solid. ESI-MS m/z calc. 488.3. Found 489.5 (M+1)⁺; Retention time: 1.45 minutes (3 min run).

Step 3:

[8-Benzyl-10-(1H-imidazol-2-yl)-11-oxa-3,8-diazaspiro[5.5]undecan-3-yl]-(4-isopropoxy-3-methyl-phenyl)methanone (233 mg, 0.48 mmol) was suspended in a mixture of anhydrous DMF (1.5 mL)/THF (0.1 mL) under an atmosphere of nitrogen at 0° C. NaH (19 mg, 0.48 mmol) was added and the reaction mixture was stirred for 30 minutes, then MeI (68 mg, 30 μL, 0.48 mmol) was added and the reaction mixture was stirred for 10 minutes. The reaction mixture was quenched with water and diluted with EtOAc, the layers were separated and the aqueous layer was extracted once more with EtOAc. The combined organics were washed with brine solution (2×5 mL), dried over $Na_2SO_4$, filtered and concentrated in vacuo to an oil. The residue was purified by silica gel column chromatography using 0-5% MeOH in DCM to yield [8-benzyl-10-(1-methylimidazol-2-yl)-11-oxa-3,8-diazaspiro[5.5]undecan-3-yl]-(4-isopropoxy-3-methyl-phenyl)methanone (205 mg, 86%) as a white foam. ESI-MS m/z calc. 502.3. Found 503.1 $(M+1)^+$; Retention time: 1.51 minutes (3 min run); $^1H$ NMR (400 MHz, DMSO) δ 7.38-7.30 (m, 4H), 7.25 (ddd, J=8.4, 5.9, 2.2 Hz, 1H), 7.19 (d, J=7.0 Hz, 2H), 7.10 (d, J=1.1 Hz, 1H), 6.96 (t, J=5.9 Hz, 1H), 6.75 (d, J=1.1 Hz, 1H), 4.96 (ddd, J=9.9, 6.7, 2.4 Hz, 1H), 4.68-4.59 (m, 1H), 3.70 (s, 3H), 3.53 (td, J=13.6, 9.0 Hz, 3H), 3.30-3.15 (m, 2H), 2.93 (dd, J=11.1, 0.7 Hz, 1H), 2.74-2.69 (m, 1H), 2.66-2.52 (m, 2H), 2.13 (s, 3H), 1.95-1.86 (m, 1H), 1.61-1.33 (m, 4H), 1.28 (d, J=6.9 Hz, 6H).

Step 4:

To a solution of [8-benzyl-10-(1-methylimidazol-2-yl)-11-oxa-3,8-diazaspiro[5.5]undecan-3-yl]-(4-isopropoxy-3-methyl-phenyl)methanone (50 mg, 0.10 mmol) in EtOH (500 μL) was added $Pd(OH)_2$ (6.98 mg, 0.01 mmol) and ammonium formate (29 mg, 0.46 mmol) and the reaction mixture was heated at 65° C. for 1.5 hours. The reaction mixture was cooled to room temperature, diluted with ethyl acetate, filtered and washed with sat. aq. $NaHCO_3$ (pH 10)/brine. The aqueous was extracted further with ethyl acetate. The combined organics were dried over $Na_2SO_4$, filtered and concentrated in vacuo to give (4-isopropoxy-3-methyl-phenyl)-[10-(1-methylimidazol-2-yl)-11-oxa-3,8-diazaspiro[5.5]undecan-3-yl]methanone (38 mg, 94%) as a clear colorless oil. ESI-MS m/z calc. 412.2. Found 413.3 $(M+1)^+$; Retention time: 1.16 minutes (3 min run).

Step 5:

2,2-Difluoroethyl trifluoromethanesulfonate (24 mg, 0.11 mmol) was added to a mixture of (4-isopropoxy-3-methyl-phenyl)-[10-(1-methylimidazol-2-yl)-11-oxa-3,8-diazaspiro[5.5]undecan-3-yl]methanone (38 mg, 0.09 mmol) and $NaHCO_3$ (23 mg, 0.28 mmol) in EtOH (0.3 mL). The reaction mixture was purged with argon, sealed and heated at 50° C. for 1 hour. The reaction mixture was cooled to room temperature, diluted with DMF (1 mL), and microfiltered. The residue was purified by Waters mass directed LC/MS: (1-99% ACN/$H_2O$ (5 mM HCl)) to yield [8-(2,2-difluoroethyl)-10-(1-methylimidazol-2-yl)-11-oxa-3,8-diazaspiro[5.5]undecan-3-yl]-(4-isopropoxy-3-methyl-phenyl)methanone hydrochloride salt (28 mg, 58%). ESI-MS m/z calc. 476.3. Found 477.3 $(M+1)^+$; Retention time: 1.5 minutes (3 min run); $^1H$ NMR (400 MHz, DMSO) δ 7.74 (d, J=1.9 Hz, 1H), 7.69 (d, J=1.9 Hz, 1H), 7.18 (dd, J=6.0, 2.0 Hz, 2H), 7.04-6.90 (m, 1H), 6.20 (tt, J=55.5, 4.0 Hz, 1H), 5.34-5.28 (m, 1H), 4.69-4.57 (m, 1H), 3.91 (s, 3H), 3.69-3.41 (m, 1H), 3.37-3.09 (m, 3H), 2.87 (ddd, J=19.6, 18.4, 7.9 Hz, 3H), 2.57-2.51 (m, 2H), 2.46-2.31 (m, 1H), 2.26 (d, J=11.6 Hz, 1H), 2.13 (s, 3H), 1.70-1.52 (m, 3H), 1.29 (d, J=6.0 Hz, 6H).

Preparation of 8-(2,2-difluoroethyl)-10-(1-ethylpyrazol-3-yl)-11-oxa-3,8-diazaspiro[5.5]undecan-3-yl]-(4-isopropoxy-3-methyl-phenyl)methanone and 8-(2,2-difluoroethyl)-10-(2-ethylpyrazol-3-yl)-11-oxa-3,8-diazaspiro[5.5]undecan-3-yl]-(4-isopropoxy-3-methyl-phenyl)methanone

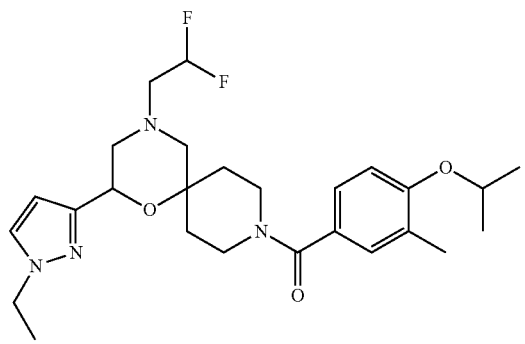

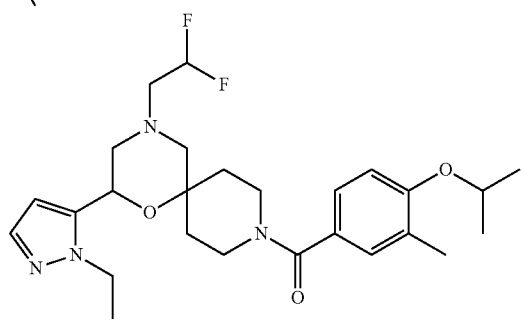

To 8-(2,2-difluoroethyl)-10-(1H-pyrazol-3-yl)-11-oxa-3,8-diazaspiro[5.5]undecane (193 mg, 0.54 mmol), 4-isopropoxy-3-methyl-benzoic acid (110 mg, 0.56 mmol) and HATU (215 mg, 0.56 mmol) was added N,N-dimethylformamide (1.3 mL). The reaction mixture was stirred for 5 minutes at room temperature, then diisopropylethylamine (374 μL, 2.15 mmol) was added and the reaction mixture was stirred overnight. The reaction mixture was then diluted with sat. $NaHCO_3$ (5 mL) and the aqueous layer was extracted with ethyl acetate (2×10 mL). The combined organic layer was washed with water (5 mL), dried over $MgSO_4$, filtered and concentrated in vacuo. The residue was passed through a silica gel plug, eluting with 30% EtOAc/DCM. The solvent was concentrated in vacuo and the residue was dissolved in N,N-dimethylformamide (1.3 mL) under an atmosphere of nitrogen, cooled to 0° C., then treated with NaH (21 mg, 0.54 mmol). The reaction mixture was stirred at 0° C. for 10 minutes, then at room temperature for 5 minutes, then iodoethane (50 μL, 0.63 mmol) was added and the reaction mixture stirred for 1 hour. The reaction mixture was diluted with methanol, microfiltered and purified by preparative LCMS (10-99% ACN/Water, 5 mM HCl modifier) to give 8-(2,2-difluoroethyl)-10-(1-ethylpyrazol-3-yl)-11-oxa-3,8-diazaspiro[5.5]undecan-3-yl]-(4-isopropoxy-3-methyl-phenyl)methanone (26 mg, 14%) and 8-(2,2-difluoroethyl)-10-(2-ethylpyrazol-3-yl)-11-oxa-3,8-diazaspiro[5.5]undecan-3-yl]-(4-isopropoxy-3-methyl-phenyl)methanone (24 mg, 13%).

Data for 8-(2,2-difluoroethyl)-10-(1-ethylpyrazol-3-yl)-11-oxa-3,8-diazaspiro[5.5]undecan-3-yl-(4-isopropoxy-3-methyl-phenyl)methanone: ESI-MS m/z calc. 490.3. Found 491.3 (M+1); Retention time: 1.89 minutes (3 min run); $^1$H NMR (400 MHz, CD$_3$CN) δ 7.54 (d, J=2.3 Hz, 1H), 7.20-7.17 (m, 2H), 7.00-6.71 (m, 1H), 6.92 (d, J=9.0 Hz, 1H), 6.34 (d, J=2.3 Hz, 1H), 5.26 (d, J=10.2 Hz, 1H), 4.66-4.60 (m, 1H), 4.14 (q, J=7.3 Hz, 2H), 3.63-3.35 (m, 5H), 3.37-3.13 (m, 3H), 3.08 (d, J=13.2 Hz, 1H), 2.95 (d, J=12.6 Hz, 1H), 2.18 (s, 3H), 1.75-1.55 (m, 4H), 1.41 (t, J=8 Hz, 3H), 1.32 (d, J=6.0 Hz, 6H).

Data for 8-(2,2-difluoroethyl)-10-(2-ethylpyrazol-3-yl)-11-oxa-3,8-diazaspiro[5.5]undecan-3-yl-(4-isopropoxy-3-methyl-phenyl)methanone: ESI-MS m/z calc. 490.3. Found 491.5 (M+1)$^+$; Retention time: 1.82 minutes (3 min run); $^1$H NMR (400 MHz, CD$_3$CN) δ 7.45 (s, 1H), 7.22-7.20 (m, 2H), 6.94 (d, J=8 Hz, 1H), 6.63-6.34 (m, 1H), 6.34 (s, 1H), 6.29 (s, 1H), 5.29 (d, J=8.6 Hz, 1H), 4.74-4.54 (m, 1H), 4.24 (q, J=7.0 Hz, 2H), 3.40-3.09 (m, 6H), 3.05-2.59 (m, 3H), 2.20 (s, 3H), 1.89-1.50 (m, 4H), 1.43 (t, J=8 Hz, 3H), 1.34 (d, J=6 Hz, 6H).

Preparation of tert-butyl 8-(2,2-difluoroethyl)-10-(1-methylpyrazol-3-yl)-11-oxa-3,8-diazaspiro[5.5]undecane-3-carboxylate and tert-butyl 8-(2,2-difluoroethyl)-10-(2-methylpyrazol-3-yl)-11-oxa-3,8-diazaspiro[5.5]undecane-3-carboxylate

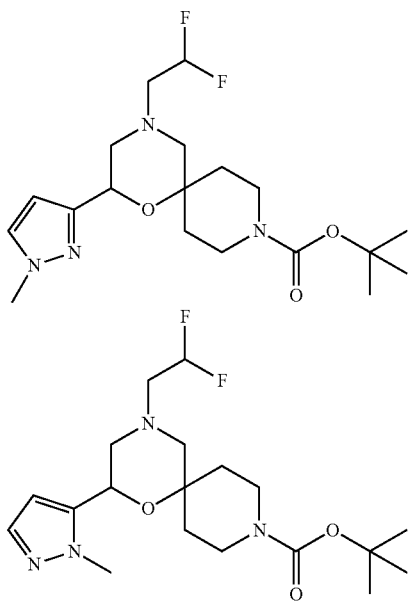

A solution tert-butyl 8-(2,2-difluoroethyl)-10-prop-2-ynoyl-11-oxa-3,8-diazaspiro[5.5]undecane-3-carboxylate (40 mg, 0.11 mmol), hydrazine (69 mg, 67 µL, 2.15 mmol) and ethanol (800 µL) was stirred for one hour at room temperature. The reaction mixture was concentrated in vacuo, diluted with 1:1 of 1M aq. NaOH/sat. aq. NaHCO$_3$ (2 mL), and extracted with DCM (3×3 mL). The combined organics were dried over MgSO$_4$, filtered and concentrated in vacuo to give the pyrazole intermediate, which was dissolved in N,N-dimethylformamide (0.5 mL) and NaH (8 mg, 0.20 mmol) was added. The reaction mixture was stirred for 20 minutes at room temperature, then iodomethane (30 mg, 13 µL, 0.21 mmol) was added and the reaction mixture was stirred for 2 hours. The reaction mixture was concentrated in vacuo and the residue was purified by silica gel column chromatography using 0-100% EtOAc/DCM as eluent to give tert-butyl 8-(2,2-difluoroethyl)-10-(1-methylpyrazol-3-yl)-11-oxa-3,8-diazaspiro[5.5]undecane-3-carboxylate and tert-butyl 8-(2,2-difluoroethyl)-10-(2-methylpyrazol-3-yl)-11-oxa-3,8-diazaspiro[5.5]undecane-3-carboxylate as a colorless foam in a 1:1 mixture (36 mg, 84%). ESI-MS m/z calc. 400.2. Found 401.5 (M+1)$^+$; Retention time: 1.63 and 1.71 minutes (3 min run); $^1$H NMR (400 MHz, CDCl$_3$) δ 7.34-7.21 (m, 1H), 6.17-6.10 (m, 1H), 5.95-5.64 (m, 1H), 4.85-4.78 (m, 1H), 3.89-3.79 (m, 3H), 3.74-3.48 (m, 2H), 3.28-3.04 (m, 2H), 2.99-2.94 (m, 1H), 2.75-2.60 (m, 3H), 2.50-2.32 (m, 2H), 1.60-1.41 (m, 4H), 1.39-1.37 (m, 9H).

Preparation of 8-(2,2-difluoroethyl)-10-(1-methylpyrazol-3-yl)-11-oxa-3,8-diazaspiro[5.5]undecan-3-yl]-(4-isopropoxy-3-methyl-phenyl)methanone and 8-(2,2-difluoroethyl)-10-(2-methylpyrazol-3-yl)-11-oxa-3,8-diazaspiro[5.5]undecan-3-yl]-(4-isopropoxy-3-methyl-phenyl)methanone

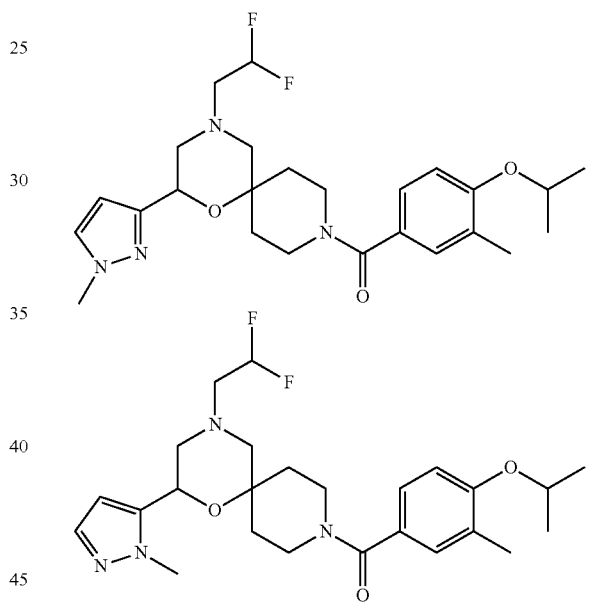

The mixture of regioisomeric pyrazoles, tert-butyl 8-(2,2-difluoroethyl)-10-(2-methylpyrazol-3-yl)-11-oxa-3,8-diazaspiro[5.5]undecane-3-carboxylate and tert-butyl difluoroethyl)-10-(2-methylpyrazol-3-yl)-11-oxa-3,8-diazaspiro[5.5]undecane-3-carboxylate (31 mg, 0.08 mmol) was dissolved in ethanol (100 µL) and HCl (193.5 µL of 4 M in dioxane, 0.77 mmol) was added. The reaction mixture was stirred for 2 hours at room temperature, and then concentrated in vacuo. 4-Isopropoxy-3-methyl-benzoic acid (15.04 mg, 0.08 mmol), HATU (29 mg, 0.08 mmol) and N,N-dimethylformamide (484 µL) were added, followed by the addition of diisopropylethylamine (54 µL, 0.31 mmol). The reaction mixture was stirred for 2 hours at room temperature, then diluted with methanol, microfiltered and purified by preparative LCMS (10-99% ACN/Water, 5 mM HCl modifier) to give the title compounds as white solids.

Data for 8-(2,2-difluoroethyl)-10-(1-methylpyrazol-3-yl)-11-oxa-3,8-diazaspiro[5.5]undecan-3-yl-(4-isopropoxy-3-methyl-phenyl)methanone: ESI-MS m/z calc. 476.3. Found 477.3 (M+1)$^+$; Retention time: 1.77 minutes (3 min run); $^1$H NMR (400 MHz, CD$_3$CN) δ 7.50 (d, J=2.3 Hz, 1H), 7.21-7.17 (m, 2H), 7.00-6.69 (m, 1H), 6.92 (d, J=9.1 Hz, 1H), 6.35 (d, J=2.3 Hz, 1H), 5.26 (d, J=9.6 Hz, 1H), 4.66-4.60 (m, 1H), 3.85 (s, 3H), 3.67-3.37 (m, 5H), 3.36-3.01 (m, 4H), 2.95 (d, J=12.7 Hz, 1H), 2.18 (s, 3H), 1.81-1.51 (m, 4H), 1.32 (t, J=5.4 Hz, 6H).

Data for 8-(2,2-difluoroethyl)-10-(2-methylpyrazol-3-yl)-11-oxa-3,8-diazaspiro[5.5]undecan-3-yl-(4-isopropoxy-3-methyl-phenyl)methanone: $^1$H NMR (400 MHz, CD$_3$CN) δ 7.39 (d, J=1.9 Hz, 1H), 7.24-7.19 (m, 2H), 6.92 (d, J=9.0 Hz, 1H), 6.72-6.39 (m, 1H), 6.28 (d, J=1.9 Hz, 1H), 5.32-5.26 (m, 1H), 4.70-4.61 (m, 1H), 3.90 (s, 3H), 3.49-3.19 (m, 6H), 3.05-2.69 (m, 4H), 2.21 (s, 3H), 1.85-1.54 (m, 4H), 1.30 (t, J=10.1 Hz, 6H); ESI-MS m/z calc. 476.3. Found 477.4 (M+1); Retention time: 6.04 minutes (15 min run).

(4-(2,2-Difluoroethyl)-2-(1-methyl-1H-pyrazol-3-yl)-1-oxa-4,9-diazaspiro[5.5]undecan-9-yl)(3-fluoro-4-isopropoxyphenyl)methanone was prepared using the procedure as described above, using 3-fluoro-4-isopropoxy-benzoic acid as the acid reagent.

Preparation of 8-(2,2-difluoroethyl)-9-phenyl-11-oxa-3,8-diazaspiro[5.5]undecan-3-yl]-(4-isopropoxy-3-methoxy-phenyl)methanone

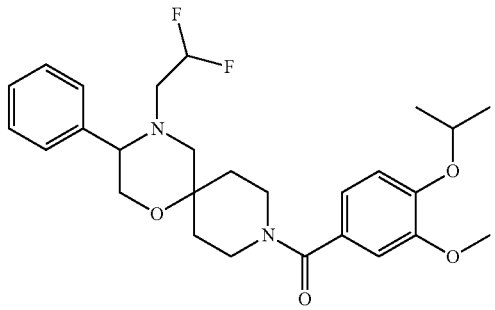 [SMILES: COc1cc(C(=O)N2CCC3(CC2)CN(CC(F)F)C(c2ccccc2)CO3)ccc1OC(C)C]

Step 1:
To a solution of tert-butyl 8-[(4-methoxyphenyl)methyl]-9-phenyl-11-oxa-3,8-diazaspiro[5.5]undecane-3-carboxylate (500 mg, 1.11 mmol) in DCM (1 mL) was added HCl (3 mL of 4 M in dioxane, 11.05 mmol) dropwise. The reaction mixture was stirred overnight at room temperature. The solvent was concentrated in vacuo and the residue was dissolved in the minimum amount of DCM and precipitated with ether. The solvent was decanted and the residue was again washed with ether and dried to give 8-[(4-methoxyphenyl)methyl]-9-phenyl-11-oxa-3,8-diazaspiro[5.5]undecane (400 mg, 93%). ESI-MS m/z calc. 352.2. Found 353.7 (M+1)$^+$; Retention time: 0.99 minutes (3 min run).

Step 2:
To a solution of 8-[(4-methoxyphenyl)methyl]-9-phenyl-11-oxa-3,8-diazaspiro[5.5]undecane (400 mg, 1.03 mmol) in DMF (2 mL) was added DIEA (266 mg, 358 µL, 2.06 mmol) followed by the addition of 4-isopropoxy-3-methoxy-benzoic acid (238 mg, 1.13 mmol) and HATU (469 mg, 1.23 mmol). The reaction mixture was stirred for 10 minutes at room temperature. The reaction mixture was quenched with water and the aqueous layer was extracted with ethyl acetate. The organic layer was washed with water (3×10 mL), dried over MgSO$_4$, filtered and concentrated in vacuo. The crude material was purified by silica gel column chromatography using 0 to 60% EtOAc in hexanes as eluent to obtain (4-isopropoxy-3-methoxy-phenyl)-[8-(4-methoxyphenyl)methyl]-9-phenyl-11-oxa-3,8-diazaspiro[5.5]undecan-3-yl]methanone (300 mg, 54%). $^1$H NMR (400 MHz, CDCl$_3$) δ 7.40-7.18 (m, 7H), 6.97-6.78 (m, 5H), 4.94-4.71 (m, 1H), 4.59-4.50 (m, 1H), 4.33-4.17 (m, 1H), 3.83 (d, J=13.0 Hz, 6H), 3.69-3.39 (m, 3H), 3.32 (d, J=13.0 Hz, 1H), 3.02-2.89 (m, 1H), 2.80 (s, 2H), 2.69-2.48 (m, 2H), 2.09-1.85 (m, 2H), 1.37 (d, J=6.1 Hz, 6H), 1.29-1.14 (m, 1H), 0.95-0.79 (m, 1H); ESI-MS m/z calc. 544.7. Found 545.3 (M+1)$^+$; Retention time: 1.58 minutes (3 min run).

Step 3:
To (4-isopropoxy-3-methoxy-phenyl)-[8-[(4-methoxyphenyl)methyl]-9-phenyl-11-oxa-3,8-diazaspiro[5.5]undecan-3-yl]methanone (175 mg, 0.32 mmol), Pd(OH)$_2$ (129 mg, 0.9186 mmol) and ammonium formate (405 mg, 6.43 mmol) was added ethanol. The reaction mixture was then heated at 65° C. for 16 hours. The reaction mixture was filtered, the solvent evaporated and the residue was purified by silica gel column chromatography using 0 to 60% EtOAc in hexanes as eluent to give (4-isopropoxy-3-methoxy-phenyl)-(9-phenyl-11-oxa-3,8-diazaspiro[5.5]undecan-3-yl) methanone. ESI-MS m/z calc. 424.5. Found 425.5 (M+1)$^+$; Retention time: 1.28 minutes (3 min run).

Step 4:
To a solution of (4-isopropoxy-3-methoxy-phenyl)-(9-phenyl-11-oxa-3,8-diazaspiro[5.5]undecan-3-yl)methanone (15 mg, 0.04 mmol) in ethanol (375 µL) was added NaHCO$_3$ (12 mg, 0.14 mmol), followed by the addition of 2,2-difluoroethyl trifluoromethanesulfonate (11 mg, 0.05 mmol). The reaction mixture was heated at 80° C. for 16 hours. The reaction mixture was filtered and purified by Waters mass directed LC/MS: (1-99% ACN/H$_2$O (5 mM HCl) to obtain [8-(2,2-difluoroethyl)-9-phenyl-11-oxa-3,8-diazaspiro[5.5] undecan-3-yl]-(4-isopropoxy-3-methoxy-phenyl)methanone (5 mg, 29%). $^1$H NMR (400 MHz, CDCl$_3$) δ 7.45-7.36 (m, 5H), 6.98-6.83 (m, 3H), 5.25 (d, J=10.4 Hz, 1H), 4.57 (dt, J=12.2, 6.1 Hz, 1H), 3.85 (s, 3H), 3.60 (d, J=10.9 Hz, 1H), 3.47-3.12 (m, 6H), 2.86-2.60 (m, 3H), 1.88-1.50 (m, 5H), 1.38 (d, J=6.1 Hz, 6H); ESI-MS m/z calc. 488.5. Found 489.7 (M+1)$^+$; Retention time: 2.17 minutes (3 min run).

(4-Isopropoxy-3-methoxy-phenyl)-[9-phenyl-8-(2,2,2-trifluoroethyl)-11-oxa-3,8-diazaspiro[5.5]undecan-3-yl] methanone was prepared using the chemistry described above using 2,2,2-trifluoroethyl trifluoromethanesulfonate in step 4. ESI-MS m/z calc. 506.6. Found 507.5 (M+1)$^+$; Retention time: 2.27 minutes (3 min run).

Preparation of [10-ethyl-8-(2,2,2-trifluoroethyl)-11-oxa-3,8-diazaspiro[5.5]undecan-3-yl]-(4-isopropoxy-3-methyl-phenyl)methanone

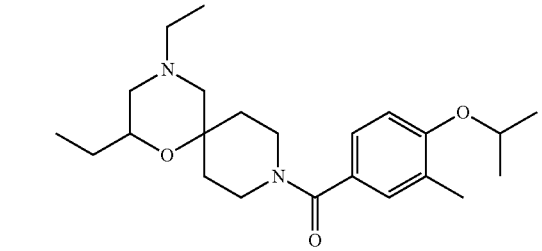 [SMILES: CCC1CN(CC)CC2(CCN(C(=O)c3ccc(OC(C)C)c(C)c3)CC2)O1]

Step 1:
To tert-butyl 8-benzyl-10-vinyl-11-oxa-3,8-diazaspiro [5.5]undecane-3-carboxylate (600 mg, 1.61 mmol) in ethanol (1 mL) was added HCl (4.028 mL of 4 M in dioxane, 16.11 mmol) and the reaction mixture was stirred for 30 minutes. The reaction mixture was concentrated in vacuo, then DMF (4 mL), 4-isopropoxy-3-methyl-benzoic acid (313 mg, 1.61 mmol) and HATU (613 mg, 1.61 mmol) were added and the reaction mixture was stirred for 10 minutes. Triethylamine (898 µL, 6.44 mmol) was added and the reaction mixture was stirred for 16 hours, The reaction mixture was concentrated in vacuo, diluted with DCM (5 mL), washed with 1 N aq. NaOH (2 mL) and brine (2 mL), dried over MgSO₄, filtered and concentrated in vacuo. The crude material was purified by silica gel column chromatography using 0-100% EtOAc/hexanes eluent to give (8-benzyl-10-vinyl-11-oxa-3,8-diazaspiro [5.5]undecan-3-yl)-(4-isopropoxy-3-methyl-phenyl)methanone (715 mg, 99%) as a pale yellow oil. ¹H NMR (400 MHz, CDCl₃) δ 7.35-7.22 (m, 5H), 7.20-7.14 (m, 2H), 6.79 (d, J=8.2 Hz, 1H), 5.83-5.74 (m, 1H), 5.34-5.26 (m, 1H), 5.15 (d, J=10.6 Hz, 1H), 4.59-4.50 (m, 1H), 4.33-4.14 (m, 2H), 3.59-3.14 (m, 7H), 2.79 (d, J=11.0 Hz, 1H), 2.56 (d, J=11.1 Hz, 1H), 2.19 (s, 3H), 1.91-1.80 (m, 2H), 1.69-1.39 (m, 2H), 1.34 (d, J=6.0 Hz, 6H); ESI-MS m/z calc. 448.6. Found 449.5 (M+1)⁺; Retention time: 1.48 minutes (3 min run).

Step 2:
To (8-benzyl-10-vinyl-11-oxa-3,8-diazaspiro[5.5]undecan-3-yl)-(4-isopropoxy-3-methyl-phenyl)methanone (150 mg, 0.33 mmol), ammonium formate (74 mg, 1.17 mmol) and Pd (17 mg, 0.02 mmol) (10% on activated carbon) was added methanol (2 mL) and the reaction mixture was heated at 75° C. for 30 minutes. The reaction mixture was cooled, microfiltered and concentrated in vacuo, then diluted with DCM (20 mL), washed with aq. 1M NaOH (10 mL), extracted with DCM (120 mL), washed with brine (10 mL), dried over MgSO₄ and concentrated in vacuo to give (10-ethyl-11-oxa-3,8-diazaspiro[5.5]undecan-3-yl)-(4-isopropoxy-3-methyl-phenyl)methanone (100 mg, 83%) as a colorless oil. ESI-MS m/z calc. 360.5. Found 361.3 (M+1)⁺; Retention time: 1.25 minutes (3 min run).

Step 3:
To (10-ethyl-11-oxa-3,8-diazaspiro[5.5]undecan-3-yl)-(4-isopropoxy-3-methyl-phenyl)methanone (33 mg, 0.09 mmol) in ethanol (0.5 mL) was added NaHCO₃ (15 mg, 0.18 mmol) then iodoethane (21 mg, 11 µL, 0.14 mmol). The reaction mixture was heated at 50° C. for 16 hours, then microfiltered and purified by prep LCMS (1-99% ACN/Water, 5 mM HCl modifier) to give (8,10-diethyl-11-oxa-3,8-diazaspiro[5.5]undecan-3-yl)-(4-isopropoxy-3-methyl-phenyl)methanone hydrochloride salt (39 mg, 100%); ESI-MS m/z calc. 388.3. Found 389.7 (M+1)⁺; Retention time: 1.36 (3 min run).

[10-ethyl-8-(2,2,2-trifluoroethyl)-11-oxa-3,8-diazaspiro [5.5]undecan-3-yl]-(4-isopropoxy-3-methyl-phenyl)methanone was also prepared using the procedure above using 2,2,2-trifluoroethyl trifluoromethanesulfonate in step 3. ESI-MS m/z calc. 442.2. Found 443.7 (M+1)⁺; Retention time: 2.33 (3 min run).

Preparation of (8-benzyl-10-ethyl-11-oxa-3,8-diazaspiro[5.5]undecan-3-yl)-(4-isopropoxy-3-methyl-phenyl)methanone

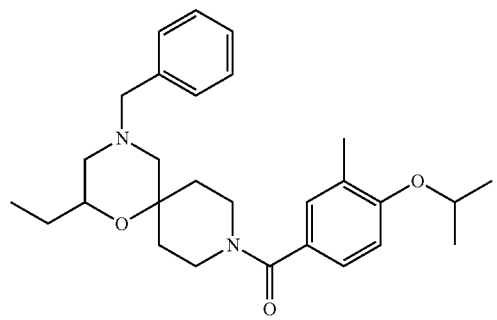 [SMILES: CCC1CN(Cc2ccccc2)CC2(CCN(C(=O)c3ccc(OC(C)C)c(C)c3)CC2)O1]

A mixture of (8-benzyl-10-vinyl-11-oxa-3,8-diazaspiro [5.5]undecan-3-yl)-(4-isopropoxy-3-methyl-phenyl)methanone (50 mg, 0.11 mmol) and Pd (4 mg, 0.003 mmol) (10% on activated carbon) in methanol (1 mL) was stirred under an atmosphere of hydrogen for 2 hours. The reaction mixture was microfiltered and purified by prep LCMS (10-99% ACN/Water, 5 mM HCl modifier) to give (8-benzyl-10-ethyl-11-oxa-3,8-diazaspiro[5.5]undecan-3-yl)-(4-isopropoxy-3-methyl-phenyl)methanone hydrochloride salt (8 mg, 15%) as a white solid. ESI-MS m/z calc. 450.3. Found 451.5 (M+1)⁺; Retention time: 1.36 minutes (3 min run).

Preparation of [8-benzyl-10-(hydroxymethyl)-11-oxa-3,8-diazaspiro[5.5]undecan-3-yl]-(4-isopropoxy-3-methyl-phenyl)methanone

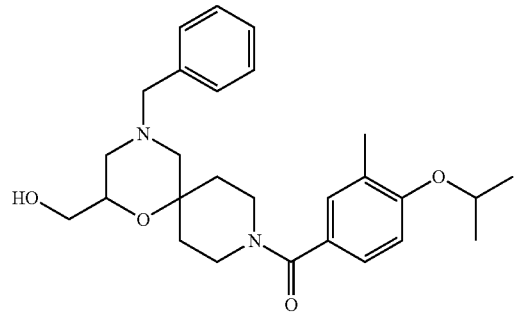 [SMILES: Cc1cc(C(=O)N2CCC3(CC2)CN(Cc2ccccc2)CC(CO)O3)ccc1OC(C)C]

To (8-benzyl-10-vinyl-11-oxa-3,8-diazaspiro[5.5]undecan-3-yl)-(4-isopropoxy-3-methyl-phenyl)methanone (135 mg, 0.30 mmol) in DCM (4 mL) and methanol (1 mL) at −78° C. was bubbled ozone until the solution turned faint blue. NaBH₄ (91 mg, 2.41 mmol) and methanol (~2 mL) was added under an atmosphere of nitrogen and the reaction mixture was stirred at −78° C. for 30 minutes, then at 0° C. for 1 hour. The reaction mixture was concentrated in vacuo, quenched with 4N HCl/dioxane, concentrated in vacuo, then diluted with methanol-water (1:1), microfiltered and purified by prep LCMS (1-99% ACN/Water, 5 mM HCl modifier) to give [8-benzyl-10-(hydroxymethyl)-11-oxa-3,8-diazaspiro[5.5] undecan-3-yl]-(4-isopropoxy-3-methyl-phenyl)methanone (50 mg, 34%). ESI-MS m/z calc. 452.6. Found 453.5 (M+1)⁺; Retention time: 1.18 minutes (3 min run).

Preparation of [10-(ethoxymethyl)-8-ethyl-11-oxa-3,8-diazaspiro[5.5]undecan-3-yl]-(4-isopropoxy-3-methyl-phenyl)methanone

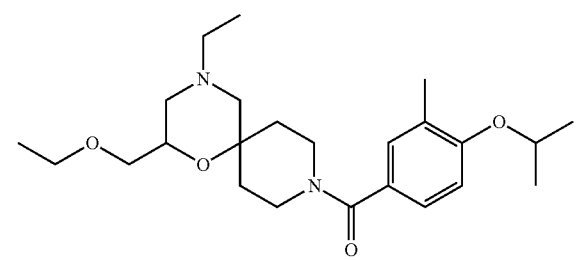 [SMILES: CCOCC1CN(CC)CC2(CCN(C(=O)c3ccc(OC(C)C)c(C)c3)CC2)O1]

Step 1:
To [8-benzyl-10-(hydroxymethyl)-11-oxa-3,8-diazaspiro [5.5]undecan-3-yl]-(4-isopropoxy-3-methyl-phenyl)methanone hydrochloride salt (43 mg, 0.09 mmol) in DMF (0.5 mL) was added sodium hydride (11 mg, 0.30 mmol) and the reaction mixture was stirred for 20 minutes. Iodoethane (30 µL, 0.38 mmol) was added and the reaction mixture was stirred for 3 hours, then diluted with EtOAc, filtered, concentrated in vacuo. The residue was purified by silica gel column chromatography using 10-100 EtOAc/hexanes eluent to give the ether intermediate as pale yellow oil. The oil was dissolved in methanol (0.6 mL), and Pd (5 mg, 0.004 mmol) and ammonium formate (27 mg, 0.44 mmol) were added and the reaction mixture was heated at 75° C. for 40 minutes. The reaction mixture was filtered, concentrated in vacuo, diluted with ethyl acetate, washed with 1:1 3M NaOH/sat. aq. NaHCO₃, dried over MgSO₄, filtered and concentrated in vacuo to give [10-(ethoxymethyl)-11-oxa-3,8-diazaspiro[5.5]undecan-3-yl]-(4-isopropoxy-3-methyl-phenyl)methanone (25 mg, 74%) as a pale yellow oil. ESI-MS m/z calc. 390.5. Found 391.3 (M+1)⁺; Retention time: 1.17 minutes (3 min run).

Step 2:
To [10-(ethoxymethyl)-11-oxa-3,8-diazaspiro[5.5]undecan-3-yl]-(4-isopropoxy-3-methyl-phenyl)methanone (25 mg, 0.06 mmol) and NaHCO₃ (16 mg, 0.19 mmol) in ethanol (0.5 mL) was added iodoethane (15 mg, 8 μL, 0.10 mmol) and the reaction mixture was heated in a sealed vial at 70° C. for 24 hours. The reaction mixture was microfiltered and purified by prep LCMS (1-99% ACN/Water, 5 mM HCl modifier) to give [10-(ethoxymethyl)-8-ethyl-11-oxa-3,8-diazaspiro[5.5]undecan-3-yl]-(4-isopropoxy-3-methyl-phenyl)methanone hydrochloride salt (19 mg, 66%) as a colorless oil. ESI-MS m/z calc. 418.3. Found 419.7 (M+1)⁺; Retention time: 1.20 minutes (3 min run).

Preparation of [8-benzyl-10-(1-hydroxy-1-methyl-ethyl)-11-oxa-3,8-diazaspiro[5.5]undecan-3-yl]-(4-isopropoxy-3-methyl-phenyl)methanone

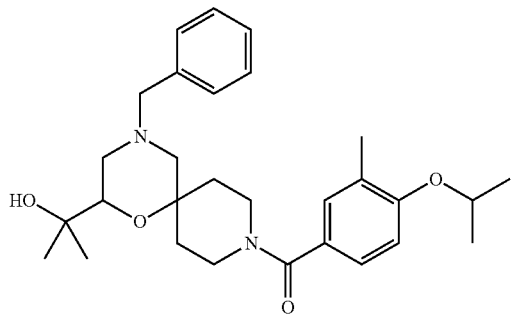 [SMILES: Cc1cc(C(=O)N2CCC3(CC2)CN(Cc2ccccc2)CC(C(C)(C)O)O3)ccc1OC(C)C]

Step 1:
8-Benzyl-3-(4-isopropoxy-3-methyl-benzoyl)-11-oxa-3,8-diazaspiro[5.5]undecane-10-carboxylic acid (10 mg, 0.02 mmol), K₂CO₃ (12 mg, 0.09 mmol) and iodomethane (2 μL, 0.03 mmol) in DMF (0.1 mL) was stirred for 1 hour. The mixture was diluted with ethyl acetate (5 mL), washed with water (2 mL) and brine (2 mL), dried over magnesium sulfate, filtered and evaporated to give methyl 8-benzyl-3-(4-isopropoxy-3-methyl-benzoyl)-11-oxa-3,8-diazaspiro[5.5]undecane-10-carboxylate (10 mg, 100%). ESI-MS m/z calc. 480.6. Found 481.5 (M+1)⁺; Retention time: 1.82 minutes (3 min run).

Step 2:
To methyl 8-benzyl-3-(4-isopropoxy-3-methyl-benzoyl)-11-oxa-3,8-diazaspiro[5.5]undecane-10-carboxylate (100 mg, 0.21 mmol) in THF (0.5 mL) at −78° C. was added chloro(methyl)magnesium (150 μL, of 3 M in THF, 0.45 mmol) and the reaction mixture was stirred for 2 hours then allowed to warm to room temperature. The reaction mixture was diluted with water, extracted with ethyl acetate and dried over MgSO₄, then purified by silica gel column chromatography using 0-100% EtOAc/DCM as eluent to give [8-benzyl-10-(1-hydroxy-1-methyl-ethyl)-11-oxa-3,8-diazaspiro[5.5] undecan-3-yl]-(4-isopropoxy-3-methyl-phenyl)methanone (81 mg, 80%) as a white foam. ESI-MS m/z calc. 480.6. Found 481.7 (M+1)⁺; Retention time: 1.22 minutes (3 min run).

Preparation of [10-(1-hydroxy-1-methyl-ethyl)-8-(2,2,2-trifluoroethyl)-11-oxa-3,8-diazaspiro[5.5]undecan-3-yl]-(4-isopropoxy-3-methyl-phenyl)methanone

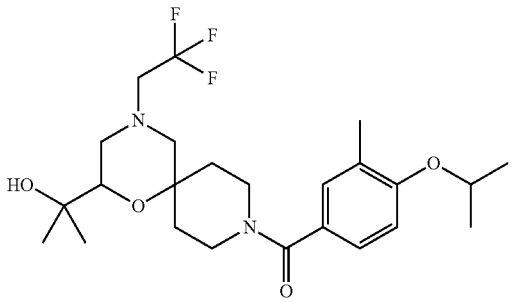 [SMILES: Cc1cc(C(=O)N2CCC3(CC2)CN(CC(F)(F)F)CC(C(C)(C)O)O3)ccc1OC(C)C]

Step 1:
[8-Benzyl-10-(1-hydroxy-1-methyl-ethyl)-11-oxa-3,8-diazaspiro[5.5]undecan-3-yl]-(4-isopropoxy-3-methyl-phenyl)methanone (75 mg, 0.16 mmol) was dissolved in ethanol (3 mL) and Pd (8 mg, 0.008 mmol) and ammonium formate (50 mg, 0.80 mmol) were added and the reaction mixture was heated at 75° C. for 30 minutes. The reaction mixture was filtered, concentrated in vacuo, diluted with ethyl acetate, washed with 3M NaOH, dried over MgSO₄, filtered and concentrated in vacuo to give (2-(2-hydroxypropan-2-yl)-1-oxa-4,9-diazaspiro[5.5]undecan-9-yl)(4-isopropoxy-3-methylphenyl)methanone (60 mg, 94%). ESI-MS m/z calc. 390.3. Found 391.5 (M+1)⁺; Retention time: 1.27 minutes (3 min run).

Step 2:
(2-(2-Hydroxypropan-2-yl)-1-oxa-4,9-diazaspiro[5.5]undecan-9-yl)(4-isopropoxy-3-methylphenyl)methanone (25 mg, 0.06 mmol) was dissolved in dry ethanol (300 μL) and NaHCO₃ (50 mg, 0.60 mmol) and 2,2,2-trifluoroethyl trifluoromethanesulfonate (20 μL, 0.13 mmol) were added and the reaction mixture was heated at 80° C. for 16 hours. The reaction mixture was filtered, concentrated in vacuo and purified by silica gel column chromatography using 0-100% EtOAc/hexanes as eluent to give [10-(1-hydroxy-1-methyl-ethyl)-8-(2,2,2-trifluoroethyl)-11-oxa-3,8-diazaspiro[5.5]undecan-3-yl]-(4-isopropoxy-3-methyl-phenyl)methanone (15 mg, 53%) as a colorless oil. ESI-MS m/z calc. 472.5. Found 473.5 (M+1)⁺; Retention time: 1.93 minutes (3 min run).

Preparation of [8-benzyl-10-(2-hydroxyethyl)-11-oxa-3,8-diazaspiro[5.5]undecan-3-yl]-(4-isopropoxy-3-methyl-phenyl)methanone

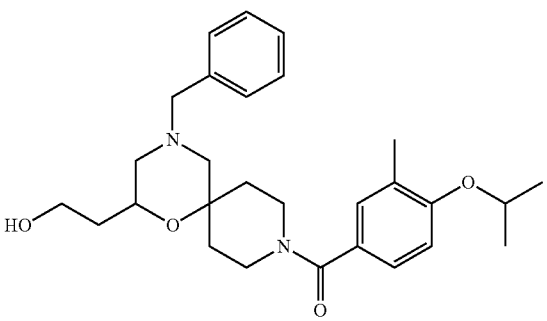 [SMILES: Cc1cc(C(=O)N2CCC3(CC2)CN(Cc2ccccc2)CC(CCO)O3)ccc1OC(C)C]

To (8-benzyl-10-vinyl-11-oxa-3,8-diazaspiro[5.5]undecan-3-yl)-(4-isopropoxy-3-methyl-phenyl)methanone (95 mg, 0.21 mmol) and chloro-tris(triphenylphosphoranyl)rhodium (6 mg, 0.006 mmol) in THF (1 mL) was added catecholborane (635 µL of 1 M in THF, 0.64 mmol) at 0° C. and the reaction mixture was stirred at room temperature for 1 hour. Sodium hydroxide (0.3 mL of 3 M, 0.90 mmol) was added slowly, followed by the addition of $H_2O_2$ (0.3 mL of 30% w/w, 2.94 mmol) and the reaction mixture was stirred for 15 minutes. The reaction mixture was extracted three times with ethyl acetate and the combined organics were concentrated in vacuo and purified by prep LCMS (1-99% ACN/Water, 5 mM HCl modifier) to give [8-benzyl-10-(2-hydroxyethyl)-11-oxa-3,8-diazaspiro[5.5]undecan-3-yl]-(4-isopropoxy-3-methyl-phenyl)methanone hydrochloride salt (55 mg, 50%) as a pale yellow solid. ESI-MS m/z calc. 466.3. Found 467.3 (M+1)$^+$; Retention time: 1.01 minutes (3 min run).

Preparation of [10-(2-hydroxyethyl)-8-(2,2,2-trifluoroethyl)-11-oxa-3,8-diazaspiro[5.5]undecan-3-yl]-(4-isopropoxy-3-methyl-phenyl)methanone

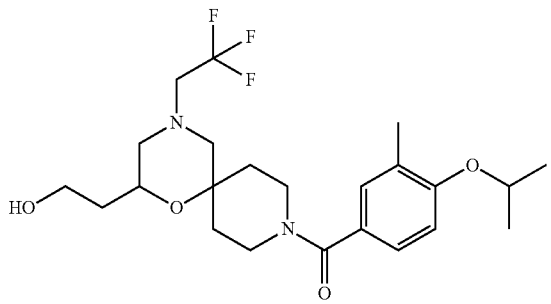 [SMILES: Cc1cc(C(=O)N2CCC3(CC2)CN(CC(F)(F)F)CC(CCO)O3)ccc1OC(C)C]

Step 1:
To a solution of [8-benzyl-10-(2-hydroxyethyl)-11-oxa-3,8-diazaspiro[5.5]undecan-3-yl]-(4-isopropoxy-3-methyl-phenyl)methanone hydrochloride salt (40 mg, 0.08 mmol) in methanol (750 µL) was added Pd (4 mg, 0.004 mmol) and ammonium formate (25 mg, 0.39 mmol), and the reaction mixture was heated at 75° C. for 1 hour. The reaction mixture was microfiltered and purified by prep LCMS (1-99% ACN/Water, 5 mM HCl modifier) to give [10-(2-hydroxyethyl)-11-oxa-3,8-diazaspiro[5.5]undecan-3-yl]-(4-isopropoxy-3-methyl-phenyl)methanone hydrochloride salt (20 mg, 62%). ESI-MS m/z calc. 376.2. Found 377.3 (M+1)$^+$; Retention time: 1.01 minutes (3 min run).

Step 2:
To [10-(2-hydroxyethyl)-11-oxa-3,8-diazaspiro[5.5]undecan-3-yl]-(4-isopropoxy-3-methyl-phenyl)methanone hydrochloride salt (20 mg, 0.05 mmol) and $NaHCO_3$ (16 mg, 0.19 mmol) in ethanol (0.5 mL) was added 2,2,2-trifluoroethyl trifluoromethanesulfonate (11 µL, 0.07 mmol) and the reaction mixture heated in a sealed vial at 80° C. for 5 hours. The reaction mixture was microfiltered and purified by prep LCMS (10-99% ACN/Water, 5 mM HCl modifier) to give [10-(2-hydroxyethyl)-8-(2,2,2-trifluoroethyl)-11-oxa-3,8-diazaspiro[5.5]undecan-3-yl]-(4-isopropoxy-3-methyl-phenyl)methanone (16 mg, 87%) as a colorless oil ESI-MS m/z calc. 458.2. Found 459.7 (M+1)$^+$; Retention time: 1.78 minutes (3 min run).

Preparation of (4-isopropoxy-3-methyl-phenyl)-[10-(5-methyloxazol-2-yl)-8-(2,2,2-trifluoroethyl)-11-oxa-3,8-diazaspiro[5.5]undecan-3-yl]methanone

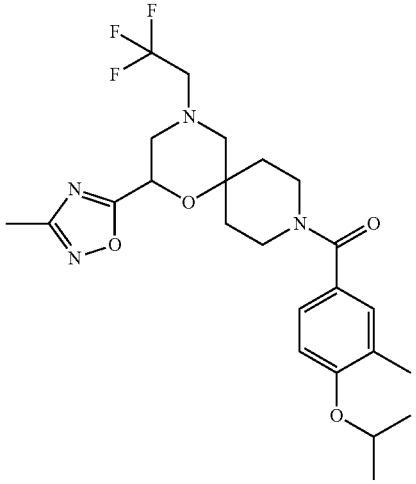 [SMILES: Cc1noc(C2CN(CC(F)(F)F)CC3(CCN(C(=O)c4ccc(OC(C)C)c(C)c4)CC3)O2)n1]

Step 1:
T3P (546 mg, 510 µL of 50% w/w, 0.86 mmol) was added to a solution of 8-benzyl-3-(4-isopropoxy-3-methyl-benzoyl)-11-oxa-3,8-diazaspiro[5.5]undecane-10-carboxylic acid (160 mg, 0.34 mmol), N'-hydroxyacetamidine (25 mg, 0.34 mmol) and triethylamine (173 mg, 239 µL, 1.71 mmol) in 2-methyltetrahydrofuran (800 µL) and the reaction mixture was heated at 75° C. for 2 hours. The reaction mixture was cooled to room temperature and partitioned between EtOAc/saturated aq. $NaHCO_3$. The layers were separated and the aqueous layer was extracted with EtOAc (2×). The combined organics were dried over $Na_2SO_4$, filtered and concentrated in vacuo to a dark foam. The crude product was purified by silica gel column chromatography using 0-30% EtOAc in DCM as eluent to afford [8-benzyl-10-(3-methyl-1,2,4-oxadiazol-5-yl)-11-oxa-3,8-diazaspiro[5.5]undecan-3-yl]-(4-isopropoxy-3-methyl-phenyl)methanone (67 mg, 39%) as a white solid. ESI-MS m/z calc. 504.6. Found 505.3 (M+1)$^+$; Retention time: 1.63 minutes (3 min run).

Step 2:
A solution of 1-chloroethyl chloroformate (89 µL, 0.80 mmol) in DCE (0.1 mL) was added to a stirred solution of [8-benzyl-10-(3-methyl-1,2,4-oxadiazol-5-yl)-11-oxa-3,8-diazaspiro[5.5]undecan-3-yl]-(4-isopropoxy-3-methyl-phenyl)methanone (67 mg, 0.13 mmol) in DCE (488 µL) under an atmosphere of nitrogen and the reaction mixture was heated to reflux. After 1 hour, an additional aliquot of 1-chloroethyl chloroformate (89 µL, 0.80 mmol) was added and the reaction mixture was heated to reflux for a further 8 hours. After 8 hours, an additional 1-chloroethyl chloroformate (89 µL, 0.80 mmol) was added and the reaction mixture was heated to reflux for a further 15 hours. The excess solvent was removed under reduced pressure and the carbamate intermediate was dissolved in MeOH (2 mL) and heated at reflux for 1 hour. The reaction mixture was cooled to room temperature, filtered and purified by Waters mass directed LC/MS-HPLC: (10-99% ACN/H2O (5 mM HCl)) to afford (4-isopropoxy-3-methyl-phenyl)-[10-(3-methyl-1,2,4-oxadiazol-5-yl)-11-oxa-3,8-diazaspiro[5.5]undecan-3-yl]methanone hydrochloride salt (28 mg, 47%). ESI-MS m/z calc. 414.2. Found 415.7 (M+1)$^+$; Retention time: 1.54 minutes (3 min run).

Step 3:

A mixture of (4-isopropoxy-3-methyl-phenyl)-[10-(3-methyl-1,2,4-oxadiazol-5-yl)-11-oxa-3,8-diazaspiro[5.5]undecan-3-yl]methanone hydrochloride salt (28 mg, 0.06 mmol), 2,2,2-trifluoroethyl trifluoromethanesulfonate (14 μL, 0.09 mmol) and NaHCO$_3$ (21 mg, 0.23 mmol) was heated at 80° C. in a sealed vial for 18 hours. The reaction mixture was allowed to cool to room temperature, microfiltered and purified by Waters mass directed LC/MS: (10-99% ACN/H$_2$0 (5 mM HCl)) and concentrated to yield (4-isopropoxy-3-methyl-phenyl)-[10-(5-methyloxazol-2-yl)-8-(2,2,2-trifluoro-ethyl)-11-oxa-3,8-diazaspiro[5.5]undecan-3-yl]methanone (3 mg, 10%) as a white solid. ESI-MS m/z calc. 496.5. Found 497.7 (M+1)$^+$; Retention time: 1.99 minutes (3 min run); $^1$H NMR (400 MHz, DMSO) δ 7.27-7.06 (m, 2H), 6.96 (d, J=9.1 Hz, 1H), 5.17 (dd, J=13.6, 4.2 Hz, 1H), 4.63 (dt, J=12.1, 6.2 Hz, 1H), 3.31-3.19 (m, 5H), 2.92-2.81 (m, 1H), 2.67 (dd, J=12.0, 10.1 Hz, 1H), 2.43-2.27 (m, 6H), 2.15 (s, 3H), 1.70-1.40 (m, 4H), 1.29 (d, J=6.0 Hz, 6H).

Preparation of 8-ethyl-3-(4-isopropoxy-3-methyl-benzoyl)-10-phenyl-11-oxa-3,8-diazaspiro[5.5]undecan-9-one

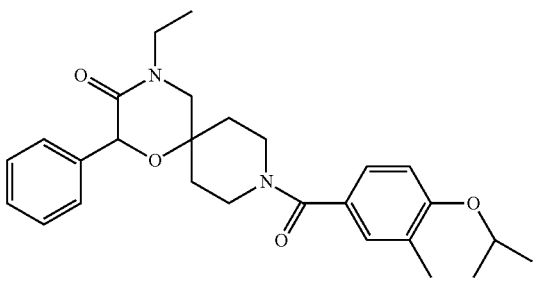 [SMILES: CCN1CC2(CCN(C(=O)c3ccc(OC(C)C)c(C)c3)CC2)OC(c2ccccc2)C1=O]

Step 1:

To a mixture of tert-butyl 4-hydroxy-4-[[(4-methoxyphenyl)methylamino]methyl]piperidine-1-carboxylate (1.06 g, 3.01 mmol) and diisopropylethylamine (1 mL, 5.74 mmol) in DCM (15 mL) at 0° C. was added 2-chloro-2-phenyl-acetyl chloride (654 mg, 3.46 mmol) and the reaction mixture was stirred at room temperature for 16 hours. The reaction mixture was concentrated in vacuo and the residue was purified by silica gel column chromatography using 0-100% EtOAc/DCM as eluent to give tert-butyl 4-[[(2-chloro-2-phenyl-acetyl)-[(4-methoxyphenyl)methyl]amino]methyl]-4-hydroxy-piperidine-1-carboxylate (1.11 g, 73%) as a pale yellow oil. ESI-MS m/z calc. 502.2. Found 503.5 (M+1)$^+$; Retention time: 1.90 minutes (3 min run).

Step 2:

To a suspension of tert-butyl 4-[[(2-chloro-2-phenyl-acetyl)-[(4-methoxyphenyl)methyl]amino]methyl]-4-hydroxy-piperidine-1-carboxylate (322 mg, 0.64 mmol) in DMF (3 mL) at 0° C. was added NaH (27 mg, 0.67 mmol). The reaction mixture was allowed to warm to room temperature overnight, then diluted with water (10 mL) and extracted with ethyl acetate (3×15 mL). The combined organic layers were washed with water (10 mL) and brine (10 mL), dried over MgSO$_4$, filtered, and concentrated in vacuo. The crude product was purified by silica gel column chromatography using 0-40% EtOAc/DCM to give tert-butyl 10-[(4-methoxyphenyl)methyl]-9-oxo-8-phenyl-7-oxa-3,10-diazaspiro[5.5]undecane-3-carboxylate (215 mg, 72%) as a colorless oil. ESI-MS m/z calc. 502.2. Found 503.5 (M+1)$^+$; Retention time: 1.90 minutes (3 min run).

Step 3:

To tert-butyl 10-[(4-methoxyphenyl)methyl]-9-oxo-8-phenyl-7-oxa-3,10-diazaspiro[5.5]undecane-3-carboxylate (215 mg, 0.46 mmol) in acetonitrile (2.5 mL) was added water (2.5 mL) followed by the addition of ceric ammonium nitrate (500 mg, 0.91 mmol). The reaction mixture was stirred for 2 hours. After this time, a further aliquot of ceric ammonium nitrate (250 mg, 0.46 mmol) was added and the reaction mixture was stirred for an additional 45 minutes, it was then diluted with 1M aq. HCl, extracted with ethyl acetate (2×25 mL), dried over MgSO$_4$ and concentrated in vacuo. The residue was dissolved in methanol (1 mL) and HCl (1 mL of 4 M in dioxane, 4.00 mmol) was added. The reaction mixture was stirred for 1 hour, then concentrated in vacuo to give 10-phenyl-11-oxa-3,8-diazaspiro[5.5]undecan-9-one hydrochloride salt (130 mg, 100%). ESI-MS m/z calc. 246.1. Found 247.5 (M+1)$^+$; Retention time: 0.46 minutes (3 min run).

Step 4:

To 4-isopropoxy-3-methyl-benzoic acid (114 mg, 0.59 mmol), 4-phenyl-5-oxa-2,9-diazaspiro[5.5]undecan-3-one hydrochloride salt (166 mg, 0.59 mmol) and HATU (223 mg, 0.59 mmol) in DMF (0.5 mL) was added diisopropylethylamine (228 mg, 307 μL, 1.76 mmol) and the reaction mixture was stirred for 16 hours. The reaction mixture was concentrated in vacuo, diluted with methanol and purified by prep LCMS (1-99% ACN/H$_2$O, 5 mM HCl modifier) to give 3-(4-isopropoxy-3-methyl-benzoyl)-8-phenyl-7-oxa-3,10-diazaspiro[5.5]undecan-9-one (100 mg, 40%) as a yellow foam. ESI-MS m/z calc. 422.2. Found 423.5 (M+1)$^+$; Retention time: 1.61 minutes (3 min run).

Step 5:

To a solution of 3-(4-isopropoxy-3-methyl-benzoyl)-8-phenyl-7-oxa-3,10-diazaspiro[5.5]undecan-9-one (65 mg, 0.15 mmol) in THF (1 mL) at 0° C. was added NaH (6 mg, 0.15 mmol) and the reaction mixture was stirred for 30 minutes. Bromoethane (34 mg, 23 μL, 0.31 mmol) was added and the reaction mixture was stirred at room temperature for 16 hours. The reaction mixture was concentrated in vacuo and purified by silica gel column chromatography using 0-100% EtOAc/DCM as eluent to give 2-ethyl-9-(4-isopropoxy-3-methyl-benzoyl)-4-phenyl-5-oxa-2,9-diazaspiro[5.5]undecan-3-one as a viscous oil. $^1$H NMR (400 MHz, CDCl$_3$) δ 7.48-7.43 (m, 2H), 7.39-7.29 (m, 3H), 7.23-7.17 (m, 2H), 6.81 (d, J=8.2 Hz, 1H), 5.11 (s, 1H), 4.56 (dt, J=12.1, 6.0 Hz, 1H), 3.63 (d, J=12.4 Hz, 1H), 3.59-3.19 (m, 5H), 3.09 (d, J=12.4 Hz, 1H), 2.92 (d, J=28.7 Hz, 1H), 2.22 (s, 1H), 2.23-2.16 (m, 3H), 1.59 (s, 3H), 1.35 (d, J=6.0 Hz, 6H), 1.14 (t, J=7.2 Hz, 3H). ESI-MS m/z calc. 450.3. Found 451.1 (M+1)$^+$; Retention time: 1.76 minutes (3 min run).

Preparation of 2-isopentyl-9-[4-methoxy-3-(trifluoromethyl)benzoyl]-4-phenyl-5-oxa-2,9-diazaspiro[5.5]undecan-3-one

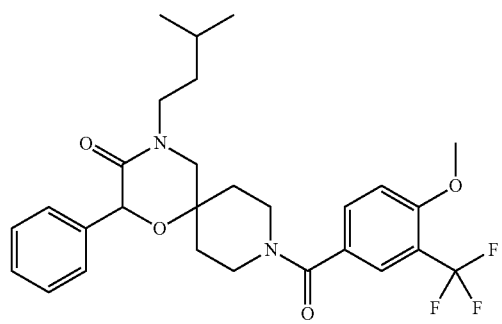 [SMILES: COc1ccc(C(=O)N2CCC3(CC2)CN(CCC(C)C)C(=O)C(c2ccccc2)O3)cc1C(F)(F)F]

Step 1:

NaBH₄ (66 mg, 1.75 mmol) was added portionwise to a stirred solution of 4-(aminomethyl)-1-benzyl-piperidin-4-ol (167 mg, 0.76 mmol) and 3-methylbutanal (74 μL, 0.68 mmol) in MeOH (7.5 mL) and acetic acid (350 μL). The reaction mixture was stirred for 16 hours at room temperature, then quenched with H₂O (5 mL). The aqueous layer was extracted with EtOAc (3×50 mL). The combined organics were dried over Na₂SO₄, filtered and concentrated in vacuo to provide an oil. To the oil was added pyridine (1 mL) followed by dropwise addition of (2,2,2-trifluoroacetyl) 2,2,2-trifluoroacetate (105 μL, 0.76 mmol) at room temperature. The reaction mixture was stirred vigorously for 30 minutes. The reaction mixture was quenched with water and aqueous layer was extracted with EtOAc (3×100 mL), dried over Na₂SO₄, filtered and concentrated in vacuo. The residue was purified by silica gel column chromatography using 0-100% hexanes/EtOAc to provide N-[(1-benzyl-4-hydroxy-4-piperidyl)methyl]-2,2,2-trifluoro-N-isopentyl-acetamide (112 mg, 38%) as a pale tan oil.

Step 2:

Palladium (50.8 mg, 0.48 mmol) 10% on activated carbon and N-[(1-benzyl-4-hydroxy-4-piperidyl)methyl]-2,2,2-trifluoro-N-isopentyl-acetamide (112 mg, 0.29 mmol) in propan-2-ol (3 mL) was stirred under an atmosphere of hydrogen for 18 hours. The catalyst was filtered through Celite® and washed with MeOH. The organics were concentrated in vacuo to provide a clear oil. To the oil was added DMF (2 mL) and triethylamine (40 μL, 0.29 mmol) and this solution was added dropwise to a solution 4-methoxy-3-(trifluoromethyl)benzoic acid (64 mg, 0.29 mmol) and HATU (110 mg, 0.29 mmol) in DMF (1 mL). The reaction mixture was stirred for 16 hours. The solution was partitioned between water and EtOAc and the layers were separated. The aqueous layer was extracted with EtOAc (3×100 mL). The combined organics were dried over Na₂SO₄, filtered, and concentrated in vacuo. The residue was taken up in MeOH and purified by reverse phase HPLC (Gilson 20-99% water/MeOH) to give 2,2,2-trifluoro-N-[[4-hydroxy-1-[4-methoxy-3-(trifluoromethyl)benzoyl]-4-piperidyl]methyl]-N-isopentyl-acetamide (82 mg, 56%). ESI-MS m/z calc. 498.5. Found 499.5 (M+1)⁺; Retention time: 1.86 minutes (3 min run).

Step 3:

Sodium hydroxide (1.4 mL of 0.2 M, 0.29 mmol) was added to a solution of 2,2,2-trifluoro-N-[[4-hydroxy-1-[4-methoxy-3-(trifluoromethyl)benzoyl]-4-piperidyl]methyl]-N-isopentyl-acetamide (72 mg, 0.14 mmol) in MeOH (722 μL) and the reaction mixture was heated to 65° C. for 16 hours. The solution was partitioned between water (5 mL) and EtOAc (5 mL) and the aqueous layer was extracted with EtOAc (3×5 mL). The combined organics were dried over Na₂SO₄, filtered, and concentrated in vacuo to provide the crude amine as a clear oil (54 mg, 92%). ESI-MS m/z calc. 402.4. Found 403.7 (M+1)⁺; Retention time: 1.34 minutes (3 min run). The residue was taken up in THF (480 μL) and added dropwise to a solution of potassium tert-butoxide (36 mg, 0.32 mmol) in tert-butanol (480 μL) and the reaction mixture was heated at 83° C. for 20 minutes. The solution was neutralized with AcOH, and partitioned between water (2 mL) and EtOAc (2 mL), the aqueous layer was extracted with EtOAc (3×2 mL). The combined organics were dried over Na₂SO₄, filtered, and concentrated in vacuo. The residue was dissolved in MeOH (3 mL) and purified by reverse phase HPLC (Gilson) 20-99% water/MeOH to provide 2-isopentyl-9-[4-methoxy-3-(trifluoromethyl)benzoyl]-4-phenyl-5-oxa-2,9-diazaspiro[5.5]undecan-3-one (39 mg, 45%) as a white foam. ESI-MS m/z calc. 518.6. Found 519.5 (M+1)⁺; Retention time: 2.03 minutes (3 min run).

Preparation of (3,3-dimethyl-1-oxa-4,9-diazaspiro[5.5]undecan-9-yl)(4-isopropoxy-3-methylphenyl)methanone

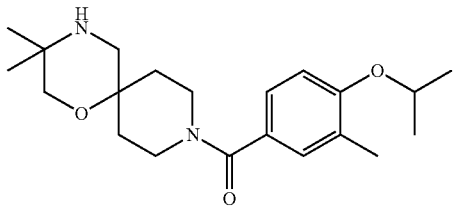 [SMILES: Cc1cc(C(=O)N2CCC3(CC2)CNC(C)(C)CO3)ccc1OC(C)C]

Step 1:

2-(Benzylamino)-2-methyl-propan-1-ol hydrochloride (539 mg, 2.50 mmol) was treated with aqueous sodium hydroxide (50 mL of 2 M, 100 mmol), then diethyl ether (50 mL) was added to the solution and stirred for 3 min. The organic layer was separated, washed with brine, dried over Na₂SO₄, filtered and concentrated in vacuo to provide the 2-(benzylamino)-2-methyl-propan-1-ol free base as a white powder. The 2-(benzylamino)-2-methyl-propan-1-ol (2.50 mmol) and tert-butyl 1-oxa-6-azaspiro[2.5]octane-6-carboxylate (500 mg, 2.344 mmol) were dissolved in ethanol (2 mL) and the reaction mixture was heated in a sealed tube at 100° C. for 48 h. The ethanol was evaporated and the crude material purified by silica gel column chromatography (1-100% ethyl acetate/hexanes) to provide tert-butyl 4-((benzyl(1-hydroxy-2-methylpropan-2-yl)amino)methyl)-4-hydroxypiperidine-1-carboxylate as white powder (551 mg, 60%). ESI-MS m/z calc. 392.5. Found 373.3 (M+1)⁺; Retention time: 1.14 minutes (3 min run). ¹H NMR (400 MHz, DMSO-d₆) δ 7.43 (d, J=7.4 Hz, 2H), 7.24 (t, J=7.6 Hz, 2H), 7.13 (t, J=7.3 Hz, 1H), 4.66 (t, J=5.1 Hz, 1H), 4.43 (s, 1H), 3.91 (s, 2H), 3.62 (s, 2H), 3.22 (d, J=4.8 Hz, 2H), 2.97 (s, 2H), 2.58 (s, 2H), 1.44-1.27 (m, 13H), 0.88 (s, 6H).

Step 2:

To a solution of tert-butyl 4-[[benzyl-(2-hydroxy-1,1-dimethyl-ethyl)amino]methyl]-4-hydroxy-piperidine-1-carboxylate (330 mg, 0.841 mmol) in tetrahydrofuran was added N,N-diisopropylethylamine (439 μL, 2.52 mmol) and methanesulfonic anhydride (439 mg, 2.52 mmol) under a nitrogen atmosphere. The reaction mixture was heated at 65° C. for 18 h. The reaction mixture was diluted with ethyl acetate, washed with saturated sodium bicarbonate (2×50 mL) and brine (50 mL), dried over Na₂SO₄, filtered and concentrated in vacuo. The crude material was purified by silica gel chromatography (0-80% of ethyl acetate/hexanes) to provide tert-butyl 8-benzyl-9,9-dimethyl-11-oxa-3,8-diazaspiro[5.5]undecane-3-carboxylate (89 mg, 28%) as white solid. ESI-MS m/z calc. 374.5. Found 375.3 (M+1)⁺; Retention time: 1.30 minutes (3 min run).

Step 3:

Tert-butyl 8-benzyl-9,9-dimethyl-11-oxa-3,8-diazaspiro[5.5]undecane-3-carboxylate (89 mg, 0.24 mmol) was treated with hydrogen chloride solution in dioxane (240 μL of 4 M, 0.95 mmol). The reaction mixture was stirred for 18 h. The reaction mixture was concentrated in vacuo to provide 8-benzyl-9,9-dimethyl-11-oxa-3,8-diazaspiro[5.5]undecane hydrochloride (56 mg, 86%). ESI-MS m/z calc. 274.4. Found 275.5 (M+1)⁺; Retention time: 0.80 minutes (3 min run).

Step 4:

A solution of 4-isopropoxy-3-methylbenzoic acid (31.0 mg, 0.161 mmol) and O-(7-azabenzotriazol-1-yl)-N,N,N',N'-tetramethyluronium hexafluorophosphate (61.3 mg, 0.161 mmol) in acetonitrile was treated with triethylamine (67 μL, 0.48 mmol) and stirred for 5 min. 8-Benzyl-9,9-dimethyl-11-oxa-3,8-diazaspiro[5.5]undecane hydrochloride (56.0 mg, 0.161 mmol) was added and the reaction mixture stirred for 3 h. The reaction mixture was filtered and concentrated in vacuo. The crude material was purified by chromatography (0-80% of ethyl acetate/hexanes) to provide (8-benzyl-9,9-dimethyl-11-oxa-3,8-diazaspiro[5.5]undecan-3-yl)-(4-isopropoxy-3-methyl-phenyl)methanone (51.0 mg, 70%) as colorless oil. ESI-MS m/z calc. 450.6. Found 451.3 (M+1)$^+$; Retention time: 1.54 minutes (3 min run).

Step 5:

To a solution of (8-benzyl-9,9-dimethyl-11-oxa-3,8-diazaspiro[5.5]undecan-3-yl)-(4-isopropoxy-3-methyl-phenyl)methanone (51 mg, 0.11 mmol) in ethanol (2 mL) was added Pd(OH)$_2$ (16 mg, 0.11 mmol) followed by ammonium formate (29 mg, 0.45 mmol). The reaction mixture was stirred at 40° C. for 18 h, then filtered and concentrated in vacuo to afford (9,9-dimethyl-11-oxa-3,8-diazaspiro[5.5]undecan-3-yl)-(4-isopropoxy-3-methyl-phenyl)methanone (40 mg, 98%). ESI-MS m/z calc. 360.5. Found 361.3 (M+1)$^+$; Retention time: 1.29 minutes (3 min run).

Preparation of (8-but-2-ynyl-9,9-dimethyl-11-oxa-3,8-diazaspiro[5.5]undecan-3-yl)-(4-isopropoxy-3-methyl-phenyl)methanone

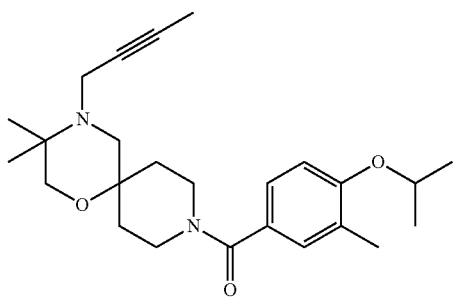 [SMILES: CC#CCN1CC2(CCN(C(=O)c3ccc(OC(C)C)c(C)c3)CC2)OCC1(C)C]

To a mixture of (9,9-dimethyl-11-oxa-3,8-diazaspiro[5.5]undecan-3-yl)-(4-isopropoxy-3-methyl-phenyl)methanone (20.1 mg, 0.0557 mmol) and potassium carbonate (15 mg, 0.11 mmol) in N,N-dimethylformamide (310 μL) was added 1-bromobut-2-yne (8.1 mg, 0.061 mmol) and reaction mixture was heated at 45° C. for 1 h. The reaction mixture was filtered and crude material was purified by HPLC (15-75% CH$_3$CN/5 mM HCl) to provide (8-but-2-ynyl-9,9-dimethyl-11-oxa-3,8-diazaspiro[5.5]undecan-3-yl)-(4-isopropoxy-3-methyl-phenyl)methanone hydrochloride (11 mg, 41%). ESI-MS m/z calc. 412.3. Found 413.3 (M+1)$^+$; Retention time: 1.43 minutes (3 min run).

Preparation of (3,3-dimethyl-4-(pyrimidin-2-yl)-1-oxa-4,9-diazaspiro[5.5]undecan-9-yl)(4-isopropoxy-3-methylphenyl)methanone

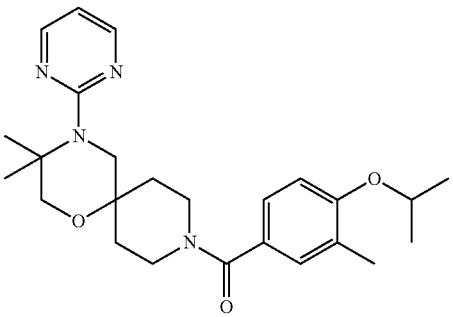 [SMILES: Cc1cc(C(=O)N2CCC3(CC2)CN(c2ncccn2)C(C)(C)CO3)ccc1OC(C)C]

A solution of (9,9-dimethyl-11-oxa-3,8-diazaspiro[5.5]undecan-3-yl)-(4-isopropoxy-3-methyl-phenyl)methanone (11.0 mg, 0.0305 mmol), potassium carbonate (4.2 mg, 0.031 mmol) and 2-chloropyrimidine (3.7 mg, 0.031 mmol) in DMSO (90 μL) was heated at 90° C. for 2 h. The reaction was filtered and purified by HPLC (1-99% CH$_3$CN/5 mM HCl) to provide (3,3-dimethyl-4-(pyrimidin-2-yl)-1-oxa-4,9-diazaspiro[5.5]undecan-9-yl)(4-isopropoxy-3-methylphenyl)methanone hydrochloride (6.0 mg, 0.012 mmol, 38%). ESI-MS m/z calc. 438.3. Found 439.3 (M+1)$^+$; Retention time: 1.92 minutes (3 min run).

Preparation of (4-isopropoxy-3-methylphenyl)(2-(methoxymethyl)-4-(4-(trifluoromethyl)phenyl)-1-oxa-4,9-diazaspiro[5.5]undecan-9-yl)methanone

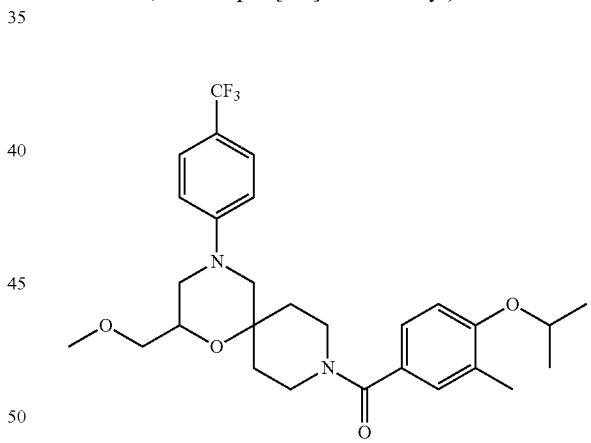

To a vial charged with (4-isopropoxy-3-methyl-phenyl)-[10-(methoxymethyl)-11-oxa-3,8-diazaspiro[5.5]undecan-3-yl]methanone (30.0 mg, 0.08 mmol), 1-bromo-4-(trifluoromethyl)benzene (19.7 mg, 0.088 mmol), Pd$_2$(dba)$_3$ (23 mg, 0.04 mmol), rac-BINAP (24.8 mg, 0.04 mmol) and sodium tert-butoxide (9.8 mg, 0.088 mmol) were added N-methyl-2-pyrrolidone (0.2 mL) and toluene (1.0 mL). The reaction mixture was heated at 100° C. under nitrogen 18 h. The reaction mixture was cooled to room temperature, filtered and purified via HPLC (1-90% CH$_3$CN/5 mM HCl) to provide (4-isopropoxy-3-methylphenyl)(2-(methoxymethyl)-4-(4-(trifluoromethyl)phenyl)-1-oxa-4,9-diazaspiro[5.5]undecan-9-yl)methanone (5.0 mg, 0.0077 mmol, 10%). ESI-MS m/z calc. 520.2549. Found 521.3 (M+1)$^+$; Retention time: 2.21 minutes (3 min run).

Preparation of (4-cyclobutyl-2-(methoxymethyl)-1-oxa-4,9-diazaspiro[5.5]undecan-9-yl)(4-isopropoxy-3-methylphenyl)methanone

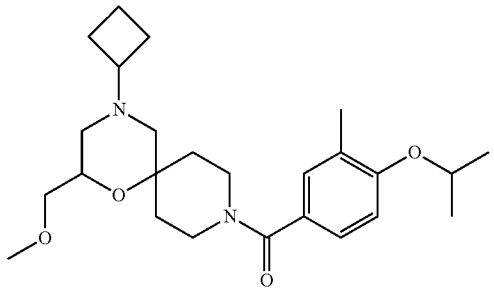 [SMILES: COCC1CN(C2CCC2)CC2(CCN(C(=O)c3ccc(OC(C)C)c(C)c3)CC2)O1]

Step 1:
A solution of (4-isopropoxy-3-methyl-phenyl)-[10-(methoxymethyl)-11-oxa-3,8-diazaspiro[5.5]undecan-3-yl]methanone (343 mg, 0.912 mmol) and cyclobutanone (96.0 mg, 1.36 mmol) in dichloroethane (3 mL) was treated with acetic acid (78 μL, 1.4 mmol) and stirred for 30 min. NaBH(OAc)$_3$ (387 mg, 1.82 mmol) was added and the reaction mixture stirred for 16 h. The reaction mixture was diluted with MTBE and washed with 1N NaOH (100 mL). The organic layer was separated and washed with brine, dried over Na$_2$SO$_4$, filtered and concentrated in vacuo. Silica gel chromatography (5-80% ethyl acetate/hexane) provided (4-cyclobutyl-2-(methoxymethyl)-1-oxa-4,9-diazaspiro[5.5]undecan-9-yl)(4-isopropoxy-3-methylphenyl)methanone (330 mg, 84%). ESI-MS m/z calc. 430.3. Found 431.3 (M+1)$^+$; Retention time: 1.24 minutes (3 min run). $^1$H NMR (400 MHz, CDCl$_3$) δ 7.19 (d, J=8.4 Hz, 2H), 6.80 (d, J=8.1 Hz, 1H), 4.55 (hept, J=6.2 Hz, 1H), 4.30-4.10 (m, 1H), 3.94-3.75 (m, 1H), 3.62-3.46 (m, 1H), 3.48-3.33 (m, 6H), 3.30-3.16 (m, 1H), 2.75 (d, J=10.8 Hz, 1H), 2.67-2.57 (m, 1H), 2.55 (d, J=11.1 Hz, 1H), 2.47-2.27 (m, 1H), 2.20 (s, 3H), 1.98 (d, J=7.3 Hz, 2H), 1.91-1.76 (m, 1H), 1.76-1.61 (m, 4H), 1.57-1.39 (m, 3H), 1.34 (d, J=6.0 Hz, 6H).

Table 2 below recites the analytical data for the compounds of Table 1.

TABLE 2

| Cmpd. No. | LC/MS M + 1 | LC/RT min | NMR |
|---|---|---|---|
| 1 | 467.50 | 1.63 | |
| 2 | 467.30 | 1.01 | |
| 3 | 490.20 | 1.22 | |
| 4 | 507.14 | 1.87 | |
| 5 | 473.39 | 1.42 | |
| 6 | 411.50 | 1.90 | |
| 7 | 423.50 | 1.31 | |
| 8 | 497.23 | 2.41 | |
| 9 | 451.10 | 1.76 | 1H NMR (400 MHz, CDCl3) δ 7.48-7.43 (m, 2H), 7.39-7.29 (m, 3H), 7.23-7.17 (m, 2H), 6.81 (d, J = 8.2 Hz, 1H), 5.11 (s, 1H), 4.56 (dt, J = 12.1, 6.0 Hz, 1H), 3.63 (d, J = 12.4 Hz, 1H), 3.59-3.19 (m, 5H), 3.09 (d, J = 12.4 Hz, 1H), 2.92 (d, J = 28.7 Hz, 1H), 2.22 (s, 1H), 2.23-2.16 (m, 3H), 1.59 (s, 4H), 1.35 (d, J = 6.0 Hz, 6H), 1.14 (t, J = 7.2 Hz, 3H). |
| 10 | 437.70 | 1.43 | |
| 11 | 477.40 | 6.04 | 1H NMR (400 MHz, CD3CN) δ 7.39 (d, J = 1.9 Hz, 1H), 7.26-7.10 (m, 2H), 6.92 (d, J = 9.0 Hz, 1H), 6.54 (t, J = 52.5 Hz, 1H), 6.28 (d, J = 1.9 Hz, 1H), 5.28 (d, J = 9.5 Hz, 1H), 4.63 (dt, J = 12.1, 6.0 Hz, 1H), 3.90 (s, 4H), 3.42 (d, J = 12.1 Hz, 1H), 3.24 (d, J = 12.4 Hz, 6H), 2.92 (d, J = 27.2 Hz, 3H), 2.74 (s, 2H), 2.51-2.01 (m, 33H), 1.87-1.46 (m, 5H), 1.30 (t, J = 10.1 Hz, 7H). |
| 12 | 539.29 | 1.97 | |
| 13 | 492.30 | 2.26 | |
| 14 | 468.19 | 2.37 | |
| 15 | 471.29 | 2.33 | |
| 16 | 468.30 | 1.51 | |
| 17 | 468.50 | 1.25 | |
| 18 | 417.30 | 1.43 | |
| 19 | 459.29 | 2.78 | |
| 20 | 491.50 | 1.82 | 1H NMR (400 MHz, CD3CN) δ 7.45 (d, J = 1.7 Hz, 1H), 7.23-7.16 (m, 2H), 7.13 (t, J = 3.8 Hz, 1H), 6.98-6.88 (m, 1H), 6.63 (s, 1H), 6.50 (s, 1H), 6.34 (s, 1H), 6.29 (d, J = 1.7 Hz, 1H), 5.29 (d, J = 8.6 Hz, 1H), 4.74-4.54 (m, 1H), 4.24 (q, J = 7.0 Hz, 2H), 3.50-3.09 (m, 6H), 3.05-2.59 (m, 3H), 2.46-2.03 (m, 6H), 1.89-1.75 (m, 2H), 1.75-1.50 (m, 2H), 1.49-1.39 (m, 3H), 1.34 (dd, J = 6.0, 5.1 Hz, 6H), 1.29 (s, 1H), 1.17 (d, J = 6.1 Hz, 2H). |
| 21 | 463.30 | 1.71 | 1H NMR (400 MHz, MeOD) δ 7.70 (d, J = 2.3 Hz, 1H), 7.30-7.16 (m, 2H), 6.96 (d, J = 8.7 Hz, 1H), 6.43 (d, J = 2.3 Hz, 1H), 6.27 (s, 1H), 6.14 (s, 1H), 6.00 (s, 1H), 5.01 (d, J = 43.6 Hz, 1H), 4.66 (dt, J = 12.0, 6.0 Hz, 1H), 4.30 (s, 1H), 3.49 (ddd, J = 49.9, 49.0, 23.7 Hz, 3H), 3.19-2.96 (m, 3H), 2.60 (dd, J = 42.6, 23.4 Hz, 3H), 2.19 (s, 3H), 1.68 (s, 3H), 1.34 (d, J = 6.0 Hz, 6H). |
| 22 | 437.70 | 1.36 | |
| 23 | 416.29 | 1.62 | |
| 24 | 481.70 | 1.49 | |

TABLE 2-continued

| Cmpd. No. | LC/MS M + 1 | LC/RT min | NMR |
|---|---|---|---|
| 25 | 453.20 | 1.08 | |
| 26 | 495.50 | 7.63 | |
| 27 | 491.25 | 2.17 | |
| 28 | 389.70 | 1.03 | |
| 29 | 465.70 | 1.72 | |
| 30 | 439.10 | 1.38 | |
| 31 | 454.30 | 1.29 | |
| 32 | 391.30 | 1.20 | |
| 33 | 474.50 | 1.61 | |
| 34 | 389.70 | 1.36 | |
| 35 | 477.30 | 1.50 | 1H NMR (400 MHz, DMSO) δ 7.74 (d, J = 1.9 Hz, 1H), 7.69 (d, J = 1.9 Hz, 1H), 7.18 (dd, J = 6.0, 2.0 Hz, 2H), 7.04-6.90 (m, 1H), 6.20 (tt, J = 55.5, 4.0 Hz, 1H), 5.34-5.28 (m, 1H), 4.69-4.57 (m, 1H), 3.91 (s, 3H), 3.69-3.41 (m, 1H), 3.37-3.09 (m, 3H), 2.87 (ddd, J = 19.6, 18.4, 7.9 Hz, 3H), 2.57-2.51 (m, 2H), 2.46-2.31 (m, 1H), 2.26 (d, J = 11.6 Hz, 1H), 2.13 (s, 3H), 1.70-1.52 (m, 3H), 1.29 (d, J = 6.0 Hz, 6H). |
| 36 | 499.30 | 1.76 | |
| 37 | 488.40 | 1.50 | |
| 38 | 485.50 | 7.23 | |
| 39 | 509.50 | 1.97 | |
| 40 | 389.70 | 1.33 | |
| 41 | 442.50 | 1.12 | |
| 42 | 492.20 | 2.17 | |
| 43 | 453.50 | 1.24 | |
| 44 | 491.30 | 2.27 | 1H NMR (400 MHz, CDCl3) δ 7.53 (t, J = 6.9 Hz, 1H), 7.33-7.27 (m, 1H), 7.20-7.09 (m, 3H), 7.07-7.01 (m, 1H), 6.96 (t, J = 8.2 Hz, 1H), 6.14-5.75 (m, 1H), 5.25-5.07 (m, 1H), 4.66-4.52 (m, 1H), 4.45-4.21 (m, 1H), 3.73-3.31 (m, 2H), 3.08 (d, J = 10.8 Hz, 1H), 2.85-2.61 (m, 4H), 2.39-2.17 (m, 2H), 1.66-1.45 (m, 3H), 1.37 (d, J = 6.1 Hz, 6H). |
| 45 | 495.50 | 2.14 | 1H NMR (400 MHz, CDCl3) δ 7.53 (t, J = 6.9 Hz, 1H), 7.33-7.27 (m, 1H), 7.20-7.09 (m, 3H), 7.07-7.01 (m, 1H), 6.96 (t, J = 8.2 Hz, 1H), 6.14-5.75 (m, 1H), 5.25-5.07 (m, 1H), 4.66-4.52 (m, 1H), 4.45-4.21 (m, 1H), 3.73-3.31 (m, 2H), 3.08 (d, J = 10.8 Hz, 1H), 2.85-2.61 (m, 4H), 2.39-2.17 (m, 2H), 1.66-1.45 (m, 3H), 1.37 (d, J = 6.1 Hz, 6H). |
| 46 | 415.50 | 1.41 | |
| 47 | 445.37 | 1.33 | |
| 48 | 447.33 | 1.34 | |
| 49 | 470.30 | 1.38 | |
| 50 | 465.50 | 1.64 | |
| 51 | 439.30 | 1.92 | |
| 52 | 433.11 | 1.47 | |
| 53 | 459.29 | 2.18 | |
| 54 | 464.50 | 1.29 | |
| 55 | 449.34 | 1.32 | |
| 56 | 505.40 | 2.16 | |
| 57 | 478.20 | 1.06 | |
| 58 | 525.29 | 1.81 | |
| 59 | 489.28 | 1.85 | |
| 60 | 521.50 | 2.15 | |
| 61 | 535.20 | 3.25 | |
| 62 | 525.00 | 2.00 | |
| 63 | 487.30 | 2.39 | |
| 64 | 458.18 | 2.22 | |
| 65 | 522.40 | 1.13 | |
| 66 | 503.15 | 2.65 | |
| 67 | 465.50 | 1.60 | 1H NMR (400 MHz, DMSO) δ 8.35 (d, J = 4.4 Hz, 2H), 7.52 (d, J = 7.8 Hz, 2H), 7.33 (d, J = 7.2 Hz, 2H), 6.62 (s, 1H), 4.75 (s, 1H), 4.65-4.48 (m, 2H), 4.10 (br s, 1H), 3.56 (br s, 1H), 3.39 (br s, 1H), 3.03 (br s, 1H), 2.75 (d, J = 13.3 Hz, 1H), 2.60-2.52 (m, 1H), 1.99 (br s, 1H), 1.81-1.17 (m, 16H), 0.96 (t, J = 7.3 Hz, 3H). |
| 68 | 448.24 | 1.64 | |
| 69 | 469.20 | 2.17 | |
| 70 | 478.30 | 1.94 | |
| 71 | 467.10 | 2.10 | |
| 72 | 427.29 | 2.52 | |
| 73 | 419.31 | 1.28 | |
| 74 | 483.30 | 2.03 | |
| 75 | 468.30 | 1.14 | |
| 76 | 474.50 | 1.07 | |
| 77 | 477.30 | 2.15 | |

TABLE 2-continued

| Cmpd. No. | LC/MS M + 1 | LC/RT min | NMR |
|---|---|---|---|
| 78 | 518.38 | 2.05 | |
| 79 | 484.30 | 1.59 | |
| 80 | 492.50 | 1.16 | |
| 81 | 507.00 | 1.86 | 1H NMR (400 MHz, MeOD) δ 7.47 (dd, J = 8.7, 5.4 Hz, 2H), 7.23 (dd, J = 11.7, 3.5 Hz, 2H), 7.12 (t, J = 8.8 Hz, 2H), 6.96 (d, J = 8.3 Hz, 1H), 6.24 (t, J = 54.0 Hz, 1H), 4.95 (s, 1H), 4.33 (s, 1H), 4.13 (t, J = 6.2 Hz, 2H), 3.77 (t, J = 6.3 Hz, 2H), 3.73-3.61 (m, 1H), 2.73 (s, 2H), 2.61-2.46 (m, 1H), 2.22 (s, 3H), 2.11-1.96 (m, 2H), 1.75 (s, 3H). |
| 82 | 453.50 | 1.19 | |
| 83 | 504.50 | 1.70 | |
| 84 | 481.50 | 1.62 | |
| 85 | 534.40 | 1.15 | |
| 86 | 493.40 | 2.13 | |
| 87 | 499.30 | 7.16 | 1H NMR (400 MHz, CDCl3) δ 7.15 (dd, J = 15.8, 5.3 Hz, 2H), 7.06-6.86 (m, 1H), 6.17 (s, 1H), 5.01 (s, 1H), 4.58 (dt, J = 12.2, 6.1 Hz, 1H), 4.30 (s, 1H), 3.60 (s, 3H), 3.15 (d, J = 11.6 Hz, 1H), 3.01 (q, J = 9.3 Hz, 2H), 2.74 (d, J = 11.1 Hz, 1H), 2.59 (dd, J = 20.7, 9.9 Hz, 2H), 2.47 (d, J = 11.4 Hz, 1H), 2.44 (s, 3H), 2.02 (d, J = 6.7 Hz, 1H), 1.78 (d, J = 45.0 Hz, 1H), 1.53 (d, J = 6.1 Hz, 2H), 1.44-1.23 (m, 6H). |
| 88 | 506.30 | 2.09 | |
| 89 | 443.36 | 1.42 | |
| 90 | 485.12 | 2.07 | |
| 91 | 451.30 | 1.55 | |
| 92 | 441.30 | 1.55 | 1H NMR (400 MHz, CDCl3) δ 8.40 (s, 2H), 7.20 (d, J = 9.0 Hz, 2H), 6.80 (d, J = 8.0 Hz, 1H), 6.65 (s, 1H), 4.80 (dd, J = 22.7, 12.7 Hz, 2H), 4.55 (dt, J = 12.0, 6.0 Hz, 1H), 3.92 (dt, J = 7.4, 6.6 Hz, 1H), 3.83-3.64 (m, 3H), 3.59-3.42 (m, 1H), 3.28 (s, 1H), 3.08-2.88 (m, 2H), 2.19 (s, 3H), 2.11-1.87 (m, 2H), 1.80-1.52 (m, 3H), 1.34 (d, J = 6.0 Hz, 6H). |
| 93 | 467.50 | 1.29 | |
| 94 | 495.40 | 2.27 | |
| 95 | 468.32 | 2.40 | |
| 96 | 553.12 | 1.75 | |
| 97 | 438.50 | 1.11 | |
| 98 | 491.30 | 2.12 | |
| 99 | 538.28 | 1.91 | |
| 100 | 489.70 | 2.17 | 1H NMR (400 MHz, CDCl3) δ 7.45-7.36 (m, 5H), 6.98-6.83 (m, 3H), 5.25 (d, J = 10.4 Hz, 1H), 4.57 (dt, J = 12.2, 6.1 Hz, 1H), 3.85 (s, 3H), 3.60 (d, J = 10.9 Hz, 1H), 3.47-3.12 (m, 6H), 2.86-2.60 (m, 3H), 1.88-1.50 (m, 5H), 1.38 (d, J = 6.1 Hz, 6H). |
| 101 | 433.35 | 1.34 | |
| 102 | 485.16 | 2.65 | |
| 103 | 464.50 | 1.25 | |
| 104 | 507.50 | 2.26 | |
| 105 | 477.30 | 2.05 | |
| 106 | 459.20 | 1.91 | |
| 107 | 463.38 | 1.40 | |
| 108 | 511.26 | 1.85 | |
| 109 | 539.15 | 1.95 | |
| 110 | 501.30 | 7.66 | |
| 111 | 433.35 | 1.29 | |
| 112 | 461.36 | 1.42 | |
| 113 | 433.29 | 1.19 | |
| 114 | 483.50 | 1.89 | |
| 115 | 464.24 | 1.59 | |
| 116 | 474.30 | 2.08 | |
| 117 | 507.00 | 1.94 | |
| 118 | 487.05 | 2.28 | |
| 119 | 477.32 | 2.14 | |
| 120 | 455.30 | 1.86 | 1H NMR (400 MHz, CDCl3) δ 8.45 (d, J = 4.5 Hz, 2H), 7.23-7.17 (m, 2H), 6.80 (d, J = 8.1 Hz, 1H), 6.71 (s, 1H), 4.97-4.76 (m, 2H), 4.55 (dt, J = 12.1, 6.0 Hz, 1H), 4.36-4.08 (m, 1H), 4.03-3.84 (m, 1H), 3.81-3.61 (m, 1H), 3.61-3.50 (m, 3H), 3.42 (s, 3H), 3.35-3.21 (m, 1H), 3.07-2.91 (m, 2H), 2.19 (s, 3H), 2.07-1.93 (m, 1H), 1.84-1.52 (m, 3H), 1.34 (d, J = 6.0 Hz, 6H). |

TABLE 2-continued

| Cmpd. No. | LC/MS M + 1 | LC/RT min | NMR |
|---|---|---|---|
| 121 | 502.35 | 1.17 | |
| 122 | 507.20 | 2.17 | |
| 123 | 505.30 | 2.50 | 1H NMR (501 MHz, DMSO) δ 7.38-7.26 (m, 5H), 7.15 (s, 2H), 6.92 (d, J = 8.5 Hz, 1H), 4.59 (dt, J = 11.1, 5.4 Hz, 1H), 4.29 (s, 1H), 3.52-3.44 (m, 2H), 3.24-2.98 (m, 3H), 2.91 (d, J = 11.6 Hz, 1H), 2.71-2.47 (m, 3H), 2.46-2.27 (m, 1H), 2.10 (s, 3H), 1.67-1.38 (m, 3H), 1.26 (d, J = 5.8 Hz, 6H), 0.79 (d, J = 5.1 Hz, 3H). |
| 124 | 521.30 | 2.22 | |
| 125 | 487.29 | 2.14 | |
| 126 | 484.30 | 1.40 | |
| 127 | 473.50 | 1.94 | |
| 128 | 521.34 | 2.16 | |
| 129 | 427.50 | 1.61 | |
| 130 | 451.50 | 2.03 | |
| 131 | 477.29 | 1.30 | |
| 132 | 472.18 | 2.48 | |
| 133 | 491.30 | 2.09 | 1H NMR (400 MHz, CDCl3) δ 7.43-7.30 (m, 8H), 7.26 (s, 1H), 4.86 (s, 1H), 4.47-4.27 (m, 1H), 3.66-3.12 (m, 3H), 3.04 (dd, J = 18.6, 9.3 Hz, 3H), 2.84 (s, 2H), 2.81 (s, 2H), 2.73-2.54 (m, 1H), 2.52-2.37 (m, 2H), 1.86-1.74 (m, 2H), 1.26 (s, 6H). |
| 134 | 475.34 | 1.23 | |
| 135 | 495.13 | 2.22 | |
| 136 | 441.29 | 2.70 | |
| 137 | 524.10 | 2.22 | |
| 138 | 521.30 | 2.04 | |
| 139 | 417.30 | 1.37 | |
| 140 | 454.30 | 0.28 | |
| 141 | 385.30 | 1.22 | |
| 142 | 451.50 | 1.35 | |
| 143 | 523.29 | 1.89 | |
| 144 | 432.18 | 1.87 | |
| 145 | 439.70 | 1.26 | |
| 146 | 459.70 | 1.78 | |
| 147 | 447.33 | 1.42 | |
| 148 | 505.30 | 1.63 | |
| 149 | 497.70 | 1.99 | 1H NMR (400 MHz, DMSO) δ 7.27-7.06 (m, 2H), 6.96 (d, J = 9.1 Hz, 1H), 5.17 (dd, J = 13.6, 4.2 Hz, 1H), 4.63 (dt, J = 12.1, 6.2 Hz, 1H), 3.31-3.19 (m, 5H), 2.92-2.81 (m, 1H), 2.67 (dd, J = 12.0, 10.1 Hz, 1H), 2.43-2.27 (m, 6H), 2.15 (s, 3H), 1.70-1.40 (m, 4H), 1.29 (d, J = 6.0 Hz, 6H). |
| 150 | 477.30 | 1.59 | |
| 151 | 491.14 | 1.72 | |
| 152 | 528.50 | 1.92 | |
| 153 | 473.26 | 2.23 | |
| 154 | 421.30 | 2.00 | 1H NMR (400 MHz, CDCl3) δ 7.25-7.16 (m, 2H), 6.81 (d, J = 8.2 Hz, 1H), 4.56 (dt, J = 12.1, 6.0 Hz, 1H), 3.85-3.57 (m, 2H), 3.41 (br s, 2H), 3.36 (d, J = 2.3 Hz, 2H), 2.88-2.76 (m, 2H), 2.51 (s, 2H), 2.20 (s, 3H), 2.09 (d, J = 14.2 Hz, 2H), 1.85 (t, J = 2.3 Hz, 3H), 1.54 (br s, 2H), 1.34 (d, J = 6.0 Hz, 6H). |
| 155 | 453.10 | 2.13 | |
| 156 | 511.16 | 2.14 | |
| 157 | 441.20 | 1.82 | |
| 158 | 423.70 | 0.93 | |
| 159 | 510.30 | 1.98 | |
| 160 | 433.50 | 1.25 | |
| 161 | 441.29 | 2.00 | |
| 162 | 522.60 | 1.43 | |
| 163 | 409.50 | 1.32 | 1H NMR (400 MHz, MeOD) δ 7.49-7.32 (m, 5H), 7.24-7.16 (m, 2H), 6.98-6.90 (m, 1H), 5.08-4.96 (m, 1H), 4.70-4.60 (m, 1H), 4.48-4.28 (m, 1H), 3.86-3.62 (m, 1H), 3.60-3.32 (m, 3H), 3.21-2.91 (m, 3H), 2.69-2.43 (m, 1H), 2.19 (s, 3H), 1.96-1.55 (m, 3H), 1.34 (d, J = 6.0 Hz, 6H). |
| 164 | 449.24 | 2.42 | |
| 165 | 539.29 | 2.02 | |
| 166 | 453.50 | 1.08 | |
| 167 | 484.70 | 0.99 | |
| 168 | 473.26 | 1.83 | |
| 169 | 467.30 | 1.21 | 1H NMR (400 MHz, DMSO) δ 7.36-7.27 (m, 4H), 7.24 (t, J = 6.7 Hz, 1H), 7.20-7.12 (m, 2H), 6.94 (d, J = 8.8 Hz, 1H), 4.63 (dt, J = 12.1, 6.0 Hz, 1H), 3.95-3.78 (m, 1H), 3.44 (dd, J = 30.4, 13.6 Hz, 3H), 3.34 (d, J = 5.5 Hz, 2H), 3.29-3.19 (m, 5H), 3.18-3.01 (m, 1H), 2.73 |

TABLE 2-continued

| Cmpd. No. | LC/MS M + 1 | LC/RT min | NMR |
|---|---|---|---|
| | | | (d, J = 10.3 Hz, 1H), 2.69-2.56 (m, 1H), 2.33 (d, J = 1.9 Hz, 1H), 2.12 (s, 3H), 1.75 (t, J = 11.0 Hz, 2H), 1.53-1.34 (m, 3H), 1.28 (d, J = 6.0 Hz, 6H). |
| 170 | 521.00 | 1.93 | 1H NMR (400 MHz, MeOD) δ 7.48 (dd, J = 8.7, 5.4 Hz, 2H), 7.32-7.19 (m, 2H), 7.13 (dd, J = 12.2, 5.4 Hz, 2H), 6.93 (d, J = 8.1 Hz, 1H), 6.22 (d, J = 55.6 Hz, 1H), 4.95 (s, 1H), 4.36 (s, 1H), 3.82 (s, 2H), 3.75-3.64 (m, 1H), 3.57-3.36 (m, 4H), 2.84 (d, J = 9.5 Hz, 2H), 2.65 (s, 1H), 2.27 (s, 3H), 1.76 (s, 3H), 1.35 (s, 6H). |
| 171 | 491.50 | 1.86 | 1H NMR (400 MHz, CDCl3) δ 8.30 (d, J = 4.8 Hz, 2H), 7.24-7.15 (m, 2H), 6.80 (d, J = 8.1 Hz, 1H), 6.53 (t, J = 4.7 Hz, 1H), 6.29 (t, J = 74.3 Hz, 1H), 4.75 (d, J = 13.0 Hz, 1H), 4.65 (d, J = 13.3 Hz, 1H), 4.55 (dt, J = 12.1, 6.1 Hz, 1H), 3.93 (m, 3H), 3.52 (br s, 2H), 3.37-3.17 (m, 1H), 2.88-2.73 (m, 2H), 2.19 (s, 3H), 2.03 (br s, 1H), 1.71-1.53 (m, 3H), 1.34 (d, J = 6.1 Hz, 6H). |
| 172 | 527.26 | 1.82 | |
| 173 | 471.29 | 2.50 | |
| 174 | 484.30 | 1.39 | |
| 175 | 449.34 | 1.28 | |
| 176 | 450.50 | 1.17 | |
| 177 | 478.10 | 2.21 | 1H NMR (400 MHz, CDCl3) δ 8.23 (d, J = 2.7 Hz, 1H), 7.63 (d, J = 8.7 Hz, 1H), 7.43-7.30 (m, 5H), 7.28-7.25 (m, 1H), 4.85 (dd, J = 33.8, 8.9 Hz, 1H), 4.64 (dq, J = 12.0, 6.0 Hz, 1H), 4.40 (d, J = 13.0 Hz, 1H), 3.88-3.77 (m, 1H), 3.70-3.14 (m, 2H), 3.07-2.91 (m, 3H), 2.82-2.55 (m, 2H), 2.40 (dd, J = 22.0, 10.9 Hz, 2H), 1.76-1.60 (m, 3H), 1.40 (d, J = 6.0 Hz, 6H). |
| 178 | 441.30 | 1.48 | |
| 179 | 481.70 | 1.24 | |
| 180 | 460.30 | 1.40 | |
| 181 | 495.70 | 1.95 | |
| 182 | 463.57 | 1.82 | |
| 183 | 483.30 | 1.95 | |
| 184 | 451.29 | 1.32 | |
| 185 | 413.36 | 1.43 | |
| 186 | 519.50 | 2.03 | |
| 187 | 473.30 | 1.91 | |
| 188 | 435.30 | 1.24 | |
| 189 | 511.26 | 1.87 | |
| 190 | 511.50 | 2.25 | 1H NMR (400 MHz, DMSO) δ 7.61 (dd, J = 7.8, 1.2 Hz, 1H), 7.50-7.31 (m, 3H), 7.30-7.12 (m, 3H), 6.36-6.00 (m, 1H), 5.08 (d, J = 13.4 Hz, 1H), 4.74-4.64 (m, 1H), 4.12-3.91 (m, 1H), 3.73-3.59 (m, 2H), 3.32 (dd, J = 32.0, 10.6 Hz, 1H), 3.06 (dd, J = 11.0, 3.1 Hz, 1H), 2.91 (dd, J = 11.6, 2.6 Hz, 1H), 2.86-2.65 (m, 2H), 2.44-2.30 (m, 1H), 2.19 (d, J = 9.6 Hz, 1H), 2.13-1.99 (m, 1H), 1.70-1.55 (m, 3H), 1.30 (d, J = 6.0 Hz, 6H). |
| 191 | 469.33 | 3.47 | |
| 192 | 453.50 | 1.10 | |
| 193 | 475.30 | 1.38 | |
| 194 | 507.29 | 1.94 | |
| 195 | 492.20 | 1.31 | |
| 196 | 512.70 | 2.17 | 1H NMR (400 MHz, CDCl3) δ 7.47 (s, 1H), 7.20 (d, J = 8.8 Hz, 2H), 6.81 (d, J = 8.1 Hz, 1H), 5.20 (dd, J = 9.3, 1.1 Hz, 1H), 4.62-4.52 (m, 1H), 3.76 (ddd, J = 36.3, 29.5, 14.8 Hz, 1H), 3.50 (dd, J = 10.4, 1.0 Hz, 2H), 3.33-3.13 (m, 1H), 3.05 (q, J = 9.3 Hz, 2H), 2.77 (d, J = 11.3 Hz, 1H), 2.60-2.42 (m, 6H), 2.20 (s, 3H), 1.79-1.46 (m, 4H), 1.35 (d, J = 6.0 Hz, 6H). |
| 197 | 455.29 | 2.34 | |
| 198 | 502.27 | 2.21 | |
| 199 | 493.00 | 1.87 | |
| 200 | 539.00 | 2.06 | |
| 201 | 473.39 | 1.40 | |
| 202 | 511.16 | 1.80 | |
| 203 | 439.70 | 1.21 | |
| 204 | 459.30 | 1.44 | |
| 205 | 419.31 | 1.26 | |
| 206 | 473.39 | 1.44 | |
| 207 | 481.50 | 1.43 | |
| 208 | 487.22 | 2.12 | |

TABLE 2-continued

| Cmpd. No. | LC/MS M + 1 | LC/RT min | NMR |
|---|---|---|---|
| 209 | 464.30 | 1.77 | 1H NMR (400 MHz, CDCl3) δ 7.74 (d, J = 0.7 Hz, 1H), 7.22-7.17 (m, 2H), 7.16 (d, J = 0.7 Hz, 1H), 7.04-6.70 (m, 2H), 5.44 (dd, J = 10.9, 1.9 Hz, 1H), 4.64-4.52 (m, 1H), 4.41-4.22 (m, 1H), 4.17-3.98 (m, 1H), 3.93-3.80 (m, 1H), 3.47-3.27 (m, 6H), 3.23 (d, J = 15.1 Hz, 1H), 2.81 (d, J = 12.3 Hz, 1H), 2.20 (s, 3H), 1.82-1.62 (m, 3H), 1.36 (d, J = 6.0 Hz, 6H). |
| 210 | 479.20 | 1.10 | |
| 211 | 481.30 | 7.73 | 1H NMR (400 MHz, CDCl3) δ 7.65 (d, J = 2.1 Hz, 1H), 7.19 (d, J = 8.6 Hz, 2H), 6.80 (d, J = 8.1 Hz, 1H), 6.37 (s, 1H), 5.06 (s, 1H), 4.55 (dt, J = 12.1, 6.1 Hz, 1H), 3.41 (d, J = 73.7 Hz, 4H), 3.15 (d, J = 10.6 Hz, 1H), 3.01 (q, J = 9.3 Hz, 2H), 2.77 (d, J = 11.4 Hz, 1H), 2.59 (dd, J = 19.2, 8.3 Hz, 2H), 2.47 (d, J = 11.3 Hz, 1H), 2.15 (d, J = 37.6 Hz, 3H), 2.01 (s, 1H), 1.64 (d, J = 48.9 Hz, 3H), 1.34 (d, J = 6.0 Hz, 6H). |
| 212 | 449.20 | 1.83 | |
| 213 | 511.70 | 2.48 | |
| 214 | 492.30 | 2.00 | |
| 215 | 449.34 | 1.27 | |
| 216 | 485.50 | 1.32 | |
| 217 | 413.50 | 1.50 | |
| 218 | 429.33 | 1.08 | |
| 219 | 489.22 | 2.00 | |
| 220 | 495.30 | 1.36 | |
| 221 | 478.50 | 1.47 | |
| 222 | 494.20 | 1.49 | |
| 223 | 519.30 | 1.78 | |
| 224 | 489.23 | 1.83 | |
| 225 | 551.50 | 1.87 | |
| 226 | 467.30 | 1.57 | |
| 227 | 441.70 | 1.23 | |
| 228 | 478.31 | 1.83 | |
| 229 | 491.30 | 1.89 | 1H NMR (400 MHz, CD3CN) δ 7.54 (d, J = 2.3 Hz, 1H), 7.18 (dd, J = 8.2, 1.2 Hz, 2H), 6.98 (t, J = 4.1 Hz, 1H), 6.92 (d, J = 9.0 Hz, 1H), 6.78 (dt, J = 53.9, 4.1 Hz, 1H), 6.34 (d, J = 2.3 Hz, 1H), 5.26 (d, J = 10.2 Hz, 1H), 4.63 (dt, J = 12.1, 6.0 Hz, 1H), 4.14 (q, J = 7.3 Hz, 2H), 3.63-3.35 (m, 5H), 3.37-3.13 (m, 3H), 3.08 (d, J = 13.2 Hz, 1H), 2.95 (d, J = 12.6 Hz, 1H), 2.64-2.02 (m, 11H), 1.73 (ddd, J = 26.1, 9.6, 3.2 Hz, 2H), 1.58 (d, J = 14.5 Hz, 1H), 1.48-1.36 (m, 3H), 1.32 (d, J = 6.0 Hz, 6H). |
| 230 | 520.30 | 2.34 | |
| 231 | 424.15 | 1.35 | |
| 232 | 473.33 | 1.42 | |
| 233 | 443.70 | 2.33 | |
| 234 | 525.00 | 2.28 | |
| 235 | 469.50 | 1.77 | 1H NMR (400 MHz, CDCl3) δ 8.40 (d, J = 4.5 Hz, 2H), 7.20 (d, J = 8.8 Hz, 2H), 6.80 (d, J = 8.1 Hz, 1H), 6.64 (s, 1H), 4.85 (d, J = 12.9 Hz, 1H), 4.76 (d, J = 13.1 Hz, 1H), 4.55 (dt, J = 12.1, 6.1 Hz, 1H), 4.16 (s, 1H), 3.94 (s, 1H), 3.64-3.44 (m, 5H), 3.28 (t, J = 11.5 Hz, 1H), 3.28 (t, J = 11.5 Hz, 1H), 2.92 (dd, J = 26.7, 12.5 Hz, 2H), 2.19 (s, 3H), 2.03 (s, 2H), 1.65 (d, J = 47.5 Hz, 4H), 1.34 (d, J = 6.1 Hz, 5H), 1.22 (t, J = 7.0 Hz, 3H). |
| 236 | 439.50 | 1.87 | 1H NMR (400 MHz, CDCl3) δ 8.44 (d, J = 4.8 Hz, 2H), 7.21 (d, J = 8.8 Hz, 2H), 6.80 (d, J = 8.1 Hz, 1H), 6.69 (s, 1H), 4.86 (d, J = 13.3 Hz, 1H), 4.77 (d, J = 12.4 Hz, 1H), 4.55 (dt, J = 12.3, 6.1 Hz, 1H), 3.66 (br s, 1H), 3.47 (br s, 1H), 3.17 (br s, 1H), 2.97 (d, J = 13.4 Hz, 1H), 2.81 (t, J = 12.2 Hz, 1H), 2.20 (s, 3H), 2.03 (br s, 1H), 1.78-1.52 (m, 6H), 1.34 (d, J = 6.1 Hz, 6H), 1.05 (t, J = 7.5 Hz, 3H). |
| 237 | 481.50 | 1.43 | |
| 238 | 487.50 | 1.48 | |
| 239 | 417.15 | 1.38 | |
| 240 | 455.29 | 2.13 | |
| 241 | 459.23 | 1.75 | |
| 242 | 399.30 | 1.37 | |
| 243 | 468.50 | 1.61 | |
| 244 | 495.20 | 2.07 | |
| 245 | 505.28 | 1.98 | |
| 246 | 474.24 | 2.03 | |
| 247 | 521.20 | 2.12 | |
| 248 | 413.30 | 1.47 | |
| 249 | 459.35 | 1.26 | |
| 250 | 458.70 | 1.28 | |

TABLE 2-continued

| Cmpd. No. | LC/MS M + 1 | LC/RT min | NMR |
|---|---|---|---|
| 251 | 489.50 | 2.00 | |
| 252 | 474.28 | 1.38 | |
| 253 | 504.40 | 1.29 | |
| 254 | 405.28 | 1.24 | |
| 255 | 433.29 | 1.28 | |
| 256 | 484.30 | 1.94 | |
| 257 | 495.50 | 2.12 | |
| 258 | 521.30 | 2.26 | |
| 259 | 459.30 | 1.17 | |
| 260 | 459.30 | 1.94 | |
| 261 | 492.20 | 1.32 | |
| 262 | 459.50 | 1.51 | |
| 263 | 481.10 | 1.66 | |
| 264 | 453.50 | 1.23 | |
| 265 | 536.70 | 1.23 | |
| 266 | 465.50 | 1.93 | |
| 267 | 455.29 | 2.20 | |
| 268 | 474.30 | 1.33 | |
| 269 | 539.15 | 1.90 | |
| 270 | 461.30 | 1.21 | |
| 271 | 469.50 | 1.54 | |
| 272 | 419.70 | 1.20 | |
| 273 | 507.30 | 1.96 | |
| 274 | 507.20 | 1.93 | |
| 275 | 434.20 | 1.55 | |
| 276 | 499.33 | 3.20 | |
| 277 | 414.18 | 1.20 | |
| 278 | 507.40 | 2.15 | |
| 279 | 508.40 | 1.44 | |
| 280 | 538.17 | 1.83 | |
| 281 | 451.50 | 1.38 | |
| 282 | 456.31 | 2.33 | |
| 283 | 448.20 | 2.01 | |
| 284 | 481.24 | 2.79 | |
| 285 | 431.34 | 1.25 | |
| 286 | 453.30 | 1.98 | |
| 287 | 431.33 | 1.03 | |
| 288 | 450.50 | 1.17 | |
| 289 | 479.40 | 1.98 | |
| 290 | 470.15 | 1.98 | |
| 291 | 454.20 | 1.32 | |
| 292 | 549.50 | 2.28 | |
| 293 | 536.40 | 1.95 | |
| 294 | 455.37 | 1.57 | |
| 295 | 438.70 | 1.39 | 1H NMR (400 MHz, CDCl3) δ 8.21 (d, J = 5.7 Hz, 1H), 7.86 (t, J = 7.7 Hz, 1H), 7.25-7.19 (m, 2H), 6.92 (d, J = 9.2 Hz, 1H), 6.88 (t, J = 6.6 Hz, 1H), 6.80 (d, J = 8.2 Hz, 1H), 4.55 (dt, J = 12.1, 6.1 Hz, 1H), 4.48 (d, J = 13.6 Hz, 1H), 4.35 (d, J = 12.5 Hz, 1H), 3.77 (br s, 1H), 3.43 (br s, 1H), 3.20 (d, J = 13.4 Hz, 1H), 3.12 (br s, 1H), 3.04-2.91 (m, 1H), 2.20 (s, 3H), 2.09 (br s, 1H), 1.72-1.59 (m, 6H), 1.34 (d, J = 5.9 Hz, 6H), 1.07 (t, J = 7.4 Hz, 3H). |
| 296 | 476.20 | 0.96 | |
| 297 | 508.70 | 1.51 | |
| 298 | 481.30 | 1.48 | 1H NMR (400 MHz, DMSO) δ 7.48 (s, 1H), 7.35-7.13 (m, 3H), 6.60-6.25 (m, 1H), 5.06-4.91 (m, 1H), 4.75-4.64 (m, 1H), 4.27-3.99 (m, 1H), 3.58-2.55 (m, 9H), 2.07 (s, 3H), 1.67-1.39 (m, 4H), 1.30 (d, J = 6.0 Hz, 6H). |
| 299 | 503.26 | 2.07 | |
| 300 | 467.50 | 1.29 | |
| 301 | 491.50 | 2.33 | |
| 302 | 445.31 | 1.30 | |
| 303 | 466.29 | 2.67 | |
| 304 | 501.41 | 1.58 | |
| 305 | 490.20 | 1.11 | |
| 306 | 477.30 | 1.77 | 1H NMR (400 MHz, CD3CN) δ 7.50 (d, J = 2.3 Hz, 1H), 7.24-7.14 (m, 2H), 6.98 (s, 1H), 6.92 (d, J = 9.1 Hz, 1H), 6.81 (dd, J = 31.0, 26.9 Hz, 1H), 6.35 (d, J = 2.3 Hz, 1H), 5.26 (d, J = 9.6 Hz, 1H), 4.63 (dt, J = 12.0, 6.0 Hz, 1H), 3.85 (s, 4H), 3.67-3.37 (m, 5H), 3.36-3.14 (m, 3H), 3.08 (d, J = 13.9 Hz, 1H), 2.95 (d, J = 12.7 Hz, 1H), 2.70-2.03 (m, 14H), 1.97 (s, 1H), 1.81-1.51 (m, 4H), 1.32 (t, J = 5.4 Hz, 7H). |
| 307 | 495.10 | 1.88 | |
| 308 | 424.50 | 1.14 | |

TABLE 2-continued

| Cmpd. No. | LC/MS M + 1 | LC/RT min | NMR |
|---|---|---|---|
| 309 | 496.70 | 1.99 | 1H NMR (400 MHz, DMSO) δ 7.27-7.13 (m, 2H), 6.96 (d, J = 9.0 Hz, 1H), 6.82 (d, J = 1.2 Hz, 1H), 4.86 (dd, J = 12.0, 4.7 Hz, 1H), 4.71-4.54 (m, 1H), 3.32-3.14 (m, 5H), 3.07 (dd, J = 11.5, 2.6 Hz, 1H), 2.90-2.83 (m, 1H), 2.70 (dd, J = 18.3, 7.2 Hz, 1H), 2.41-2.23 (m, 6H), 2.13 (s, 3H), 1.64-1.39 (m, 3H), 1.29 (d, J = 6.0 Hz, 6H). |

Assays for Detecting and Measuring NaV Inhibition Properties of Compound
E-VIPR Optical Membrane Potential Assay Method with Electrical Stimulation Sodium channels are voltage-dependent proteins that can be activated by inducing membrane voltage changes by applying electric fields. The electrical stimulation instrument and methods of use are described in Ion Channel Assay Methods PCT/US01/21652, herein incorporated by reference and are referred to as E-VIPR. The instrument comprises a microtiter plate handler, an optical system for exciting the coumarin dye while simultaneously recording the coumarin and oxonol dye emissions, a waveform generator, a current- or voltage-controlled amplifier, and a device for inserting electrodes in well. Under integrated computer control, this instrument passes user-programmed electrical stimulus protocols to cells within the wells of the microtiter plate.

24 hours before the assay on E-VIPR, HEK cells expressing human NaV subtype, like NaV 1.7, are seeded in 384-well poly-lysine coated plates at 15,000-20,000 cells per well. Other subtypes are performed in an analogous mode in a cell line expressing the NaV of interest. HEK cells are grown in media (exact composition is specific to each cell type and NaV subtype) supplemented with 10% FBS (Fetal Bovine Serum, qualified; GibcoBRL #16140-071) and 1% Pen-Strep (Penicillin-Streptomycin; GibcoBRL #15140-122). Cells are grown in vented cap flasks, in 90% humidity and 10% $CO_2$, to 100% confluence. They are usually split by trypsinization 1:10 or 1:20, depending on scheduling needs, and grown for 2-3 days before the next split.

Reagents and Solutions 100 mg/mL Pluronic F-127 (Sigma #P2443), in dry DMSO
Compound Plates: 384-well round bottom plate, e.g. Corning 384-well Polypropylene Round Bottom #3656
Cell Plates: 384-well tissue culture treated plate, e.g. Greiner #781091-1B
10 mM $DiSBAC_6(3)$ (Aurora #00-100-010) in dry DMSO
10 mM CC2-DMPE (Aurora #00-100-008) in dry DMSO
200 mM ABSC1 in $H_2O$
Bath1 buffer. Glucose 10 mM (1.8 g/L), Magnesium Chloride (Anhydrous), 1 mM (0.095 g/L), Calcium Chloride, 2 mM (0.222 g/L), HEPES 10 mM (2.38 g/L), Potassium Chloride, 4.5 mM (0.335 g/L), Sodium Chloride 160 mM (9.35 g/L).
Hexyl Dye Solution: Bath1 Buffer+0.5% β-cyclodextrin (make this prior to use, Sigma #C4767), 8 μM CC2-DMPE+ 2.5 μM DiSBAC6(3). To make the solution Add volume of 10% Pluronic F127 stock equal to volumes of CC2-DMPE+ DiSBAC6(3). The order of preparation is first mix Pluronic and CC2-DMPE, then add DiSBAC6(3) while vortexing, then add Bath1+β-Cyclodextrin.

Assay Protocol

1) Pre-spot compounds (in neat DMSO) into compound plates. Vehicle control (neat DMSO), the positive control (20 mM DMSO stock tetracaine, 125 μM final in assay) and test compounds are added to each well at 160× desired final concentration in neat DMSO. Final compound plate volume will be 80 μL (80-fold intermediate dilution from 1 μL DMSO spot; 160-fold final dilution after transfer to cell plate). Final DMSO concentration for all wells in assay is 0.625%.

2) Prepare Hexyl Dye Solution.

3) Prepare cell plates. On the day of the assay, medium is aspirated and cells are washed three times with 100 μL of Bath1 Solution, maintaining 25 μL residual volume in each well.

4) Dispense 25 μL per well of Hexyl Dye Solution into cell plates. Incubate for 20-35 minutes at room temp or ambient conditions.

5) Dispense 80 μL per well of Bath1 into compound plates. Acid Yellow-17 (1 mM) is added and Potassium Chloride can be altered from 4.5 to 20 mM depending on the NaV subtype and assay sensitivity.

6) Wash cell plates three times with 100 μL per well of Bath1, leaving 25 μL of residual volume. Then transfer 25 uL per well from Compound Plates to Cell Plates. Incubate for 20-35 minutes at room temp/ambient condition 7) Read Plate on E-VIPR. Use the current-controlled amplifier to deliver stimulation wave pulses for typically 9 seconds and a scan rate of 400 Hz. A pre-stimulus recording is performed for 0.5 seconds to obtain the un-stimulated intensities baseline. The stimulatory waveform is applied for 9 seconds followed by 0.5 seconds of post-stimulation recording to examine the relaxation to the resting state. The stimulatory waveform of the electrical stimulation is specific for each cell type and can vary the magnitude, duration and frequency of the applied current to provide an optimal assay signal.

Data Analysis

Data are analyzed and reported as normalized ratios of background-subtracted emission intensities measured in the 460 nm and 580 nm channels. Background intensities are then subtracted from each assay channel. Background intensities are obtained by measuring the emission intensities during the same time periods from identically treated assay wells in which there are no cells. The response as a function of time is then reported as the ratios obtained using the following formula:

$$R(t) = \frac{(intensity_{460\ nm} - background_{460\ nm})}{(intensity_{580\ nm} - background_{580\ nm})}$$

The data is further reduced by calculating the initial ($R_i$) and final ($R_f$) ratios. These are the average ratio values during part or all of the pre-stimulation period, and during sample points during the stimulation period. The response to the stimulus $R=R_f/R_i$ is then calculated and reported as a function of time.

Control responses are obtained by performing assays in the presence of a compound with the desired properties (positive control), such as tetracaine, and in the absence of pharmacological agents (negative control). Responses to the negative (N) and positive (P) controls are calculated as above. The compound antagonist activity A is defined as:

$$A = \frac{R-P}{N-P} * 100.$$

where R is the ratio response of the test compound

Electrophysiology Assays for NaV Activity and Inhibition of Test Compounds

Patch clamp electrophysiology was used to assess the efficacy and selectivity of sodium channel blockers in dorsal root ganglion neurons. Rat neurons were isolated from the dorsal root ganglions and maintained in culture for 2 to 10 days in the presence of NGF (50 ng/ml) (culture media consisted of NeurobasalA supplemented with B27, glutamine and antibiotics). Small diameter neurons (nociceptors, 8-12 μm in diameter) have been visually identified and probed with fine tip glass electrodes connected to an amplifier (Axon Instruments). The "voltage clamp" mode has been used to assess the compound's IC50 holding the cells at −60 mV. In addition, the "current clamp" mode has been employed to test the efficacy of the compounds in blocking action potential generation in response to current injections. The results of these experiments have contributed to the definition of the efficacy profile of the compounds.

IonWorks Assays.

Sodium currents were recorded using the automated patch clamp system, IonWorks (Molecular Devices Corporation, Inc.). Cells expressing Nav subtypes are harvested from tissue culture and placed in suspension at 0.5-4 million cells per mL Bath1. The IonWorks instrument measures changes in sodium currents in response to applied voltage clamp similarly to the traditional patch clamp assay, except in a 384-well format. Using the IonWorks, dose-response relationships were determined in voltage clamp mode by depolarizing the cell from the experiment specific holding potential to a test potential of about 0 mV before and following addition of the test compound. The influence of the compound on currents are measured at the test potential.

1-Benzazepin-2-One Binding Assay

The sodium channel inhibiting properties of the compounds of the invention can also be determined by assay methods described in Williams, B. S. et al., "Characterization of a New Class of Potent Inhibitors of the Voltage-Gated Sodium Channel NaV 1.7," *Biochemistry*, 2007, 46, 14693-14703, the entire contents of which are incorporated herein by reference.

The exemplified compounds of Table 1 herein are active against one or more sodium channels as measured using the assays described herein above as presented in Table 3.

TABLE 3

| Cmpd. No. | Binned Activity Data |
| --- | --- |
| 1 | ++ |
| 2 | + |
| 3 | +++ |
| 4 | ++ |

TABLE 3-continued

| Cmpd. No. | Binned Activity Data |
| --- | --- |
| 5 | +++ |
| 6 | ++ |
| 7 | +++ |
| 8 | ++ |
| 9 | ++ |
| 10 | +++ |
| 11 | +++ |
| 12 | +++ |
| 13 | +++ |
| 14 | + |
| 15 | + |
| 16 | +++ |
| 17 | +++ |
| 18 | +++ |
| 19 | +++ |
| 20 | +++ |
| 21 | +++ |
| 22 | +++ |
| 23 | + |
| 24 | +++ |
| 25 | ++ |
| 26 | ++ |
| 27 | +++ |
| 28 | + |
| 29 | +++ |
| 30 | + |
| 31 | + |
| 32 | + |
| 33 | +++ |
| 34 | + |
| 35 | + |
| 36 | + |
| 37 | +++ |
| 38 | ++ |
| 39 | ++ |
| 40 | + |
| 41 | +++ |
| 42 | +++ |
| 43 | ++ |
| 44 | +++ |
| 45 | +++ |
| 46 | +++ |
| 47 | +++ |
| 48 | +++ |
| 49 | +++ |
| 50 | +++ |
| 51 | + |
| 52 | +++ |
| 53 | ++ |
| 54 | +++ |
| 55 | +++ |
| 56 | ++ |
| 57 | ++ |
| 58 | +++ |
| 59 | +++ |
| 60 | +++ |
| 61 | +++ |
| 62 | +++ |
| 63 | ++ |
| 64 | + |
| 65 | + |
| 66 | +++ |
| 67 | +++ |
| 68 | ++ |
| 69 | + |
| 70 | +++ |
| 71 | + |
| 72 | + |
| 73 | +++ |
| 74 | +++ |
| 75 | +++ |
| 76 | ++ |
| 77 | +++ |
| 78 | +++ |
| 79 | +++ |
| 80 | + |
| 81 | + |
| 82 | ++ |

TABLE 3-continued

| Cmpd. No. | Binned Activity Data |
|---|---|
| 83 | +++ |
| 84 | + |
| 85 | ++ |
| 86 | +++ |
| 87 | ++ |
| 88 | +++ |
| 89 | +++ |
| 90 | + |
| 91 | +++ |
| 92 | + |
| 93 | +++ |
| 94 | +++ |
| 95 | + |
| 96 | + |
| 97 | +++ |
| 98 | +++ |
| 99 | +++ |
| 100 | +++ |
| 101 | +++ |
| 102 | +++ |
| 103 | +++ |
| 104 | +++ |
| 105 | +++ |
| 106 | + |
| 107 | +++ |
| 108 | + |
| 109 | ++ |
| 110 | +++ |
| 111 | +++ |
| 112 | +++ |
| 113 | + |
| 114 | +++ |
| 115 | ++ |
| 116 | +++ |
| 117 | +++ |
| 118 | + |
| 119 | +++ |
| 120 | +++ |
| 121 | + |
| 122 | + |
| 123 | ++ |
| 124 | +++ |
| 125 | + |
| 126 | +++ |
| 127 | ++ |
| 128 | +++ |
| 129 | +++ |
| 130 | + |
| 131 | +++ |
| 132 | ++ |
| 133 | +++ |
| 134 | + |
| 135 | +++ |
| 136 | ++ |
| 137 | +++ |
| 138 | +++ |
| 139 | + |
| 140 | +++ |
| 141 | + |
| 142 | + |
| 143 | +++ |
| 144 | ++ |
| 145 | + |
| 146 | ++ |
| 147 | +++ |
| 148 | ++ |
| 149 | ++ |
| 150 | +++ |
| 151 | + |
| 152 | +++ |
| 153 | +++ |
| 154 | + |
| 155 | + |
| 156 | +++ |
| 157 | + |
| 158 | + |
| 159 | + |
| 160 | ++ |
| 161 | + |
| 162 | + |
| 163 | + |
| 164 | + |
| 165 | +++ |
| 166 | ++ |
| 167 | + |
| 168 | +++ |
| 169 | +++ |
| 170 | +++ |
| 171 | +++ |
| 172 | + |
| 173 | ++ |
| 174 | +++ |
| 175 | +++ |
| 176 | +++ |
| 177 | +++ |
| 178 | +++ |
| 179 | + |
| 180 | +++ |
| 181 | + |
| 182 | +++ |
| 183 | +++ |
| 184 | +++ |
| 185 | + |
| 186 | +++ |
| 187 | +++ |
| 188 | ++ |
| 189 | +++ |
| 190 | +++ |
| 191 | +++ |
| 192 | +++ |
| 193 | +++ |
| 194 | +++ |
| 195 | +++ |
| 196 | +++ |
| 197 | ++ |
| 198 | + |
| 199 | ++ |
| 200 | +++ |
| 201 | +++ |
| 202 | + |
| 203 | ++ |
| 204 | +++ |
| 205 | +++ |
| 206 | +++ |
| 207 | +++ |
| 208 | + |
| 209 | +++ |
| 210 | + |
| 211 | +++ |
| 212 | +++ |
| 213 | +++ |
| 214 | ++ |
| 215 | ++ |
| 216 | ++ |
| 217 | +++ |
| 218 | +++ |
| 219 | +++ |
| 220 | +++ |
| 221 | +++ |
| 222 | +++ |
| 223 | +++ |
| 224 | +++ |
| 225 | +++ |
| 226 | ++ |
| 227 | +++ |
| 228 | +++ |
| 229 | ++ |
| 230 | +++ |
| 231 | + |
| 232 | +++ |
| 233 | +++ |
| 234 | +++ |
| 235 | +++ |
| 236 | +++ |
| 237 | +++ |
| 238 | ++ |

TABLE 3-continued

| Cmpd. No. | Binned Activity Data |
|---|---|
| 239 | + |
| 240 | + |
| 241 | ++ |
| 242 | ++ |
| 243 | +++ |
| 244 | +++ |
| 245 | +++ |
| 246 | +++ |
| 247 | ++ |
| 248 | +++ |
| 249 | ++ |
| 250 | +++ |
| 251 | +++ |
| 252 | ++ |
| 253 | ++ |
| 254 | ++ |
| 255 | + |
| 256 | +++ |
| 257 | +++ |
| 258 | +++ |
| 259 | +++ |
| 260 | +++ |
| 261 | +++ |
| 262 | +++ |
| 263 | +++ |
| 264 | + |
| 265 | ++ |
| 266 | ++ |
| 267 | ++ |
| 268 | ++ |
| 269 | ++ |
| 270 | ++ |
| 271 | +++ |
| 272 | + |
| 273 | ++ |
| 274 | +++ |
| 275 | + |
| 276 | +++ |
| 277 | ++ |
| 278 | +++ |
| 279 | +++ |
| 280 | ++ |
| 281 | +++ |
| 282 | +++ |
| 283 | +++ |
| 284 | +++ |
| 285 | +++ |
| 286 | +++ |
| 287 | +++ |
| 288 | +++ |
| 289 | ++ |
| 290 | + |
| 291 | +++ |
| 292 | ++ |
| 293 | +++ |
| 294 | +++ |
| 295 | +++ |
| 296 | + |
| 297 | +++ |
| 298 | +++ |
| 299 | + |
| 300 | +++ |
| 301 | +++ |
| 302 | +++ |
| 303 | +++ |
| 304 | +++ |
| 305 | ++ |
| 306 | +++ |
| 307 | +++ |
| 308 | + |
| 309 | +++ |

IC50: +++ <= 2.0 µM < ++ <= 5.0 µM < +

Many modifications and variations of the embodiments described herein may be made without departing from the scope, as is apparent to those skilled in the art. The specific embodiments described herein are offered by way of example only.

We claim:
1. A compound of formula I:

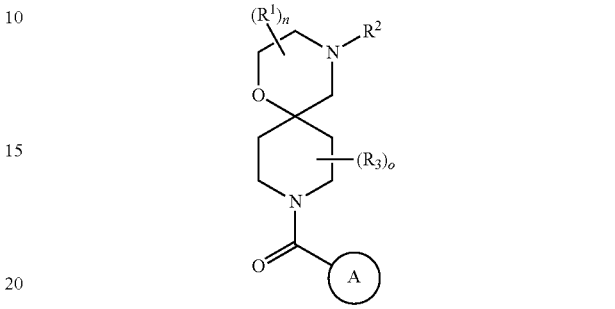

or a pharmaceutically acceptable salt thereof,
wherein, independently for each occurrence:
$R^1$ is C1-C6 alkyl, C1-C6 fluoroalkyl, C3-C8 cycloalkyl, halo, $NR^8SO_2R^8$, $SO_2R^8$, $SR^8$, $SOR^8$, $NR^8COR^8$, $NR8CO_2R^8$, CN, $CON(R^8)_2$, $SO_2N(R^8)_2$, $CF_3$, optionally substituted heterocycloalkyl, phenyl, heteroaryl, or a straight chain, branched, or cyclic-(C3-C8)—$R^9$ wherein up to two $CH_2$ units may be replaced with O, CO, S, SO, $SO_2$, N, $CF_2$, or $NR^8$;

$R^2$ is H, C1-C6 alkyl, C1-C6 fluoroalkyl, an optionally substituted cycloalkyl, aryl, heteroaryl, or heterocycloalkyl, $COR^8$, $CO_2R^8$, $CON(R^8)_2$, $CF_3$, $CHF_2$, or a straight chain, branched, or cyclic-(C3-C8)—$R^9$ wherein up to two $CH_2$ units may be replaced with O, CO, S, SO, $SO_2$, N, $CF_2$, or $NR^8$;

$R^3$ is C1-C6 alkyl or halo;

$R^8$ is H, C1-C6 alkyl, or C3-C8 cycloalkyl, a straight chain, branched, or cyclic (C3-C8)—$R^9$ wherein up to two $CH_2$ units may be replaced with O, CO, S, SO, $SO_2$, N, $CF_2$, or NR, or 2 $R^8$ taken together with the atoms to which they are attached form a ring;

$R^9$ is H, $CF_3$, $CHF_2$, $CH_2F$, $CO_2R$, OH, optionally substituted aryl, heteroaryl, C3-C8 cycloalkyl, heterocycloalkyl, $N(R)_2$, NRCOR, $CON(R)_2$, CN, or $SO_2R$;

R is H, C1-C6 alkyl, optionally substituted aryl, heteroaryl, C3-C8 cycloalkyl, or heterocycloalkyl;

A is an aryl, heteroaryl or heterocyclic in which each is optionally substituted with C1-C6 alkyl, C3-C8 cycloalkyl, C3-C8 cycloalkoxy, C1-C6 alkoxy, halo, CN, OH, $OR^8$, $N(R^8)_2$, $NR^8SO_2R^8$, $SO_2R^8$, $SOR^8$, $SR^8$, $CO_2R^8$, $NR^8COR^8$, $NR^8CO_2R^8$ $CON(R^8)_2$, $SO_2N(R^8)_2$, $CHF_2$, $CF_3$, $OCF_3$, $OCHF_2$, $R^9$, heterocycloalkyl, heterocycloalkoxy, aryl, heteroaryl, or a straight chain, branched, or cyclic (C3-C8)—$R^9$ wherein up to three $CH_2$ units may be replaced with O, CO, S, SO, $SO_2$, N, $CF_2$, or $NR^8$;

n is an integer from 0 to 4 inclusive; and
o is an integer from 0 to 4 inclusive.

2. The compound of claim 1, wherein $R^1$ is optionally substituted aryl, heteroaryl, C1-C6 alkyl, C1-C6 fluoroalkyl, a straight chain, branched, or cyclic-(C3-C8)—$R^9$ wherein up to two $CH_2$ units may be replaced with O, CO, S, SO, $SO_2$, N, or $NR^8$.

3. The compound of claim 1, wherein $R^1$ is F, or optionally substituted phenyl, pyridyl, oxazole, thiazole, pyrazole, oxadiazole, CH$_2$OCH$_3$, CH$_2$F, CH$_2$OCH(CH$_3$)$_2$, CH$_2$OCHF$_2$, CH$_3$, CH$_2$CH$_3$, CH$_2$OH, C(CH$_3$)$_2$OH, CH$_2$CH$_2$OH, CH$_2$OCH$_2$CH$_3$, CH(CH$_2$)$_2$,

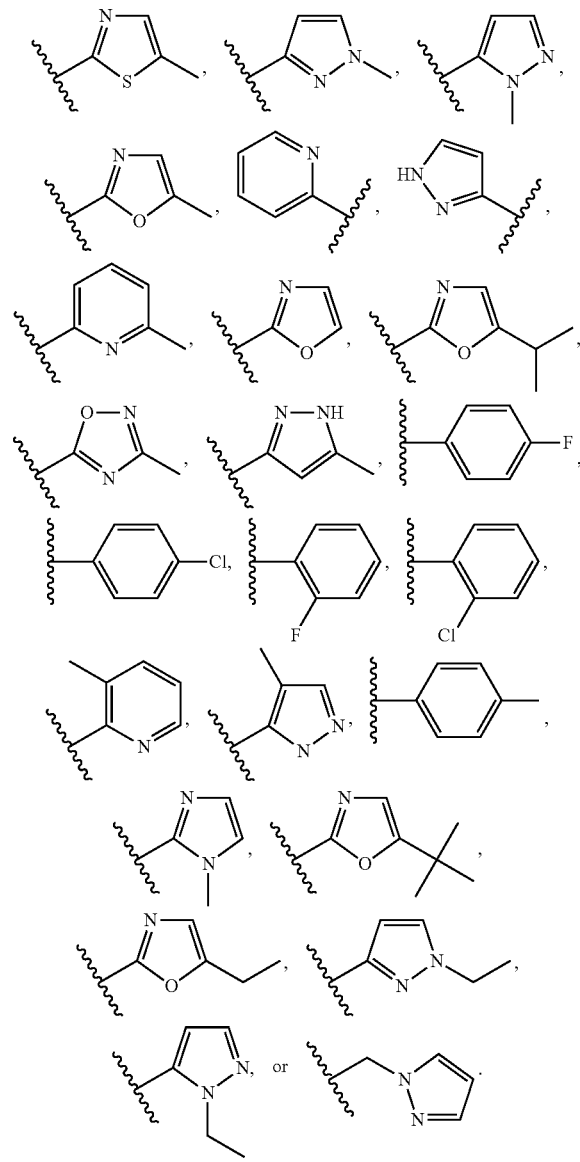

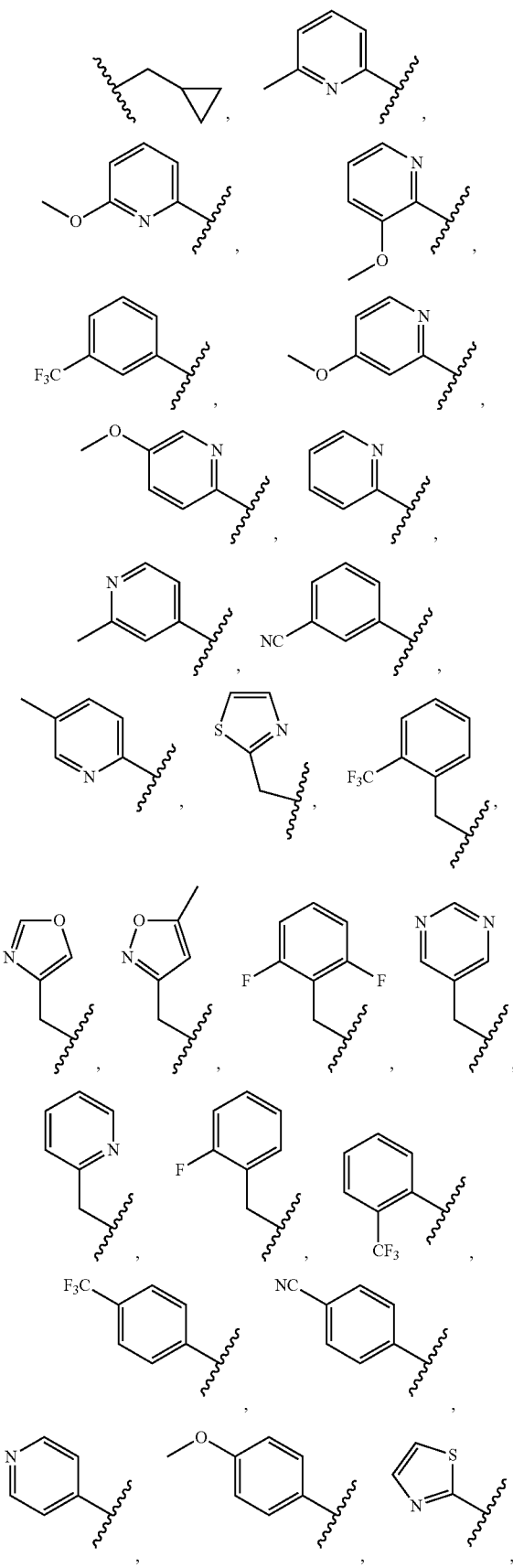

4. The compound of claim 1, wherein R$^2$ is H, C1-C6 alkyl, C1-C6 fluoroalkyl, CF$_3$, cycloalkyl, aryl, heterocycloalkyl, heteroaryl, or a straight chain, branched, or cyclic-(C3-C8)—R$^9$ wherein up to two CH$_2$ units may be replaced with O, CO, S, SO, SO$_2$, N, or NR$^8$.

5. The compound of claim 1, wherein R$^2$ is H, CH$_2$CHF$_2$, CH$_2$CF$_3$, CH(CH$_3$)CH$_2$F, CH$_2$CH(CH$_3$)$_2$, CH$_3$, CH$_2$CH$_3$, tBu, CH$_2$CN, CH(CH$_3$)$_2$, CH$_2$C(CH$_3$)$_2$OH, CH$_2$CH$_2$CH(CH$_3$)$_2$, CH$_2$CH$_2$OH, C(O)CH$_2$CH$_3$, C(O)CH(CH$_3$)$_2$, CH(CH$_3$)CH$_2$F, CH$_2$CH(CH$_3$)$_2$, CH(CH$_2$CH$_3$)$_2$, CH$_2$C(CH$_3$)$_2$OH, CH$_2$CH$_2$CH(CH$_3$)$_2$, CH$_2$CH$_2$OH, C(O)CH$_3$, C(O)CH$_2$CH$_3$, C(O)CH(CH$_3$)$_2$, CH$_2$CF$_2$CH$_3$, CH$_2$CCCH$_3$, CH$_2$C(O)tBu, CH$_2$CH$_2$OCH$_3$, CH$_2$OCH$_3$, CH$_2$C(O)CH$_3$, CH$_2$C(O)OCH$_3$, CH$_2$CH$_2$OCH$_2$CH$_2$CH$_3$, CH$_2$CCCH$_2$CH$_3$, CH$_2$CH$_2$OCH$_2$CH$_3$, CH$_2$CH$_2$SCH$_3$, CH$_2$CH$_2$CH$_2$OCH$_3$, CH$_2$CH(CH$_2$CH$_3$)$_2$, n-butyl, n-propyl, -continued

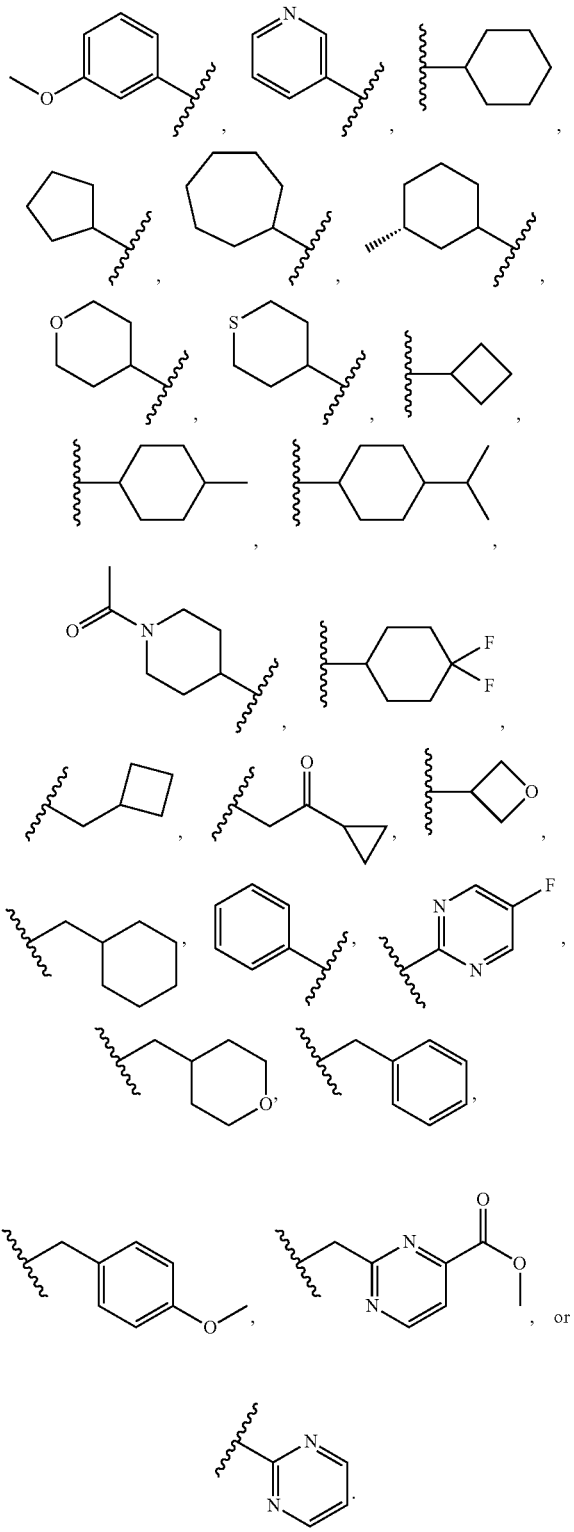

6. The compound of claim 1, wherein n is 0, 1, 2, or 3.
7. The compound of claim 1, wherein n is 1 or 2.
8. The compound of claim 1, wherein n is 1.
9. The compound of claim 1, wherein o is 0 or 1.
10. The compound of claim 1, wherein o is 0.

11. The compound of claim 1, wherein A is

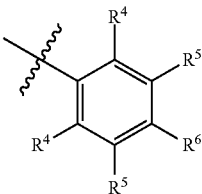

wherein:
$R^4$ is H, C1-C6 alkyl, C3-C8 cycloalkyl, C1-C6 alkoxy, halo, CN, OH, $OR^8$, $N(R^8)_2$, $NR^8SO_2R^8$, $SO_2R^8$, $SOR^8$, $SR^8$, $CO_2R^8$, $NR^8COR^8$, $NR^8CO_2R^8$, $CON(R^8)_2$, $SO_2N(R^8)_2$, $CHF_2$, $CF_3$, $OCF_3$, $OCHF_2$, $R^9$, heterocycloalkyl, heterocycloalkoxy, aryl, heteroaryl, or a straight chain, branched, or cyclic-(C3-C8)—$R^9$ wherein up to three $CH_2$ units may be replaced with O, CO, S, SO, $SO_2$, N, $CF_2$, or $NR^8$;

$R^5$ is H, C1-C6 alkyl, C3-C8 cycloalkyl, C1-C6 alkoxy, C3-C8 cycloalkoxy, halo, CN, OH, $OR^8$, $N(R^8)_2$, $NR^8SO_2R^8$, $SO_2R^8$, $SOR^8$, $SR^8$, $CO_2R^8$, $NR^8COR^8$, $NR^8CO_2R^8$, $CON(R^8)_2$, $SO_2N(R^8)_2$, $CF_3$, $OCF_3$, $OCHF_2$, $R^9$, heterocycloalkyl, heterocycloalkoxy, aryl, heteroaryl, or a straight chain, branched, or cyclic-(C3-C8)—$R^9$ wherein up to three $CH_2$ units may be replaced with O, CO, S, SO, $SO_2$, N, $CF_2$, or $NR^8$;

$R^6$ is H, C1-C6 alkyl, C3-C8 cycloalkyl, C1-C6 alkoxy, halo, CN, OH, $OR^8$, $N(R^8)_2$, $NR^8SO_2R^8$, $SO_2R^8$, $SOR^8$, $SR^8$, $CO_2R^8$, $NR^8COR^8$, $NR^8CO_2R^8$, $CON(R^8)_2$, $SO_2N(R^8)_2$, $CF_3$, $OCF_3$, $OCHF_2$, $R^9$, heterocycloalkyl, heterocycloalkoxy, aryl, heteroaryl, or a straight chain, branched, or cyclic-(C3-C8)—$R^9$ wherein up to three $CH_2$ units may be replaced with O, CO, S, SO, $SO_2$, N, $CF_2$, or $NR^8$; or two occurrences of $R^4$ and $R^5$, or $R^5$ and $R^6$ together with the carbons to which they are attached form an optionally substituted ring comprising up to 2 heteroatoms.

12. The compound of claim 11, wherein $R^4$ is H, C1-C6 alkyl, halo, or $OCHF_2$.

13. The compound of claim 11, wherein $R^4$ is H, F, $CH_3$, or $OCHF_2$.

14. The compound of claim 11, wherein $R^5$ is H, C1-C6 alkyl, C1-C6 alkoxy, halo, $CF_3$, CN, or a straight chain, branched, or cyclic-(C3-C8)—$R^9$ wherein up to three $CH_2$ units may be replaced with O, CO, S, SO, $SO_2$, N, or $NR^8$.

15. The compound of claim 11, wherein $R^5$ is H, $CH_3$, $OCH_3$, $OCH_2CH_3$, $OCH(CH_3)_2$, F, Cl, $CF_3$, CN, or $CH_2OH$.

16. The compound of claim 11, wherein $R^6$ is H, C1-C6 alkyl, C1-C6 alkoxy, $SO_2R^8$, $SO_2N(R^8)_2$, $R^9$, or a straight chain, branched, or cyclic (C3-C8)—$R^9$, wherein up to three $CH_2$ units may be replaced with O, S, SO, $SO_2$, N, or $NR^8$.

17. The compound of claim 11, wherein $R^6$ is H, $CH_2OH$, $OCH_3$, $OCH_2CH_3$, $OCH_2CH_2CH_3$, $OCH_2CH_2CH(CH_3)_2$, OtBu, tBu, $OCH(CH_3)_2$, $OCH_2C(CH_3)_2OCH_3$, $CH(OH)CH(CH_3)_2$, $C(OH)(CH_2CH_3)_2$, $OCH_2C(CH_3)_2OH$, $C(CH_3)_2OH$, $OCH_2CH_2OCH_3$, $OCH_2CH_2OH$, $OCH_2CH_2CH_2OH$, $CCCH_2OCH_3$, $SO_2CH_3$, $SO_2CH_2CH(CH_3)_2$, $SO_2CH(CH_3)_2$, $SO_2CH_2CH_3$, $SO_2C(CH_3)_3$, $CON(CH_2CH_3)_2$, $C(CH_3)_2CO_2CH_3$,

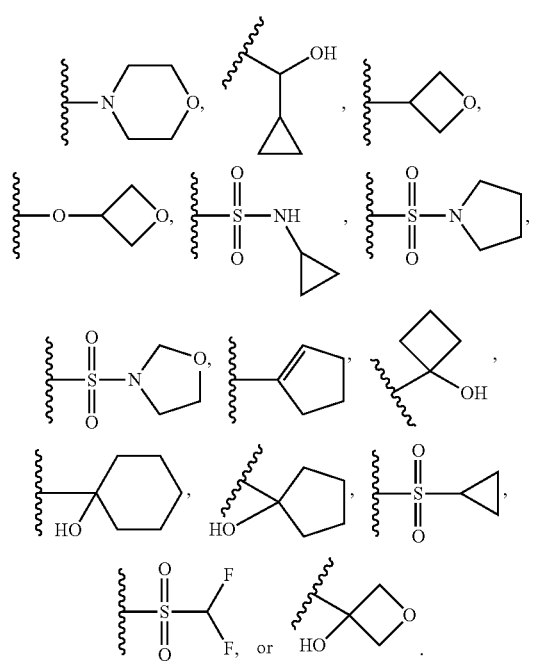
18. The compound of claim 11, wherein
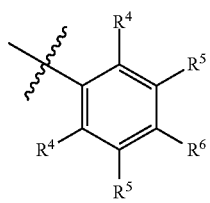
is:
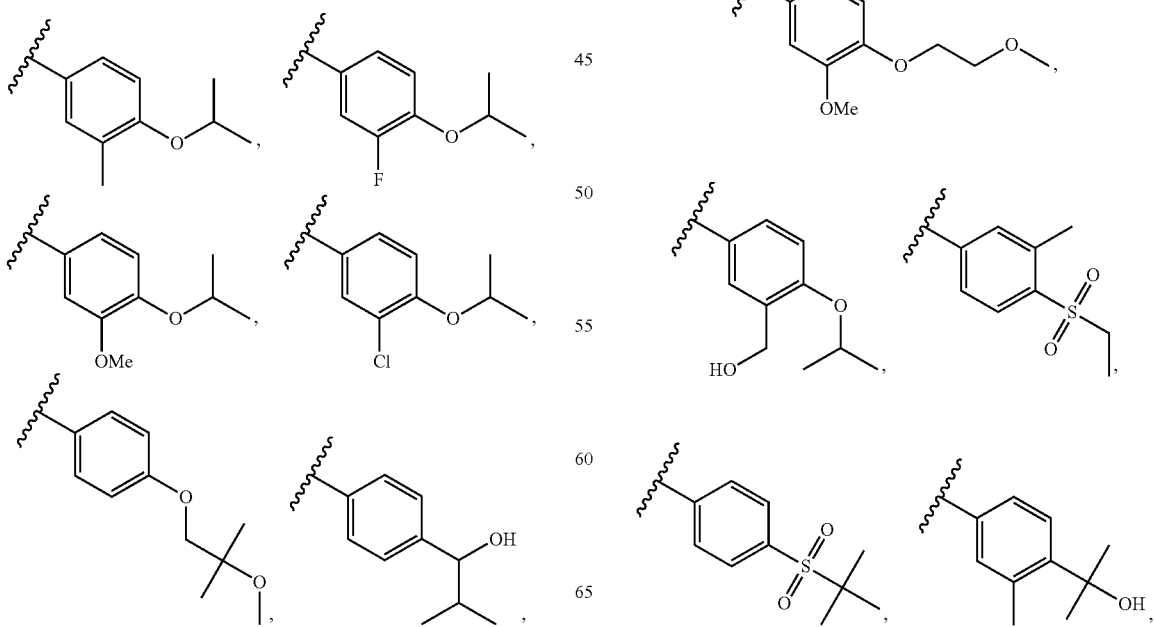

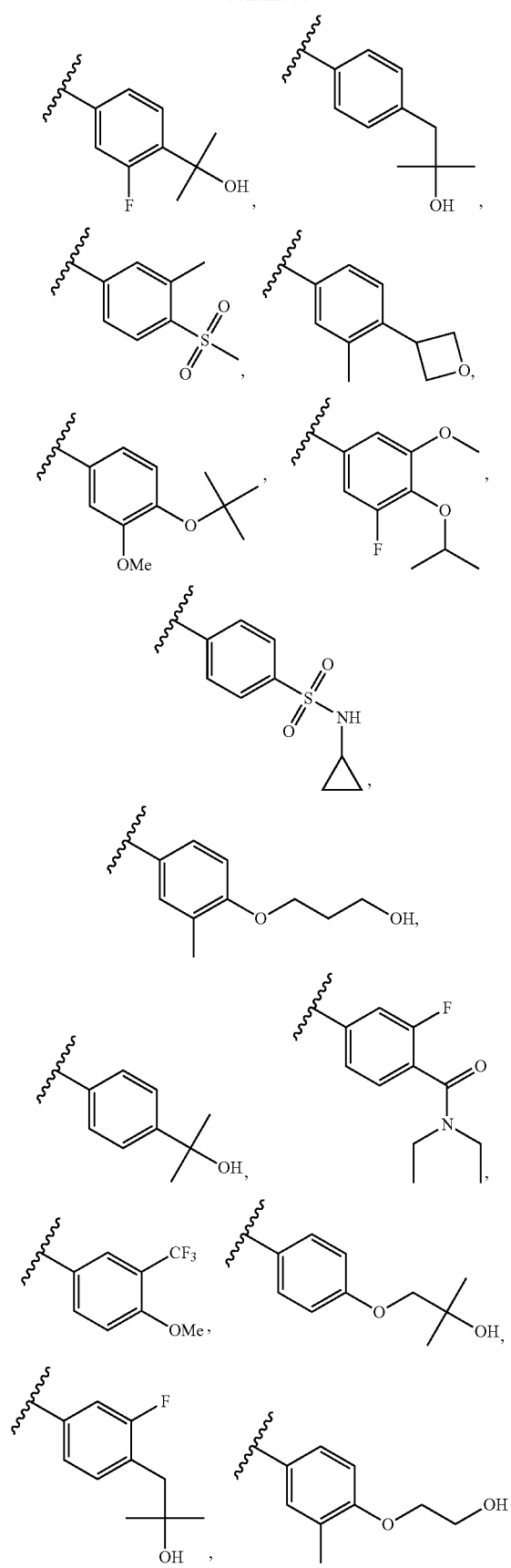
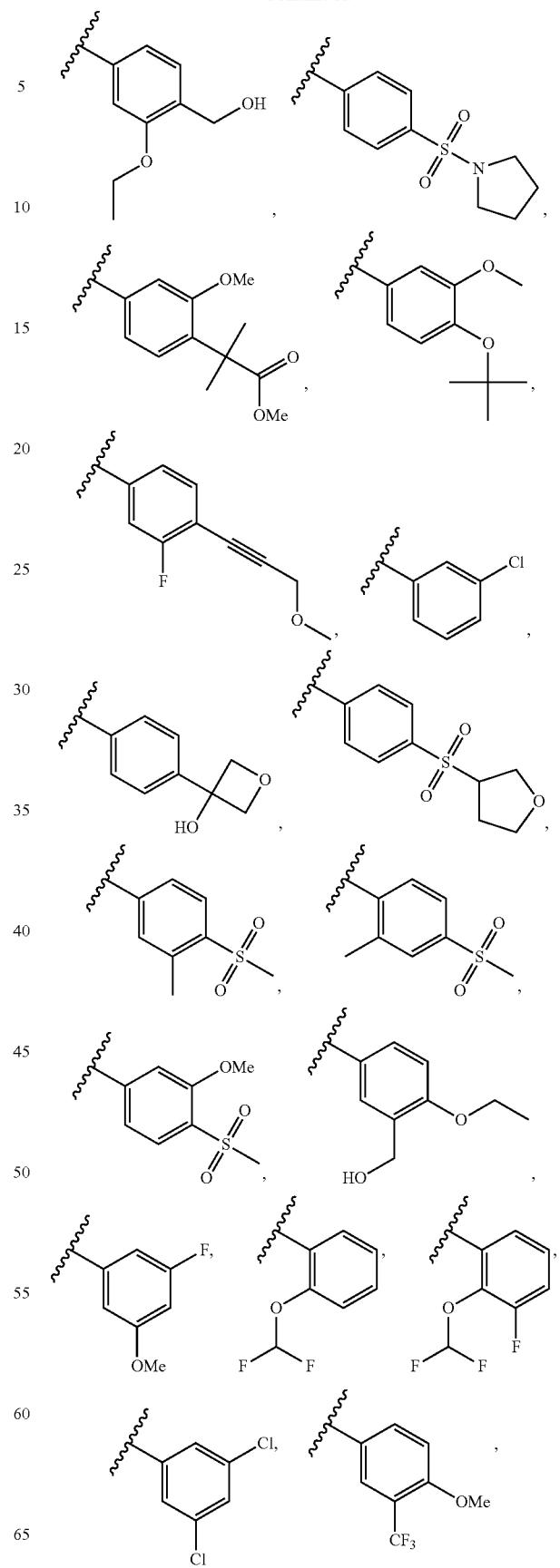

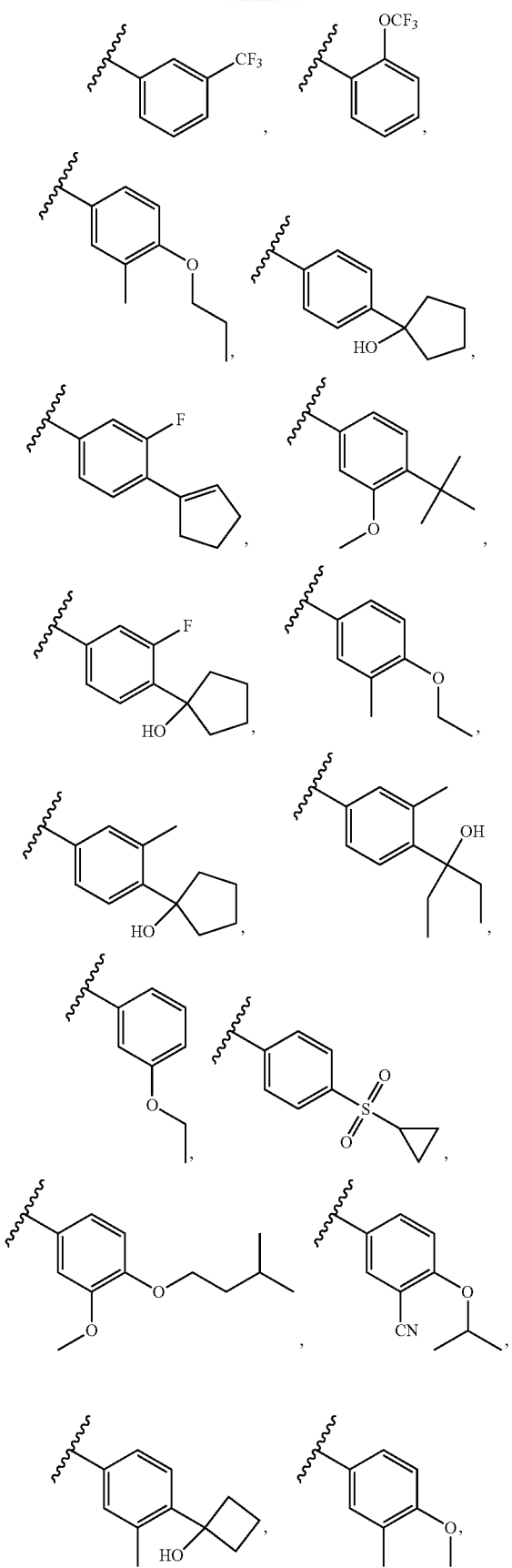
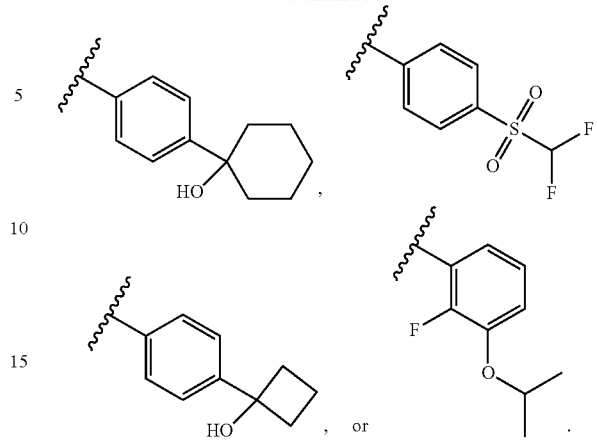
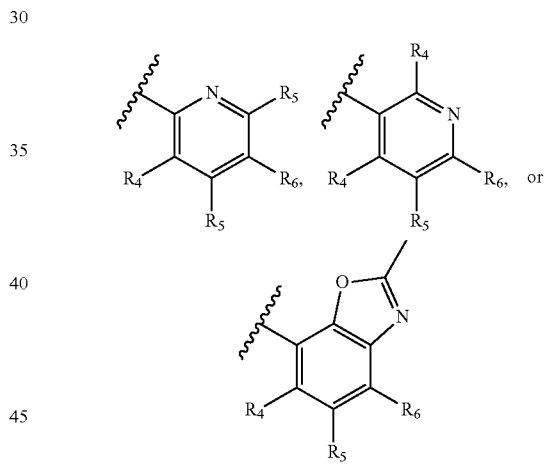

19. The compound of claim 1, wherein A is heteroaryl or heterocyclic.

20. The compound of claim 19, wherein A is a monocyclic heteroaryl comprising 1 to 3 heteroatoms, wherein said heteroatoms are independently N, O, or S.

21. The compound of claim 19, wherein A is a bicyclic heteroaryl comprising from 1 to 3 heteoratoms, wherein said heteroatoms are independently N, O, or S.

22. The compound of claim 19, wherein A is wherein:
$R^4$ is H, C1-C6 alkyl, C3-C8 cycloalkyl, C1-C6 alkoxy, halo, CN, OH, $OR^8$, $N(R^8)_2$, $NR^8SO_2R^8$, $SO_2R^8$, $SOR^8$, $SR^8$, $CO_2R^8$, $NR^8COR^8$, $NR^8CO_2R^8$, $CON(R^8)_2$, $SO_2N(R^8)_2$, $CHF_2$, $CF_3$, $OCF_3$, $OCHF_2$, $R^9$, heterocycloalkyl, heterocycloalkoxy, aryl, heteroaryl, or a straight chain, branched, or cyclic-(C3-C8)—$R^9$ wherein up to three $CH_2$ units may be replaced with O, CO, S, SO, $SO_2$, N, $CF_2$, or $NR^8$;

$R^5$ is H, C1-C6 alkyl, C3-C8 cycloalkyl, C1-C6 alkoxy, C3-C8 cycloalkoxy, halo, CN, OH, $OR^8$, $N(R^8)_2$, $NR^8SO_2R^8$, $SO_2R^8$, $SOR^8$, $SR^8$, $CO_2R^8$, $NR^8COR^8$, $NR^8CO_2R^8$, $CON(R^8)_2$, $SO_2N(R^8)_2$, $CF_3$, $OCF_3$, $OCHF_2$, $R^9$, heterocycloalkyl, heterocycloalkoxy, aryl, heteroaryl, or a straight chain, branched, or cyclic-(C3-C8)—$R^9$ wherein up to three $CH_2$ units may be replaced with O, CO, S, SO, $SO_2$, N, $CF_2$, or $NR^8$;

$R^6$ is H, C1-C6 alkyl, C3-C8 cycloalkyl, C1-C6 alkoxy, halo, CN, OH, $OR^8$, $N(R^8)_2$, $NR^8SO_2R^8$, $SO_2R^8$, $SOR^8$, SR⁸, CO₂R⁸, NR⁸COR⁸, NR⁸CO₂R⁸, CON(R⁸)₂, SO₂N(R⁸)₂, CF₃, OCF₃, OCHF₂, R⁹, heterocycloalkyl, heterocycloalkoxy, aryl, heteroaryl, or a straight chain, branched, or cyclic-(C3-C8)—R⁹ wherein up to three CH₂ units may be replaced with O, CO, S, SO, SO₂, N, CF₂, or NR⁸; or two occurrences of R⁴ and R⁵, or R⁵ and R⁶ together with the carbons to which they are attached form an optionally substituted ring comprising up to 2 heteroatoms.

23. The compound of claim 22, wherein R⁴ is H or C1-C6 alkyl.

24. The compound of claim 22, wherein R⁴ is H.

25. The compound of claim 22, wherein R⁵ is H, C1-C6 alkyl, or C1-C6 alkoxy.

26. The compound of claim 22, wherein R⁵ is H, CH₃, or OCH₃.

27. The compound of claim 22, wherein R⁶ is H, CN, C1-C6 alkoxy, or CF₃.

28. The compound of claim 22, wherein R⁶ is H, CN, OCH₃, or CF₃.

29. The compound of claim 22, wherein A is:

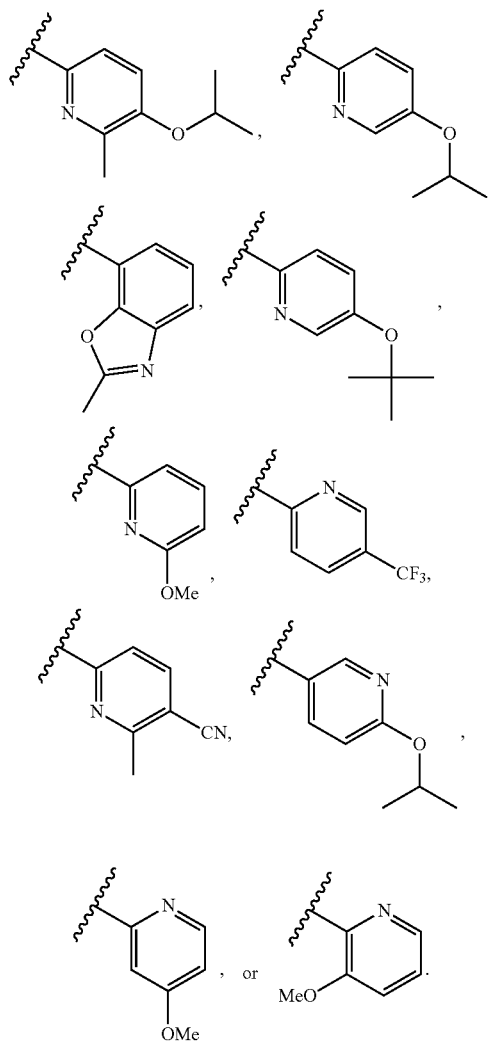

30. The compound of claim 1, wherein the compound has formula IA:

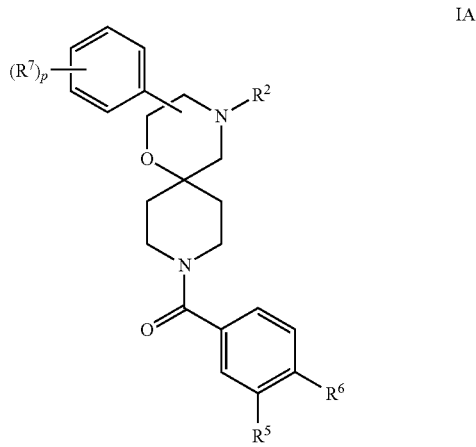

wherein:
R² is H, C1-C6 alkyl, C1-C6 fluoroalkyl, an optionally substituted cycloalkyl, aryl, heteroaryl, or heterocycloalkyl, or a straight chain, branched, or cyclic (C3-C8)—R⁹ wherein up to two CH₂ units may be replaced with O, CO, S, SO, SO₂, N, CF₂, or NR⁸;

R⁵ is H, C1-C6 alkyl, C1-C6 alkoxy, C1-C6 fluoroalkyl, halo, CF₃, OCF₃, OCHF₂, or a straight chain, branched, or cyclic-(C3-C8)—R⁹ wherein up to three CH₂ units may be replaced with O, CO, S, SO, SO₂, N, CF₂, or NR⁸;

R⁶ is H, C1-C6 alkyl, C1-C6 alkoxy, CN, SO₂R⁸, CON(R⁸)₂, SO₂N(R⁸)₂, heterocycloalkyl, or a straight chain, branched, or cyclic-(C3-C8)—R⁹ wherein up to three CH₂ units may be replaced with O, CO, S, SO, SO₂, N, CF₂, or NR8;

R⁷ is C1-C6 alkyl, C3-C8 cycloalkyl, C1-C6 alkoxy, halo, CN, OH, OR⁸, N(R⁸)₂, CF₃, OCF₃, or OCHF₂; and p is an integer from 0 to 3 inclusive.

31. The compound of claim 30, wherein R² is C1-C6 alkyl, C1-C6 fluoroalkyl, cycloalkyl, aryl, heterocycloalkyl, heteroaryl, or a straight chain, branched, or cyclic-(C3-C8)—R⁹ wherein up to two CH₂ units may be replaced with O, CO, S, SO, SO₂, N, CF₂, or NR⁸.

32. The compound of claim 30, wherein R² is CH₃, CH₂CH₃, CH(CH₃)₂, CH₂CH(CH₃)₂, CH₂CHF₂, CH₂CF₃, CH(CH₃)CH₂F, CH₂CN, CH₂CH₂OH, CH₂C(CH₃)₂OH, COCH₂CH₃, or COCH(CH₃)₂.

33. The compound of claim 30, wherein R⁵ is H, C1-C6 alkyl, C1-C6 alkoxy, C1-C6 fluroalkyl, halo, or a straight chain, branched, or cyclic (C3-C8)—R⁹ wherein up to three CH₂ units may be replaced with O, CO, S, SO, SO₂, N, CF₂, or NR⁸.

34. The compound of claim 30, wherein R⁵ is H, CH₃, OCH₃, OCH₂CH₃, CF₃, Cl, F, or CH₂OH.

35. The compound of claim 30, wherein R⁶ is H, C1-C6 alkoxy, or a straight chain, branched, or cyclic-(C3-C8)—R⁹ wherein up to three CH₂ units may be replaced with O, CO, S, SO, SO₂, N, CF₂, or NR⁸.

36. The compound of claim 30, wherein R⁶ is H, CH₂OH, OCH₂CH₃, OtBu, OCH(CH₃)₂, OCH₂C(CH₃)₂OCH₃, CH(OH)CH(CH₃)₂, OCH₂C(CH₃)₂OH, C(CH₃)₂OH, OCH₂CH₂OCH₃, OCH₂CH₂OH, OCH₂CH₂CH₂OH, CCCH$_2$OCH$_3$, SO$_2$CH$_3$, SO$_2$CH$_2$CH(CH$_3$)$_2$, SO$_2$CH(CH$_3$)$_2$, SO$_2$CH$_2$CH$_3$, SO$_2$C(CH$_3$)$_3$, CON(CH$_2$CH$_3$)$_2$, C(CH$_3$)$_2$CO$_2$CH$_3$,
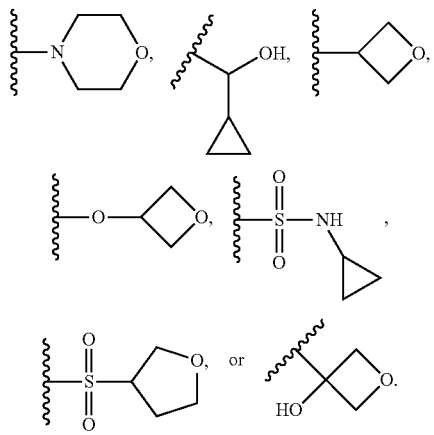
37. The compound of claim 30, wherein R$^7$ is halo.
38. The compound of claim 30, wherein R$^7$ is F.
39. The compound of claim 30, wherein the
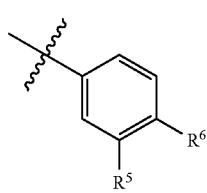
moiety is:
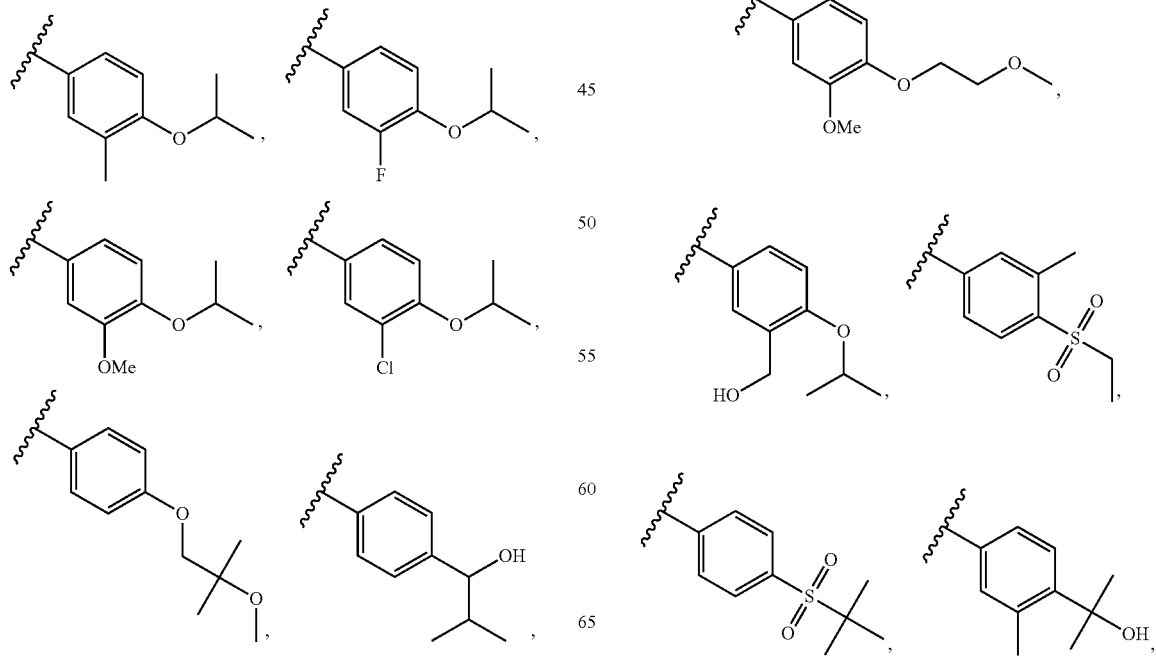

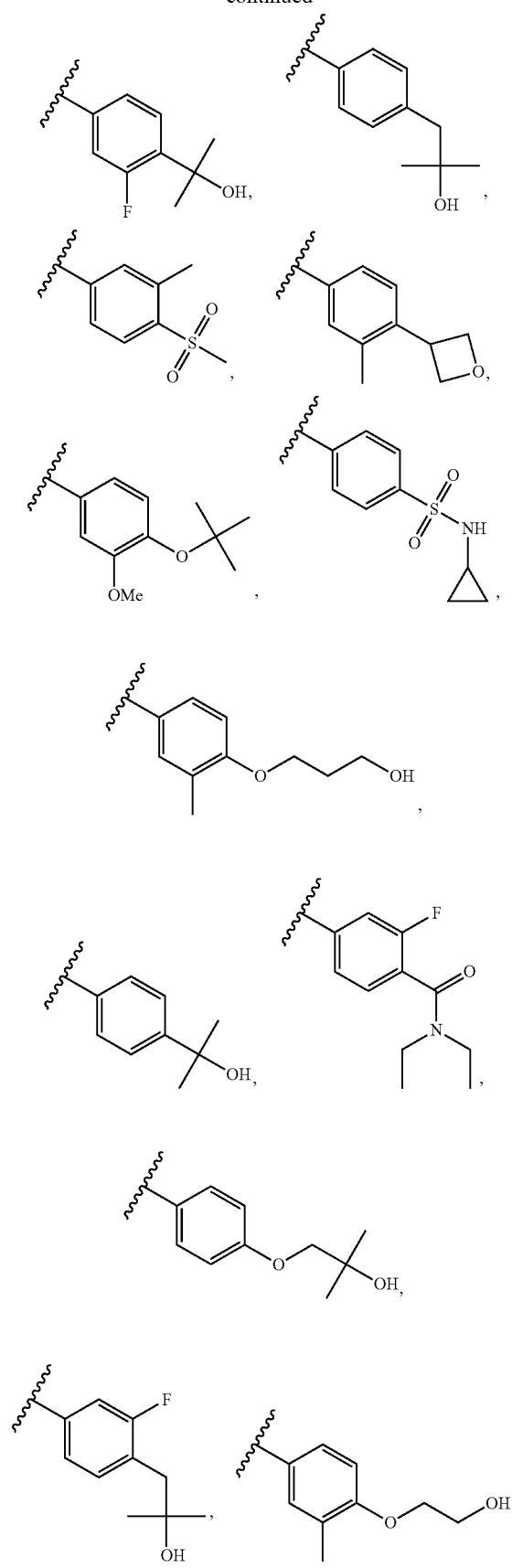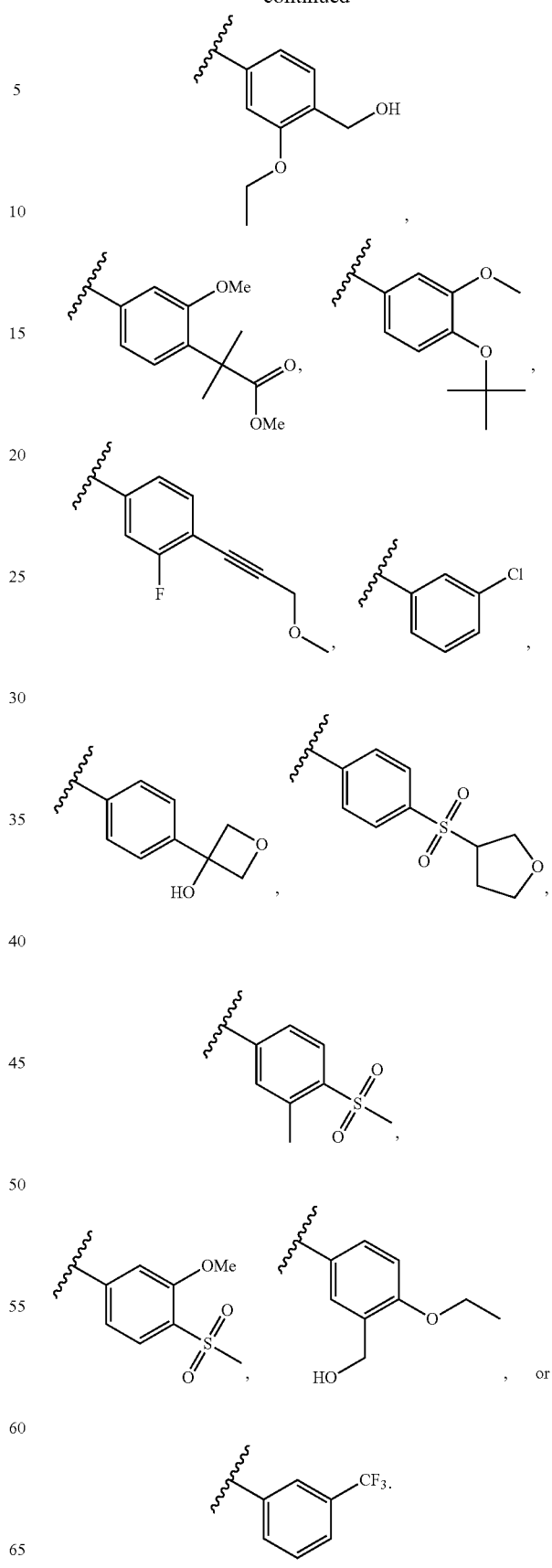

40. The compound of claim 30, wherein the compound has formula IB:

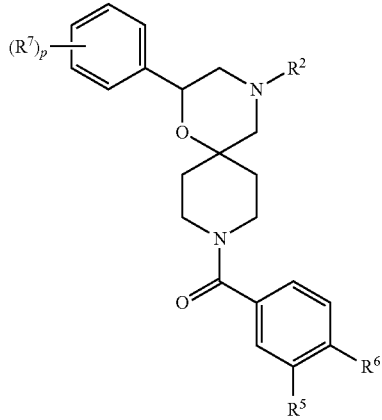

IB wherein:
R² is H, C1-C6 alkyl, C1-C6 fluoroalkyl, an optionally substituted cycloalkyl, aryl, heteroaryl, or heterocycloalkyl, or a straight chain, branched, or cyclic (C3-C8)—R⁹ wherein up to two CH₂ units may be replaced with O, CO, S, SO, SO₂, N, CF₂, or NR⁸;

R⁵ is H, C1-C6 alkyl, C1-C6 alkoxy, C1-C6 flunronlkyl, halo, CF₃, OCF₃, OCHF₂, or a straight chain, branched, or cyclic-(C3-C8)—R⁹ wherein up to three CH₂ units may be replaced with O, CO, S, SO, SO₂, N, CF₂, or NR⁸;

R⁶ is H, C1-C6 alkyl, C1-C6 alkoxy, CN, SO₂R⁸, CON(R⁸)₂, SO₂N(R⁸)₂, heterocycloalkyl, or a straight chain, branched, or cyclic-(C3-C8)—R⁹ wherein up to three CH₂ units may be replaced with O, CO, S, SO, SO₂, N, CF₂, or NR⁸;

R⁷ is C1-C6 alkyl, C3-C8 cycloalkyl, C1-C6 alkoxy, halo, CN, OH, OR⁸, N(R⁸)₂, CF₃, OCF₃, or OCHF₂; and p is an integer from 0 to 3 inclusive.

41. The compound of claim 40, wherein R² is C1-C6 alkyl, C1-C6 fluoroalkyl, or a straight chain, branched, or cyclic-(C3-C8)—R⁹ wherein up to two CH₂ units may be replaced with O, CO, S, SO, SO₂, N, CF₂, or NR8.

42. The compound of claim 40, wherein R² is CH₃, CH₂CH₃, CH(CH₃)₂, CH₂CH(CH₃)₂, CH₂CHF₂, CH₂CF₃, CH(CH₃)CH₂F, CH₂CN, CH₂CH₂OH, CH₂C(CH₃)₂OH, COCH₂CH₃, or COCH(CH₃)₂.

43. The compound of claim 40, wherein R⁵ is H, C1-C6 alkyl, C1-C6 alkoxy, C1-C6 fluroroalkyl, halo, or a straight chain, branched, or cyclic (C3-C8)—R⁹ wherein up to three CH₂ units may be replaced with O, CO, S, SO, SO₂, N, CF₂, or NR⁸.

44. The compound of claim 40, wherein R⁵ is H, CH₃, OCH₃, OCH₂CH₃, CF₃, Cl, F, or CH₂OH.

45. The compound of claim 40, wherein R⁶ is H, C1-C6 alkoxy, or a straight chain, branched, or cyclic-(C3-C8)—R⁹ wherein up to three CH₂ units may be replaced with O, CO, S, SO, SO₂, N, CF₂, or NR⁸.

46. The compound of claim 40, wherein R⁶ is H, CH₂OH, OCH₂CH₃, OtBu, OCH(CH₃)₂, OCH₂C(CH₃)₂OCH₃, CH(OH)CH(CH₃)₂, OCH₂C(CH₃)₂OH, C(CH₃)₂OH, OCH₂CH₂OCH₃, OCH₂CH₂OH, OCH₂CH₂CH₂OH, CCCH₂OCH₃, SO₂CH₃, SO₂CH₂CH(CH₃)₂, SO₂CH(CH₃)₂, SO₂CH₂CH₃, SO₂C(CH₃)₃, CON(CH₂CH₃)₂, C(CH₃)₂CO₂CH₃,

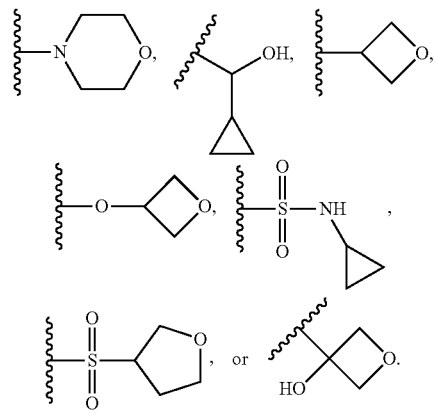

47. The compound of claim 40, wherein R⁷ is halo.
48. The compound of claim 40, wherein R⁷ is F.
49. The compound of claim 40, wherein the

moiety is:

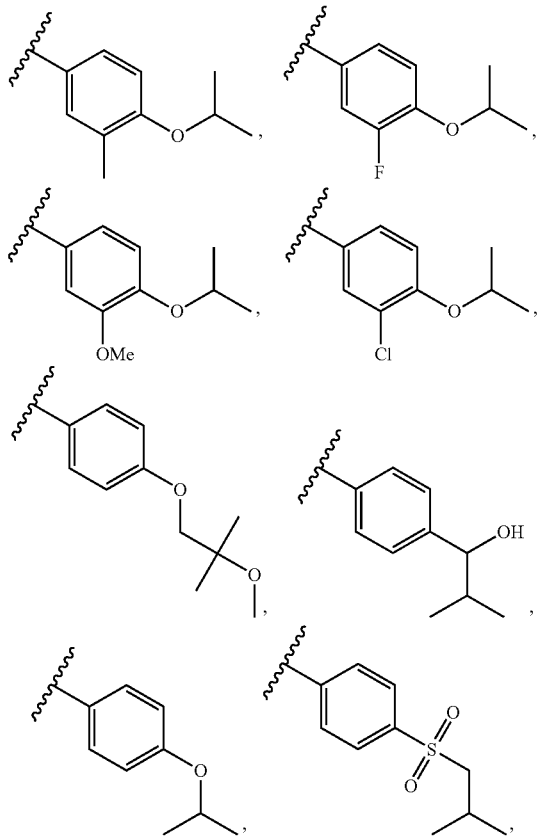

-continued
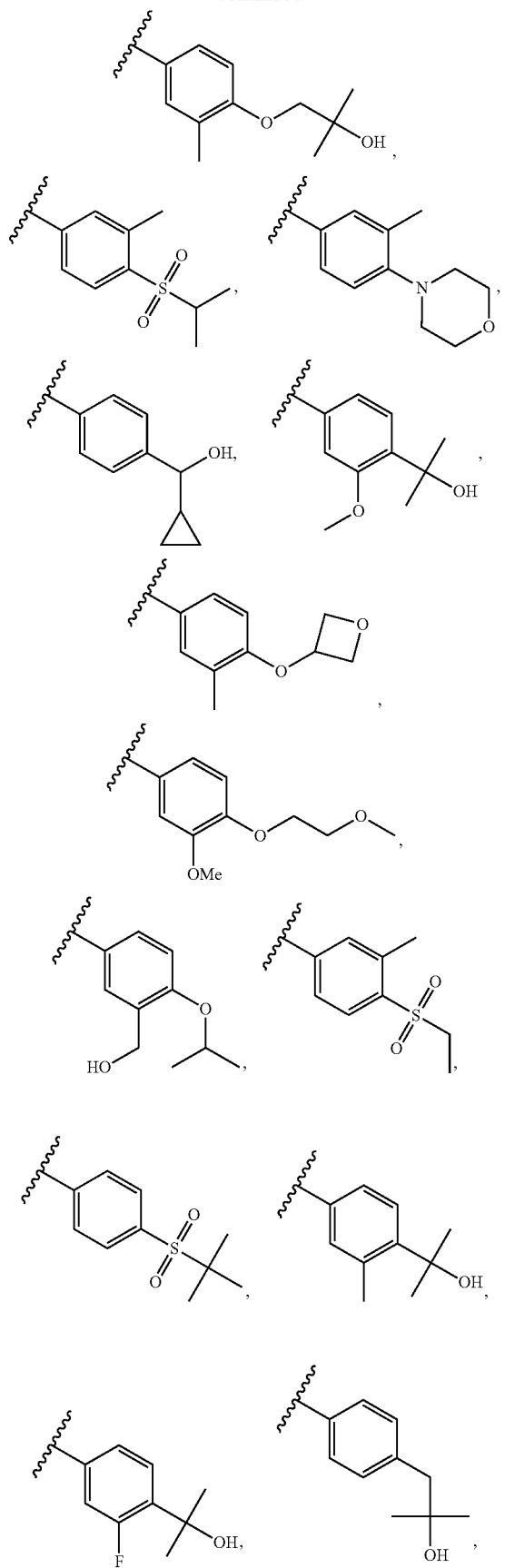
-continued
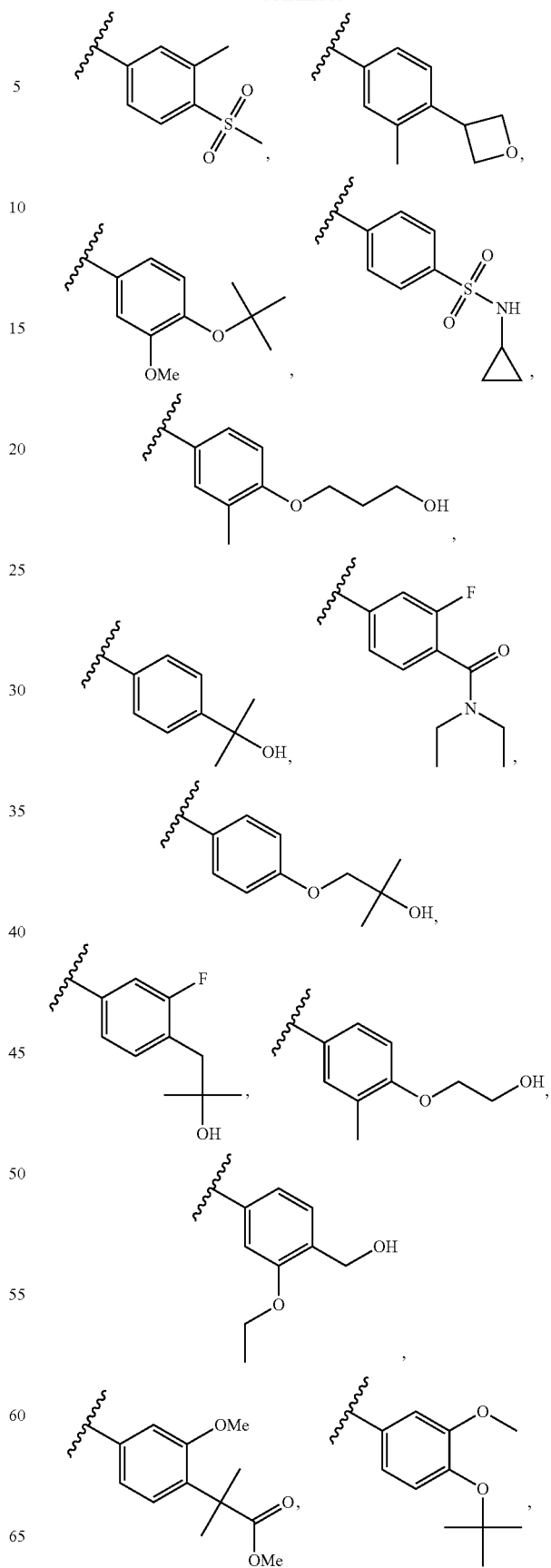

-continued

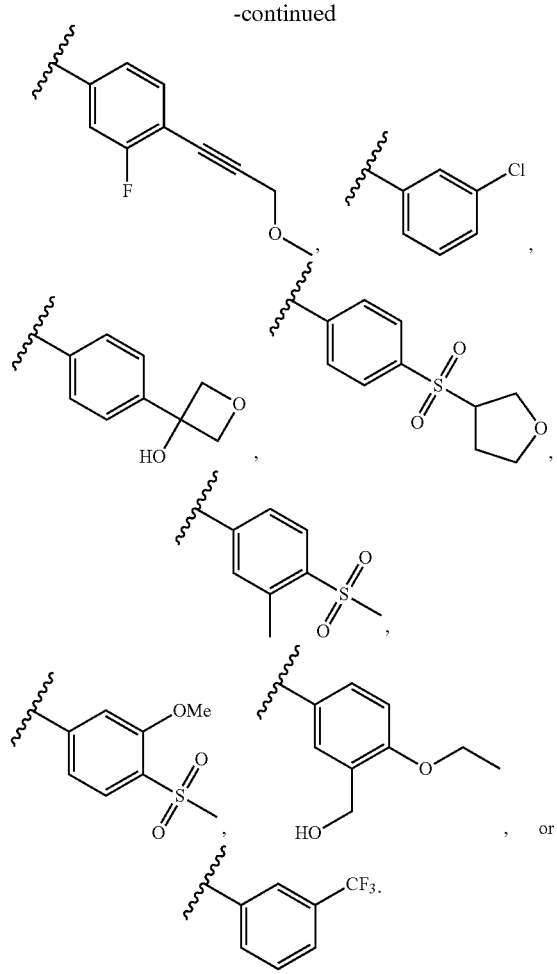

50. The compound of claim 1, wherein the compound has formula IC:

(IC)

wherein,
the Het ring is a mono or bicyclic optionally substituted heterocyclic or heteroaryl ring;
$R^2$ is H, C1-C6 alkyl, C1-C6 fluoroalkyl, an optionally substituted aryl, heteroaryl, or heterocycloalkyl, or a straight chain, branched, or cyclic-(C3-C8)—$R^9$ wherein up to two $CH_2$ units may be replaced with O, CO, S, SO, $SO_2$, N, $CF_2$, or $NR^8$;

$R^5$ is H, C1-C6 alkyl, C1-C6 alkoxy, halo, $CF_3$, $OCF_3$, $OCHF_2$, or a straight chain, branched, or cyclic-(C3-C8)—$R^9$ wherein up to three $CH_2$ units may be replaced with O, CO, S, SO, $SO_2$, N, $CF_2$, or $NR^8$;

$R^6$ is H, C1-C6 alkyl, C1-C6 alkoxy, CN, $SO_2R^8$, $CON(R^8)_2$, $SO_2N(R^8)_2$, heterocycloalkyl, or a straight chain, branched, or cyclic-(C3-C8)—$R^9$ wherein up to three $CH_2$ units may be replaced with O, CO, S, SO, $SO_2$, N, $CF_2$, or $NR^8$ $R^7$ is C1-C6 alkyl, C3-C8 cycloalkyl, C1-C6 alkoxy, halo, CN, OH, $OR^8$, $N(R^8)_2$, $CF_3$, $OCF_3$, or $OCHF_2$; and p is an integer from 0 to 3 inclusive.

51. The compound of claim 50, wherein the Het ring is an optionally substituted thiazole, pyridine, pyrazole, oxazole, or oxadiazole.

52. The compound of claim 50, wherein p is 0 or 1.

53. The compound of claim 50, wherein, $R^7$ is C1-C6 alkyl.

54. The compound of claim 50, wherein, $R^7$ is $CH_3$, $CH_2CH_3$, $CH(CH_3)_2$, or tBu.

55. The compound of claim 50, wherein the Het ring is

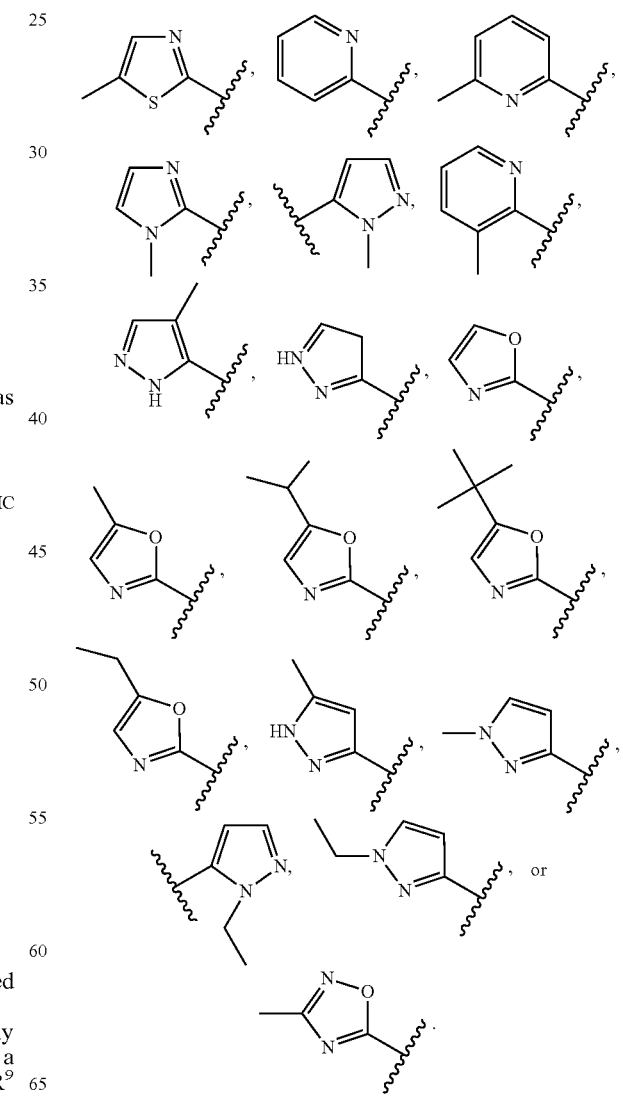

56. The compound of claim 50, wherein $R^2$ is C1-C6 alkyl or a straight chain, branched, or cyclic-(C3-C8)—$R^9$ wherein up to two $CH_2$ units may be replaced with O, CO, S, SO, $SO_2$, N, $CF_2$, or $NR^8$.

57. The compound of claim 50, wherein $R^2$ is $CH_2CH_3$, tBu, $CH_2CHF_2$, $CH_2CF_3$, or

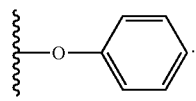

58. The compound of claim 50, wherein $R^5$ is H, C1-C6 alkyl, C1-C6 alkoxy, or halo.

59. The compound of claim 50, wherein $R^5$ is H, $CH_3$, $OCH_3$, F, or Cl.

60. The compound of claim 50, wherein $R^6$ is H, C1-C6 alkoxy, or a straight chain, branched, or cyclic-(C3-C8)—$R^9$ wherein up to three $CH_2$ units may be replaced with O, CO, S, SO, $SO_2$, N, $CF_2$, or $NR^8$.

61. The compound of claim 50, wherein $R^6$ is $OCH(CH_3)_2$, $C(CH_3)_2OH$, $OCH_2CH_2OH$, $OCH_2CH_2CH_2OH$,

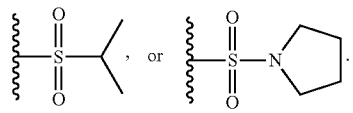

62. The compound of claim 1, wherein the compound has formula ID:

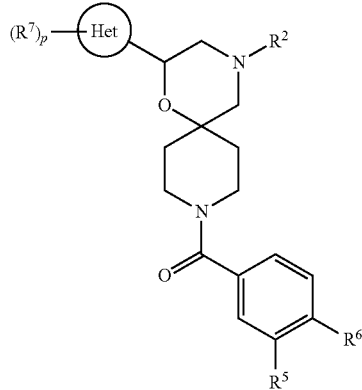

wherein,
the Het ring is a mono or bicyclic optionally substituted heterocyclic or heteroaryl ring;
$R^2$ is H, C1-C6 alkyl, C1-C6 fluoroalkyl, an optionally substituted aryl, heteroaryl, or heterocycloalkyl, or a straight chain, branched, or cyclic-(C3-C8)—$R^9$ wherein up to two $CH_2$ units may be replaced with O, CO, S, SO, $SO_2$, N, $CF_2$, or $NR^8$;
$R^5$ is H, C1-C6 alkyl, C1-C6 alkoxy, halo, $CF_3$, $OCF_3$, $OCHF_2$, or a straight chain, branched, or cyclic-(C3-C8)—$R^9$ wherein up to three $CH_2$ units may be replaced with O, CO, S, SO, $SO_2$, N, $CF_2$, or $NR^8$;
$R^6$ is H, C1-C6 alkyl, C1-C6 alkoxy, CN, $SO_2R^8$, $CON(R^8)_2$, $SO_2N(R^8)_2$, heterocycloalkyl, or a straight chain, branched, or cyclic-(C3-C8)—$R^9$ wherein up to three $CH_2$ units may be replaced with O, CO, S, SO, $SO_2$, N, $CF_2$, or NR8

$R^7$ is C1-C6 alkyl, C3-C8 cycloalkyl, C1-C6 alkoxy, halo, CN, OH, $OR^8$, $N(R^8)_2$, $CF_3$, $OCF_3$, or $OCHF_2$; and
p is an integer from 0 to 3 inclusive.

63. The compound of claim 62, wherein the Het ring is an optionally substituted thiazole, pyridine, pyrazole, oxazole, or oxadiazole.

64. The compound of claim 62, wherein p is 0 or 1.

65. The compound of claim 62, wherein $R^7$ is C1-C6 alkyl.

66. The compound of claim 62, wherein $R^7$ is $CH_3$, $CH_2CH_3$, $CH(CH_3)_2$, or tBu.

67. The compound of claim 62, wherein the Het ring is

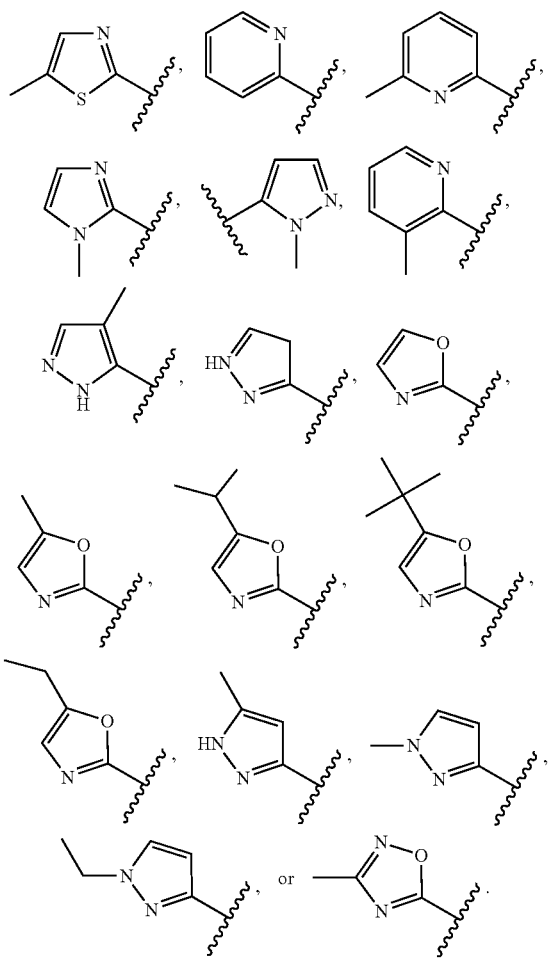

68. The compound of claim 62, wherein $R^2$ is C1-C6 alkyl or a straight chain, branched, or cyclic-(C3-C8)—$R^9$ wherein up to two $CH_2$ units may be replaced with O, CO, S, SO, $SO_2$, N, $CF_2$, or $NR^8$.

69. The compound of claim 62, wherein $R^2$ is $CH_2CH_3$, tBu, $CH_2CHF_2$, $CH_2CF_3$, or

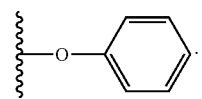

70. The compound of claim 62, wherein $R^5$ is H, C1-C6 alkyl, C1-C6 alkoxy, or halo.

71. The compound of claim 62, wherein $R^5$ is H, $CH_3$, $OCH_3$, F, or Cl.

72. The compound of claim 62, wherein $R^6$ is H, C1-C6 alkoxy, or a straight chain, branched, or cyclic-(C3-C8)—$R^9$ wherein up to three $CH_2$ units may be replaced with O, CO, S, SO, $SO_2$, N, $CF_2$, or $NR^8$.

73. The compound of claim 62, wherein $R^6$ is $OCH(CH_3)_2$, $C(CH_3)_2OH$, $OCH_2CH_2OH$, $OCH_2CH_2CH_2OH$,

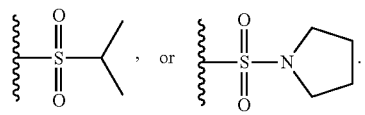

74. The compound of claim 1, wherein the compound is selected from the following table:

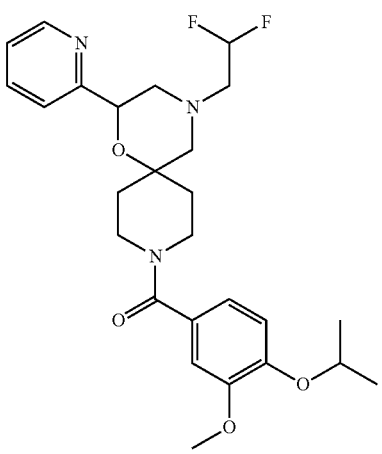

3

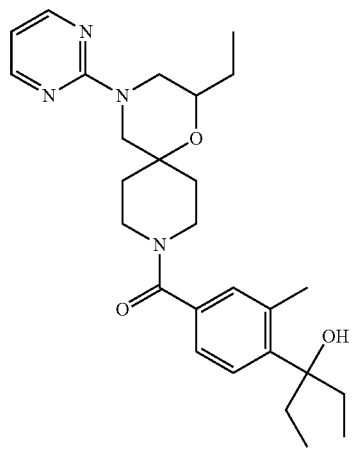 [SMILES: CCC1CN(c2ncccn2)CC2(CCN(C(=O)c3ccc(C(O)(CC)CC)c(C)c3)CC2)O1]

1

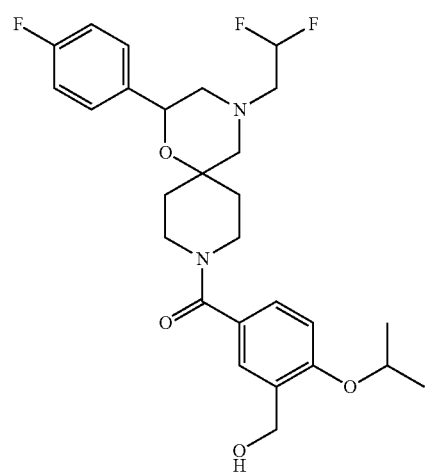

4

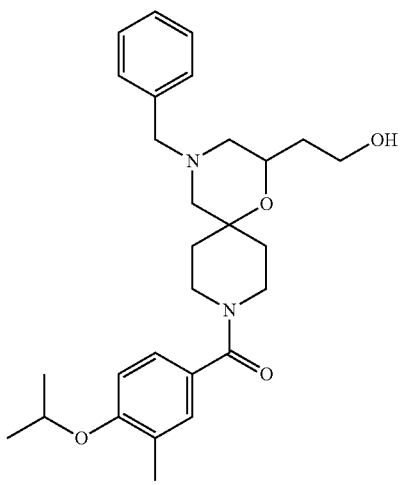 [SMILES: Cc1cc(C(=O)N2CCC3(CC2)CN(Cc2ccccc2)CC(CCO)O3)ccc1OC(C)C]

2

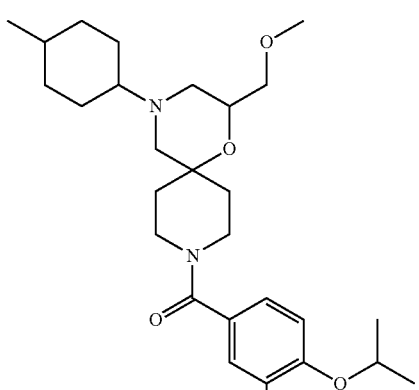

5

-continued

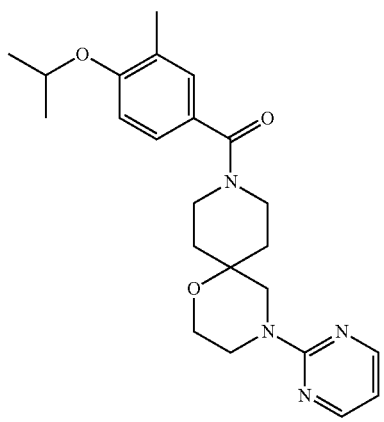 [SMILES: Cc1cc(C(=O)N2CCC3(CC2)CN(c2ncccn2)CCO3)ccc1OC(C)C]
6
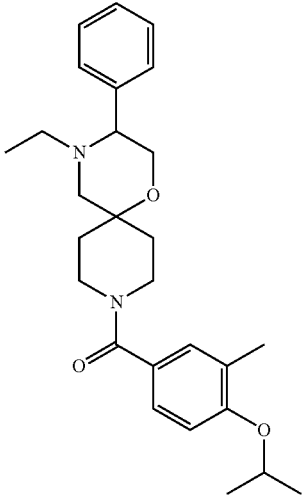
10
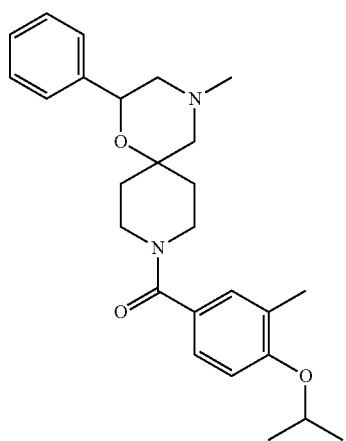
7
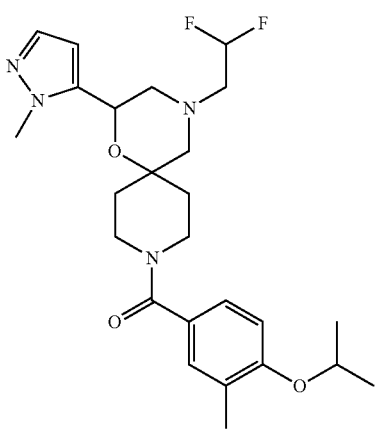
11
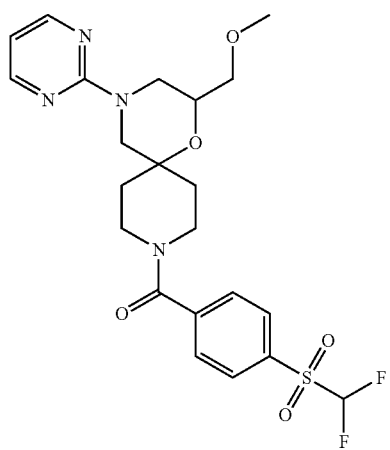 [SMILES: COCC1CN(c2ncccn2)CC2(CCN(C(=O)c3ccc(S(=O)(=O)C(F)F)cc3)CC2)O1]
8
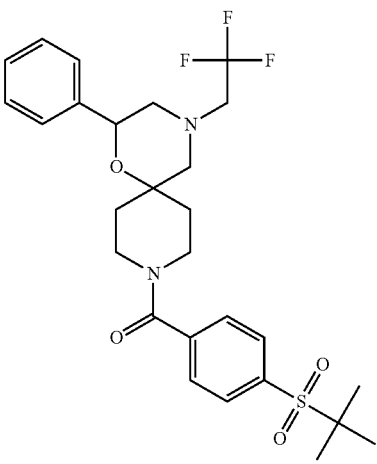 [SMILES: CC(C)(C)S(=O)(=O)c1ccc(C(=O)N2CCC3(CC2)CN(CC(F)(F)F)CC(c2ccccc2)O3)cc1]
12

| 357 -continued | 358 -continued |
|---|---|
| 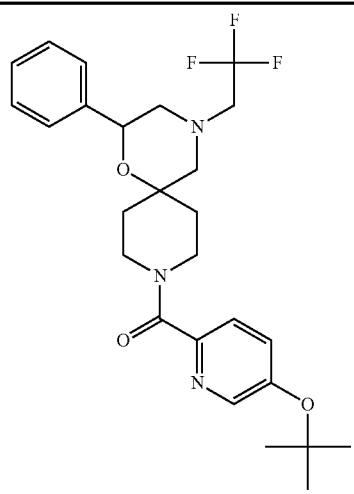 13 | 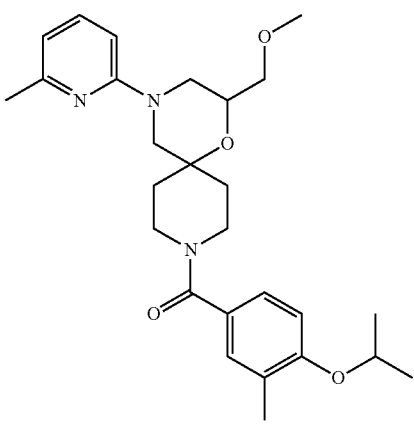 16 |
| 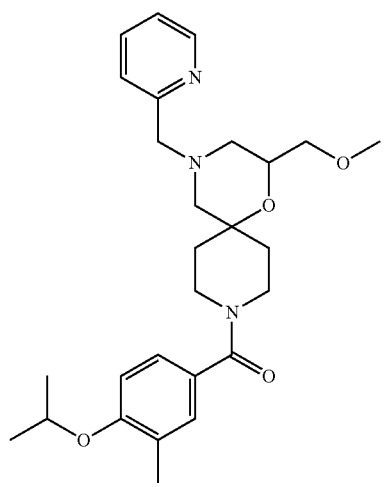 [SMILES: COCC1CN(Cc2ccccn2)CC2(CCN(C(=O)c3ccc(OC(C)C)c(C)c3)CC2)O1] 14 | 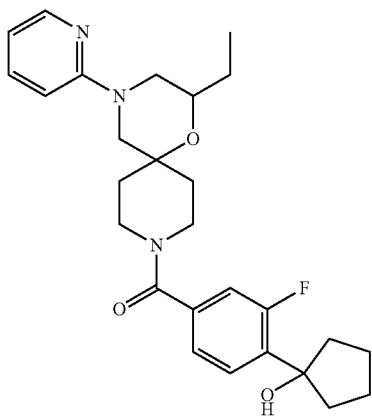 17 |
| 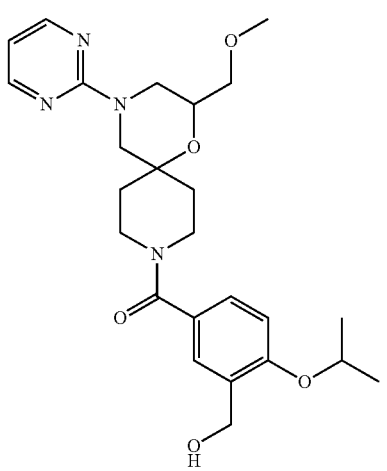 [SMILES: COCC1CN(c2ncccn2)CC2(CCN(C(=O)c3ccc(OC(C)C)c(CO)c3)CC2)O1] 15 | 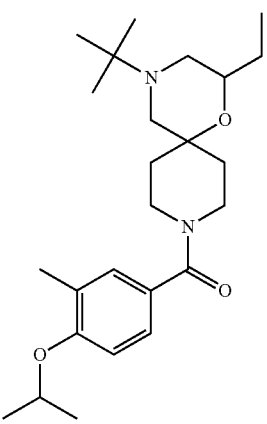 [SMILES: CCC1CN(C(C)(C)C)CC2(CCN(C(=O)c3ccc(OC(C)C)c(C)c3)CC2)O1] 18 |

| 19 | 22 |
|---|---|
| 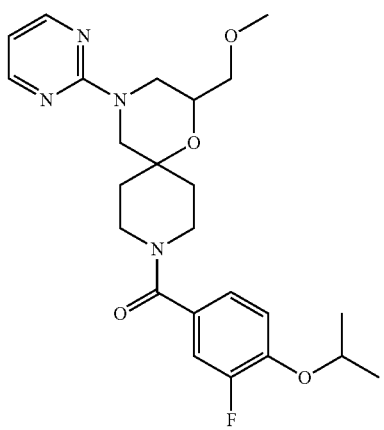 [SMILES: COCC1CN(c2ncccn2)CC2(CCN(C(=O)c3ccc(OC(C)C)c(F)c3)CC2)O1] | 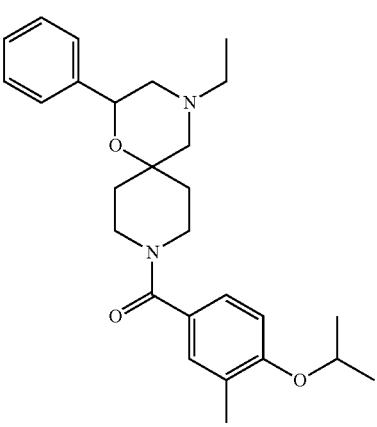 |
| 20 | 23 |
| 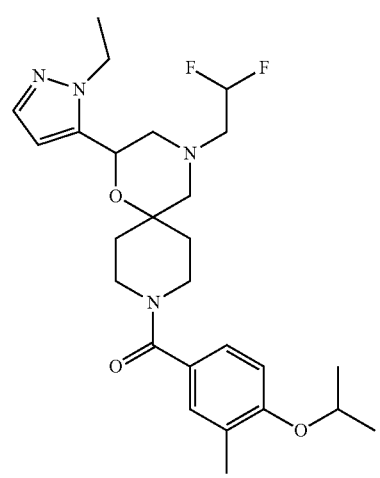 [SMILES: CCn1nccc1C1CN(CC(F)F)CC2(CCN(C(=O)c3ccc(OC(C)C)c(C)c3)CC2)O1] | 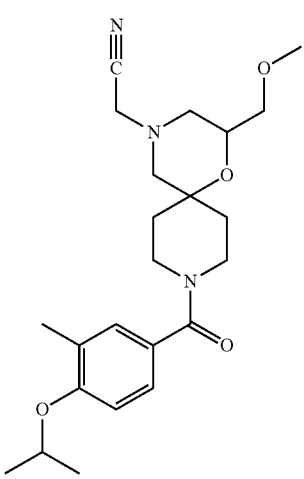 |
| 21 | 24 |
| 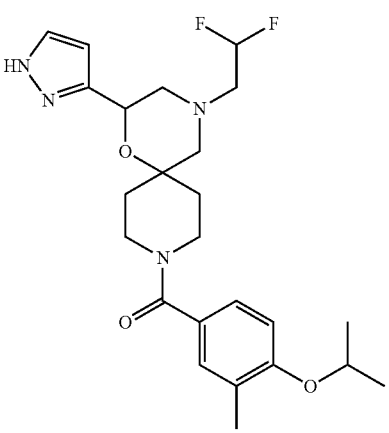 [SMILES: Cc1cc(C(=O)N2CCC3(CC2)CN(CC(F)F)CC(c2cc[nH]n2)O3)ccc1OC(C)C] | 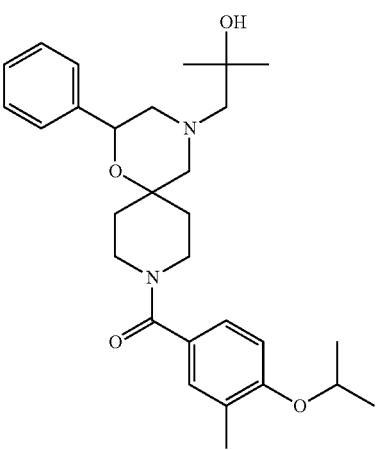 [SMILES: Cc1cc(C(=O)N2CCC3(CC2)CN(CC(C)(C)O)CC(c2ccccc2)O3)ccc1OC(C)C] |

| 361 -continued | 362 -continued |
|---|---|
| 25 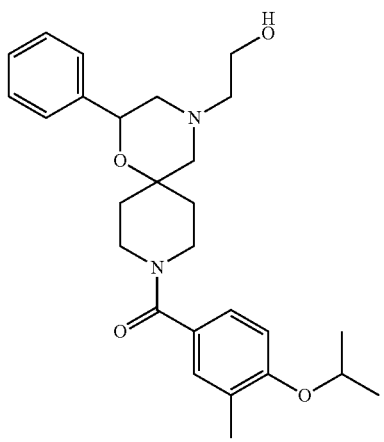 [SMILES: Cc1cc(C(=O)N2CCC3(CC2)CN(CCO)CC(c2ccccc2)O3)ccc1OC(C)C] | 28 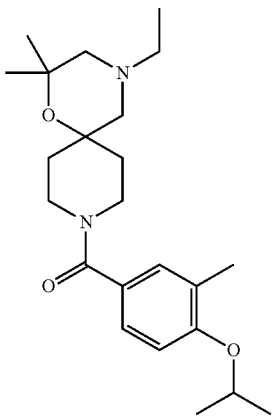 |
| 26 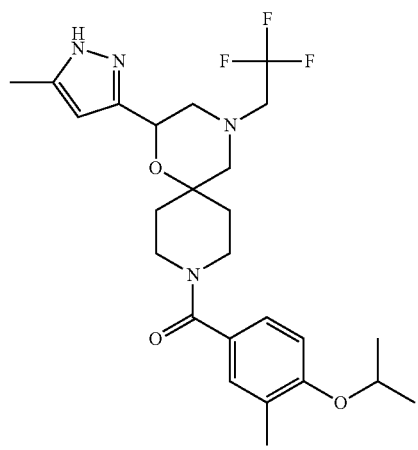 [SMILES: Cc1cc(C2CN(CC(F)(F)F)CC3(CCN(C(=O)c4ccc(OC(C)C)c(C)c4)CC3)O2)n[nH]1] | 29 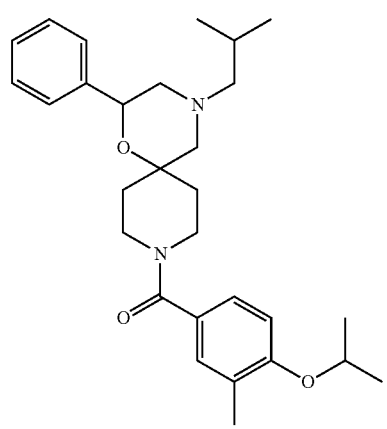 |
| 27 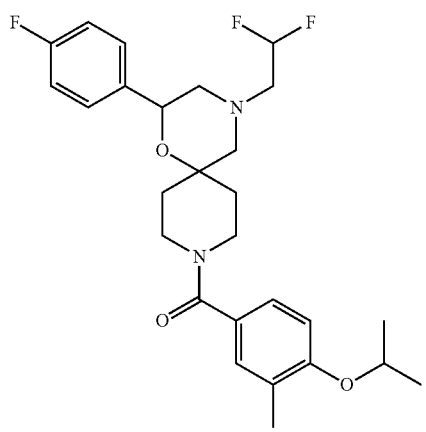 [SMILES: Cc1cc(C(=O)N2CCC3(CC2)CN(CC(F)F)CC(c2ccc(F)cc2)O3)ccc1OC(C)C] | 30 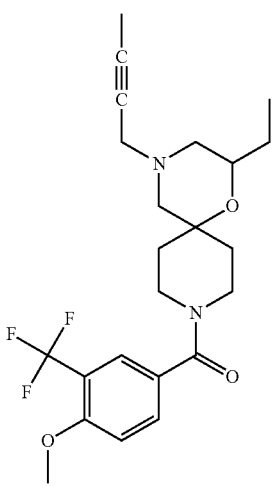 |

| 363 -continued | 364 -continued |
|---|---|
| 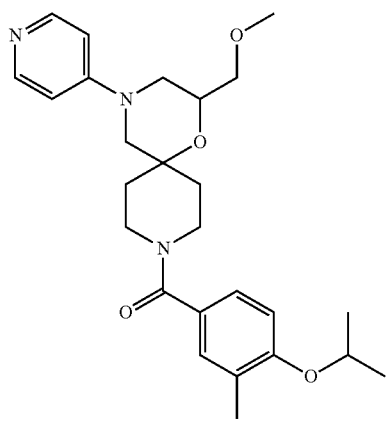 [SMILES: COCC1CN(c2ccncc2)CC2(CCN(C(=O)c3ccc(OC(C)C)c(C)c3)CC2)O1] 31 | 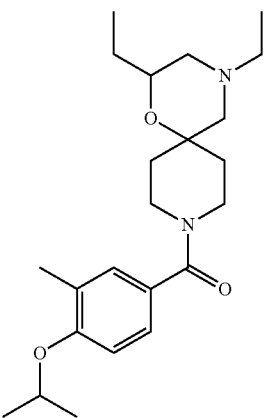 34 |
| 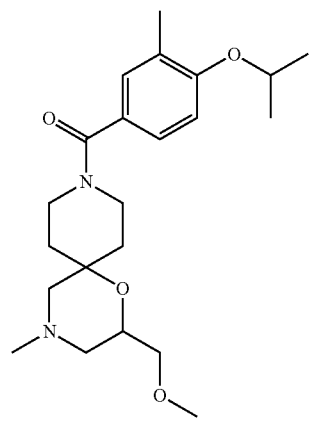 [SMILES: COCC1CN(C)CC2(CCN(C(=O)c3ccc(OC(C)C)c(C)c3)CC2)O1] 32 | 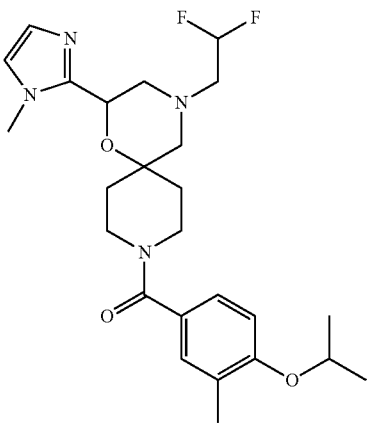 [SMILES: Cc1cc(C(=O)N2CCC3(CC2)CN(CC(F)F)CC(c2nccn2C)O3)ccc1OC(C)C] 35 |
| 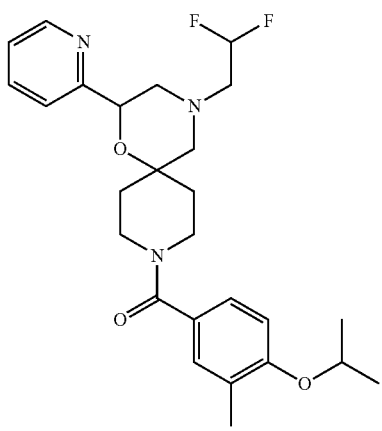 33 | 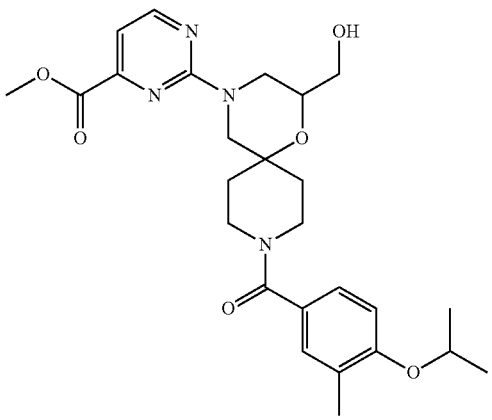 [SMILES: COC(=O)c1ccnc(N2CC(CO)OC3(CCN(C(=O)c4ccc(OC(C)C)c(C)c4)CC3)C2)n1] 36 |

| 37 | 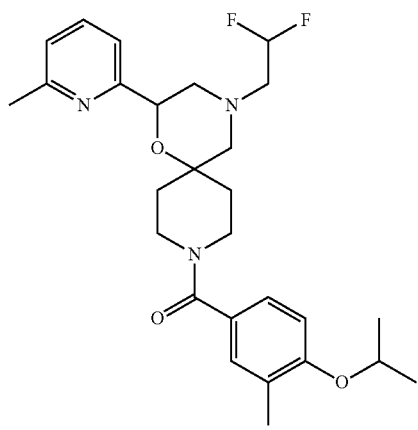 [SMILES: Cc1cccc(C2CN(CC(F)F)CC3(CCN(C(=O)c4ccc(OC(C)C)c(C)c4)CC3)O2)n1] | 40 | 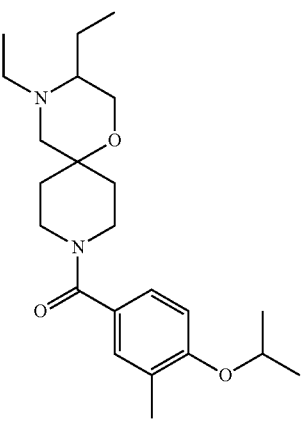 |
| 38 | 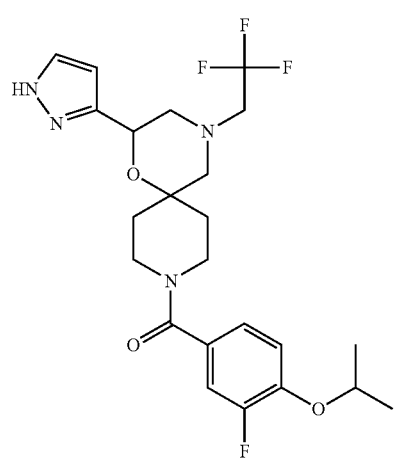 [SMILES: CC(C)Oc1ccc(C(=O)N2CCC3(CC2)CN(CC(F)(F)F)CC(c2cc[nH]n2)O3)cc1F] | 41 | 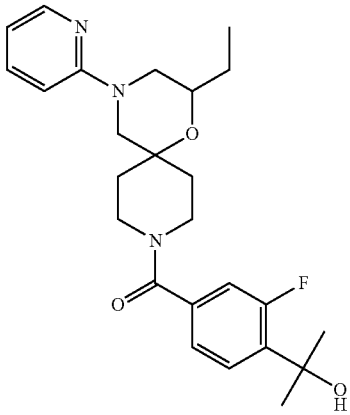 |
| 39 | 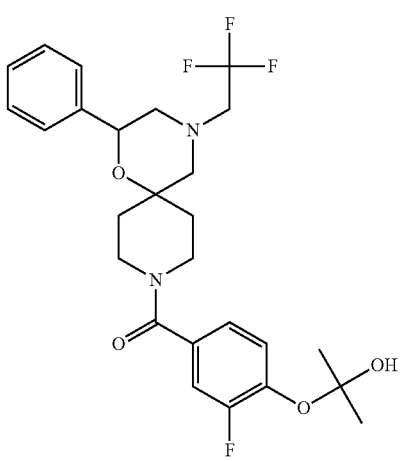 [SMILES: CC(C)(O)Oc1ccc(C(=O)N2CCC3(CC2)CN(CC(F)(F)F)CC(c2ccccc2)O3)cc1F] | 42 | 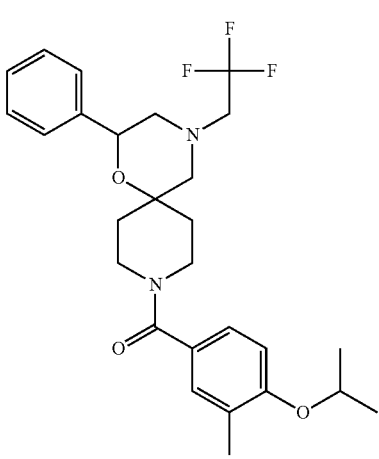 [SMILES: Cc1cc(C(=O)N2CCC3(CC2)CN(CC(F)(F)F)CC(c2ccccc2)O3)ccc1OC(C)C] |

-continued
43
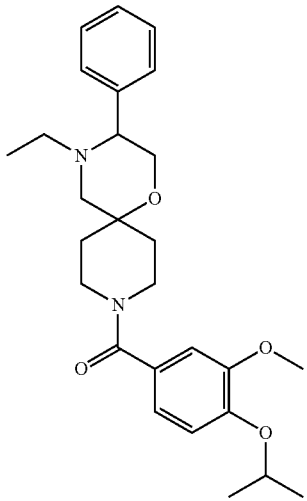 [SMILES: CCN1CC2(CCN(C(=O)c3ccc(OC(C)C)c(OC)c3)CC2)OCC1c1ccccc1]
44
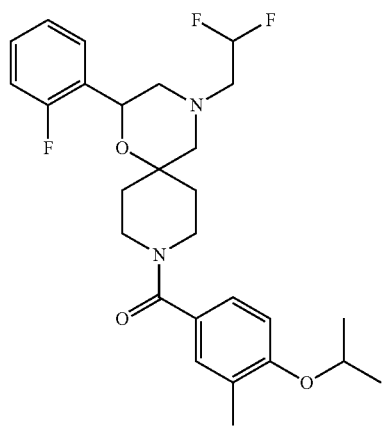 [SMILES: Cc1cc(C(=O)N2CCC3(CC2)CN(CC(F)F)CC(c2ccccc2F)O3)ccc1OC(C)C]
45
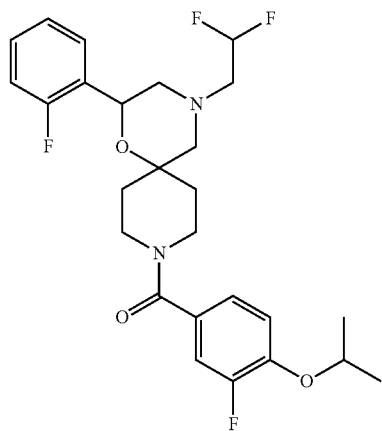 [SMILES: CC(C)Oc1ccc(C(=O)N2CCC3(CC2)CN(CC(F)F)CC(c2ccccc2F)O3)cc1F]
-continued
46
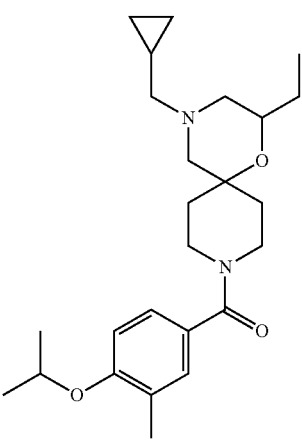 [SMILES: CCC1CN(CC2CC2)CC2(CCN(C(=O)c3ccc(OC(C)C)c(C)c3)CC2)O1]
47
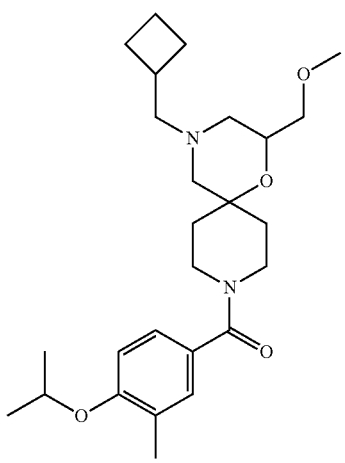 [SMILES: COCC1CN(CC2CCC2)CC2(CCN(C(=O)c3ccc(OC(C)C)c(C)c3)CC2)O1]
48
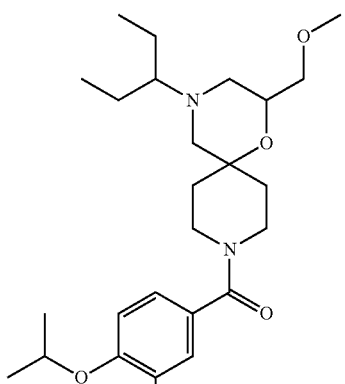

| 369 -continued | 370 -continued |
|---|---|
| 49 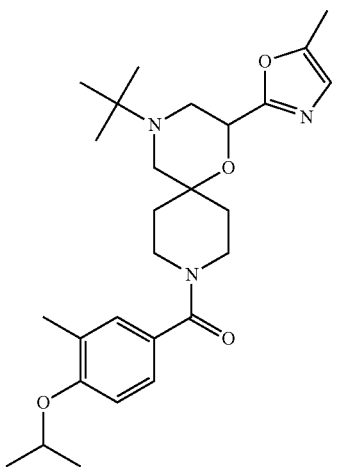 | 52 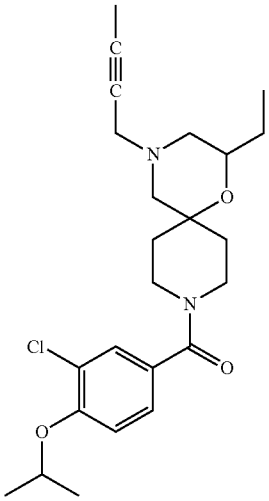 |
| 50 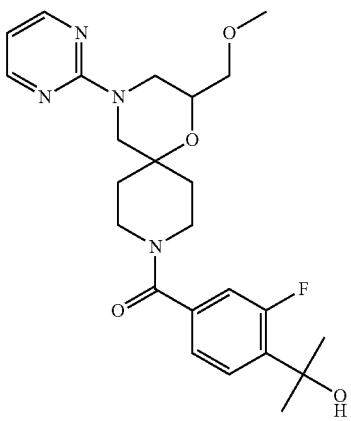 | 53 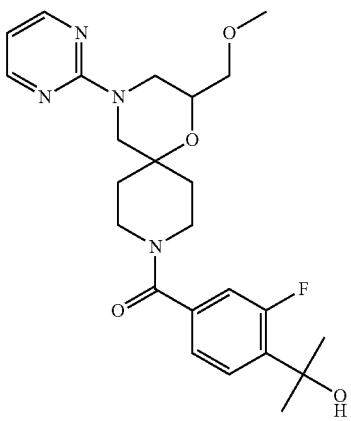 |
| 51 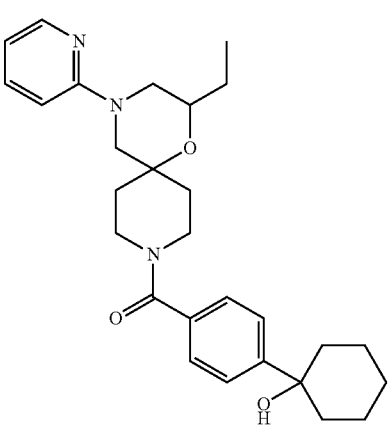 [SMILES: CCC1CN(c2ccccn2)CC2(CCN(C(=O)c3ccc(C4(O)CCCCC4)cc3)CC2)O1] | 54 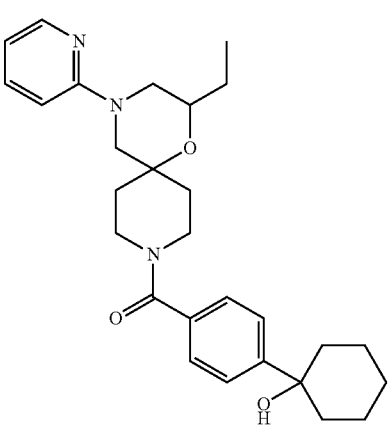 [SMILES: CCC1CN(c2ccccn2)CC2(CCN(C(=O)c3ccc(C4(O)CCCCC4)cc3)CC2)O1] |

| 55 | 58 |
|---|---|
| 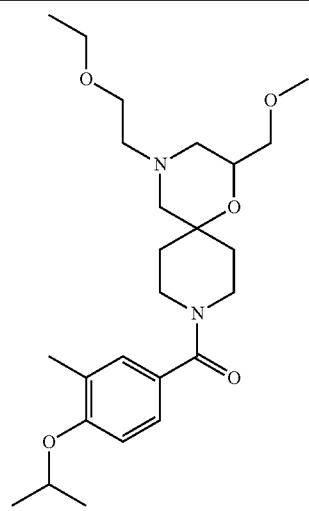 | 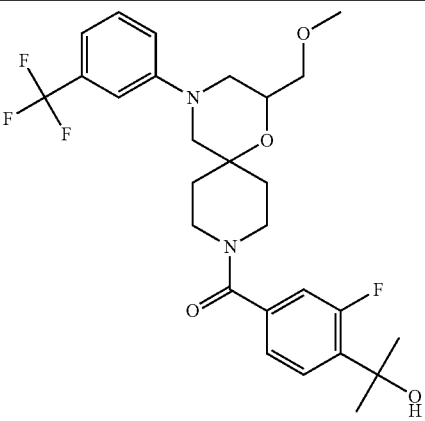 |
| 56 | 59 |
| 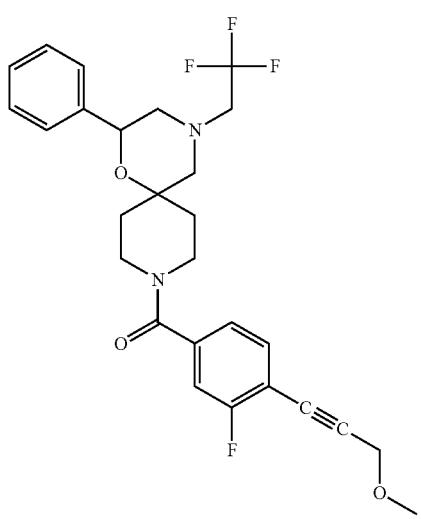 [SMILES: COCC#Cc1ccc(C(=O)N2CCC3(CC2)CN(CC(F)(F)F)CC(c2ccccc2)O3)cc1F] | 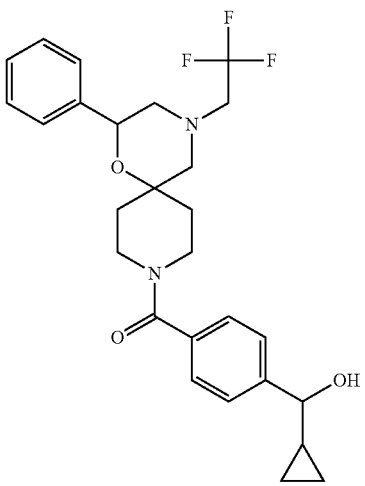 |
| 57 | 60 |
| 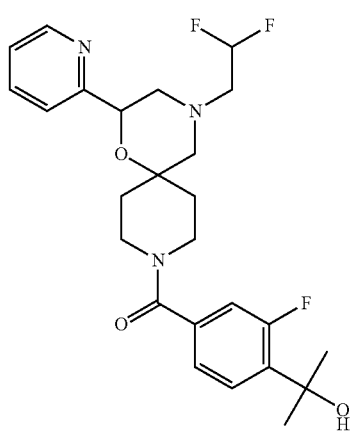 [SMILES: CC(C)(O)c1ccc(C(=O)N2CCC3(CC2)CN(CC(F)F)CC(c2ccccn2)O3)cc1F] | 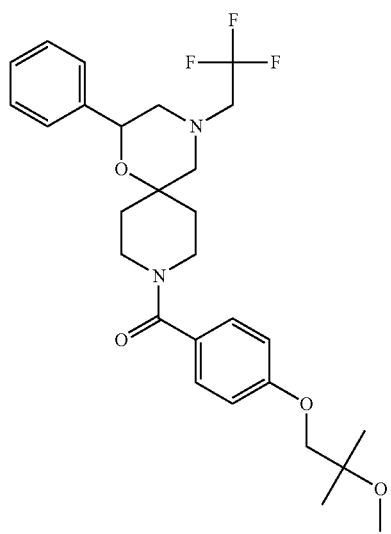 [SMILES: COC(C)(C)COc1ccc(C(=O)N2CCC3(CC2)CN(CC(F)(F)F)CC(c2ccccc2)O3)cc1] |

| 61 | 64 |
|---|---|
| 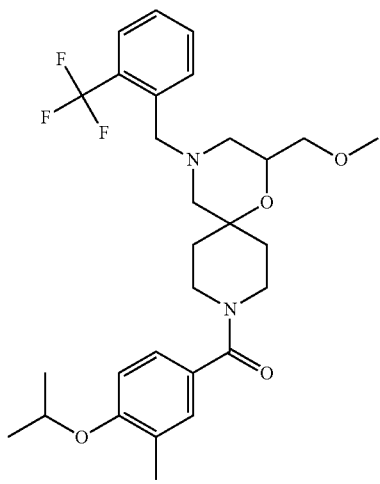 [SMILES: COCC1CN(Cc2ccccc2C(F)(F)F)CC2(CCN(C(=O)c3ccc(OC(C)C)c(C)c3)CC2)O1] | 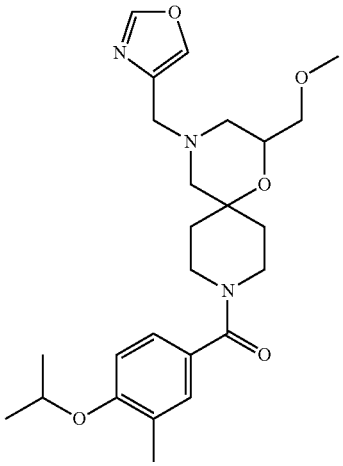 |
| 62 | 65 |
| 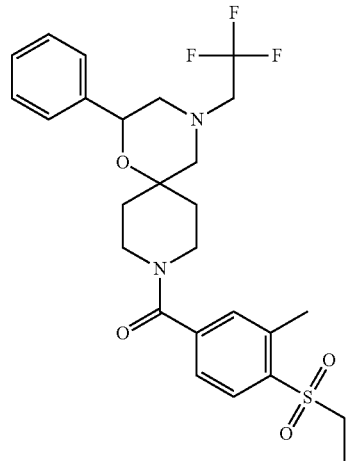 [SMILES: CCS(=O)(=O)c1ccc(C(=O)N2CCC3(CC2)CN(CC(F)(F)F)CC(c2ccccc2)O3)cc1C] | 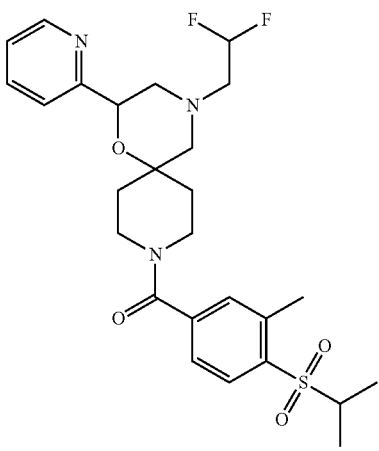 |
| 63 | 66 |
| 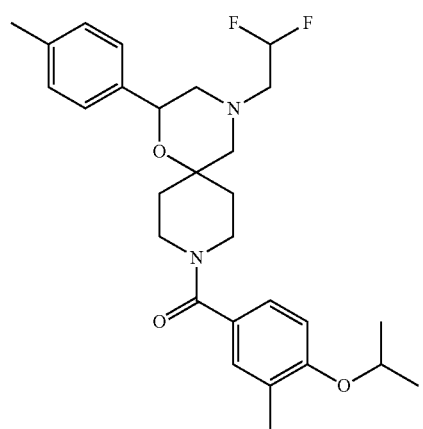 [SMILES: Cc1ccc(C2CN(CC(F)F)CC3(CCN(C(=O)c4ccc(OC(C)C)c(C)c4)CC3)O2)cc1] | 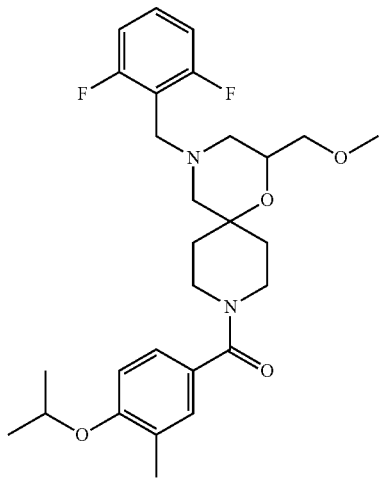 [SMILES: COCC1CN(Cc2c(F)cccc2F)CC2(CCN(C(=O)c3ccc(OC(C)C)c(C)c3)CC2)O1] |

| 375 -continued | 376 -continued |
|---|---|
| 67 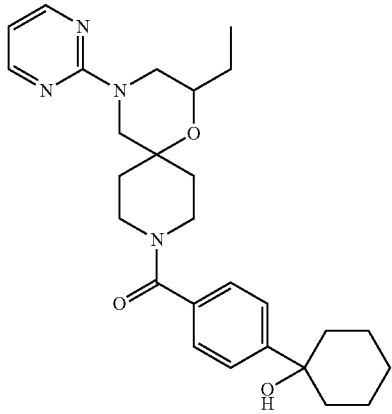 [SMILES: CCC1CN(c2ncccn2)CC2(CCN(C(=O)c3ccc(C4(O)CCCCC4)cc3)CC2)O1] | 70 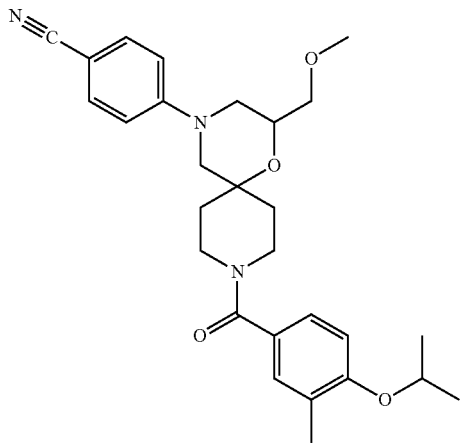 |
| 68 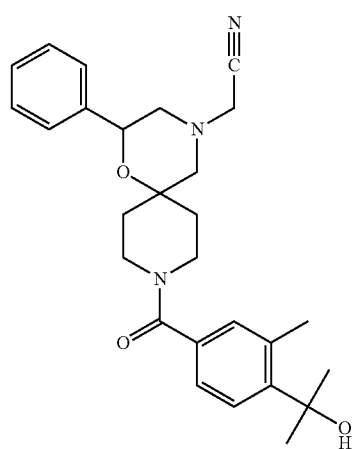 [SMILES: Cc1cc(C(=O)N2CCC3(CC2)CN(CC#N)CC(c2ccccc2)O3)ccc1C(C)(C)O] | 71 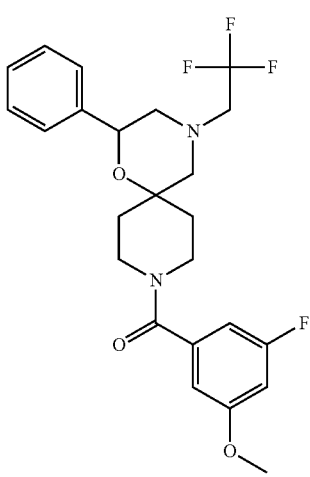 |
| 69 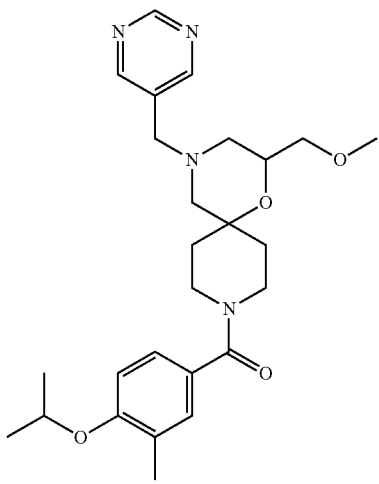 | 72 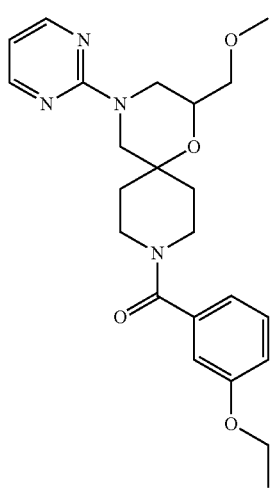 [SMILES: CCOc1cccc(C(=O)N2CCC3(CC2)CN(c2ncccn2)CC(COC)O3)c1] |

| 73 | 76 |
|---|---|
| 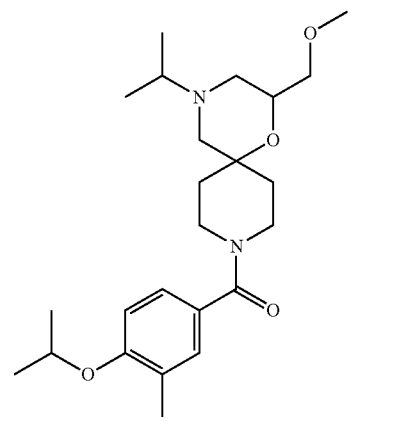 [SMILES: COCC1CN(C(C)C)CC2(CCN(C(=O)c3ccc(OC(C)C)c(C)c3)CC2)O1] | 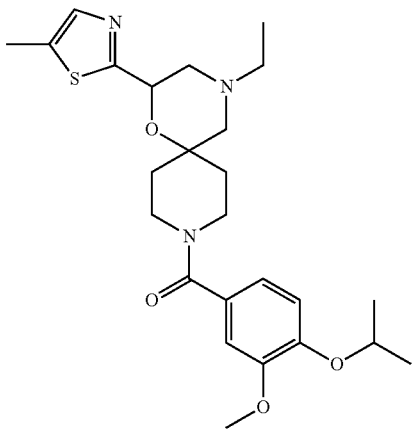 |
| 74 | 77 |
|---|---|
| 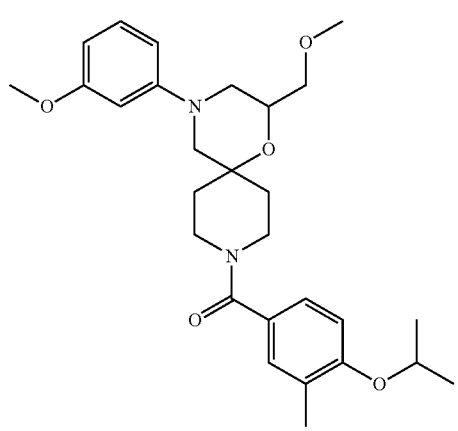 | 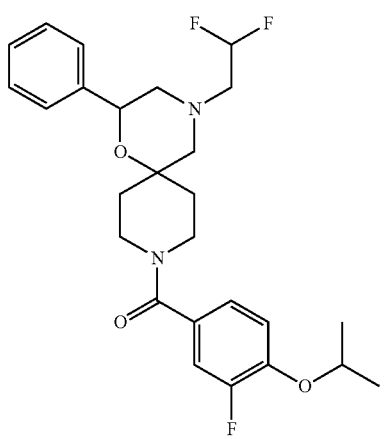 |
| 75 | 78 |
|---|---|
| 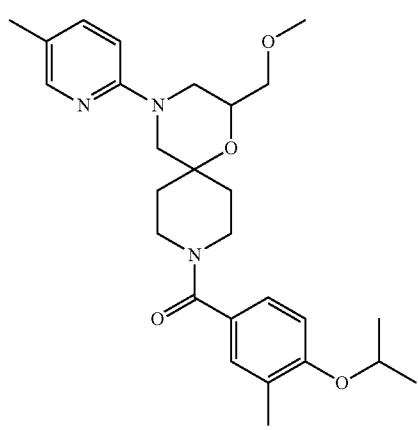 [SMILES: COCC1CN(c2ccc(C)cn2)CC2(CCN(C(=O)c3ccc(OC(C)C)c(C)c3)CC2)O1] | 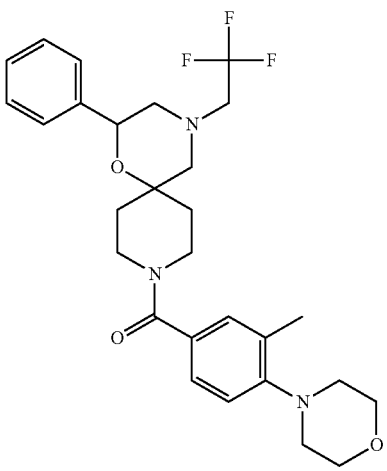 [SMILES: Cc1cc(C(=O)N2CCC3(CC2)CN(CC(F)(F)F)CC(c2ccccc2)O3)ccc1N1CCOCC1] |

| 379 -continued | 380 -continued |
|---|---|
| 79 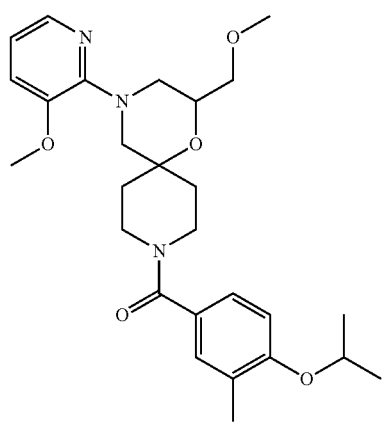 [SMILES: COCC1CN(c2ncccc2OC)CC2(CCN(C(=O)c3ccc(OC(C)C)c(C)c3)CC2)O1] | 82 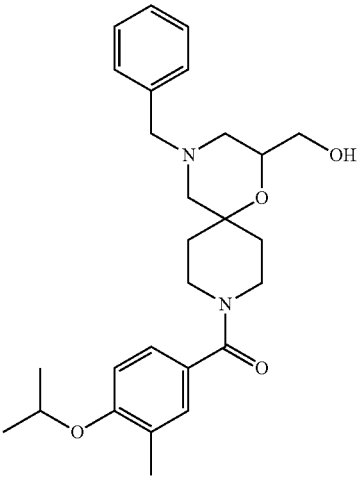 |
| 80 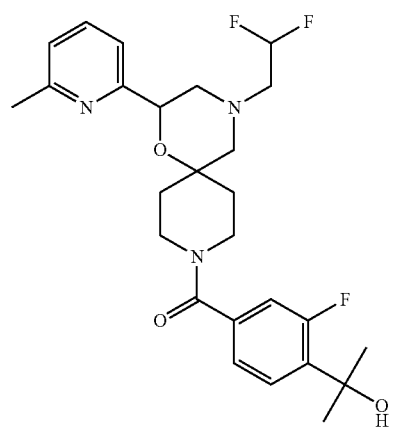 [SMILES: Cc1cccc(C2CN(CC(F)F)CC3(CCN(C(=O)c4ccc(C(C)(C)O)c(F)c4)CC3)O2)n1] | 83 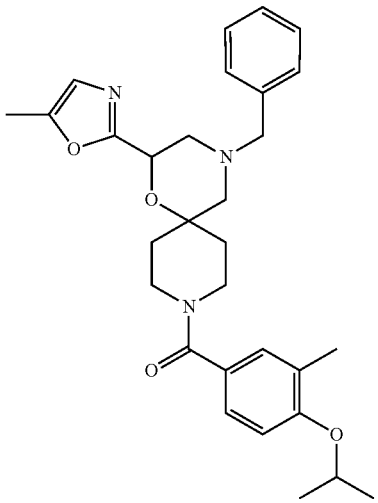 |
| 81 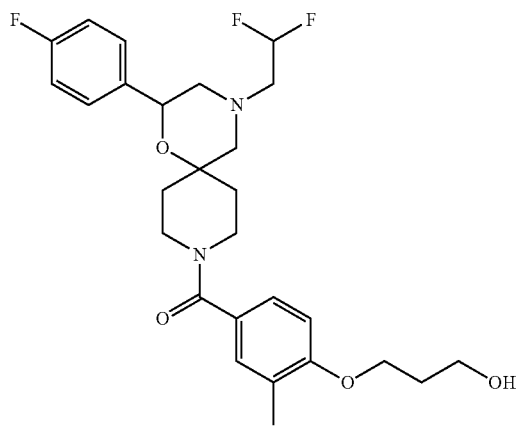 [SMILES: Cc1cc(C(=O)N2CCC3(CC2)CN(CC(F)F)CC(c2ccc(F)cc2)O3)ccc1OCCCO] | 84 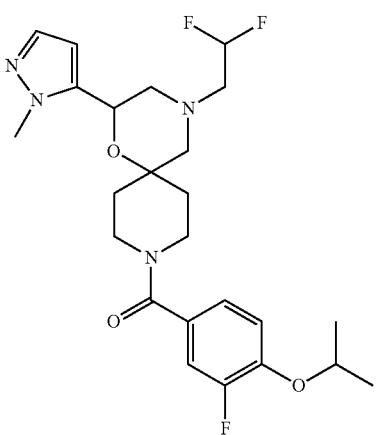 [SMILES: CC(C)Oc1ccc(C(=O)N2CCC3(CC2)CN(CC(F)F)CC(c2ccnn2C)O3)cc1F] |

| 381 -continued | 382 -continued |
|---|---|
| 85 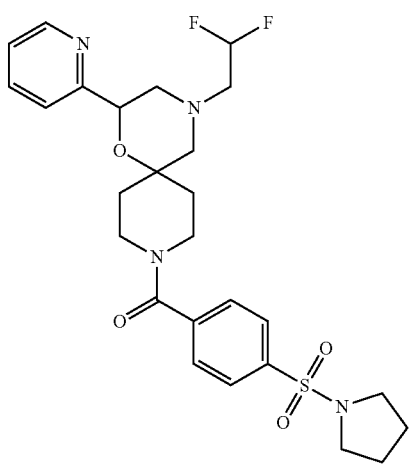 [SMILES: O=C(c1ccc(S(=O)(=O)N2CCCC2)cc1)N1CCC2(CC1)CN(CC(F)F)CC(c1ccccn1)O2] | 88 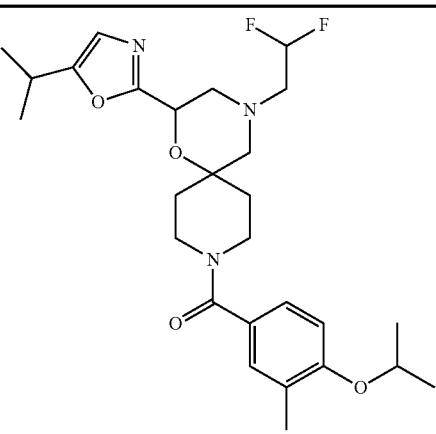 |
| 86 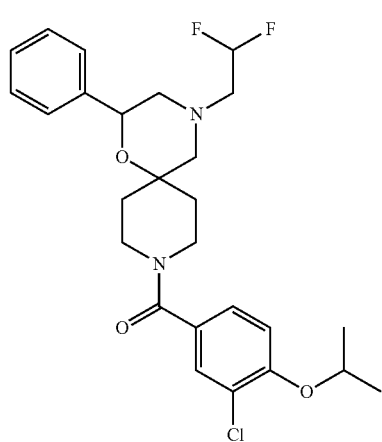 | 89 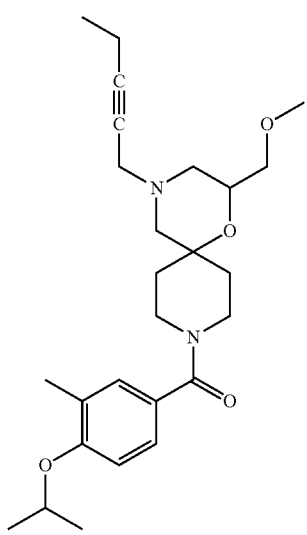 |
| 87 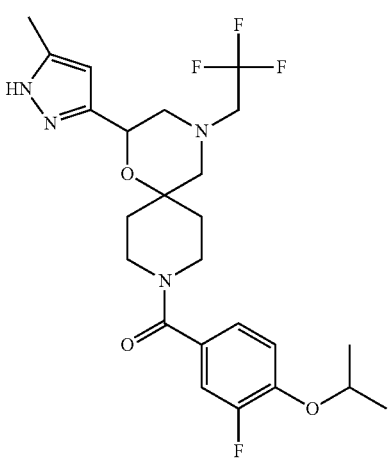 [SMILES: Cc1cc(C2CN(CC(F)(F)F)CC3(CCN(C(=O)c4ccc(OC(C)C)c(F)c4)CC3)O2)n[nH]1] | 90 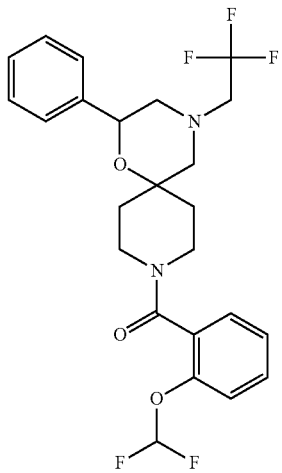 [SMILES: O=C(c1ccccc1OC(F)F)N1CCC2(CC1)CN(CC(F)(F)F)CC(c1ccccc1)O2] |

| 383 -continued | 384 -continued |
|---|---|
| 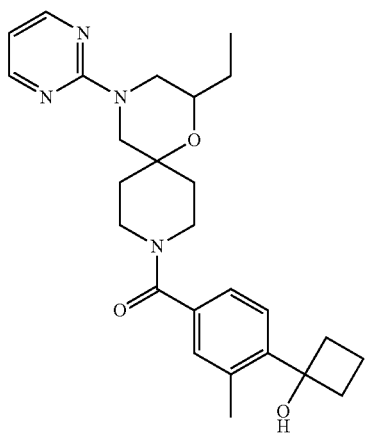 91 | 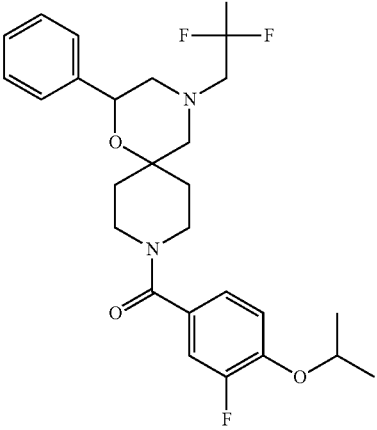 94 |
| 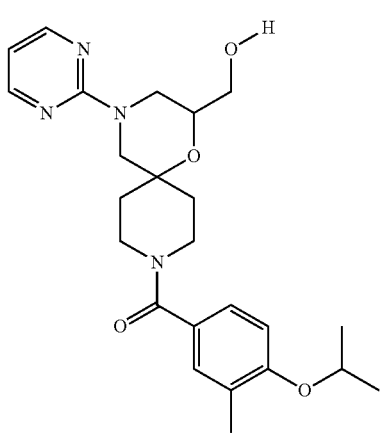 [SMILES: Cc1cc(C(=O)N2CCC3(CC2)CN(c2ncccn2)CC(CO)O3)ccc1OC(C)C] 92 | 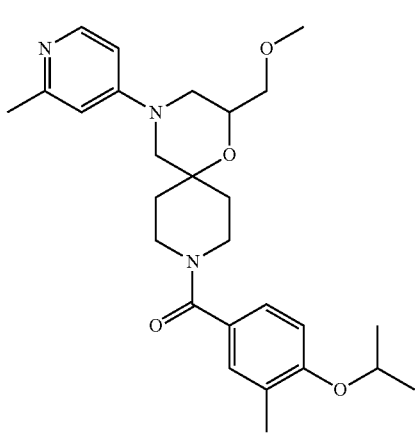 95 |
| 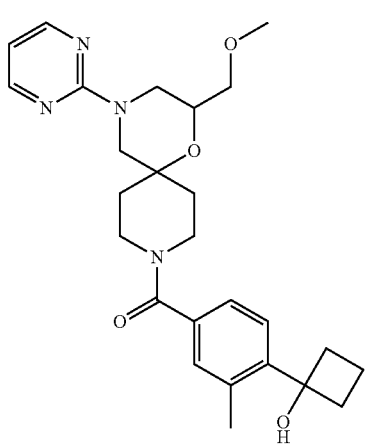 [SMILES: COCC1CN(c2ncccn2)CC2(CCN(C(=O)c3ccc(C4(O)CCC4)c(C)c3)CC2)O1] 93 | 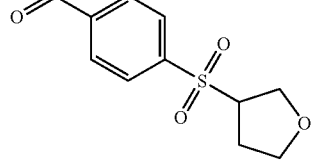 96 |

97 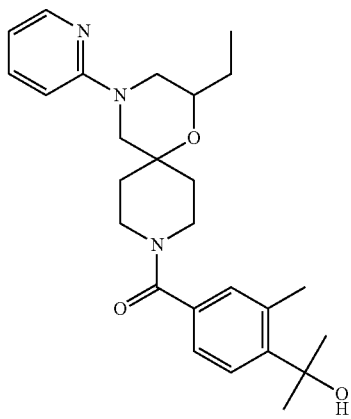 [SMILES: CCC1CN(c2ccccn2)CC2(CCN(C(=O)c3ccc(C(C)(C)O)c(C)c3)CC2)O1]
98 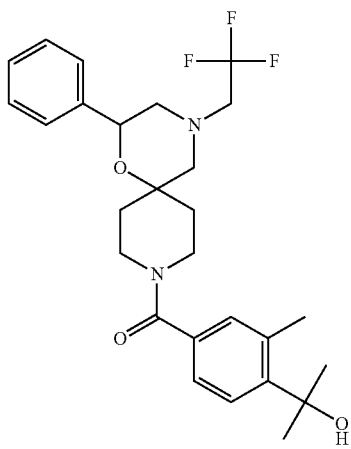 [SMILES: Cc1cc(C(=O)N2CCC3(CC2)CN(CC(F)(F)F)CC(c2ccccc2)O3)ccc1C(C)(C)O]
99 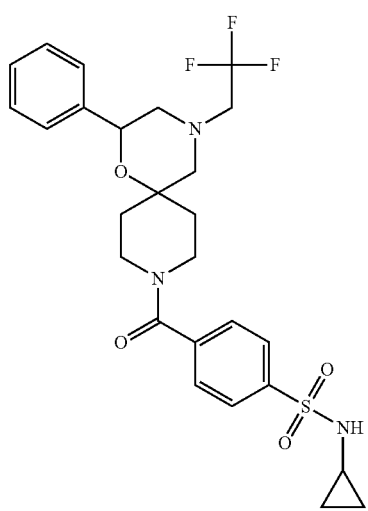 [SMILES: O=C(c1ccc(S(=O)(=O)NC2CC2)cc1)N1CCC2(CC1)CN(CC(F)(F)F)CC(c1ccccc1)O2]
100 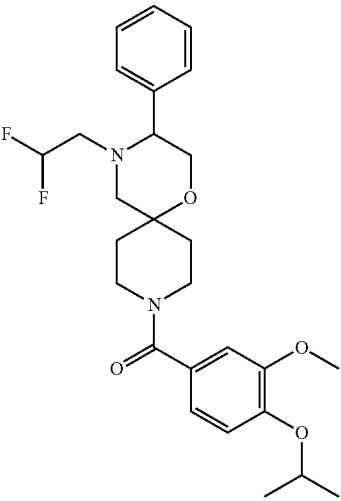 [SMILES: COc1cc(C(=O)N2CCC3(CC2)CN(CC(F)F)C(c2ccccc2)CO3)ccc1OC(C)C]
101 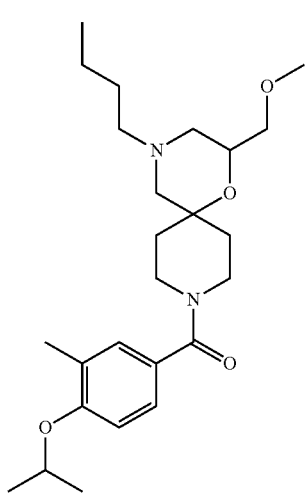
102 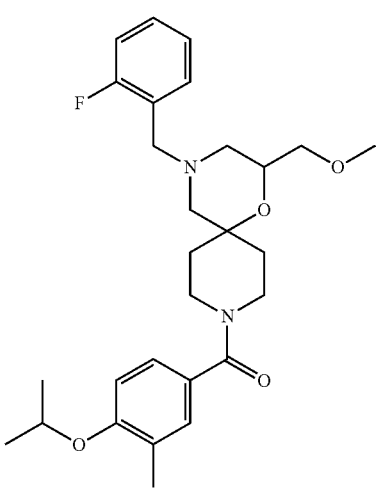 [SMILES: COCC1CN(Cc2ccccc2F)CC2(CCN(C(=O)c3ccc(OC(C)C)c(C)c3)CC2)O1]

| 387 | 388 |
|---|---|
| 103 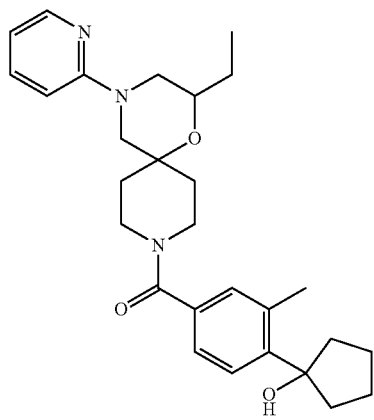 [SMILES: CCC1CN(c2ccccn2)CC2(CCN(C(=O)c3ccc(C4(O)CCCC4)c(C)c3)CC2)O1] | 106 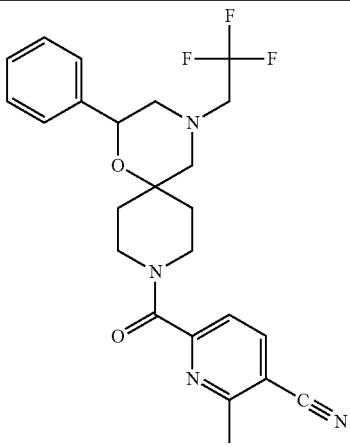 |
| 104 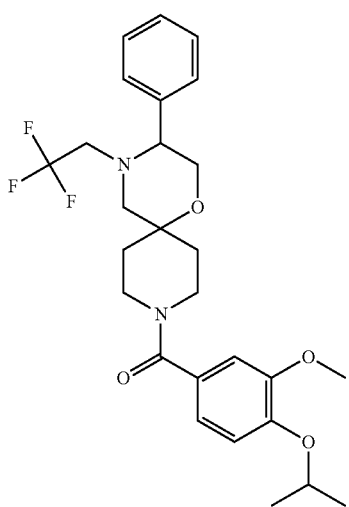 [SMILES: COc1cc(C(=O)N2CCC3(CC2)CN(CC(F)(F)F)C(c2ccccc2)CO3)ccc1OC(C)C] | 107 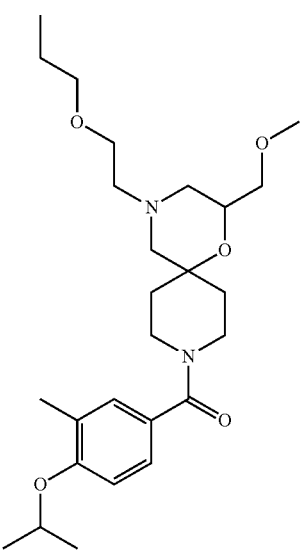 |
| 105 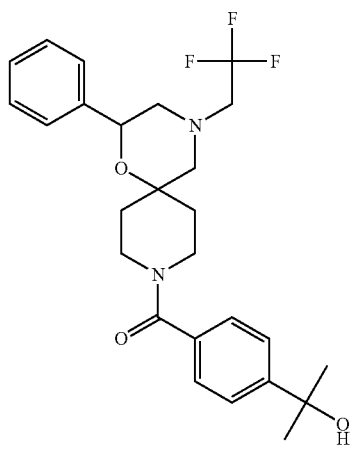 [SMILES: CC(C)(O)c1ccc(C(=O)N2CCC3(CC2)CN(CC(F)(F)F)CC(c2ccccc2)O3)cc1] | 108 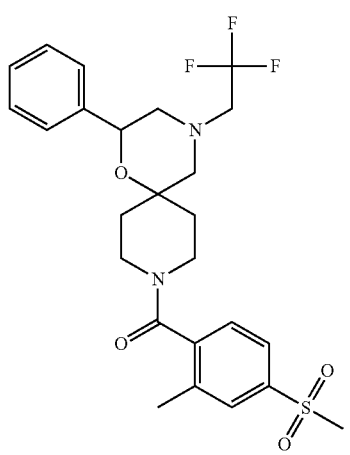 [SMILES: Cc1cc(S(C)(=O)=O)ccc1C(=O)N1CCC2(CC1)CN(CC(F)(F)F)CC(c1ccccc1)O2] |

| 389 -continued | 390 -continued |
|---|---|
| 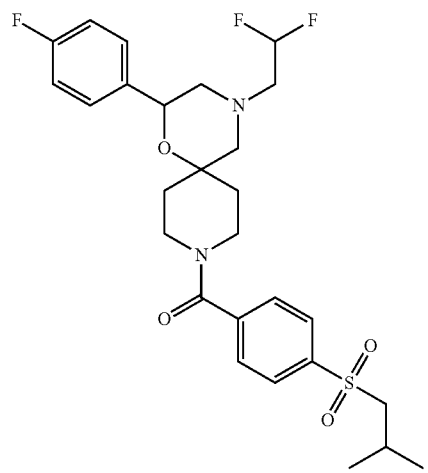 [SMILES: CC(C)CS(=O)(=O)c1ccc(C(=O)N2CCC3(CC2)CN(CC(F)F)CC(c2ccc(F)cc2)O3)cc1] 109 | 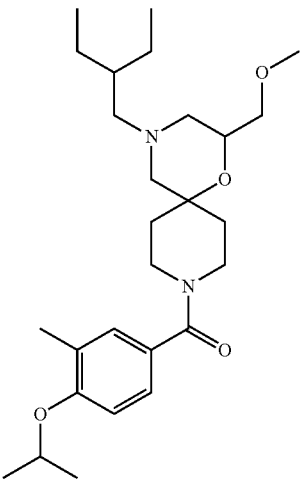 112 |
| 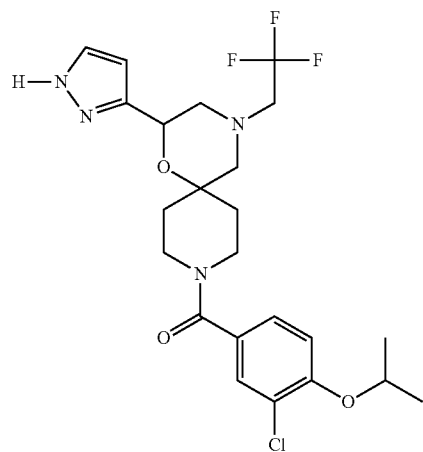 [SMILES: CC(C)Oc1ccc(C(=O)N2CCC3(CC2)CN(CC(F)(F)F)CC(c2cc[nH]n2)O3)cc1Cl] 110 | 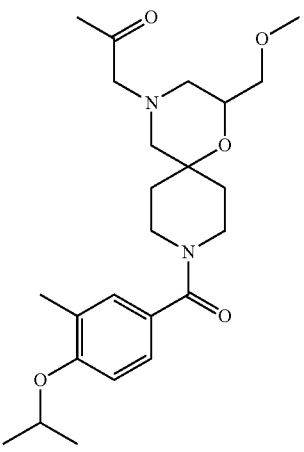 113 |
| 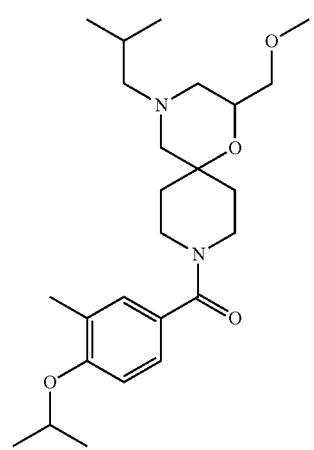 [SMILES: COCC1CN(CC(C)C)CC2(CCN(C(=O)c3ccc(OC(C)C)c(C)c3)CC2)O1] 111 | 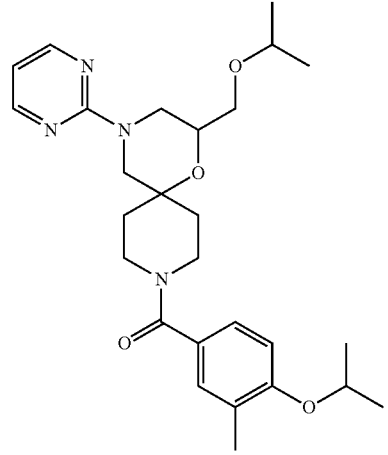 [SMILES: Cc1cc(C(=O)N2CCC3(CC2)CN(c2ncccn2)CC(COC(C)C)O3)ccc1OC(C)C] 114 |

| 115 | 118 |
|---|---|
| 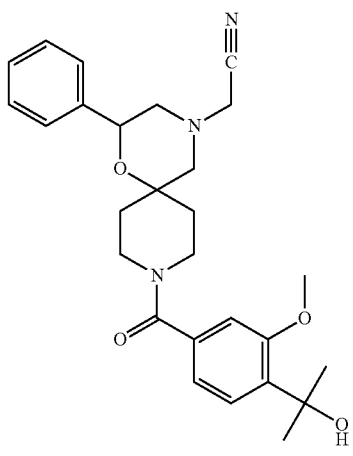 [SMILES: COc1cc(C(=O)N2CCC3(CC2)CN(CC#N)CC(c2ccccc2)O3)ccc1C(C)(C)O] | 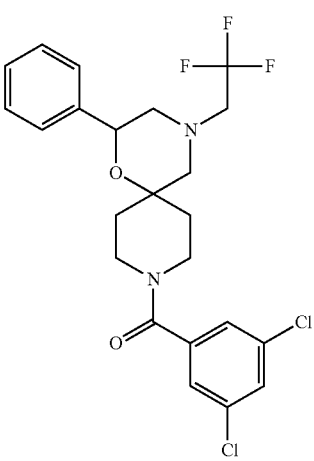 |
| 116 | 119 |
| 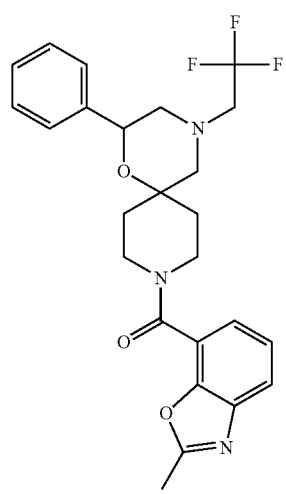 [SMILES: Cc1nc2cccc(C(=O)N3CCC4(CC3)CN(CC(F)(F)F)CC(c3ccccc3)O4)c2o1] | 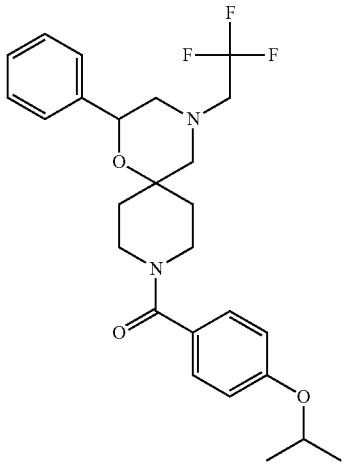 |
| 117 | 120 |
| 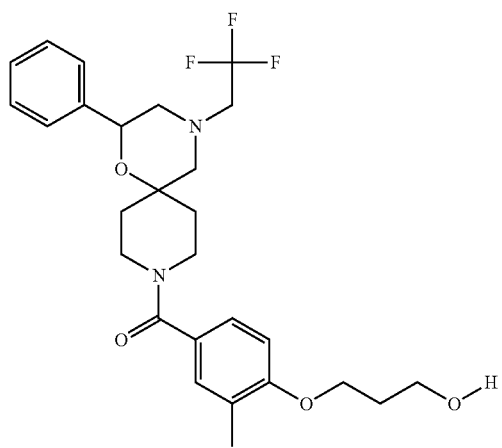 [SMILES: Cc1cc(C(=O)N2CCC3(CC2)CN(CC(F)(F)F)CC(c2ccccc2)O3)ccc1OCCCO] | 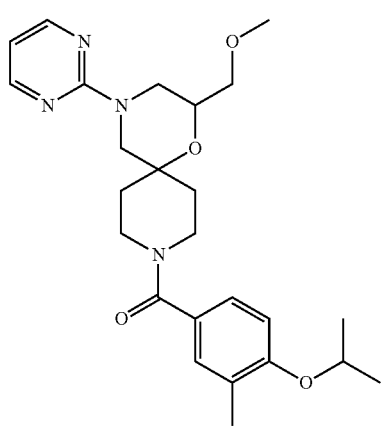 [SMILES: COCC1CN(c2ncccn2)CC2(CCN(C(=O)c3ccc(OC(C)C)c(C)c3)CC2)O1] |

| 393 -continued | 394 -continued |
|---|---|
| 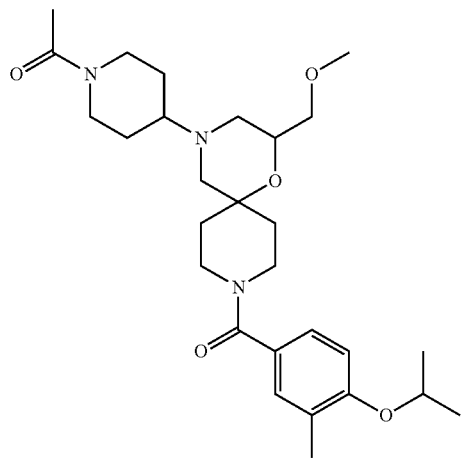 [SMILES: COCC1CN(C2CCN(C(C)=O)CC2)CC2(CCN(C(=O)c3ccc(OC(C)C)c(C)c3)CC2)O1] 121 | 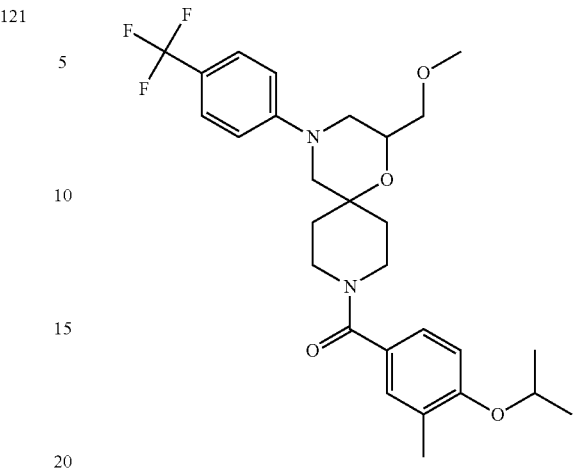 124 |
| 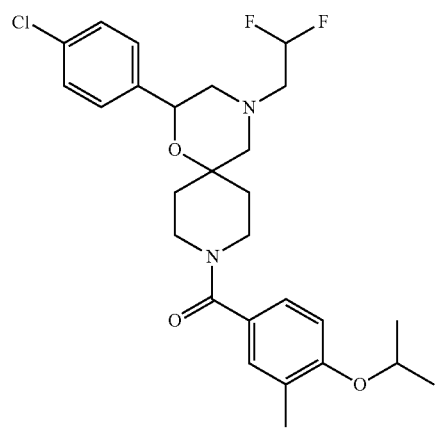 [SMILES: Cc1cc(C(=O)N2CCC3(CC2)CN(CC(F)F)CC(c2ccc(Cl)cc2)O3)ccc1OC(C)C] 122 | 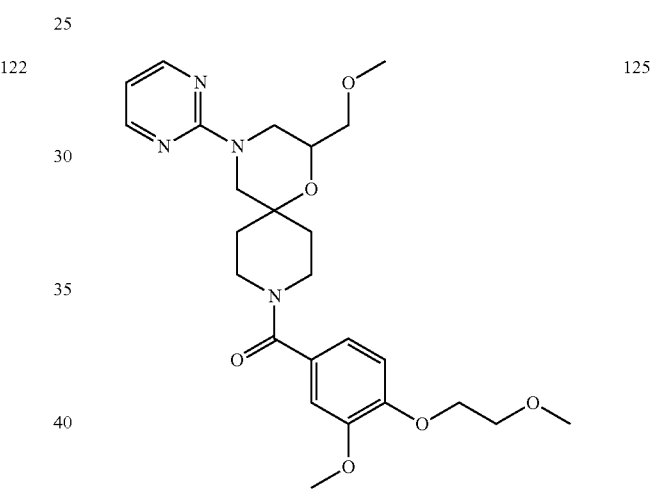 125 |
| 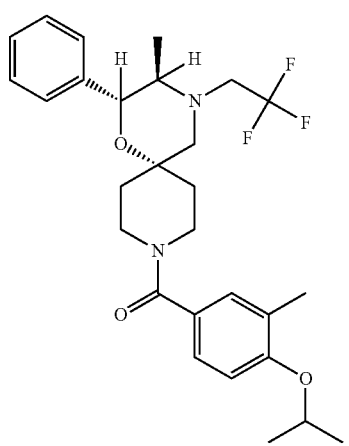 123 | 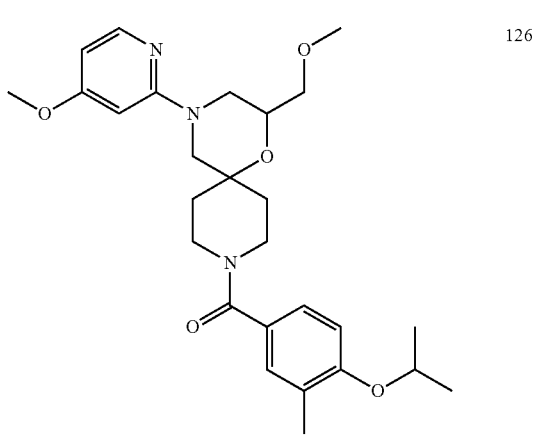 126 |

| 127 | 130 |
|---|---|
| 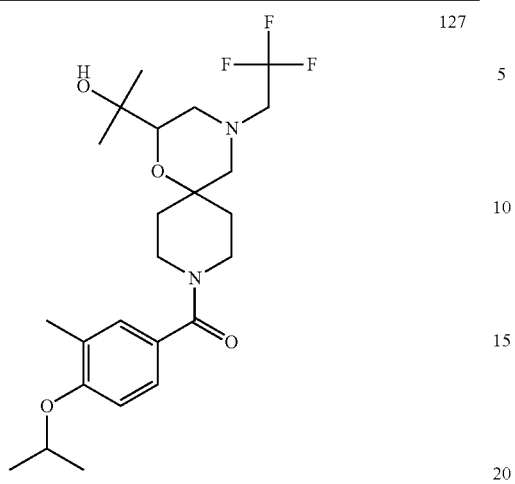 | 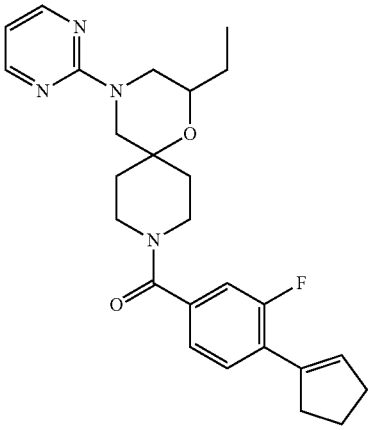 [SMILES: CCC1CN(c2ncccn2)CC2(CCN(C(=O)c3ccc(C4=CCCC4)c(F)c3)CC2)O1] |
| 128 | 131 |
| 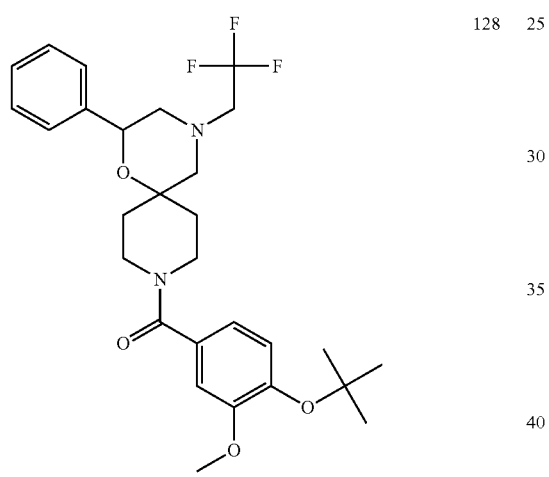 | 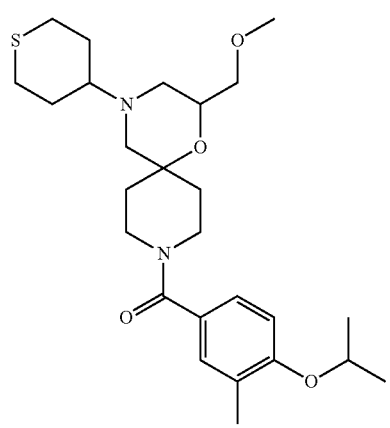 [SMILES: COCC1CN(C2CCSCC2)CC2(CCN(C(=O)c3ccc(OC(C)C)c(C)c3)CC2)O1] |
| 129 | 132 |
| 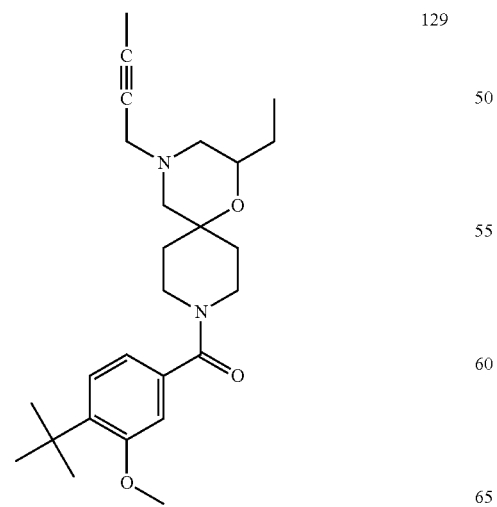 | 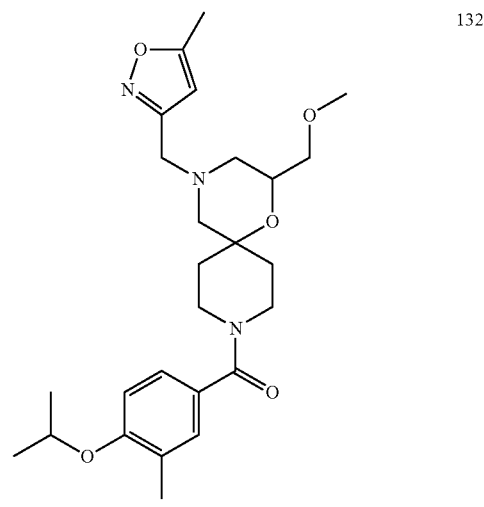 |

-continued
| 133 | 136 |
|---|---|
| 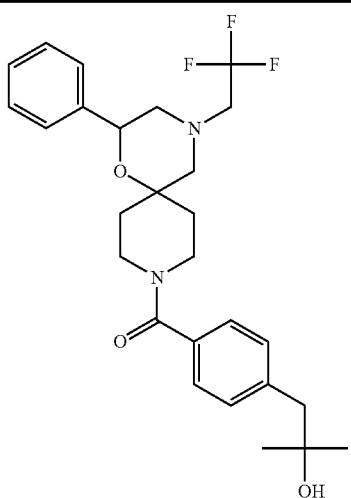 | 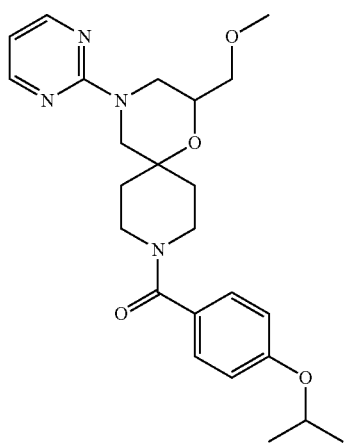 |
| 134 | 137 |
| 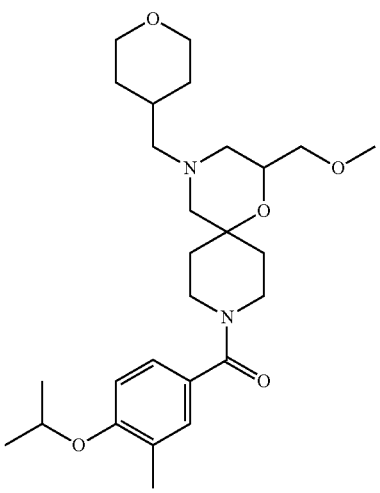 [SMILES: COCC1CN(CC2CCOCC2)CC2(CCN(C(=O)c3ccc(OC(C)C)c(C)c3)CC2)O1] | 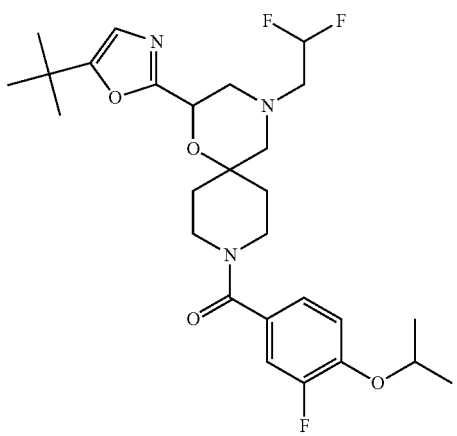 |
| 135 | 138 |
| 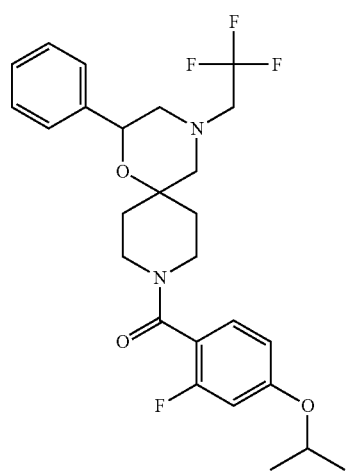 [SMILES: CC(C)Oc1ccc(C(=O)N2CCC3(CC2)CN(CC(F)(F)F)CC(c2ccccc2)O3)c(F)c1] | 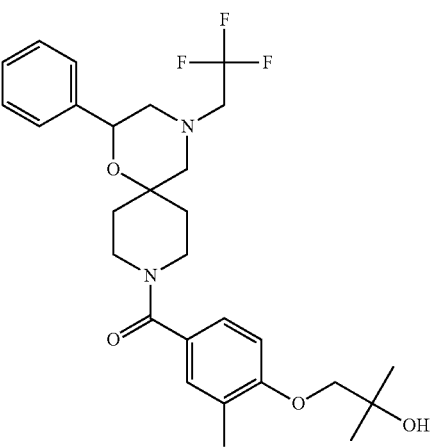 [SMILES: Cc1cc(C(=O)N2CCC3(CC2)CN(CC(F)(F)F)CC(c2ccccc2)O3)ccc1OCC(C)(C)O] |

| 399 -continued | 400 -continued |
|---|---|
| 139 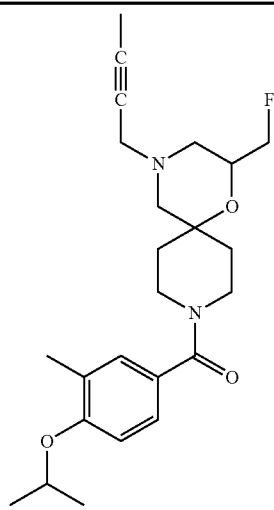 | 142 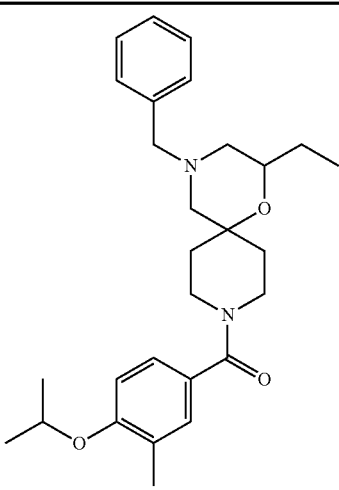 |
| 140 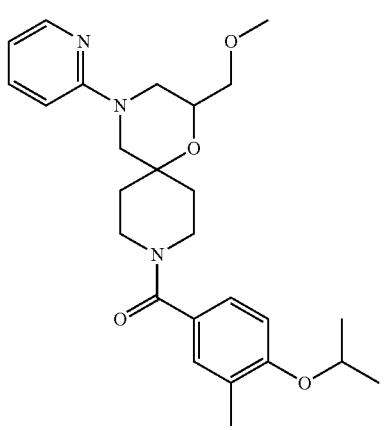 [SMILES: COCC1CN(c2ccccn2)CC2(CCN(C(=O)c3ccc(OC(C)C)c(C)c3)CC2)O1] | 143 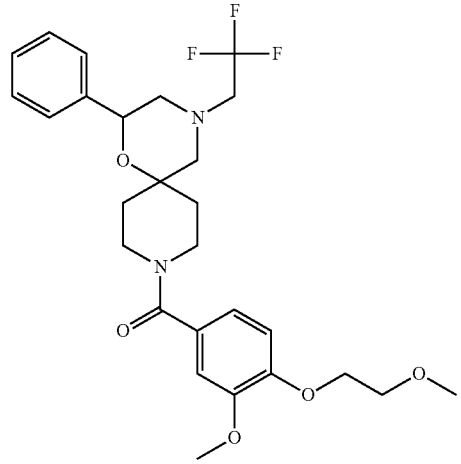 |
| 141 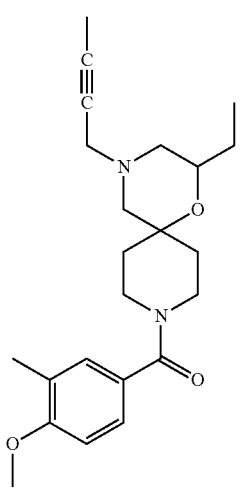 [SMILES: CC#CCN1CC(CC)OC2(CCN(C(=O)c3ccc(OC)c(C)c3)CC2)C1] | 144 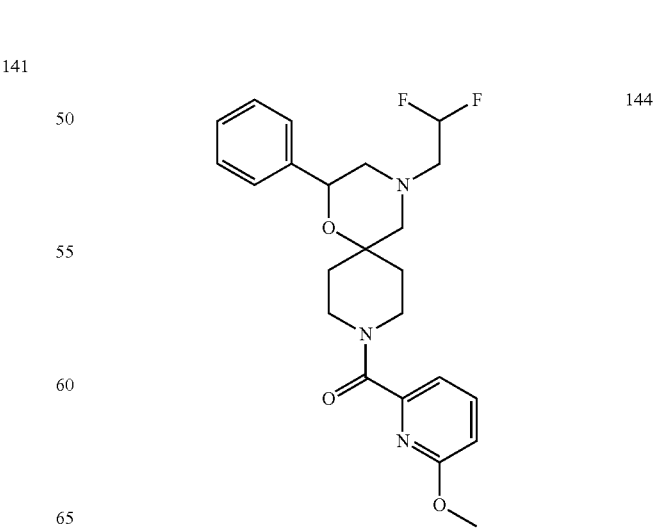 |

| 145 | 148 |
|---|---|
| 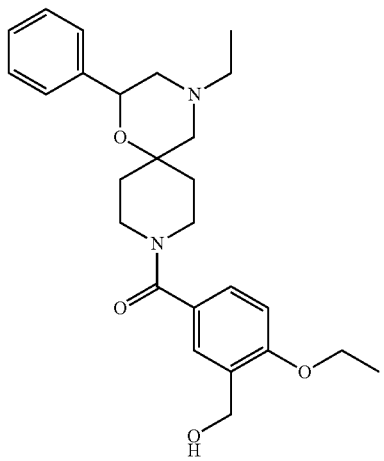 [SMILES: CCOc1ccc(C(=O)N2CCC3(CC2)CN(CC)CC(c2ccccc2)O3)cc1CO] | 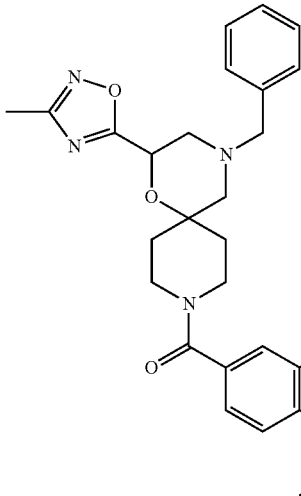 |
| 146 | 149 |
|---|---|
| 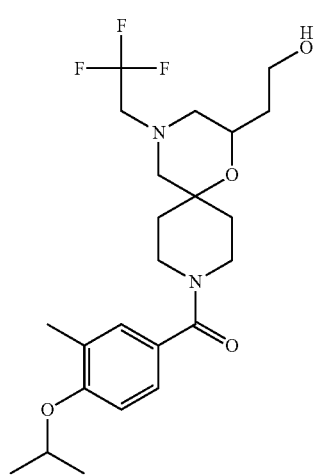 [SMILES: Cc1cc(C(=O)N2CCC3(CC2)CN(CC(F)(F)F)CC(CCO)O3)ccc1OC(C)C] | 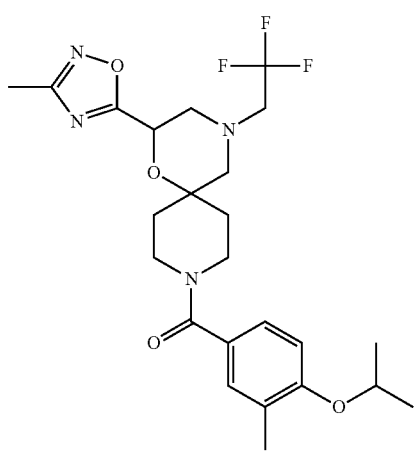 |
| 147 | 150 |
|---|---|
| 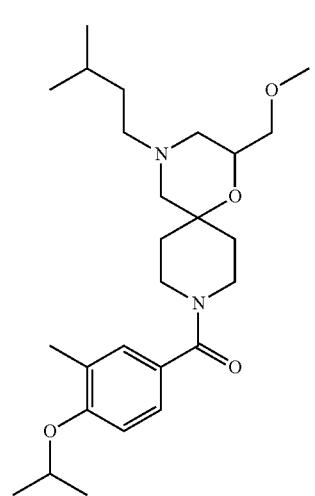 [SMILES: COCC1CN(CCC(C)C)CC2(CCN(C(=O)c3ccc(OC(C)C)c(C)c3)CC2)O1] | 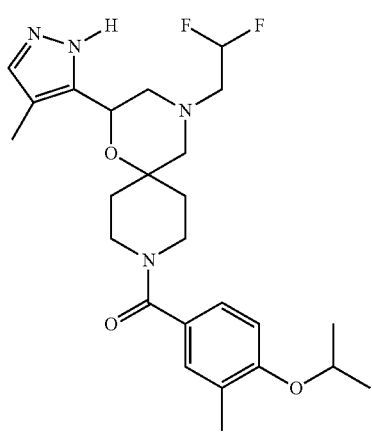 [SMILES: Cc1cc(C(=O)N2CCC3(CC2)CN(CC(F)F)CC(c2[nH]ncc2C)O3)ccc1OC(C)C] |

| 403 -continued | 404 -continued |
|---|---|
| 151 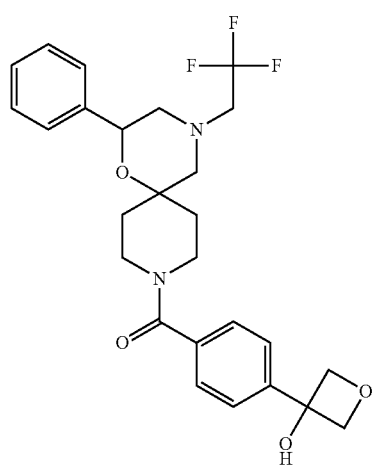 [SMILES: O=C(c1ccc(C2(O)COC2)cc1)N1CCC2(CC1)CN(CC(F)(F)F)CC(c1ccccc1)O2] | 154 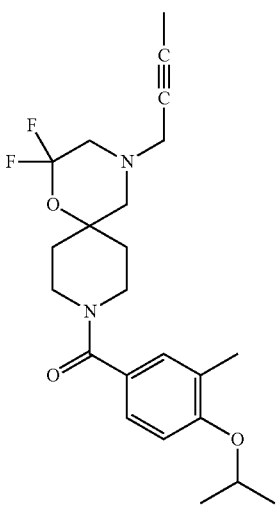 |
| 152 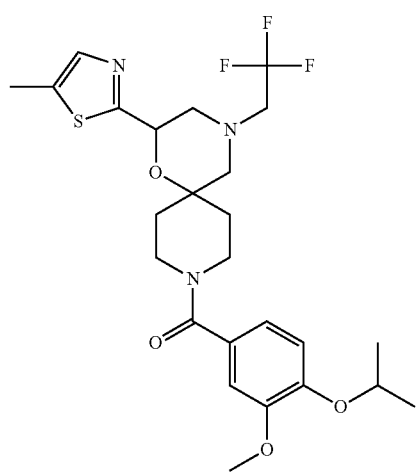 [SMILES: COc1cc(C(=O)N2CCC3(CC2)CN(CC(F)(F)F)CC(c2ncc(C)s2)O3)ccc1OC(C)C] | 155 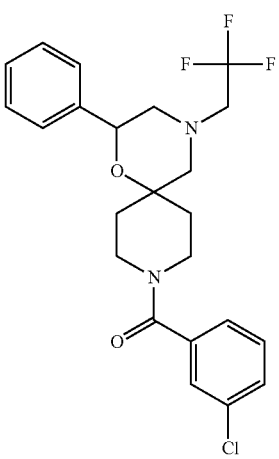 |
| 153 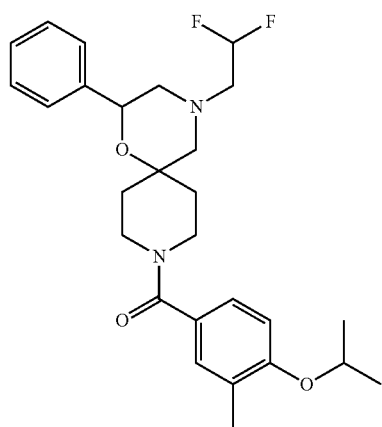 [SMILES: Cc1cc(C(=O)N2CCC3(CC2)CN(CC(F)F)CC(c2ccccc2)O3)ccc1OC(C)C] | 156 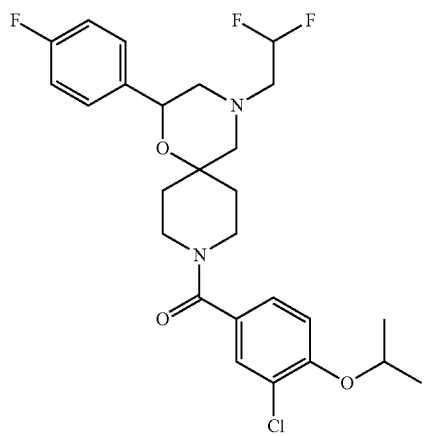 [SMILES: CC(C)Oc1ccc(C(=O)N2CCC3(CC2)CN(CC(F)F)CC(c2ccc(F)cc2)O3)cc1Cl] |

405
-continued
| | |
|---|---|
| 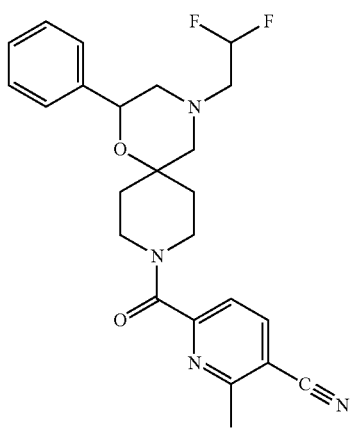 [SMILES: Cc1nc(C(=O)N2CCC3(CC2)CN(CC(F)F)CC(c2ccccc2)O3)ccc1C#N] 157 | 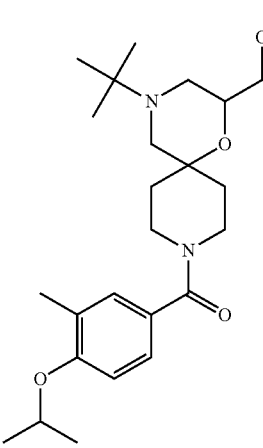 160 |
| 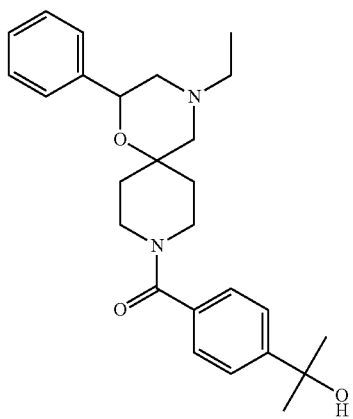 [SMILES: CCN1CC(c2ccccc2)OC2(CCN(C(=O)c3ccc(C(C)(C)O)cc3)CC2)C1] 158 | 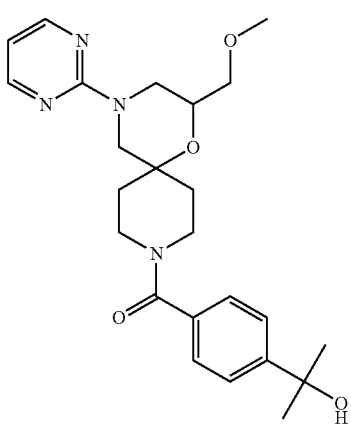 161 |
| 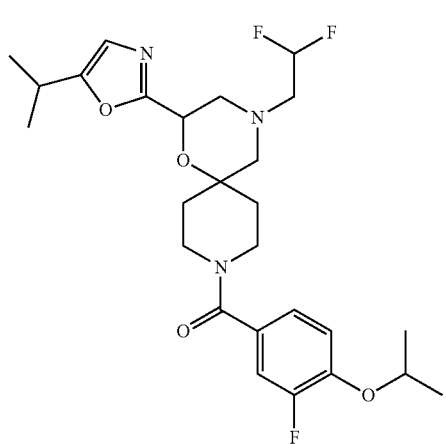 [SMILES: CC(C)Oc1ccc(C(=O)N2CCC3(CC2)CN(CC(F)F)CC(c2ncc(C(C)C)o2)O3)cc1F] 159 | 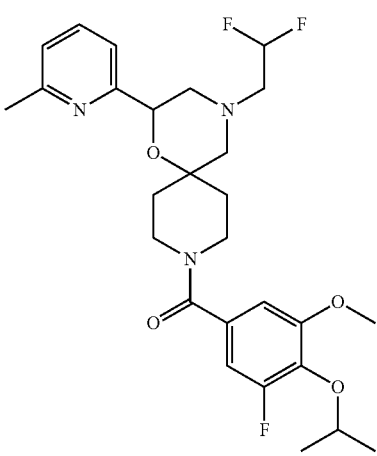 162 |

| 163 | 166 |
|---|---|
| 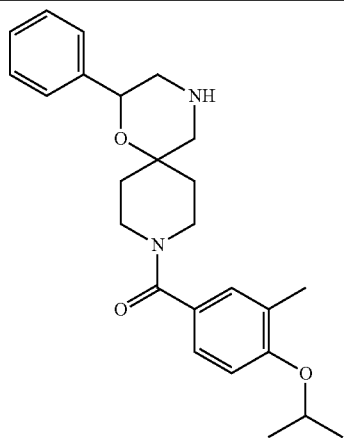 | 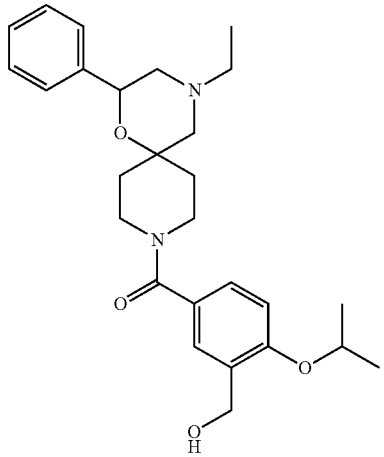 |
| 164 | 167 |
| 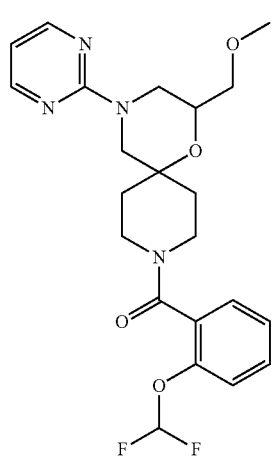 [SMILES: COCC1CN(c2ncccn2)CC2(CCN(C(=O)c3ccccc3OC(F)F)CC2)O1] | 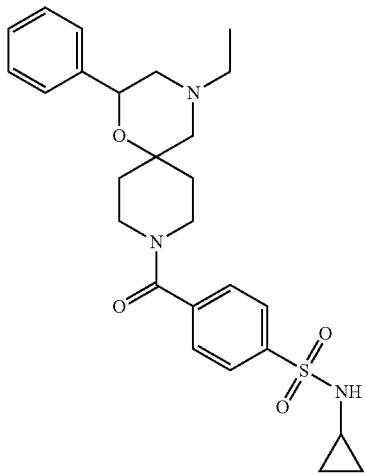 |
| 165 | 168 |
| 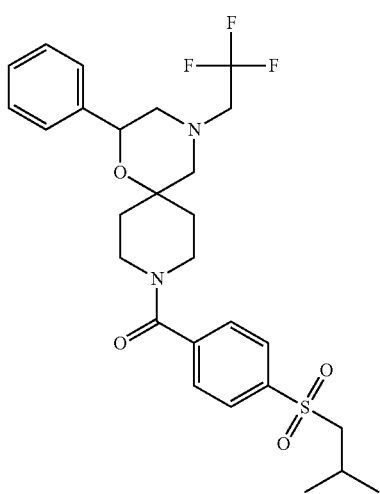 [SMILES: CC(C)CS(=O)(=O)c1ccc(C(=O)N2CCC3(CC2)CN(CC(F)(F)F)CC(c2ccccc2)O3)cc1] | 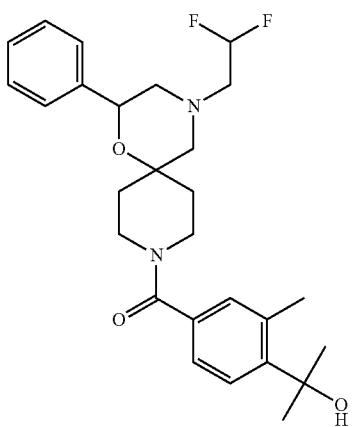 [SMILES: Cc1cc(C(=O)N2CCC3(CC2)CN(CC(F)F)CC(c2ccccc2)O3)ccc1C(C)(C)O] |

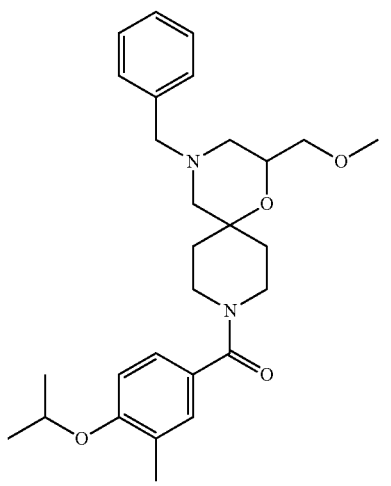 [SMILES: COCC1CN(Cc2ccccc2)CC2(CCN(C(=O)c3ccc(OC(C)C)c(C)c3)CC2)O1]
169
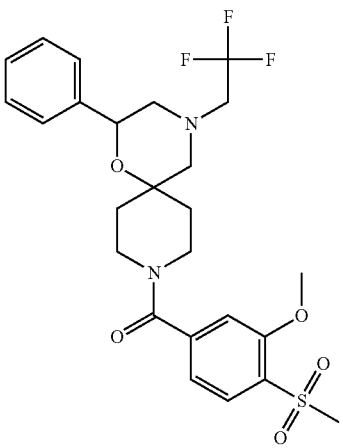 [SMILES: COc1cc(C(=O)N2CCC3(CC2)CN(CC(F)(F)F)CC(c2ccccc2)O3)ccc1S(C)(=O)=O]
172
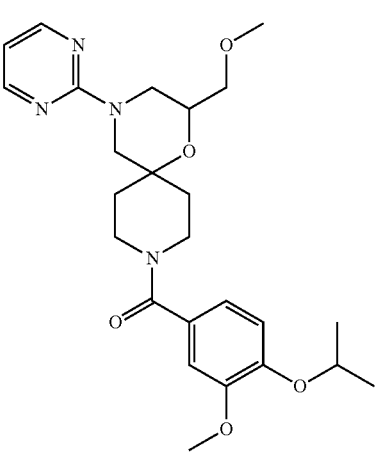 [SMILES: COCC1CN(c2ncccn2)CC2(CCN(C(=O)c3ccc(OC(C)C)c(OC)c3)CC2)O1]
173
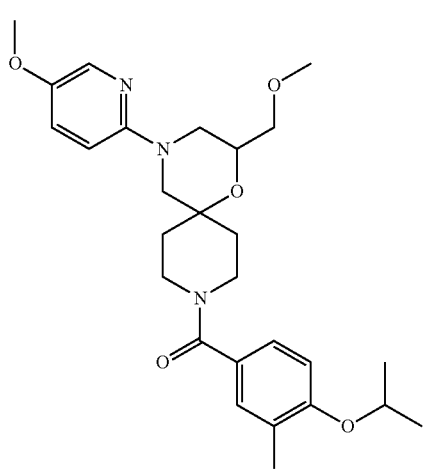 [SMILES: COCC1CN(c2ccc(OC)cn2)CC2(CCN(C(=O)c3ccc(OC(C)C)c(C)c3)CC2)O1]
174

| 411 | 412 |
|---|---|
| 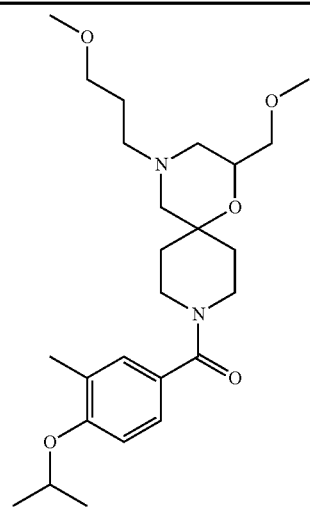 175 | 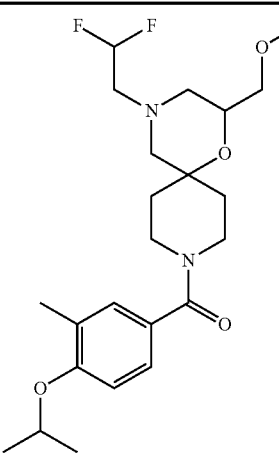 178 |
| 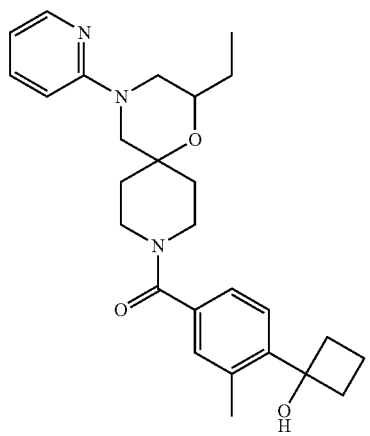 [SMILES: CCC1CN(c2ccccn2)CC2(CCN(C(=O)c3ccc(C4(O)CCC4)c(C)c3)CC2)O1] 176 | 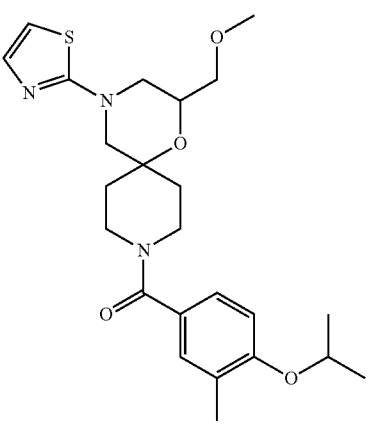 [SMILES: COCC1CN(c2nccs2)CC2(CCN(C(=O)c3ccc(OC(C)C)c(C)c3)CC2)O1] 179 |
| 177 | 180 |

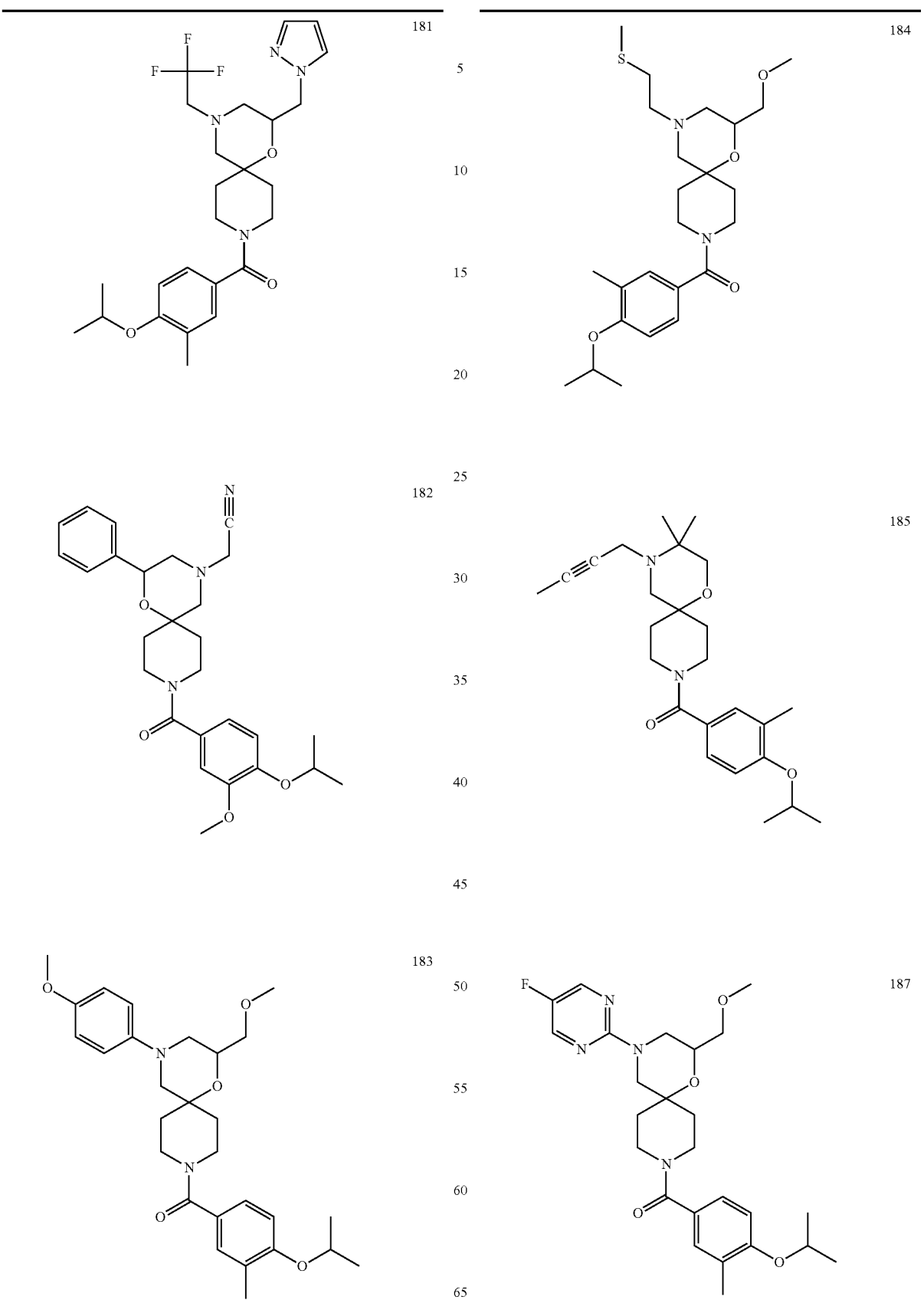

188
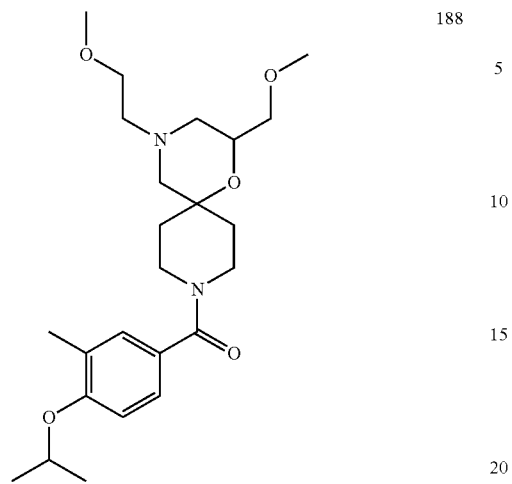
189
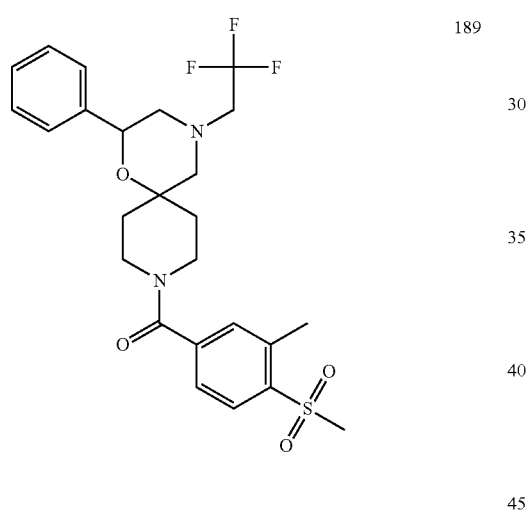
190
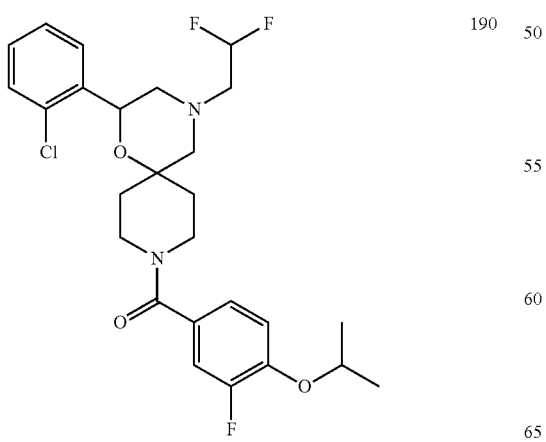
191
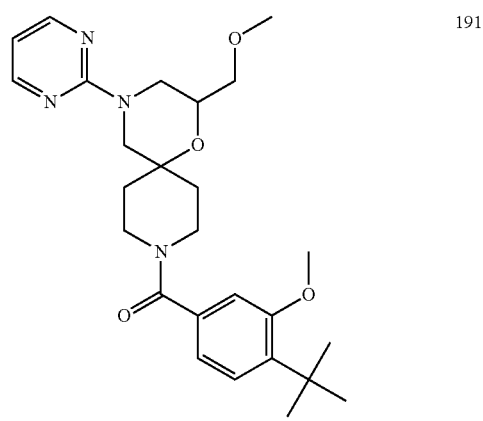
192
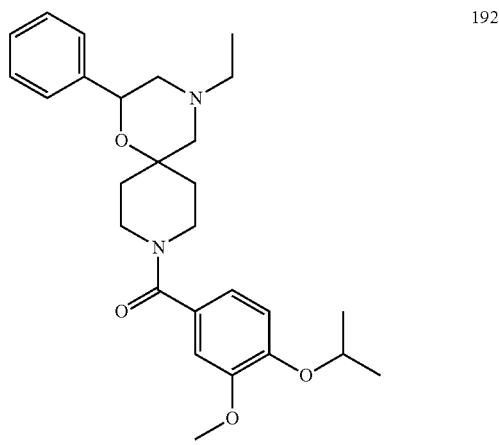
193
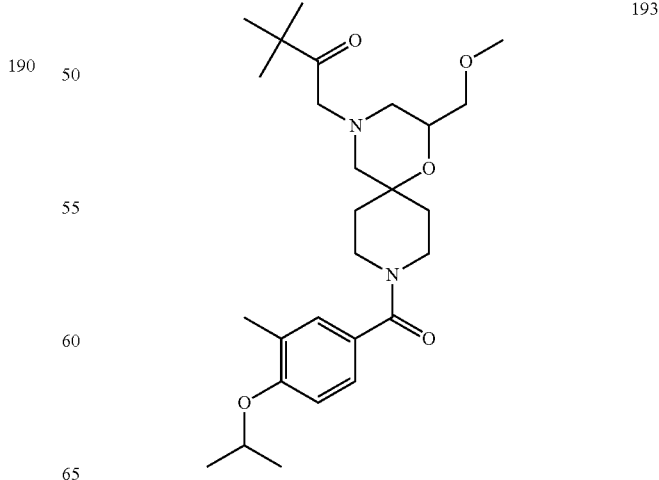

| 417 -continued | 418 -continued |
|---|---|
| 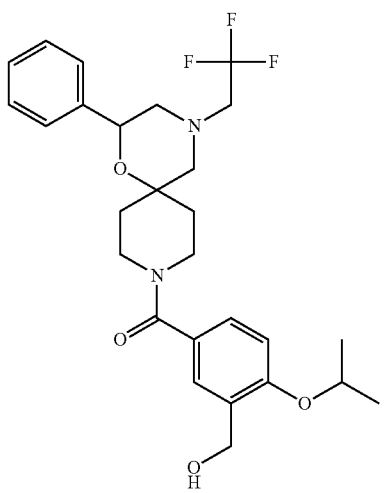 [SMILES: CC(C)Oc1ccc(C(=O)N2CCC3(CC2)CN(CC(F)(F)F)CC(c2ccccc2)O3)cc1CO] 194 | 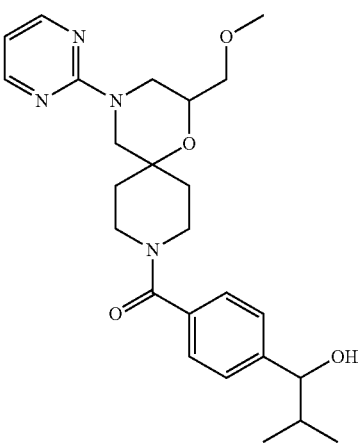 197 |
| 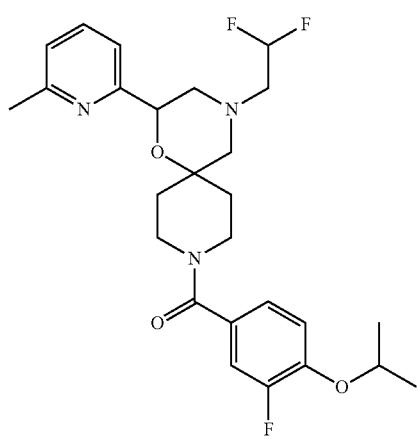 195 | 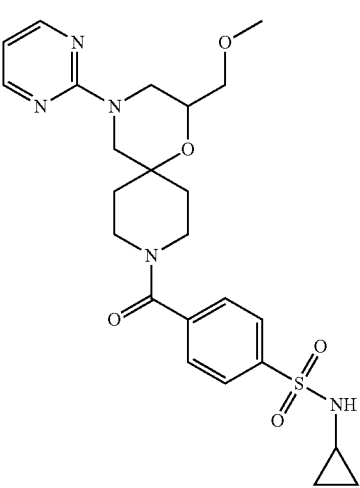 198 |
| 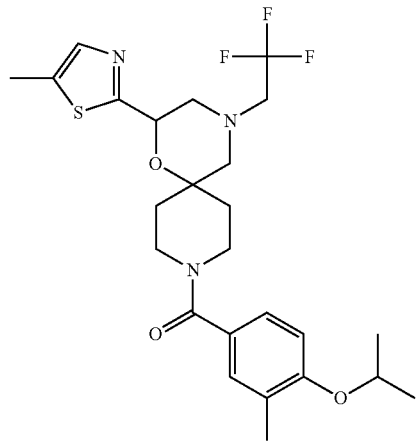 [SMILES: Cc1cnc(C2CN(CC(F)(F)F)CC3(CCN(C(=O)c4ccc(OC(C)C)c(C)c4)CC3)O2)s1] 196 | 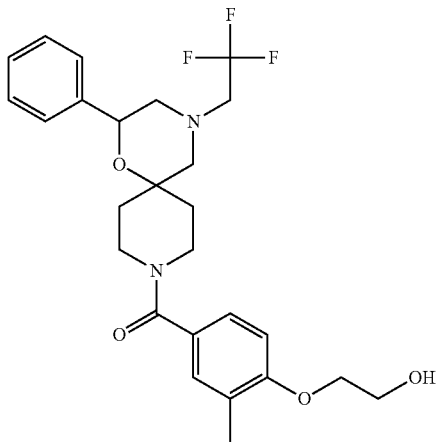 [SMILES: Cc1cc(C(=O)N2CCC3(CC2)CN(CC(F)(F)F)CC(c2ccccc2)O3)ccc1OCCO] 199 |

419
-continued
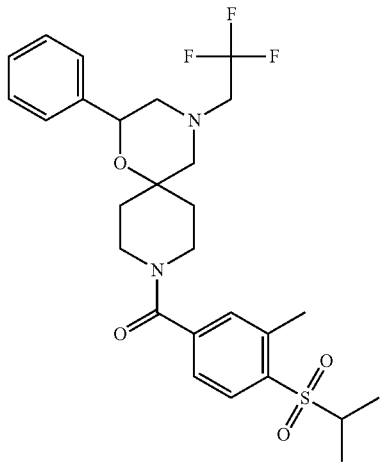 [SMILES: Cc1cc(C(=O)N2CCC3(CC2)CN(CC(F)(F)F)CC(c2ccccc2)O3)ccc1S(=O)(=O)C(C)C]
200
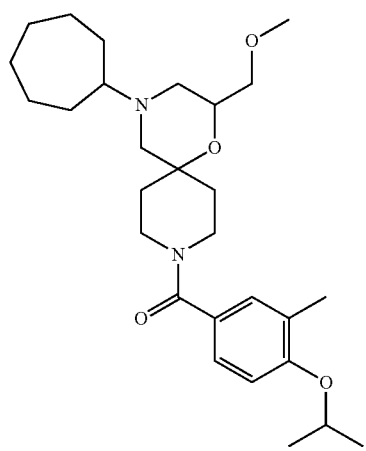 [SMILES: COCC1CN(C2CCCCCC2)CC2(CCN(C(=O)c3ccc(OC(C)C)c(C)c3)CC2)O1]
201
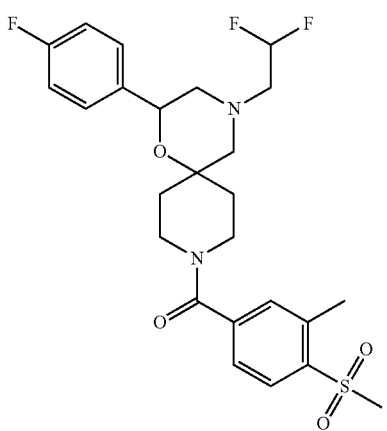 [SMILES: Cc1cc(C(=O)N2CCC3(CC2)CN(CC(F)F)CC(c2ccc(F)cc2)O3)ccc1S(C)(=O)=O]
202
420
-continued
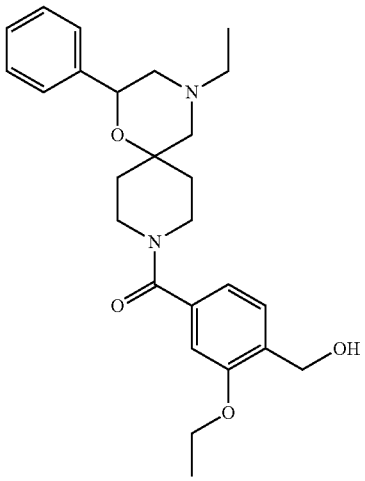 [SMILES: CCOc1cc(C(=O)N2CCC3(CC2)CN(CC)CC(c2ccccc2)O3)ccc1CO]
203
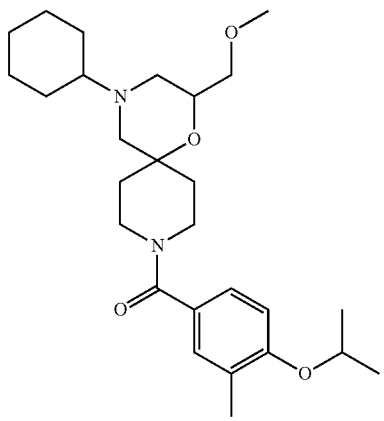 [SMILES: COCC1CN(C2CCCCC2)CC2(CCN(C(=O)c3ccc(OC(C)C)c(C)c3)CC2)O1]
204
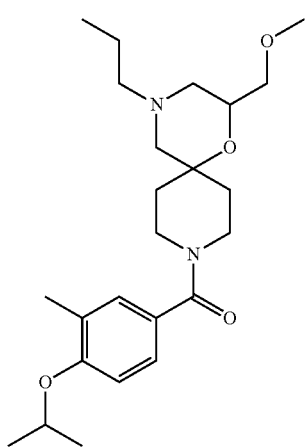 [SMILES: CCCN1CC(COC)OC2(CCN(C(=O)c3ccc(OC(C)C)c(C)c3)CC2)C1]
205

| 421 -continued | | 422 -continued | |
|---|---|---|---|
| 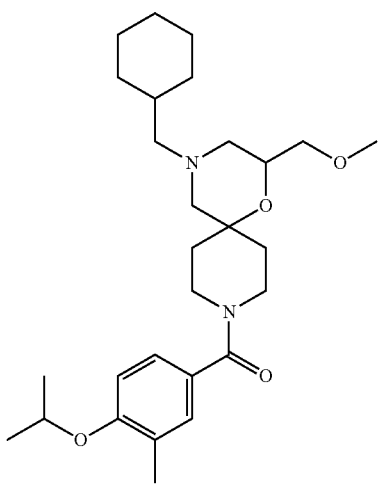 [SMILES: COCC1CN(CC2CCCCC2)CC2(CCN(C(=O)c3ccc(OC(C)C)c(C)c3)CC2)O1] | 206 | 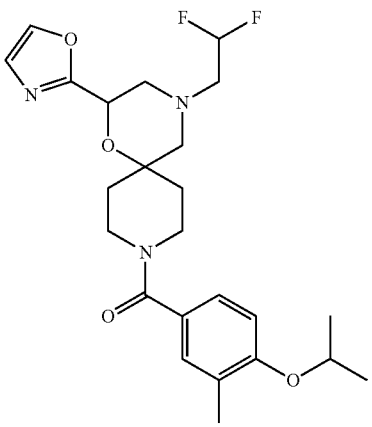 | 209 |
| 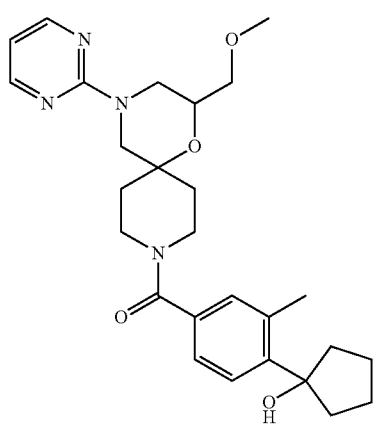 [SMILES: COCC1CN(c2ncccn2)CC2(CCN(C(=O)c3ccc(C4(O)CCCC4)c(C)c3)CC2)O1] | 207 | 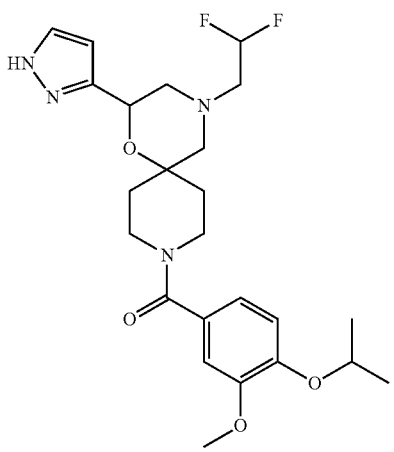 | 210 |
| 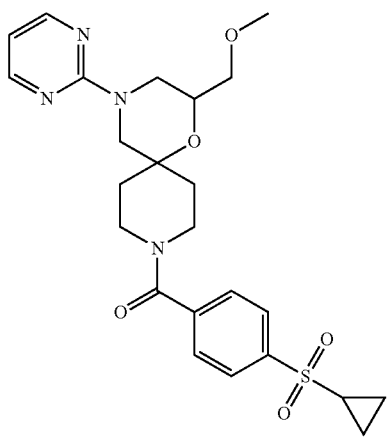 [SMILES: COCC1CN(c2ncccn2)CC2(CCN(C(=O)c3ccc(S(=O)(=O)C4CC4)cc3)CC2)O1] | 208 | 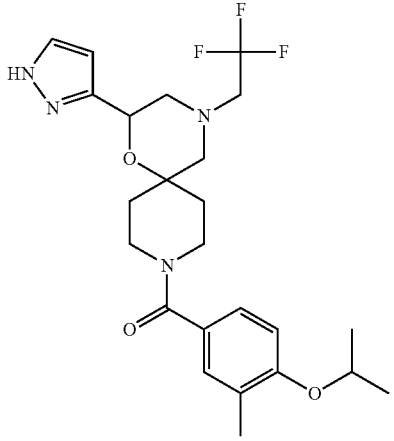 [SMILES: Cc1cc(C(=O)N2CCC3(CC2)CN(CC(F)(F)F)CC(c2cc[nH]n2)O3)ccc1OC(C)C] | 211 |

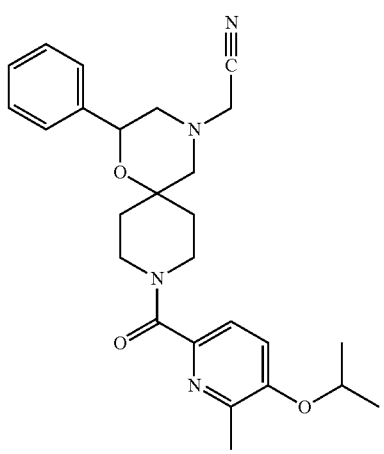 [SMILES: Cc1nc(C(=O)N2CCC3(CC2)CN(CC#N)CC(c2ccccc2)O3)ccc1OC(C)C]
212
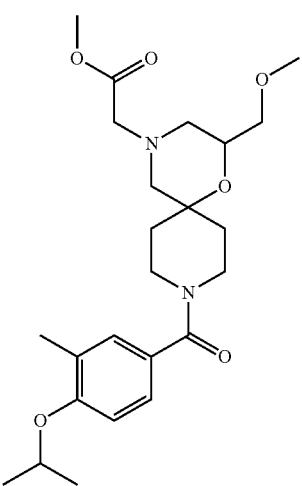
215
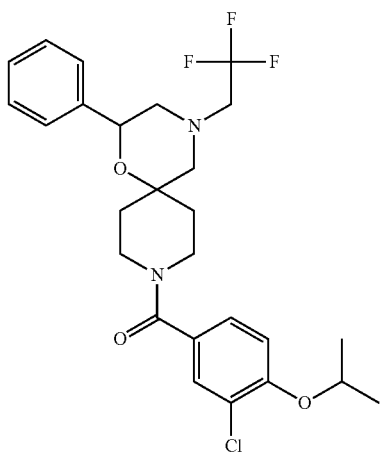
213
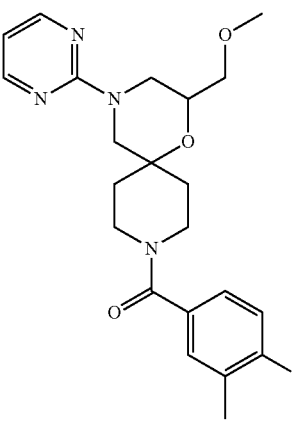
216
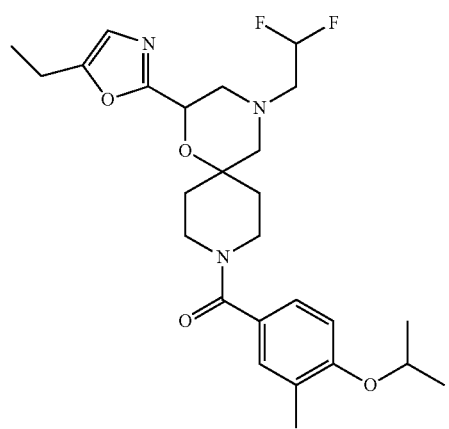 [SMILES: CCc1cnc(C2CN(CC(F)F)CC3(CCN(C(=O)c4ccc(OC(C)C)c(C)c4)CC3)O2)o1]
214
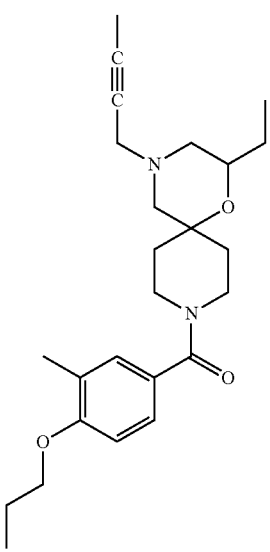 [SMILES: CC#CCN1CC(CC)OC2(CCN(C(=O)c3ccc(OCCC)c(C)c3)CC2)C1]
217

-continued
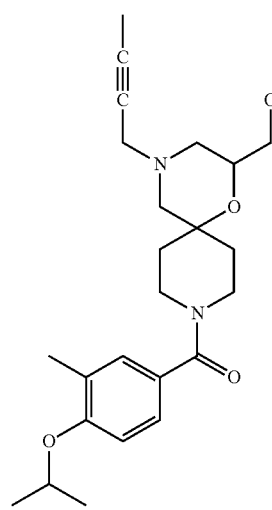
218
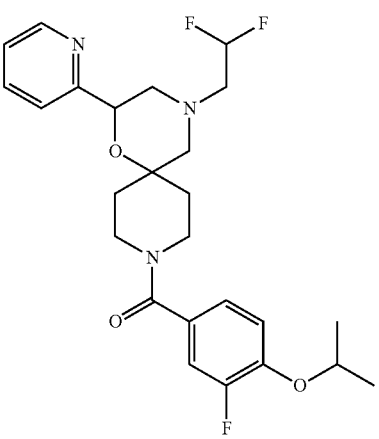
221
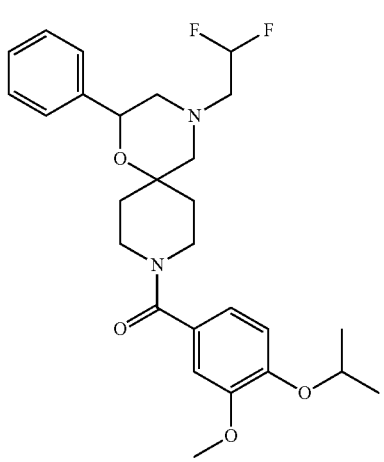 [SMILES: COc1cc(C(=O)N2CCC3(CC2)CN(CC(F)F)CC(c2ccccc2)O3)ccc1OC(C)C]
219
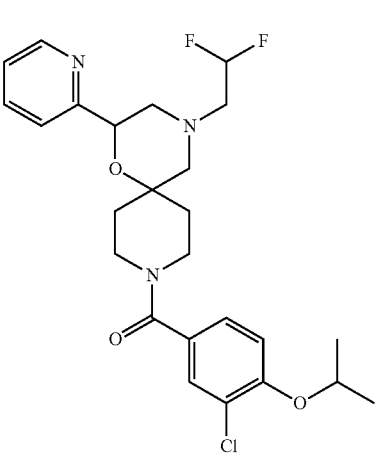
222
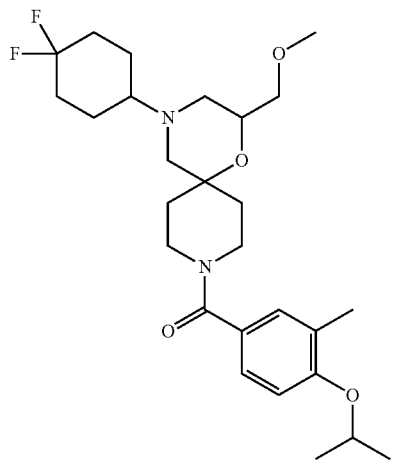 [SMILES: COCC1CN(C2CCC(F)(F)CC2)CC2(CCN(C(=O)c3ccc(OC(C)C)c(C)c3)CC2)O1]
220
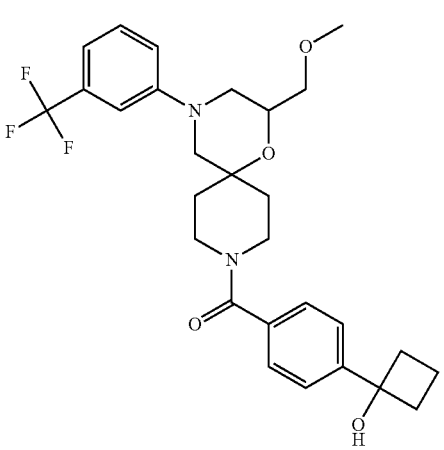 [SMILES: COCC1CN(c2cccc(C(F)(F)F)c2)CC2(CCN(C(=O)c3ccc(C4(O)CCC4)cc3)CC2)O1]
223

| 427 -continued | | 428 -continued | |
|---|---|---|---|
| 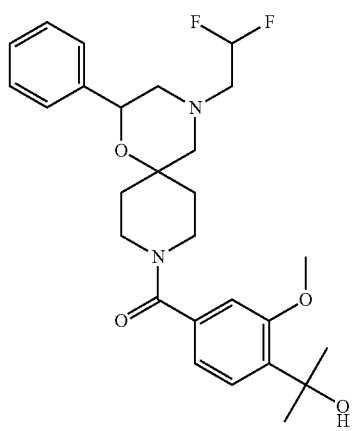 [SMILES: COc1cc(C(=O)N2CCC3(CC2)CN(CC(F)F)CC(c2ccccc2)O3)ccc1C(C)(C)O] | 224 | 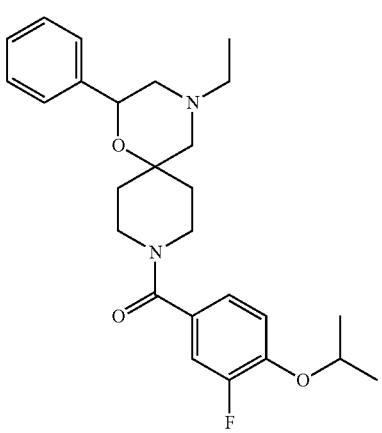 | 227 |
| 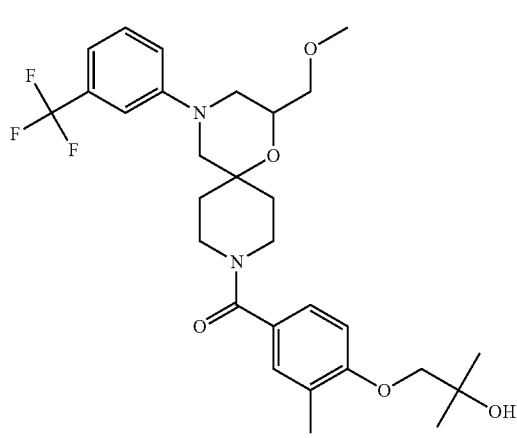 [SMILES: COCC1CN(c2cccc(C(F)(F)F)c2)CC2(CCN(C(=O)c3ccc(OCC(C)(C)O)c(C)c3)CC2)O1] | 225 | 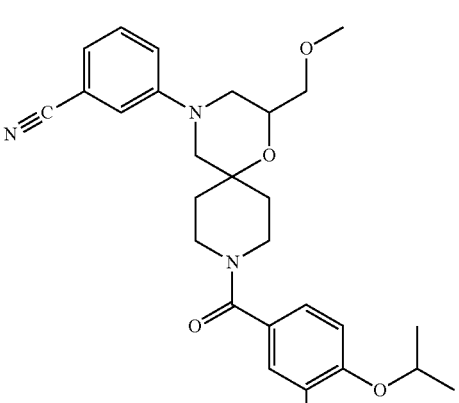 | 228 |
| 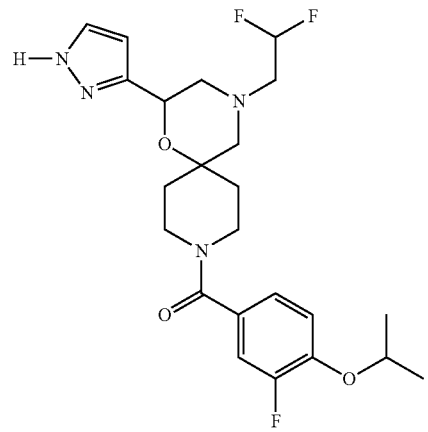 [SMILES: CC(C)Oc1ccc(C(=O)N2CCC3(CC2)CN(CC(F)F)CC(c2cc[nH]n2)O3)cc1F] | 226 | | 229 |

| 230 | 233 |
|---|---|
| 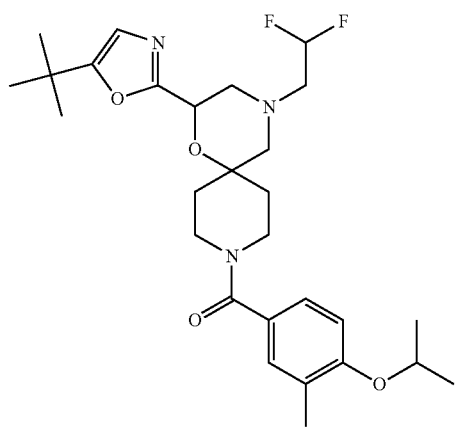 [SMILES: Cc1cc(C(=O)N2CCC3(CC2)CN(CC(F)F)CC(c2ncc(C(C)(C)C)o2)O3)ccc1OC(C)C] | 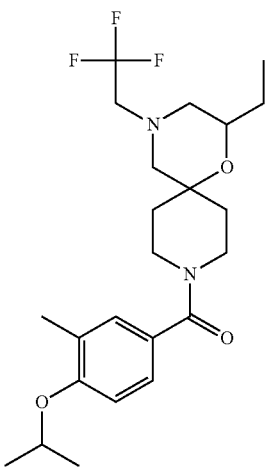 |
| 231 | 234 |
|---|---|
| 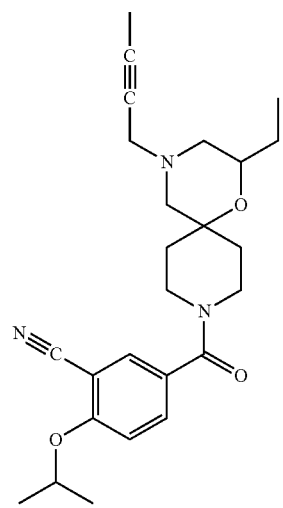 [SMILES: CC#CCN1CC(CC)OC2(CCN(C(=O)c3ccc(OC(C)C)c(C#N)c3)CC2)C1] | 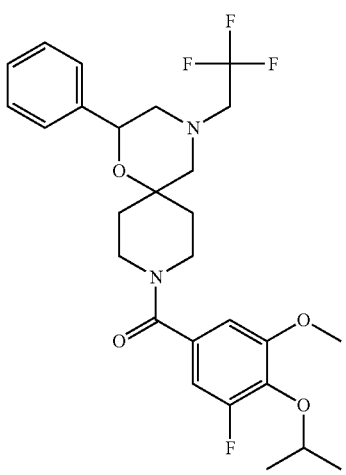 |
| 232 | 235 |
|---|---|
| 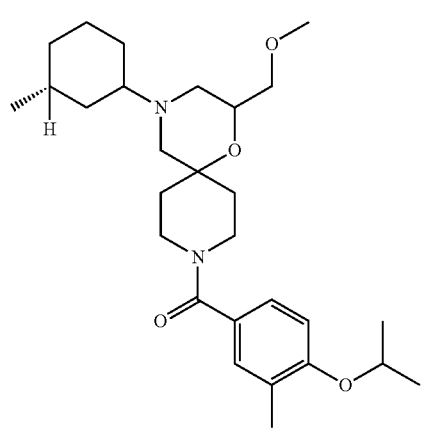 [SMILES: COCC1CN(C2CCC[C@@H](C)C2)CC2(CCN(C(=O)c3ccc(OC(C)C)c(C)c3)CC2)O1] | 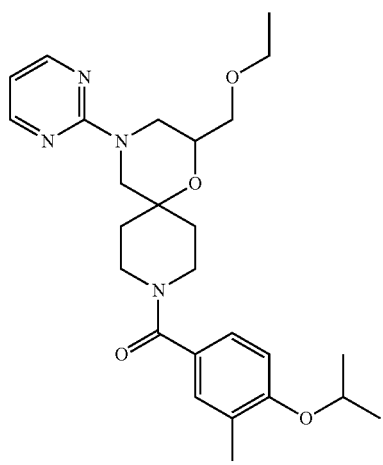 [SMILES: CCOCC1CN(c2ncccn2)CC2(CCN(C(=O)c3ccc(OC(C)C)c(C)c3)CC2)O1] |

| 236 | 239 |
|---|---|
| 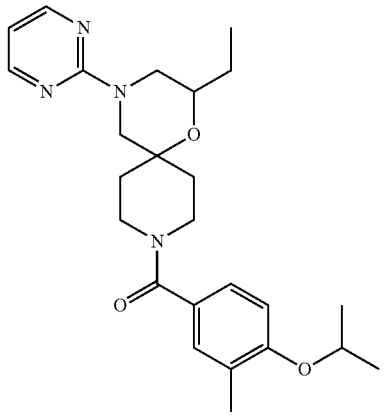 [SMILES: CCC1CN(c2ncccn2)CC2(CCN(C(=O)c3ccc(OC(C)C)c(C)c3)CC2)O1] | 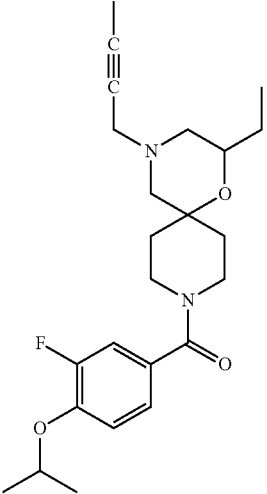 |
| 237 | 240 |
| 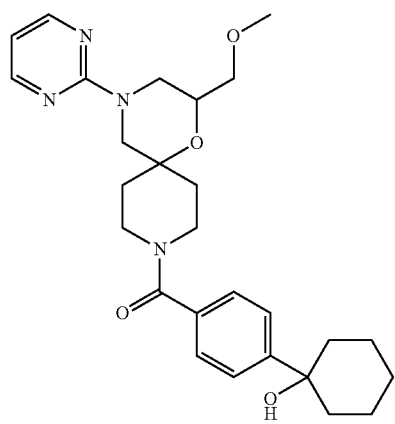 [SMILES: COCC1CN(c2ncccn2)CC2(CCN(C(=O)c3ccc(C4(O)CCCCC4)cc3)CC2)O1] | 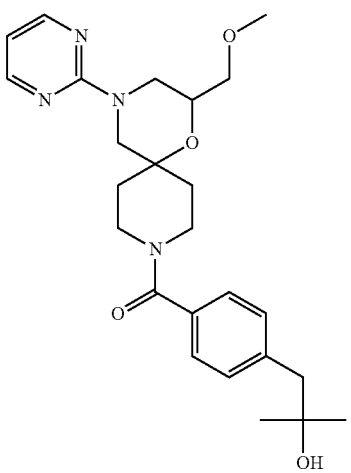 |
| 238 | 241 |
| 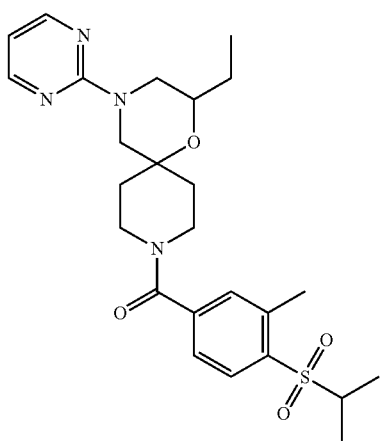 [SMILES: CCC1CN(c2ncccn2)CC2(CCN(C(=O)c3ccc(S(=O)(=O)C(C)C)c(C)c3)CC2)O1] | 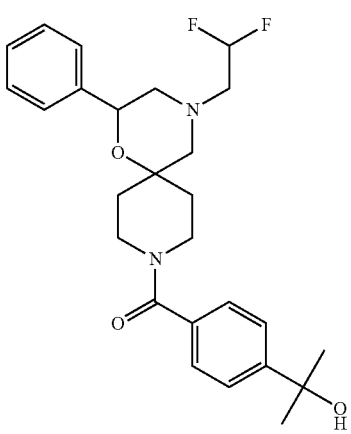 [SMILES: CC(C)(O)c1ccc(C(=O)N2CCC3(CC2)CN(CC(F)F)CC(c2ccccc2)O3)cc1] |

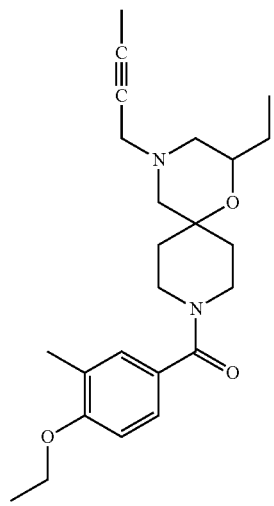 [SMILES: CC#CCN1CC(CC)OC2(CCN(C(=O)c3ccc(OCC)c(C)c3)CC2)C1]
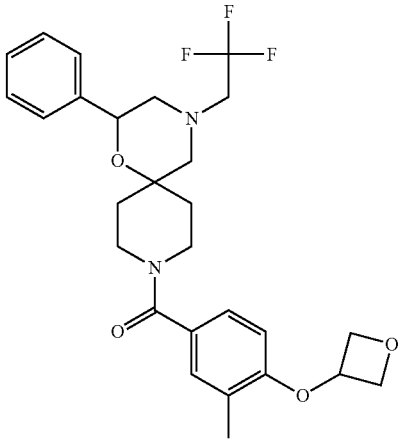 [SMILES: Cc1cc(C(=O)N2CCC3(CC2)CN(CC(F)(F)F)CC(c2ccccc2)O3)ccc1OC1COC1]
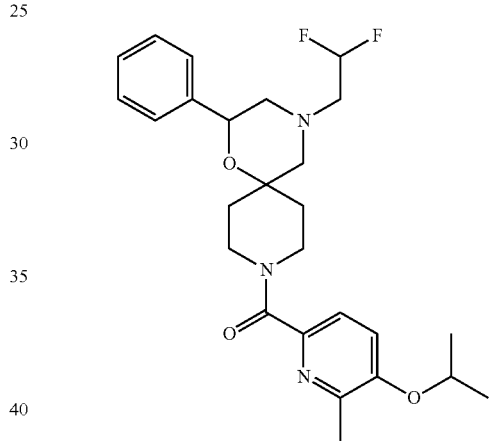
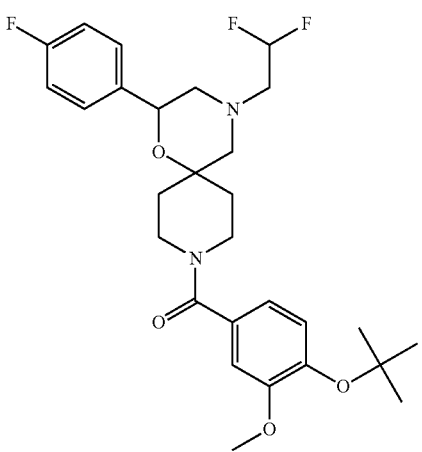 [SMILES: COc1cc(C(=O)N2CCC3(CC2)CN(CC(F)F)CC(c2ccc(F)cc2)O3)ccc1OC(C)(C)C]

| 435 -continued | 436 -continued |
|---|---|
| 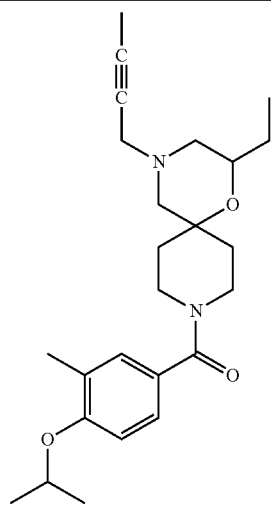 248 | 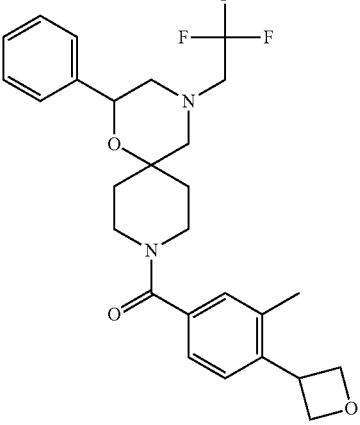 251 |
| 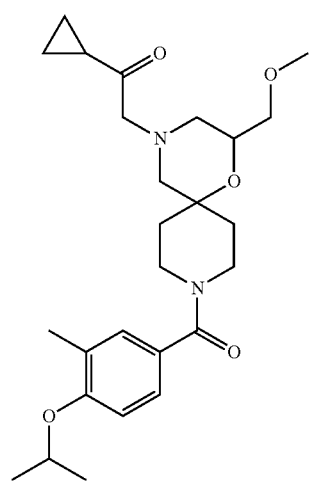 [SMILES: COCC1CN(CC(=O)C2CC2)CC2(CCN(C(=O)c3ccc(OC(C)C)c(C)c3)CC2)O1] 249 | 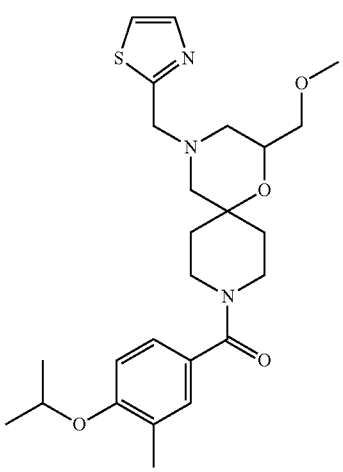 252 |
| 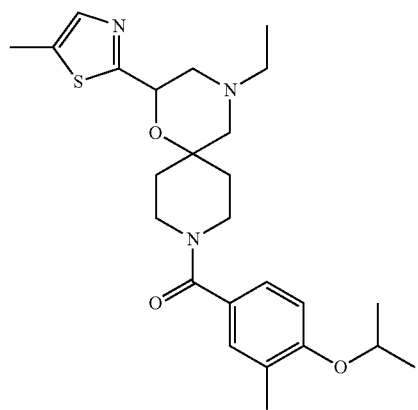 [SMILES: CCN1CC(c2ncc(C)s2)OC2(CCN(C(=O)c3ccc(OC(C)C)c(C)c3)CC2)C1] 250 | 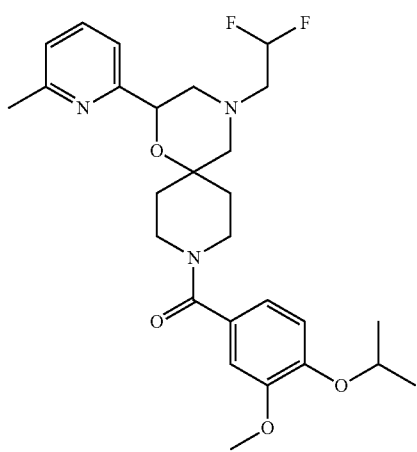 [SMILES: COc1cc(C(=O)N2CCC3(CC2)CN(CC(F)F)CC(c2cccc(C)n2)O3)ccc1OC(C)C] 253 |

| 437 -continued | 438 -continued |
|---|---|
| 254 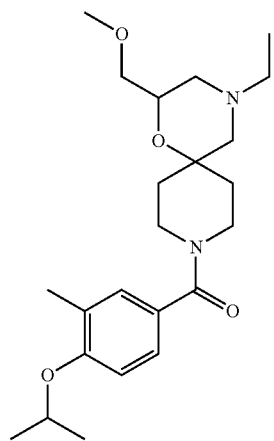 [SMILES: CCN1CC(COC)OC2(CCN(C(=O)c3ccc(OC(C)C)c(C)c3)CC2)C1] | 257 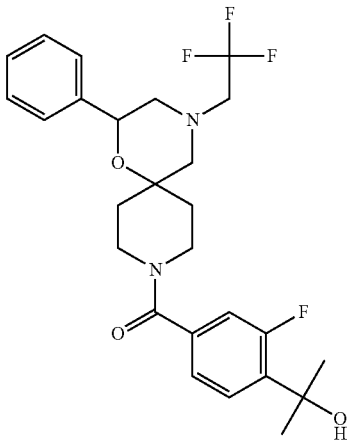 [SMILES: CC(C)(O)c1ccc(C(=O)N2CCC3(CC2)CN(CC(F)(F)F)CC(c2ccccc2)O3)cc1F] |
| 255 | 258 |
| 256 | 259 |
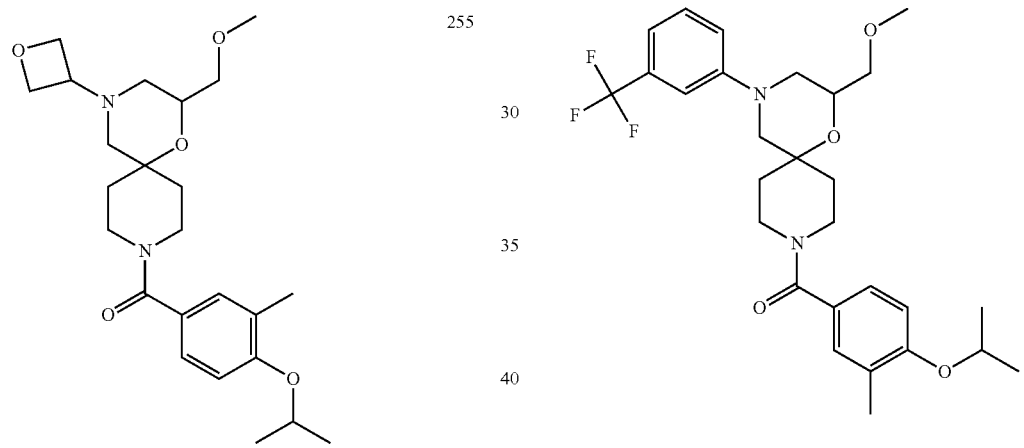
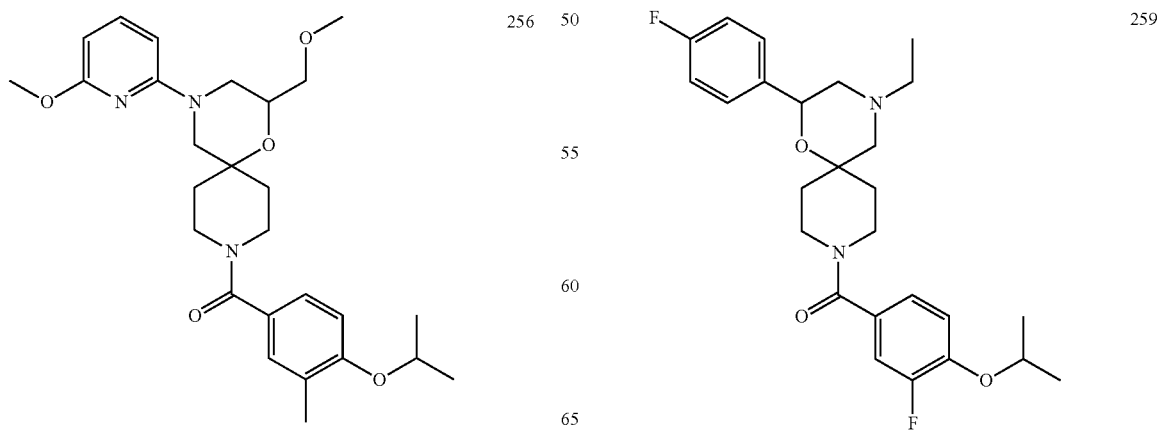

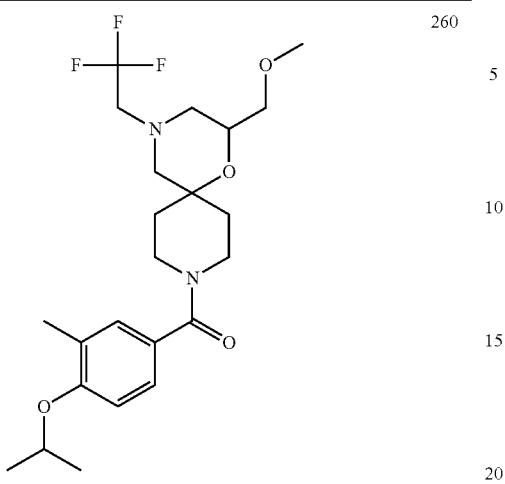
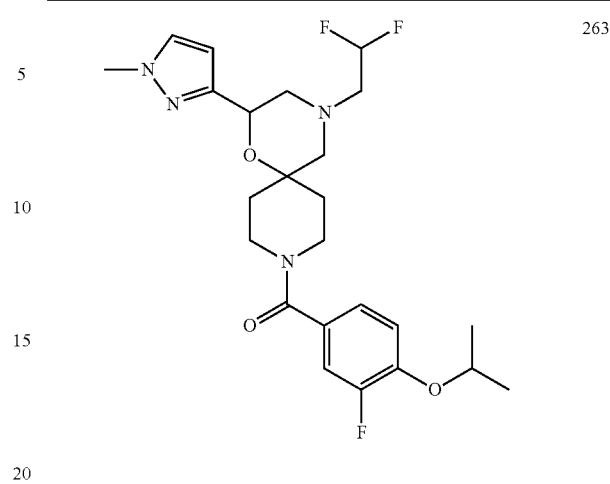
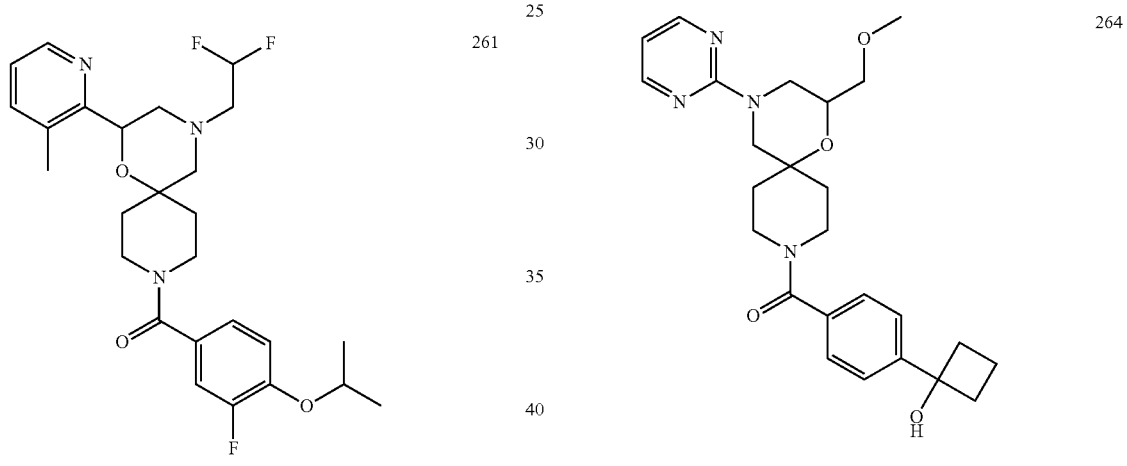
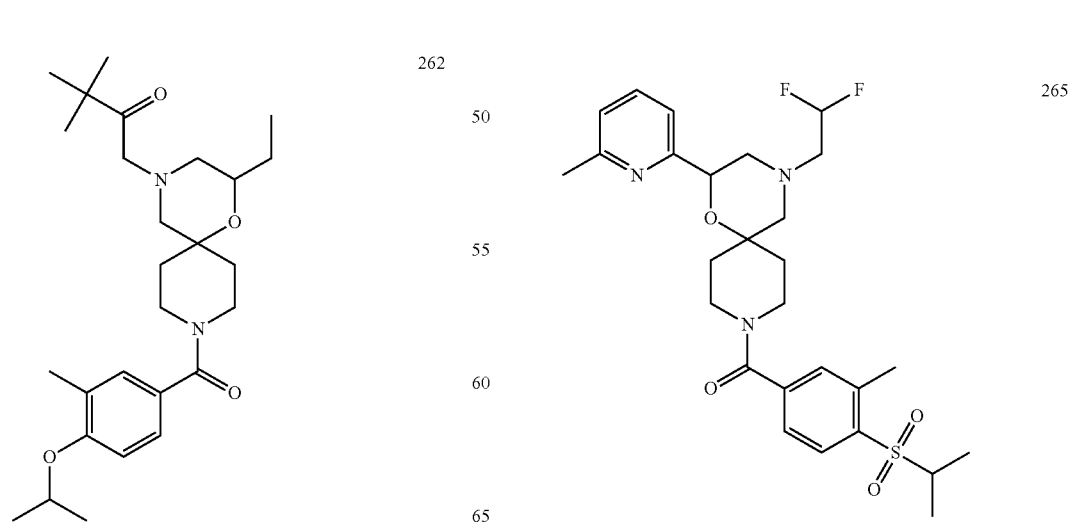

441
-continued
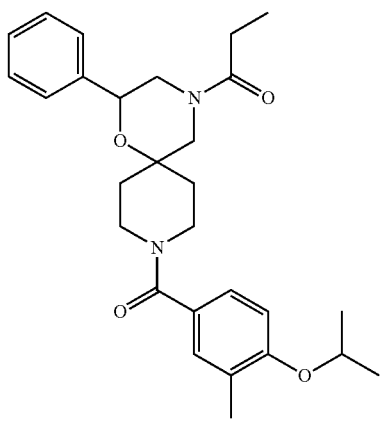 [SMILES: CCC(=O)N1CC(c2ccccc2)OC2(CCN(C(=O)c3ccc(OC(C)C)c(C)c3)CC2)C1]
266
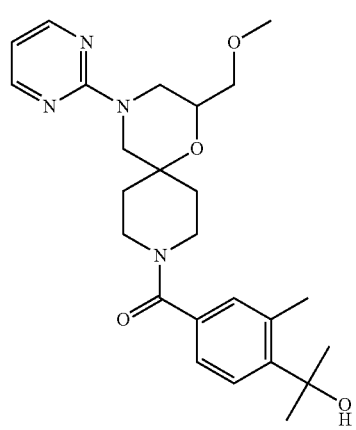 [SMILES: COCC1CN(c2ncccn2)CC2(CCN(C(=O)c3ccc(C(C)(C)O)c(C)c3)CC2)O1]
267
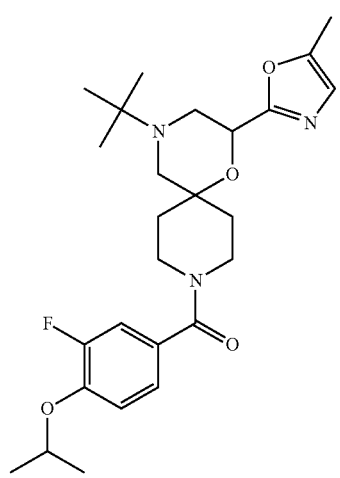
268
442
-continued
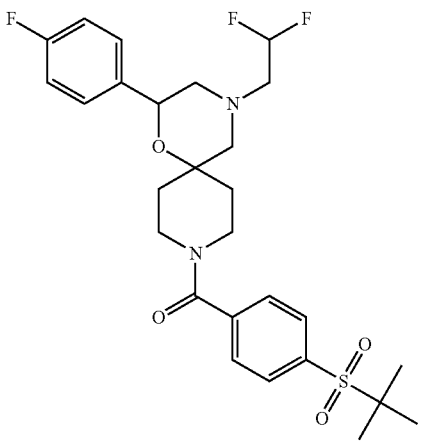 [SMILES: CC(C)(C)S(=O)(=O)c1ccc(C(=O)N2CCC3(CC2)CN(CC(F)F)CC(c2ccc(F)cc2)O3)cc1]
269
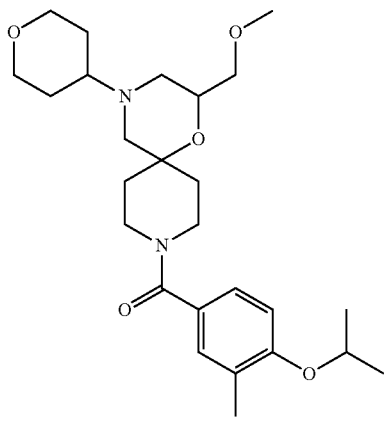 [SMILES: COCC1CN(C2CCOCC2)CC2(CCN(C(=O)c3ccc(OC(C)C)c(C)c3)CC2)O1]
270
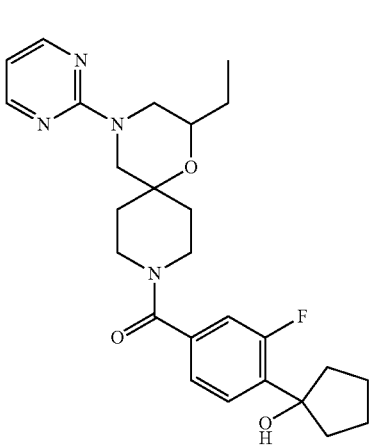
271

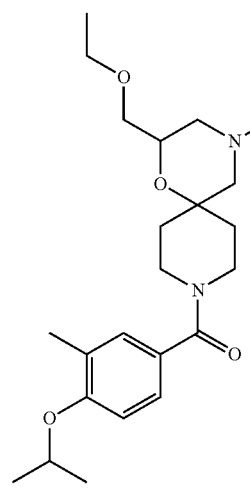
272
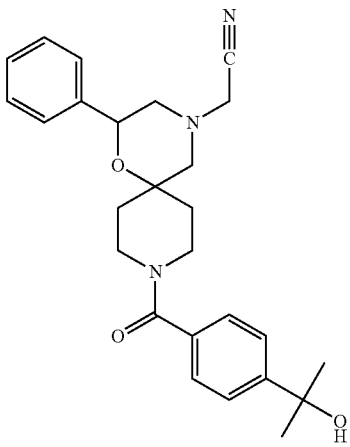
275
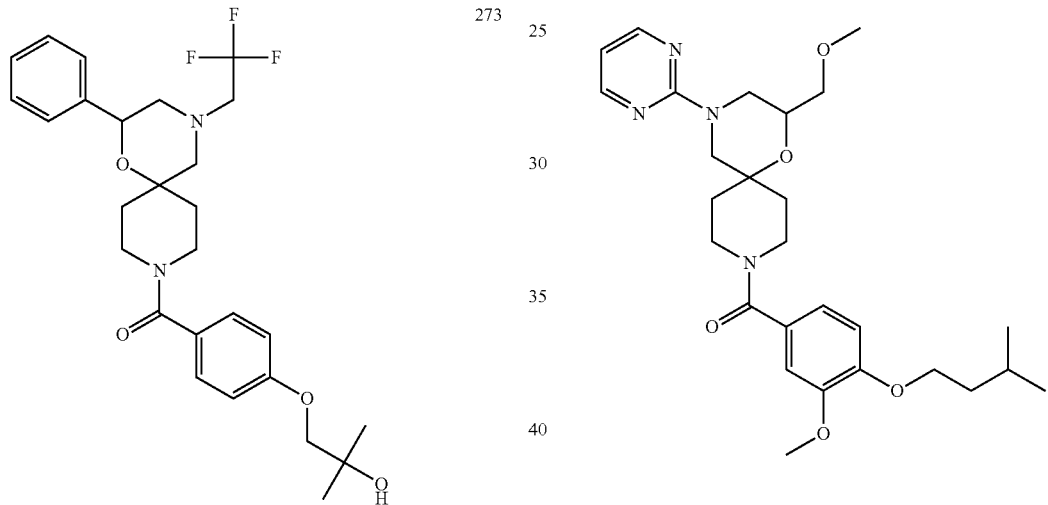
273
276
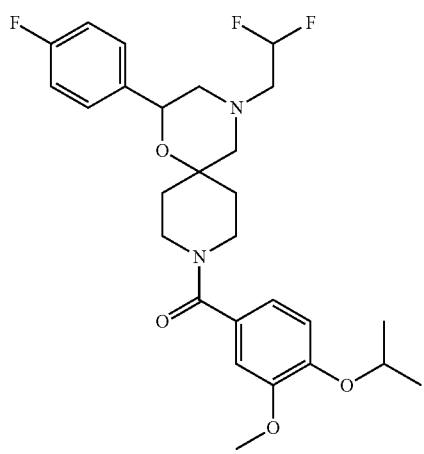 [SMILES: COc1cc(C(=O)N2CCC3(CC2)CN(CC(F)F)CC(c2ccc(F)cc2)O3)ccc1OC(C)C]
274
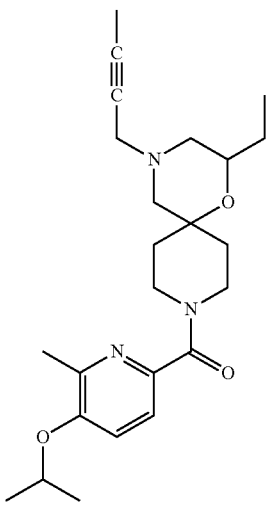
277

| 445 -continued | 446 -continued |
|---|---|
| 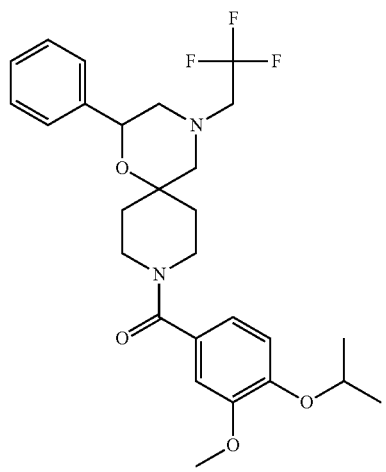 [SMILES: COc1cc(C(=O)N2CCC3(CC2)CN(CC(F)(F)F)CC(c2ccccc2)O3)ccc1OC(C)C] 278 | 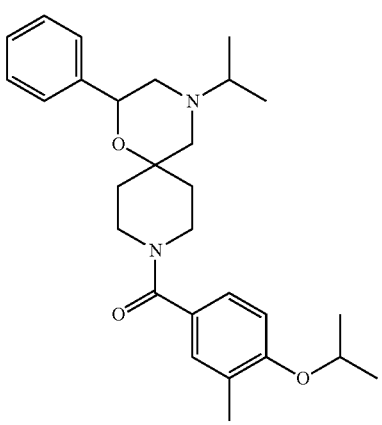 281 |
| 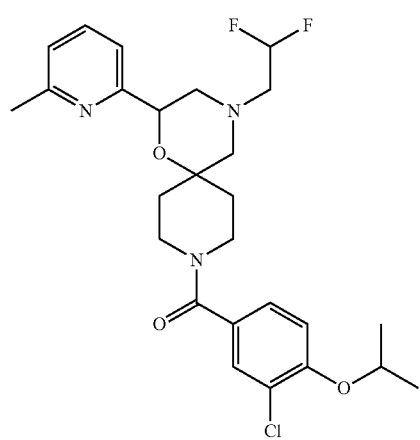 279 | 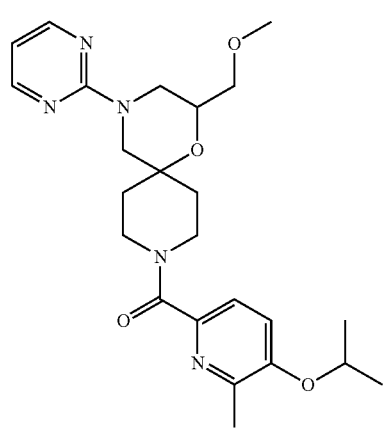 282 |
| 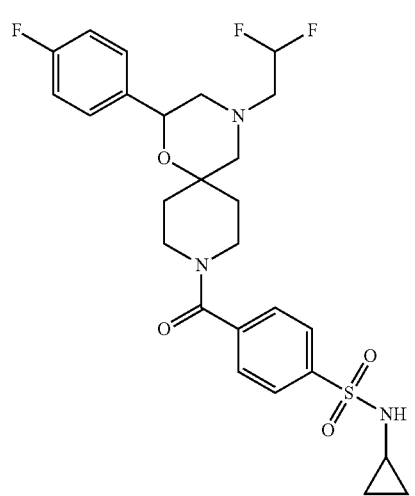 [SMILES: O=C(c1ccc(S(=O)(=O)NC2CC2)cc1)N1CCC2(CC1)CN(CC(F)F)CC(c1ccc(F)cc1)O2] 280 | 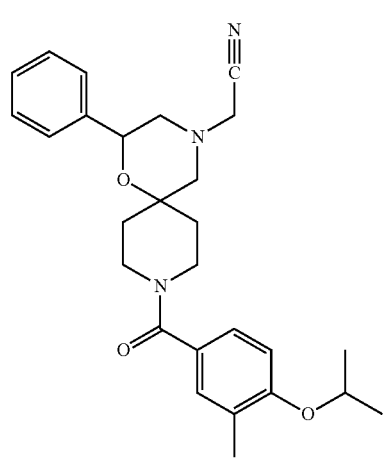 [SMILES: Cc1cc(C(=O)N2CCC3(CC2)CN(CC#N)CC(c2ccccc2)O3)ccc1OC(C)C] 283 |

| 284 | 287 |
|---|---|
| 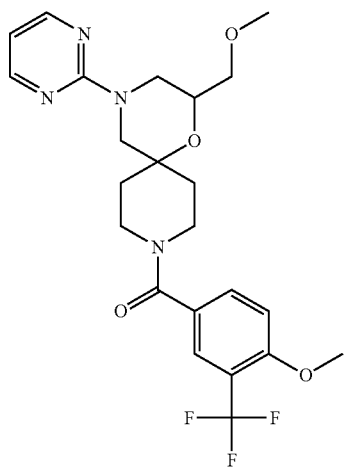 [SMILES: COCC1CN(c2ncccn2)CC2(CCN(C(=O)c3ccc(OC)c(C(F)(F)F)c3)CC2)O1] | 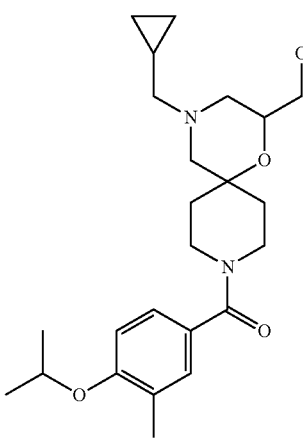 |
| 285 | 288 |
|---|---|
| | 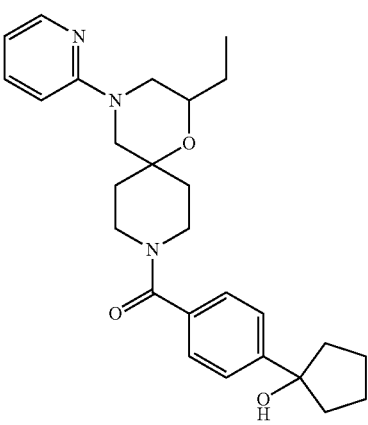 |
| 286 | 289 |
|---|---|
| 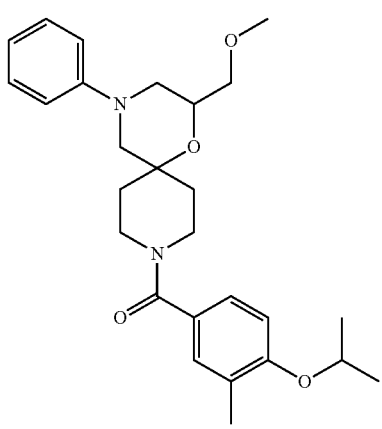 [SMILES: COCC1CN(c2ccccc2)CC2(CCN(C(=O)c3ccc(OC(C)C)c(C)c3)CC2)O1] | 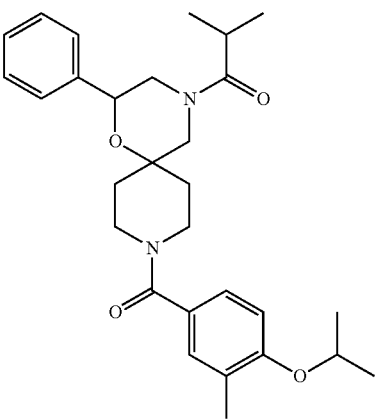 [SMILES: Cc1cc(C(=O)N2CCC3(CC2)CN(C(=O)C(C)C)CC(c2ccccc2)O3)ccc1OC(C)C] |

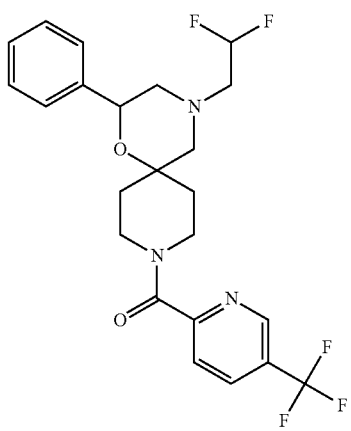 [SMILES: O=C(c1ccc(C(F)(F)F)cn1)N1CCC2(CC1)CN(CC(F)F)CC(c1ccccc1)O2]
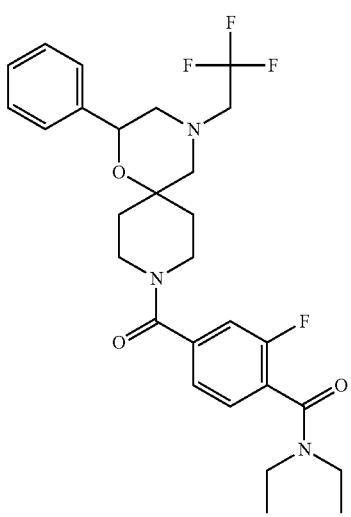 [SMILES: CCN(CC)C(=O)c1ccc(C(=O)N2CCC3(CC2)CN(CC(F)(F)F)CC(c2ccccc2)O3)cc1F]

| 451 -continued | 452 -continued |
|---|---|
| 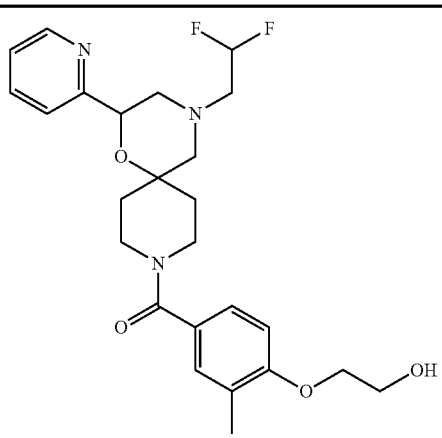 296 | 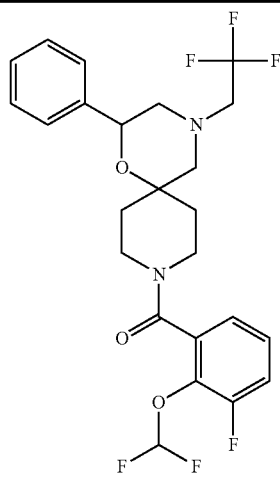 299 |
| 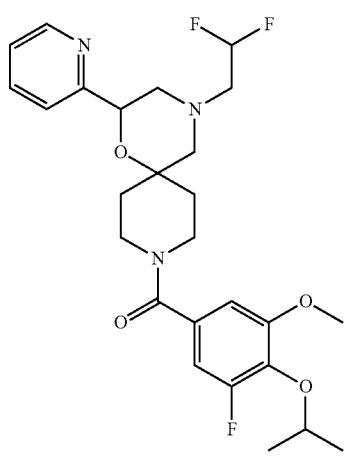 [SMILES: COc1cc(C(=O)N2CCC3(CC2)CN(CC(F)F)CC(c2ccccn2)O3)cc(F)c1OC(C)C] 297 | 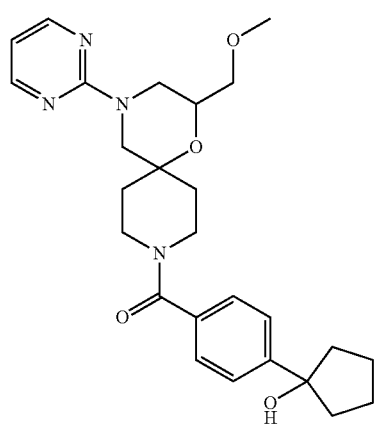 300 |
| 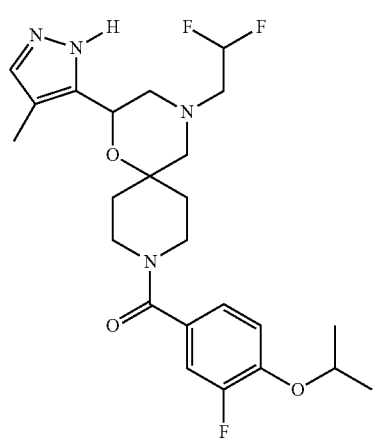 [SMILES: Cc1cn[nH]c1C1CN(CC(F)F)CC2(CCN(C(=O)c3ccc(OC(C)C)c(F)c3)CC2)O1] 298 | 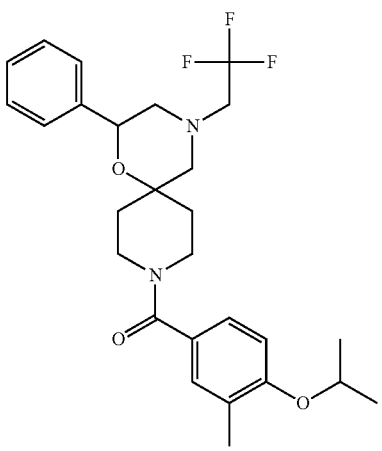 [SMILES: Cc1cc(C(=O)N2CCC3(CC2)CN(CC(F)(F)F)CC(c2ccccc2)O3)ccc1OC(C)C] 301 |

| 453 -continued | 454 -continued |
|---|---|
| 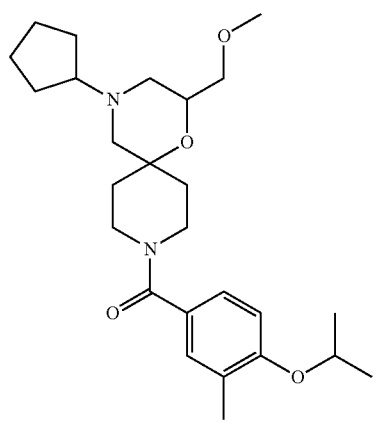 [SMILES: COCC1CN(C2CCCC2)CC2(CCN(C(=O)c3ccc(OC(C)C)c(C)c3)CC2)O1] 302 | 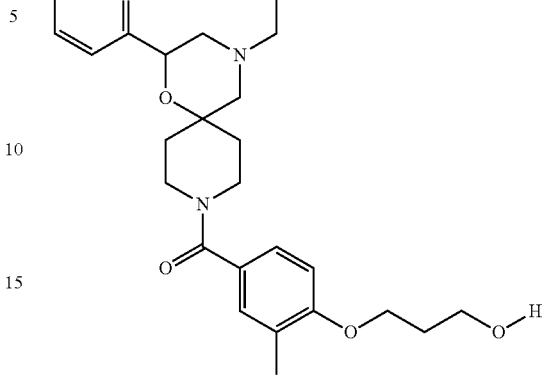 305 |
| 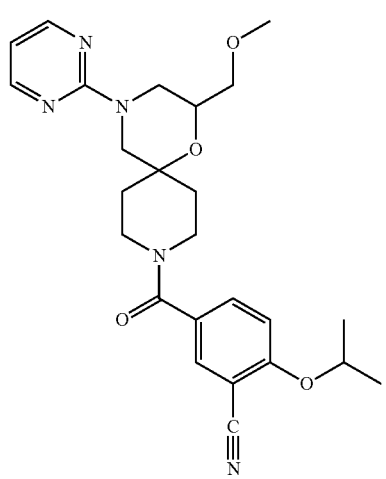 [SMILES: COCC1CN(c2ncccn2)CC2(CCN(C(=O)c3ccc(OC(C)C)c(C#N)c3)CC2)O1] 303 | 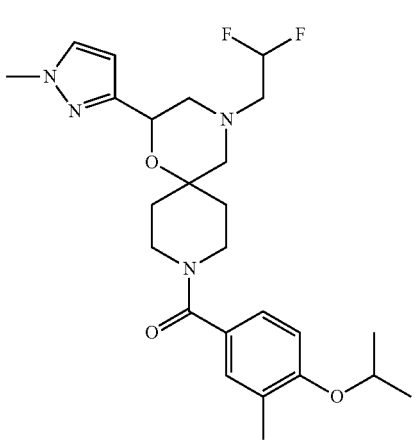 306 |
| 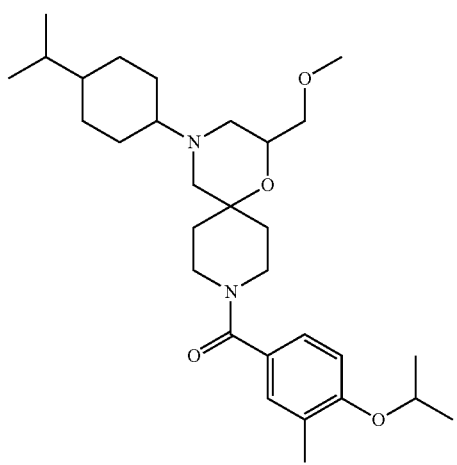 [SMILES: COCC1CN(C2CCC(C(C)C)CC2)CC2(CCN(C(=O)c3ccc(OC(C)C)c(C)c3)CC2)O1] 304 | 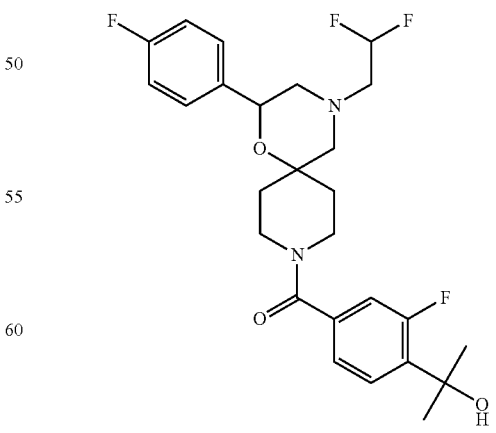 307 |

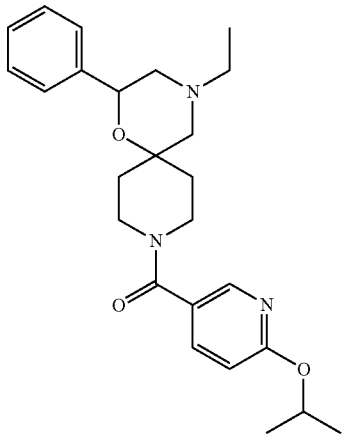 [SMILES: CCN1CC(c2ccccc2)OC2(CCN(C(=O)c3ccc(OC(C)C)nc3)CC2)C1]

308

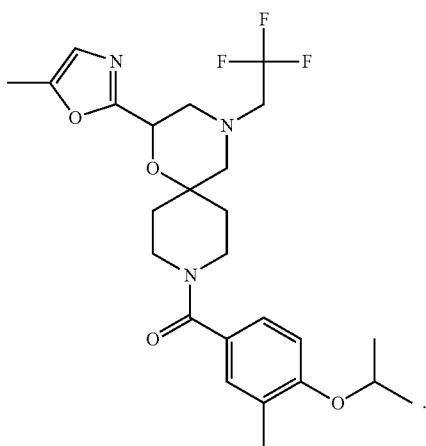 [SMILES: Cc1cnc(C2CN(CC(F)(F)F)CC3(CCN(C(=O)c4ccc(OC(C)C)c(C)c4)CC3)O2)o1]

309

75. A pharmaceutical composition comprising the compound of claim 1 and a pharmaceutically acceptable carrier.

76. A method of inhibiting a voltage-gated sodium ion channel in:
 a patient; or
 a biological sample;
 comprising administering to the patient, or contacting the biological sample, with the compound or composition of claim 1.

77. The method of claim 76, wherein the voltage-gated sodium ion channel is NaV 1.7.

78. A method of treating or lessening the severity in a subject of acute, chronic, neuropathic, or inflammatory pain, arthritis, migraine, cluster headaches, trigeminal neuralgia, herpatic neuralgia, general neuralgias, epilepsy or epilepsy conditions, neurodegenerative disorders, psychiatric disorders, anxiety, depression, bipolar disorder, myotonia, arrhythmia, movement disorders, neuroendocrine disorders, ataxia, multiple sclerosis, irritable bowel syndrome, incontinence, visceral pain, osteoarthritis pain, postherpetic neuralgia, diabetic neuropathy, radicular pain, sciatica, back pain, head or neck pain, severe or intractable pain, nociceptive pain, breakthrough pain, postsurgical pain, cancer pain, stroke, cerebral ischemia, traumatic brain injury, amyotrophic lateral sclerosis, stress- or exercise induced angina, palpitations, hypertension, migraine, or abormal gastro-intestinal motility, comprising administering an effective amount of a compound of claim 1.

79. The method of claim 78, wherein said method is used for treating or lessening the severity of femur cancer pain; non-malignant chronic bone pain; rheumatoid arthritis; osteoarthritis; spinal stenosis; neuropathic low back pain; neuropathic low back pain; myofascial pain syndrome; fibromyalgia; temporomandibular joint pain; chronic visceral pain, abdominal pain; pancreatic; IBS pain; chronic and acute headache pain; migraine; tension headache, including, cluster headaches; chronic and acute neuropathic pain, post-herpatic neuralgia; diabetic neuropathy; HIV-associated neuropathy; trigeminal neuralgia; Charcot-Marie Tooth neuropathy; hereditary sensory neuropathies; peripheral nerve injury; painful neuromas; ectopic proximal and distal discharges; radiculopathy; chemotherapy induced neuropathic pain; radiotherapy-induced neuropathic pain; post-mastectomy pain; central pain; spinal cord injury pain; post-stroke pain; thalamic pain; complex regional pain syndrome; phantom pain; intractable pain; acute pain, acute post-operative pain; acute musculoskeletal pain; joint pain; mechanical low back pain; neck pain; tendonitis; injury/exercise pain; acute visceral pain, abdominal pain; pyelonephritis; appendicitis; cholecystitis; intestinal obstruction; hernias; chest pain, cardiac pain; pelvic pain, renal colic pain, acute obstetric pain, labor pain; cesarean section pain; acute inflammatory, burn and trauma pain; acute intermittent pain, endometriosis; acute herpes zoster pain; sickle cell anemia; acute pancreatitis; breakthrough pain; orofacial pain including sinusitis pain, dental pain; multiple sclerosis (MS) pain; pain in depression; leprosy pain; Behcet's disease pain; adiposis dolorosa; phlebitic pain; Guillain-Barre pain; painful legs and moving toes; Haglund syndrome; erythromelalgia pain; Fabry's disease pain; bladder and urogenital disease, including, urinary incontinence; hyperactivity bladder; painful bladder syndrome; interstitial cyctitis (IC); prostatitis; complex regional pain syndrome (CRPS), type I and type II; widespread pain, paroxysmal extreme pain, pruritic, tinnitus, or angina-induced pain.

* * * * *

UNITED STATES PATENT AND TRADEMARK OFFICE
CERTIFICATE OF CORRECTION

PATENT NO. : 8,828,996 B2
APPLICATION NO. : 13/418737
DATED : September 9, 2014
INVENTOR(S) : Sara Sabine Hadida-Ruah et al.

It is certified that error appears in the above-identified patent and that said Letters Patent is hereby corrected as shown below:

In the Claims

In claim 17, col. 333, line 15, " 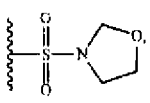 " should be -- 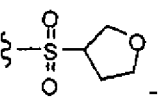 --.

In claim 40, col. 345, line 29, "C1-C6 flunronlkyl" should be --C1-C6 fluoroalkyl--.

In claim 79, col. 456, line 49, "pruritic" should be --pruritis--.

Signed and Sealed this
Thirteenth Day of January, 2015

Michelle K. Lee
*Deputy Director of the United States Patent and Trademark Office*